United States Patent
Kates et al.

(10) Patent No.: US 11,795,192 B2
(45) Date of Patent: Oct. 24, 2023

(54) ANTIMICROBIAL COMPOUNDS, COMPOSITIONS, AND USES THEREOF

(71) Applicant: Lakewood Amedex, Inc., University Park, FL (US)

(72) Inventors: Steven A. Kates, Needham, MA (US); Randolph B. Sleet, Venice, FL (US); Steven Parkinson, University Park, FL (US)

(73) Assignee: Lakewood Amedex, Inc., University Park, FL (US)

( * ) Notice: Subject to any disclaimer, the term of this patent is extended or adjusted under 35 U.S.C. 154(b) by 0 days.

(21) Appl. No.: 17/890,102

(22) Filed: Aug. 17, 2022

(65) Prior Publication Data

US 2023/0026056 A1    Jan. 26, 2023

Related U.S. Application Data

(63) Continuation-in-part of application No. 16/492,861, filed as application No. PCT/US2018/022068 on Mar. 12, 2018, now abandoned.

(60) Provisional application No. 62/470,025, filed on Mar. 10, 2017, provisional application No. 62/470,039, filed on Mar. 10, 2017.

(51) Int. Cl.
| | |
|---|---|
| *C07H 19/10* | (2006.01) |
| *C07H 19/20* | (2006.01) |
| *A61P 31/04* | (2006.01) |
| *C07H 19/207* | (2006.01) |
| *A61K 9/08* | (2006.01) |
| *A61K 9/00* | (2006.01) |
| *A61K 9/06* | (2006.01) |

(52) U.S. Cl.
CPC .......... *C07H 19/10* (2013.01); *A61K 9/0014* (2013.01); *A61K 9/0034* (2013.01); *A61K 9/0046* (2013.01); *A61K 9/0078* (2013.01); *A61K 9/06* (2013.01); *A61K 9/08* (2013.01); *A61P 31/04* (2018.01); *C07H 19/207* (2013.01)

(58) Field of Classification Search
None
See application file for complete search history.

(56) References Cited

U.S. PATENT DOCUMENTS

| | | | |
|---|---|---|---|
| 4,421,769 A | 12/1983 | Dixon et al. | |
| 5,167,950 A | 12/1992 | Lins | |
| 5,824,666 A | 10/1998 | Deckner et al. | |
| 6,211,349 B1 | 4/2001 | Dale et al. | |
| 6,521,213 B1 | 2/2003 | Mautone | |
| 7,314,923 B2 | 1/2008 | Kaneko et al. | |
| 7,868,162 B2 | 1/2011 | Dale | |
| 10,711,028 B2 * | 7/2020 | Sleet | A61P 27/16 |
| 10,752,651 B2 | 8/2020 | Sleet | |
| 10,981,943 B2 | 4/2021 | Sleet | |
| 11,123,357 B2 * | 9/2021 | Kates | A61K 9/06 |
| 2005/0232891 A1 | 10/2005 | Moloney et al. | |
| 2009/0233879 A1 | 9/2009 | Reddy et al. | |
| 2010/0092526 A1 | 4/2010 | Baker et al. | |
| 2011/0135713 A1 | 6/2011 | Dale | |
| 2011/0201674 A1 | 8/2011 | Schramm et al. | |
| 2016/0120936 A1 | 5/2016 | Troxel | |
| 2016/0166498 A1 | 6/2016 | Anastassov et al. | |
| 2016/0271217 A1 | 9/2016 | Grönberg et al. | |

FOREIGN PATENT DOCUMENTS

| | | |
|---|---|---|
| CN | 101724001 A | 6/2010 |
| CN | 102223876 A | 10/2011 |
| WO | 0040591 A1 | 7/2000 |
| WO | 0057890 A1 | 10/2000 |
| WO | 02089581 A1 | 11/2002 |
| WO | 2008133704 A2 | 11/2008 |
| WO | 2012017434 A2 | 2/2012 |
| WO | 2014124430 A1 | 8/2014 |
| WO | 2018165673 A1 | 9/2018 |
| WO | 2018231863 A1 | 12/2018 |

OTHER PUBLICATIONS

Mexican Patent Office, Office Action and translated summary dated Dec. 16, 2021 in corresponding Maxican application No. MX/a/2019/010695, 5 pgs.
Mexican Patent Office, Office Action and translated summary dated Aug. 17, 2021 in corresponding Maxican application No. MX/a/2019/010695, 10 pgs.
The International Bureau of WIPO, International Preliminary Report on Patentability issued in Application No. PCT/US2018/022068, dated Sep. 19, 2019, 6 pp.
International Searching Authority / US, International Search Report & Written Opinion issued in Application No. PCT/US2018/022068, dated Jun. 1, 2018, 10 pp.
The International Bureau of WIPO, International Preliminary Report on Patentability issued in Application No. PCT/US2018/022071, dated Sep. 19, 2019, 7 pp.
International Searching Authority / US, International Search Report & Written Opinion issued in Application No. PCT/US2018/022071, dated Jul. 3, 2018, 13 pp.
Brazilian Patent Office, Office Action and translation dated Sep. 26, 2021 in corresponding Brazilian application No. 12 2021 00404 6, 5 pgs.
Goodman, S., "What Causes Skin Ulcers?", Embarrassing issues website via Internet Archive dated Mar. 3, 2016, access online at https://archive.org/we/20160303203020/hrrp://www.embarrassingissues.co.uk/Ulcers.html on Jul. 15, 2021.
The International Bureau of WIPO, International Preliminary Report on Patentability issued in Application No. PCT/US2019/056772, dated Apr. 29, 2021, 10 pp.
International Searching Authority / US, International Search Report & Written Opinion issued in Application No. PCT/US2019/056772, dated Dec. 27, 2019, 14 pp.

(Continued)

*Primary Examiner* — Traviss C McIntosh, III
(74) *Attorney, Agent, or Firm* — Taft Stettinius & Hollister LLP

(57) ABSTRACT

Antimicrobial compounds and compositions of Formulas (V), (VI), (VII), (VIII), and (IX), and methods of use are disclosed.

21 Claims, 3 Drawing Sheets

(56) References Cited

OTHER PUBLICATIONS

European Patent Office, Extended European Search Report issued in Application No. 18763136.1, dated Dec. 15, 2020, 13 pp.

Chinese Patent Office, First Office Action issued in Application No. 201880030624.4, dated Nov. 2, 2020, 11 pp.

Abramova et al., "Synthesis of nucleotide-amino acid conjugates designed for photo-CIDNP experiments by a phosphotriester approach," Beilstein J. Org. Chem., 2013, vol. 9, pp. 2898-2909.

Acharya et al., "Measurement of Nucleobase pKa Values in Model Mononucleotides Shows RNA-RNA Duplexes To Be More Stable Than DNA-DNA Duplexes," J. Am. Chem. Soc., 2004, vol. 126, pp. 2862-2869.

Aksungur et al., "Chitosan delivery systems for the treatment of oral mucositis: in vitro and in vivo studies," Journal of Controlled Release, vol. 98, 2004, pp. 269-279.

Barman et al., "Non-identical electronic characters of the internucleotidic phosphates in RNA modulate the chemical reactivity of the phosphodiester bonds," Org. Biomol. Chem., 2006, vol. 4, pp. 928-941.

Berge et al., "Pharmaceutical Salts," Journal of Pharmaceutical Sciences, Jan. 1977, vol. 66, No. 1, 19 pp.

Chatterjee et al., "The chemical nature of the 2'-substituent in the pentose-sugar dictates the pseudoaromatic character of the nucleobase (pKa) in DNA/RNA," Org. Biomol. Chem., 2006, vol. 4, pp. 1675-1686.

Chomicz et al., "Electron induced single strand break and cyclization: a DFT study on the radiosensitization mechanism of the nucleotide of 8-bromoguanine," Phys. Chem. Chem. Phys., 2014, vol. 16, pp. 6568-6574.

Chomicz et al., "The radiosensitivity of 5- and 6-bromocytidine derivatives—electron induced DNA degradation," Phys. Chem. Chem. Phys., 2014, vol. 16, pp. 19424-19428.

Donnelly et al., "Antimicrobial therapy to prevent or treat oral mucositis," The Lancet, Infectious Diseases, vol. 3, Jul. 2003, pp. 405-412.

Feng et al., "Efficacy and tolerability of amorolfine 5% nail lacquer in combination with systemic antifungal agents for onychomycosis: A meta-analysis and systemic review," Dermatologic Therapy, vol. 30, 2017, 6 pp.

Jagtap et al., "Development and Evaluation of Herbal Wound Healing Formulations," International Journal of PharmTech Research, vol. 1, No. 4, 2009, pp. 1104-1108.

Lison et al., "Update on the genotoxicity and carcinogenicity of cobalt compounds," Occup Environ Med, 2001, vol. 58, pp. 619-625.

Mason et al., "Oligonucleotide transition state analogues of saporin L3," European Journal of Medicinal Chemistry, vol. 127, 2017, pp. 793-809.

Melekos et al., "Complicated urinary tract infections," International Journal of Antimicrobial Agents, vol. 15, 2000, pp. 247-256.

Moura et al., "Recent advances on the development of wound dressings for diabetic foot ulcer treatment—A review," Acta Biomaterialia, vol. 9, 2013, pp. 7093-7114.

Nandanan et al., "Structure-Activity Relationships of Bisphosphate Nucleotide Derivatives as P2Y1 Receptor Antagonists and Partial Agonists," J. Med. Chem., 1999, vol. 42, pp. 1625-1638.

Olsthoorn et al., "Conformational Characteristics of the Trinucleoside Diphosphate dApdApdA and Its Constituents from Nuclear Magnetic Resonance and Circular Dichroism Studies," Eur. J. Biochem., vol. 112, 1980, pp. 95-110.

Polak et al., "The change in the electronic character upon cisplatin binding to guanine nucleotide is transmitted to drive the conformation of the local sugar-phosphate backbone—a quantitative study," J. Chem. Soc., Perkin Trans. 1, 1999, pp. 2835-2843.

Tyagi et al., "Recent Advances in Intravesical Drug/Gene Delivery," Molecular Pharmaceutics, Jan. 3, 2006; vol. 3, No. 4, pp. 369-379.

Valanne et al., "CAMP factor homologues in Propionibacterium acnes: a new protein family differentially expressed by types I and II," Microbiology, 2005, vol. 151, pp. 1369-1379.

Wagh et al., "Formulation and Evaluation of in situ Gel Drug Delivery System of Sesbania grandiflora Flower Extract for the Treatment of Bacterial Conjunctivitis," J. Pharm. Sci. & Res., vol. 4, No. 8, 2012, pp. 1880-1884.

Wong et al., "Bisphosphocins: a novel antimicrobials for enhanced killing of drug-resistant and biofilm-forming bacteria," Future Microbiol., 2015, vol. 10, No. 11, pp. 1751-1758.

Canadian Office Action, Canadian Intellectual Property Office, Canadian Patent Application No. 3,055,932, dated Feb. 14, 2023, 5 pages.

Korean Office Action, Korean Intellectual Property Office, Korean Patent Application No. 10-2021-7031132, dated Feb. 21, 2023, 5 pages.

Indian Office Action, Intellectual Property India, Indian Patent Application No. 201927040425, dated Mar. 7, 2023, 7 pages.

Chinese Search Report, China National Intellectual Property Administration, Chinese Patent Application No. 2021106620116, dated Jun. 25, 2023, 2 pages.

Cao et al.,"Antimicrobial activity and mechanism of action of Nu-3, a protonated modified nucleotide", Annuals of Clinical Microbiology and Antimicrobials, Jan. 14, 2011, 9 pages.

* cited by examiner

ANTIMICROBIAL COMPOUNDS, COMPOSITIONS, AND USES THEREOF

CROSS REFERENCE TO RELATED APPLICATIONS

This application is a continuation-in-part of U.S. Patent Application Ser. No. 16/492,861 filed on Sep. 10, 2019, which is a U.S. National Phase of International PCT Application No. PCT/US2018/022068 filed Mar. 12, 2018, which claims priority to U.S. Provisional Patent Application Ser. Nos. 62/470,025 and 62/470,039 filed on Mar. 10, 2017, each of which is incorporated by reference herein in its entirety.

FIELD

The present disclosure provides novel antimicrobial compounds and compositions and uses thereof.

BACKGROUND

Bisphosphocin® compounds have antimicrobial activity. U.S. Pat. No. 7,868,162 discloses Bisphosphocin® compounds.

SUMMARY

The present disclosure provides a compound having the formula:

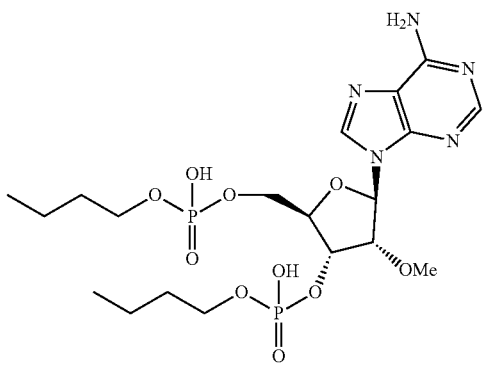

Formula (V)

or a pharmaceutically acceptable salt thereof.

The present disclosure also provides a compound having the formula:

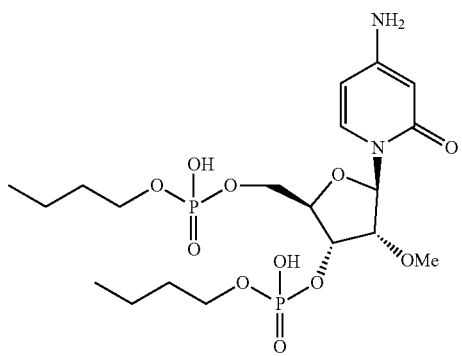

Formula (VI)

or a pharmaceutically acceptable salt thereof.

The present disclosure also provides a compound having the formula:

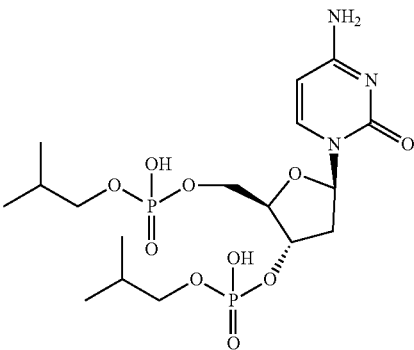

Formula (VII)

or a pharmaceutically acceptable salt thereof.

The present disclosure also provides a compound having the formula:

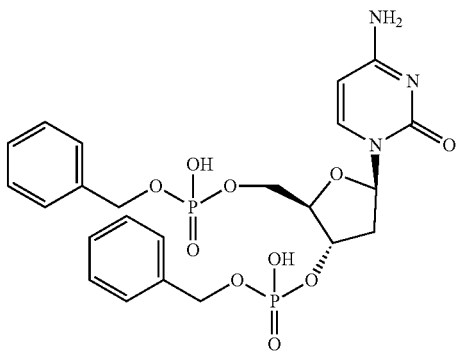

Formula (VIII)

or a pharmaceutically acceptable salt thereof.

The present disclosure also provides a compound having the formula:

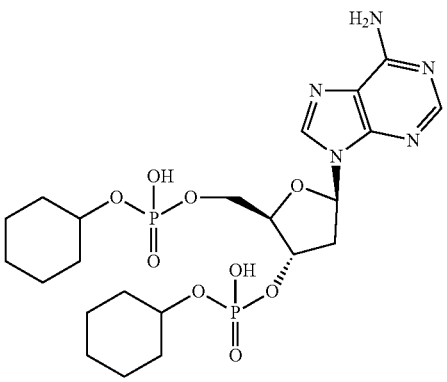

Formula (IX)

or a pharmaceutically acceptable salt thereof.

The present disclosure also provides a pharmaceutical composition comprising a compound of any one of Formula (V), (VI), (VII), (VIII), and (IX), or a pharmaceutically acceptable salt thereof, and one or more pharmaceutically acceptable carriers, excipients, or diluents.

The present disclosure also provides a method of treating an infection in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating an infection of a lower extremity in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating an infection of a diabetic foot ulcer in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating a bladder and/or a urinary tract infection in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating a lung infection in a patient in need thereof, the method comprising administering an effective amount of a compound of any one of Formula (V), (VI), (VII), (VIII), and (IX), or a pharmaceutically acceptable salt thereof, to the patient. In some embodiments, the lung infection arises from a pulmonary condition. In some embodiments, the pulmonary condition is selected from the group consisting of genetic conditions, acquired conditions, primary conditions, secondary conditions, asthma, chronic obstructive pulmonary disease, cystic fibrosis, bronchiolitis, pneumonia, bronchitis, emphysema, adult respiratory distress syndrome, allergies, lung cancer, small cell lung cancer, primary lung cancer, metastatic lung cancer, bronchiestasis, bronchopulmonary dysplasia, chronic bronchitis, chronic lower respiratory diseases, croup, high altitude pulmonary edema, pulmonary fibrosis, interstitial lung disease, reactive airway disease, lymphangioleiomyomatosis, neonatal respiratory distress syndrome, parainfluenza, pleural effusion, pleurisy, pneumothorax, primary pulmonary hypertension, psittacosis, pulmonary edema secondary to various causes, pulmonary embolism, pulmonary hypertension secondary to various causes, respiratory failure secondary to various causes, sleep apnea, sarcoidosis, smoking, stridor, acute respiratory distress syndrome, infectious diseases, SARS, tuberculosis, psittacosis infection, Q fever, parainfluenza, respiratory syncytial virus, combinations thereof, and conditions caused by any one or combination of the above.

The present disclosure also provides a method of treating a lung infection arising from cystic fibrosis in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating pneumonia in a patient in need thereof, the method comprising administering an effective amount of a compound of any one of Formula (V), (VI), (VII), (VIII), and (IX), or a pharmaceutically acceptable salt thereof, to the patient. In some embodiments, the pneumonia is ventilator acquired pneumonia.

The present disclosure also provides a method of treating an infection in a burn wound in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating otitis externa in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating bacterial vaginosis in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating impetigo in a patient in need thereof, the method comprising administering an effective amount of a compound of any one of Formula (V), (VI), (VII), (VIII), and (IX), or a pharmaceutically acceptable salt thereof, to the patient.

The present disclosure also provides a method of treating oral mucositis in a patient in need thereof, the method comprising administering an effective amount of a compound of any one of Formula (V), (VI), (VII), (VIII), and (IX), or a pharmaceutically acceptable salt thereof, to the patient.

The present disclosure also provides a compound of any one of Formula (V), (VI), (VII), (VIII), and (IX), or a pharmaceutically acceptable salt thereof, for use in therapy.

The present disclosure also provides the use of a compound of any one of Formula (V), (VI), (VII), (VIII), and (IX), or a pharmaceutically acceptable salt thereof, for the manufacture of a medicament.

The present disclosure also provides a compound having the formula:

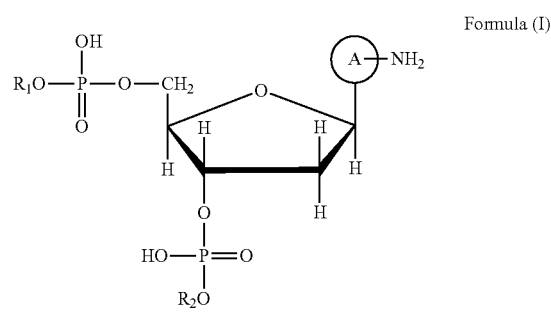

Formula (I)

wherein:

A is a monocyclic, bicyclic, or tricyclic carbocyclic or heterocyclic moiety, and $R_1$ and $R_2$ are each a $C_1$-$C_8$ alkyl moiety; or a pharmaceutically acceptable salt thereof.

In some embodiments, $R_1$ and $R_2$ are each butyl.

Another aspect of the present disclosure provides a compound having the formula:

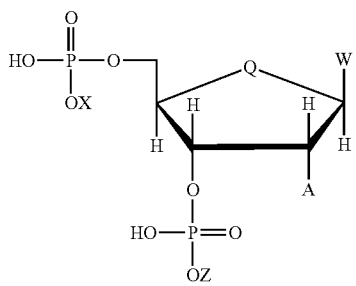

Formula (II)

wherein:
Q is oxygen or sulfur;
W is an amino-substituted or guanidino-substituted nitrogen containing heterocyclic moiety;
X and Z are end blocking groups; and
A is H, alkyl, halogen, alkoxy, alkyl-(O-alkyl), aryl, alkenyl, alkanol or phenol.

Another aspect of the present disclosure provides a compound selected from any one of Cmpds 1 to 2,520 as described in TABLE 1 in the Detailed Description.

Another aspect of the present disclosure provides a compound having the formula:

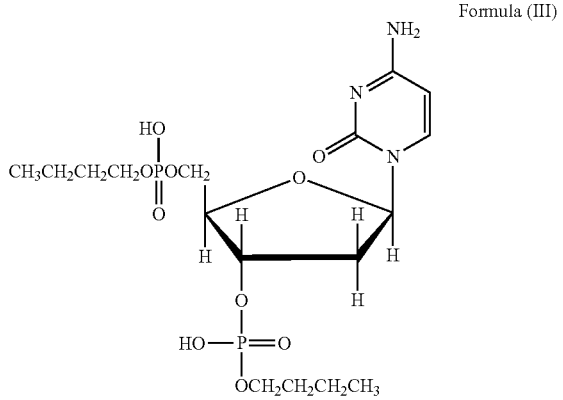

Formula (III)

or a pharmaceutically acceptable salt thereof.

Another aspect of the present disclosure provides a pharmaceutical composition comprising a compound according to Formula (I) to (III), or a pharmaceutically acceptable salt thereof, and one or more pharmaceutically acceptable carriers, excipients, or diluents.

Another aspect of the present disclosure provides a method of treating an infection of a diabetic foot ulcer in a patient in need thereof, the method comprising administering an effective amount of a compound according to Formula (I) to (III), or a pharmaceutically acceptable salt thereof, to the patient.

Another aspect of the present disclosure provides a method of treating a complicated urinary tract infection in a patient in need thereof, the method comprising administering an effective amount of a compound according to Formula (I) to (III), or a pharmaceutically acceptable salt thereof, to the patient.

Another aspect of the present disclosure provides a method of treating a lung infection arising from cystic fibrosis in a patient in need thereof, the method comprising administering an effective amount of a compound according to Formula (I) to (III), or a pharmaceutically acceptable salt thereof, to the patient.

Another aspect of the present disclosure provides a method of treating ventilator acquired pneumonia in a patient in need thereof, the method comprising administering an effective amount of a compound according to Formula (I) to (III), or a pharmaceutically acceptable salt thereof, to the patient.

Another aspect of the present disclosure provides a method of treating an infection in a burn wound in a patient in need thereof, the method comprising administering an effective amount of a compound according to Formula (I) to (III), or a pharmaceutically acceptable salt thereof, to the patient.

Another aspect of the present disclosure provides a method of treating otitis externa in a patient in need thereof, the method comprising administering an effective amount of a compound according to Formula (I) to (III), or a pharmaceutically acceptable salt thereof, to the patient.

Another aspect of the present disclosure provides a method of treating bacterial vaginosis in a patient in need thereof, the method comprising administering an effective amount of a compound according to Formula (I) to (III), or a pharmaceutically acceptable salt thereof, to the patient.

Another aspect of the present disclosure provides a method of treating impetigo in a patient in need thereof, the method comprising administering an effective amount of a compound according to Formula (I) to (III), or a pharmaceutically acceptable salt thereof, to the patient.

Another aspect of the present disclosure provides a compound according to Formula (I) to (III), or a pharmaceutically acceptable salt thereof, for use in therapy.

Another aspect of the present disclosure provides the use of a compound according to Formula (I) to (III), or a pharmaceutically acceptable salt thereof, for the manufacture of a medicament.

In some embodiments, a compound of Formula (I) to (IX), or a pharmaceutically acceptable salt thereof, has certain surprising features and advantages that could not have been predicted prior to the present disclosure. One advantage of a compound of Formula (I) to (IX), or a pharmaceutically acceptable salt thereof, in accordance with some embodiments of the present disclosure is that such compound and/or salt has a high level of biological activity when such compound and/or salt is formulated at higher (less acidic) pH levels. Without being bound by any theory, it is believed that the free amino or guanidino group of a compound of Formula (I) to (IX), or a pharmaceutically acceptable salt thereof, in accordance with some embodiments confers the desired biological activity at higher pH levels. It has been discovered that a compound of Formula (I) to (IX), or a pharmaceutically acceptable salt thereof, in accordance with some embodiments of the present disclosure is unexpectedly more potent at pH levels above about pH 3. Accordingly, it is believed that a compound of Formula (I) to (IX), or a pharmaceutically acceptable salt thereof, in accordance with some embodiments will be useful for indications in which prolonged exposure to antimicrobials is advantageous, such as, for example, microbial infections. Unlike some drugs formulated at below about pH 3 resulting in unacceptable contact irritation in topical, inhalation or intravesical administration routes, a compound of Formula (I) to (IX), or a pharmaceutically acceptable salt thereof, in accordance with some embodiments is compatible with topical, inhalation and intravesical administration routes. Additionally, a compound of Formula (I) to (IX), or a pharmaceutically acceptable salt thereof, in accordance with some embodiments is effective against slow growth bacteria since a compound or salt thereof exhibits, in a short period of time, a high level of biological activity at a higher pH (fast acting antimicrobial mechanism).

Additional aspects and embodiments will be apparent from the Detailed Description and from the claims.

BRIEF DESCRIPTION OF THE DRAWINGS

The teachings of some embodiments of the present disclosure will be better understood by reference to the description taken in conjunction with the accompanying drawings, wherein.

DETAILED DESCRIPTION

Figure 1:
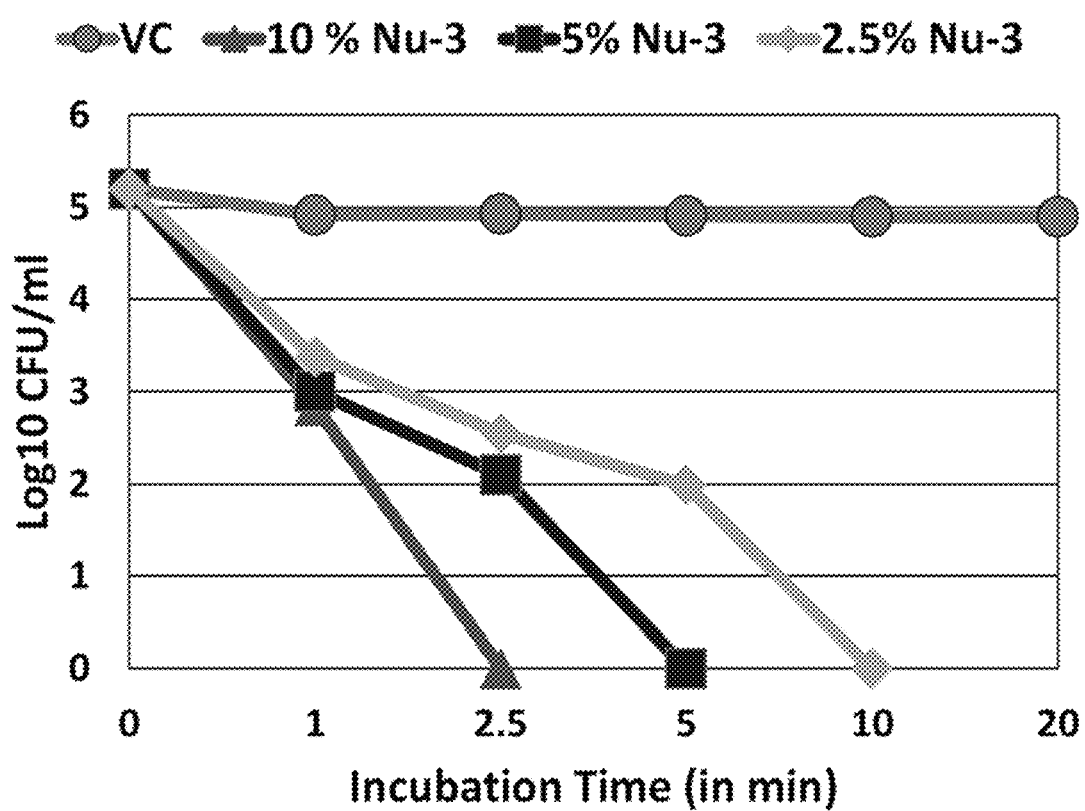
FIG. 1 shows a graph of $Log_{10}$ CFU vs. time for Nu-3 at 2.5%, 5%, and 10% solutions according to embodiments.

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

The present disclosure provides a compound having the formula:

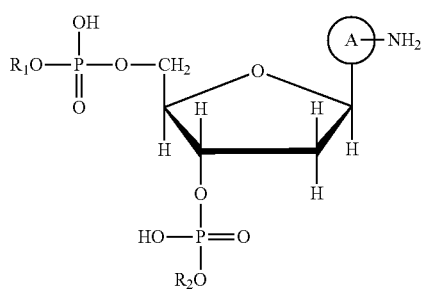

Formula (I)

wherein:
A is a monocyclic, bicyclic, or tricyclic carbocyclic or heterocyclic moiety, and
$R_1$ and $R_2$ are each a $C_1$-$C_8$ alkyl moiety; or
a pharmaceutically acceptable salt thereof.

In some embodiments, the $R_1$ and $R_2$ are each butyl as shown below:

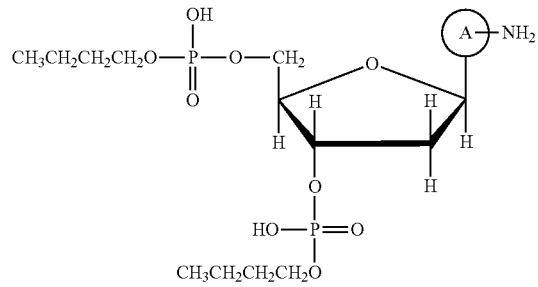

or a pharmaceutically acceptable salt thereof.

The present disclosure also provides a compound having the formula:

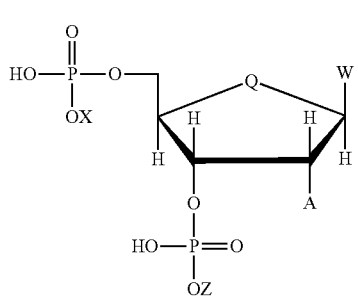

Formula (II)

wherein:
Q is oxygen or sulfur;
W is an amino-substituted or guanidino-substituted nitrogen containing heterocyclic moiety;
X and Z are end blocking groups; and
A is H, alkyl, halogen, alkoxy, alkyl-(O-alkyl), aryl, alkenyl, alkanol or phenol.

As used herein, the term "end blocking group" refers to any chemical moiety that prevents substantial nuclease degradation, and in particular exonuclease degradation, of a protonated compound. The end group may be any chemical moiety that allows for proper protonation of a compound of Formula (II), including without limitation H, OH, SH, NH2, an alkyl group, an alkanol group, and the like.

In some embodiments, A is an alkyl. In some embodiments, the alkyl is $CH_3$— or $CH_3$—$CH_2$—. In some embodiments, A is a halogen. In some embodiments, the halogen is F—, Cl—, Br— or I—. In some embodiments, A is an alkoxy. In some embodiments, the alkoxy is $CH_3$—O—$CH_2$-or $CH_3$—$CH_2$—O—$CH_2$—. In some embodiments, A is an alkyl-(O-alkyl). In some embodiments, the alkyl-(O-alkyl) is $CH_3$—O— or $CH_3$—$CH_2$—O—. In some embodiments, A is an aryl. In some embodiments, the aryl is:

In some embodiments, A is an alkenyl. In some embodiments, the alkenyl is:

In some embodiments, A is an alkanol. In some embodiments, the alkanol is —$CH_2$—OH or —$CH_2$—$CH_2$—OH. In some embodiments, A is a phenol. In some embodiments, the phenol is:

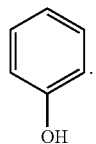

In some embodiments, W is an amino substituted aziridine as illustrated below:

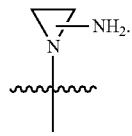

In some embodiments, W is an amino substituted azetidine as illustrated below:

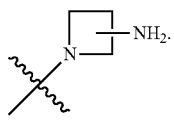

In some embodiments, W is an amino substituted 1,3-azetidine as illustrated below:

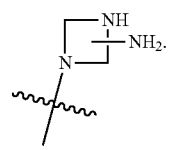

In some embodiments, W is an amino substituted azetidin-2-one (β-lactam) as illustrated below:

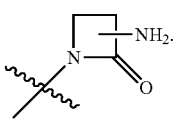

In some embodiments, W is an amino substituted pyrrolidine as illustrated below:

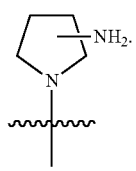

In some embodiments, W is an amino substituted 3-pyrroline as illustrated below:

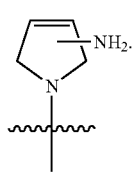

In some embodiments, W is an amino substituted 2-pyrroline as illustrated below:

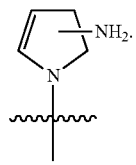

In some embodiments, W is an amino substituted 1H-pyrrole as illustrated below:

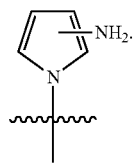

In some embodiments, W is an amino substituted pyrazolidine as illustrated below:

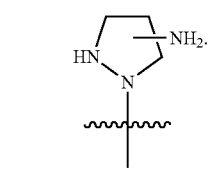

In some embodiments, W is an amino substituted imidazolidine as illustrated below:

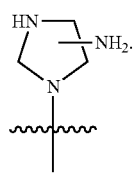

In some embodiments, W is an amino substituted 2-pyrazoline as illustrated below:

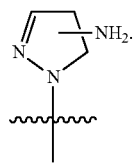

In some embodiments, W is an amino substituted 2-imidazoline as illustrated below:

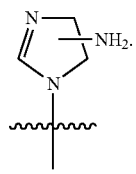

In some embodiments, W is an amino substituted succinimide as illustrated below:

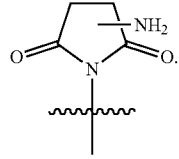

In some embodiments, W is an amino substituted hydantoin as illustrated below:

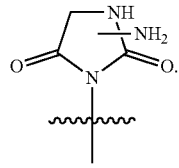

In some embodiments, W is an amino substituted 2,4-thiazolidinedione as illustrated below:

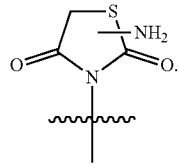

In some embodiments, W is an amino substituted piperidine as illustrated below:

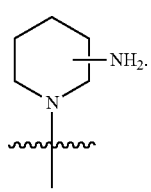

In some embodiments, W is an amino substituted piperazine as illustrated below:

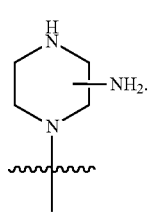

In some embodiments, W is an amino substituted morpholine as illustrated below:

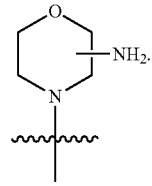

In some embodiments, W is an amino substituted 2H-1,2-oxazdine as illustrated below:

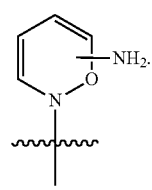

In some embodiments, W is an amino substituted 4H-1,4-oxazdine as illustrated below:

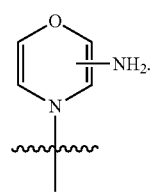

In some embodiments, W is an amino substituted thiomorpholine as illustrated below:

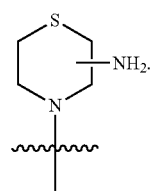

In some embodiments, W is an amino substituted 2H-1,2-thiazine as illustrated below:

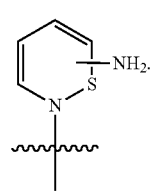

In some embodiments, W is an amino substituted 4H-1,4-thiazine as illustrated below:

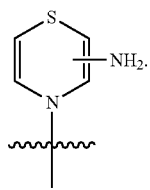

In some embodiments, W is an amino substituted thiomorpholine dioxide as illustrated below:

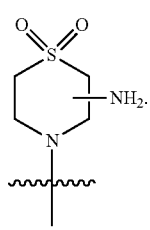

In some embodiments, W is an amino substituted 1,4,5,6-tetrahydrocyclo-penta[b]pyrrole as illustrated below:

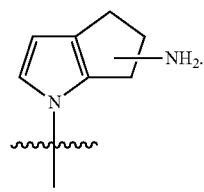

In some embodiments, W is an amino substituted 1,3a,4,6a-tetrahydropyrrolo-[3,2-b]pyrrole as illustrated below:

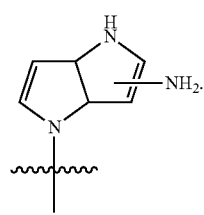

In some embodiments, W is an amino substituted 1,4-dihydropyrolo-[3,2-b]pyrrole as illustrated below:

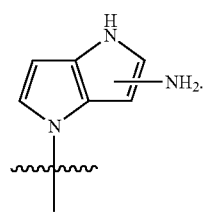

In some embodiments, W is an amino substituted 1,6-dihydropyrolo-[2,3,-b]pyrrole as illustrated below:

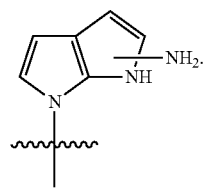

In some embodiments, W is an amino substituted 6H-furo[2,3-b]pyrrole as illustrated below:

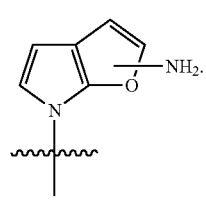

In some embodiments, W is an amino substituted 4H-furo[3,2-b]pyrrole as illustrated below:

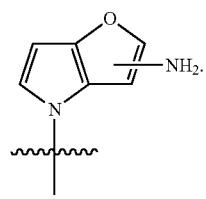

In some embodiments, W is an amino substituted 6H-thieno[2,3-b]pyrrole as illustrated below:

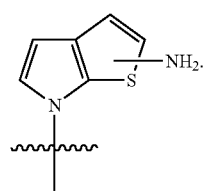

In some embodiments, W is an amino substituted 4H-thieno[3,2-b]pyrrole as illustrated below:

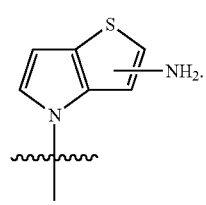

In some embodiments, W is an amino substituted indoline as illustrated below:

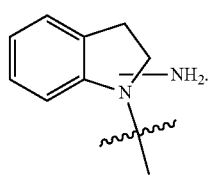

In some embodiments, W is an amino substituted 1H-indole as illustrated below:

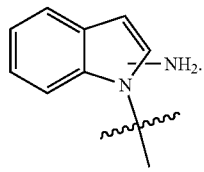

In some embodiments, W is an amino substituted 2H-isoindole as illustrated below:

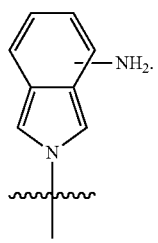

In some embodiments, W is an amino substituted 1H-indazole as illustrated below:

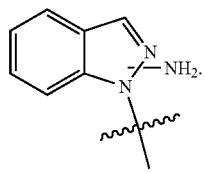

In some embodiments, W is an amino substituted benzimidazole as illustrated below:

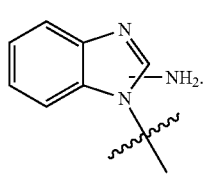

In some embodiments, W is an amino substituted 4-azaindole as illustrated below:

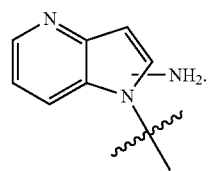

In some embodiments, W is an amino substituted 5-azaindole as illustrated below:

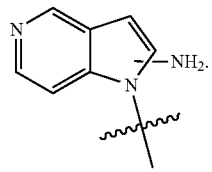

In some embodiments, W is an amino substituted 6-azaindole as illustrated below:

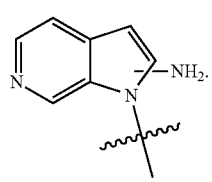

In some embodiments, W is an amino substituted 7-azaindole as illustrated below:

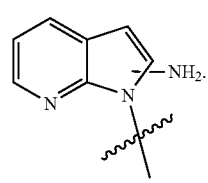

In some embodiments, W is an amino substituted 7-azaindazole as illustrated below:

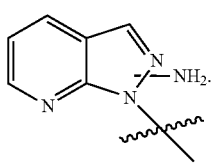

In some embodiments, W is an amino substituted purine as illustrated below:

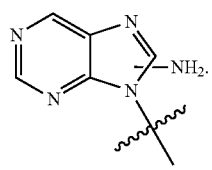

In some embodiments, W is an amino substituted 1,2-benzoisothiazole-3(2H)-one as illustrated below:

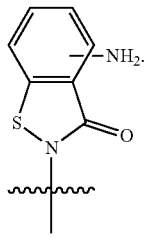

In some embodiments, W is an amino substituted guanine as illustrated below:

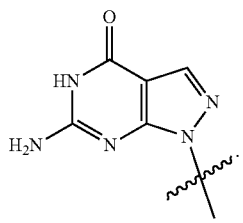

In some embodiments, W is an amino substituted adenine as illustrated below:

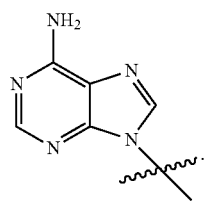

In some embodiments, W is an amino substituted decahydroisoquinoline as illustrated below:

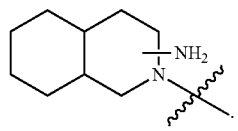

In some embodiments, W is an amino substituted decahydroquinoline as illustrated below:

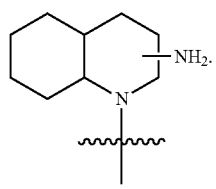

In some embodiments, W is an amino substituted 1,2,3,4-tetrahydro-quinoline as illustrated below:

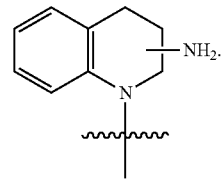

In some embodiments, W is an amino substituted 1,2-dihydroquinoline as illustrated below:

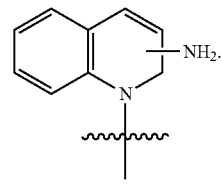

In some embodiments, W is an amino substituted 1,2-dihydroisoquinoline as illustrated below:

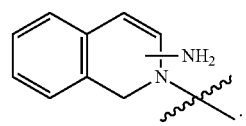

In some embodiments, W is an amino substituted 2H-benzo-[e][1,2]oxazine as illustrated below:

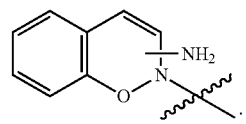

In some embodiments, W is an amino substituted quinolin 2(1H)-one as illustrated below:

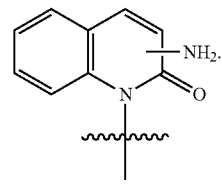

In some embodiments, W is an amino substituted isoquinolin 1(2H)-one as illustrated

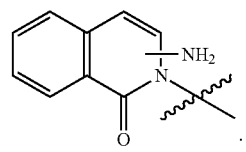

In some embodiments, W is an amino substituted carbazole as illustrated below:

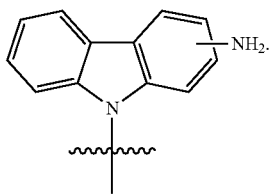

In some embodiments, W is an amino substituted phenoxazine as illustrated below:

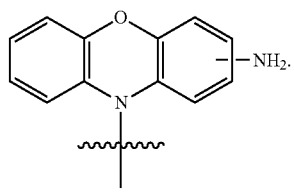

In some embodiments, W is an amino substituted phenothiazine as illustrated below:

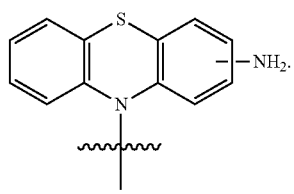

In some embodiments, W is an amino substituted 2-aza-adamantane as illustrated below:

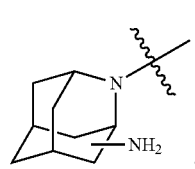

In some embodiments, W is an amino substituted 2,3-dihydroazepine as illustrated below:

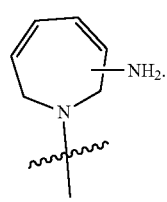

In some embodiments, W is an amino substituted 2,5-dihydroazepine as illustrated below:

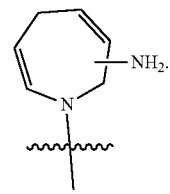

In some embodiments, W is an amino substituted azepine as illustrated below:

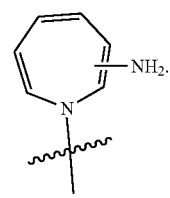

In some embodiments, W is an amino substituted 1,2-azepine as illustrated below:

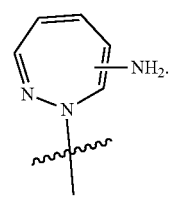

In some embodiments, W is an amino substituted 1,3-azepine as illustrated below:

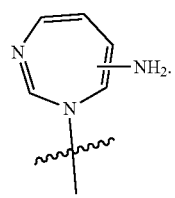

In some embodiments, W is an amino substituted 1,4-azepine as illustrated below:

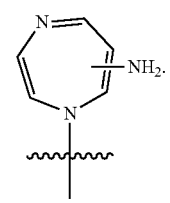

In some embodiments, W is an amino substituted azocane as illustrated below:

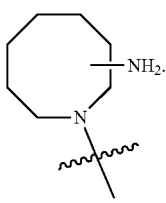

In some embodiments, W is a guanidino substituted aziridine. In some embodiments, W is a guanidino substituted azetidine. In some embodiments, W is a guanidino substituted 1,3-azetidine. In some embodiments, W is a guanidino substituted azetidin-2-one (β-lactam). In some embodiments, W is a guanidino substituted pyrrolidine. In some embodiments, W is a guanidino substituted 3-pyrroline. In some embodiments, W is a guanidino substituted 2-pyrroline. In some embodiments, W is a guanidino substituted 1H-pyrrole. In some embodiments, W is a guanidino substituted pyrazolidine.

In some embodiments, W is a guanidino substituted imidazolidine. In some embodiments, W is a guanidino substituted 2-pyrazoline. In some embodiments, W is a guanidino substituted 2-imidazoline. In some embodiments, W is a guanidino substituted succinimide. In some embodiments, W is a guanidino substituted hydantoin. In some embodiments, W is a guanidino substituted 2,4-thiazolidinedione.

In some embodiments, W is a guanidino substituted piperidine. In some embodiments, W is a guanidino substituted piperazine. In some embodiments, W is a guanidino substituted morpholine. In some embodiments, W is a guanidino substituted 2H-1,2-oxazdine. In some embodiments, W is a guanidino substituted 4H-1,4-oxazdine. In some embodiments, W is a guanidino substituted thiomorpholine.

In some embodiments, W is a guanidino substituted 2H-1,2-thiazine. In some embodiments, W is a guanidino substituted 4H-1,4-thiazine. In some embodiments, W is a guanidino substituted thiomorpholine dioxide. In some embodiments, W is a guanidino substituted 1,4,5,6-tetrahydrocyclopenta[b]pyrrole. In some embodiments, W is a guanidino substituted 1,3a,4,6a-tetrahydropyrrolo-[3,2-b]pyrrole. In some embodiments, W is a guanidino substituted 1,4-dihydropyrolo-[3,2-b]pyrrole.

In some embodiments, W is a guanidino substituted 1,6-dihydropyrolo-[2,3,-b]pyrrole. In some embodiments, W is a guanidino substituted 6H-furo[2,3-b]pyrrole. In some embodiments, W is a guanidino substituted 4H-furo[3,2-b]pyrrole. In some embodiments, W is a guanidino substituted 6H-thieno[2,3-b]pyrrole. In some embodiments, W is a guanidino substituted 4H-thieno[3,2-b]pyrrole. In some embodiments, W is a guanidino substituted indoline.

In some embodiments, W is a guanidino substituted 1H-indole. In some embodiments, W is a guanidino substituted 2H-isoindole. In some embodiments, W is a guanidino substituted 1H-indazole. In some embodiments, W is a guanidino substituted benzimidazole. In some embodiments, W is a guanidino substituted 4-azaindole. In some embodiments, W is a guanidino substituted 5-azaindole.

In some embodiments, W is a guanidino substituted 6-azaindole. In some embodiments, W is a guanidino substituted 7-azaindole. In some embodiments, W is a guanidino substituted 7-azaindazole. In some embodiments, W is a guanidino substituted purine. In some embodiments, W is a guanidino substituted 1,2-benzoisothiazole-3(2H)-one.

In some embodiments, W is a guanidino substituted guanine. In some embodiments, W is a guanidino substituted adenine. In some embodiments, W is a guanidino substituted decahydroisoquinoline. In some embodiments, W is a guanidino substituted decahydroquinoline. In some embodiments, W is a guanidino substituted 1,2,3,4-tetrahydroquinoline. In some embodiments, W is a guanidino substituted 1,2-dihydroquinoline.

In some embodiments, W is a guanidino substituted 1,2-dihydroisoquinoline. In some embodiments, W is a guanidino substituted 2H-benzo-[e][1,2]oxazine. In some embodiments, W is a guanidino substituted quinolin 2(1H)-one. In some embodiments, W is a guanidino substituted isoquinolin 1(2H)-one. In some embodiments, W is a guanidino substituted carbazole. In some embodiments, W is a guanidino substituted phenoxazine.

In some embodiments, W is a guanidino substituted phenothiazine. In some embodiments, W is a guanidino substituted 2-azaadamantane. In some embodiments, W is a guanidino substituted 2,3-dihydroazepine. In some embodiments, W is a guanidino substituted 2,5-dihydroazepine. In some embodiments, W is a guanidino substituted azepine. In some embodiments, W is a guanidino substituted 1,2-azepine.

In some embodiments, W is a guanidino substituted 1,3-azepine. In some embodiments, W is a guanidino substituted 1,4-azepine. In some embodiments, W is a guanidino substituted azocane.

In some embodiments, X and/or Z is a straight alkyl chain. In some embodiments, the straight alkyl chain is:

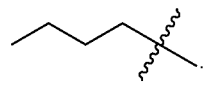 [SMILES: *CCCC]

In some embodiments, X and/or Z is a branched alkyl chain. In some embodiments, the branched alkyl chain is:

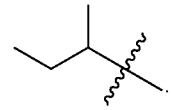

In some embodiments, X and/or Z is a branched alkyl chain. In some embodiments, the branched alkyl chain is:

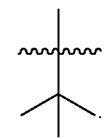 [SMILES: *C(C)(C)C]

In some embodiments, X and/or Z is a cyclic alkyl. In some embodiments, the cyclic alkyl is:

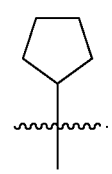

In some embodiments, X and/or Z is a cyclic alkyl. In some embodiments, the cyclic alkyl is:

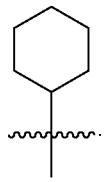

In some embodiments, X and/or Z is an aryl. In some embodiments, the aryl is:

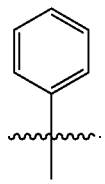

In some embodiments, X and/or Z is a benzyl. In some embodiments, the benzyl is:

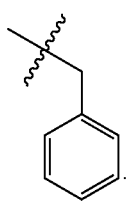

In some embodiments, X and/or Z is a straight chain alkanol. In some embodiments, the straight chain alkanol is:

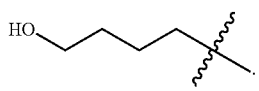 [SMILES: *CCCCO]

In some embodiments, X and/or Z is a branched chain alkanol. In some embodiments, the branched chain alkanol is:

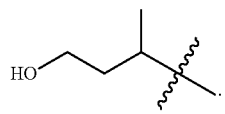 [SMILES: *C(C)CCO]

In some embodiments, X and/or Z is a cyclic alkanol. In some embodiments, the cyclic alkanol is:

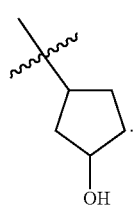

In some embodiments, X and/or Z is a cyclic alkanol. In some embodiments, the cyclic alkanol is:

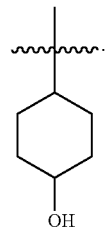 [SMILES: *C1CCC(O)CC1]

In some embodiments, X and/or Z is a phenolic. In some embodiments, the phenolic is:

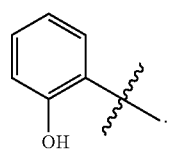 [SMILES: *c1ccccc1O]

In some embodiments, X and/or Z is a 4-hydroxybenzyl. In some embodiments, the 4-hydroxybenzyl is:

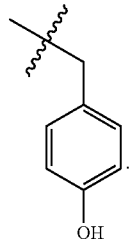

The present disclosure also provides the compounds as described in TABLE 1. As used herein, the term "Cmpd" refers to the compound of Formula (II), or a pharmaceutically acceptable salt thereof, where W, X, Z, A, and Q are defined as W, X, Z, A, and Q in one of the rows of Table 1 labeled Cmpd 1 to Cmpd 2520. For example, in the present disclosure or the claims, "Cmpd 1 as described in TABLE 1" refers specifically to the compound of Formula (II), or a pharmaceutically acceptable salt thereof, where W, X, Z, A, and Q of the compound of Formula (II), or a pharmaceutically acceptable salt thereof, are as follows:

| W | X | Z | A | Q |
|---|---|---|---|---|
| 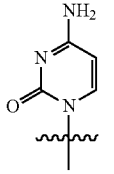 [SMILES: *n1ccc(N)nc1=O] | 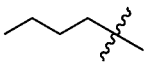 [SMILES: *CCCC] | 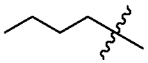 | H | O |

Cmpds 1 to 2520 may be made by referencing the compound of Formula (II), TABLE 1, and the synthesis schemes described in EXAMPLES 1 to 3.

TABLE 1

| Cmpd | W | X | Z | A | Q |
|------|---|---|---|---|---|
| 1 | cytosin-1-yl | pentyl | pentyl | H | O |
| 2 | 3-aminoaziridin-1-yl | pentyl | pentyl | H | O |
| 3 | 2-aminoazetidin-1-yl | pentyl | pentyl | H | O |
| 4 | 3-aminoazetidin-1-yl | pentyl | pentyl | H | O |
| 5 | 2-amino-2,3-dihydro-1H-imidazol-1-yl | pentyl | pentyl | H | O |
| 6 | 3-amino-2-oxoazetidin-1-yl | pentyl | pentyl | H | O |
| 7 | 3-amino-4-oxoazetidin-1-yl | pentyl | pentyl | H | O |
| 8 | 2-aminopyrrolidin-1-yl | pentyl | pentyl | H | O |
| 9 | 3-aminopyrrolidin-1-yl | pentyl | pentyl | H | O |

TABLE 1-continued

| Cmpd | W | X | Z | A | Q |
|---|---|---|---|---|---|
| 10 | 2-amino-2,5-dihydro-1H-pyrrol-1-yl | pentyl | pentyl | H | O |
| 11 | 3-amino-2,5-dihydro-1H-pyrrol-1-yl | pentyl | pentyl | H | O |
| 12 | 2-amino-4,5-dihydro-1H-pyrrol-1-yl | pentyl | pentyl | H | O |
| 13 | 3-amino-4,5-dihydro-1H-pyrrol-1-yl | pentyl | pentyl | H | O |
| 14 | 3-amino-2,3-dihydro-1H-pyrrol-1-yl | pentyl | pentyl | H | O |
| 15 | 2-amino-2,3-dihydro-1H-pyrrol-1-yl | pentyl | pentyl | H | O |
| 16 | 2-amino-1H-pyrrol-1-yl | pentyl | pentyl | H | O |
| 17 | 3-amino-1H-pyrrol-1-yl | pentyl | pentyl | H | O |

TABLE 1-continued

| Cmpd | W | X | Z | A | Q |
|---|---|---|---|---|---|
| 18 | 3-amino-pyrazolidin-1-yl (H2N on C3, NH on N2, attachment at N1) | pentyl | pentyl | H | O |
| 19 | 4-amino-pyrazolidin-1-yl | pentyl | pentyl | H | O |
| 20 | 5-amino-pyrazolidin-1-yl (H2N on C5, HN on N2) | pentyl | pentyl | H | O |
| 21 | 4-amino-imidazolidin-1-yl | pentyl | pentyl | H | O |
| 22 | 5-amino-imidazolidin-1-yl (HN on N3) | pentyl | pentyl | H | O |
| 23 | 2-amino-imidazolidin-1-yl | pentyl | pentyl | H | O |
| 24 | 3-amino-4,5-dihydro-pyrazol-1-yl | pentyl | pentyl | H | O |
| 25 | 4-amino-4,5-dihydro-pyrazol-1-yl | pentyl | pentyl | H | O |

TABLE 1-continued

| Cmpd | W | X | Z | A | Q |
|---|---|---|---|---|---|
| 26 | 4,5-dihydro-1H-pyrazol-5-amine (N-linked) | pentyl | pentyl | H | O |
| 27 | 4,5-dihydro-1H-imidazol-2-amine (N-linked) | pentyl | pentyl | H | O |
| 28 | 4,5-dihydro-1H-imidazol-4-amine (N-linked) | pentyl | pentyl | H | O |
| 29 | 4,5-dihydro-1H-imidazol-5-amine (N-linked) | pentyl | pentyl | H | O |
| 30 | 3-aminopyrrolidine-2,5-dione (N-linked) | pentyl | pentyl | H | O |
| 31 | 5-aminoimidazolidine-2,4-dione (N-linked) | pentyl | pentyl | H | O |
| 32 | 5-amino-thiazolidine-2,4-dione (N-linked) | pentyl | pentyl | H | O |
| 33 | piperidin-2-amine (N-linked) | pentyl | pentyl | H | O |

TABLE 1-continued

| Cmpd | W | X | Z | A | Q |
|---|---|---|---|---|---|
| 34 | 3-aminopiperidin-1-yl | pentyl | pentyl | H | O |
| 35 | 4-aminopiperidin-1-yl | pentyl | pentyl | H | O |
| 36 | 3-aminopiperazin-1-yl | pentyl | pentyl | H | O |
| 37 | 2-aminopiperazin-4-yl | pentyl | pentyl | H | O |
| 38 | 3-aminomorpholin-4-yl | pentyl | pentyl | H | O |
| 39 | 2-aminomorpholin-4-yl | pentyl | pentyl | H | O |
| 40 | 3-amino-2H-1,2-oxazin-2-yl | pentyl | pentyl | H | O |

TABLE 1-continued

| Cmpd | W | X | Z | A | Q |
|------|---|---|---|---|---|
| 41 | 4-amino-2H-1,2-oxazine (N-linked) | pentyl | pentyl | H | O |
| 42 | 5-amino-2H-1,2-oxazine (N-linked) | pentyl | pentyl | H | O |
| 43 | 6-amino-2H-1,2-oxazine (N-linked) | pentyl | pentyl | H | O |
| 44 | 3-amino-4H-1,4-oxazine (N-linked) | pentyl | pentyl | H | O |
| 45 | 2-amino-4H-1,4-oxazine (N-linked) | pentyl | pentyl | H | O |
| 46 | 3-amino-thiomorpholine (N-linked) | pentyl | pentyl | H | O |
| 47 | 2-amino-thiomorpholine (N-linked) | pentyl | pentyl | H | O |
| 48 | 3-amino-2H-1,2-thiazine (N-linked) | pentyl | pentyl | H | O |

TABLE 1-continued

| Cmpd | W | X | Z | A | Q |
|---|---|---|---|---|---|
| 49 | 4-amino-2H-1,2-thiazine (N-linked) | pentyl | pentyl | H | O |
| 50 | 5-amino-2H-1,2-thiazine (N-linked) | pentyl | pentyl | H | O |
| 51 | 6-amino-2H-1,2-thiazine (N-linked) | pentyl | pentyl | H | O |
| 52 | 3-amino-4H-1,4-thiazine (N-linked) | pentyl | pentyl | H | O |
| 53 | 2-amino-4H-1,4-thiazine (N-linked) | pentyl | pentyl | H | O |
| 54 | 3-amino-1,1-dioxo-thiomorpholine (N-linked) | pentyl | pentyl | H | O |
| 55 | 2-amino-1,1-dioxo-thiomorpholine (N-linked) | pentyl | pentyl | H | O |

TABLE 1-continued

| Cmpd | W | X | Z | A | Q |
|---|---|---|---|---|---|
| 56 | 2-amino-1-substituted-cyclopenta[b]pyrrole | pentyl | pentyl | H | O |
| 57 | 3-amino-1-substituted-cyclopenta[b]pyrrole | pentyl | pentyl | H | O |
| 58 | 4-amino-1-substituted-5,6-dihydro-4H-cyclopenta[b]pyrrole | pentyl | pentyl | H | O |
| 59 | 5-amino-1-substituted-5,6-dihydro-4H-cyclopenta[b]pyrrole | pentyl | pentyl | H | O |
| 60 | 6-amino-1-substituted-5,6-dihydro-4H-cyclopenta[b]pyrrole | pentyl | pentyl | H | O |
| 61 | 2-amino-1-substituted-pyrrolo[3,2-b]pyrrole | pentyl | pentyl | H | O |
| 62 | 3-amino-1-substituted-pyrrolo[3,2-b]pyrrole | pentyl | pentyl | H | O |

TABLE 1-continued

| Cmpd | W | X | Z | A | Q |
|---|---|---|---|---|---|
| 63 | 2-amino-N-substituted pyrrolo[3,2-b]pyrrole | pentyl | pentyl | H | O |
| 64 | 3-amino-N-substituted pyrrolo[3,2-b]pyrrole | pentyl | pentyl | H | O |
| 65 | 5-amino-N-substituted pyrrolo[3,2-b]pyrrole | pentyl | pentyl | H | O |
| 66 | 6-amino-N-substituted pyrrolo[3,2-b]pyrrole | pentyl | pentyl | H | O |
| 67 | 2-amino-N-substituted pyrrolo[3,2-b]pyrrole | pentyl | pentyl | H | O |
| 68 | 2-amino-N-substituted pyrrolo[3,2-b]pyrrole | pentyl | pentyl | H | O |
| 69 | 2-amino-N-substituted pyrrolo[2,3-b]pyrrole | pentyl | pentyl | H | O |

TABLE 1-continued

| Cmpd | W | X | Z | A | Q |
|---|---|---|---|---|---|
| 70 | 4-amino-1H-pyrrolo[2,3-b]pyrrole, N-linked | pentyl | pentyl | H | O |
| 71 | 3-amino-1H-pyrrolo[2,3-b]pyrrole, N-linked | pentyl | pentyl | H | O |
| 72 | 2-amino-1H-pyrrolo[2,3-b]pyrrole, N-linked | pentyl | pentyl | H | O |
| 73 | 5-amino-furo[2,3-b]pyrrole, N-linked | pentyl | pentyl | H | O |
| 74 | 4-amino-furo[2,3-b]pyrrole, N-linked | pentyl | pentyl | H | O |
| 75 | 3-amino-furo[2,3-b]pyrrole, N-linked | pentyl | pentyl | H | O |
| 76 | 2-amino-furo[2,3-b]pyrrole, N-linked | pentyl | pentyl | H | O |

TABLE 1-continued

| Cmpd | W | X | Z | A | Q |
|---|---|---|---|---|---|
| 77 | 5-amino-furo[3,2-b]pyrrole N-linked | pentyl | pentyl | H | O |
| 78 | 6-amino-furo[3,2-b]pyrrole N-linked | pentyl | pentyl | H | O |
| 79 | 2-amino-furo[3,2-b]pyrrole N-linked | pentyl | pentyl | H | O |
| 80 | 3-amino-furo[3,2-b]pyrrole N-linked | pentyl | pentyl | H | O |
| 81 | 5-amino-thieno[2,3-b]pyrrole N-linked | pentyl | pentyl | H | O |
| 82 | 6-amino-thieno[2,3-b]pyrrole N-linked | pentyl | pentyl | H | O |
| 83 | 3-amino-thieno[2,3-b]pyrrole N-linked | pentyl | pentyl | H | O |

TABLE 1-continued

| Cmpd | W | X | Z | A | Q |
|---|---|---|---|---|---|
| 84 | 2-amino-4H-thieno[3,2-b]pyrrol-4-yl (N-linked) | pentyl | pentyl | H | O |
| 85 | 5-amino-4H-thieno[3,2-b]pyrrol-4-yl (N-linked) | pentyl | pentyl | H | O |
| 86 | 6-amino-4H-thieno[3,2-b]pyrrol-4-yl (N-linked) | pentyl | pentyl | H | O |
| 87 | 2-amino-4H-thieno[2,3-b]pyrrol-4-yl (N-linked) | pentyl | pentyl | H | O |
| 88 | 3-amino-4H-thieno[2,3-b]pyrrol-4-yl (N-linked) | pentyl | pentyl | H | O |
| 89 | 7-aminoindolin-1-yl | pentyl | pentyl | H | O |
| 90 | 6-aminoindolin-1-yl | pentyl | pentyl | H | O |
| 91 | 4-aminoindolin-1-yl | pentyl | pentyl | H | O |

TABLE 1-continued

| Cmpd | W | X | Z | A | Q |
|---|---|---|---|---|---|
| 92 | 3-amino-indoline, N-linked | pentyl (branched) | pentyl (branched) | H | O |
| 93 | 2-amino-indoline, N-linked | pentyl (branched) | pentyl (branched) | H | O |
| 94 | 7-amino-indole, N-linked | pentyl (branched) | pentyl (branched) | H | O |
| 95 | 6-amino-indole, N-linked | pentyl (branched) | pentyl (branched) | H | O |
| 96 | 5-amino-indoline, N-linked | pentyl (branched) | pentyl (branched) | H | O |
| 97 | 4-amino-indole, N-linked | pentyl (branched) | pentyl (branched) | H | O |
| 98 | 3-amino-indole, N-linked | pentyl (branched) | pentyl (branched) | H | O |
| 99 | 2-amino-indole, N-linked | pentyl (branched) | pentyl (branched) | H | O |

TABLE 1-continued
| Cmpd | W | X | Z | A | Q |
|---|---|---|---|---|---|
| 100 | 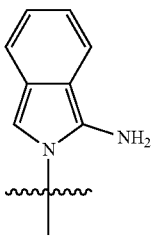 | 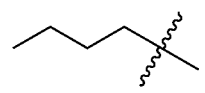 [SMILES: *CCCC] | 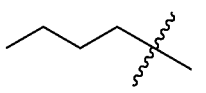 [SMILES: *CCCC] | H | O |
| 101 | 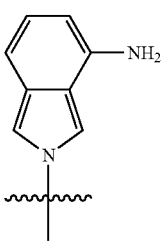 | 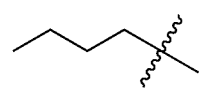 [SMILES: *CCCC] | 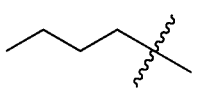 [SMILES: *CCCC] | H | O |
| 102 | 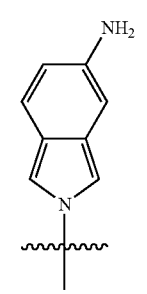 [SMILES: *n1cc2ccc(N)cc2c1] | 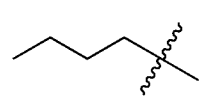 [SMILES: *CCCC] | 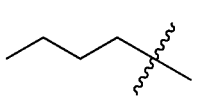 [SMILES: *CCCC] | H | O |
| 103 | 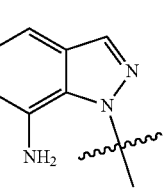 | 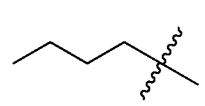 [SMILES: *CCCC] | 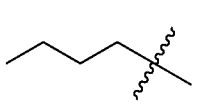 [SMILES: *CCCC] | H | O |
| 104 | 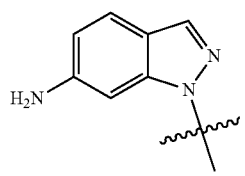 [SMILES: *n1ncc2ccc(N)cc21] | 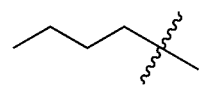 | 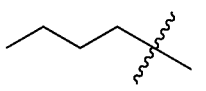 | H | O |
| 105 | 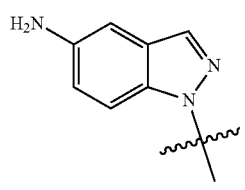 [SMILES: *n1ncc2cc(N)ccc21] | 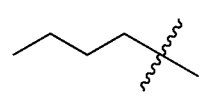 [SMILES: *CCCC] | 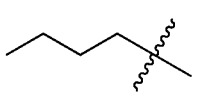 [SMILES: *CCCC] | H | O |
| 106 | 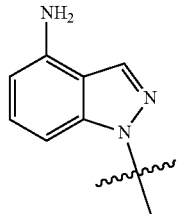 [SMILES: *n1ncc2c(N)cccc21] | 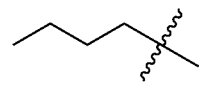 | 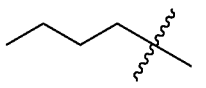 [SMILES: *CCCC] | H | O |

TABLE 1-continued

| Cmpd | W | X | Z | A | Q |
|---|---|---|---|---|---|
| 107 | 3-amino-1H-indazol-1-yl | pentyl | pentyl | H | O |
| 108 | 7-amino-1H-benzimidazol-1-yl | pentyl | pentyl | H | O |
| 109 | 6-amino-1H-benzimidazol-1-yl | pentyl | pentyl | H | O |
| 110 | 5-amino-1H-benzimidazol-1-yl | pentyl | pentyl | H | O |
| 111 | 4-amino-1H-benzimidazol-1-yl | pentyl | pentyl | | O |
| 112 | 2-amino-1H-benzimidazol-1-yl | pentyl | pentyl | H | O |
| 113 | 7-amino-1H-pyrrolo[3,2-b]pyridin-1-yl | pentyl | pentyl | H | O |
| 114 | 6-amino-1H-pyrrolo[3,2-b]pyridin-1-yl | pentyl | pentyl | H | O |

TABLE 1-continued
| Cmpd | W | X | Z | A | Q |
|------|---|---|---|---|---|
| 115 | 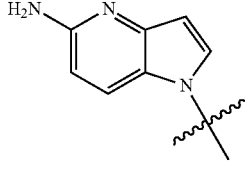 [SMILES: *n1ccc2nc(N)ccc21] | 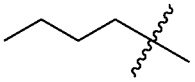 [SMILES: *CCCC] | 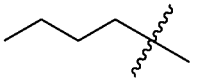 [SMILES: *CCCC] | H | O |
| 116 | 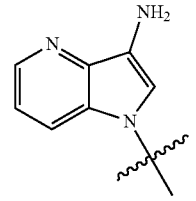 [SMILES: *n1cc(N)c2ncccc21] | 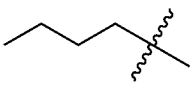 | 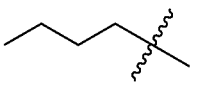 | H | O |
| 117 | 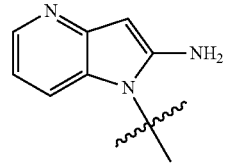 [SMILES: *n1c(N)cc2ncccc21] | 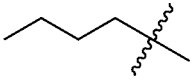 [SMILES: *CCCC] | 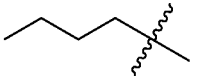 [SMILES: *CCCC] | H | O |
| 118 | 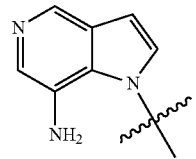 [SMILES: *n1ccc2cncc(N)c21] | 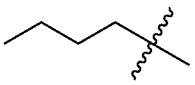 [SMILES: *CCCC] | 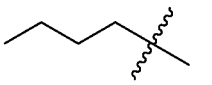 [SMILES: *CCCC] | H | O |
| 119 | 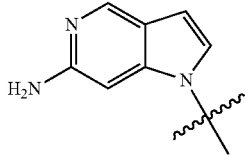 | 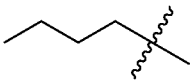 [SMILES: *CCCC] | 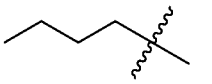 [SMILES: *CCCC] | H | O |
| 120 | 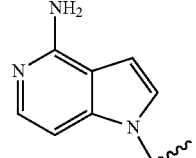 | 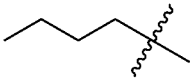 [SMILES: *CCCC] | 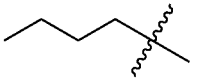 [SMILES: *CCCC] | H | O |
| 121 | 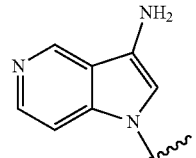 | 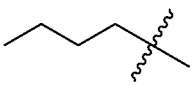 | 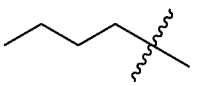 | H | O |
| 122 | 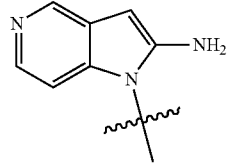 [SMILES: *n1c(N)cc2cnccc21] | 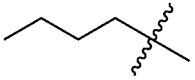 [SMILES: *CCCC] |  | H | O |

TABLE 1-continued

| Cmpd | W | X | Z | A | Q |
|---|---|---|---|---|---|
| 123 | 7-amino-1H-pyrrolo[2,3-c]pyridine (N1-linked) | pentyl | pentyl | H | O |
| 124 | 5-amino-1H-pyrrolo[2,3-c]pyridine (N1-linked) | pentyl | pentyl | H | O |
| 125 | 4-amino-1H-pyrrolo[2,3-c]pyridine (N1-linked) | pentyl | pentyl | H | O |
| 126 | 3-amino-1H-pyrrolo[2,3-c]pyridine (N1-linked) | pentyl | pentyl | H | O |
| 127 | 2-amino-1H-pyrrolo[2,3-c]pyridine (N1-linked) | pentyl | pentyl | H | O |
| 128 | 6-amino-1H-pyrrolo[2,3-b]pyridine (N1-linked) | pentyl | pentyl | H | O |
| 129 | 5-amino-1H-pyrrolo[2,3-b]pyridine (N1-linked) | pentyl | pentyl | H | O |
| 130 | 4-amino-1H-pyrrolo[2,3-b]pyridine (N1-linked) | pentyl | pentyl | H | O |

TABLE 1-continued

| Cmpd | W | X | Z | A | Q |
|---|---|---|---|---|---|
| 131 | 3-amino-7-azaindole (N1-linked) | pentyl (gem-dimethyl) | pentyl (gem-dimethyl) | H | O |
| 132 | 2-amino-7-azaindole (N1-linked) | pentyl (gem-dimethyl) | pentyl (gem-dimethyl) | H | O |
| 133 | 6-amino-pyrazolo[3,4-b]pyridine (N1-linked) | pentyl (gem-dimethyl) | pentyl (gem-dimethyl) | H | O |
| 134 | 5-amino-pyrazolo[3,4-b]pyridine (N1-linked) | pentyl (gem-dimethyl) | pentyl (gem-dimethyl) | H | O |
| 135 | 4-amino-pyrazolo[3,4-b]pyridine (N1-linked) | pentyl (gem-dimethyl) | pentyl (gem-dimethyl) | H | O |
| 136 | 3-amino-pyrazolo[3,4-b]pyridine (N1-linked) | pentyl (gem-dimethyl) | pentyl (gem-dimethyl) | H | O |
| 137 | 2-amino-purine (N9-linked) | pentyl (gem-dimethyl) | pentyl (gem-dimethyl) | H | O |
| 138 | 6-amino-purine (adenine, N9-linked) | pentyl (gem-dimethyl) | pentyl (gem-dimethyl) | H | O |

TABLE 1-continued

| Cmpd | W | X | Z | A | Q |
|---|---|---|---|---|---|
| 139 | imidazo[4,5-d]pyrimidin-7-amine (N-linked) | pentyl (branched) | pentyl (branched) | H | O |
| 140 | 7-amino-benzo[d]isothiazol-3(2H)-one (N-linked) | pentyl (branched) | pentyl (branched) | H | O |
| 141 | 6-amino-benzo[d]isothiazol-3(2H)-one (N-linked) | pentyl (branched) | pentyl (branched) | H | O |
| 142 | 5-amino-benzo[d]isothiazol-3(2H)-one (N-linked) | pentyl (branched) | pentyl (branched) | H | O |
| 143 | 4-amino-benzo[d]isothiazol-3(2H)-one (N-linked) | pentyl (branched) | pentyl (branched) | H | O |
| 144 | 6-amino-1H-pyrazolo[3,4-d]pyrimidin-4(5H)-one (N1-linked) | pentyl (branched) | pentyl (branched) | H | O |

TABLE 1-continued
| Cmpd | W | X | Z | A | Q |
|---|---|---|---|---|---|
| 145 | 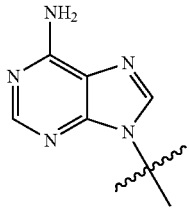 [SMILES: *n1cnc2c(N)ncnc21] | 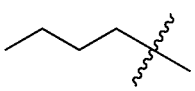 [SMILES: *CCCC] | 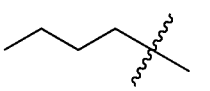 [SMILES: *CCCC] | H | O |
| 146 | 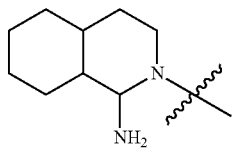 | 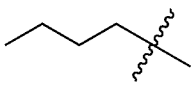 [SMILES: *CCCC] | 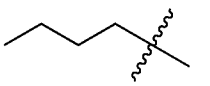 [SMILES: *CCCC] | H | O |
| 147 | 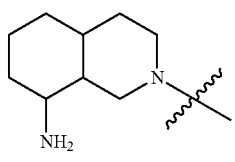 | 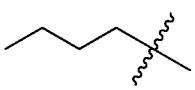 [SMILES: *CCCC] | 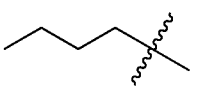 [SMILES: *CCCC] | H | O |
| 148 | 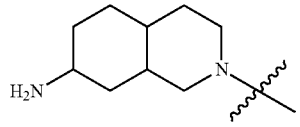 | 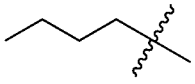 [SMILES: *CCCC] | 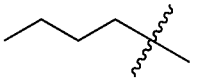 [SMILES: *CCCC] | H | O |
| 149 | 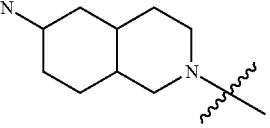 | 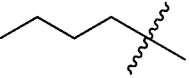 [SMILES: *CCCC] | 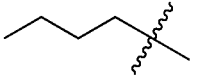 [SMILES: *CCCC] | H | O |
| 150 | 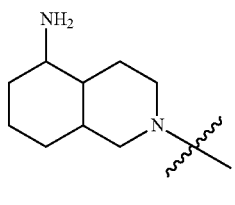 [SMILES: *N1CCC2C(N)CCCC2C1] | 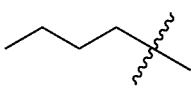 [SMILES: *CCCC] | 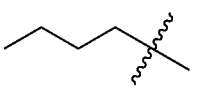 [SMILES: *CCCC] | H | O |
| 151 | 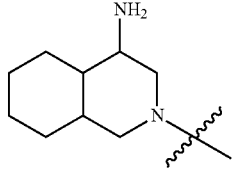 [SMILES: *N1CC(N)C2CCCCC2C1] | 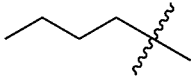 [SMILES: *CCCC] | 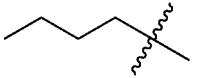 | H | O |
| 152 | 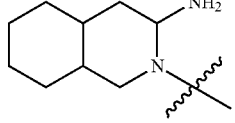 | 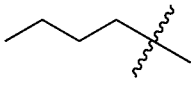 [SMILES: *CCCC] | 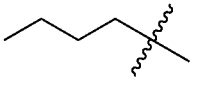 [SMILES: *CCCC] | H | O |
| 153 | 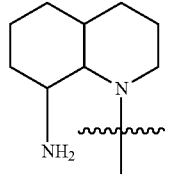 [SMILES: *N1CCCC2CCCC(N)C21] | 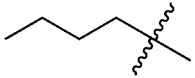 [SMILES: *CCCC] | 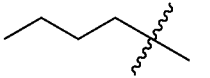 [SMILES: *CCCC] | H | O |

TABLE 1-continued
| Cmpd | W | X | Z | A | Q |
|---|---|---|---|---|---|
| 154 |  |  |  | H | O |
| 155 | 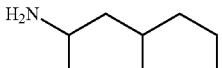 | 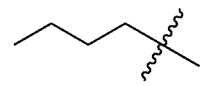 [SMILES: *CCCC] | 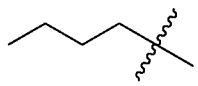 [SMILES: *CCCC] | H | O |
| 156 |  |  |  | H | O |
| 157 | 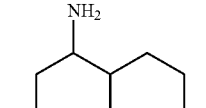 | 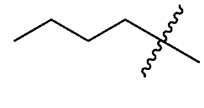 [SMILES: *CCCC] | 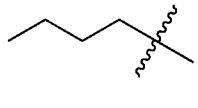 [SMILES: *CCCC] | H | O |
| 158 | 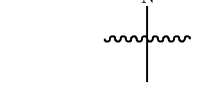 |  |  | H | O |
| 159 | 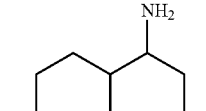 | 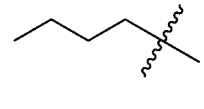 [SMILES: *CCCC] | 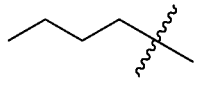 [SMILES: *CCCC] | H | O |
| 160 | 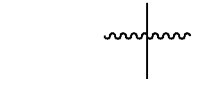 |  |  | H | O |

TABLE 1-continued

| Cmpd | W | X | Z | A | Q |
|---|---|---|---|---|---|
| 161 | 7-amino-1,2,3,4-tetrahydroquinolin-1-yl | pentyl | pentyl | H | O |
| 162 | 6-amino-1,2,3,4-tetrahydroquinolin-1-yl | pentyl | pentyl | H | O |
| 163 | 5-amino-1,2,3,4-tetrahydroquinolin-1-yl | pentyl | pentyl | H | O |
| 164 | 4-amino-1,2,3,4-tetrahydroquinolin-1-yl | pentyl | pentyl | H | O |
| 165 | 3-amino-1,2,3,4-tetrahydroquinolin-1-yl | pentyl | pentyl | H | O |
| 166 | 2-amino-1,2,3,4-tetrahydroquinolin-1-yl | pentyl | pentyl | H | O |
| 167 | 8-amino-2H-quinolin-1-yl | pentyl | pentyl | H | O |

TABLE 1-continued
| Cmpd | W | X | Z | A | Q |
|---|---|---|---|---|---|
| 168 | 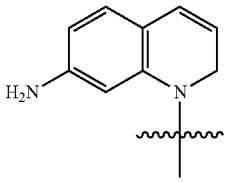 [SMILES: *N1CC=Cc2ccc(N)cc21] | 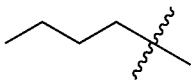 [SMILES: *CCCC] | 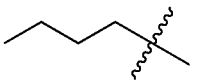 [SMILES: *CCCC] | H | O |
| 169 | 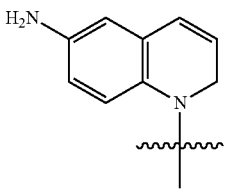 [SMILES: *N1CC=Cc2cc(N)ccc21] | 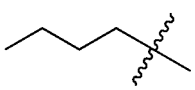 [SMILES: *CCCC] | 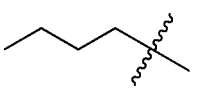 [SMILES: *CCCC] | H | O |
| 170 | 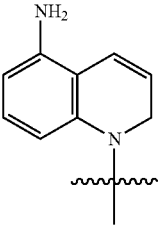 [SMILES: *N1CC=Cc2c(N)cccc21] | 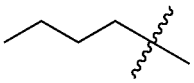 [SMILES: *CCCC] | 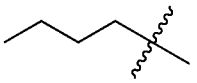 [SMILES: *CCCC] | H | O |
| 171 | 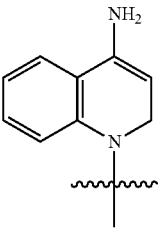 | 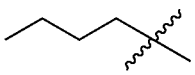 [SMILES: *CCCC] | 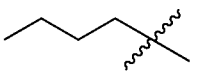 | H | O |
| 172 | 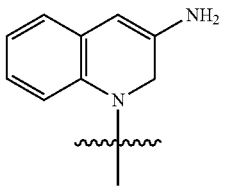 [SMILES: *N1CC(N)=Cc2ccccc21] | 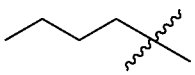 | 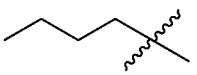 | H | O |
| 173 | 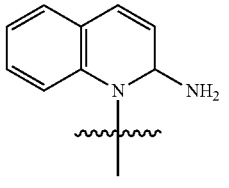 [SMILES: *N1c2ccccc2C=CC1N] | 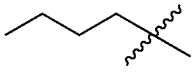 | 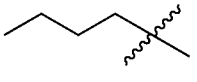 | H | O |
| 174 | 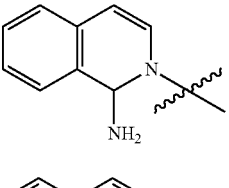 | 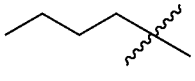 [SMILES: *CCCC] | 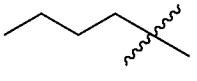 [SMILES: *CCCC] | H | O |
| 175 | 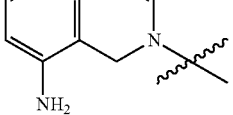 | 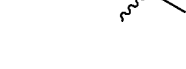 | 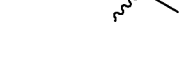 | H | O |

TABLE 1-continued
| Cmpd | W | X | Z | A | Q |
|---|---|---|---|---|---|
| 176 | 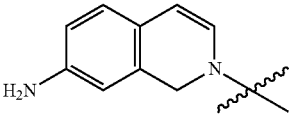 [SMILES: *N1C=Cc2ccc(N)cc2C1] | 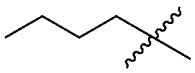 [SMILES: *CCCC] | 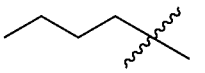 [SMILES: *CCCC] | H | O |
| 177 | 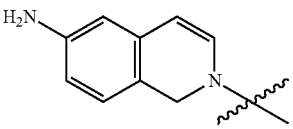 [SMILES: *N1C=Cc2cc(N)ccc2C1] | 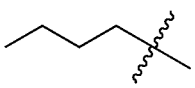 [SMILES: *CCCC] | 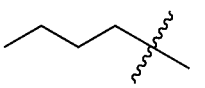 [SMILES: *CCCC] | H | O |
| 178 | 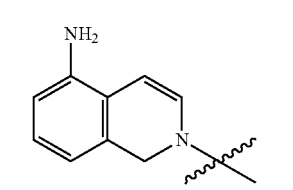 [SMILES: *N1C=Cc2c(N)cccc2C1] | 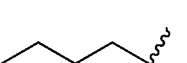 | 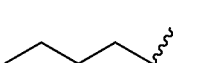 | H | O |
| 179 | 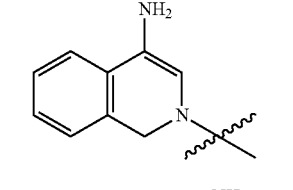 [SMILES: *N1C=C(N)c2ccccc2C1] | 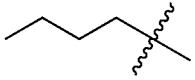 | 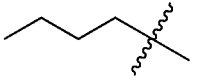 [SMILES: *CCCC] | H | O |
| 180 | 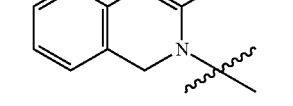 | 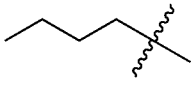 [SMILES: *CCCC] | 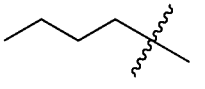 [SMILES: *CCCC] | H | O |
| 181 | 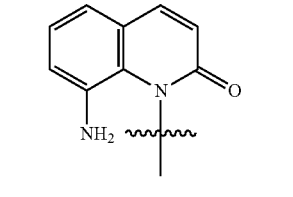 [SMILES: *n1c(=O)ccc2cccc(N)c21] | 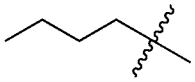 | 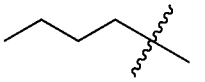 | H | O |
| 182 | 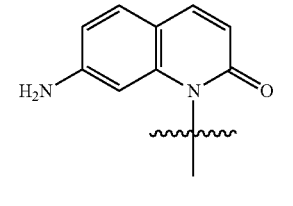 | 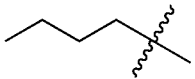 [SMILES: *CCCC] | 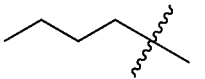 [SMILES: *CCCC] | H | O |
| 183 | 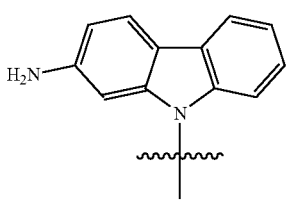 | 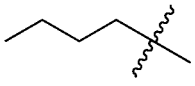 [SMILES: *CCCC] | 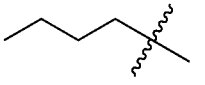 [SMILES: *CCCC] | H | O |
| 184 | 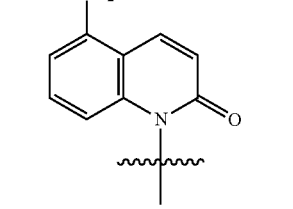 | 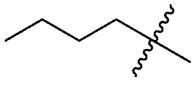 [SMILES: *CCCC] | 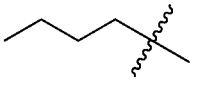 [SMILES: *CCCC] | H | O |

TABLE 1-continued

| Cmpd | W | X | Z | A | Q |
|---|---|---|---|---|---|
| 185 | 4-amino-1-substituted quinolin-2(1H)-one | pentyl | pentyl | H | O |
| 186 | 3-amino-1-substituted quinolin-2(1H)-one | pentyl | pentyl | H | O |
| 187 | 8-amino-2-substituted isoquinolin-1(2H)-one | pentyl | pentyl | H | O |
| 188 | 7-amino-2-substituted isoquinolin-1(2H)-one | pentyl | pentyl | H | O |
| 189 | 6-amino-2-substituted isoquinolin-1(2H)-one | pentyl | pentyl | H | O |
| 190 | 5-amino-2-substituted isoquinolin-1(2H)-one | pentyl | pentyl | H | O |
| 191 | 4-amino-2-substituted isoquinolin-1(2H)-one | pentyl | pentyl | H | O |
| 192 | 3-amino-2-substituted isoquinolin-1(2H)-one | pentyl | pentyl | H | O |

TABLE 1-continued
| Cmpd | W | X | Z | A | Q |
|---|---|---|---|---|---|
| 193 | 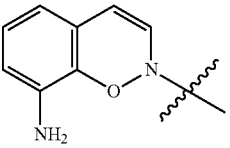 [SMILES: *N1C=Cc2cccc(N)c2O1] |  |  | H | O |
| 194 | 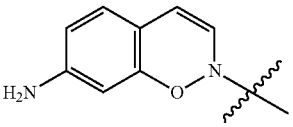 [SMILES: *N1C=Cc2ccc(N)cc2O1] | 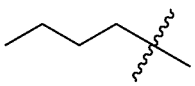 [SMILES: *CCCC] | 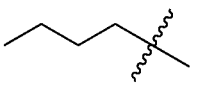 [SMILES: *CCCC] | H | O |
| 195 | 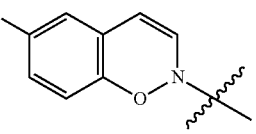 | 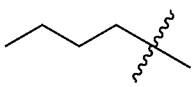 | 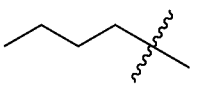 [SMILES: *CCCC] | H | O |
| 196 | 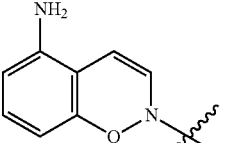 | 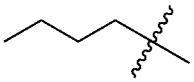 [SMILES: *CCCC] | 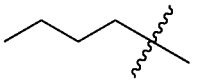 [SMILES: *CCCC] | H | O |
| 197 | 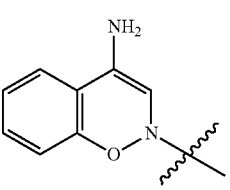 [SMILES: *N1C=C(N)c2ccccc2O1] | 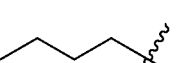 | 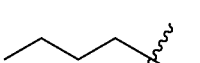 | H | O |
| 198 | 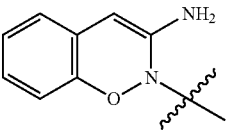 [SMILES: *N1Oc2ccccc2C=C1N] | 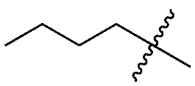 [SMILES: *CCCC] | 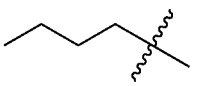 [SMILES: *CCCC] | H | O |
| 199 | 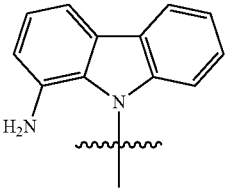 [SMILES: *n1c2ccccc2c2cccc(N)c21] | 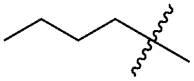 [SMILES: *CCCC] | 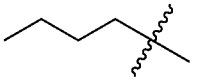 [SMILES: *CCCC] | H | O |
| 200 | 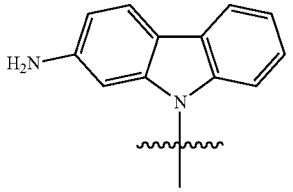 [SMILES: *n1c2ccccc2c2ccc(N)cc21] | 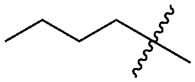 [SMILES: *CCCC] | 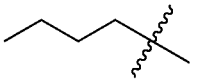 [SMILES: *CCCC] | H | O |
| 201 | 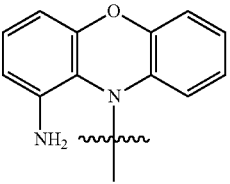 | 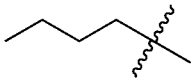 [SMILES: *CCCC] | 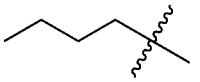 [SMILES: *CCCC] | H | O |

TABLE 1-continued

| Cmpd | W | X | Z | A | Q |
|---|---|---|---|---|---|
| 202 | 2-amino-phenoxazin-10-yl | pentyl | pentyl | H | O |
| 203 | 1-amino-phenothiazin-10-yl | pentyl | pentyl | H | O |
| 204 | 2-amino-phenothiazin-10-yl | pentyl | pentyl | H | O |
| 205 | amino-azaadamantyl | pentyl | pentyl | H | O |
| 206 | 4-amino-2,7-dihydro-1H-azepin-1-yl | pentyl | pentyl | H | O |
| 207 | 5-amino-2,3-dihydro-1H-azepin-1-yl | pentyl | pentyl | H | O |
| 208 | 4-amino-1H-azepin-1-yl | pentyl | pentyl | H | O |

TABLE 1-continued
| Cmpd | W | X | Z | A | Q |
|---|---|---|---|---|---|
| 209 | 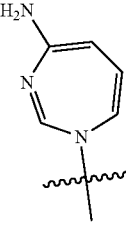 | 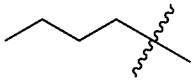 [SMILES: *CCCC] | 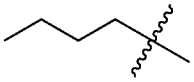 [SMILES: *CCCC] | H | O |
| 210 | 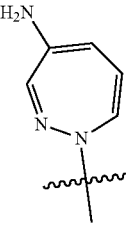 | 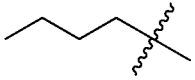 | 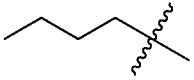 [SMILES: *CCCC] | H | O |
| 211 | 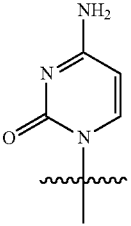 | 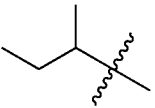 | 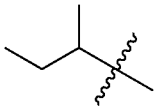 | H | O |
| 212 | 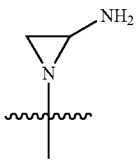 [SMILES: *N1CC1N] | 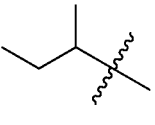 [SMILES: *C(C)CC] | 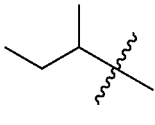 [SMILES: *C(C)CC] | H | O |
| 213 | 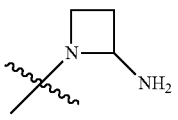 | 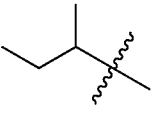 | 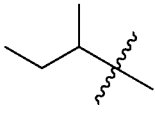 [SMILES: *C(C)CC] | H | O |
| 214 | 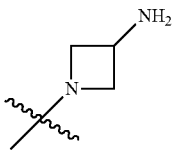 [SMILES: *N1CC(N)C1] | 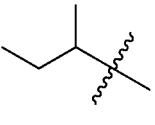 [SMILES: *C(C)CC] | 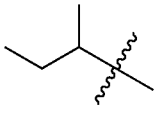 [SMILES: *C(C)CC] | H | O |
| 215 | 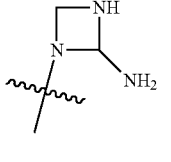 | 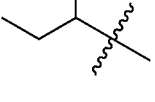 | 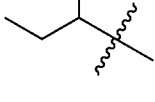 | H | O |
| 216 | 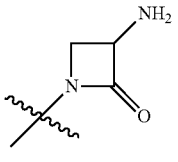 [SMILES: *N1CC(N)C1=O] | 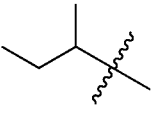 [SMILES: *C(C)CC] | 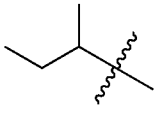 [SMILES: *C(C)CC] | H | O |

TABLE 1-continued

| Cmpd | W | X | Z | A | Q |
|---|---|---|---|---|---|
| 217 | 4-amino-azetidinone (N-linked) | 3-methylpentan-3-yl | 3-methylpentan-3-yl | H | O |
| 218 | 2-aminopyrrolidine (N-linked) | 3-methylpentan-3-yl | 3-methylpentan-3-yl | H | O |
| 219 | 3-aminopyrrolidine (N-linked) | 3-methylpentan-3-yl | 3-methylpentan-3-yl | H | O |
| 220 | 2-amino-2,5-dihydro-1H-pyrrole (N-linked) | 3-methylpentan-3-yl | 3-methylpentan-3-yl | H | O |
| 221 | 3-amino-2,5-dihydro-1H-pyrrole (N-linked) | 3-methylpentan-3-yl | 3-methylpentan-3-yl | H | O |
| 222 | 2-amino-3,4-dihydro-2H-pyrrole (N-linked) | 3-methylpentan-3-yl | 3-methylpentan-3-yl | H | O |
| 223 | 3-amino-4,5-dihydro-1H-pyrrole (N-linked) | 3-methylpentan-3-yl | 3-methylpentan-3-yl | H | O |
| 224 | 3-amino-2,3-dihydro-1H-pyrrole (N-linked) | 3-methylpentan-3-yl | 3-methylpentan-3-yl | H | O |

TABLE 1-continued

| Cmpd | W | X | Z | A | Q |
|------|---|---|---|---|---|
| 225 | 2-amino-2,5-dihydro-1H-pyrrol-1-yl | 3-pentyl | 3-pentyl | H | O |
| 226 | 2-amino-1H-pyrrol-1-yl | 3-pentyl | 3-pentyl | H | O |
| 227 | 3-amino-1H-pyrrol-1-yl | 3-pentyl | 3-pentyl | H | O |
| 228 | 3-aminopyrazolidin-1-yl | 3-pentyl | 3-pentyl | H | O |
| 229 | 4-aminopyrazolidin-1-yl | 3-pentyl | 3-pentyl | H | O |
| 230 | 5-aminopyrazolidin-1-yl | 3-pentyl | 3-pentyl | H | O |
| 231 | 4-aminoimidazolidin-1-yl | 3-pentyl | 3-pentyl | H | O |
| 232 | 5-aminoimidazolidin-1-yl | 3-pentyl | 3-pentyl | H | O |

TABLE 1-continued

| Cmpd | W | X | Z | A | Q |
|---|---|---|---|---|---|
| 233 | 2-amino-imidazolidin-1-yl (HN, H₂N-C=N, N-) | 3-pentyl | 3-pentyl | H | O |
| 234 | 3-amino-4,5-dihydro-pyrazol-1-yl | 3-pentyl | 3-pentyl | H | O |
| 235 | 4-amino-4,5-dihydro-pyrazol-1-yl | 3-pentyl | 3-pentyl | H | O |
| 236 | 5-amino-4,5-dihydro-pyrazol-1-yl | 3-pentyl | 3-pentyl | H | O |
| 237 | 2-amino-4,5-dihydro-imidazol-1-yl | 3-pentyl | 3-pentyl | H | O |
| 238 | 4-amino-4,5-dihydro-imidazol-1-yl | 3-pentyl | 3-pentyl | H | O |
| 239 | 5-amino-4,5-dihydro-imidazol-1-yl | 3-pentyl | 3-pentyl | H | O |
| 240 | 3-amino-2,5-dioxopyrrolidin-1-yl | 3-pentyl | 3-pentyl | H | O |

TABLE 1-continued

| Cmpd | W | X | Z | A | Q |
|---|---|---|---|---|---|
| 241 | 5-amino-hydantoin N-linked | 3-methylpentyl | 3-methylpentyl | H | O |
| 242 | 5-amino-thiazolidine-2,4-dione N-linked | 3-methylpentyl | 3-methylpentyl | H | O |
| 243 | 2-aminopiperidin-1-yl | 3-methylpentyl | 3-methylpentyl | H | O |
| 244 | 3-aminopiperidin-1-yl | 3-methylpentyl | 3-methylpentyl | H | O |
| 245 | 4-aminopiperidin-1-yl | 3-methylpentyl | 3-methylpentyl | H | O |
| 246 | 3-aminopiperazin-1-yl | 3-methylpentyl | 3-methylpentyl | H | O |
| 247 | 2-aminopiperazin-4-yl | 3-methylpentyl | 3-methylpentyl | H | O |

TABLE 1-continued

| Cmpd | W | X | Z | A | Q |
|---|---|---|---|---|---|
| 248 | 3-amino-morpholinyl (N-linked) | 3-methylpentan-3-yl | 3-methylpentan-3-yl | H | O |
| 249 | 2-amino-morpholinyl (N-linked) | 3-methylpentan-3-yl | 3-methylpentan-3-yl | H | O |
| 250 | 3-amino-2H-1,2-oxazinyl (N-linked) | 3-methylpentan-3-yl | 3-methylpentan-3-yl | H | O |
| 251 | 4-amino-2H-1,2-oxazinyl (N-linked) | 3-methylpentan-3-yl | 3-methylpentan-3-yl | H | O |
| 252 | 5-amino-2H-1,2-oxazinyl (N-linked) | 3-methylpentan-3-yl | 3-methylpentan-3-yl | H | O |
| 253 | 6-amino-2H-1,2-oxazinyl (N-linked) | 3-methylpentan-3-yl | 3-methylpentan-3-yl | H | O |
| 254 | 3-amino-4H-1,4-oxazinyl (N-linked) | 3-methylpentan-3-yl | 3-methylpentan-3-yl | H | O |
| 255 | 2-amino-4H-1,4-oxazinyl (N-linked) | 3-methylpentan-3-yl | 3-methylpentan-3-yl | H | O |

TABLE 1-continued

| Cmpd | W | X | Z | A | Q |
|---|---|---|---|---|---|
| 256 | 3-amino-thiomorpholinyl (N-linked) | 3-methylpentan-3-yl | 3-methylpentan-3-yl | H | O |
| 257 | 2-amino-thiomorpholinyl (N-linked) | 3-methylpentan-3-yl | 3-methylpentan-3-yl | H | O |
| 258 | 3-amino-2H-1,2-thiazine (N-linked) | 3-methylpentan-3-yl | 3-methylpentan-3-yl | H | O |
| 259 | 4-amino-2H-1,2-thiazine (N-linked) | 3-methylpentan-3-yl | 3-methylpentan-3-yl | H | O |
| 260 | 5-amino-2H-1,2-thiazine (N-linked) | 3-methylpentan-3-yl | 3-methylpentan-3-yl | H | O |
| 261 | 6-amino-2H-1,2-thiazine (N-linked) | 3-methylpentan-3-yl | 3-methylpentan-3-yl | H | O |
| 262 | 3-amino-4H-1,4-thiazine (N-linked) | 3-methylpentan-3-yl | 3-methylpentan-3-yl | H | O |

TABLE 1-continued

| Cmpd | W | X | Z | A | Q |
|---|---|---|---|---|---|
| 263 | 2-amino-thiazine N-linked | 3-pentyl | 3-pentyl | H | O |
| 264 | 3-amino-1,1-dioxo-thiomorpholine N-linked | 3-pentyl | 3-pentyl | H | O |
| 265 | 2-amino-1,1-dioxo-thiomorpholine N-linked | 3-pentyl | 3-pentyl | H | O |
| 266 | 2-amino-5,6-dihydro-4H-cyclopenta[b]pyrrole N-linked | 3-pentyl | 3-pentyl | H | O |
| 267 | 3-amino-5,6-dihydro-4H-cyclopenta[b]pyrrole N-linked | 3-pentyl | 3-pentyl | H | O |
| 268 | 4-amino-5,6-dihydro-4H-cyclopenta[b]pyrrole N-linked | 3-pentyl | 3-pentyl | H | O |
| 269 | 5-amino-5,6-dihydro-4H-cyclopenta[b]pyrrole N-linked | 3-pentyl | 3-pentyl | H | O |

TABLE 1-continued

| Cmpd | W | X | Z | A | Q |
|---|---|---|---|---|---|
| 270 | (bicyclic pyrrole with NH₂, N-linked) | 3-pentyl | 3-pentyl | H | O |
| 271 | (bicyclic pyrrolopyrrole with H₂N and NH, N-linked) | 3-pentyl | 3-pentyl | H | O |
| 272 | (bicyclic pyrrolopyrrole with H₂N and NH, N-linked) | 3-pentyl | 3-pentyl | H | O |
| 273 | (bicyclic pyrrolopyrrole with NH₂ and NH, N-linked) | 3-pentyl | 3-pentyl | H | O |
| 274 | (bicyclic pyrrolopyrrole with NH₂ and NH, N-linked) | 3-pentyl | 3-pentyl | H | O |
| 275 | (bicyclic pyrrolopyrrole with H₂N and NH, N-linked) | 3-pentyl | 3-pentyl | H | O |
| 276 | (bicyclic pyrrolopyrrole with H₂N and NH, N-linked) | 3-pentyl | 3-pentyl | H | O |

US 11,795,192 B2
TABLE 1-continued
| Cmpd | W | X | Z | A | Q |
|------|---|---|---|---|---|
| 277 | 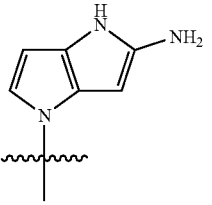 | 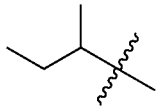 [SMILES: *C(C)CC] | 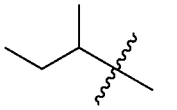 [SMILES: *C(C)CC] | H | O |
| 278 | 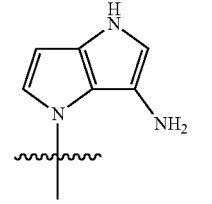 | 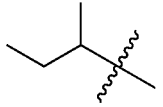 [SMILES: *C(C)CC] | 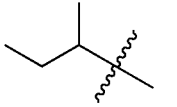 [SMILES: *C(C)CC] | H | O |
| 279 | 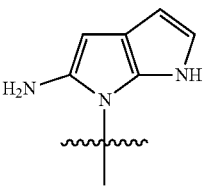 | 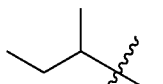 | 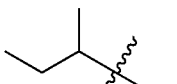 | H | O |
| 280 | 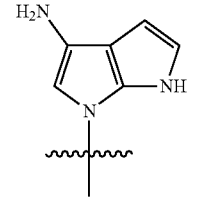 | 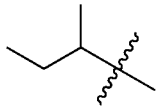 [SMILES: *C(C)CC] | 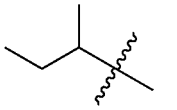 [SMILES: *C(C)CC] | H | O |
| 281 | 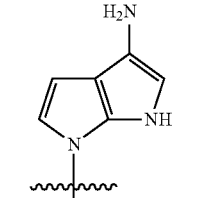 | 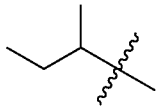 [SMILES: *C(C)CC] | 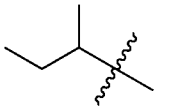 | H | O |
| 282 | 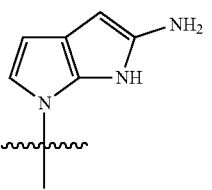 [SMILES: *n1ccc2cc(N)[nH]c21] | 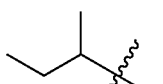 | 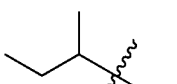 | H | O |
| 283 | 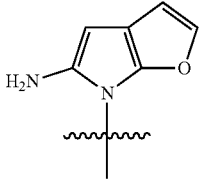 | 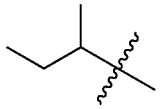 [SMILES: *C(C)CC] | 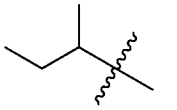 [SMILES: *C(C)CC] | H | O |

TABLE 1-continued

| Cmpd | W | X | Z | A | Q |
|---|---|---|---|---|---|
| 284 | 6-amino-furo[2,3-b]pyrrole, N-linked | 3-pentyl | 3-pentyl | H | O |
| 285 | 3-amino-furo[2,3-b]pyrrole, N-linked | 3-pentyl | 3-pentyl | H | O |
| 286 | 2-amino-furo[2,3-b]pyrrole, N-linked | 3-pentyl | 3-pentyl | H | O |
| 287 | 5-amino-furo[3,2-b]pyrrole, N-linked | 3-pentyl | 3-pentyl | H | O |
| 288 | 6-amino-furo[3,2-b]pyrrole, N-linked | 3-pentyl | 3-pentyl | H | O |
| 289 | 2-amino-furo[3,2-b]pyrrole, N-linked | 3-pentyl | 3-pentyl | H | O |
| 290 | 3-amino-furo[3,2-b]pyrrole, N-linked | 3-pentyl | 3-pentyl | H | O |

TABLE 1-continued

| Cmpd | W | X | Z | A | Q |
|------|---|---|---|---|---|
| 291 | (H₂N-substituted pyrrolothiophene, N-methyl) | 3-methylpentyl | 3-methylpentyl | H | O |
| 292 | (H₂N-substituted pyrrolothiophene, N-methyl) | 3-methylpentyl | 3-methylpentyl | H | O |
| 293 | (H₂N-substituted pyrrolothiophene, N-methyl) | 3-methylpentyl | 3-methylpentyl | H | O |
| 294 | (NH₂-substituted pyrrolothiophene, N-methyl) | 3-methylpentyl | 3-methylpentyl | H | O |
| 295 | (H₂N-substituted pyrrolothiophene, N-methyl) | 3-methylpentyl | 3-methylpentyl | H | O |
| 296 | (H₂N-substituted pyrrolothiophene, N-methyl) | 3-methylpentyl | 3-methylpentyl | H | O |
| 297 | (NH₂-substituted pyrrolothiophene, N-methyl) | 3-methylpentyl | 3-methylpentyl | H | O |

TABLE 1-continued
| Cmpd | W | X | Z | A | Q |
|---|---|---|---|---|---|
| 298 |  |  |  | H | O |
| 299 | 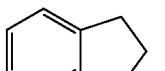 | 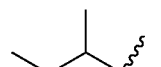 | 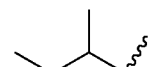 | H | O |
| 300 | 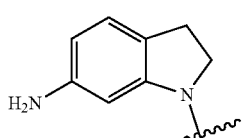 | 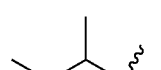 | 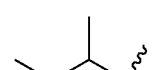 | H | O |
| 301 | 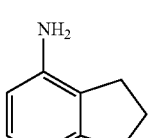 |  |  | H | O |
| 302 | 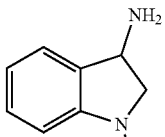 | 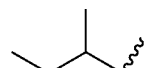 | 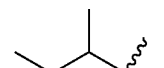 | H | O |
| 303 | 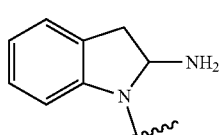 | 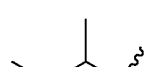 | 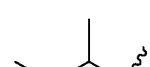 | H | O |
| 304 | 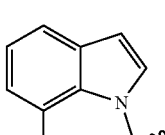 |  | 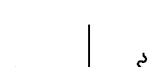 | H | O |
| 305 | 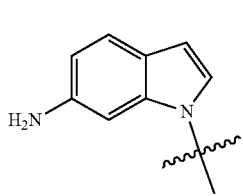 |  |  | H | O |

TABLE 1-continued

| Cmpd | W | X | Z | A | Q |
|------|---|---|---|---|---|
| 306 | 5-amino-indol-1-yl (H₂N on indole) | 3-pentyl (CH(Et)(CH₃)) | 3-pentyl | H | O |
| 307 | 4-amino-indol-1-yl | 3-pentyl | 3-pentyl | H | O |
| 308 | 3-amino-indol-1-yl | 3-pentyl | 3-pentyl | H | O |
| 309 | 2-amino-indol-1-yl | 3-pentyl | 3-pentyl | H | O |
| 310 | 1-amino-isoindol-2-yl | 3-pentyl | 3-pentyl | H | O |
| 311 | 4-amino-isoindol-2-yl | 3-pentyl | 3-pentyl | H | O |
| 312 | 5-amino-isoindol-2-yl | 3-pentyl | 3-pentyl | H | O |

TABLE 1-continued

| Cmpd | W | X | Z | A | Q |
|---|---|---|---|---|---|
| 313 | 7-amino-1H-indazol-1-yl (attached via N1) | 3-pentyl | 3-methylpentan-3-yl | H | O |
| 314 | 6-amino-1H-indazol-1-yl | 3-pentyl | 3-methylpentan-3-yl | H | O |
| 315 | 5-amino-1H-indazol-1-yl | 3-pentyl | 3-methylpentan-3-yl | H | O |
| 316 | 4-amino-1H-indazol-1-yl | 3-pentyl | 3-methylpentan-3-yl | H | O |
| 317 | 3-amino-1H-indazol-1-yl | 3-pentyl | 3-methylpentan-3-yl | H | O |
| 318 | 7-amino-1H-benzimidazol-1-yl | 3-pentyl | 3-methylpentan-3-yl | H | O |
| 319 | 6-amino-1H-benzimidazol-1-yl | 3-pentyl | 3-methylpentan-3-yl | H | O |
| 320 | 5-amino-1H-benzimidazol-1-yl | 3-pentyl | 3-methylpentan-3-yl | H | O |

TABLE 1-continued

| Cmpd | W | X | Z | A | Q |
|---|---|---|---|---|---|
| 321 | 4-aminobenzimidazol-1-yl (structure) | 3-pentyl | 3-pentyl | | O |
| 322 | 2-aminobenzimidazol-1-yl | 3-pentyl | 3-pentyl | H | O |
| 323 | 7-amino-4-azaindol-1-yl | 3-pentyl | 3-pentyl | H | O |
| 324 | 6-amino-4-azaindol-1-yl | 3-pentyl | 3-pentyl | H | O |
| 325 | 5-amino-4-azaindol-1-yl | 3-pentyl | 3-pentyl | H | O |
| 326 | 3-amino-4-azaindol-1-yl | 3-pentyl | 3-pentyl | H | O |
| 327 | 2-amino-4-azaindol-1-yl | 3-pentyl | 3-pentyl | H | O |
| 328 | 7-amino-5-azaindol-1-yl | 3-pentyl | 3-pentyl | H | O |
| 329 | 6-amino-5-azaindol-1-yl | 3-pentyl | 3-pentyl | H | O |

TABLE 1-continued

| Cmpd | W | X | Z | A | Q |
|---|---|---|---|---|---|
| 330 | 4-amino-1H-pyrrolo[3,2-c]pyridine (N1-linked) | 3-pentyl | 3-pentyl | H | O |
| 331 | 3-amino-1H-pyrrolo[3,2-c]pyridine (N1-linked) | 3-pentyl | 3-pentyl | H | O |
| 332 | 2-amino-1H-pyrrolo[3,2-c]pyridine (N1-linked) | 3-pentyl | 3-pentyl | H | O |
| 333 | 7-amino-1H-pyrrolo[2,3-c]pyridine (N1-linked) | 3-pentyl | 3-pentyl | H | O |
| 334 | 5-amino-1H-pyrrolo[2,3-c]pyridine (N1-linked) | 3-pentyl | 3-pentyl | H | O |
| 335 | 4-amino-1H-pyrrolo[2,3-c]pyridine (N1-linked) | 3-pentyl | 3-pentyl | H | O |
| 336 | 3-amino-1H-pyrrolo[2,3-c]pyridine (N1-linked) | 3-pentyl | 3-pentyl | H | O |
| 337 | 2-amino-1H-pyrrolo[2,3-c]pyridine (N1-linked) | 3-pentyl | 3-pentyl | H | O |

TABLE 1-continued

| Cmpd | W | X | Z | A | Q |
|---|---|---|---|---|---|
| 338 | 6-amino-7-azaindole (N1-linked) | 3-pentyl | 3-methylpentyl (3° C linked) | H | O |
| 339 | 5-amino-7-azaindole (N1-linked) | 3-pentyl | 3-methylpentyl (3° C linked) | H | O |
| 340 | 4-amino-7-azaindole (N1-linked) | 3-pentyl | 3-methylpentyl (3° C linked) | H | O |
| 341 | 3-amino-7-azaindole (N1-linked) | 3-pentyl | 3-methylpentyl (3° C linked) | H | O |
| 342 | 2-amino-7-azaindole (N1-linked) | 3-pentyl | 3-methylpentyl (3° C linked) | H | O |
| 343 | 6-amino-pyrazolo[3,4-b]pyridine (N1-linked) | 3-pentyl | 3-methylpentyl (3° C linked) | H | O |
| 344 | 5-amino-pyrazolo[3,4-b]pyridine (N1-linked) | 3-pentyl | 3-methylpentyl (3° C linked) | H | O |
| 345 | 4-amino-pyrazolo[3,4-b]pyridine (N1-linked) | 3-pentyl | 3-methylpentyl (3° C linked) | H | O |

TABLE 1-continued

| Cmpd | W | X | Z | A | Q |
|---|---|---|---|---|---|
| 346 | 3-amino-pyrazolo[3,4-b]pyridin-1-yl | 3-pentyl | 3-methylpentyl | H | O |
| 347 | 2-amino-purin-9-yl | 3-pentyl | 3-methylpentyl | H | O |
| 348 | adenin-9-yl (6-amino-purin-9-yl) | 3-pentyl | 3-methylpentyl | H | O |
| 349 | 8-amino-purin-9-yl | 3-pentyl | 3-methylpentyl | H | O |
| 350 | 7-amino-benzo[d]isothiazol-3(2H)-on-2-yl | 3-pentyl | 3-methylpentyl | H | O |
| 351 | 6-amino-benzo[d]isothiazol-3(2H)-on-2-yl | 3-pentyl | 3-methylpentyl | H | O |
| 352 | 5-amino-benzo[d]isothiazol-3(2H)-on-2-yl | 3-pentyl | 3-methylpentyl | H | O |

TABLE 1-continued

| Cmpd | W | X | Z | A | Q |
|---|---|---|---|---|---|
| 353 | 4-amino-2-alkyl-benzisothiazol-3(2H)-one | 3-pentyl | 3-methyl-pentyl | H | O |
| 354 | 6-amino-1-alkyl-1H-pyrazolo[3,4-d]pyrimidin-4(5H)-one | 3-pentyl | 3-methyl-pentyl | H | O |
| 355 | 9-alkyl-9H-adenine | 3-pentyl | 3-methyl-pentyl | H | O |
| 356 | 1-amino-2-alkyl-decahydroisoquinoline | 3-pentyl | 3-methyl-pentyl | H | O |
| 357 | 8-amino-2-alkyl-decahydroisoquinoline | 3-pentyl | 3-methyl-pentyl | H | O |
| 358 | 7-amino-2-alkyl-decahydroisoquinoline | 3-pentyl | 3-methyl-pentyl | H | O |
| 359 | 6-amino-2-alkyl-decahydroisoquinoline | 3-pentyl | 3-methyl-pentyl | H | O |
| 360 | 5-amino-2-alkyl-decahydroisoquinoline | 3-pentyl | 3-methyl-pentyl | H | O |

TABLE 1-continued

| Cmpd | W | X | Z | A | Q |
|---|---|---|---|---|---|
| 361 | decahydroisoquinoline with NH₂ at 4-position, N-linked | 3-pentyl | 3-pentyl | H | O |
| 362 | decahydroisoquinoline with NH₂ at 3-position, N-linked | 3-pentyl | 3-pentyl | H | O |
| 363 | decahydroquinoline with NH₂ at 8-position, N-linked | 3-pentyl | 3-pentyl | H | O |
| 364 | decahydroquinoline with NH₂ at 7-position, N-linked | 3-pentyl | 3-pentyl | H | O |
| 365 | decahydroquinoline with NH₂ at 6-position, N-linked | 3-pentyl | 3-pentyl | H | O |
| 366 | decahydroquinoline with NH₂ at 5-position, N-linked | 3-pentyl | 3-pentyl | H | O |
| 367 | decahydroquinoline with NH₂ at 4-position, N-linked | 3-pentyl | 3-pentyl | H | O |
| 368 | decahydroquinoline with NH₂ at 3-position, N-linked | 3-pentyl | 3-pentyl | H | O |

TABLE 1-continued

| Cmpd | W | X | Z | A | Q |
| --- | --- | --- | --- | --- | --- |
| 369 | decahydroquinoline-2-amine | 3-pentyl | 3-pentyl | H | O |
| 370 | 8-amino-1,2,3,4-tetrahydroquinoline | 3-pentyl | 3-pentyl | H | O |
| 371 | 7-amino-1,2,3,4-tetrahydroquinoline | 3-pentyl | 3-pentyl | H | O |
| 372 | 6-amino-1,2,3,4-tetrahydroquinoline | 3-pentyl | 3-pentyl | H | O |
| 373 | 5-amino-1,2,3,4-tetrahydroquinoline | 3-pentyl | 3-pentyl | H | O |
| 374 | 4-amino-1,2,3,4-tetrahydroquinoline | 3-pentyl | 3-pentyl | H | O |
| 375 | 3-amino-1,2,3,4-tetrahydroquinoline | 3-pentyl | 3-pentyl | H | O |

TABLE 1-continued

| Cmpd | W | X | Z | A | Q |
|---|---|---|---|---|---|
| 376 | 3,4-dihydroquinolin-2-amine, N1-linked | 3-methylpentan-3-yl | 3-methylpentan-3-yl | H | O |
| 377 | 8-amino-2H-quinoline, N1-linked | 3-methylpentan-3-yl | 3-methylpentan-3-yl | H | O |
| 378 | 7-amino-2H-quinoline, N1-linked | 3-methylpentan-3-yl | 3-methylpentan-3-yl | H | O |
| 379 | 6-amino-2H-quinoline, N1-linked | 3-methylpentan-3-yl | 3-methylpentan-3-yl | H | O |
| 380 | 5-amino-2H-quinoline, N1-linked | 3-methylpentan-3-yl | 3-methylpentan-3-yl | H | O |
| 381 | 4-amino-2H-quinoline, N1-linked | 3-methylpentan-3-yl | 3-methylpentan-3-yl | H | O |
| 382 | 3-amino-2H-quinoline, N1-linked | 3-methylpentan-3-yl | 3-methylpentan-3-yl | H | O |

TABLE 1-continued

| Cmpd | W | X | Z | A | Q |
|---|---|---|---|---|---|
| 383 | 2-amino-quinoline N-substituted | 3-pentyl | 3-pentyl | H | O |
| 384 | 1-amino-1,2,3,4-tetrahydroisoquinoline N-substituted | 3-pentyl | 3-pentyl | H | O |
| 385 | 8-amino-1,2,3,4-tetrahydroisoquinoline N-substituted | 3-pentyl | 3-pentyl | H | O |
| 386 | 7-amino-1,2,3,4-tetrahydroisoquinoline N-substituted | 3-pentyl | 3-pentyl | H | O |
| 387 | 6-amino-1,2,3,4-tetrahydroisoquinoline N-substituted | 3-pentyl | 3-pentyl | H | O |
| 388 | 5-amino-1,2,3,4-tetrahydroisoquinoline N-substituted | 3-pentyl | 3-pentyl | H | O |
| 389 | 4-amino-1,2,3,4-tetrahydroisoquinoline N-substituted | 3-pentyl | 3-pentyl | H | O |
| 390 | 3-amino-1,2,3,4-tetrahydroisoquinoline N-substituted | 3-pentyl | 3-pentyl | H | O |
| 391 | 8-amino-2-oxo-quinoline N-substituted | 3-pentyl | 3-pentyl | H | O |

TABLE 1-continued

| Cmpd | W | X | Z | A | Q |
|---|---|---|---|---|---|
| 392 | 7-H2N-quinolin-2(1H)-one (N-substituted) | 3-pentyl | 3-pentyl | H | O |
| 393 | 6-H2N-quinolin-2(1H)-one (N-substituted) | 3-pentyl | 3-pentyl | H | O |
| 394 | 5-NH2-quinolin-2(1H)-one (N-substituted) | 3-pentyl | 3-pentyl | H | O |
| 395 | 4-NH2-quinolin-2(1H)-one (N-substituted) | 3-pentyl | 3-pentyl | H | O |
| 396 | 3-NH2-quinolin-2(1H)-one (N-substituted) | 3-pentyl | 3-pentyl | H | O |
| 397 | 8-NH2-isoquinolin-1(2H)-one (N-substituted) | 3-pentyl | 3-pentyl | H | O |
| 398 | 7-H2N-isoquinolin-1(2H)-one (N-substituted) | 3-pentyl | 3-pentyl | H | O |
| 399 | 6-H2N-isoquinolin-1(2H)-one (N-substituted) | 3-pentyl | 3-pentyl | H | O |

| Cmpd | W | X | Z | A | Q |
|---|---|---|---|---|---|
| 400 | 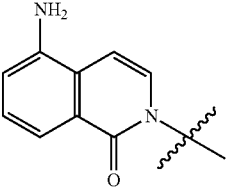 [SMILES: *n1ccc2c(N)cccc2c1=O] | 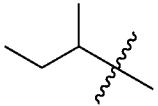 [SMILES: *C(C)CC] | 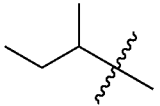 [SMILES: *C(C)CC] | H | O |
| 401 | 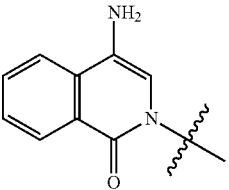 [SMILES: *n1cc(N)c2ccccc2c1=O] | 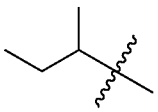 [SMILES: *C(C)CC] | 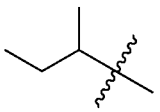 [SMILES: *C(C)CC] | H | O |
| 402 | 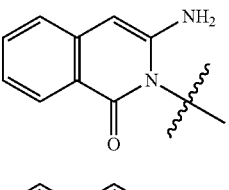 | 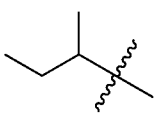 [SMILES: *C(C)CC] | 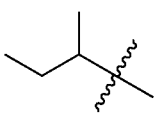 [SMILES: *C(C)CC] | H | O |
| 403 | 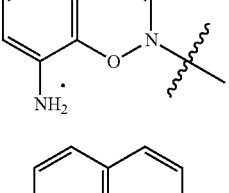 | 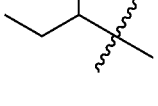 | 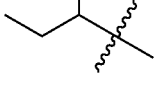 | H | O |
| 404 | 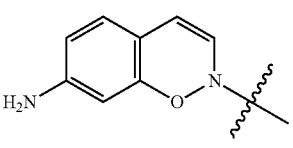 | 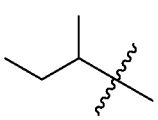 [SMILES: *C(C)CC] | 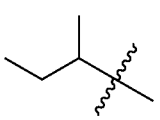 [SMILES: *C(C)CC] | H | O |
| 405 | 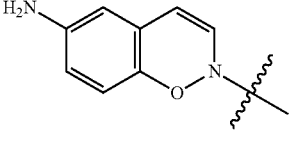 | 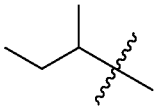 | 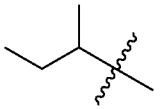 [SMILES: *C(C)CC] | H | O |
| 406 | 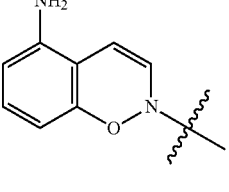 | 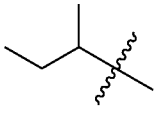 [SMILES: *C(C)CC] | 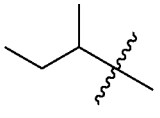 [SMILES: *C(C)CC] | H | O |
| 407 | 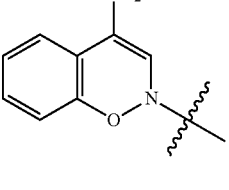 | 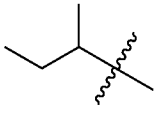 [SMILES: *C(C)CC] | 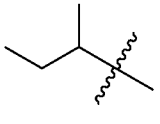 [SMILES: *C(C)CC] | H | O |
| 408 | 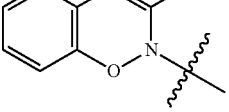 | 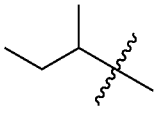 [SMILES: *C(C)CC] | 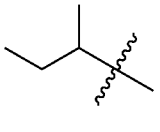 [SMILES: *C(C)CC] | H | O |

TABLE 1-continued

| Cmpd | W | X | Z | A | Q |
|---|---|---|---|---|---|
| 409 | 1-amino-9H-carbazol-9-yl (N-linked with methyl) | 3-methylpentan-3-yl | 3-methylpentan-3-yl | H | O |
| 410 | 2-amino-9H-carbazol-9-yl (N-linked with methyl) | 3-methylpentan-3-yl | 3-methylpentan-3-yl | H | O |
| 411 | 1-amino-10H-phenoxazin-10-yl | 3-methylpentan-3-yl | 3-methylpentan-3-yl | H | O |
| 412 | 2-amino-10H-phenoxazin-10-yl | 3-methylpentan-3-yl | 3-methylpentan-3-yl | H | O |
| 413 | 1-amino-10H-phenothiazin-10-yl | 3-methylpentan-3-yl | 3-methylpentan-3-yl | H | O |
| 414 | 2-amino-10H-phenothiazin-10-yl | 3-methylpentan-3-yl | 3-methylpentan-3-yl | H | O |
| 415 | amino-adamantyl-N | 3-methylpentan-3-yl | 3-methylpentan-3-yl | H | O |

TABLE 1-continued

| Cmpd | W | X | Z | A | Q |
|---|---|---|---|---|---|
| 416 | 4-amino-2,5-dihydro-1H-azepine (N-linked) | 3-pentyl (at C3) | 3-pentyl (at C3) | H | O |
| 417 | 4-amino-2,3-dihydro-1H-azepine (N-linked) | 3-pentyl (at C3) | 3-pentyl (at C3) | H | O |
| 418 | 4-amino-1H-azepine (N-linked) | 3-pentyl (at C3) | 3-pentyl (at C3) | H | O |
| 419 | 4-amino-1H-1,3-diazepine (N1-linked) | 3-pentyl (at C3) | 3-pentyl (at C3) | H | O |
| 420 | 4-amino-1H-1,2-diazepine (N1-linked) | 3-pentyl (at C3) | 3-pentyl (at C3) | H | O |
| 421 | 4-amino-2-oxo-pyrimidin-1-yl (cytosin-1-yl) | cyclohexyl | cyclohexyl | H | O |
| 422 | 3-amino-aziridin-1-yl | cyclohexyl | cyclohexyl | H | O |

TABLE 1-continued

| Cmpd | W | X | Z | A | Q |
|---|---|---|---|---|---|
| 423 | azetidine-N-linked, 2-NH₂ | cyclohexyl | cyclohexyl | H | O |
| 424 | azetidine-N-linked, 3-NH₂ | cyclohexyl | cyclohexyl | H | O |
| 425 | 2-amino-azetidine with NH | cyclohexyl | cyclohexyl | H | O |
| 426 | 3-amino-2-oxo-azetidin-N-yl | cyclohexyl | cyclohexyl | H | O |
| 427 | 4-amino-2-oxo-azetidin-N-yl | cyclohexyl | cyclohexyl | H | O |
| 428 | 2-amino-pyrrolidin-1-yl | cyclohexyl | cyclohexyl | H | O |
| 429 | 3-amino-pyrrolidin-1-yl | cyclohexyl | cyclohexyl | H | O |
| 430 | 2-amino-2,5-dihydro-pyrrol-1-yl | cyclohexyl | cyclohexyl | H | O |

TABLE 1-continued

| Cmpd | W | X | Z | A | Q |
|---|---|---|---|---|---|
| 431 | 3-amino-2,5-dihydro-1H-pyrrol-1-yl (H2N on pyrroline, N-attached) | cyclohexyl | cyclohexyl | H | O |
| 432 | 2-amino-2,3-dihydro-1H-pyrrol-1-yl | cyclohexyl | cyclohexyl | H | O |
| 433 | 3-amino-4,5-dihydro-1H-pyrrol-1-yl | cyclohexyl | cyclohexyl | H | O |
| 434 | 3-amino-2,5-dihydro-1H-pyrrol-1-yl | cyclohexyl | cyclohexyl | H | O |
| 435 | 2-amino-2,5-dihydro-1H-pyrrol-1-yl | cyclohexyl | cyclohexyl | H | O |
| 436 | 2-amino-1H-pyrrol-1-yl | cyclohexyl | cyclohexyl | H | O |
| 437 | 3-amino-1H-pyrrol-1-yl | cyclohexyl | cyclohexyl | H | O |

TABLE 1-continued
| Cmpd | W | X | Z | A | Q |
|---|---|---|---|---|---|
| 438 | 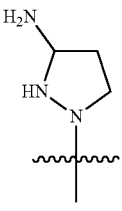 | 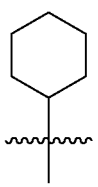 [SMILES: *C1CCCCC1] | 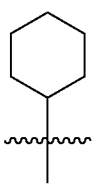 [SMILES: *C1CCCCC1] | H | O |
| 439 | 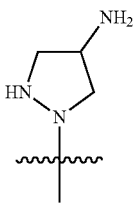 [SMILES: *N1CC(N)CN1] | 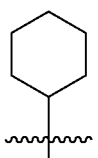 | 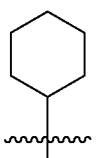 | H | O |
| 440 | 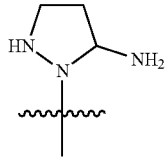 | 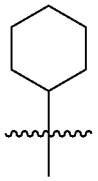 | 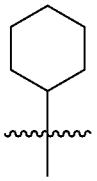 | H | O |
| 441 | 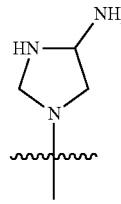 | 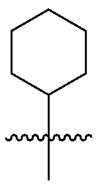 | 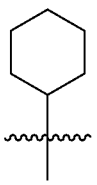 | H | O |
| 442 | 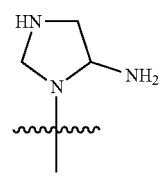 | 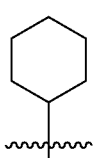 | 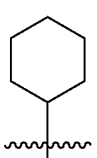 | H | O |
| 443 | 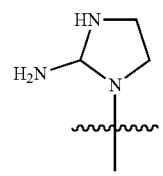 | 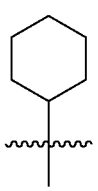 | 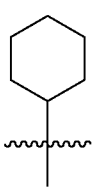 [SMILES: *C1CCCCC1] | H | O |
| 444 | 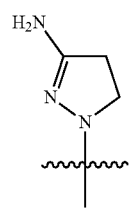 | 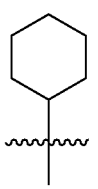 [SMILES: *C1CCCCC1] | 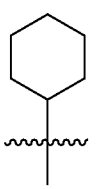 [SMILES: *C1CCCCC1] | H | O |

TABLE 1-continued

| Cmpd | W | X | Z | A | Q |
|---|---|---|---|---|---|
| 445 | 4-amino-4,5-dihydropyrazol-1-yl (N-linked) | cyclohexyl | cyclohexyl | H | O |
| 446 | 5-amino-4,5-dihydropyrazol-1-yl (N-linked) | cyclohexyl | cyclohexyl | H | O |
| 447 | 2-amino-4,5-dihydroimidazol-1-yl (N-linked) | cyclohexyl | cyclohexyl | H | O |
| 448 | 4-amino-4,5-dihydroimidazol-1-yl (N-linked) | cyclohexyl | cyclohexyl | H | O |
| 449 | 5-amino-4,5-dihydroimidazol-1-yl (N-linked) | cyclohexyl | cyclohexyl | H | O |
| 450 | 3-amino-2,5-dioxopyrrolidin-1-yl (N-linked) | cyclohexyl | cyclohexyl | H | O |
| 451 | 5-amino-2,4-dioxoimidazolidin-3-yl (N-linked hydantoin) | cyclohexyl | cyclohexyl | H | O |

TABLE 1-continued

| Cmpd | W | X | Z | A | Q |
|---|---|---|---|---|---|
| 452 | 4-amino-3-(thiazolidine-2,4-dione-N-yl) | cyclohexyl | cyclohexyl | H | O |
| 453 | 2-aminopiperidin-1-yl | cyclohexyl | cyclohexyl | H | O |
| 454 | 3-aminopiperidin-1-yl | cyclohexyl | cyclohexyl | H | O |
| 455 | 4-aminopiperidin-1-yl | cyclohexyl | cyclohexyl | H | O |
| 456 | 3-aminopiperazin-1-yl | cyclohexyl | cyclohexyl | H | O |
| 457 | 2-aminopiperazin-4-yl | cyclohexyl | cyclohexyl | H | O |
| 458 | 3-aminomorpholin-4-yl | cyclohexyl | cyclohexyl | H | O |

TABLE 1-continued

| Cmpd | W | X | Z | A | Q |
|---|---|---|---|---|---|
| 459 | 2-amino-morpholine (N-linked) | cyclohexyl | cyclohexyl | H | O |
| 460 | 3-amino-2H-1,2-oxazine (N-linked) | cyclohexyl | cyclohexyl | H | O |
| 461 | 4-amino-2H-1,2-oxazine (N-linked) | cyclohexyl | cyclohexyl | H | O |
| 462 | 5-amino-2H-1,2-oxazine (N-linked) | cyclohexyl | cyclohexyl | H | O |
| 463 | 6-amino-2H-1,2-oxazine (N-linked) | cyclohexyl | cyclohexyl | H | O |
| 464 | 3-amino-morpholine (N-linked) | cyclohexyl | cyclohexyl | H | O |
| 465 | 2-amino-morpholine (N-linked, O adjacent) | cyclohexyl | cyclohexyl | H | O |
| 466 | 3-amino-thiomorpholine (N-linked) | cyclohexyl | cyclohexyl | H | O |

TABLE 1-continued

| Cmpd | W | X | Z | A | Q |
|------|---|---|---|---|---|
| 467 | 2-amino-thiomorpholinyl (N-linked) | cyclohexyl | cyclohexyl | H | O |
| 468 | 3-amino-2H-1,2-thiazinyl (N-linked) | cyclohexyl | cyclohexyl | H | O |
| 469 | 4-amino-2H-1,2-thiazinyl (N-linked) | cyclohexyl | cyclohexyl | H | O |
| 470 | 5-amino-2H-1,2-thiazinyl (N-linked) | cyclohexyl | cyclohexyl | H | O |
| 471 | 6-amino-2H-1,2-thiazinyl (N-linked) | cyclohexyl | cyclohexyl | H | O |
| 472 | 3-amino-4H-1,4-thiazinyl (N-linked) | cyclohexyl | cyclohexyl | H | O |
| 473 | 3-amino-4H-1,4-thiazinyl (N-linked, alt) | cyclohexyl | cyclohexyl | H | O |

TABLE 1-continued
| Cmpd | W | X | Z | A | Q |
|---|---|---|---|---|---|
| 474 | 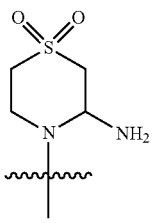 [SMILES: *N1CCS(=O)(=O)CC1N] | 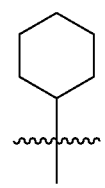 | 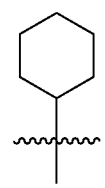 [SMILES: *C1CCCCC1] | H | O |
| 475 | 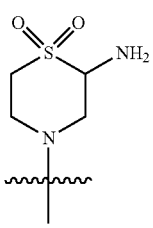 | 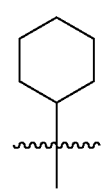 | 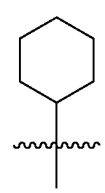 [SMILES: *C1CCCCC1] | H | O |
| 476 | 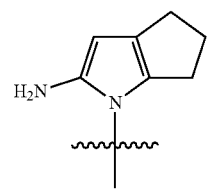 | 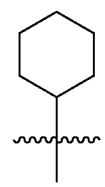 | 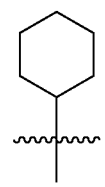 [SMILES: *C1CCCCC1] | H | O |
| 477 | 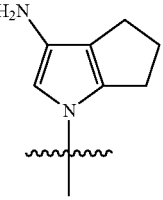 | 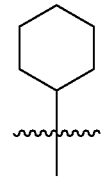 [SMILES: *C1CCCCC1] | 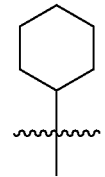 [SMILES: *C1CCCCC1] | H | O |
| 478 | 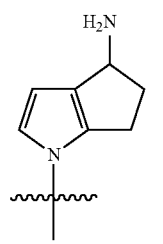 [SMILES: *n1ccc2c1CCC2N] | 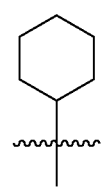 | 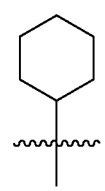 [SMILES: *C1CCCCC1] | H | O |
| 479 | 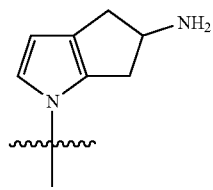 [SMILES: *n1ccc2c1CC(N)C2] | 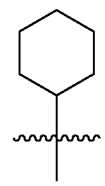 | 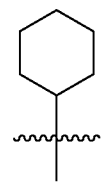 [SMILES: *C1CCCCC1] | H | O |
| 480 | 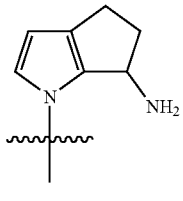 [SMILES: *n1ccc2c1C(N)CC2] | 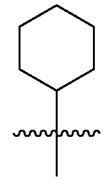 | 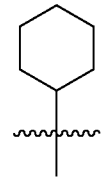 [SMILES: *C1CCCCC1] | H | O |

TABLE 1-continued

| Cmpd | W | X | Z | A | Q |
|---|---|---|---|---|---|
| 481 | (pyrrolopyrrole with H₂N, N-linked) | cyclohexyl | cyclohexyl | H | O |
| 482 | (pyrrolopyrrole with H₂N, N-linked) | cyclohexyl | cyclohexyl | H | O |
| 483 | (pyrrolopyrrole with NH₂, N-linked) | cyclohexyl | cyclohexyl | H | O |
| 484 | (pyrrolopyrrole with NH₂, N-linked) | cyclohexyl | cyclohexyl | H | O |
| 485 | (pyrrolopyrrole with H₂N, N-linked) | cyclohexyl | cyclohexyl | H | O |
| 486 | (pyrrolopyrrole with H₂N, N-linked) | cyclohexyl | cyclohexyl | H | O |
| 487 | (pyrrolopyrrole with NH₂, N-linked) | cyclohexyl | cyclohexyl | H | O |

TABLE 1-continued

| Cmpd | W | X | Z | A | Q |
|------|---|---|---|---|---|
| 488 | pyrrolo[3,2-b]pyrrole-NH₂ | cyclohexyl | cyclohexyl | H | O |
| 489 | 5-amino-pyrrolo[2,3-b]pyrrole | cyclohexyl | cyclohexyl | H | O |
| 490 | 4-amino-pyrrolo[2,3-b]pyrrole | cyclohexyl | cyclohexyl | H | O |
| 491 | 3-amino-pyrrolo[2,3-b]pyrrole | cyclohexyl | cyclohexyl | H | O |
| 492 | 2-amino-pyrrolo[2,3-b]pyrrole | cyclohexyl | cyclohexyl | H | O |
| 493 | 5-amino-pyrrolo[2,3-b]furan | cyclohexyl | cyclohexyl | H | O |
| 494 | 4-amino-pyrrolo[2,3-b]furan | cyclohexyl | cyclohexyl | H | O |

TABLE 1-continued

| Cmpd | W | X | Z | A | Q |
|------|---|---|---|---|---|
| 495 | (3-amino-furo[3,2-b]pyrrole, N-linked) | cyclohexyl | cyclohexyl | H | O |
| 496 | (2-amino-furo[3,2-b]pyrrole, N-linked) | cyclohexyl | cyclohexyl | H | O |
| 497 | (5-amino-4H-furo[3,2-b]pyrrole, N-linked) | cyclohexyl | cyclohexyl | H | O |
| 498 | (6-amino-4H-furo[3,2-b]pyrrole, N-linked) | cyclohexyl | cyclohexyl | H | O |
| 499 | (2-amino-4H-furo[3,2-b]pyrrole, N-linked) | cyclohexyl | cyclohexyl | H | O |
| 500 | (3-amino-furo[3,2-b]pyrrole, N-linked) | cyclohexyl | cyclohexyl | H | O |
| 501 | (5-amino-thieno[2,3-b]pyrrole, N-linked) | cyclohexyl | cyclohexyl | H | O |

TABLE 1-continued
| Cmpd | W | X | Z | A | Q |
|---|---|---|---|---|---|
| 502 | 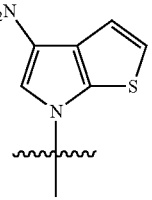 | 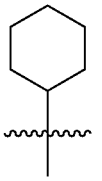 | 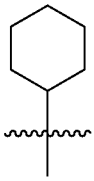 [SMILES: *C1CCCCC1] | H | O |
| 503 | 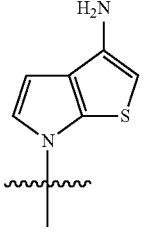 | 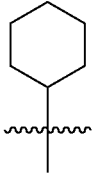 | 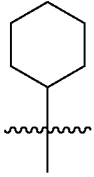 [SMILES: *C1CCCCC1] | H | O |
| 504 | 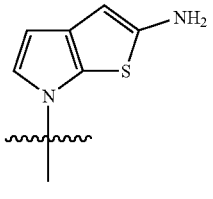 | 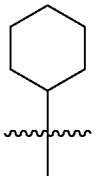 | 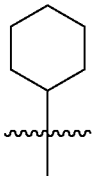 [SMILES: *C1CCCCC1] | H | O |
| 505 | 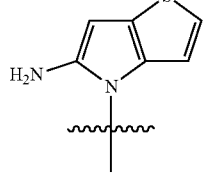 | 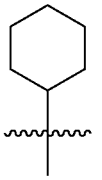 | 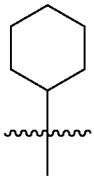 [SMILES: *C1CCCCC1] | H | O |
| 506 | 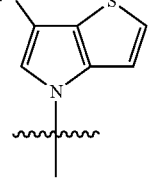 | 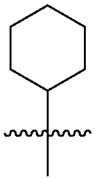 | 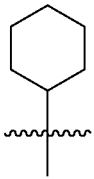 [SMILES: *C1CCCCC1] | H | O |
| 507 | 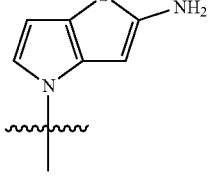 | 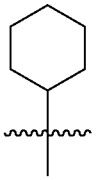 | 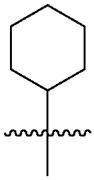 [SMILES: *C1CCCCC1] | H | O |
| 508 | 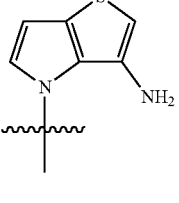 | 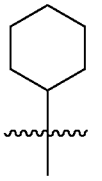 [SMILES: *C1CCCCC1] | 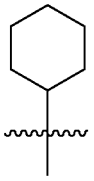 [SMILES: *C1CCCCC1] | H | O |

TABLE 1-continued
| Cmpd | W | X | Z | A | Q |
|---|---|---|---|---|---|
| 509 | 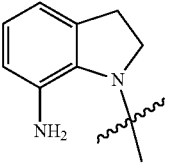 [SMILES: *N1CCc2cccc(N)c21] | 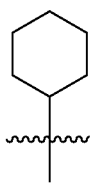 [SMILES: *C1CCCCC1] | 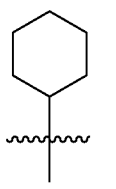 [SMILES: *C1CCCCC1] | H | O |
| 510 | 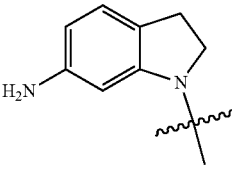 [SMILES: *N1CCc2ccc(N)cc21] | 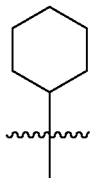 [SMILES: *C1CCCCC1] | 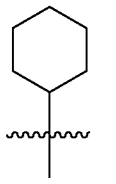 [SMILES: *C1CCCCC1] | H | O |
| 511 | 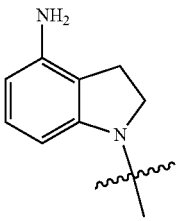 | 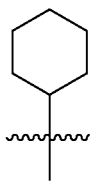 [SMILES: *C1CCCCC1] | 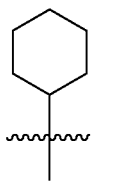 [SMILES: *C1CCCCC1] | H | O |
| 512 | 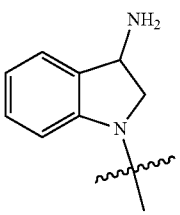 [SMILES: *N1CC(N)c2ccccc21] | 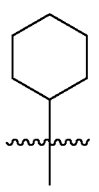 [SMILES: *C1CCCCC1] | 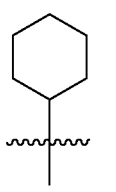 [SMILES: *C1CCCCC1] | H | O |
| 513 | 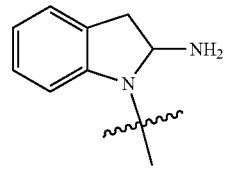 [SMILES: *N1c2ccccc2CC1N] | 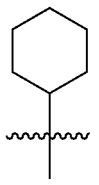 [SMILES: *C1CCCCC1] | 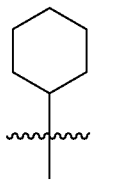 [SMILES: *C1CCCCC1] | H | O |
| 514 | 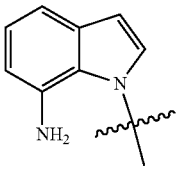 | 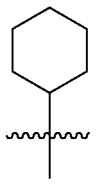 | 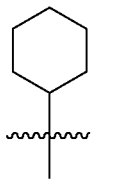 [SMILES: *C1CCCCC1] | H | O |
| 515 | 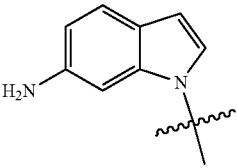 [SMILES: *n1ccc2ccc(N)cc21] | 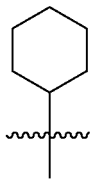 [SMILES: *C1CCCCC1] | 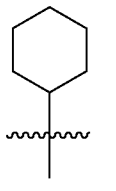 [SMILES: *C1CCCCC1] | H | O |
| 516 | 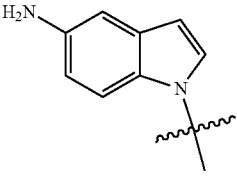 [SMILES: *n1ccc2cc(N)ccc21] | 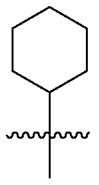 [SMILES: *C1CCCCC1] | 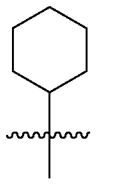 [SMILES: *C1CCCCC1] | H | O |

TABLE 1-continued
| Cmpd | W | X | Z | A | Q |
|---|---|---|---|---|---|
| 517 | 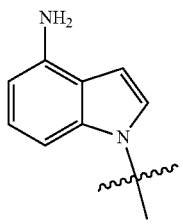 | 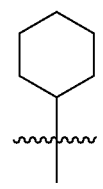 [SMILES: *C1CCCCC1] | 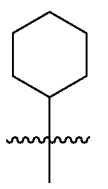 [SMILES: *C1CCCCC1] | H | O |
| 518 | 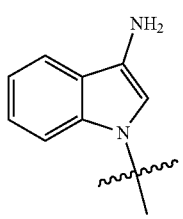 | 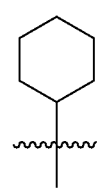 [SMILES: *C1CCCCC1] | 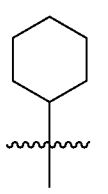 [SMILES: *C1CCCCC1] | H | O |
| 519 | 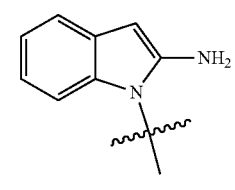 [SMILES: *n1c(N)cc2ccccc21] | 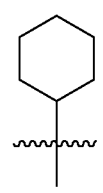 [SMILES: *C1CCCCC1] | 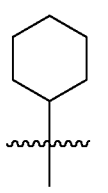 [SMILES: *C1CCCCC1] | H | O |
| 520 | 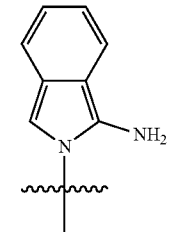 | 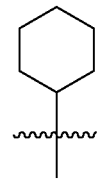 [SMILES: *C1CCCCC1] | 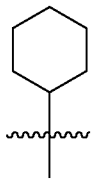 [SMILES: *C1CCCCC1] | H | O |
| 521 | 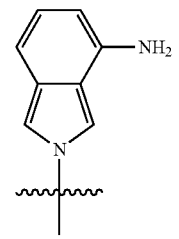 | 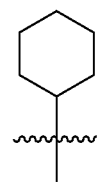 [SMILES: *C1CCCCC1] | 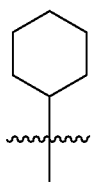 [SMILES: *C1CCCCC1] | H | O |
| 522 | 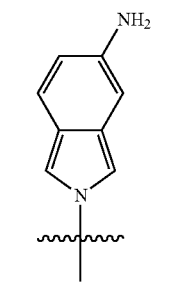 [SMILES: *n1cc2ccc(N)cc2c1] | 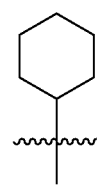 [SMILES: *C1CCCCC1] | 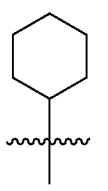 [SMILES: *C1CCCCC1] | H | O |
| 523 | 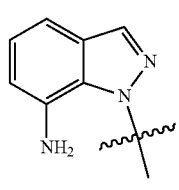 [SMILES: *n1ncc2cccc(N)c21] | 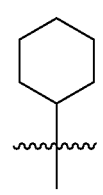 [SMILES: *C1CCCCC1] | 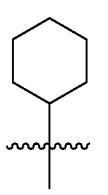 [SMILES: *C1CCCCC1] | H | O |

US 11,795,192 B2
TABLE 1-continued
| Cmpd | W | X | Z | A | Q |
|---|---|---|---|---|---|
| 524 | 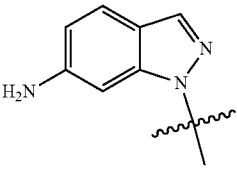 [SMILES: *n1ncc2ccc(N)cc21] | 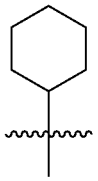 | 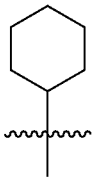 [SMILES: *C1CCCCC1] | H | O |
| 525 | 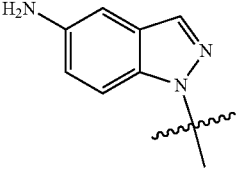 [SMILES: *n1ncc2cc(N)ccc21] | 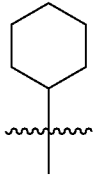 [SMILES: *C1CCCCC1] | 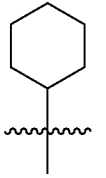 [SMILES: *C1CCCCC1] | H | O |
| 526 | 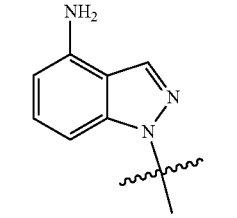 [SMILES: *n1ncc2c(N)cccc21] | 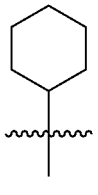 | 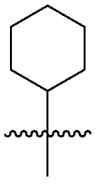 [SMILES: *C1CCCCC1] | H | O |
| 527 | 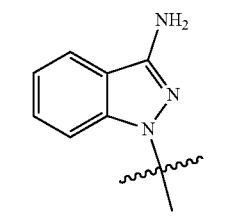 | 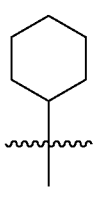 | 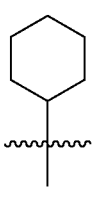 [SMILES: *C1CCCCC1] | H | O |
| 528 | 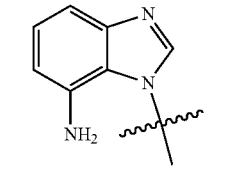 [SMILES: *n1cnc2cccc(N)c21] | 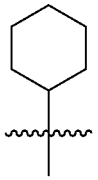 | 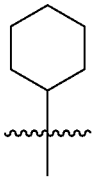 [SMILES: *C1CCCCC1] | H | O |
| 529 | 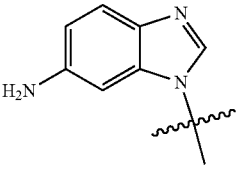 [SMILES: *n1cnc2ccc(N)cc21] | 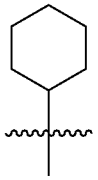 [SMILES: *C1CCCCC1] | 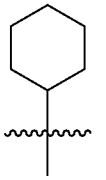 [SMILES: *C1CCCCC1] | H | O |
| 530 | 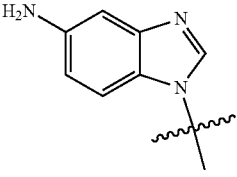 [SMILES: *n1cnc2cc(N)ccc21] | 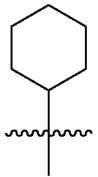 | 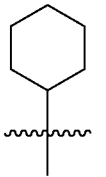 [SMILES: *C1CCCCC1] | H | O |

TABLE 1-continued

| Cmpd | W | X | Z | A | Q |
|---|---|---|---|---|---|
| 531 | 4-aminobenzimidazol-1-yl (NH₂ at 4-position) | cyclohexyl | cyclohexyl |  | O |
| 532 | 2-aminobenzimidazol-1-yl | cyclohexyl | cyclohexyl | H | O |
| 533 | 7-amino-pyrrolo[3,2-b]pyridin-1-yl | cyclohexyl | cyclohexyl | H | O |
| 534 | 6-amino-pyrrolo[3,2-b]pyridin-1-yl | cyclohexyl | cyclohexyl | H | O |
| 535 | 5-amino-pyrrolo[3,2-b]pyridin-1-yl | cyclohexyl | cyclohexyl | H | O |
| 536 | 3-amino-pyrrolo[3,2-b]pyridin-1-yl | cyclohexyl | cyclohexyl | H | O |
| 537 | 2-amino-pyrrolo[3,2-b]pyridin-1-yl | cyclohexyl | cyclohexyl | H | O |
| 538 | 7-amino-pyrrolo[2,3-c]pyridin-1-yl | cyclohexyl | cyclohexyl | H | O |

TABLE 1-continued
| Cmpd | W | X | Z | A | Q |
|---|---|---|---|---|---|
| 539 | 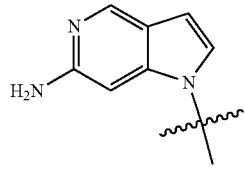 [SMILES: *n1ccc2cnc(N)cc21] | 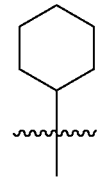 [SMILES: *C1CCCCC1] | 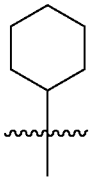 [SMILES: *C1CCCCC1] | H | O |
| 540 | 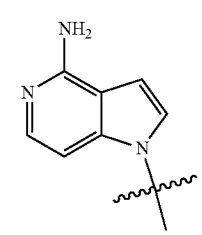 [SMILES: *n1ccc2c(N)nccc21] | 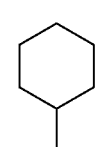 | 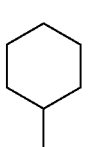 | H | O |
| 541 | 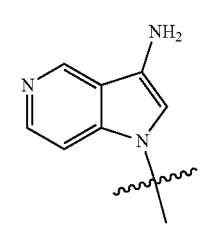 | 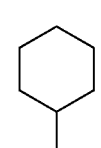 | 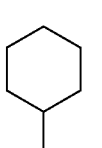 | H | O |
| 542 | 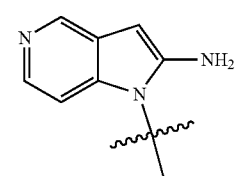 | 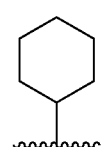 | 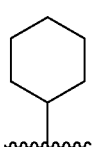 | H | O |
| 543 | 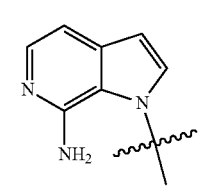 | 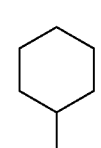 | 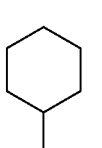 | H | O |
| 544 | 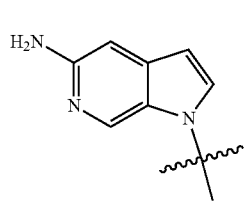 [SMILES: *n1ccc2cc(N)ncc21] | 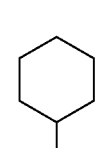 | 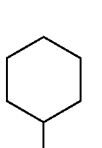 | H | O |
| 545 | 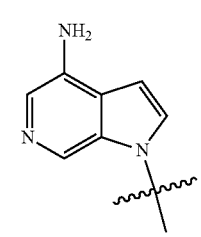 | 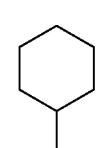 | 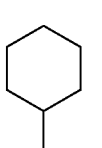 | H | O |

TABLE 1-continued
| Cmpd | W | X | Z | A | Q |
|---|---|---|---|---|---|
| 546 | 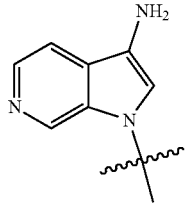 | 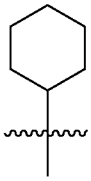 [SMILES: *C1CCCCC1] | 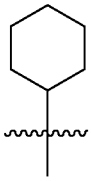 [SMILES: *C1CCCCC1] | H | O |
| 547 | 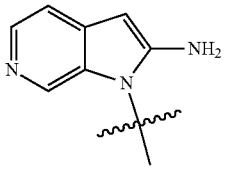 [SMILES: *n1c(N)cc2ccncc21] | 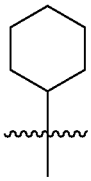 [SMILES: *C1CCCCC1] | 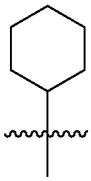 [SMILES: *C1CCCCC1] | H | O |
| 548 | 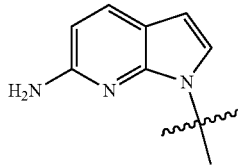 [SMILES: *n1ccc2ccc(N)nc21] | 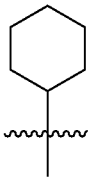 | 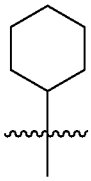 [SMILES: *C1CCCCC1] | H | O |
| 549 | 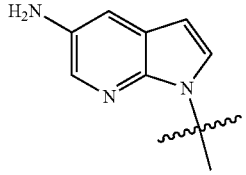 [SMILES: *n1ccc2cc(N)cnc21] | 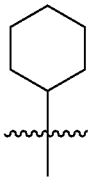 [SMILES: *C1CCCCC1] | 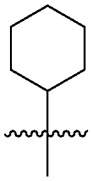 [SMILES: *C1CCCCC1] | H | O |
| 550 | 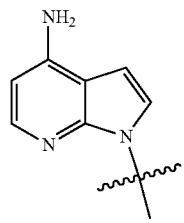 [SMILES: *n1ccc2c(N)ccnc21] | 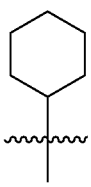 [SMILES: *C1CCCCC1] | 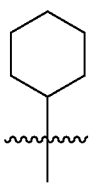 [SMILES: *C1CCCCC1] | H | O |
| 551 | 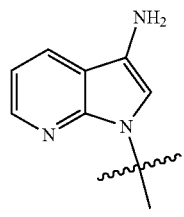 [SMILES: *n1cc(N)c2cccnc21] | 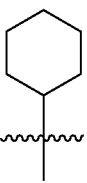 [SMILES: *C1CCCCC1] | 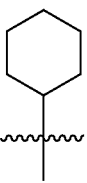 [SMILES: *C1CCCCC1] | H | O |
| 552 | 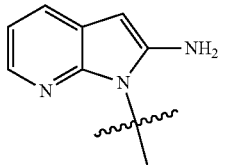 | 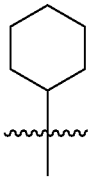 [SMILES: *C1CCCCC1] | 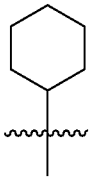 [SMILES: *C1CCCCC1] | H | O |

TABLE 1-continued
| Cmpd | W | X | Z | A | Q |
|---|---|---|---|---|---|
| 553 | 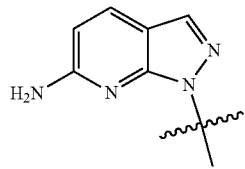 | 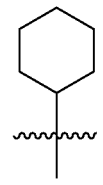 [SMILES: *C1CCCCC1] | 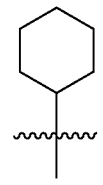 [SMILES: *C1CCCCC1] | H | O |
| 554 | 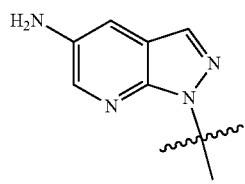 [SMILES: *n1ncc2cc(N)cnc21] | 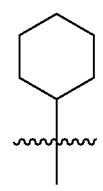 [SMILES: *C1CCCCC1] | 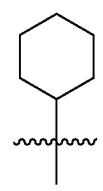 [SMILES: *C1CCCCC1] | H | O |
| 555 | 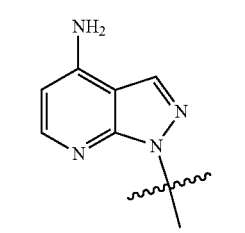 | 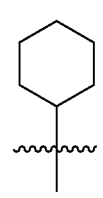 [SMILES: *C1CCCCC1] | 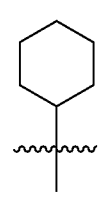 [SMILES: *C1CCCCC1] | H | O |
| 556 | 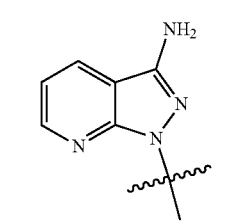 | 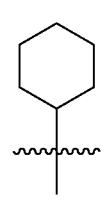 | 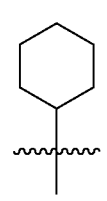 [SMILES: *C1CCCCC1] | H | O |
| 557 | 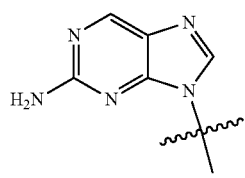 | 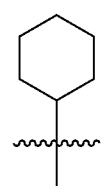 | 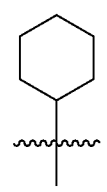 [SMILES: *C1CCCCC1] | H | O |
| 558 | 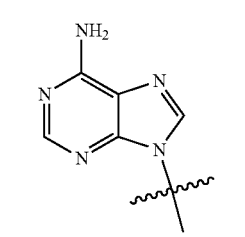 | 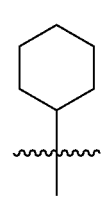 | 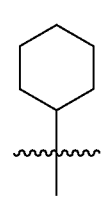 [SMILES: *C1CCCCC1] | H | O |
| 559 | 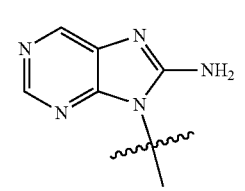 [SMILES: *n1c(N)nc2cncnc21] | 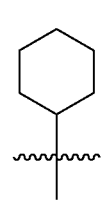 | 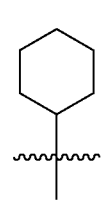 [SMILES: *C1CCCCC1] | H | O |

TABLE 1-continued
| Cmpd | W | X | Z | A | Q |
|---|---|---|---|---|---|
| 560 | 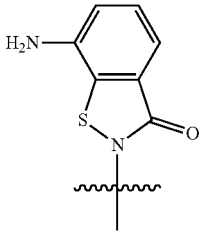 |  |  | H | O |
| 561 | 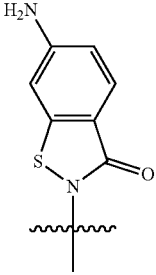 [SMILES: *n1sc2cc(N)ccc2c1=O] | 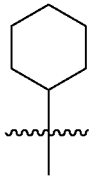 [SMILES: *C1CCCCC1] | 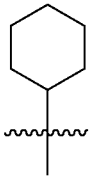 [SMILES: *C1CCCCC1] | H | O |
| 562 | 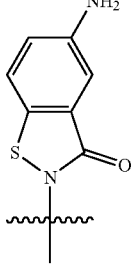 | 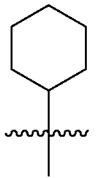 [SMILES: *C1CCCCC1] | 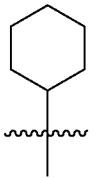 [SMILES: *C1CCCCC1] | H | O |
| 563 | 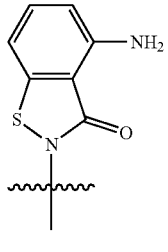 | 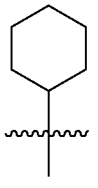 | 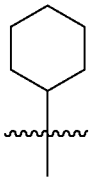 [SMILES: *C1CCCCC1] | H | O |
| 564 | 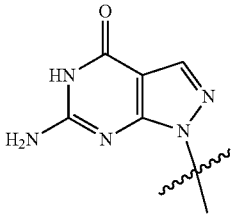 [SMILES: *n1ncc2c(=O)[nH]c(N)nc21] | 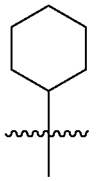 [SMILES: *C1CCCCC1] | 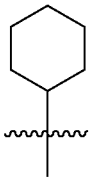 [SMILES: *C1CCCCC1] | H | O |
| 565 | 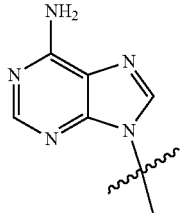 [SMILES: *n1cnc2c(N)ncnc21] | 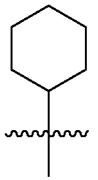 [SMILES: *C1CCCCC1] | 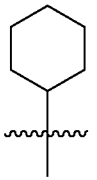 [SMILES: *C1CCCCC1] | H | O |

TABLE 1-continued

| Cmpd | W | X | Z | A | Q |
|---|---|---|---|---|---|
| 566 | decahydroisoquinoline with NH₂ and N-linker | cyclohexyl | cyclohexyl | H | O |
| 567 | decahydroisoquinoline with NH₂ and N-linker | cyclohexyl | cyclohexyl | H | O |
| 568 | decahydroisoquinoline with H₂N and N-linker | cyclohexyl | cyclohexyl | H | O |
| 569 | decahydroisoquinoline with H₂N and N-linker | cyclohexyl | cyclohexyl | H | O |
| 570 | decahydroisoquinoline with NH₂ and N-linker | cyclohexyl | cyclohexyl | H | O |
| 571 | decahydroisoquinoline with NH₂ and N-linker | cyclohexyl | cyclohexyl | H | O |
| 572 | decahydroisoquinoline with NH₂ and N-linker | cyclohexyl | cyclohexyl | H | O |
| 573 | decahydroquinoline with NH₂ and N-linker | cyclohexyl | cyclohexyl | H | O |

TABLE 1-continued
| Cmpd | W | X | Z | A | Q |
|---|---|---|---|---|---|
| 574 | 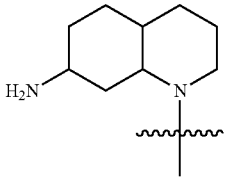 [SMILES: *N1CCCC2CCC(N)CC21] | 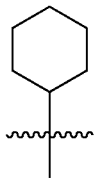 | 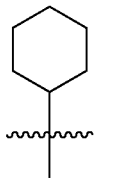 [SMILES: *C1CCCCC1] | H | O |
| 575 | 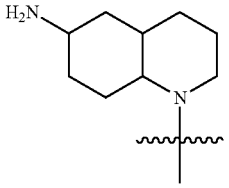 | 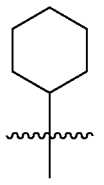 | 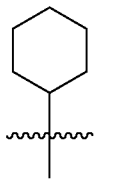 [SMILES: *C1CCCCC1] | H | O |
| 576 | 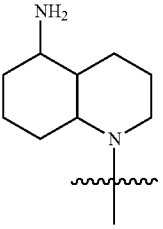 [SMILES: *N1CCCC2C(N)CCCC21] | 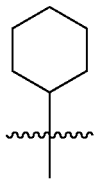 | 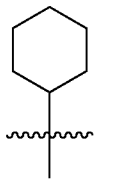 [SMILES: *C1CCCCC1] | H | O |
| 577 | 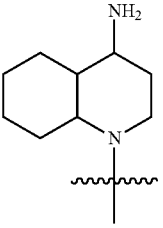 [SMILES: *N1CCC(N)C2CCCCC21] | 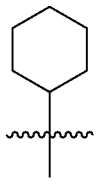 | 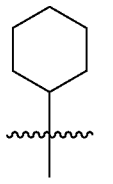 [SMILES: *C1CCCCC1] | H | O |
| 578 | 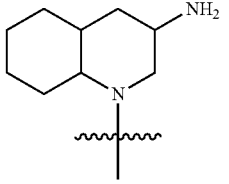 [SMILES: *N1CC(N)CC2CCCCC21] | 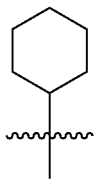 | 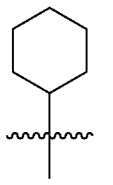 [SMILES: *C1CCCCC1] | H | O |
| 579 | 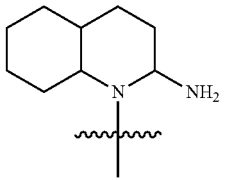 [SMILES: *N1C(N)CCC2CCCCC21] | 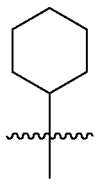 | 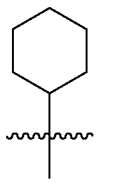 [SMILES: *C1CCCCC1] | H | O |
| 580 | 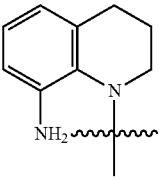 [SMILES: *N1CCCc2cccc(N)c21] | 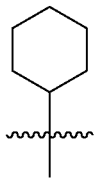 | 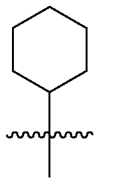 [SMILES: *C1CCCCC1] | H | O |

TABLE 1-continued
| Cmpd | W | X | Z | A | Q |
|---|---|---|---|---|---|
| 581 |  |  | 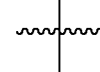 | H | O |
| 582 | 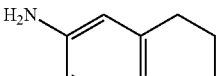 |  | 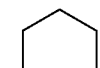 | H | O |
| 583 | 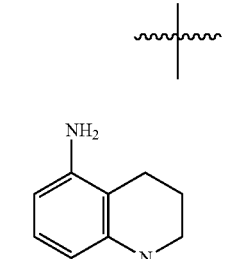 | 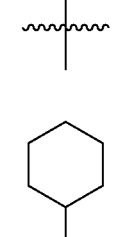 | 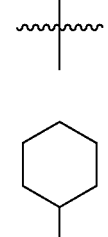 | H | O |
| 584 | 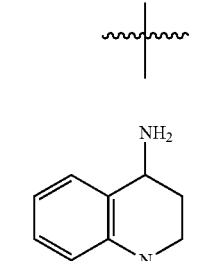 | 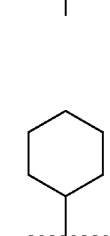 |  | H | O |
| 585 | 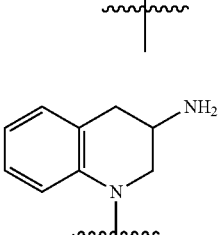 | 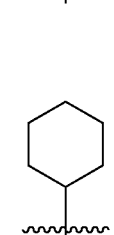 | 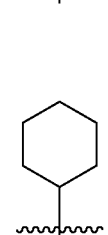 | H | O |
| 586 | 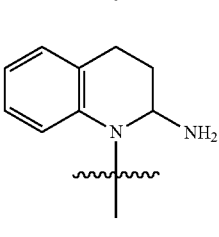 | 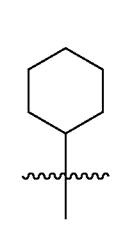 | 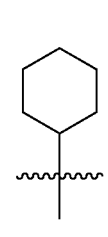 [SMILES: *C1CCCCC1] | H | O |
| 587 | 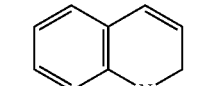 |  | 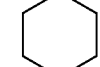 | H | O |

| Cmpd | W | X | Z | A | Q |
|---|---|---|---|---|---|
| 588 | 7-amino-2H-quinolin-1-yl | cyclohexyl | cyclohexyl | H | O |
| 589 | 6-amino-2H-quinolin-1-yl | cyclohexyl | cyclohexyl | H | O |
| 590 | 5-amino-2H-quinolin-1-yl | cyclohexyl | cyclohexyl | H | O |
| 591 | 4-amino-2H-quinolin-1-yl | cyclohexyl | cyclohexyl | H | O |
| 592 | 3-amino-2H-quinolin-1-yl | cyclohexyl | cyclohexyl | H | O |
| 593 | 2-amino-2H-quinolin-1-yl | cyclohexyl | cyclohexyl | H | O |
| 594 | 1-amino-1H-isoquinolin-2-yl | cyclohexyl | cyclohexyl | H | O |

TABLE 1-continued
| Cmpd | W | X | Z | A | Q |
|---|---|---|---|---|---|
| 595 | 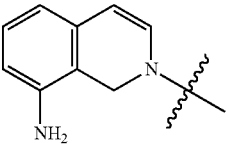 | 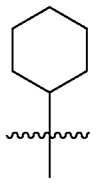 [SMILES: *C1CCCCC1] | 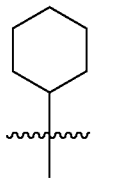 [SMILES: *C1CCCCC1] | H | O |
| 596 | 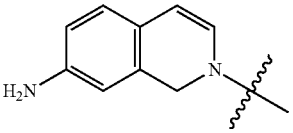 [SMILES: *N1C=Cc2ccc(N)cc2C1] | 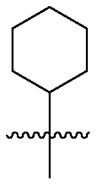 [SMILES: *C1CCCCC1] | 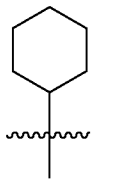 [SMILES: *C1CCCCC1] | H | O |
| 597 | 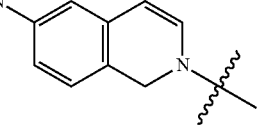 | 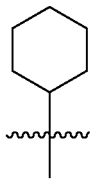 [SMILES: *C1CCCCC1] | 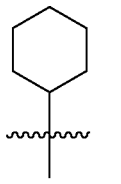 [SMILES: *C1CCCCC1] | H | O |
| 598 | 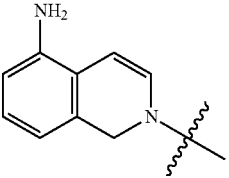 [SMILES: *N1C=Cc2c(N)cccc2C1] | 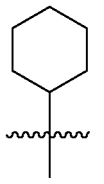 [SMILES: *C1CCCCC1] | 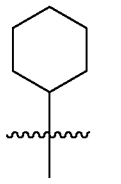 [SMILES: *C1CCCCC1] | H | O |
| 599 | 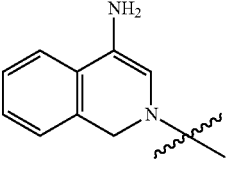 [SMILES: *N1C=C(N)c2ccccc2C1] | 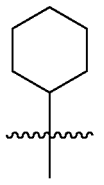 | 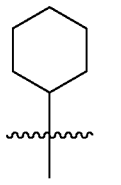 | H | O |
| 600 | 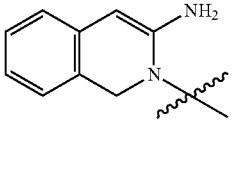 [SMILES: *N1Cc2ccccc2C=C1N] | 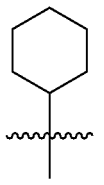 | 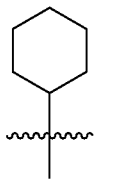 | H | O |
| 601 | 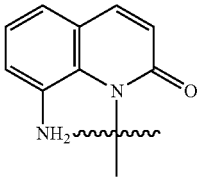 [SMILES: *n1c(=O)ccc2cccc(N)c21] | 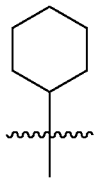 | 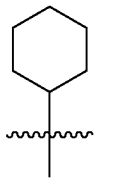 [SMILES: *C1CCCCC1] | H | O |
| 602 | 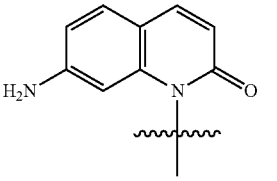 | 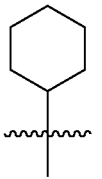 | 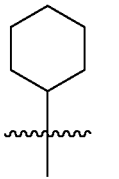 | H | O |

TABLE 1-continued
| Cmpd | W | X | Z | A | Q |
|---|---|---|---|---|---|
| 603 | 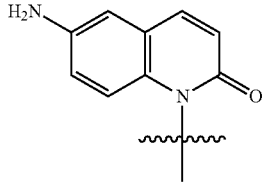 | 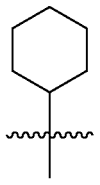 | 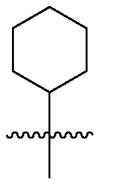 | H | O |
| 604 | 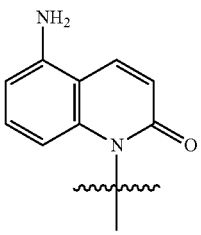 [SMILES: *n1c(=O)ccc2c(N)cccc21] | 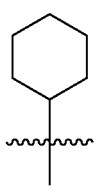 | 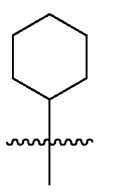 | H | O |
| 605 | 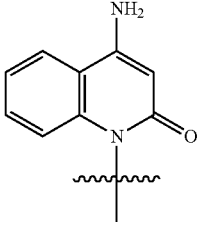 [SMILES: *n1c(=O)cc(N)c2ccccc21] | 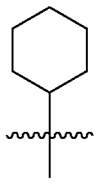 [SMILES: *C1CCCCC1] | 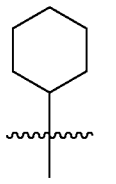 | H | O |
| 606 | 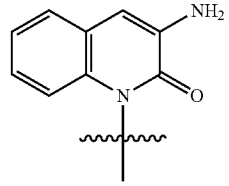 [SMILES: *n1c(=O)c(N)cc2ccccc21] | 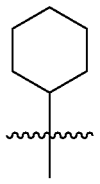 | 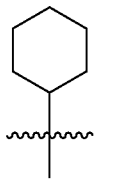 | H | O |
| 607 | 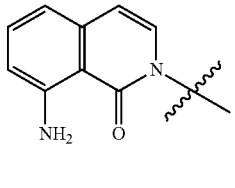 [SMILES: *n1ccc2cccc(N)c2c1=O] | 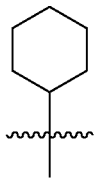 | 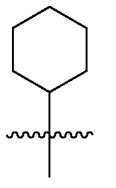 | H | O |
| 608 | 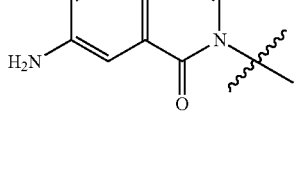 | 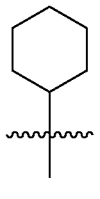 | 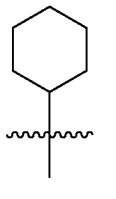 | H | O |
| 609 | 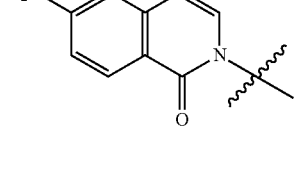 | 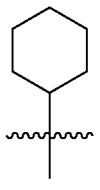 | 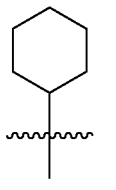 | H | O |

TABLE 1-continued
| Cmpd | W | X | Z | A | Q |
|---|---|---|---|---|---|
| 610 | 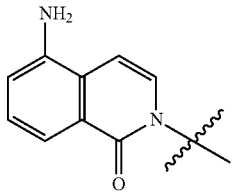 [SMILES: *n1ccc2c(N)cccc2c1=O] | 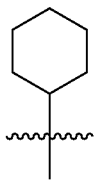 | 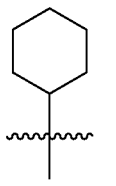 | H | O |
| 611 | 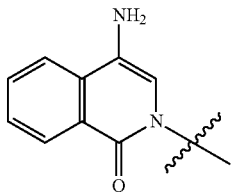 [SMILES: *n1cc(N)c2ccccc2c1=O] | 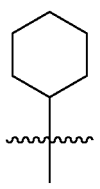 | 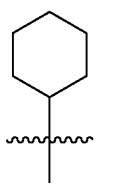 | H | O |
| 612 | 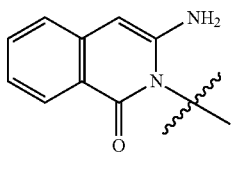 [SMILES: *n1c(N)cc2ccccc2c1=O] | 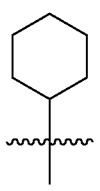 | 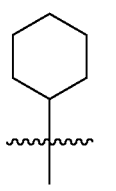 | H | O |
| 613 | 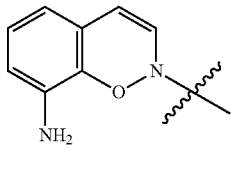 | 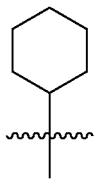 | 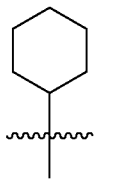 [SMILES: *C1CCCCC1] | H | O |
| 614 | 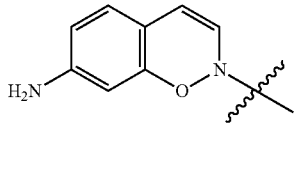 [SMILES: *N1C=Cc2ccc(N)cc2O1] | 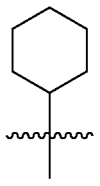 | 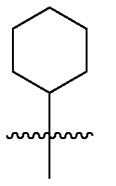 | H | O |
| 615 | 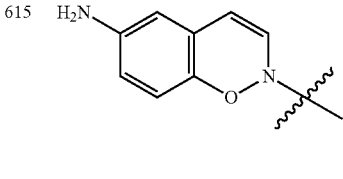 | 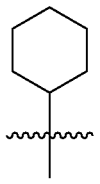 | 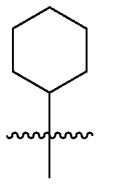 | H | O |
| 616 | 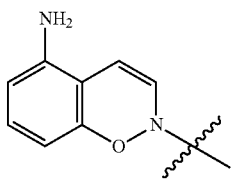 [SMILES: *N1C=Cc2c(N)cccc2O1] | 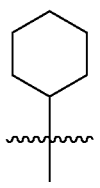 | 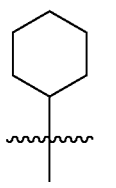 | H | O |
| 617 | 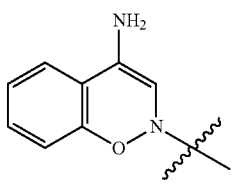 [SMILES: *N1C=C(N)c2ccccc2O1] | 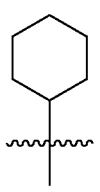 | 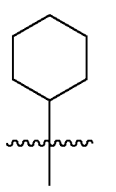 | H | O |

TABLE 1-continued

| Cmpd | W | X | Z | A | Q |
|---|---|---|---|---|---|
| 618 | benzoxazine-3-amine | cyclohexyl | cyclohexyl | H | O |
| 619 | 1-amino-carbazol-9-yl | cyclohexyl | cyclohexyl | H | O |
| 620 | 2-amino-carbazol-9-yl | cyclohexyl | cyclohexyl | H | O |
| 621 | 1-amino-phenoxazin-10-yl | cyclohexyl | cyclohexyl | H | O |
| 622 | 2-amino-phenoxazin-10-yl | cyclohexyl | cyclohexyl | H | O |
| 623 | 1-amino-phenothiazin-10-yl | cyclohexyl | cyclohexyl | H | O |
| 624 | 2-amino-phenothiazin-10-yl | cyclohexyl | cyclohexyl | H | O |
| 625 | amino-adamantyl-azetidinyl | cyclohexyl | cyclohexyl | H | O |

TABLE 1-continued
| Cmpd | W | X | Z | A | Q |
|---|---|---|---|---|---|
| 626 | 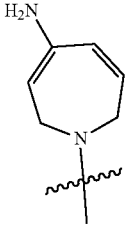 | 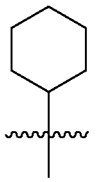 [SMILES: *C1CCCCC1] | 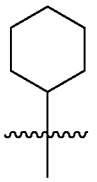 | H | O |
| 627 | 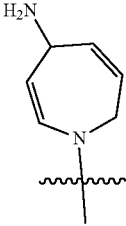 | 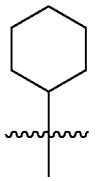 [SMILES: *C1CCCCC1] | 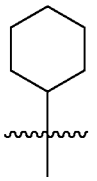 | H | O |
| 628 | 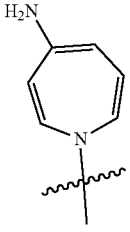 | 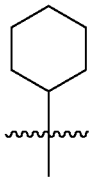 [SMILES: *C1CCCCC1] | 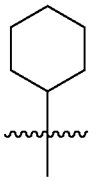 | H | O |
| 629 | 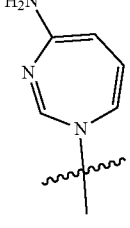 | 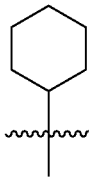 [SMILES: *C1CCCCC1] | 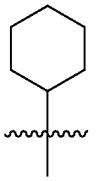 | H | O |
| 630 | 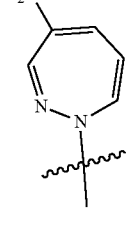 | 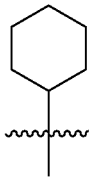 [SMILES: *C1CCCCC1] | 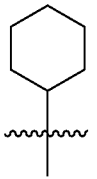 | H | O |
| 631 | 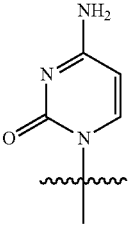 [SMILES: *n1ccc(N)nc1=O] | 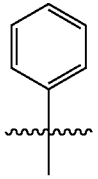 |  | H | O |

TABLE 1-continued
| Cmpd | W | X | Z | A | Q |
|---|---|---|---|---|---|
| 632 | 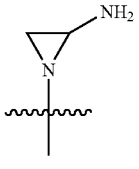 [SMILES: *N1CC1N] | 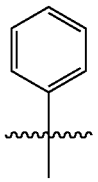 | 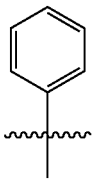 | H | O |
| 633 | 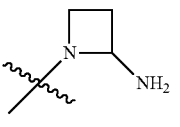 | 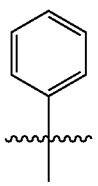 [SMILES: *c1ccccc1] | 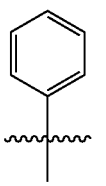 | H | O |
| 634 | 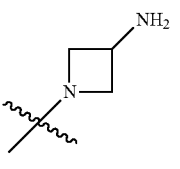 [SMILES: *N1CC(N)C1] | 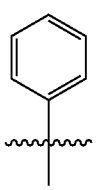 [SMILES: *c1ccccc1] | 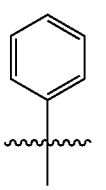 | H | O |
| 635 | 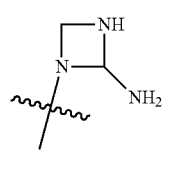 | 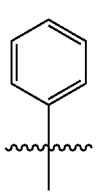 | 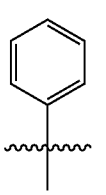 | H | O |
| 636 | 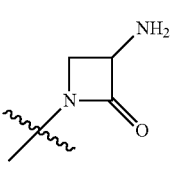 | 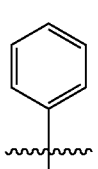 | 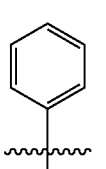 | H | O |
| 637 | 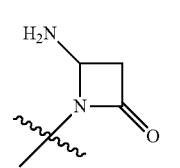 [SMILES: *N1C(=O)CC1N] | 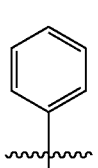 | 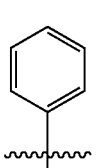 | H | O |
| 638 | 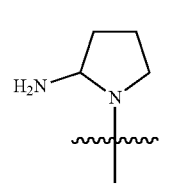 | 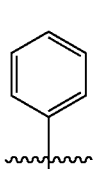 | 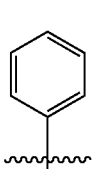 | H | O |
| 639 | 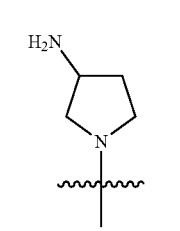 [SMILES: *N1CCC(N)C1] | 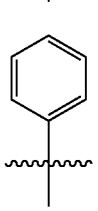 | 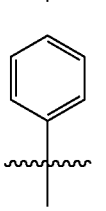 | H | O |

TABLE 1-continued
| Cmpd | W | X | Z | A | Q |
|---|---|---|---|---|---|
| 640 | 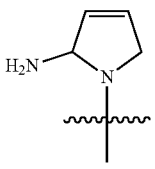 | 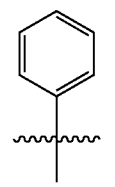 | 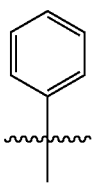 | H | O |
| 641 | 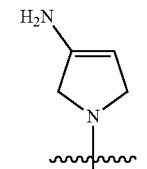 | 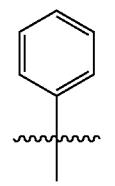 | 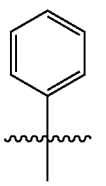 | H | O |
| 642 | 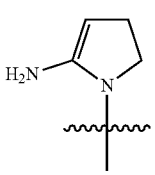 | 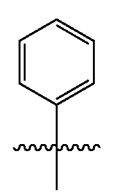 | 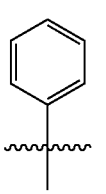 | H | O |
| 643 | 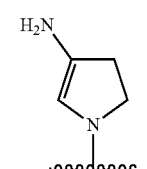 | 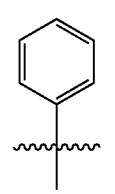 [SMILES: *c1ccccc1] | 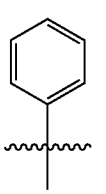 | H | O |
| 644 | 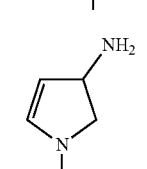 | 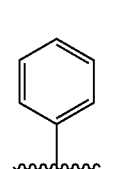 | 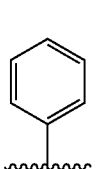 | H | O |
| 645 | 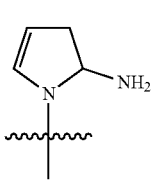 [SMILES: *N1C=CCC1N] | 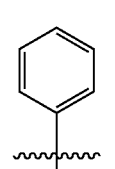 | 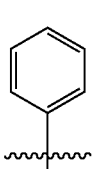 | H | O |
| 646 | 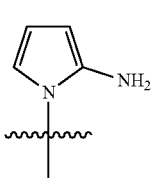 [SMILES: *n1cccc1N] | 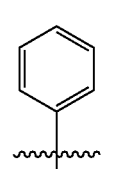 | 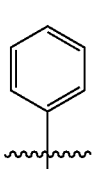 | H | O |
| 647 | 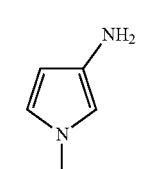 | 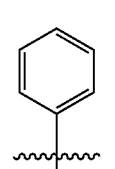 | 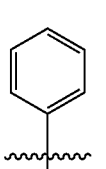 | H | O |

TABLE 1-continued

| Cmpd | W | X | Z | A | Q |
|---|---|---|---|---|---|
| 648 | 3-amino-pyrazolidin-1-yl | phenyl | phenyl | H | O |
| 649 | 4-amino-pyrazolidin-1-yl | phenyl | phenyl | H | O |
| 650 | 5-amino-pyrazolidin-1-yl | phenyl | phenyl | H | O |
| 651 | 4-amino-imidazolidin-1-yl | phenyl | phenyl | H | O |
| 652 | 5-amino-imidazolidin-1-yl | phenyl | phenyl | H | O |
| 653 | 2-amino-imidazolidin-1-yl | phenyl | phenyl | H | O |
| 654 | 3-amino-4,5-dihydro-pyrazol-1-yl | phenyl | phenyl | H | O |

TABLE 1-continued
| Cmpd | W | X | Z | A | Q |
|---|---|---|---|---|---|
| 655 | 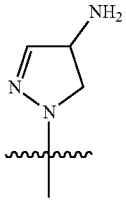 | 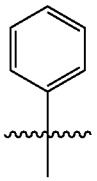 | 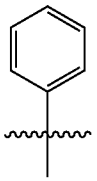 | H | O |
| 656 | 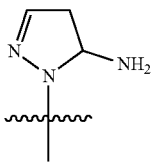 | 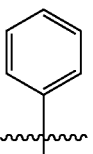 | 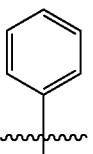 | H | O |
| 657 | 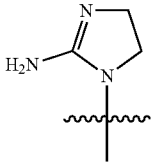 | 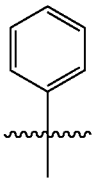 [SMILES: *c1ccccc1] | 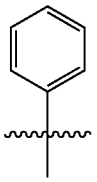 | H | O |
| 658 | 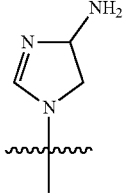 | 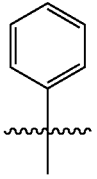 | 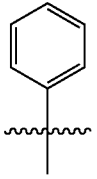 | H | O |
| 659 | 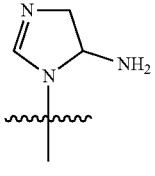 | 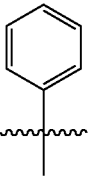 | 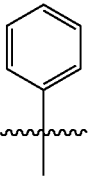 | H | O |
| 660 | 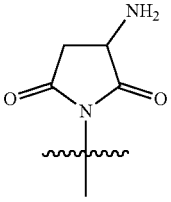 [SMILES: *N1C(=O)CC(N)C1=O] | 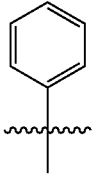 | 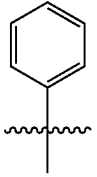 | H | O |
| 661 | 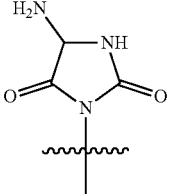 | 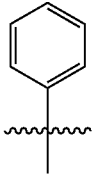 | 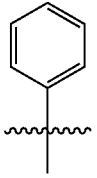 | H | O |

TABLE 1-continued
| Cmpd | W | X | Z | A | Q |
|---|---|---|---|---|---|
| 662 | 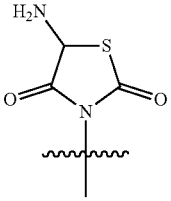 | 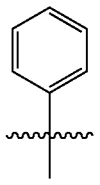 | 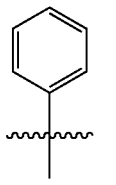 | H | O |
| 663 | 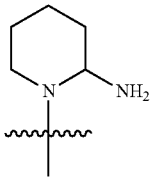 [SMILES: *N1CCCCC1N] | 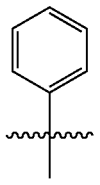 | 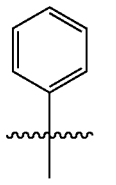 | H | O |
| 664 | 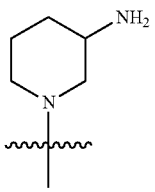 | 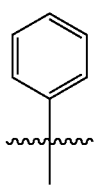 | 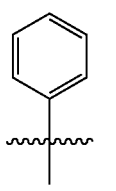 | H | O |
| 665 | 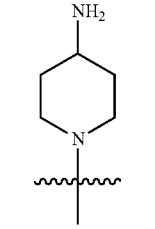 | 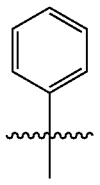 [SMILES: *c1ccccc1] | 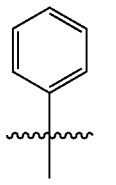 | H | O |
| 666 | 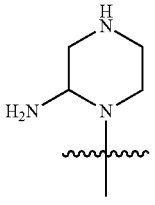 [SMILES: *N1CCNCC1N] | 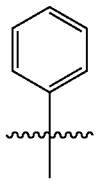 | 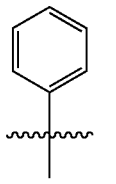 | H | O |
| 667 | 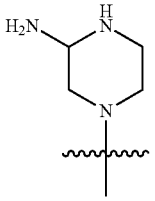 [SMILES: *N1CCNC(N)C1] | 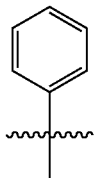 | 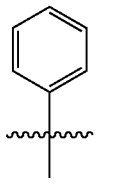 | H | O |
| 668 | 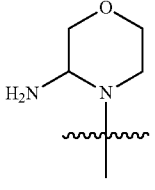 | 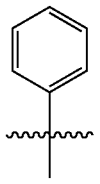 | 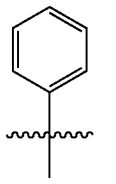 | H | O |

| Cmpd | W | X | Z | A | Q |
|---|---|---|---|---|---|
| 669 | 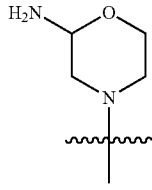 [SMILES: *N1CCOC(N)C1] | 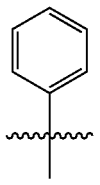 [SMILES: *c1ccccc1] | 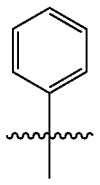 | H | O |
| 670 | 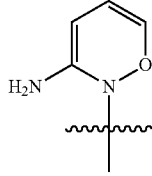 [SMILES: *N1OC=CC=C1N] | 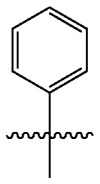 | 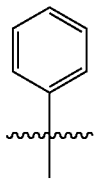 | H | O |
| 671 | 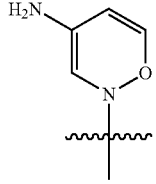 [SMILES: *N1C=C(N)C=CO1] | 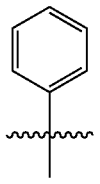 | 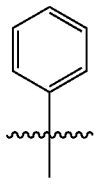 | H | O |
| 672 | 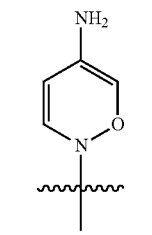 | 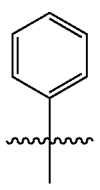 | 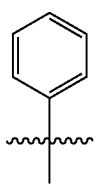 | H | O |
| 673 | 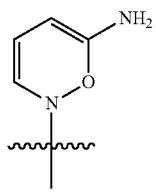 [SMILES: *N1C=CC=C(N)O1] | 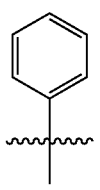 | 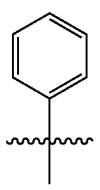 | H | O |
| 674 | 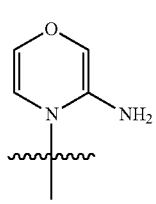 [SMILES: *N1C=COC=C1N] | 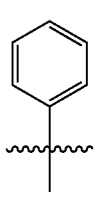 [SMILES: *c1ccccc1] | 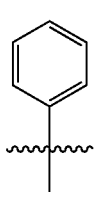 | H | O |
| 675 | 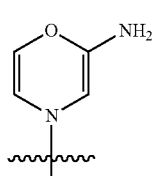 | 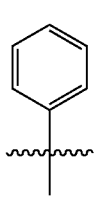 | 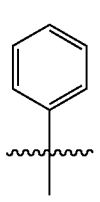 | H | O |
| 676 | 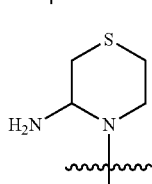 | 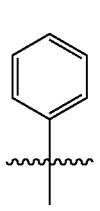 | 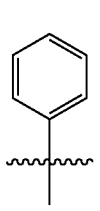 | H | O |

TABLE 1-continued

| Cmpd | W | X | Z | A | Q |
|---|---|---|---|---|---|
| 677 | 2-amino-thiomorpholin-4-yl | phenyl | phenyl | H | O |
| 678 | 3-amino-2H-1,2-thiazin-2-yl | phenyl | phenyl | H | O |
| 679 | 4-amino-2H-1,2-thiazin-2-yl | phenyl | phenyl | H | O |
| 680 | 5-amino-2H-1,2-thiazin-2-yl | phenyl | phenyl | H | O |
| 681 | 6-amino-2H-1,2-thiazin-2-yl | phenyl | phenyl | H | O |
| 682 | 3-amino-4H-1,4-thiazin-4-yl | phenyl | phenyl | H | O |
| 683 | 2-amino-4H-1,4-thiazin-4-yl | phenyl | phenyl | H | O |

TABLE 1-continued
| Cmpd | W | X | Z | A | Q |
|---|---|---|---|---|---|
| 684 | 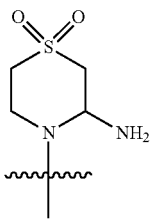 [SMILES: *N1CCS(=O)(=O)CC1N] | 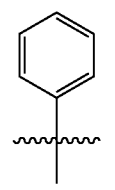 |  | H | O |
| 685 | 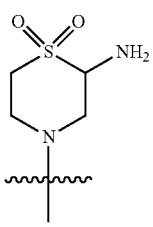 [SMILES: *N1CCS(=O)(=O)C(N)C1] | 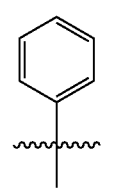 |  | H | O |
| 686 | 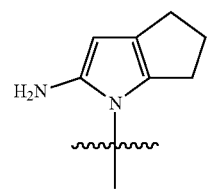 | 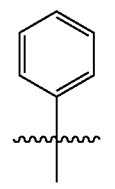 |  | H | O |
| 687 | 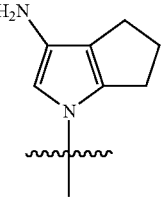 | 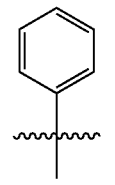 |  | H | O |
| 688 | 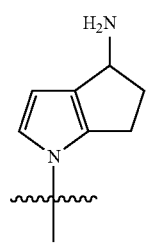 [SMILES: *n1ccc2c1CCC2N] | 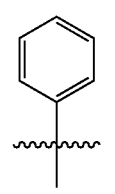 |  | H | O |
| 689 | 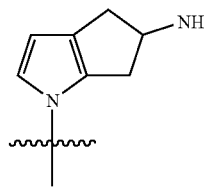 | 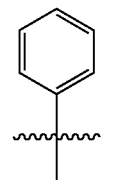 |  | H | O |
| 690 | 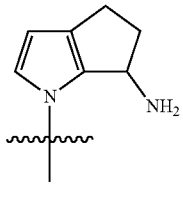 [SMILES: *n1ccc2c1C(N)CC2] | 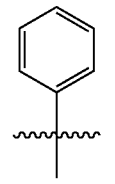 |  | H | O |

TABLE 1-continued
| Cmpd | W | X | Z | A | Q |
|---|---|---|---|---|---|
| 691 | 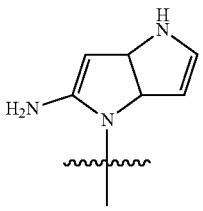 [SMILES: *N1C(N)=CC2NC=CC21] | 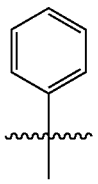 | 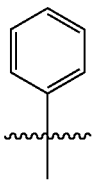 | H | O |
| 692 | 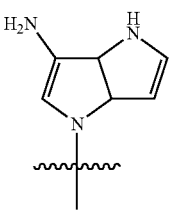 [SMILES: *N1C=C(N)C2NC=CC21] | 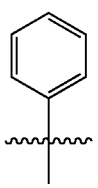 | 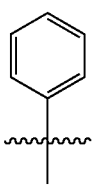 | H | O |
| 693 | 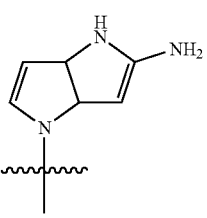 [SMILES: *N1C=CC2NC(N)=CC21] | 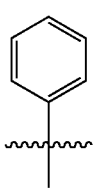 | 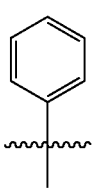 | H | O |
| 694 | 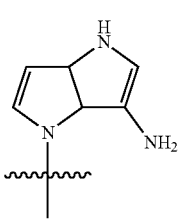 [SMILES: *N1C=CC2NC=C(N)C21] | 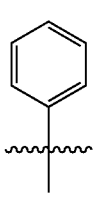 | 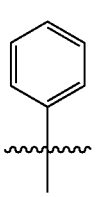 | H | O |
| 695 | 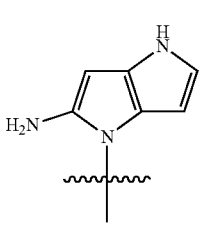 [SMILES: *n1c(N)cc2[nH]ccc21] | 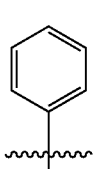 | 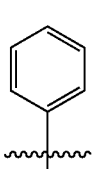 | H | O |
| 696 | 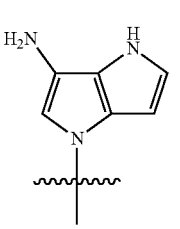 [SMILES: *n1cc(N)c2[nH]ccc21] | 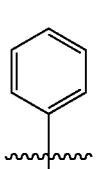 | 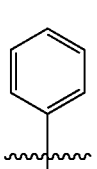 | H | O |
| 697 | 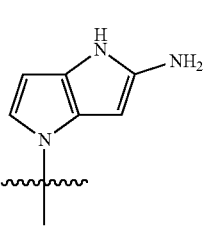 [SMILES: *n1ccc2[nH]c(N)cc21] | 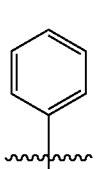 | 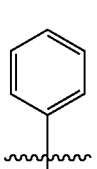 | H | O |

TABLE 1-continued

| Cmpd | W | X | Z | A | Q |
|---|---|---|---|---|---|
| 698 | pyrrolo-pyrrole with NH and NH₂ | phenyl | phenyl | H | O |
| 699 | pyrrolo-pyrrole with H₂N and NH | phenyl | phenyl | H | O |
| 700 | pyrrolo-pyrrole with H₂N and NH | phenyl | phenyl | H | O |
| 701 | pyrrolo-pyrrole with H₂N and NH | phenyl | phenyl | H | O |
| 702 | pyrrolo-pyrrole with NH₂ and NH | phenyl | phenyl | H | O |
| 703 | pyrrolo-furan with H₂N and O | phenyl | phenyl | H | O |
| 704 | pyrrolo-furan with H₂N and O | phenyl | phenyl | H | O |

TABLE 1-continued
| Cmpd | W | X | Z | A | Q |
|---|---|---|---|---|---|
| 705 | 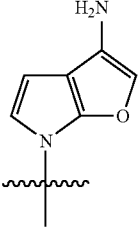 [SMILES: *n1ccc2c(N)coc21] | 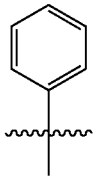 | 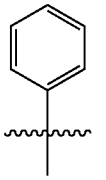 | H | O |
| 706 | 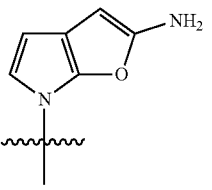 [SMILES: *n1ccc2cc(N)oc21] | 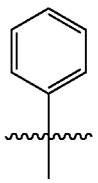 | 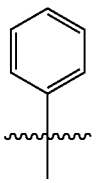 | H | O |
| 707 | 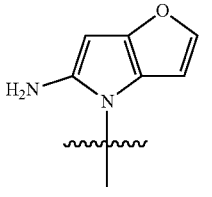 | 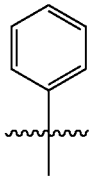 | 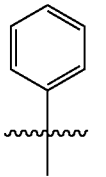 | H | O |
| 708 | 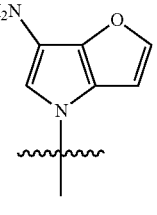 | 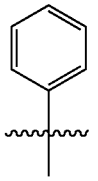 | 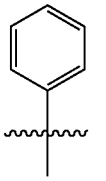 | H | O |
| 709 | 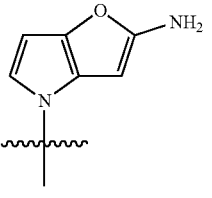 [SMILES: *n1ccc2oc(N)cc21] | 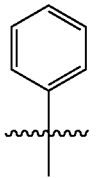 | 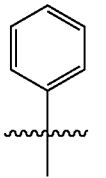 | H | O |
| 710 | 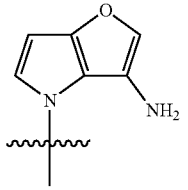 | 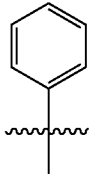 | 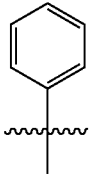 | H | O |
| 711 | 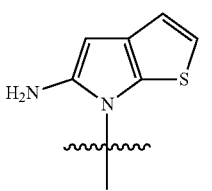 | 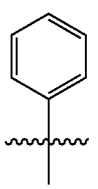 | 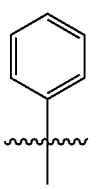 | H | O |

TABLE 1-continued

| Cmpd | W | X | Z | A | Q |
|---|---|---|---|---|---|
| 712 | 4-amino-7H-thieno[2,3-b]pyrrol-7-yl | phenyl | phenyl | H | O |
| 713 | 3-amino-4H-thieno[3,2-b]pyrrol-4-yl | phenyl | phenyl | H | O |
| 714 | 2-amino-4H-thieno[3,2-b]pyrrol-4-yl | phenyl | phenyl | H | O |
| 715 | 5-amino-4H-thieno[3,2-b]pyrrol-4-yl | phenyl | phenyl | H | O |
| 716 | 5-amino-4H-thieno[2,3-b]pyrrol-4-yl | phenyl | phenyl | H | O |
| 717 | 2-amino-4H-thieno[3,2-b]pyrrol-4-yl | phenyl | phenyl | H | O |
| 718 | 3-amino-4H-thieno[3,2-b]pyrrol-4-yl | phenyl | phenyl | H | O |

TABLE 1-continued
| Cmpd | W | X | Z | A | Q |
|---|---|---|---|---|---|
| 719 | 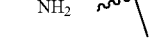 |  |  | H | O |
| 720 | 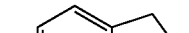 |  |  | H | O |
| 721 | 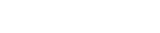 |  |  | H | O |
| 722 | 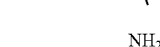 |  |  | H | O |
| 723 | 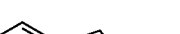 |  |  | H | O |
| 724 | 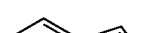 |  |  | H | O |
| 725 | 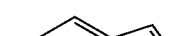 |  |  | H | O |
| 726 | 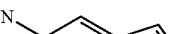 |  |  | H | O |

TABLE 1-continued

| Cmpd | W | X | Z | A | Q |
|---|---|---|---|---|---|
| 727 | 4-amino-indol-1-yl | phenyl | phenyl | H | O |
| 728 | 3-amino-indol-1-yl | phenyl | phenyl | H | O |
| 729 | 2-amino-indol-1-yl | phenyl | phenyl | H | O |
| 730 | 1-amino-isoindol-2-yl | phenyl | phenyl | H | O |
| 731 | 7-amino-isoindol-2-yl | phenyl | phenyl | H | O |
| 732 | 2-amino-isoindol-5-yl | phenyl | phenyl | H | O |
| 733 | 7-amino-indazol-1-yl | phenyl | phenyl | H | O |

TABLE 1-continued

| Cmpd | W | X | Z | A | Q |
|------|---|---|---|---|---|
| 734 | 6-aminoindazol-1-yl | phenyl | phenyl | H | O |
| 735 | 5-aminoindazol-1-yl | phenyl | phenyl | H | O |
| 736 | 4-aminoindazol-1-yl | phenyl | phenyl | H | O |
| 737 | 3-aminoindazol-1-yl | phenyl | phenyl | H | O |
| 738 | 7-aminobenzimidazol-1-yl | phenyl | phenyl | H | O |
| 739 | 6-aminobenzimidazol-1-yl | phenyl | phenyl | H | O |
| 740 | 5-aminobenzimidazol-1-yl | phenyl | phenyl | H | O |

TABLE 1-continued

| Cmpd | W | X | Z | A | Q |
|---|---|---|---|---|---|
| 741 | 4-aminobenzimidazol-1-yl (methyl linker) | phenyl | phenyl | | O |
| 742 | 2-aminobenzimidazol-1-yl (methyl linker) | phenyl | phenyl | H | O |
| 743 | 7-amino-pyrrolo[3,2-b]pyridin-1-yl (methyl linker) | phenyl | phenyl | H | O |
| 744 | 6-amino-pyrrolo[3,2-b]pyridin-1-yl (methyl linker) | phenyl | phenyl | H | O |
| 745 | 5-amino-pyrrolo[3,2-b]pyridin-1-yl (methyl linker) | phenyl | phenyl | H | O |
| 746 | 3-amino-pyrrolo[3,2-b]pyridin-1-yl (methyl linker) | phenyl | phenyl | H | O |
| 747 | 2-amino-pyrrolo[3,2-b]pyridin-1-yl (methyl linker) | phenyl | phenyl | H | O |
| 748 | 7-amino-pyrrolo[3,2-c]pyridin-1-yl (methyl linker) | phenyl | phenyl | H | O |

TABLE 1-continued

| Cmpd | W | X | Z | A | Q |
|---|---|---|---|---|---|
| 749 | 6-amino-1H-pyrrolo[3,2-c]pyridin-1-yl | phenyl | phenyl | H | O |
| 750 | 4-amino-1H-pyrrolo[3,2-c]pyridin-1-yl | phenyl | phenyl | H | O |
| 751 | 3-amino-1H-pyrrolo[3,2-c]pyridin-1-yl | phenyl | phenyl | H | O |
| 752 | 2-amino-1H-pyrrolo[3,2-c]pyridin-1-yl | phenyl | phenyl | H | O |
| 753 | 7-amino-1H-pyrrolo[2,3-c]pyridin-1-yl | phenyl | phenyl | H | O |
| 754 | 5-amino-1H-pyrrolo[2,3-c]pyridin-1-yl | phenyl | phenyl | H | O |
| 755 | 4-amino-1H-pyrrolo[2,3-c]pyridin-1-yl | phenyl | phenyl | H | O |

TABLE 1-continued

| Cmpd | W | X | Z | A | Q |
|---|---|---|---|---|---|
| 756 | 3-amino-1H-pyrrolo[3,2-c]pyridine (N1-linked) | phenyl | phenyl | H | O |
| 757 | 2-amino-1H-pyrrolo[3,2-c]pyridine (N1-linked) | phenyl | phenyl | H | O |
| 758 | 6-amino-1H-pyrrolo[2,3-b]pyridine (N1-linked) | phenyl | phenyl | H | O |
| 759 | 5-amino-1H-pyrrolo[2,3-b]pyridine (N1-linked) | phenyl | phenyl | H | O |
| 760 | 4-amino-1H-pyrrolo[2,3-b]pyridine (N1-linked) | phenyl | phenyl | H | O |
| 761 | 3-amino-1H-pyrrolo[2,3-b]pyridine (N1-linked) | phenyl | phenyl | H | O |
| 762 | 2-amino-1H-pyrrolo[2,3-b]pyridine (N1-linked) | phenyl | phenyl | H | O |

TABLE 1-continued
| Cmpd | W | X | Z | A | Q |
|---|---|---|---|---|---|
| 763 |  | 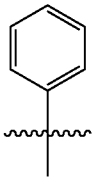 [SMILES: *c1ccccc1] | 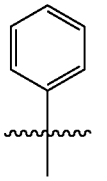 | H | O |
| 764 | 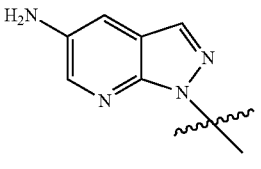 [SMILES: *n1ncc2cc(N)cnc21] | 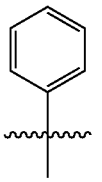 | 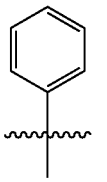 | H | O |
| 765 | 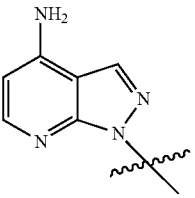 [SMILES: *n1ncc2c(N)ccnc21] | 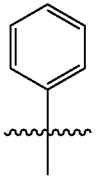 | 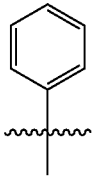 | H | O |
| 766 | 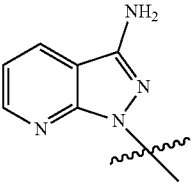 [SMILES: *n1nc(N)c2cccnc21] | 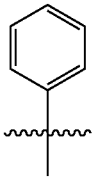 | 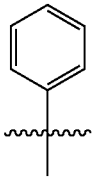 | H | O |
| 767 | 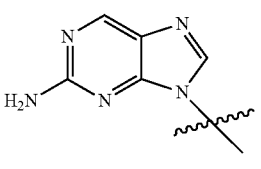 [SMILES: *n1cnc2cnc(N)nc21] | 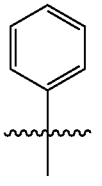 [SMILES: *c1ccccc1] | 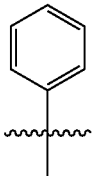 | H | O |
| 768 | 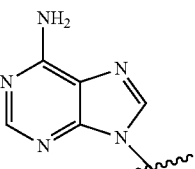 | 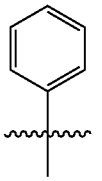 [SMILES: *c1ccccc1] | 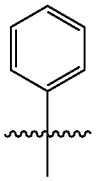 | H | O |
| 769 | 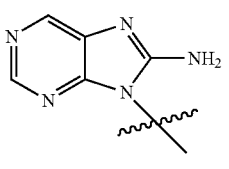 [SMILES: *n1c(N)nc2cncnc21] | 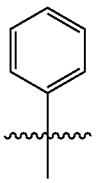 | 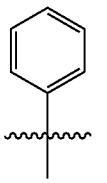 | H | O |

US 11,795,192 B2
231                                                                                   232
TABLE 1-continued
| Cmpd | W | X | Z | A | Q |
|---|---|---|---|---|---|
| 770 | 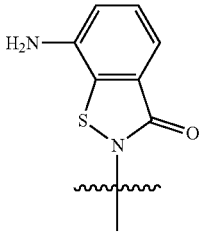 | 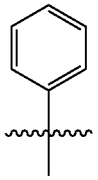 [SMILES: *c1ccccc1] | 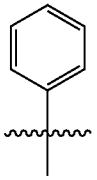 | H | O |
| 771 | 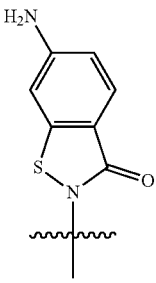 | 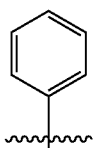 | 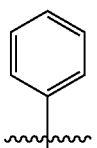 | H | O |
| 772 | 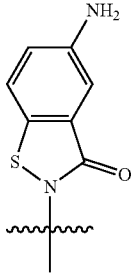 [SMILES: *n1sc2ccc(N)cc2c1=O] | 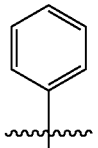 | 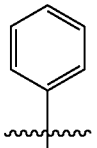 | H | O |
| 773 | 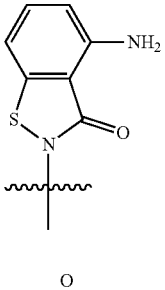 | 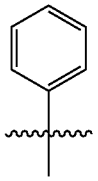 | 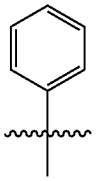 | H | O |
| 774 | 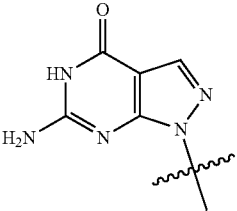 [SMILES: *n1ncc2c(=O)[nH]c(N)nc21] | 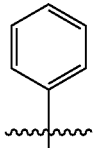 | 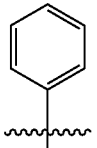 | H | O |
| 775 | 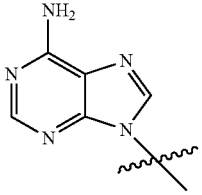 [SMILES: *n1cnc2c(N)ncnc21] | 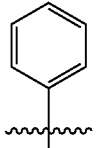 | 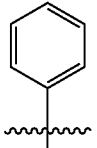 | H | O |

TABLE 1-continued

| Cmpd | W | X | Z | A | Q |
|---|---|---|---|---|---|
| 776 | decahydroisoquinoline with NH₂ at 1-position, N-linked | phenyl | phenyl | H | O |
| 777 | decahydroisoquinoline with NH₂ at 8-position, N-linked | phenyl | phenyl | H | O |
| 778 | decahydroisoquinoline with H₂N at 7-position, N-linked | phenyl | phenyl | H | O |
| 779 | decahydroisoquinoline with H₂N at 6-position, N-linked | phenyl | phenyl | H | O |
| 780 | decahydroisoquinoline with NH₂ at 5-position, N-linked | phenyl | phenyl | H | O |
| 781 | decahydroisoquinoline with NH₂ at 4-position, N-linked | phenyl | phenyl | H | O |
| 782 | decahydroisoquinoline with NH₂ at 3-position, N-linked | phenyl | phenyl | H | O |
| 783 | decahydroquinoline with NH₂ at 8-position, N-linked | phenyl | phenyl | H | O |

TABLE 1-continued
| Cmpd | W | X | Z | A | Q |
|------|---|---|---|---|---|
| 784 | 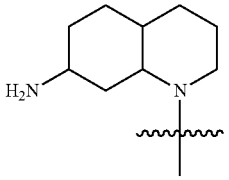 [SMILES: *N1CCCC2CCC(N)CC21] | 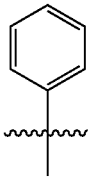 [SMILES: *c1ccccc1] | 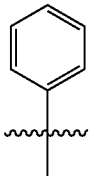 | H | O |
| 785 | 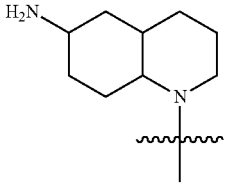 [SMILES: *N1CCCC2CC(N)CCC21] | 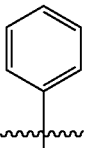 | 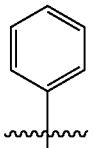 | H | O |
| 786 | 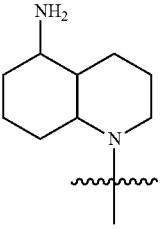 [SMILES: *N1CCCC2C(N)CCCC21] | 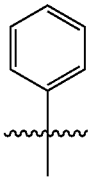 [SMILES: *c1ccccc1] | 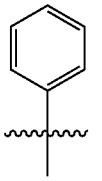 | H | O |
| 787 | 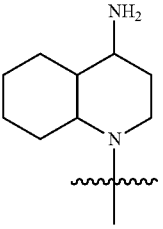 [SMILES: *N1CCC(N)C2CCCCC21] | 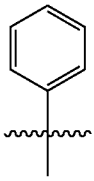 | 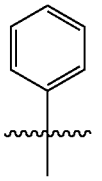 | H | O |
| 788 | 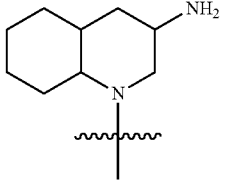 [SMILES: *N1CC(N)CC2CCCCC21] | 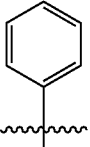 | 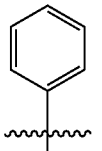 | H | O |
| 789 | 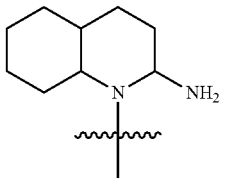 [SMILES: *N1C(N)CCC2CCCCC21] | 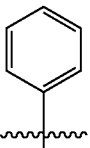 | 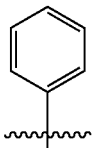 | H | O |
| 790 | 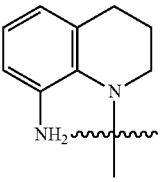 [SMILES: *N1CCCc2cccc(N)c21] | 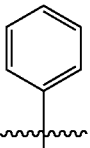 | 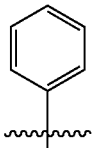 | H | O |

TABLE 1-continued

| Cmpd | W | X | Z | A | Q |
|---|---|---|---|---|---|
| 791 | 7-amino-1,2,3,4-tetrahydroquinolin-1-yl | phenyl | phenyl | H | O |
| 792 | 6-amino-1,2,3,4-tetrahydroquinolin-1-yl | phenyl | phenyl | H | O |
| 793 | 5-amino-1,2,3,4-tetrahydroquinolin-1-yl | phenyl | phenyl | H | O |
| 794 | 4-amino-1,2,3,4-tetrahydroquinolin-1-yl | phenyl | phenyl | H | O |
| 795 | 3-amino-1,2,3,4-tetrahydroquinolin-1-yl | phenyl | phenyl | H | O |
| 796 | 2-amino-1,2,3,4-tetrahydroquinolin-1-yl | phenyl | phenyl | H | O |
| 797 | 8-amino-2H-quinolin-1-yl | phenyl | phenyl | H | O |

TABLE 1-continued

| Cmpd | W | X | Z | A | Q |
|---|---|---|---|---|---|
| 798 | 7-amino-1,2-dihydroquinolin-1-yl | phenyl | phenyl | H | O |
| 799 | 6-amino-1,2-dihydroquinolin-1-yl | phenyl | phenyl | H | O |
| 800 | 5-amino-1,2-dihydroquinolin-1-yl | phenyl | phenyl | H | O |
| 801 | 4-amino-1,2-dihydroquinolin-1-yl | phenyl | phenyl | H | O |
| 802 | 3-amino-1,2-dihydroquinolin-1-yl | phenyl | phenyl | H | O |
| 803 | 2-amino-1,2-dihydroquinolin-1-yl | phenyl | phenyl | H | O |
| 804 | 1-amino-1,2-dihydroisoquinolin-2-yl | phenyl | phenyl | H | O |

TABLE 1-continued
| Cmpd | W | X | Z | A | Q |
|---|---|---|---|---|---|
| 805 |  |  |  | H | O |
| 806 | 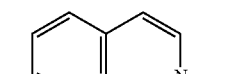 |  |  | H | O |
| 807 | 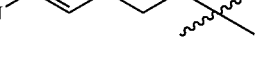 |  |  | H | O |
| 808 |  |  |  | H | O |
| 809 | 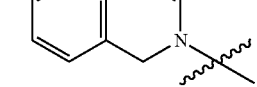 |  |  | H | O |
| 810 |  |  |  | H | O |
| 811 |  |  |  | H | O |
| 812 | 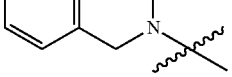 |  |  | H | O |

TABLE 1-continued

| Cmpd | W | X | Z | A | Q |
|---|---|---|---|---|---|
| 813 | 6-amino-quinolin-2(1H)-one (N-linked) | phenyl | phenyl | H | O |
| 814 | 5-amino-quinolin-2(1H)-one (N-linked) | phenyl | phenyl | H | O |
| 815 | 4-amino-quinolin-2(1H)-one (N-linked) | phenyl | phenyl | H | O |
| 816 | 3-amino-quinolin-2(1H)-one (N-linked) | phenyl | phenyl | H | O |
| 817 | 8-amino-isoquinolin-1(2H)-one (N-linked) | phenyl | phenyl | H | O |
| 818 | 7-amino-isoquinolin-1(2H)-one (N-linked) | phenyl | phenyl | H | O |
| 819 | 6-amino-isoquinolin-1(2H)-one (N-linked) | phenyl | phenyl | H | O |

TABLE 1-continued
| Cmpd | W | X | Z | A | Q |
|---|---|---|---|---|---|
| 820 | 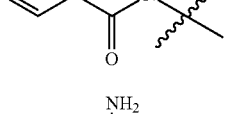 | 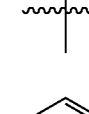 | 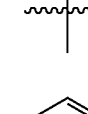 | H | O |
| 821 | 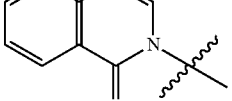 | 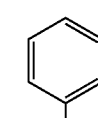 | 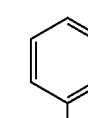 | H | O |
| 822 | 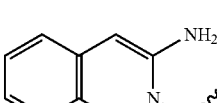 | 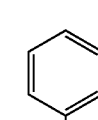 | 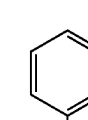 | H | O |
| 823 | 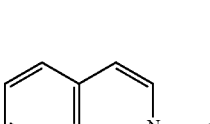 | 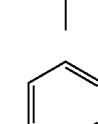 | 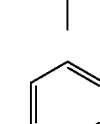 | H | O |
| 824 | 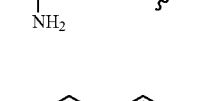 | 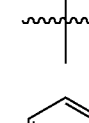 | 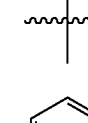 | H | O |
| 825 | 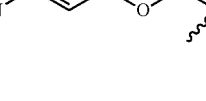 | 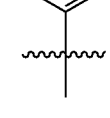 | 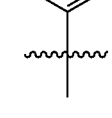 | H | O |
| 826 | 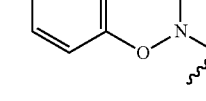 | 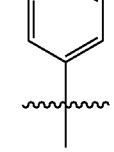 | 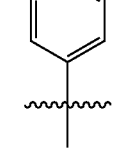 | H | O |
| 827 | 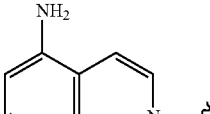 | 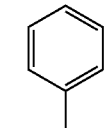 | 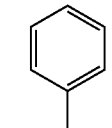 | H | O |

TABLE 1-continued

| Cmpd | W | X | Z | A | Q |
|---|---|---|---|---|---|
| 828 | benzoxazine-NH2 | phenyl | phenyl | H | O |
| 829 | 1-aminocarbazol-9-yl | phenyl | phenyl | H | O |
| 830 | 2-aminocarbazol-9-yl | phenyl | phenyl | H | O |
| 831 | 1-aminophenoxazin-10-yl | phenyl | phenyl | H | O |
| 832 | 2-aminophenoxazin-10-yl | phenyl | phenyl | H | O |
| 833 | 1-aminophenothiazin-10-yl | phenyl | phenyl | H | O |
| 834 | 2-aminophenothiazin-10-yl | phenyl | phenyl | H | O |
| 835 | aminoadamantyl-azabicyclic | phenyl | phenyl | H | O |

TABLE 1-continued

| Cmpd | W | X | Z | A | Q |
|------|---|---|---|---|---|
| 836 | 4-amino-2,3-dihydro-1H-1,2-diazepine (H2N on diazepine, N-linked) | phenyl | phenyl | H | O |
| 837 | 4-amino-2,3-dihydro-1H-azepine | phenyl | phenyl | H | O |
| 838 | 4-amino-2,3-dihydro-1H-azepine (isomer) | phenyl | phenyl | H | O |
| 839 | 4-amino-1,3-diazepine | phenyl | phenyl | H | O |
| 840 | 4-amino-1,2-diazepine | phenyl | phenyl | H | O |
| 841 | cytosin-1-yl (4-amino-2-oxopyrimidin-1-yl) | benzyl (−CH2−Ph) | benzyl (−CH2−Ph) | H | O |

TABLE 1-continued
| Cmpd | W | X | Z | A | Q |
|---|---|---|---|---|---|
| 842 | 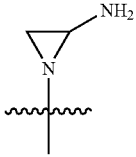 [SMILES: *N1CC1N] | 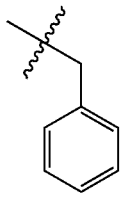 | 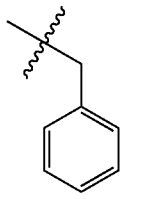 | H | O |
| 843 | 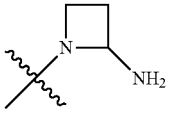 | 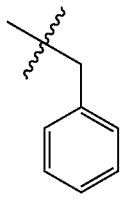 [SMILES: *Cc1ccccc1] | 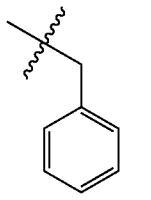 | H | O |
| 844 | 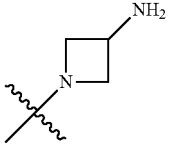 [SMILES: *N1CC(N)C1] | 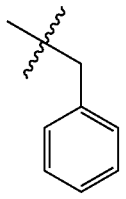 [SMILES: *Cc1ccccc1] | 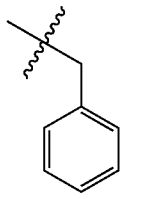 | H | O |
| 845 | 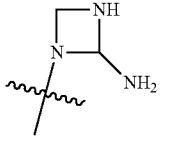 | 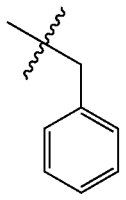 [SMILES: *Cc1ccccc1] | 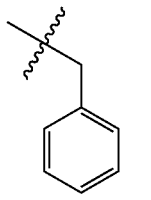 | H | O |
| 846 | 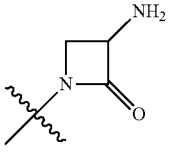 [SMILES: *N1CC(N)C1=O] | 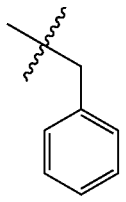 [SMILES: *Cc1ccccc1] | 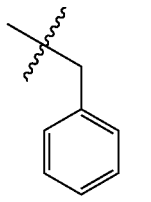 | H | O |
| 847 | 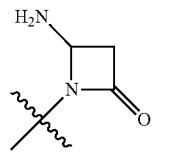 [SMILES: *N1C(=O)CC1N] | 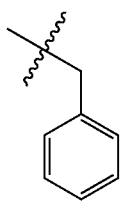 [SMILES: *Cc1ccccc1] | 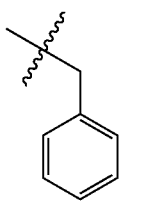 | H | O |
| 848 | 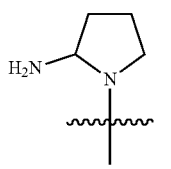 | 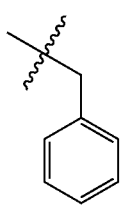 [SMILES: *Cc1ccccc1] | 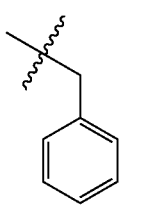 | H | O |

TABLE 1-continued

| Cmpd | W | X | Z | A | Q |
|---|---|---|---|---|---|
| 849 | 3-amino-pyrrolidin-1-yl | benzyl | benzyl | H | O |
| 850 | 2-amino-2,3-dihydro-pyrrol-1-yl | benzyl | benzyl | H | O |
| 851 | 3-amino-2,5-dihydro-pyrrol-1-yl | benzyl | benzyl | H | O |
| 852 | 5-amino-2,3-dihydro-pyrrol-1-yl | benzyl | benzyl | H | O |
| 853 | 3-amino-4,5-dihydro-pyrrol-1-yl | benzyl | benzyl | H | O |
| 854 | 3-amino-2,3-dihydro-pyrrol-1-yl | benzyl | benzyl | H | O |
| 855 | 2-amino-2,5-dihydro-pyrrol-1-yl | benzyl | benzyl | H | O |

TABLE 1-continued
| Cmpd | W | X | Z | A | Q |
|---|---|---|---|---|---|
| 856 | 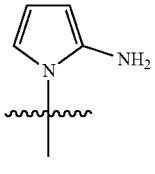 [SMILES: *n1cccc1N] | 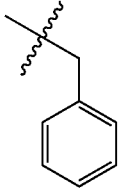 [SMILES: *Cc1ccccc1] | 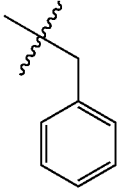 | H | O |
| 857 | 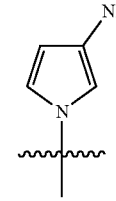 | 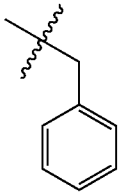 | 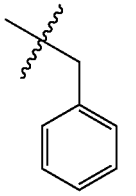 | H | O |
| 858 | 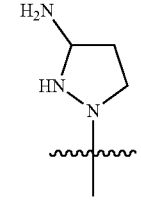 | 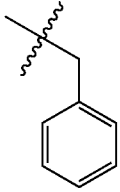 [SMILES: *Cc1ccccc1] | 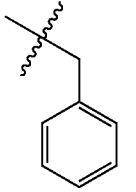 | H | O |
| 859 | 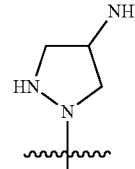 | 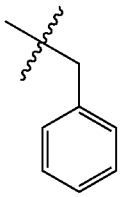 [SMILES: *Cc1ccccc1] | 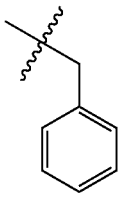 | H | O |
| 860 | 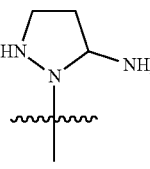 | 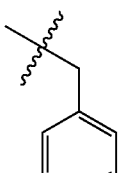 | 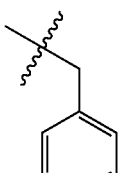 | H | O |
| 861 | 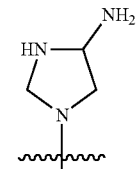 | 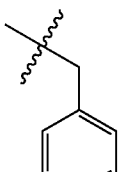 | 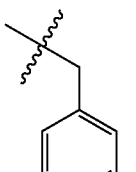 | H | O |
| 862 | 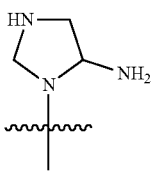 | 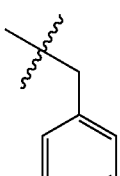 | 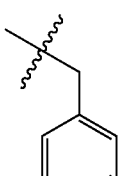 | H | O |

TABLE 1-continued

| Cmpd | W | X | Z | A | Q |
|---|---|---|---|---|---|
| 863 | 2-amino-4,5-dihydroimidazol-1-yl (N-linked) | benzyl | benzyl | H | O |
| 864 | 3-amino-4,5-dihydro-1H-pyrazol-1-yl | benzyl | benzyl | H | O |
| 865 | 4-amino-4,5-dihydro-1H-pyrazol-1-yl | benzyl | benzyl | H | O |
| 866 | 5-amino-4,5-dihydro-1H-pyrazol-1-yl | benzyl | benzyl | H | O |
| 867 | 2-amino-4,5-dihydro-1H-imidazol-1-yl | benzyl | benzyl | H | O |
| 868 | 5-amino-4,5-dihydro-1H-imidazol-1-yl | benzyl | benzyl | H | O |
| 869 | 5-amino-4,5-dihydro-1H-imidazol-1-yl (isomer) | benzyl | benzyl | H | O |

TABLE 1-continued

| Cmpd | W | X | Z | A | Q |
|---|---|---|---|---|---|
| 870 | 3-amino-pyrrolidine-2,5-dione (N-linked) | benzyl | benzyl | H | O |
| 871 | 5-amino-hydantoin (N-linked) | benzyl | benzyl | H | O |
| 872 | 5-amino-thiazolidine-2,4-dione (N-linked) | benzyl | benzyl | H | O |
| 873 | 2-aminopiperidine (N-linked) | benzyl | benzyl | H | O |
| 874 | 3-aminopiperidine (N-linked) | benzyl | benzyl | H | O |
| 875 | 4-aminopiperidine (N-linked) | benzyl | benzyl | H | O |
| 876 | 3-aminopiperazine (N-linked) | benzyl | benzyl | H | O |

TABLE 1-continued
| Cmpd | W | X | Z | A | Q |
|---|---|---|---|---|---|
| 877 | 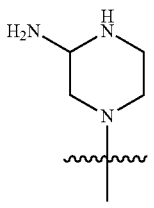 [SMILES: *N1CCNC(N)C1] | 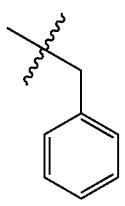 [SMILES: *Cc1ccccc1] | 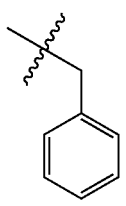 | H | O |
| 878 | 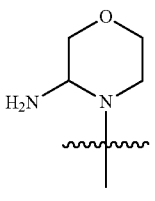 [SMILES: *N1CCOCC1N] | 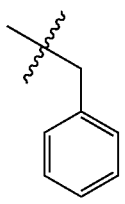 | 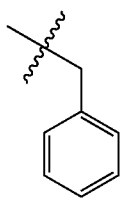 | H | O |
| 879 | 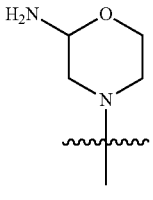 [SMILES: *N1CCOC(N)C1] | 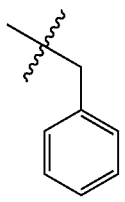 [SMILES: *Cc1ccccc1] | 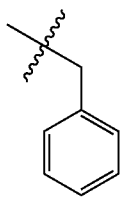 | H | O |
| 880 | 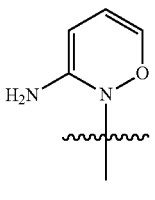 [SMILES: *N1OC=CC=C1N] | 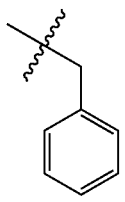 [SMILES: *Cc1ccccc1] | 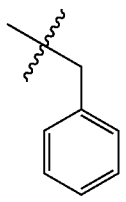 | H | O |
| 881 | 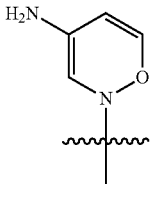 [SMILES: *N1C=C(N)C=CO1] | 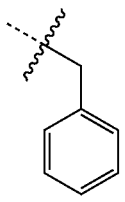 [SMILES: *Cc1ccccc1] | 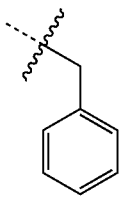 | H | O |
| 882 | 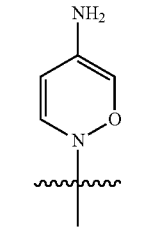 | 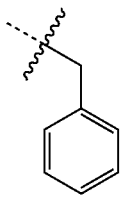 | 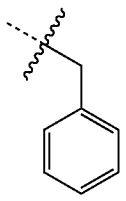 | H | O |
| 883 | 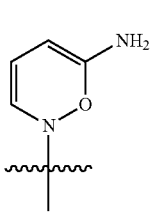 [SMILES: *N1C=CC=C(N)O1] | 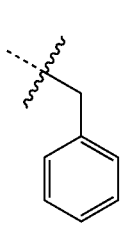 [SMILES: *Cc1ccccc1] | 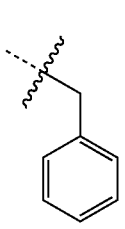 | H | O |

TABLE 1-continued

| Cmpd | W | X | Z | A | Q |
|---|---|---|---|---|---|
| 884 | 4-amino-4H-1,4-oxazine (N-linked, NH2 at 3) | CH2-phenyl | CH2-phenyl | H | O |
| 885 | 4H-1,4-oxazin-2-amine (N-linked) | CH2-phenyl | CH2-phenyl | H | O |
| 886 | 3-amino-thiomorpholine (N-linked) | CH2-phenyl | CH2-phenyl | H | O |
| 887 | 2-amino-thiomorpholine (N-linked) | CH2-phenyl | CH2-phenyl | H | O |
| 888 | 3-amino-2H-1,2-thiazine (N-linked) | CH2-phenyl | CH2-phenyl | H | O |
| 889 | 4-amino-2H-1,2-thiazine (N-linked) | CH2-phenyl | CH2-phenyl | H | O |
| 890 | 5-amino-2H-1,2-thiazine (N-linked) | CH2-phenyl | CH2-phenyl | H | O |

TABLE 1-continued

| Cmpd | W | X | Z | A | Q |
|---|---|---|---|---|---|
| 891 | 6-amino-2H-1,2-thiazine, N-linked | benzyl | benzyl | H | O |
| 892 | 3-amino-4H-1,4-thiazine, N-linked | benzyl | benzyl | H | O |
| 893 | 3-amino-1,4-thiazine, N4-linked | benzyl | benzyl | H | O |
| 894 | 3-amino-1,1-dioxo-thiomorpholine, N-linked | benzyl | benzyl | H | O |
| 895 | 2-amino-1,1-dioxo-thiomorpholine, N-linked | benzyl | benzyl | H | O |
| 896 | 2-amino-5,6-dihydro-4H-cyclopenta[b]pyrrole, N-linked | benzyl | benzyl | H | O |
| 897 | 3-amino-5,6-dihydro-4H-cyclopenta[b]pyrrole, N-linked | benzyl | benzyl | H | O |

TABLE 1-continued

| Cmpd | W | X | Z | A | Q |
|---|---|---|---|---|---|
| 898 | 4-amino-cyclopenta-pyrrole (H₂N on cyclopentane, N-linked) | benzyl | benzyl | H | O |
| 899 | 5-amino-cyclopenta-pyrrole (NH₂ on cyclopentane, N-linked) | benzyl | benzyl | H | O |
| 900 | cyclopenta-pyrrole with NH₂, N-linked | benzyl | benzyl | H | O |
| 901 | 2-amino-pyrrolo-pyrrole, N-linked | benzyl | benzyl | H | O |
| 902 | amino-pyrrolo-pyrrole, N-linked | benzyl | benzyl | H | O |
| 903 | amino-pyrrolo-pyrrole, N-linked | benzyl | benzyl | H | O |
| 904 | amino-pyrrolo-pyrrole, N-linked | benzyl | benzyl | H | O |

TABLE 1-continued

| Cmpd | W | X | Z | A | Q |
|---|---|---|---|---|---|
| 905 | 5-amino-1H-pyrrolo[3,2-b]pyrrole, N-linked | benzyl | benzyl | H | O |
| 906 | 5-amino-4H-pyrrolo[3,2-b]pyrrole, N-linked | benzyl | benzyl | H | O |
| 907 | 2-amino-4H-pyrrolo[3,2-b]pyrrole, N-linked | benzyl | benzyl | H | O |
| 908 | 6-amino-1H-pyrrolo[3,2-b]pyrrole, N-linked | benzyl | benzyl | H | O |
| 909 | 5-amino-1H-pyrrolo[2,3-b]pyrrole, N-linked | benzyl | benzyl | H | O |
| 910 | 5-amino-1H-pyrrolo[2,3-b]pyrrole, N-linked | benzyl | benzyl | H | O |
| 911 | 4-amino-1H-pyrrolo[2,3-b]pyrrole, N-linked | benzyl | benzyl | H | O |

TABLE 1-continued

| Cmpd | W | X | Z | A | Q |
|---|---|---|---|---|---|
| 912 | 2-amino-1H-pyrrolo[2,3-b]pyrrole, N1-linked | benzyl | benzyl | H | O |
| 913 | 5-amino-6H-pyrrolo[2,3-b]furan, N6-linked | benzyl | benzyl | H | O |
| 914 | 4-amino-6H-pyrrolo[2,3-b]furan, N6-linked | benzyl | benzyl | H | O |
| 915 | 3-amino-6H-pyrrolo[2,3-b]furan, N6-linked | benzyl | benzyl | H | O |
| 916 | 2-amino-7aH-pyrrolo[2,3-b]furan (N-linked) | benzyl | benzyl | H | O |
| 917 | 5-amino-4H-furo[3,2-b]pyrrole, N4-linked | benzyl | benzyl | H | O |
| 918 | 6-amino-4H-furo[3,2-b]pyrrole, N4-linked | benzyl | benzyl | H | O |

TABLE 1-continued

| Cmpd | W | X | Z | A | Q |
|---|---|---|---|---|---|
| 919 | furo-pyrrole with NH₂, N-linked | benzyl | benzyl | H | O |
| 920 | furo-pyrrole with NH₂ at 3-position, N-linked | benzyl | benzyl | H | O |
| 921 | thieno-pyrrole with H₂N, N-linked | benzyl | benzyl | H | O |
| 922 | thieno-pyrrole with H₂N, N-linked | benzyl | benzyl | H | O |
| 923 | thieno-pyrrole with H₂N, N-linked | benzyl | benzyl | H | O |
| 924 | thieno-pyrrole with NH₂, N-linked | benzyl | benzyl | H | O |
| 925 | thieno-pyrrole with H₂N, N-linked | benzyl | benzyl | H | O |

TABLE 1-continued

| Cmpd | W | X | Z | A | Q |
|---|---|---|---|---|---|
| 926 | 5-amino-4H-thieno[3,2-b]pyrrole (N-linked) | benzyl | benzyl | H | O |
| 927 | 2-amino-4H-thieno[3,2-b]pyrrole (N-linked) | benzyl | benzyl | H | O |
| 928 | 3-amino-4H-thieno[3,2-b]pyrrole (N-linked) | benzyl | benzyl | H | O |
| 929 | 7-amino-indoline (N-linked) | benzyl | benzyl | H | O |
| 930 | 6-amino-indoline (N-linked) | benzyl | benzyl | H | O |
| 931 | 4-amino-indoline (N-linked) | benzyl | benzyl | H | O |
| 932 | 3-amino-indoline (N-linked) | benzyl | benzyl | H | O |

TABLE 1-continued

| Cmpd | W | X | Z | A | Q |
|------|---|---|---|---|---|
| 933 | 2-amino-indoline (N-linked) | benzyl | benzyl | H | O |
| 934 | 7-amino-indole (N-linked) | benzyl | benzyl | H | O |
| 935 | 6-amino-indole (N-linked) | benzyl | benzyl | H | O |
| 936 | 5-amino-indole (N-linked) | benzyl | benzyl | H | O |
| 937 | 4-amino-indole (N-linked) | benzyl | benzyl | H | O |
| 938 | 3-amino-indole (N-linked) | benzyl | benzyl | H | O |
| 939 | 2-amino-indole (N-linked) | benzyl | benzyl | H | O |

TABLE 1-continued

| Cmpd | W | X | Z | A | Q |
|---|---|---|---|---|---|
| 940 | 1-amino-isoindole (2-yl linked) | benzyl | benzyl | H | O |
| 941 | 7-amino-isoindole (2-yl linked) | benzyl | benzyl | H | O |
| 942 | 5-amino-isoindole (2-yl linked) | benzyl | benzyl | H | O |
| 943 | 7-amino-indazole (1-yl linked) | benzyl | benzyl | H | O |
| 944 | 6-amino-indazole (1-yl linked) | benzyl | benzyl | H | O |
| 945 | 5-amino-indazole (1-yl linked) | benzyl | benzyl | H | O |
| 946 | 4-amino-indazole (1-yl linked) | benzyl | benzyl | H | O |

TABLE 1-continued

| Cmpd | W | X | Z | A | Q |
|---|---|---|---|---|---|
| 947 | 3-amino-1H-indazol-1-yl (benzyl attachment) | benzyl | benzyl | H | O |
| 948 | 7-amino-1H-benzimidazol-1-yl | benzyl | benzyl | H | O |
| 949 | 6-amino-1H-benzimidazol-1-yl | benzyl | benzyl | H | O |
| 950 | 5-amino-1H-benzimidazol-1-yl | benzyl | benzyl | H | O |
| 951 | 4-amino-1H-benzimidazol-1-yl | benzyl | benzyl | H | O |
| 952 | 2-amino-1H-benzimidazol-1-yl | benzyl | benzyl | H | O |
| 953 | 7-amino-1H-pyrrolo[3,2-b]pyridin-1-yl | benzyl | benzyl | H | O |

TABLE 1-continued
| Cmpd | W | X | Z | A | Q |
|---|---|---|---|---|---|
| 954 | 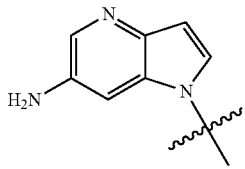 [SMILES: *n1ccc2ncc(N)cc21] | 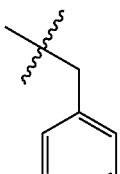 | 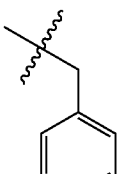 | H | O |
| 955 | 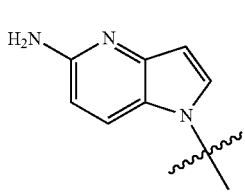 [SMILES: *n1ccc2nc(N)ccc21] | 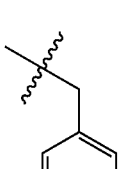 | 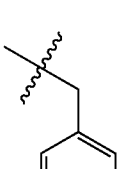 | H | O |
| 956 | 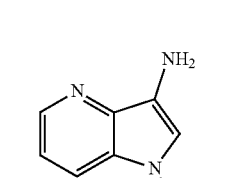 | 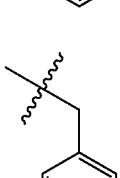 | 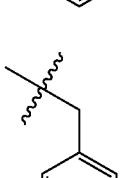 | H | O |
| 957 | 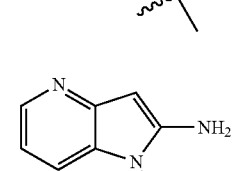 | 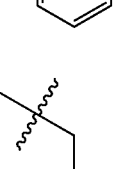 | 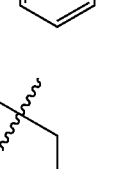 | H | O |
| 958 | 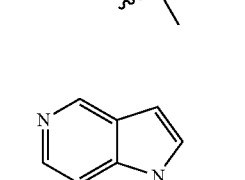 | 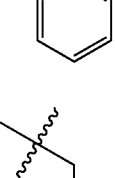 | 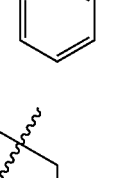 | H | O |
| 959 | 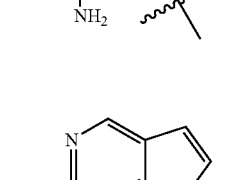 | 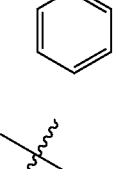 | 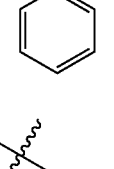 | H | O |
| 960 | 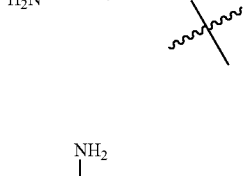 | 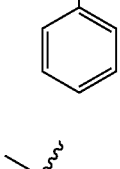 | 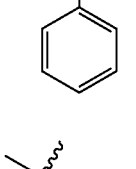 | H | O |

TABLE 1-continued

| Cmpd | W | X | Z | A | Q |
|---|---|---|---|---|---|
| 961 | 3-amino-pyrrolo[2,3-c]pyridine (N-linked) | -CH2-phenyl | -CH2-phenyl | H | O |
| 962 | 2-amino-pyrrolo[2,3-c]pyridine (N-linked) | -CH2-phenyl | -CH2-phenyl | H | O |
| 963 | 7-amino-pyrrolo[2,3-c]pyridine (N-linked) | -CH2-phenyl | -CH2-phenyl | H | O |
| 964 | 5-amino-pyrrolo[2,3-c]pyridine (N-linked) | -CH2-phenyl | -CH2-phenyl | H | O |
| 965 | 4-amino-pyrrolo[2,3-c]pyridine (N-linked) | -CH2-phenyl | -CH2-phenyl | H | O |
| 966 | 3-amino-pyrrolo[3,2-c]pyridine (N-linked) | -CH2-phenyl | -CH2-phenyl | H | O |
| 967 | 2-amino-pyrrolo[3,2-c]pyridine (N-linked) | -CH2-phenyl | -CH2-phenyl | H | O |

TABLE 1-continued
| Cmpd | W | X | Z | A | Q |
|---|---|---|---|---|---|
| 968 | 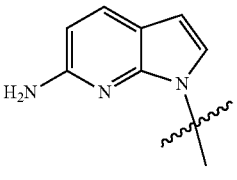 [SMILES: *n1ccc2ccc(N)nc21] | 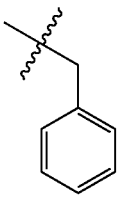 [SMILES: *Cc1ccccc1] | 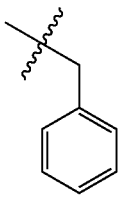 | H | O |
| 969 | 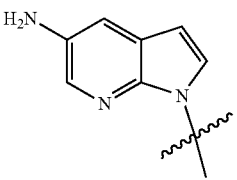 [SMILES: *n1ccc2cc(N)cnc21] | 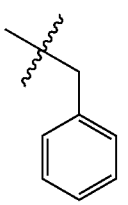 [SMILES: *Cc1ccccc1] | 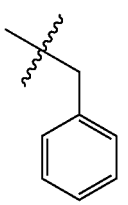 | H | O |
| 970 | 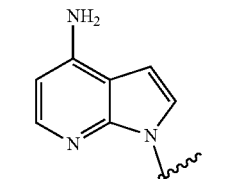 | 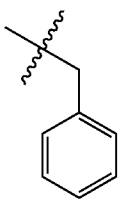 [SMILES: *Cc1ccccc1] | 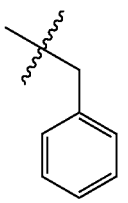 | H | O |
| 971 | 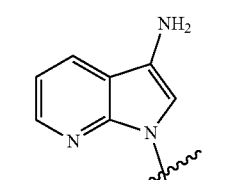 | 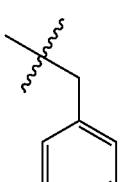 | 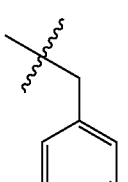 | H | O |
| 972 | 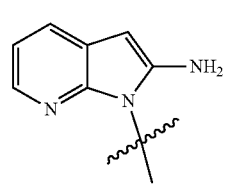 [SMILES: *n1c(N)cc2cccnc21] | 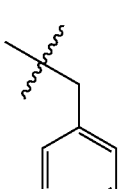 | 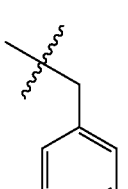 | H | O |
| 973 | 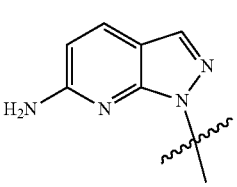 | 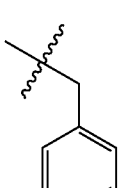 | 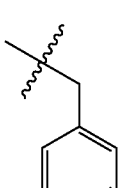 | H | O |
| 974 | 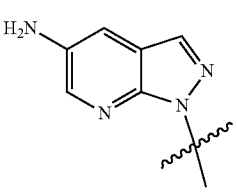 [SMILES: *n1ncc2cc(N)cnc21] | 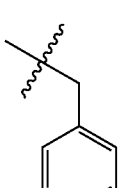 | 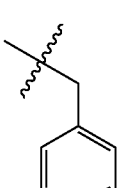 | H | O |

TABLE 1-continued

| Cmpd | W | X | Z | A | Q |
|---|---|---|---|---|---|
| 975 | 4-amino-pyrazolo[3,4-b]pyridine (N1-linked) | benzyl | benzyl | H | O |
| 976 | 3-amino-pyrazolo[3,4-b]pyridine (N1-linked) | benzyl | benzyl | H | O |
| 977 | 2-amino-purine (N9-linked) | benzyl | benzyl | H | O |
| 978 | adenine (N9-linked) | benzyl | benzyl | H | O |
| 979 | 8-amino-purine (N9-linked) | benzyl | benzyl | H | O |
| 980 | 7-amino-benzisothiazol-3(2H)-one (N2-linked) | benzyl | benzyl | H | O |
| 981 | 6-amino-benzisothiazol-3(2H)-one (N2-linked) | benzyl | benzyl | H | O |

TABLE 1-continued

| Cmpd | W | X | Z | A | Q |
|------|---|---|---|---|---|
| 982 | 5-amino-benzisothiazol-3(2H)-one (N-linked) | benzyl | benzyl | H | O |
| 983 | 4-amino-benzisothiazol-3(2H)-one (N-linked) | benzyl | benzyl | H | O |
| 984 | 6-amino-1H-pyrazolo[3,4-d]pyrimidin-4(5H)-one (N1-linked) | benzyl | benzyl | H | O |
| 985 | 4-amino-1H-pyrazolo[3,4-d]pyrimidine (N1-linked) | benzyl | benzyl | H | O |
| 986 | 1-amino-decahydroisoquinoline (N-linked) | benzyl | benzyl | H | O |
| 987 | 8-amino-decahydroisoquinoline (N-linked) | benzyl | benzyl | H | O |

TABLE 1-continued

| Cmpd | W | X | Z | A | Q |
|---|---|---|---|---|---|
| 988 | 7-amino-decahydroisoquinolin-2-yl | benzyl | benzyl | H | O |
| 989 | 6-amino-decahydroisoquinolin-2-yl | benzyl | benzyl | H | O |
| 990 | 5-amino-decahydroisoquinolin-2-yl | benzyl | benzyl | H | O |
| 991 | 4-amino-decahydroisoquinolin-2-yl | benzyl | benzyl | H | O |
| 992 | 3-amino-decahydroisoquinolin-2-yl | benzyl | benzyl | H | O |
| 993 | 8-amino-decahydroquinolin-1-yl | benzyl | benzyl | H | O |
| 994 | 7-amino-decahydroquinolin-1-yl | benzyl | benzyl | H | O |

TABLE 1-continued

| Cmpd | W | X | Z | A | Q |
|------|---|---|---|---|---|
| 995 | H2N-decahydroquinoline (amine at one position) | -CH2-phenyl | -CH2-phenyl | H | O |
| 996 | NH2-decahydroquinoline | -CH2-phenyl | -CH2-phenyl | H | O |
| 997 | NH2-decahydroquinoline | -CH2-phenyl | -CH2-phenyl | H | O |
| 998 | NH2-decahydroquinoline | -CH2-phenyl | -CH2-phenyl | H | O |
| 999 | NH2-decahydroquinoline | -CH2-phenyl | -CH2-phenyl | H | O |
| 1000 | NH2-tetrahydroquinoline | -CH2-phenyl | -CH2-phenyl | H | O |
| 1001 | H2N-tetrahydroquinoline | -CH2-phenyl | -CH2-phenyl | H | O |

TABLE 1-continued

| Cmpd | W | X | Z | A | Q |
|---|---|---|---|---|---|
| 1002 | 6-amino-1,2,3,4-tetrahydroquinolin-1-yl | benzyl | benzyl | H | O |
| 1003 | 5-amino-1,2,3,4-tetrahydroquinolin-1-yl | benzyl | benzyl | H | O |
| 1004 | 4-amino-1,2,3,4-tetrahydroquinolin-1-yl | benzyl | benzyl | H | O |
| 1005 | 3-amino-1,2,3,4-tetrahydroquinolin-1-yl | benzyl | benzyl | H | O |
| 1006 | 2-amino-1,2,3,4-tetrahydroquinolin-1-yl | benzyl | benzyl | H | O |
| 1007 | 8-amino-2H-quinolin-1-yl | benzyl | benzyl | H | O |
| 1008 | 7-amino-2H-quinolin-1-yl | benzyl | benzyl | H | O |

TABLE 1-continued

| Cmpd | W | X | Z | A | Q |
|---|---|---|---|---|---|
| 1009 | 6-amino-2H-quinolin-1-yl (with methyl) | -CH₂-phenyl | -CH₂-phenyl | H | O |
| 1010 | 5-amino-2H-quinolin-1-yl (with methyl) | -CH₂-phenyl | -CH₂-phenyl | H | O |
| 1011 | 4-amino-2H-quinolin-1-yl (with methyl) | -CH₂-phenyl | -CH₂-phenyl | H | O |
| 1012 | 3-amino-2H-quinolin-1-yl (with methyl) | -CH₂-phenyl | -CH₂-phenyl | H | O |
| 1013 | 2-amino-2H-quinolin-1-yl (with methyl) | -CH₂-phenyl | -CH₂-phenyl | H | O |
| 1014 | 1-amino-1H-isoquinolin-2-yl (with methyl) | -CH₂-phenyl | -CH₂-phenyl | H | O |
| 1015 | 8-amino-1H-isoquinolin-2-yl (with methyl) | -CH₂-phenyl | -CH₂-phenyl | H | O |

TABLE 1-continued
| Cmpd | W | X | Z | A | Q |
|---|---|---|---|---|---|
| 1016 | 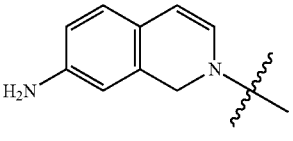 [SMILES: *N1C=Cc2ccc(N)cc2C1] | 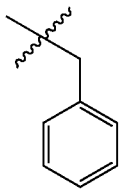 [SMILES: *Cc1ccccc1] | 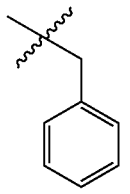 | H | O |
| 1017 | 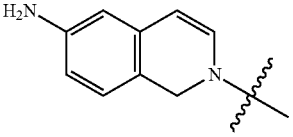 [SMILES: *N1C=Cc2cc(N)ccc2C1] | 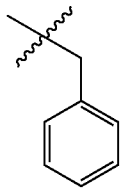 [SMILES: *Cc1ccccc1] | 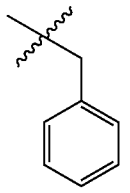 | H | O |
| 1018 | 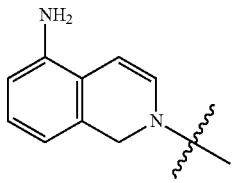 | 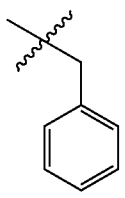 | 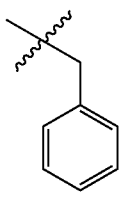 | H | O |
| 1019 | 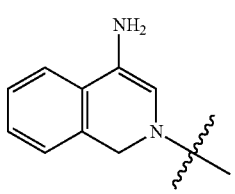 | 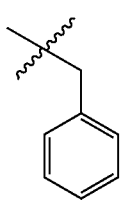 | 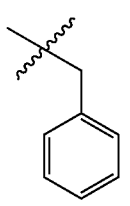 | H | O |
| 1020 | 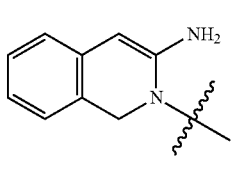 [SMILES: *N1Cc2ccccc2C=C1N] | 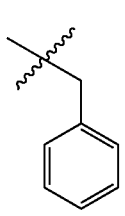 [SMILES: *Cc1ccccc1] | 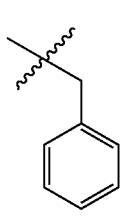 | H | O |
| 1021 | 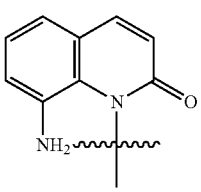 [SMILES: *n1c(=O)ccc2cccc(N)c21] | 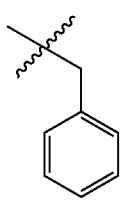 [SMILES: *Cc1ccccc1] | 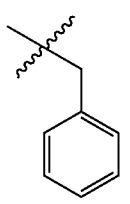 | H | O |
| 1022 | 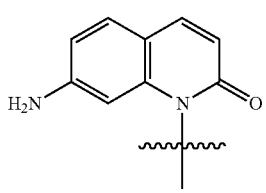 | 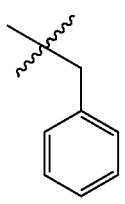 [SMILES: *Cc1ccccc1] | 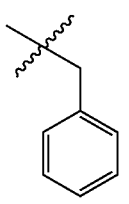 | H | O |
| 1023 | 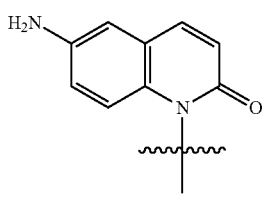 [SMILES: *n1c(=O)ccc2cc(N)ccc21] | 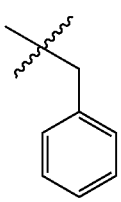 [SMILES: *Cc1ccccc1] | 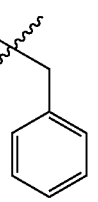 | H | O |

TABLE 1-continued

| Cmpd | W | X | Z | A | Q |
|---|---|---|---|---|---|
| 1024 | 5-amino-quinolin-2(1H)-one (N-linked) | benzyl | benzyl | H | O |
| 1025 | 4-amino-quinolin-2(1H)-one (N-linked) | benzyl | benzyl | H | O |
| 1026 | 3-amino-quinolin-2(1H)-one (N-linked) | benzyl | benzyl | H | O |
| 1027 | 8-amino-isoquinolin-1(2H)-one (N-linked) | benzyl | benzyl | H | O |
| 1028 | 7-amino-isoquinolin-1(2H)-one (N-linked) | benzyl | benzyl | H | O |
| 1029 | 6-amino-isoquinolin-1(2H)-one (N-linked) | benzyl | benzyl | H | O |
| 1030 | 5-amino-isoquinolin-1(2H)-one (N-linked) | benzyl | benzyl | H | O |

TABLE 1-continued

| Cmpd | W | X | Z | A | Q |
|---|---|---|---|---|---|
| 1031 | 4-amino-2H-isoquinolin-1-one (N-linked) | benzyl | benzyl | H | O |
| 1032 | 3-amino-2H-isoquinolin-1-one (N-linked) | benzyl | benzyl | H | O |
| 1033 | 8-amino-2H-benzo[e][1,2]oxazine (N-linked) | benzyl | benzyl | H | O |
| 1034 | 7-amino-2H-benzo[e][1,2]oxazine (N-linked) | benzyl | benzyl | H | O |
| 1035 | 6-amino-2H-benzo[e][1,2]oxazine (N-linked) | benzyl | benzyl | H | O |
| 1036 | 5-amino-2H-benzo[e][1,2]oxazine (N-linked) | benzyl | benzyl | H | O |
| 1037 | 4-amino-2H-benzo[e][1,2]oxazine (N-linked) | benzyl | benzyl | H | O |

TABLE 1-continued

| Cmpd | W | X | Z | A | Q |
|------|---|---|---|---|---|
| 1038 | benzoxazine-3-amine | benzyl | benzyl | H | O |
| 1039 | carbazol-1-amine (N-linked) | benzyl | benzyl | H | O |
| 1040 | carbazol-2-amine (N-linked) | benzyl | benzyl | H | O |
| 1041 | phenoxazin-1-amine (N-linked) | benzyl | benzyl | H | O |
| 1042 | phenoxazin-2-amine (N-linked) | benzyl | benzyl | H | O |
| 1043 | phenothiazin-1-amine (N-linked) | benzyl | benzyl | H | O |
| 1044 | phenothiazin-2-amine (N-linked) | benzyl | benzyl | H | O |

TABLE 1-continued

| Cmpd | W | X | Z | A | Q |
|------|---|---|---|---|---|
| 1045 | (aminoadamantane-N) | benzyl | benzyl | H | O |
| 1046 | 4-amino-2,7-dihydro-1H-azepin-1-yl | benzyl | benzyl | H | O |
| 1047 | 4-amino-1,4-dihydro-azepin-1-yl | benzyl | benzyl | H | O |
| 1048 | 4-amino-azepin-1-yl | benzyl | benzyl | H | O |
| 1049 | 4-amino-1,3-diazepin-1-yl | benzyl | benzyl | H | O |
| 1050 | 4-amino-1,2-diazepin-2-yl | benzyl | benzyl | H | O |
| 1051 | cytosin-1-yl | 5-hydroxypentyl | 5-hydroxypentyl | H | O |

TABLE 1-continued

| Cmpd | W | X | Z | A | Q |
|---|---|---|---|---|---|
| 1052 | aziridine-N with NH2 | HO-(CH2)4- | HO-(CH2)4- | H | O |
| 1053 | azetidine-N with 2-NH2 | HO-(CH2)4- | HO-(CH2)4- | H | O |
| 1054 | azetidine-N with 3-NH2 | HO-(CH2)4- | HO-(CH2)4- | H | O |
| 1055 | 2-amino-2,3-dihydroazete | HO-(CH2)4- | HO-(CH2)4- | H | O |
| 1056 | 3-amino-azetidin-2-one | HO-(CH2)4- | HO-(CH2)4- | H | O |
| 1057 | 4-amino-azetidin-2-one | HO-(CH2)4- | HO-(CH2)4- | H | O |
| 1058 | 2-aminopyrrolidin-1-yl | HO-(CH2)4- | HO-(CH2)4- | H | O |
| 1059 | 3-aminopyrrolidin-1-yl | HO-(CH2)4- | HO-(CH2)4- | H | O |
| 1060 | 2-amino-2,5-dihydro-1H-pyrrol-1-yl | HO-(CH2)4- | HO-(CH2)4- | H | O |

TABLE 1-continued

| Cmpd | W | X | Z | A | Q |
|---|---|---|---|---|---|
| 1061 | 3-amino-2,5-dihydro-1H-pyrrol-1-yl (H₂N on pyrrolidine ring, N-attached) | HO-(CH₂)₄-C(CH₃)< | HO-(CH₂)₄-C(CH₃)< | H | O |
| 1062 | 2-amino-2,3-dihydro-1H-pyrrol-1-yl | HO-(CH₂)₄-C(CH₃)< | HO-(CH₂)₄-C(CH₃)< | H | O |
| 1063 | 3-amino-4,5-dihydro-1H-pyrrol-1-yl | HO-(CH₂)₄-C(CH₃)< | HO-(CH₂)₄-C(CH₃)< | H | O |
| 1064 | 3-amino-2,5-dihydro-1H-pyrrol-1-yl | HO-(CH₂)₄-C(CH₃)< | HO-(CH₂)₄-C(CH₃)< | H | O |
| 1065 | 2-amino-2,3-dihydro-1H-pyrrol-1-yl | HO-(CH₂)₄-C(CH₃)< | HO-(CH₂)₄-C(CH₃)< | H | O |
| 1066 | 2-amino-1H-pyrrol-1-yl | HO-(CH₂)₄-C(CH₃)< | HO-(CH₂)₄-C(CH₃)< | H | O |
| 1067 | 3-amino-1H-pyrrol-1-yl | HO-(CH₂)₄-C(CH₃)< | HO-(CH₂)₄-C(CH₃)< | H | O |
| 1068 | 3-amino-pyrazolidin-1-yl | HO-(CH₂)₄-C(CH₃)< | HO-(CH₂)₄-C(CH₃)< | H | O |

TABLE 1-continued

| Cmpd | W | X | Z | A | Q |
|------|---|---|---|---|---|
| 1069 | 4-amino-pyrazolidin-1-yl (HN-N, NH₂) | HO-(CH₂)₄-C(CH₃)- | HO-(CH₂)₄-C(CH₃)- | H | O |
| 1070 | 3-amino-pyrazolidin-1-yl | HO-(CH₂)₄-C(CH₃)- | HO-(CH₂)₄-C(CH₃)- | H | O |
| 1071 | 4-amino-imidazolidin-1-yl | HO-(CH₂)₄-C(CH₃)- | HO-(CH₂)₄-C(CH₃)- | H | O |
| 1072 | 5-amino-imidazolidin-1-yl | HO-(CH₂)₄-C(CH₃)- | HO-(CH₂)₄-C(CH₃)- | H | O |
| 1073 | 2-amino-imidazolidin-1-yl | HO-(CH₂)₄-C(CH₃)- | HO-(CH₂)₄-C(CH₃)- | H | O |
| 1074 | 3-amino-4,5-dihydro-pyrazol-1-yl | HO-(CH₂)₄-C(CH₃)- | HO-(CH₂)₄-C(CH₃)- | H | O |
| 1075 | 4-amino-4,5-dihydro-pyrazol-1-yl | HO-(CH₂)₄-C(CH₃)- | HO-(CH₂)₄-C(CH₃)- | H | O |
| 1076 | 5-amino-4,5-dihydro-pyrazol-1-yl | HO-(CH₂)₄-C(CH₃)- | HO-(CH₂)₄-C(CH₃)- | H | O |

TABLE 1-continued
| Cmpd | W | X | Z | A | Q |
|---|---|---|---|---|---|
| 1077 | 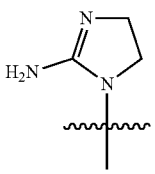 |  |  | H | O |
| 1078 | 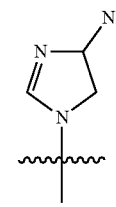 | 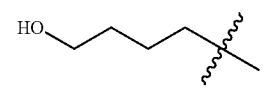 [SMILES: *CCCCO] | 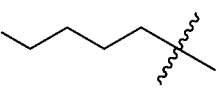 | H | O |
| 1079 | 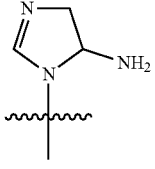 [SMILES: *N1C=NCC1N] | 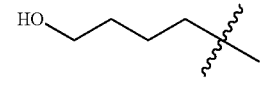 [SMILES: *CCCCO] | 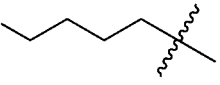 | H | O |
| 1080 | 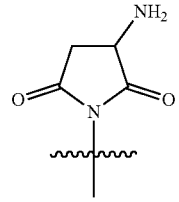 [SMILES: *N1C(=O)CC(N)C1=O] | 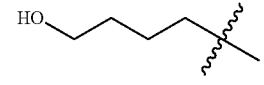 | 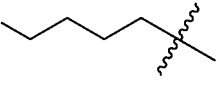 | H | O |
| 1081 | 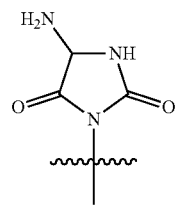 [SMILES: *N1C(=O)NC(N)C1=O] |  |  | H | O |
| 1082 | 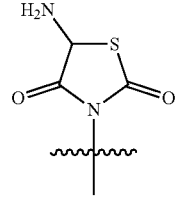 [SMILES: *N1C(=O)SC(N)C1=O] | 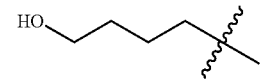 [SMILES: *CCCCO] | 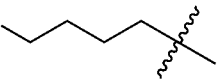 | H | O |
| 1083 | 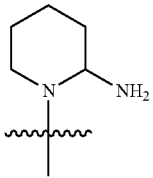 | 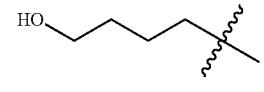 [SMILES: *CCCCO] | 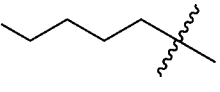 | H | O |
| 1084 | 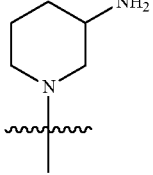 | 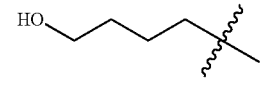 [SMILES: *CCCCO] | 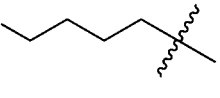 | H | O |

TABLE 1-continued
| Cmpd | W | X | Z | A | Q |
|---|---|---|---|---|---|
| 1085 | 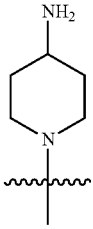 | 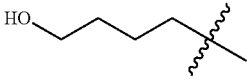 [SMILES: *CCCCO] | 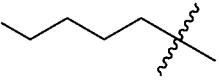 | H | O |
| 1086 | 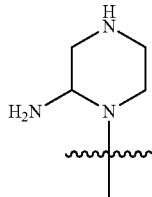 [SMILES: *N1CCNCC1N] | 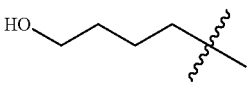 [SMILES: *CCCCO] | 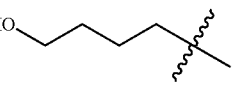 | H | O |
| 1087 | 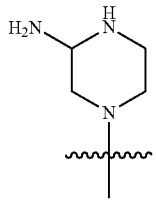 [SMILES: *N1CCNC(N)C1] | 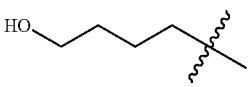 [SMILES: *CCCCO] | 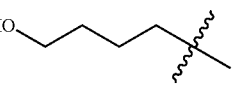 | H | O |
| 1088 | 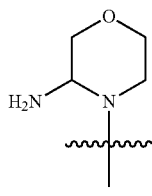 | 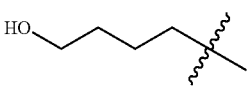 | 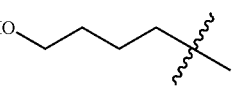 | H | O |
| 1089 | 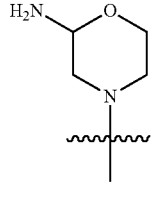 [SMILES: *N1CCOC(N)C1] | 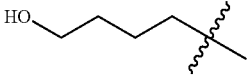 [SMILES: *CCCCO] | 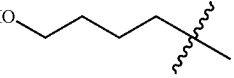 | H | O |
| 1090 | 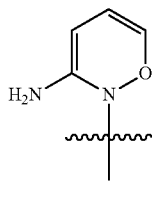 | 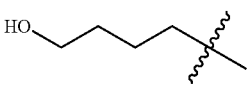 [SMILES: *CCCCO] | 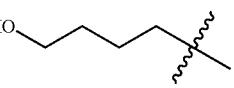 | H | O |
| 1091 | 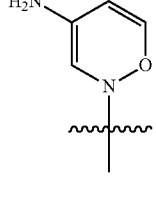 | 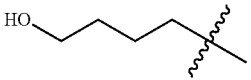 [SMILES: *CCCCO] | 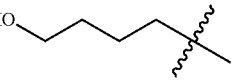 | H | O |

TABLE 1-continued

| Cmpd | W | X | Z | A | Q |
|------|---|---|---|---|---|
| 1092 | 4-amino-2H-1,2-oxazine (N-linked) | HO-(CH2)4-CH(-)CH3 | HO-(CH2)4-CH(-)CH3 | H | O |
| 1093 | 6-amino-2H-1,2-oxazine (N-linked) | HO-(CH2)4-CH(-)CH3 | HO-(CH2)4-CH(-)CH3 | H | O |
| 1094 | 3-amino-2H-1,4-oxazine (N-linked) | HO-(CH2)4-CH(-)CH3 | HO-(CH2)4-CH(-)CH3 | H | O |
| 1095 | 2-amino-2H-1,4-oxazine (N-linked) | HO-(CH2)4-CH(-)CH3 | HO-(CH2)4-CH(-)CH3 | H | O |
| 1096 | 3-aminothiomorpholine (N-linked) | HO-(CH2)4-CH(-)CH3 | HO-(CH2)4-CH(-)CH3 | H | O |
| 1097 | 2-aminothiomorpholine (N-linked) | HO-(CH2)4-CH(-)CH3 | HO-(CH2)4-CH(-)CH3 | H | O |
| 1098 | 3-amino-2H-1,2-thiazine (N-linked) | HO-(CH2)4-CH(-)CH3 | HO-(CH2)4-CH(-)CH3 | H | O |
| 1099 | 4-amino-2H-1,2-thiazine (N-linked) | HO-(CH2)4-CH(-)CH3 | HO-(CH2)4-CH(-)CH3 | H | O |

TABLE 1-continued
| Cmpd | W | X | Z | A | Q |
|---|---|---|---|---|---|
| 1100 |  |  |  | H | O |
| 1101 | 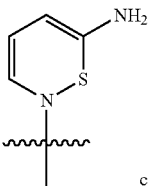 |  |  | H | O |
| 1102 | 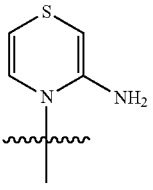 |  |  | H | O |
| 1103 |  |  |  | H | O |
| 1104 | 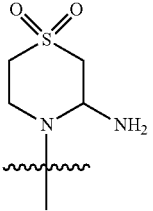 [SMILES: *N1CCS(=O)(=O)CC1N] |  |  | H | O |
| 1105 | 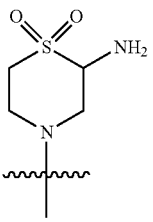 |  |  | H | O |
| 1106 | 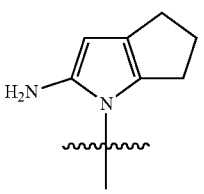 |  |  | H | O |

TABLE 1-continued
| Cmpd | W | X | Z | A | Q |
|---|---|---|---|---|---|
| 1107 | 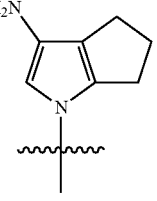 | 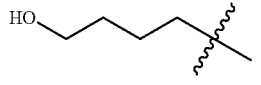 [SMILES: *CCCCO] | 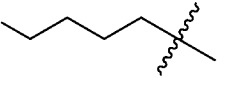 | H | O |
| 1108 | 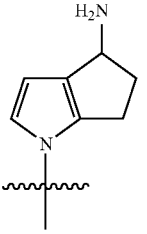 [SMILES: *n1ccc2c1CCC2N] | 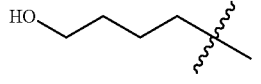 [SMILES: *CCCCO] | 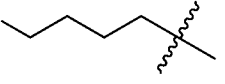 | H | O |
| 1109 | 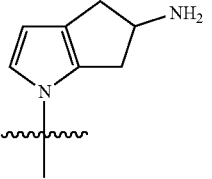 [SMILES: *n1ccc2c1CC(N)C2] | 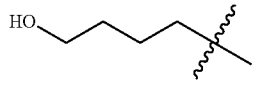 | 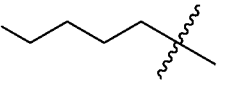 | H | O |
| 1110 | 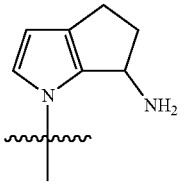 [SMILES: *n1ccc2c1C(N)CC2] | 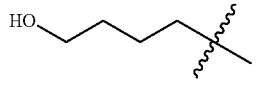 [SMILES: *CCCCO] | 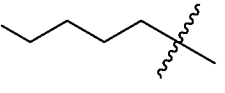 | H | O |
| 1111 | 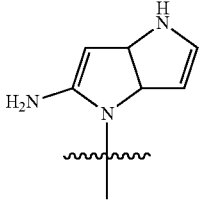 | 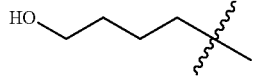 [SMILES: *CCCCO] | 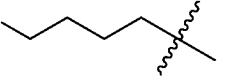 | H | O |
| 1112 | 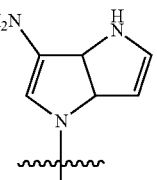 | 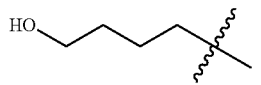 [SMILES: *CCCCO] | 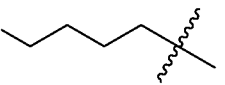 | H | O |
| 1113 | 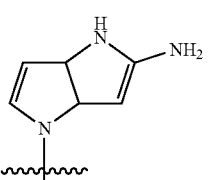 | 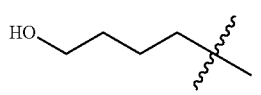 [SMILES: *CCCCO] | 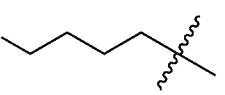 | H | O |

TABLE 1-continued

| Cmpd | W | X | Z | A | Q |
|------|---|---|---|---|---|
| 1114 | 3a-amino-1H-pyrrolo[3,2-b]pyrrole (N1-linked, with NH2 at C6) | HO-(CH2)4-C(CH3)- | HO-(CH2)4-C(CH3)- | H | O |
| 1115 | 5-amino-pyrrolo[3,2-b]pyrrole (N4-linked) | HO-(CH2)5-C(CH3)- | HO-(CH2)5-C(CH3)- | H | O |
| 1116 | 3-amino-pyrrolo[3,2-b]pyrrole (N4-linked) | HO-(CH2)4-C(CH3)- | HO-(CH2)4-C(CH3)- | H | O |
| 1117 | 2-amino-pyrrolo[3,2-b]pyrrole (N4-linked) | HO-(CH2)4-C(CH3)- | HO-(CH2)4-C(CH3)- | H | O |
| 1118 | 3-amino-pyrrolo[3,2-b]pyrrole (N1-linked) | HO-(CH2)4-C(CH3)- | HO-(CH2)4-C(CH3)- | H | O |
| 1119 | 2-amino-pyrrolo[2,3-b]pyrrole (N1-linked) | HO-(CH2)4-C(CH3)- | HO-(CH2)4-C(CH3)- | H | O |
| 1120 | 3-amino-pyrrolo[2,3-b]pyrrole (N1-linked) | HO-(CH2)4-C(CH3)- | HO-(CH2)4-C(CH3)- | H | O |

TABLE 1-continued

| Cmpd | W | X | Z | A | Q |
|---|---|---|---|---|---|
| 1121 | 3-amino-pyrrolo[2,3-b]pyrrole, N-linked | HO-(CH₂)₄-C(CH₃)< | HO-(CH₂)₄-C(CH₃)< | H | O |
| 1122 | 2-amino-pyrrolo[2,3-b]pyrrole, N-linked | HO-(CH₂)₄-C(CH₃)< | HO-(CH₂)₄-C(CH₃)< | H | O |
| 1123 | 5-amino-furo[2,3-b]pyrrole, N-linked | HO-(CH₂)₄-C(CH₃)< | HO-(CH₂)₄-C(CH₃)< | H | O |
| 1124 | 4-amino-furo[2,3-b]pyrrole, N-linked | HO-(CH₂)₄-C(CH₃)< | HO-(CH₂)₄-C(CH₃)< | H | O |
| 1125 | 3-amino-furo[2,3-b]pyrrole, N-linked | HO-(CH₂)₄-C(CH₃)< | HO-(CH₂)₄-C(CH₃)< | H | O |
| 1126 | 2-amino-furo[2,3-b]pyrrole, N-linked | HO-(CH₂)₄-C(CH₃)< | HO-(CH₂)₄-C(CH₃)< | H | O |
| 1127 | 5-amino-furo[3,2-b]pyrrole, N-linked | HO-(CH₂)₄-C(CH₃)< | HO-(CH₂)₄-C(CH₃)< | H | O |

TABLE 1-continued

| Cmpd | W | X | Z | A | Q |
|---|---|---|---|---|---|
| 1128 | 5-amino-4H-furo[3,2-b]pyrrole (N-linked) | HO-(CH2)4-C(CH3)- | HO-(CH2)4-C(CH3)- | H | O |
| 1129 | 2-amino-4H-furo[3,2-b]pyrrole (N-linked) | HO-(CH2)4-C(CH3)- | HO-(CH2)4-C(CH3)- | H | O |
| 1130 | 3-amino-4H-furo[3,2-b]pyrrole (N-linked) | HO-(CH2)4-C(CH3)- | HO-(CH2)4-C(CH3)- | H | O |
| 1131 | 5-amino-4H-thieno[2,3-b]pyrrole (N-linked) | HO-(CH2)4-C(CH3)- | HO-(CH2)4-C(CH3)- | H | O |
| 1132 | 4-amino-6H-thieno[2,3-b]pyrrole (N-linked) | HO-(CH2)4-C(CH3)- | HO-(CH2)4-C(CH3)- | H | O |
| 1133 | 3-amino-6H-thieno[2,3-b]pyrrole (N-linked) | HO-(CH2)4-C(CH3)- | HO-(CH2)4-C(CH3)- | H | O |
| 1134 | 2-amino-6H-thieno[2,3-b]pyrrole (N-linked) | HO-(CH2)4-C(CH3)- | HO-(CH2)4-C(CH3)- | H | O |

TABLE 1-continued

| Cmpd | W | X | Z | A | Q |
|---|---|---|---|---|---|
| 1135 | 5-amino-4H-thieno[3,2-b]pyrrole, N-linked | HO-(CH₂)₄-CH(*)- | HO-(CH₂)₄-CH(*)- | H | O |
| 1136 | 6-amino-4H-thieno[3,2-b]pyrrole, N-linked | HO-(CH₂)₄-CH(*)- | HO-(CH₂)₄-CH(*)- | H | O |
| 1137 | 2-amino-4H-thieno[3,2-b]pyrrole, N-linked | HO-(CH₂)₄-CH(*)- | HO-(CH₂)₄-CH(*)- | H | O |
| 1138 | 3-amino-4H-thieno[3,2-b]pyrrole, N-linked | HO-(CH₂)₄-CH(*)- | HO-(CH₂)₄-CH(*)- | H | O |
| 1139 | 7-aminoindoline, N-linked | HO-(CH₂)₄-CH(*)- | HO-(CH₂)₄-CH(*)- | H | O |
| 1140 | 6-aminoindoline, N-linked | HO-(CH₂)₄-CH(*)- | HO-(CH₂)₄-CH(*)- | H | O |
| 1141 | 4-aminoindoline, N-linked | HO-(CH₂)₄-CH(*)- | HO-(CH₂)₄-CH(*)- | H | O |
| 1142 | 3-aminoindoline, N-linked | HO-(CH₂)₄-CH(*)- | HO-(CH₂)₄-CH(*)- | H | O |

TABLE 1-continued

| Cmpd | W | X | Z | A | Q |
|---|---|---|---|---|---|
| 1143 | 2-amino-indoline, N-linked | HO-(CH2)4- | HO-(CH2)4- | H | O |
| 1144 | 7-amino-indole, N-linked | HO-(CH2)4- | HO-(CH2)4- | H | O |
| 1145 | 6-amino-indole, N-linked | HO-(CH2)4- | HO-(CH2)4- | H | O |
| 1146 | 5-amino-indole, N-linked | HO-(CH2)4- | HO-(CH2)4- | H | O |
| 1147 | 4-amino-indole, N-linked | HO-(CH2)4- | HO-(CH2)4- | H | O |
| 1148 | 3-amino-indole, N-linked | HO-(CH2)4- | HO-(CH2)4- | H | O |
| 1149 | 2-amino-indole, N-linked | HO-(CH2)4- | HO-(CH2)4- | H | O |
| 1150 | 1-amino-isoindole, N-linked | HO-(CH2)4- | HO-(CH2)4- | H | O |

TABLE 1-continued

| Cmpd | W | X | Z | A | Q |
|---|---|---|---|---|---|
| 1151 | 7-amino-2H-isoindol-2-yl | HO-(CH₂)₄-CH(-)- | HO-(CH₂)₄-CH(-)- | H | O |
| 1152 | 5-amino-2H-isoindol-2-yl | HO-(CH₂)₄-CH(-)- | HO-(CH₂)₄-CH(-)- | H | O |
| 1153 | 7-amino-1H-indazol-1-yl | HO-(CH₂)₄-CH(-)- | HO-(CH₂)₄-CH(-)- | H | O |
| 1154 | 6-amino-1H-indazol-1-yl | HO-(CH₂)₄-CH(-)- | HO-(CH₂)₄-CH(-)- | H | O |
| 1155 | 5-amino-1H-indazol-1-yl | HO-(CH₂)₄-CH(-)- | HO-(CH₂)₄-CH(-)- | H | O |
| 1156 | 4-amino-1H-indazol-1-yl | HO-(CH₂)₄-CH(-)- | HO-(CH₂)₄-CH(-)- | H | O |
| 1157 | 3-amino-1H-indazol-1-yl | HO-(CH₂)₄-CH(-)- | HO-(CH₂)₄-CH(-)- | H | O |

TABLE 1-continued

| Cmpd | W | X | Z | A | Q |
|------|---|---|---|---|---|
| 1158 | 7-aminoindazol-1-yl | HO-(CH2)4- | HO-(CH2)4- | H | O |
| 1159 | 6-aminoindazol-1-yl | HO-(CH2)4- | HO-(CH2)4- | H | O |
| 1160 | 5-aminoindazol-1-yl | HO-(CH2)4- | HO-(CH2)4- | H | O |
| 1161 | 4-aminobenzimidazol-1-yl | HO-(CH2)4- | HO-(CH2)4- | H | O |
| 1162 | 2-aminobenzimidazol-1-yl | HO-(CH2)4- | HO-(CH2)4- | H | O |
| 1163 | 7-amino-pyrrolo[3,2-b]pyridin-1-yl | HO-(CH2)4- | HO-(CH2)4- | H | O |
| 1164 | 6-amino-pyrrolo[3,2-b]pyridin-1-yl | HO-(CH2)4- | HO-(CH2)4- | H | O |
| 1165 | 5-amino-pyrrolo[3,2-b]pyridin-1-yl | HO-(CH2)4- | HO-(CH2)4- | H | O |

TABLE 1-continued

| Cmpd | W | X | Z | A | Q |
|---|---|---|---|---|---|
| 1166 | 3-amino-1H-pyrrolo[3,2-b]pyridine, N1-linked | HO-(CH2)4- | HO-(CH2)4- | H | O |
| 1167 | 2-amino-1H-pyrrolo[3,2-b]pyridine, N1-linked | HO-(CH2)4- | HO-(CH2)4- | H | O |
| 1168 | 7-amino-1H-pyrrolo[3,2-c]pyridine, N1-linked | HO-(CH2)4- | HO-(CH2)4- | H | O |
| 1169 | 6-amino-1H-pyrrolo[3,2-c]pyridine, N1-linked | HO-(CH2)4- | HO-(CH2)4- | H | O |
| 1170 | 4-amino-1H-pyrrolo[3,2-c]pyridine, N1-linked | HO-(CH2)4- | HO-(CH2)4- | H | O |
| 1171 | 3-amino-1H-pyrrolo[2,3-c]pyridine, N1-linked | HO-(CH2)4- | HO-(CH2)4- | H | O |
| 1172 | 2-amino-1H-pyrrolo[2,3-c]pyridine, N1-linked | HO-(CH2)4- | HO-(CH2)4- | H | O |
| 1173 | 7-amino-1H-pyrrolo[2,3-c]pyridine, N1-linked | HO-(CH2)4- | HO-(CH2)4- | H | O |

TABLE 1-continued
| Cmpd | W | X | Z | A | Q |
|---|---|---|---|---|---|
| 1174 | 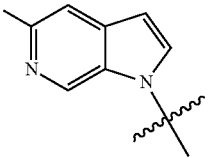 | 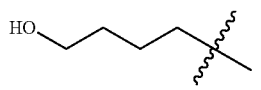 [SMILES: *CCCCO] | 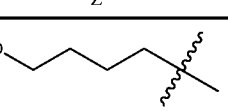 | H | O |
| 1175 | 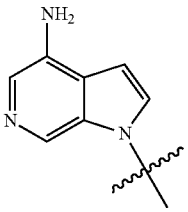 [SMILES: *n1ccc2c(N)cncc21] | 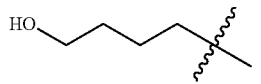 [SMILES: *CCCCO] | 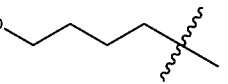 | H | O |
| 1176 | 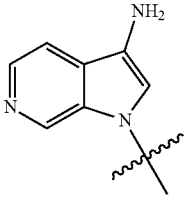 [SMILES: *n1cc(N)c2ccncc21] | 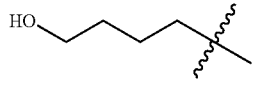 | 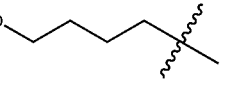 | H | O |
| 1177 | 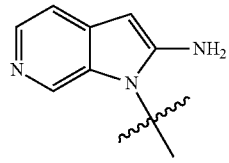 [SMILES: *n1c(N)cc2ccncc21] | 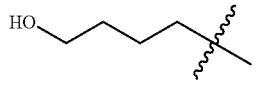 [SMILES: *CCCCO] | 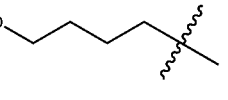 | H | O |
| 1178 | 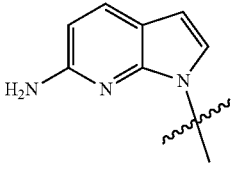 [SMILES: *n1ccc2ccc(N)nc21] | 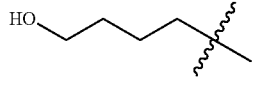 [SMILES: *CCCCO] | 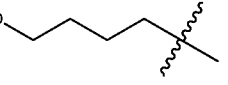 | H | O |
| 1179 | 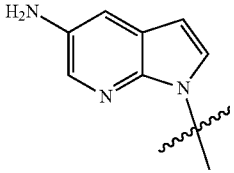 [SMILES: *n1ccc2cc(N)cnc21] | 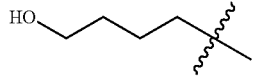 [SMILES: *CCCCO] | 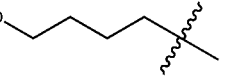 | H | O |
| 1180 | 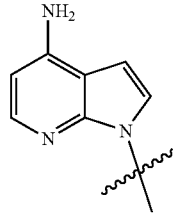 [SMILES: *n1ccc2c(N)ccnc21] | 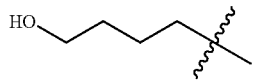 [SMILES: *CCCCO] | 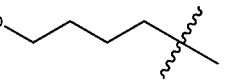 | H | O |
| 1181 | 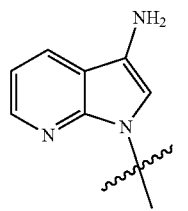 [SMILES: *n1cc(N)c2cccnc21] | 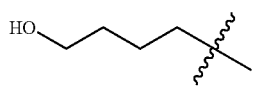 [SMILES: *CCCCO] | 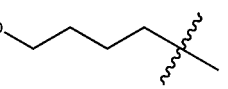 | H | O |

TABLE 1-continued

| Cmpd | W | X | Z | A | Q |
|---|---|---|---|---|---|
| 1182 | 7-azaindole with NH₂, N-linked | HO-(CH₂)₄-C(CH₃)< | HO-(CH₂)₄-C(CH₃)< | H | O |
| 1183 | 6-amino-pyrazolo[3,4-b]pyridine, N1-linked | HO-(CH₂)₄-C(CH₃)< | HO-(CH₂)₄-C(CH₃)< | H | O |
| 1184 | 5-amino-pyrazolo[3,4-b]pyridine, N1-linked | HO-(CH₂)₄-C(CH₃)< | HO-(CH₂)₄-C(CH₃)< | H | O |
| 1185 | 4-amino-pyrazolo[3,4-b]pyridine, N1-linked | HO-(CH₂)₄-C(CH₃)< | HO-(CH₂)₄-C(CH₃)< | H | O |
| 1186 | 3-amino-pyrazolo[3,4-b]pyridine, N1-linked | HO-(CH₂)₄-C(CH₃)< | HO-(CH₂)₄-C(CH₃)< | H | O |
| 1187 | 2-amino-purine, N9-linked | HO-(CH₂)₄-C(CH₃)< | HO-(CH₂)₄-C(CH₃)< | H | O |
| 1188 | adenine, N9-linked | HO-(CH₂)₄-C(CH₃)< | HO-(CH₂)₄-C(CH₃)< | H | O |
| 1189 | 8-amino-purine, N9-linked | HO-(CH₂)₄-C(CH₃)< | HO-(CH₂)₄-C(CH₃)< | H | O |

TABLE 1-continued
| Cmpd | W | X | Z | A | Q |
|------|---|---|---|---|---|
| 1190 | 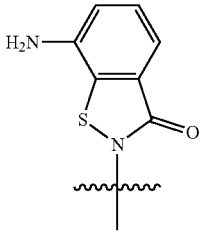 | 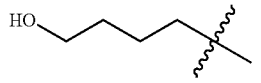 [SMILES: *CCCCO] | 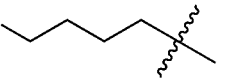 | H | O |
| 1191 | 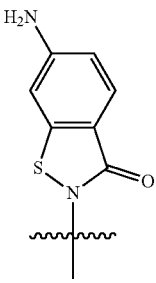 [SMILES: *n1sc2cc(N)ccc2c1=O] | 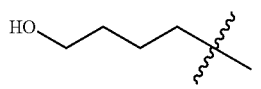 [SMILES: *CCCCO] | 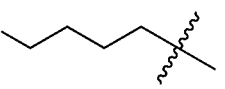 | H | O |
| 1192 | 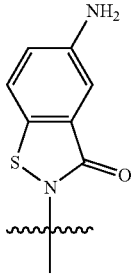 [SMILES: *n1sc2ccc(N)cc2c1=O] | 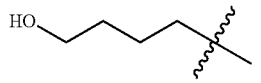 [SMILES: *CCCCO] | 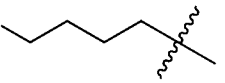 | H | O |
| 1193 | 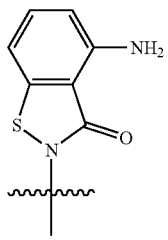 [SMILES: *n1sc2cccc(N)c2c1=O] | 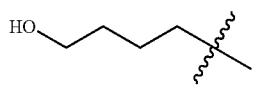 [SMILES: *CCCCO] | 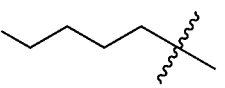 | H | O |
| 1194 | 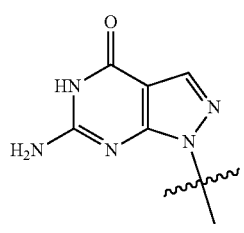 [SMILES: *n1ncc2c(=O)[nH]c(N)nc21] | 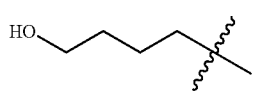 [SMILES: *CCCCO] | 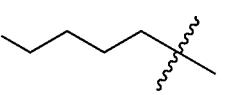 | H | O |
| 1195 | 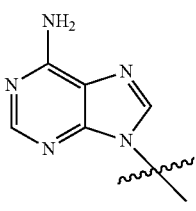 [SMILES: *n1cnc2c(N)ncnc21] | 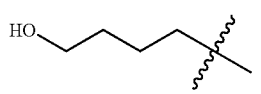 | 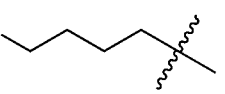 | H | O |

TABLE 1-continued

| Cmpd | W | X | Z | A | Q |
|---|---|---|---|---|---|
| 1196 | decahydroisoquinoline with NH₂ at 1-position | HO-(CH₂)₄- | HO-(CH₂)₄- | H | O |
| 1197 | decahydroisoquinoline with NH₂ substituent | HO-(CH₂)₄- | HO-(CH₂)₄- | H | O |
| 1198 | decahydroisoquinoline with H₂N substituent | HO-(CH₂)₄- | HO-(CH₂)₄- | H | O |
| 1199 | decahydroisoquinoline with H₂N substituent | HO-(CH₂)₄- | HO-(CH₂)₄- | H | O |
| 1200 | decahydroisoquinoline with NH₂ substituent | HO-(CH₂)₄- | HO-(CH₂)₄- | H | O |
| 1201 | decahydroisoquinoline with NH₂ substituent | HO-(CH₂)₄- | HO-(CH₂)₄- | H | O |
| 1202 | decahydroisoquinoline with NH₂ substituent | HO-(CH₂)₄- | HO-(CH₂)₄- | H | O |
| 1203 | decahydroquinoline with NH₂ substituent | HO-(CH₂)₄- | HO-(CH₂)₄- | H | O |
| 1204 | decahydroquinoline with H₂N substituent | HO-(CH₂)₄- | HO-(CH₂)₄- | H | O |

TABLE 1-continued
| Cmpd | W | X | Z | A | Q |
|---|---|---|---|---|---|
| 1205 | 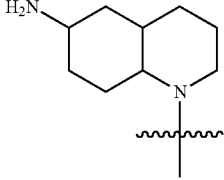 [SMILES: *N1CCCC2CC(N)CCC21] | 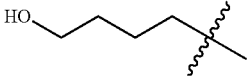 [SMILES: *CCCCO] | 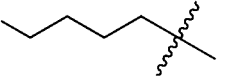 | H | O |
| 1206 | 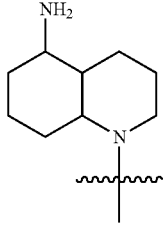 [SMILES: *N1CCCC2C(N)CCCC21] | 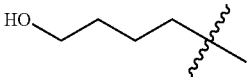 [SMILES: *CCCCO] | 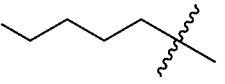 | H | O |
| 1207 | 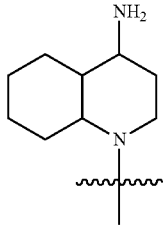 [SMILES: *N1CCC(N)C2CCCCC21] | 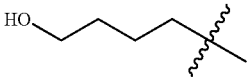 [SMILES: *CCCCO] | 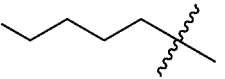 | H | O |
| 1208 | 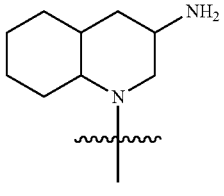 [SMILES: *N1CC(N)CC2CCCCC21] | 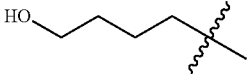 [SMILES: *CCCCO] | 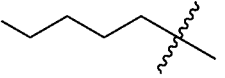 | H | O |
| 1209 | 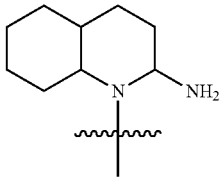 [SMILES: *N1C(N)CCC2CCCCC21] | 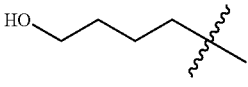 [SMILES: *CCCCO] | 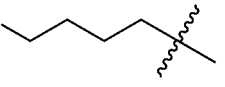 | H | O |
| 1210 | 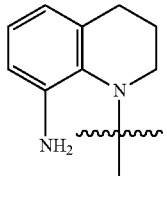 [SMILES: *N1CCCc2cccc(N)c21] | 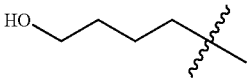 [SMILES: *CCCCO] | 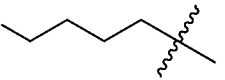 | H | O |
| 1211 | 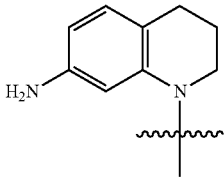 | 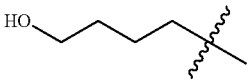 [SMILES: *CCCCO] | 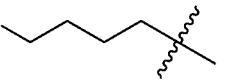 | H | O |

TABLE 1-continued

| Cmpd | W | X | Z | A | Q |
|---|---|---|---|---|---|
| 1212 | 6-amino-1,2,3,4-tetrahydroquinolin-1-yl | HO-(CH₂)₄-CH(-)- | HO-(CH₂)₄-CH(-)- | H | O |
| 1213 | 5-amino-1,2,3,4-tetrahydroquinolin-1-yl | HO-(CH₂)₄-CH(-)- | HO-(CH₂)₄-CH(-)- | H | O |
| 1214 | 4-amino-1,2,3,4-tetrahydroquinolin-1-yl | HO-(CH₂)₄-CH(-)- | HO-(CH₂)₄-CH(-)- | H | O |
| 1215 | 3-amino-1,2,3,4-tetrahydroquinolin-1-yl | HO-(CH₂)₄-CH(-)- | HO-(CH₂)₄-CH(-)- | H | O |
| 1216 | 2-amino-1,2,3,4-tetrahydroquinolin-1-yl | HO-(CH₂)₄-CH(-)- | HO-(CH₂)₄-CH(-)- | H | O |
| 1217 | 8-amino-1,2-dihydroquinolin-1-yl | HO-(CH₂)₄-CH(-)- | HO-(CH₂)₄-CH(-)- | H | O |
| 1218 | 7-amino-1,2-dihydroquinolin-1-yl | HO-(CH₂)₄-CH(-)- | HO-(CH₂)₄-CH(-)- | H | O |

TABLE 1-continued
| Cmpd | W | X | Z | A | Q |
|---|---|---|---|---|---|
| 1219 | 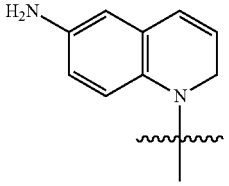 [SMILES: *N1CC=Cc2cc(N)ccc21] | 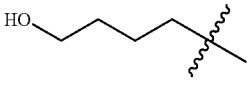 [SMILES: *CCCCO] | 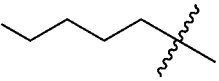 | H | O |
| 1220 | 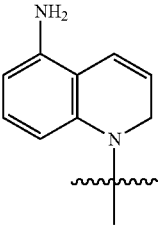 [SMILES: *N1CC=Cc2c(N)cccc21] | 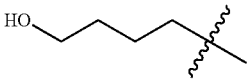 | 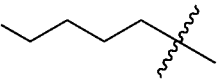 | H | O |
| 1221 | 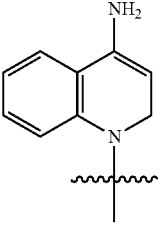 | 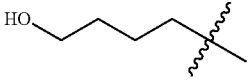 [SMILES: *CCCCO] | 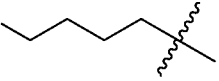 | H | O |
| 1222 | 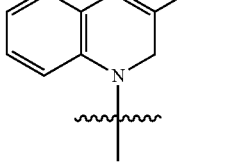 | 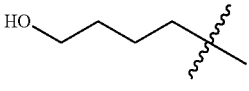 | 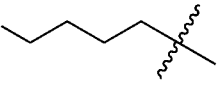 | H | O |
| 1223 | 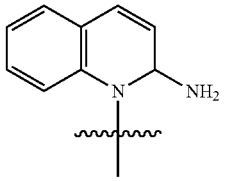 [SMILES: *N1c2ccccc2C=CC1N] | 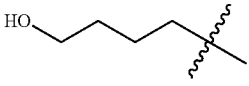 [SMILES: *CCCCO] | 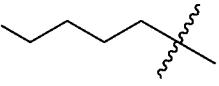 | H | O |
| 1224 | 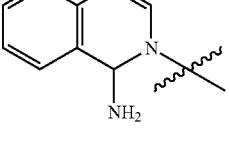 | 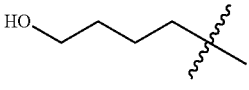 [SMILES: *CCCCO] | 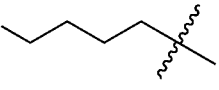 | H | O |
| 1225 | 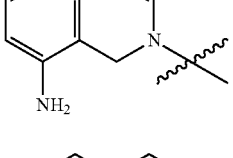 | 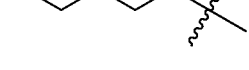 | 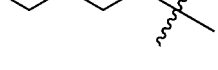 | H | O |
| 1226 | 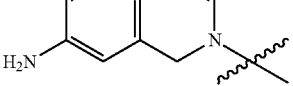 |  |  | H | O |

TABLE 1-continued

| Cmpd | W | X | Z | A | Q |
|---|---|---|---|---|---|
| 1227 | 6-amino-3,4-dihydroisoquinolin-2(1H)-yl | HO-(CH2)4-CH(-)- | HO-(CH2)4-CH(-)- | H | O |
| 1228 | 5-amino-3,4-dihydroisoquinolin-2(1H)-yl | HO-(CH2)4-CH(-)- | HO-(CH2)4-CH(-)- | H | O |
| 1229 | 4-amino-3,4-dihydroisoquinolin-2(1H)-yl | HO-(CH2)4-CH(-)- | HO-(CH2)4-CH(-)- | H | O |
| 1230 | 3-amino-3,4-dihydroisoquinolin-2(1H)-yl | HO-(CH2)4-CH(-)- | HO-(CH2)4-CH(-)- | H | O |
| 1231 | 8-amino-2-oxoquinolin-1(2H)-yl | HO-(CH2)4-CH(-)- | HO-(CH2)4-CH(-)- | H | O |
| 1232 | 7-amino-2-oxoquinolin-1(2H)-yl | HO-(CH2)4-CH(-)- | HO-(CH2)4-CH(-)- | H | O |
| 1233 | 6-amino-2-oxoquinolin-1(2H)-yl | HO-(CH2)4-CH(-)- | HO-(CH2)4-CH(-)- | H | O |
| 1234 | 5-amino-2-oxoquinolin-1(2H)-yl | HO-(CH2)4-CH(-)- | HO-(CH2)4-CH(-)- | H | O |

TABLE 1-continued
| Cmpd | W | X | Z | A | Q |
|------|---|---|---|---|---|
| 1235 | 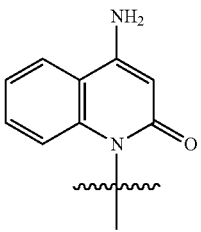 [SMILES: *n1c(=O)cc(N)c2ccccc21] | 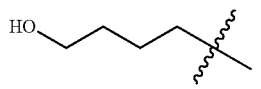 [SMILES: *CCCCO] | 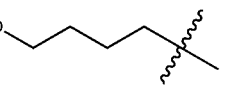 | H | O |
| 1236 | 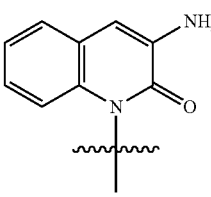 | 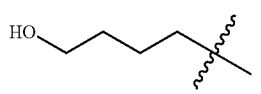 | 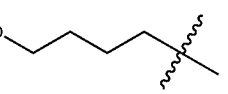 | H | O |
| 1237 | 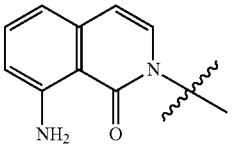 [SMILES: *n1ccc2cccc(N)c2c1=O] | 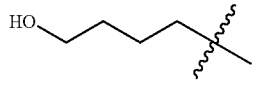 [SMILES: *CCCCO] | 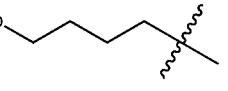 | H | O |
| 1238 | 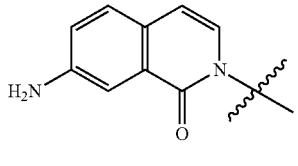 [SMILES: *n1ccc2ccc(N)cc2c1=O] | 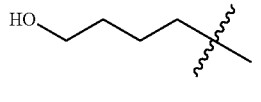 [SMILES: *CCCCO] | 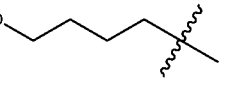 | H | O |
| 1239 | 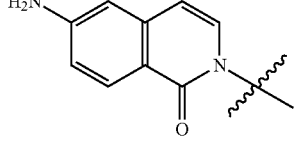 | 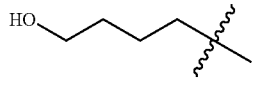 [SMILES: *CCCCO] | 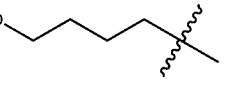 | H | O |
| 1240 | 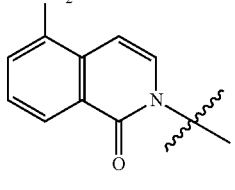 | 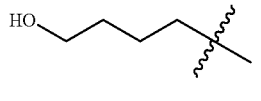 [SMILES: *CCCCO] | 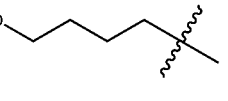 | H | O |
| 1241 | 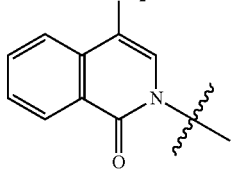 | 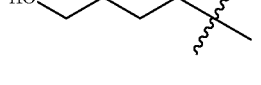 | 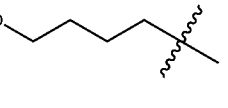 | H | O |
| 1242 | 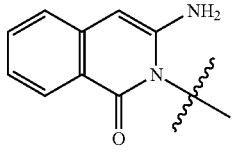 [SMILES: *n1c(N)cc2ccccc2c1=O] | 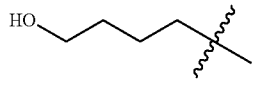 [SMILES: *CCCCO] | 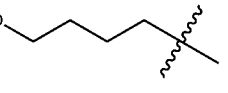 | H | O |

TABLE 1-continued
| Cmpd | W | X | Z | A | Q |
|---|---|---|---|---|---|
| 1243 | 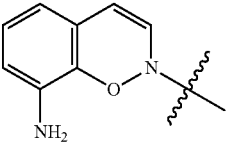 | 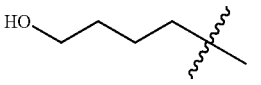 [SMILES: *CCCCO] | 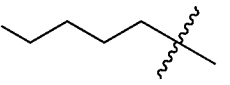 | H | O |
| 1244 | 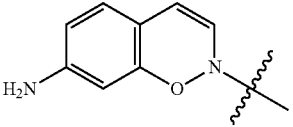 | 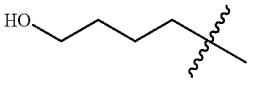 [SMILES: *CCCCO] | 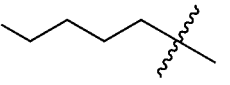 | H | O |
| 1245 | 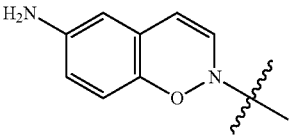 | 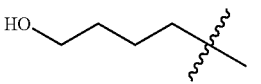 | 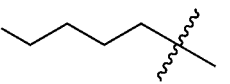 | H | O |
| 1246 | 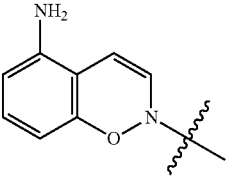 [SMILES: *N1C=Cc2c(N)cccc2O1] | 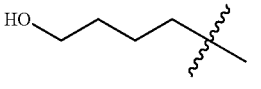 [SMILES: *CCCCO] | 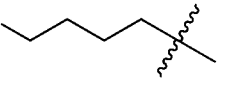 | H | O |
| 1247 | 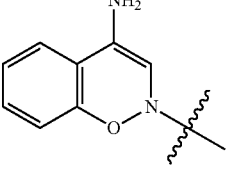 | 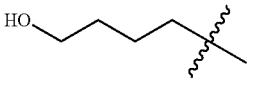 [SMILES: *CCCCO] | 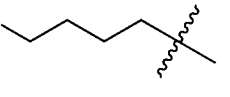 | H | O |
| 1248 | 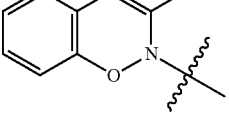 | 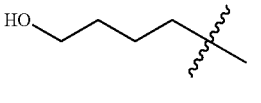 [SMILES: *CCCCO] | 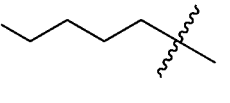 | H | O |
| 1249 | 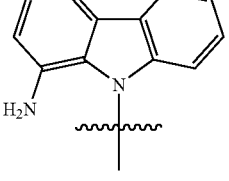 | 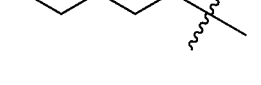 | 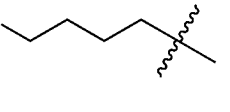 | H | O |
| 1250 | 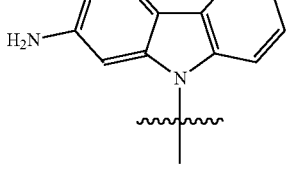 | 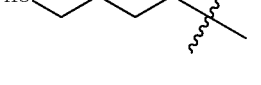 | 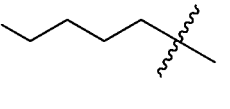 | H | O |
| 1251 | 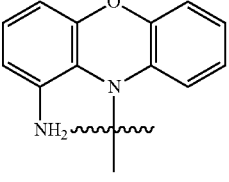 | 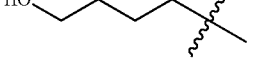 | 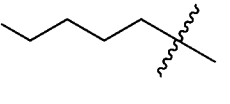 | H | O |

TABLE 1-continued

| Cmpd | W | X | Z | A | Q |
|------|---|---|---|---|---|
| 1252 | phenoxazine with H₂N substituent, N-linked | HO-(CH₂)₄-* | HO-(CH₂)₄-* | H | O |
| 1253 | phenothiazine with NH₂ substituent, N-linked | HO-(CH₂)₄-* | HO-(CH₂)₄-* | H | O |
| 1254 | phenothiazine with H₂N substituent, N-linked | HO-(CH₂)₄-* | HO-(CH₂)₄-* | H | O |
| 1255 | aminoadamantane-N linked | HO-(CH₂)₄-* | HO-(CH₂)₄-* | H | O |
| 1256 | aminoazepine, N-linked | HO-(CH₂)₄-* | HO-(CH₂)₄-* | H | O |
| 1257 | aminoazepine, N-linked | HO-(CH₂)₄-* | HO-(CH₂)₄-* | H | O |
| 1258 | aminoazepine, N-linked | HO-(CH₂)₄-* | HO-(CH₂)₄-* | H | O |

TABLE 1-continued

| Cmpd | W | X | Z | A | Q |
|---|---|---|---|---|---|
| 1259 | 4-amino-1H-1,3-diazepine (N1-linked) | HO-(CH2)4- | HO-(CH2)4- | H | O |
| 1260 | 4-amino-1H-1,2-diazepine (N1-linked) | HO-(CH2)4- | HO-(CH2)4- | H | O |
| 1261 | cytosin-1-yl | n-pentyl | n-pentyl | OMe | O |
| 1262 | 3-aminoaziridin-1-yl | n-pentyl | n-pentyl | OMe | O |
| 1263 | 2-aminoazetidin-1-yl | n-pentyl | n-pentyl | OMe | O |
| 1264 | 3-aminoazetidin-1-yl | n-pentyl | n-pentyl | OMe | O |
| 1265 | 2-amino-1,3-diazetidin-1-yl | n-pentyl | n-pentyl | OMe | O |
| 1266 | 3-amino-2-oxoazetidin-1-yl | n-pentyl | n-pentyl | OMe | O |

TABLE 1-continued

| Cmpd | W | X | Z | A | Q |
|---|---|---|---|---|---|
| 1267 | 3-amino-azetidinone (N-linked) | pentyl | pentyl | OMe | O |
| 1268 | 2-aminopyrrolidine (N-linked) | pentyl | pentyl | OMe | O |
| 1269 | 3-aminopyrrolidine (N-linked) | pentyl | pentyl | OMe | O |
| 1270 | 2-amino-2,5-dihydro-1H-pyrrole (N-linked) | pentyl | pentyl | OMe | O |
| 1271 | 3-amino-2,5-dihydro-1H-pyrrole (N-linked) | pentyl | pentyl | OMe | O |
| 1272 | 5-amino-3,4-dihydro-2H-pyrrole (N-linked) | pentyl | pentyl | OMe | O |
| 1273 | 4-amino-2,3-dihydro-1H-pyrrole (N-linked) | pentyl | pentyl | OMe | O |
| 1274 | 3-amino-2,3-dihydro-1H-pyrrole (N-linked) | pentyl | pentyl | OMe | O |

TABLE 1-continued

| Cmpd | W | X | Z | A | Q |
|---|---|---|---|---|---|
| 1275 | 2-amino-2,3-dihydro-1H-pyrrol-1-yl | pentyl | pentyl | OMe | O |
| 1276 | 5-amino-1H-pyrrol-1-yl | pentyl | pentyl | OMe | O |
| 1277 | 3-amino-1H-pyrrol-1-yl | pentyl | pentyl | OMe | O |
| 1278 | 3-amino-4,5-dihydro-1H-pyrazol-1-yl | pentyl | pentyl | OMe | O |
| 1279 | 4-amino-pyrazolidin-1-yl | pentyl | pentyl | OMe | O |
| 1280 | 3-amino-pyrazolidin-1-yl | pentyl | pentyl | OMe | O |
| 1281 | 4-amino-imidazolidin-1-yl | pentyl | pentyl | OMe | O |
| 1282 | 5-amino-imidazolidin-1-yl | pentyl | pentyl | OMe | O |

TABLE 1-continued

| Cmpd | W | X | Z | A | Q |
|---|---|---|---|---|---|
| 1283 | 2-amino-imidazolin-1-yl (HN, H₂N, N-linked) | pentyl | pentyl | OMe | O |
| 1284 | 3-amino-4,5-dihydropyrazol-1-yl | pentyl | pentyl | OMe | O |
| 1285 | 4-amino-4,5-dihydropyrazol-1-yl | pentyl | pentyl | OMe | O |
| 1286 | 5-amino-4,5-dihydropyrazol-1-yl | pentyl | pentyl | OMe | O |
| 1287 | 2-amino-4,5-dihydroimidazol-1-yl | pentyl | pentyl | OMe | O |
| 1288 | 4-amino-4,5-dihydroimidazol-1-yl | pentyl | pentyl | OMe | O |
| 1289 | 5-amino-4,5-dihydroimidazol-1-yl | pentyl | pentyl | OMe | O |
| 1290 | 3-amino-2,5-dioxopyrrolidin-1-yl | pentyl | pentyl | OMe | O |

TABLE 1-continued

| Cmpd | W | X | Z | A | Q |
|---|---|---|---|---|---|
| 1291 | 4-amino-hydantoin N-linked | pentyl | pentyl | OMe | O |
| 1292 | 5-amino-thiazolidine-2,4-dione N-linked | pentyl | pentyl | OMe | O |
| 1293 | 2-aminopiperidin-1-yl | pentyl | pentyl | OMe | O |
| 1294 | 3-aminopiperidin-1-yl | pentyl | pentyl | OMe | O |
| 1295 | 4-aminopiperidin-1-yl | pentyl | pentyl | OMe | O |
| 1296 | 3-aminopiperazin-1-yl | pentyl | pentyl | OMe | O |
| 1297 | 3-aminopiperazin-1-yl | pentyl | pentyl | OMe | O |

TABLE 1-continued

| Cmpd | W | X | Z | A | Q |
|---|---|---|---|---|---|
| 1298 | 3-amino-morpholinyl (N-linked) | pentyl | pentyl | OMe | O |
| 1299 | 2-amino-morpholinyl (N-linked) | pentyl | pentyl | OMe | O |
| 1300 | 3-amino-2H-1,2-oxazinyl (N-linked) | pentyl | pentyl | OMe | O |
| 1301 | 4-amino-2H-1,2-oxazinyl (N-linked) | pentyl | pentyl | OMe | O |
| 1302 | 5-amino-2H-1,2-oxazinyl (N-linked) | pentyl | pentyl | OMe | O |
| 1303 | 6-amino-2H-1,2-oxazinyl (N-linked) | pentyl | pentyl | OMe | O |
| 1304 | 3-amino-4H-1,4-oxazinyl (N-linked) | pentyl | pentyl | OMe | O |
| 1305 | 2-amino-4H-1,4-oxazinyl (N-linked) | pentyl | pentyl | OMe | O |

TABLE 1-continued
| Cmpd | W | X | Z | A | Q |
|---|---|---|---|---|---|
| 1306 | 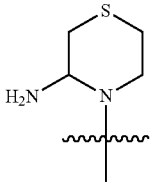 [SMILES: *N1CCSCC1N] | 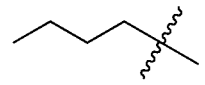 [SMILES: *CCCC] | 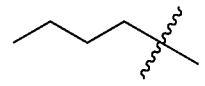 [SMILES: *CCCC] | OMe | O |
| 1307 | 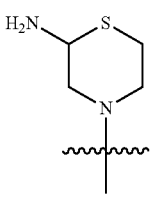 [SMILES: *N1CCSC(N)C1] | 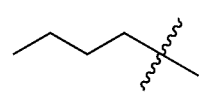 [SMILES: *CCCC] | 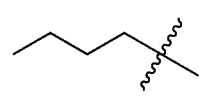 [SMILES: *CCCC] | OMe | O |
| 1308 | 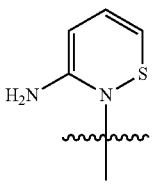 | 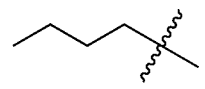 [SMILES: *CCCC] | 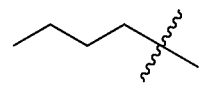 [SMILES: *CCCC] | OMe | O |
| 1309 | 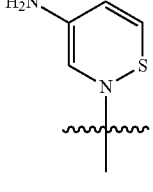 | 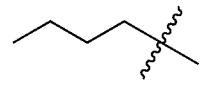 [SMILES: *CCCC] | 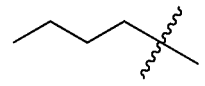 [SMILES: *CCCC] | OMe | O |
| 1310 | 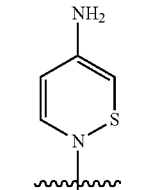 | 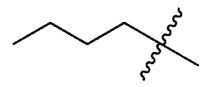 [SMILES: *CCCC] | 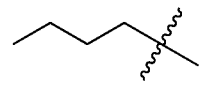 [SMILES: *CCCC] | OMe | O |
| 1311 | 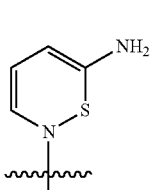 | 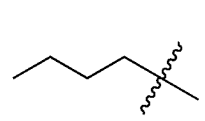 [SMILES: *CCCC] | 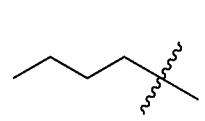 [SMILES: *CCCC] | OMe | O |
| 1312 | 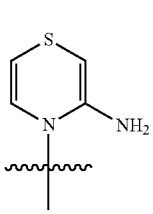 | 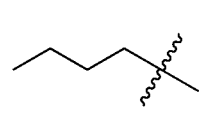 [SMILES: *CCCC] | 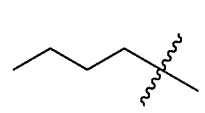 [SMILES: *CCCC] | OMe | O |

TABLE 1-continued

| Cmpd | W | X | Z | A | Q |
|---|---|---|---|---|---|
| 1313 | 2-amino-thiazine N-linked | pentyl | pentyl | OMe | O |
| 1314 | 1,1-dioxo-3-amino-thiomorpholine N-linked | pentyl | pentyl | OMe | O |
| 1315 | 1,1-dioxo-2-amino-thiomorpholine N-linked | pentyl | pentyl | OMe | O |
| 1316 | 2-amino-cyclopenta[b]pyrrole N-linked | pentyl | pentyl | OMe | O |
| 1317 | 3-amino-cyclopenta[b]pyrrole N-linked | pentyl | pentyl | OMe | O |
| 1318 | 4-amino-cyclopenta[b]pyrrole N-linked | pentyl | pentyl | OMe | O |
| 1319 | 5-amino-cyclopenta[b]pyrrole N-linked | pentyl | pentyl | OMe | O |

TABLE 1-continued

| Cmpd | W | X | Z | A | Q |
|------|---|---|---|---|---|
| 1320 | (bicyclic pyrrole with NH₂, N-linked) | pentyl | pentyl | OMe | O |
| 1321 | (bicyclic dipyrrole, H₂N-, NH, N-linked) | pentyl | pentyl | OMe | O |
| 1322 | (bicyclic dipyrrole, H₂N-, NH, N-linked) | pentyl | pentyl | OMe | O |
| 1323 | (bicyclic dipyrrole, NH₂, NH, N-linked) | pentyl | pentyl | OMe | O |
| 1324 | (bicyclic dipyrrole, NH, NH₂, N-linked) | pentyl | pentyl | OMe | O |
| 1325 | (bicyclic dipyrrole, H₂N-, NH, N-linked) | pentyl | pentyl | OMe | O |
| 1326 | (bicyclic dipyrrole, H₂N-, NH, N-linked) | pentyl | pentyl | OMe | O |

TABLE 1-continued

| Cmpd | W | X | Z | A | Q |
|---|---|---|---|---|---|
| 1327 | (pyrrolo-pyrrole with NH2, N-linked) | pentyl | pentyl | OMe | O |
| 1328 | (pyrrolo-pyrrole with NH2, N-linked) | pentyl | pentyl | OMe | O |
| 1329 | (pyrrolo-pyrrole with H2N, N-linked) | pentyl | pentyl | OMe | O |
| 1330 | (pyrrolo-pyrrole with H2N, N-linked) | pentyl | pentyl | OMe | O |
| 1331 | (pyrrolo-pyrrole with H2N, N-linked) | pentyl | pentyl | OMe | O |
| 1332 | (pyrrolo-pyrrole with NH2, N-linked) | pentyl | pentyl | OMe | O |
| 1333 | (furo-pyrrole with H2N, N-linked) | pentyl | pentyl | OMe | O |

TABLE 1-continued

| Cmpd | W | X | Z | A | Q |
|---|---|---|---|---|---|
| 1334 | 6-amino-4H-furo[3,2-b]pyrrole (N-linked) | pentyl | pentyl | OMe | O |
| 1335 | 3-amino-4H-furo[3,2-b]pyrrole (N-linked) | pentyl | pentyl | OMe | O |
| 1336 | 2-amino-4H-furo[3,2-b]pyrrole (N-linked) | pentyl | pentyl | OMe | O |
| 1337 | 5-amino-4H-furo[3,2-b]pyrrole (N-linked) | pentyl | pentyl | OMe | O |
| 1338 | 6-amino-4H-furo[2,3-b]pyrrole (N-linked) | pentyl | pentyl | OMe | O |
| 1339 | 2-amino-4H-furo[3,2-b]pyrrole (N-linked) | pentyl | pentyl | OMe | O |
| 1340 | 3-amino-4H-furo[3,2-b]pyrrole (N-linked) | pentyl | pentyl | OMe | O |

TABLE 1-continued

| Cmpd | W | X | Z | A | Q |
|---|---|---|---|---|---|
| 1341 | (H2N-pyrrolo[2,3-b]thiophene, N-substituted) | neopentyl | neopentyl | OMe | O |
| 1342 | (H2N-pyrrolo[2,3-b]thiophene isomer, N-substituted) | neopentyl | neopentyl | OMe | O |
| 1343 | (H2N-pyrrolo[2,3-b]thiophene isomer, N-substituted) | neopentyl | neopentyl | OMe | O |
| 1344 | (H2N-pyrrolo[2,3-b]thiophene isomer, N-substituted) | neopentyl | neopentyl | OMe | O |
| 1345 | (H2N-pyrrolo[3,2-b]thiophene, N-substituted) | neopentyl | neopentyl | OMe | O |
| 1346 | (H2N-pyrrolo[3,2-b]thiophene isomer, N-substituted) | neopentyl | neopentyl | OMe | O |
| 1347 | (H2N-pyrrolo[3,2-b]thiophene isomer, N-substituted) | neopentyl | neopentyl | OMe | O |

TABLE 1-continued

| Cmpd | W | X | Z | A | Q |
|---|---|---|---|---|---|
| 1348 | thieno-pyrrole-NH₂ | pentyl | pentyl | OMe | O |
| 1349 | 7-amino-indoline (N-linked) | pentyl | pentyl | OMe | O |
| 1350 | 6-amino-indoline (N-linked) | pentyl | pentyl | OMe | O |
| 1351 | 4-amino-indoline (N-linked) | pentyl | pentyl | OMe | O |
| 1352 | 3-amino-indoline (N-linked) | pentyl | pentyl | OMe | O |
| 1353 | 2-amino-indoline (N-linked) | pentyl | pentyl | OMe | O |
| 1354 | 7-amino-indole (N-linked) | pentyl | pentyl | OMe | O |
| 1355 | 6-amino-indole (N-linked) | pentyl | pentyl | OMe | O |

TABLE 1-continued

| Cmpd | W | X | Z | A | Q |
|---|---|---|---|---|---|
| 1356 | H₂N-5-aminoindole (N-substituted) | pentyl | pentyl | OMe | O |
| 1357 | 4-aminoindole (N-substituted) | pentyl | pentyl | OMe | O |
| 1358 | 3-aminoindole (N-substituted) | pentyl | pentyl | OMe | O |
| 1359 | 2-aminoindole (N-substituted) | pentyl | pentyl | OMe | O |
| 1360 | 1-amino-2H-isoindole (N-substituted) | pentyl | pentyl | OMe | O |
| 1361 | 7-amino-2H-isoindole (N-substituted) | pentyl | pentyl | OMe | O |
| 1362 | 5-amino-2H-isoindole (N-substituted) | pentyl | pentyl | OMe | O |

TABLE 1-continued

| Cmpd | W | X | Z | A | Q |
|------|---|---|---|---|---|
| 1363 | 7-amino-indazol-1-yl (gem-dimethyl linker) | pentyl (gem-dimethyl) | pentyl (gem-dimethyl) | OMe | O |
| 1364 | 6-amino-indazol-1-yl (gem-dimethyl linker) | pentyl (gem-dimethyl) | pentyl (gem-dimethyl) | OMe | O |
| 1365 | 5-amino-indazol-1-yl (gem-dimethyl linker) | pentyl (gem-dimethyl) | pentyl (gem-dimethyl) | OMe | O |
| 1366 | 4-amino-indazol-1-yl (gem-dimethyl linker) | pentyl (gem-dimethyl) | pentyl (gem-dimethyl) | OMe | O |
| 1367 | 3-amino-indazol-1-yl (gem-dimethyl linker) | pentyl (gem-dimethyl) | pentyl (gem-dimethyl) | OMe | O |
| 1368 | 7-amino-benzimidazol-1-yl (gem-dimethyl linker) | pentyl (gem-dimethyl) | pentyl (gem-dimethyl) | OMe | O |
| 1369 | 6-amino-benzimidazol-1-yl (gem-dimethyl linker) | pentyl (gem-dimethyl) | pentyl (gem-dimethyl) | OMe | O |
| 1370 | 5-amino-benzimidazol-1-yl (gem-dimethyl linker) | pentyl (gem-dimethyl) | pentyl (gem-dimethyl) | OMe | O |

TABLE 1-continued

| Cmpd | W | X | Z | A | Q |
|---|---|---|---|---|---|
| 1371 | 4-amino-benzimidazol-1-yl | pentyl | pentyl | | O |
| 1372 | 2-amino-benzimidazol-1-yl | pentyl | pentyl | OMe | O |
| 1373 | 7-amino-pyrrolo[3,2-b]pyridin-1-yl | pentyl | pentyl | OMe | O |
| 1374 | 6-amino-pyrrolo[3,2-b]pyridin-1-yl | pentyl | pentyl | OMe | O |
| 1375 | 5-amino-pyrrolo[3,2-b]pyridin-1-yl | pentyl | pentyl | OMe | O |
| 1376 | 3-amino-pyrrolo[3,2-b]pyridin-1-yl | pentyl | pentyl | OMe | O |
| 1377 | 2-amino-pyrrolo[3,2-b]pyridin-1-yl | pentyl | pentyl | OMe | O |
| 1378 | 7-amino-pyrrolo[3,2-c]pyridin-1-yl | pentyl | pentyl | OMe | O |

TABLE 1-continued
| Cmpd | W | X | Z | A | Q |
|---|---|---|---|---|---|
| 1379 | 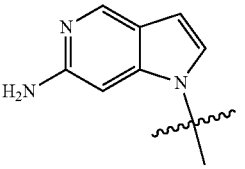 | 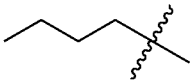 [SMILES: *CCCC] | 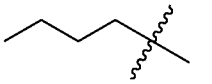 [SMILES: *CCCC] | OMe | O |
| 1380 | 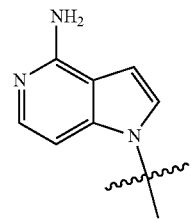 [SMILES: *n1ccc2c(N)nccc21] | 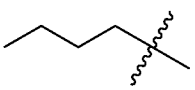 [SMILES: *CCCC] | 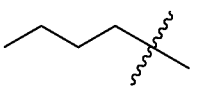 [SMILES: *CCCC] | OMe | O |
| 1381 | 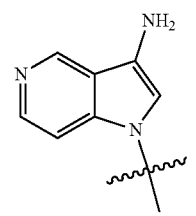 [SMILES: *n1cc(N)c2cnccc21] | 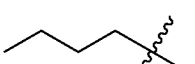 | 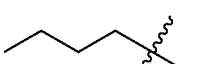 | OMe | O |
| 1382 | 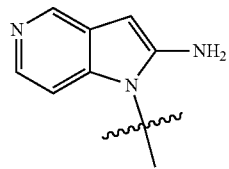 [SMILES: *n1c(N)cc2cnccc21] | 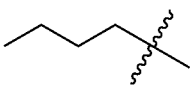 [SMILES: *CCCC] | 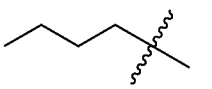 [SMILES: *CCCC] | OMe | O |
| 1383 | 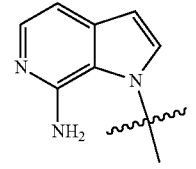 [SMILES: *n1ccc2ccnc(N)c21] | 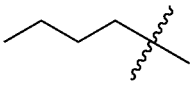 [SMILES: *CCCC] | 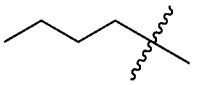 [SMILES: *CCCC] | OMe | O |
| 1384 | 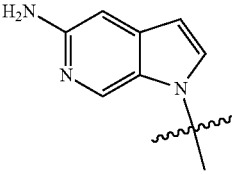 | 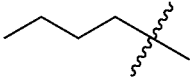 [SMILES: *CCCC] | 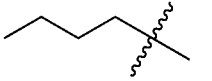 [SMILES: *CCCC] | OMe | O |
| 1385 | 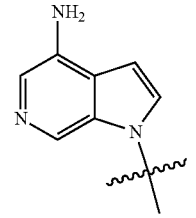 [SMILES: *n1ccc2c(N)cncc21] | 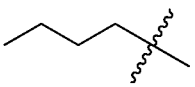 | 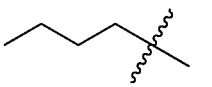 [SMILES: *CCCC] | OMe | O |
| 1386 | 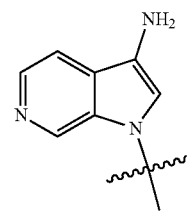 [SMILES: *n1cc(N)c2ccncc21] | 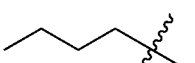 | 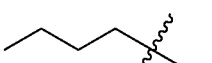 | OMe | O |

TABLE 1-continued

| Cmpd | W | X | Z | A | Q |
|---|---|---|---|---|---|
| 1387 | 2-amino-pyrrolo[3,2-c]pyridine (N-linked) | pentyl | pentyl | OMe | O |
| 1388 | 6-amino-pyrrolo[2,3-b]pyridine (N-linked) | pentyl | pentyl | OMe | O |
| 1389 | 5-amino-pyrrolo[2,3-b]pyridine (N-linked) | pentyl | pentyl | OMe | O |
| 1390 | 4-amino-pyrrolo[2,3-b]pyridine (N-linked) | pentyl | pentyl | OMe | O |
| 1391 | 3-amino-pyrrolo[2,3-b]pyridine (N-linked) | pentyl | pentyl | OMe | O |
| 1392 | 2-amino-pyrrolo[2,3-b]pyridine (N-linked) | pentyl | pentyl | OMe | O |
| 1393 | 6-amino-pyrazolo[3,4-b]pyridine (N-linked) | pentyl | pentyl | OMe | O |
| 1394 | 5-amino-pyrazolo[3,4-b]pyridine (N-linked) | pentyl | pentyl | OMe | O |

TABLE 1-continued

| Cmpd | W | X | Z | A | Q |
|---|---|---|---|---|---|
| 1395 | 4-amino-pyrazolo[3,4-b]pyridin-1-yl (N1-linked) | pentyl | pentyl | OMe | O |
| 1396 | 3-amino-pyrazolo[3,4-b]pyridin-1-yl (N1-linked) | pentyl | pentyl | OMe | O |
| 1397 | 2-amino-purin-9-yl | pentyl | pentyl | OMe | O |
| 1398 | adenin-9-yl | pentyl | pentyl | OMe | O |
| 1399 | 8-amino-purin-9-yl | pentyl | pentyl | OMe | O |
| 1400 | 7-amino-benzo[d]isothiazol-3(2H)-on-2-yl | pentyl | pentyl | OMe | O |
| 1401 | 6-amino-benzo[d]isothiazol-3(2H)-on-2-yl | pentyl | pentyl | OMe | O |

TABLE 1-continued
| Cmpd | W | X | Z | A | Q |
|---|---|---|---|---|---|
| 1402 | 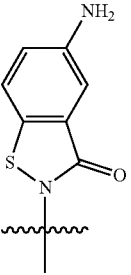 [SMILES: *n1sc2ccc(N)cc2c1=O] | 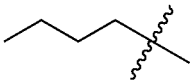 [SMILES: *CCCC] | 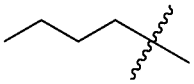 [SMILES: *CCCC] | OMe | O |
| 1403 | 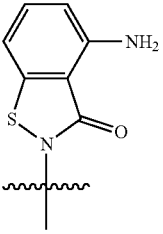 [SMILES: *n1sc2cccc(N)c2c1=O] | 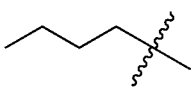 [SMILES: *CCCC] | 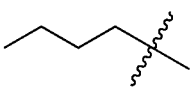 [SMILES: *CCCC] | OMe | O |
| 1404 | 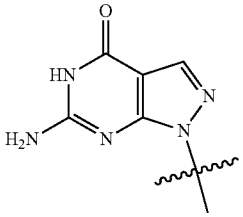 [SMILES: *n1ncc2c(=O)[nH]c(N)nc21] | 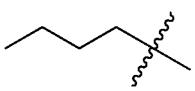 | 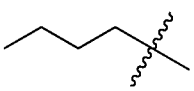 [SMILES: *CCCC] | OMe | O |
| 1405 | 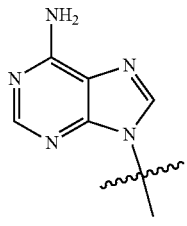 [SMILES: *n1cnc2c(N)ncnc21] | 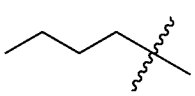 | 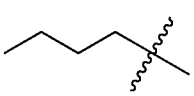 [SMILES: *CCCC] | OMe | O |
| 1406 | 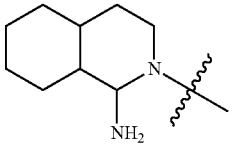 [SMILES: *N1CCC2CCCCC2C1N] | 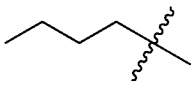 [SMILES: *CCCC] | 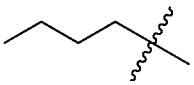 [SMILES: *CCCC] | OMe | O |
| 1407 | 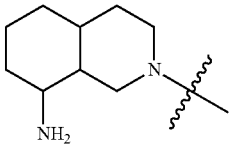 [SMILES: *N1CCC2CCCC(N)C2C1] | 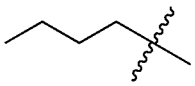 | 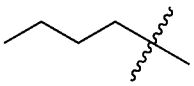 | OMe | O |
| 1408 | 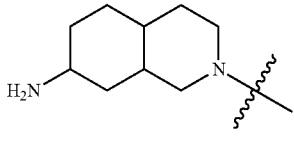 [SMILES: *N1CCC2CCC(N)CC2C1] | 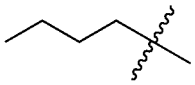 [SMILES: *CCCC] | 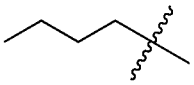 | OMe | O |
| 1409 | 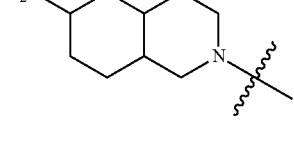 | 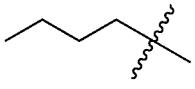 [SMILES: *CCCC] | 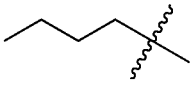 [SMILES: *CCCC] | OMe | O |

TABLE 1-continued
| Cmpd | W | X | Z | A | Q |
|---|---|---|---|---|---|
| 1410 | 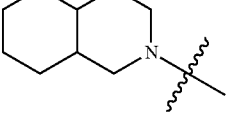 | 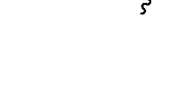 |  | OMe | O |
| 1411 | 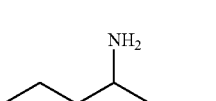 | 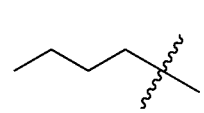 [SMILES: *CCCC] | 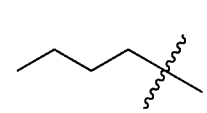 [SMILES: *CCCC] | OMe | O |
| 1412 | 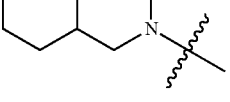 |  |  | OMe | O |
| 1413 | 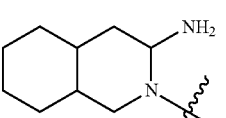 | 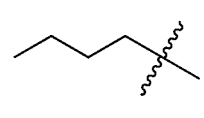 [SMILES: *CCCC] | 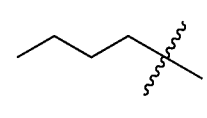 [SMILES: *CCCC] | OMe | O |
| 1414 | 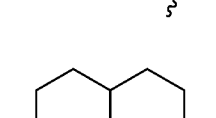 | 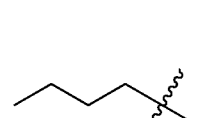 | 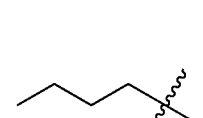 | OMe | O |
| 1415 | 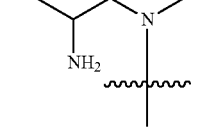 |  | 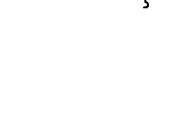 | OMe | O |
| 1416 | 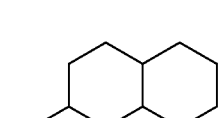 | 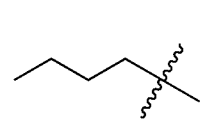 | 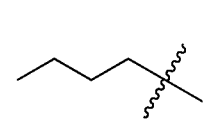 | OMe | O |

TABLE 1-continued
| Cmpd | W | X | Z | A | Q |
|------|---|---|---|---|---|
| 1417 | 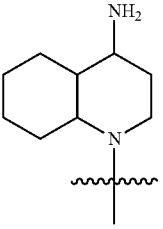 [SMILES: *N1CCC(N)C2CCCCC21] | 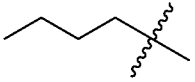 |  | OMe | O |
| 1418 | 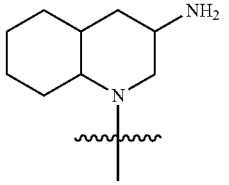 [SMILES: *N1CC(N)CC2CCCCC21] | 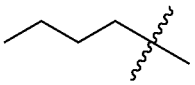 [SMILES: *CCCC] |  | OMe | O |
| 1419 | 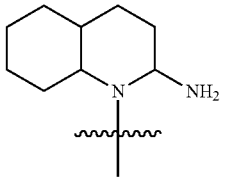 [SMILES: *N1C(N)CCC2CCCCC21] | 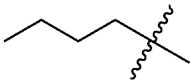 |  | OMe | O |
| 1420 | 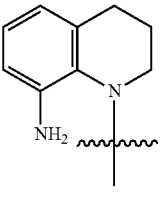 | 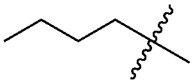 [SMILES: *CCCC] |  | OMe | O |
| 1421 | 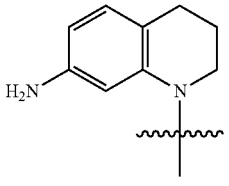 [SMILES: *N1CCCc2ccc(N)cc21] | 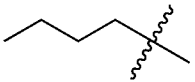 [SMILES: *CCCC] |  | OMe | O |
| 1422 | 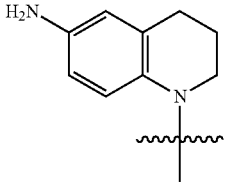 [SMILES: *N1CCCc2cc(N)ccc21] | 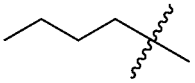 [SMILES: *CCCC] |  | OMe | O |
| 1423 | 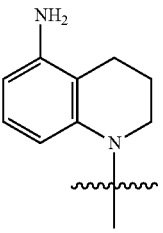 | 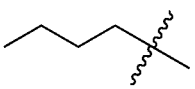 [SMILES: *CCCC] |  | OMe | O |

TABLE 1-continued

| Cmpd | W | X | Z | A | Q |
|---|---|---|---|---|---|
| 1424 | 4-amino-1,2,3,4-tetrahydroquinolin-1-yl | pentyl | pentyl | OMe | O |
| 1425 | 3-amino-1,2,3,4-tetrahydroquinolin-1-yl | pentyl | pentyl | OMe | O |
| 1426 | 2-amino-1,2,3,4-tetrahydroquinolin-1-yl | pentyl | pentyl | OMe | O |
| 1427 | 8-amino-1,2-dihydroquinolin-1-yl | pentyl | pentyl | OMe | O |
| 1428 | 7-amino-1,2-dihydroquinolin-1-yl | pentyl | pentyl | OMe | O |
| 1429 | 6-amino-1,2-dihydroquinolin-1-yl | pentyl | pentyl | OMe | O |
| 1430 | 5-amino-1,2-dihydroquinolin-1-yl | pentyl | pentyl | OMe | O |

TABLE 1-continued

| Cmpd | W | X | Z | A | Q |
|------|---|---|---|---|---|
| 1431 | 4-amino-quinoline (N-linked) | pentyl | pentyl | OMe | O |
| 1432 | 3-amino-quinoline (N-linked) | pentyl | pentyl | OMe | O |
| 1433 | 2-amino-quinoline (N-linked) | pentyl | pentyl | OMe | O |
| 1434 | 1-amino-tetrahydroisoquinoline (N-linked) | pentyl | pentyl | OMe | O |
| 1435 | 8-amino-tetrahydroisoquinoline (N-linked) | pentyl | pentyl | OMe | O |
| 1436 | 7-amino-tetrahydroisoquinoline (N-linked) | pentyl | pentyl | OMe | O |
| 1437 | 6-amino-tetrahydroisoquinoline (N-linked) | pentyl | pentyl | OMe | O |
| 1438 | 5-amino-tetrahydroisoquinoline (N-linked) | pentyl | pentyl | OMe | O |
| 1439 | 4-amino-tetrahydroisoquinoline (N-linked) | pentyl | pentyl | OMe | O |

TABLE 1-continued

| Cmpd | W | X | Z | A | Q |
|---|---|---|---|---|---|
| 1440 | 3-amino-1,2-dihydroisoquinolin-2-yl (CH-linked) | pentyl | pentyl | OMe | O |
| 1441 | 8-amino-2-oxoquinolin-1(2H)-yl | pentyl | pentyl | OMe | O |
| 1442 | 7-amino-2-oxoquinolin-1(2H)-yl | pentyl | pentyl | OMe | O |
| 1443 | 6-amino-2-oxoquinolin-1(2H)-yl | pentyl | pentyl | OMe | O |
| 1444 | 5-amino-2-oxoquinolin-1(2H)-yl | pentyl | pentyl | OMe | O |
| 1445 | 4-amino-2-oxoquinolin-1(2H)-yl | pentyl | pentyl | OMe | O |
| 1446 | 3-amino-2-oxoquinolin-1(2H)-yl | pentyl | pentyl | OMe | O |
| 1447 | 8-amino-1-oxoisoquinolin-2(1H)-yl | pentyl | pentyl | OMe | O |

TABLE 1-continued
| Cmpd | W | X | Z | A | Q |
|---|---|---|---|---|---|
| 1448 | 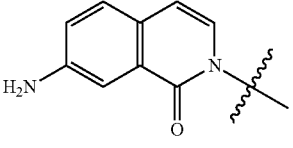 [SMILES: *n1ccc2ccc(N)cc2c1=O] | 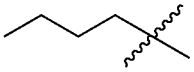 [SMILES: *CCCC] | 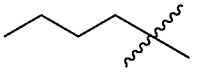 [SMILES: *CCCC] | OMe | O |
| 1449 | 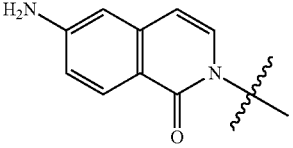 [SMILES: *n1ccc2cc(N)ccc2c1=O] | 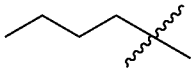 [SMILES: *CCCC] | 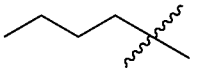 [SMILES: *CCCC] | OMe | O |
| 1450 | 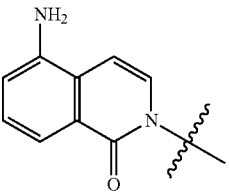 [SMILES: *n1ccc2c(N)cccc2c1=O] | 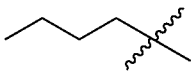 [SMILES: *CCCC] | 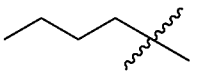 [SMILES: *CCCC] | OMe | O |
| 1451 | 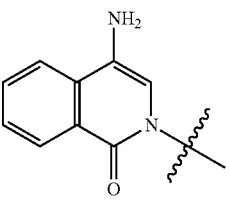 [SMILES: *n1cc(N)c2ccccc2c1=O] | 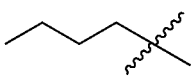 [SMILES: *CCCC] | 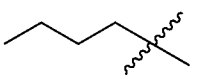 [SMILES: *CCCC] | OMe | O |
| 1452 | 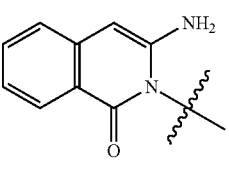 [SMILES: *n1c(N)cc2ccccc2c1=O] | 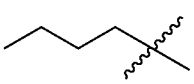 | 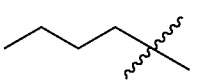 [SMILES: *CCCC] | OMe | O |
| 1453 | 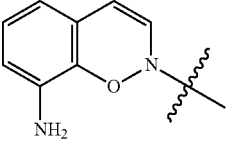 | 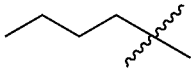 [SMILES: *CCCC] | 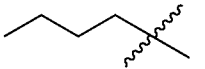 [SMILES: *CCCC] | OMe | O |
| 1454 | 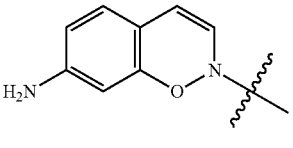 [SMILES: *N1C=Cc2ccc(N)cc2O1] | 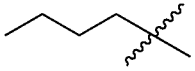 [SMILES: *CCCC] |  | OMe | O |
| 1455 | 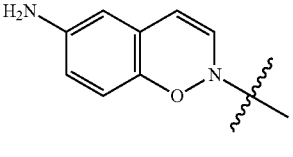 | 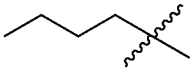 | 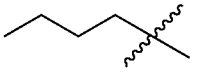 | OMe | O |
| 1456 | 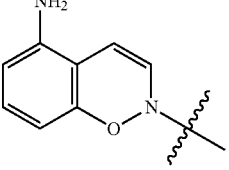 | 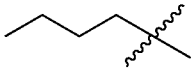 |  | OMe | O |

TABLE 1-continued

| Cmpd | W | X | Z | A | Q |
|---|---|---|---|---|---|
| 1457 | 4-amino-2H-benzo[e][1,2]oxazine (N-linked) | pentyl | pentyl | OMe | O |
| 1458 | 3-amino-2H-benzo[e][1,2]oxazine (N-linked) | pentyl | pentyl | OMe | O |
| 1459 | 1-amino-9H-carbazole (N9-linked) | pentyl | pentyl | OMe | O |
| 1460 | 2-amino-9H-carbazole (N9-linked) | pentyl | pentyl | OMe | O |
| 1461 | 1-amino-10H-phenoxazine (N10-linked) | pentyl | pentyl | OMe | O |
| 1462 | 2-amino-10H-phenoxazine (N10-linked) | pentyl | pentyl | OMe | O |
| 1463 | 1-amino-10H-phenothiazine (N10-linked) | pentyl | pentyl | OMe | O |
| 1464 | 2-amino-10H-phenothiazine (N10-linked) | pentyl | pentyl | OMe | O |

TABLE 1-continued
| Cmpd | W | X | Z | A | Q |
|---|---|---|---|---|---|
| 1465 | 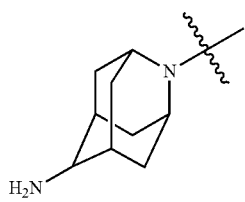 [SMILES: *N1C2CC3CC1CC(C2)C3N] | 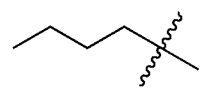 | 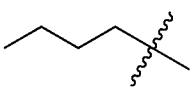 | OMe | O |
| 1466 | 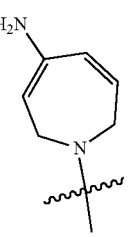 | 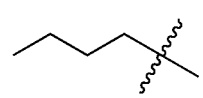 [SMILES: *CCCC] | 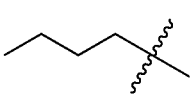 [SMILES: *CCCC] | OMe | O |
| 1467 | 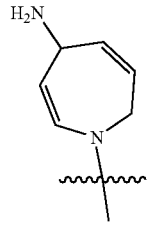 [SMILES: *N1C=CC(N)C=CC1] | 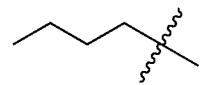 [SMILES: *CCCC] | 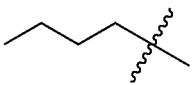 [SMILES: *CCCC] | OMe | O |
| 1468 | 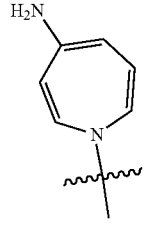 [SMILES: *N1C=CC=C(N)C=C1] | 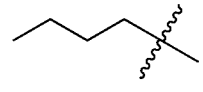 [SMILES: *CCCC] | 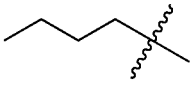 [SMILES: *CCCC] | OMe | O |
| 1469 | 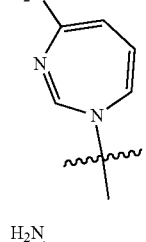 | 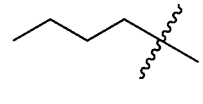 [SMILES: *CCCC] | 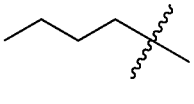 [SMILES: *CCCC] | OMe | O |
| 1470 | 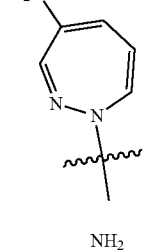 | 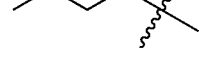 | 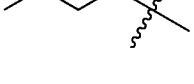 | OMe | O |
| 1471 | 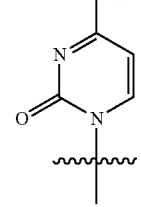 | 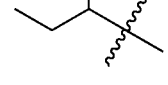 | 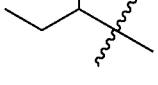 | OMe | O |

TABLE 1-continued

| Cmpd | W | X | Z | A | Q |
|---|---|---|---|---|---|
| 1472 | aziridine-NH₂ | 3-pentyl | 3-pentyl | OMe | O |
| 1473 | azetidine-2-NH₂ | 3-pentyl | 3-pentyl | OMe | O |
| 1474 | azetidine-3-NH₂ | 3-pentyl | 3-pentyl | OMe | O |
| 1475 | 2-amino-azetidine-NH | 3-pentyl | 3-pentyl | OMe | O |
| 1476 | 3-amino-azetidin-2-one | 3-pentyl | 3-pentyl | OMe | O |
| 1477 | 4-amino-azetidin-2-one | 3-pentyl | 3-pentyl | OMe | O |
| 1478 | 2-amino-pyrrolidine | 3-pentyl | 3-pentyl | OMe | O |
| 1479 | 3-amino-pyrrolidine | 3-pentyl | 3-pentyl | OMe | O |
| 1480 | 2-amino-2,5-dihydropyrrole | 3-pentyl | 3-pentyl | OMe | O |

TABLE 1-continued
| Cmpd | W | X | Z | A | Q |
|---|---|---|---|---|---|
| 1481 | 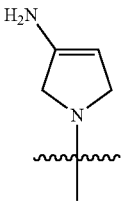 | 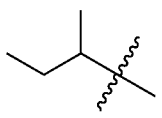 | 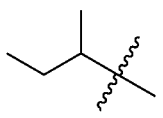 [SMILES: *C(C)CC] | OMe | O |
| 1482 | 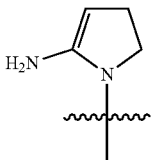 | 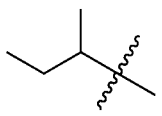 [SMILES: *C(C)CC] | 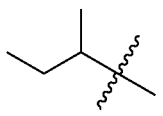 [SMILES: *C(C)CC] | OMe | O |
| 1483 | 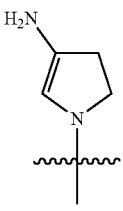 | 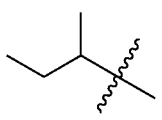 | 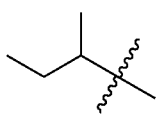 [SMILES: *C(C)CC] | OMe | O |
| 1484 | 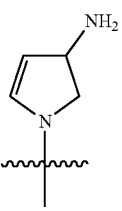 | 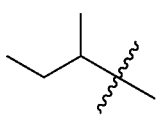 [SMILES: *C(C)CC] | 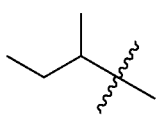 [SMILES: *C(C)CC] | OMe | O |
| 1485 | 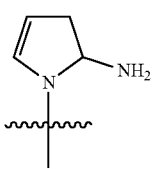 | 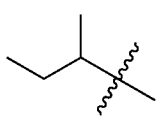 [SMILES: *C(C)CC] | 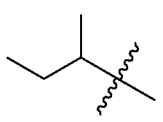 [SMILES: *C(C)CC] | OMe | O |
| 1486 | 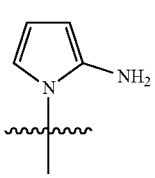 | 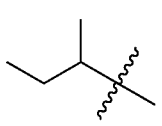 [SMILES: *C(C)CC] | 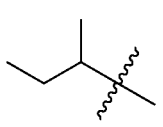 [SMILES: *C(C)CC] | OMe | O |
| 1487 | 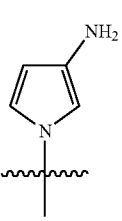 | 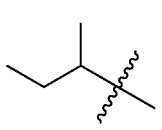 [SMILES: *C(C)CC] | 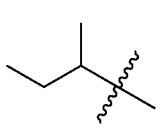 [SMILES: *C(C)CC] | OMe | O |
| 1488 | 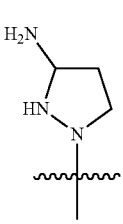 | 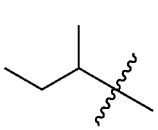 [SMILES: *C(C)CC] | 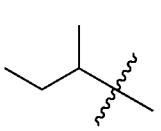 [SMILES: *C(C)CC] | OMe | O |

TABLE 1-continued

| Cmpd | W | X | Z | A | Q |
|------|---|---|---|---|---|
| 1489 | 4-amino-pyrazolidine (N1-attached) | 3-methylpentyl | 3-methylpentyl | OMe | O |
| 1490 | 3-amino-pyrazolidine (N1-attached) | 3-methylpentyl | 3-methylpentyl | OMe | O |
| 1491 | 5-amino-imidazolidine (N1-attached) | 3-methylpentyl | 3-methylpentyl | OMe | O |
| 1492 | 5-amino-imidazolidine (N1-attached, alt) | 3-methylpentyl | 3-methylpentyl | OMe | O |
| 1493 | 2-amino-imidazolidine (N1-attached) | 3-methylpentyl | 3-methylpentyl | OMe | O |
| 1494 | 3-amino-4,5-dihydropyrazole (N1-attached) | 3-methylpentyl | 3-methylpentyl | OMe | O |
| 1495 | 4-amino-4,5-dihydropyrazole (N1-attached) | 3-methylpentyl | 3-methylpentyl | OMe | O |
| 1496 | 5-amino-4,5-dihydropyrazole (N1-attached) | 3-methylpentyl | 3-methylpentyl | OMe | O |

TABLE 1-continued

| Cmpd | W | X | Z | A | Q |
|------|---|---|---|---|---|
| 1497 | 2-amino-4,5-dihydroimidazol-1-yl (N-linked) | 3-pentyl | 3-pentyl | OMe | O |
| 1498 | 5-amino-4,5-dihydroimidazol-1-yl | 3-pentyl | 3-pentyl | OMe | O |
| 1499 | 5-amino-4,5-dihydroimidazol-1-yl (alternate) | 3-pentyl | 3-pentyl | OMe | O |
| 1500 | 3-amino-2,5-dioxopyrrolidin-1-yl | 3-pentyl | 3-pentyl | OMe | O |
| 1501 | 5-amino-2,4-dioxoimidazolidin-3-yl | 3-pentyl | 3-pentyl | OMe | O |
| 1502 | 5-amino-2,4-dioxothiazolidin-3-yl | 3-pentyl | 3-pentyl | OMe | O |
| 1503 | 2-aminopiperidin-1-yl | 3-pentyl | 3-pentyl | OMe | O |
| 1504 | 3-aminopiperidin-1-yl | 3-pentyl | 3-pentyl | OMe | O |

TABLE 1-continued

| Cmpd | W | X | Z | A | Q |
|------|---|---|---|---|---|
| 1505 | 4-amino-piperidin-1-yl | 3-methylpentan-3-yl | 3-methylpentan-3-yl | OMe | O |
| 1506 | 3-aminopiperazin-1-yl | 3-methylpentan-3-yl | 3-methylpentan-3-yl | OMe | O |
| 1507 | 3-aminopiperazin-1-yl | 3-methylpentan-3-yl | 3-methylpentan-3-yl | OMe | O |
| 1508 | 3-aminomorpholin-4-yl | 3-methylpentan-3-yl | 3-methylpentan-3-yl | OMe | O |
| 1509 | 2-aminomorpholin-4-yl | 3-methylpentan-3-yl | 3-methylpentan-3-yl | OMe | O |
| 1510 | 3-amino-2H-1,2-oxazin-2-yl | 3-methylpentan-3-yl | 3-methylpentan-3-yl | OMe | O |
| 1511 | 5-amino-2H-1,2-oxazin-2-yl | 3-methylpentan-3-yl | 3-methylpentan-3-yl | OMe | O |

TABLE 1-continued
| Cmpd | W | X | Z | A | Q |
|---|---|---|---|---|---|
| 1512 | 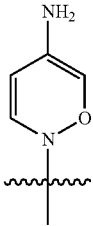 | 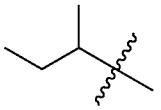 [SMILES: *C(C)CC] | 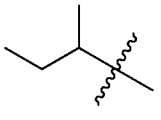 [SMILES: *C(C)CC] | OMe | O |
| 1513 | 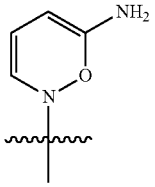 | 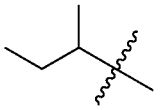 [SMILES: *C(C)CC] | 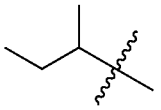 [SMILES: *C(C)CC] | OMe | O |
| 1514 | 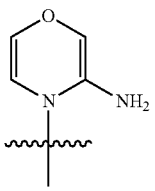 | 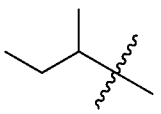 | 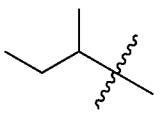 [SMILES: *C(C)CC] | OMe | O |
| 1515 | 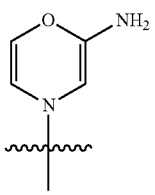 [SMILES: *N1C=COC(N)=C1] | 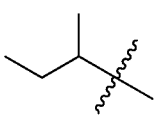 [SMILES: *C(C)CC] | 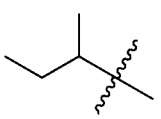 [SMILES: *C(C)CC] | OMe | O |
| 1516 | 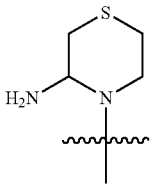 [SMILES: *N1CCSCC1N] | 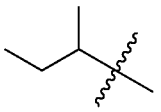 [SMILES: *C(C)CC] | 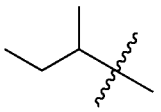 [SMILES: *C(C)CC] | OMe | O |
| 1517 | 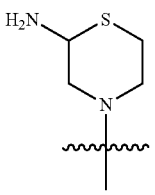 [SMILES: *N1CCSC(N)C1] | 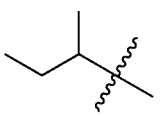 [SMILES: *C(C)CC] | 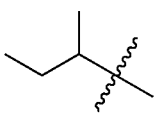 [SMILES: *C(C)CC] | OMe | O |
| 1518 | 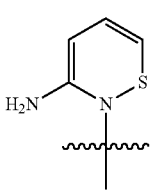 | 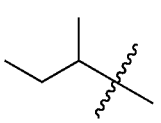 | 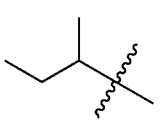 [SMILES: *C(C)CC] | OMe | O |
| 1519 | 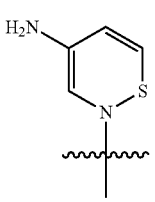 | 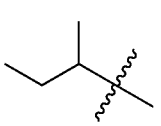 [SMILES: *C(C)CC] | 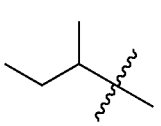 [SMILES: *C(C)CC] | OMe | O |

TABLE 1-continued

| Cmpd | W | X | Z | A | Q |
|---|---|---|---|---|---|
| 1520 | 4-amino-2H-1,2-thiazine (N-linked) | 3-pentyl | 3-pentyl | OMe | O |
| 1521 | 3-amino-2H-1,2-thiazine (N-linked) | 3-pentyl | 3-pentyl | OMe | O |
| 1522 | 3-amino-4H-1,4-thiazine (N-linked) | 3-pentyl | 3-pentyl | OMe | O |
| 1523 | 2-amino-4H-1,4-thiazine (N-linked) | 3-pentyl | 3-pentyl | OMe | O |
| 1524 | 3-amino-thiomorpholine 1,1-dioxide (N-linked) | 3-pentyl | 3-pentyl | OMe | O |
| 1525 | 2-amino-thiomorpholine 1,1-dioxide (N-linked) | 3-pentyl | 3-pentyl | OMe | O |
| 1526 | 2-amino-5,6-dihydro-4H-cyclopenta[b]pyrrole (N-linked) | 3-pentyl | 3-pentyl | OMe | O |

TABLE 1-continued
| Cmpd | W | X | Z | A | Q |
|---|---|---|---|---|---|
| 1527 | 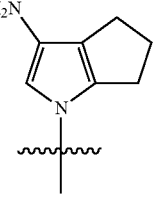 | 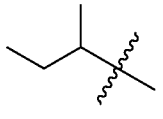 [SMILES: *C(C)CC] | 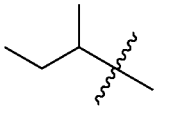 [SMILES: *C(C)CC] | OMe | O |
| 1528 | 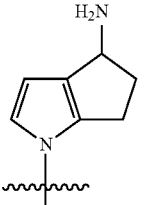 | 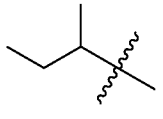 [SMILES: *C(C)CC] | 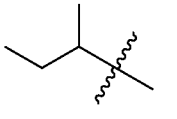 [SMILES: *C(C)CC] | OMe | O |
| 1529 | 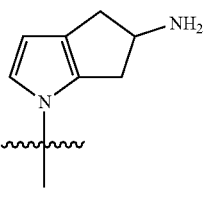 [SMILES: *n1ccc2c1CC(N)C2] | 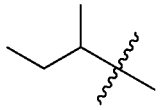 [SMILES: *C(C)CC] | 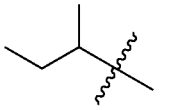 [SMILES: *C(C)CC] | OMe | O |
| 1530 | 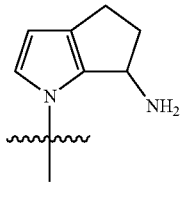 [SMILES: *n1ccc2c1C(N)CC2] | 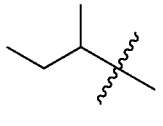 [SMILES: *C(C)CC] | 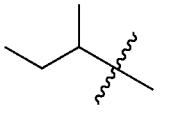 [SMILES: *C(C)CC] | OMe | O |
| 1531 | 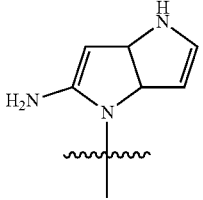 [SMILES: *N1C(N)=CC2NC=CC21] | 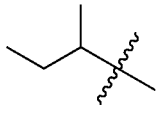 [SMILES: *C(C)CC] | 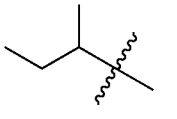 [SMILES: *C(C)CC] | OMe | O |
| 1532 | 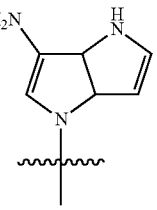 | 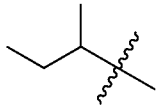 | 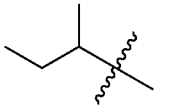 [SMILES: *C(C)CC] | OMe | O |
| 1533 | 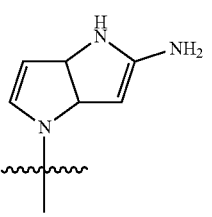 [SMILES: *N1C=CC2NC(N)=CC21] | 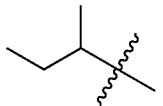 [SMILES: *C(C)CC] | 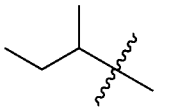 [SMILES: *C(C)CC] | OMe | O |

US 11,795,192 B2
437 438
TABLE 1-continued
| Cmpd | W | X | Z | A | Q |
|------|---|---|---|---|---|
| 1534 | 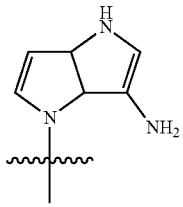 | 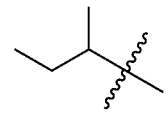 | 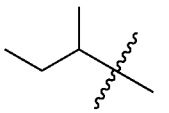 | OMe | O |
| 1535 | 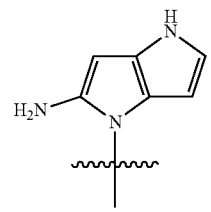 [SMILES: *n1c(N)cc2[nH]ccc21] | 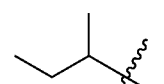 | 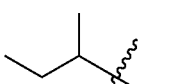 | OMe | O |
| 1536 | 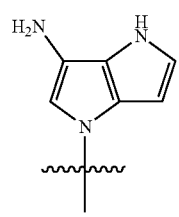 [SMILES: *n1cc(N)c2[nH]ccc21] | 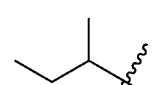 | 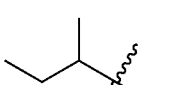 | OMe | O |
| 1537 | 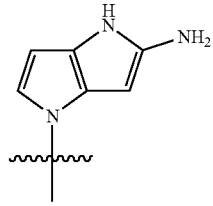 [SMILES: *n1ccc2[nH]c(N)cc21] | 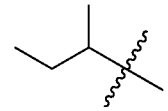 | 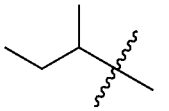 [SMILES: *C(C)CC] | OMe | O |
| 1538 | 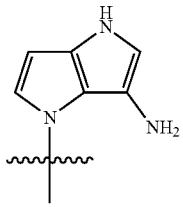 | 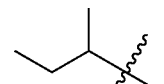 | 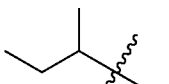 | OMe | O |
| 1539 | 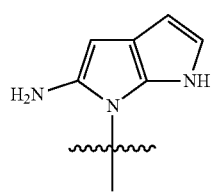 | 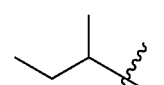 | 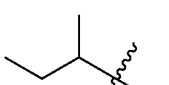 | OMe | O |
| 1540 | 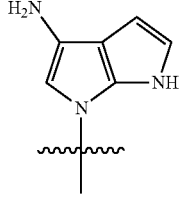 | 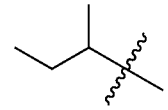 [SMILES: *C(C)CC] | 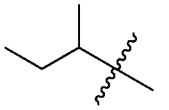 [SMILES: *C(C)CC] | OMe | O |

TABLE 1-continued

| Cmpd | W | X | Z | A | Q |
|---|---|---|---|---|---|
| 1541 | 3-amino-pyrrolo[2,3-b]pyrrole N-linked | 3-pentyl | 3-pentyl | OMe | O |
| 1542 | 2-amino-pyrrolo[2,3-b]pyrrole N-linked | 3-pentyl | 3-pentyl | OMe | O |
| 1543 | 2-amino-furo[2,3-b]pyrrole N-linked | 3-pentyl | 3-pentyl | OMe | O |
| 1544 | 3-amino-furo[2,3-b]pyrrole N-linked | 3-pentyl | 3-pentyl | OMe | O |
| 1545 | 3-amino-furo[2,3-b]pyrrole N-linked | 3-pentyl | 3-pentyl | OMe | O |
| 1546 | 2-amino-furo[2,3-b]pyrrole N-linked | 3-pentyl | 3-pentyl | OMe | O |
| 1547 | 2-amino-furo[3,2-b]pyrrole N-linked | 3-pentyl | 3-pentyl | OMe | O |

TABLE 1-continued

| Cmpd | W | X | Z | A | Q |
|---|---|---|---|---|---|
| 1548 | 5-amino-4H-furo[3,2-b]pyrrol-4-yl (N-linked) | 3-pentyl | 3-pentyl | OMe | O |
| 1549 | 2-amino-4H-furo[3,2-b]pyrrol-4-yl (N-linked) | 3-pentyl | 3-pentyl | OMe | O |
| 1550 | 3-amino-4H-furo[3,2-b]pyrrol-4-yl (N-linked) | 3-pentyl | 3-pentyl | OMe | O |
| 1551 | 5-amino-4H-thieno[3,2-b]pyrrol-4-yl (N-linked) | 3-pentyl | 3-pentyl | OMe | O |
| 1552 | 3-amino-4H-thieno[3,2-b]pyrrol-4-yl (N-linked) | 3-pentyl | 3-pentyl | OMe | O |
| 1553 | 3-amino-4H-thieno[2,3-b]pyrrol-4-yl (N-linked) | 3-pentyl | 3-pentyl | OMe | O |
| 1554 | 2-amino-4H-thieno[2,3-b]pyrrol-4-yl (N-linked) | 3-pentyl | 3-pentyl | OMe | O |

TABLE 1-continued

| Cmpd | W | X | Z | A | Q |
|---|---|---|---|---|---|
| 1555 | 5-amino-4H-thieno[3,2-b]pyrrol-4-yl | 3-pentyl | 3-pentyl | OMe | O |
| 1556 | 6-amino-4H-thieno[3,2-b]pyrrol-4-yl | 3-pentyl | 3-pentyl | OMe | O |
| 1557 | 2-amino-4H-thieno[3,2-b]pyrrol-4-yl | 3-pentyl | 3-pentyl | OMe | O |
| 1558 | 3-amino-4H-thieno[3,2-b]pyrrol-4-yl | 3-pentyl | 3-pentyl | OMe | O |
| 1559 | 7-amino-2,3-dihydro-1H-indol-1-yl | 3-pentyl | 3-pentyl | OMe | O |
| 1560 | 6-amino-2,3-dihydro-1H-indol-1-yl | 3-pentyl | 3-pentyl | OMe | O |
| 1561 | 4-amino-2,3-dihydro-1H-indol-1-yl | 3-pentyl | 3-pentyl | OMe | O |

TABLE 1-continued
| Cmpd | W | X | Z | A | Q |
|---|---|---|---|---|---|
| 1562 | 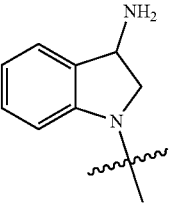 | 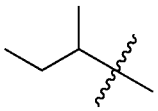 [SMILES: *C(C)CC] | 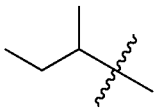 [SMILES: *C(C)CC] | OMe | O |
| 1563 | 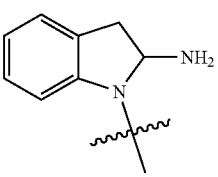 | 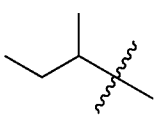 [SMILES: *C(C)CC] | 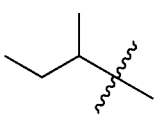 [SMILES: *C(C)CC] | OMe | O |
| 1564 | 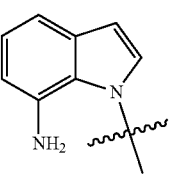 | 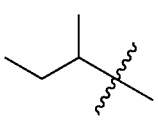 [SMILES: *C(C)CC] | 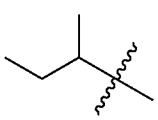 [SMILES: *C(C)CC] | OMe | O |
| 1565 | 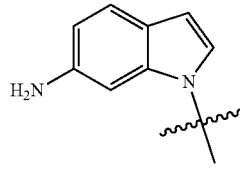 | 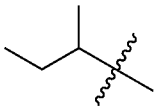 [SMILES: *C(C)CC] | 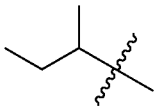 [SMILES: *C(C)CC] | OMe | O |
| 1566 | 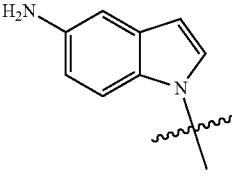 | 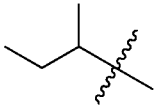 [SMILES: *C(C)CC] | 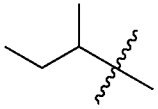 [SMILES: *C(C)CC] | OMe | O |
| 1567 | 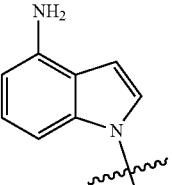 | 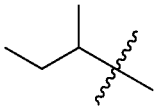 | 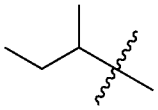 [SMILES: *C(C)CC] | OMe | O |
| 1568 | 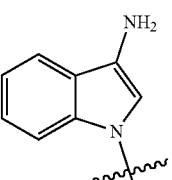 | 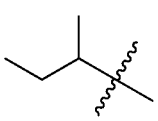 [SMILES: *C(C)CC] | 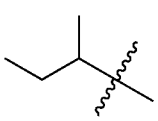 [SMILES: *C(C)CC] | OMe | O |
| 1569 | 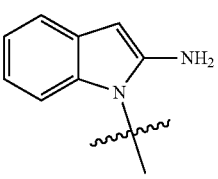 [SMILES: *n1c(N)cc2ccccc21] | 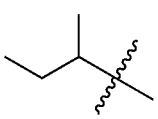 | 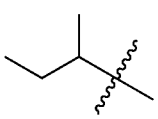 [SMILES: *C(C)CC] | OMe | O |

TABLE 1-continued

| Cmpd | W | X | Z | A | Q |
|---|---|---|---|---|---|
| 1570 | 1-aminoisoindole (N-linked, 3-amino) | 3-pentyl | 3-pentyl | OMe | O |
| 1571 | 7-aminoisoindole (N-linked) | 3-pentyl | 3-pentyl | OMe | O |
| 1572 | 5-aminoisoindole (N-linked) | 3-pentyl | 3-pentyl | OMe | O |
| 1573 | 7-aminoindazole (N1-linked) | 3-pentyl | 3-pentyl | OMe | O |
| 1574 | 6-aminoindazole (N1-linked) | 3-pentyl | 3-pentyl | OMe | O |
| 1575 | 5-aminoindazole (N1-linked) | 3-pentyl | 3-pentyl | OMe | O |
| 1576 | 4-aminoindazole (N1-linked) | 3-pentyl | 3-pentyl | OMe | O |

TABLE 1-continued

| Cmpd | W | X | Z | A | Q |
|---|---|---|---|---|---|
| 1577 | 3-amino-1H-indazol-1-yl (N1-linked) | 3-pentyl | 3-pentyl | OMe | O |
| 1578 | 7-amino-1H-benzimidazol-1-yl | 3-pentyl | 3-pentyl | OMe | O |
| 1579 | 6-amino-1H-benzimidazol-1-yl | 3-pentyl | 3-pentyl | OMe | O |
| 1580 | 5-amino-1H-benzimidazol-1-yl | 3-pentyl | 3-pentyl | OMe | O |
| 1581 | 4-amino-1H-benzimidazol-1-yl | 3-pentyl | 3-pentyl | | O |
| 1582 | 2-amino-1H-benzimidazol-1-yl | 3-pentyl | 3-pentyl | OMe | O |
| 1583 | 7-amino-1H-pyrrolo[3,2-b]pyridin-1-yl | 3-pentyl | 3-pentyl | OMe | O |
| 1584 | 6-amino-1H-pyrrolo[3,2-b]pyridin-1-yl | 3-pentyl | 3-pentyl | OMe | O |
| 1585 | 5-amino-1H-pyrrolo[3,2-b]pyridin-1-yl | 3-pentyl | 3-pentyl | OMe | O |

US 11,795,192 B2
451	452
TABLE 1-continued
| Cmpd | W | X | Z | A | Q |
|------|---|---|---|---|---|
| 1586 | 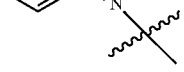 | 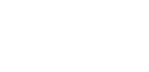 | 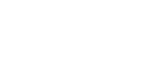 | OMe | O |
| 1587 | 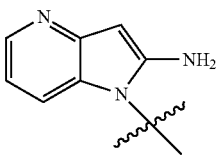 [SMILES: *n1c(N)cc2ncccc21] | 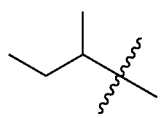 [SMILES: *C(C)CC] | 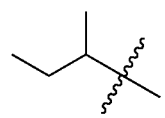 [SMILES: *C(C)CC] | OMe | O |
| 1588 | 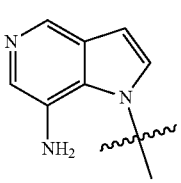 [SMILES: *n1ccc2cncc(N)c21] | 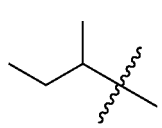 [SMILES: *C(C)CC] | 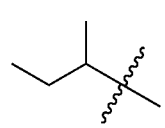 [SMILES: *C(C)CC] | OMe | O |
| 1589 | 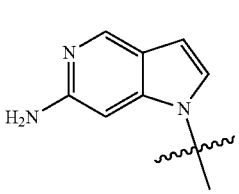 [SMILES: *n1ccc2cnc(N)cc21] | 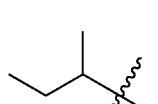 | 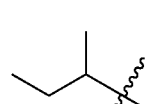 | OMe | O |
| 1590 | 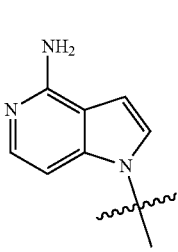 [SMILES: *n1ccc2c(N)nccc21] | 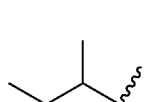 | 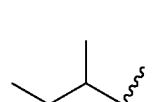 | OMe | O |
| 1591 | 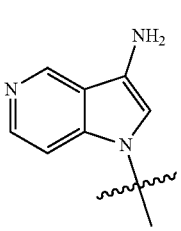 [SMILES: *n1cc(N)c2cnccc21] | 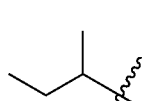 | 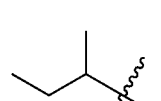 | OMe | O |
| 1592 | 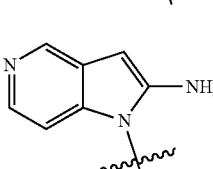 | 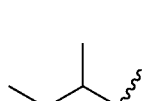 | 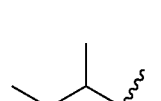 | OMe | O |
| 1593 | 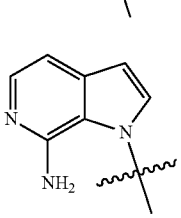 | 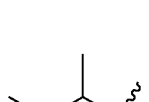 | 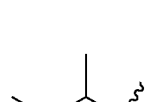 | OMe | O |

US 11,795,192 B2
TABLE 1-continued
| Cmpd | W | X | Z | A | Q |
|---|---|---|---|---|---|
| 1594 | 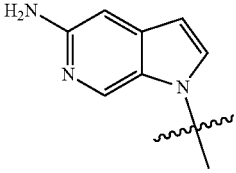 [SMILES: *n1ccc2cc(N)ncc21] | 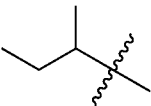 [SMILES: *C(C)CC] | 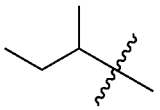 [SMILES: *C(C)CC] | OMe | O |
| 1595 | 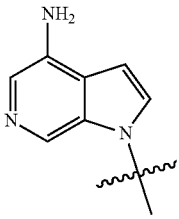 [SMILES: *n1ccc2c(N)cncc21] | 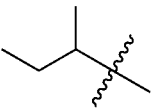 [SMILES: *C(C)CC] | 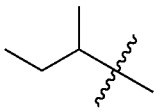 [SMILES: *C(C)CC] | OMe | O |
| 1596 | 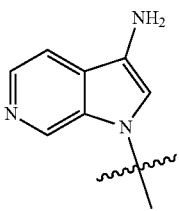 [SMILES: *n1cc(N)c2ccncc21] | 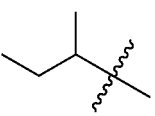 [SMILES: *C(C)CC] | 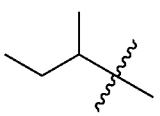 [SMILES: *C(C)CC] | OMe | O |
| 1597 | 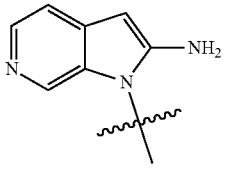 [SMILES: *n1c(N)cc2ccncc21] | 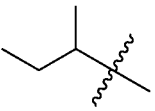 | 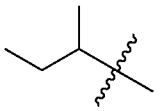 [SMILES: *C(C)CC] | OMe | O |
| 1598 | 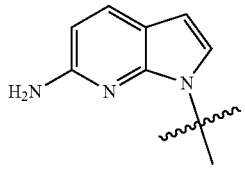 [SMILES: *n1ccc2ccc(N)nc21] | 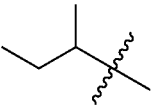 [SMILES: *C(C)CC] | 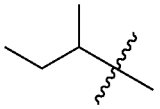 [SMILES: *C(C)CC] | OMe | O |
| 1599 | 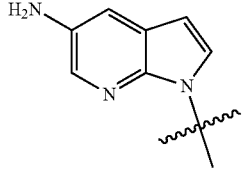 [SMILES: *n1ccc2cc(N)cnc21] | 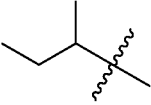 [SMILES: *C(C)CC] | 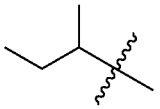 [SMILES: *C(C)CC] | OMe | O |
| 1600 | 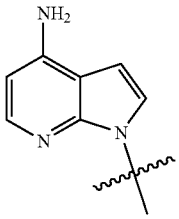 [SMILES: *n1ccc2c(N)ccnc21] | 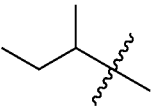 [SMILES: *C(C)CC] | 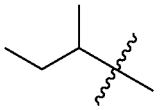 [SMILES: *C(C)CC] | OMe | O |

TABLE 1-continued

| Cmpd | W | X | Z | A | Q |
|------|---|---|---|---|---|
| 1601 | 3-amino-7-azaindole (N1-linked) | 3-pentyl | 3-pentyl | OMe | O |
| 1602 | 2-amino-7-azaindole (N1-linked) | 3-pentyl | 3-pentyl | OMe | O |
| 1603 | 6-amino-pyrazolo[3,4-b]pyridine (N1-linked) | 3-pentyl | 3-pentyl | OMe | O |
| 1604 | 5-amino-pyrazolo[3,4-b]pyridine (N1-linked) | 3-pentyl | 3-pentyl | OMe | O |
| 1605 | 4-amino-pyrazolo[3,4-b]pyridine (N1-linked) | 3-pentyl | 3-pentyl | OMe | O |
| 1606 | 3-amino-pyrazolo[3,4-b]pyridine (N1-linked) | 3-pentyl | 3-pentyl | OMe | O |
| 1607 | 2-aminopurine (N9-linked) | 3-pentyl | 3-pentyl | OMe | O |
| 1608 | adenine (N9-linked) | 3-pentyl | 3-pentyl | OMe | O |

TABLE 1-continued
| Cmpd | W | X | Z | A | Q |
|---|---|---|---|---|---|
| 1609 | 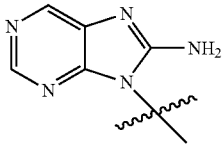 [SMILES: *n1c(N)nc2cncnc21] | 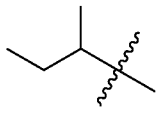 [SMILES: *C(C)CC] | 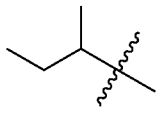 [SMILES: *C(C)CC] | OMe | O |
| 1610 | 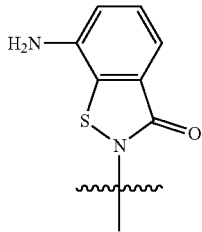 | 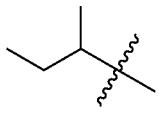 [SMILES: *C(C)CC] | 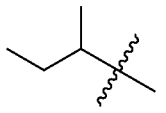 [SMILES: *C(C)CC] | OMe | O |
| 1611 | 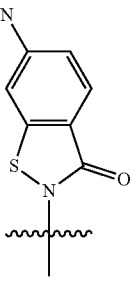 | 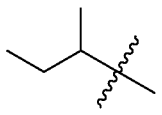 [SMILES: *C(C)CC] | 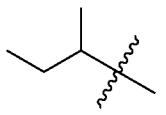 [SMILES: *C(C)CC] | OMe | O |
| 1612 | 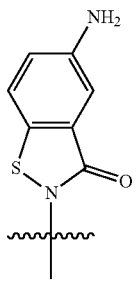 [SMILES: *n1sc2ccc(N)cc2c1=O] | 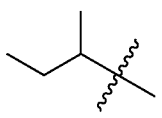 [SMILES: *C(C)CC] | 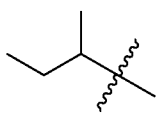 [SMILES: *C(C)CC] | OMe | O |
| 1613 | 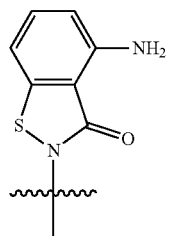 | 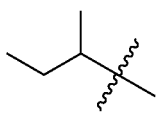 [SMILES: *C(C)CC] | 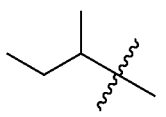 [SMILES: *C(C)CC] | OMe | O |
| 1614 | 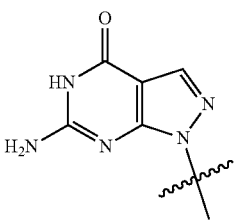 [SMILES: *n1ncc2c(=O)[nH]c(N)nc21] | 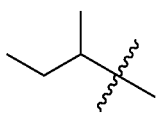 [SMILES: *C(C)CC] | 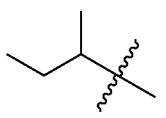 [SMILES: *C(C)CC] | OMe | O |

US 11,795,192 B2
TABLE 1-continued
| Cmpd | W | X | Z | A | Q |
|---|---|---|---|---|---|
| 1615 | 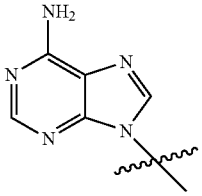 [SMILES: *n1cnc2c(N)ncnc21] | 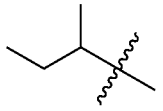 [SMILES: *C(C)CC] | 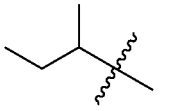 [SMILES: *C(C)CC] | OMe | O |
| 1616 | 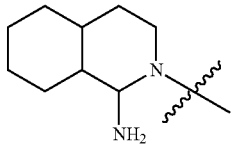 [SMILES: *N1CCC2CCCCC2C1N] | 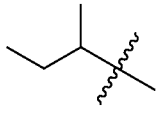 [SMILES: *C(C)CC] | 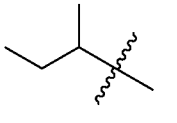 [SMILES: *C(C)CC] | OMe | O |
| 1617 | 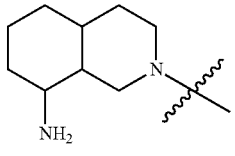 | 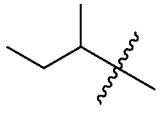 [SMILES: *C(C)CC] | 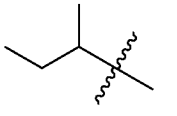 [SMILES: *C(C)CC] | OMe | O |
| 1618 | 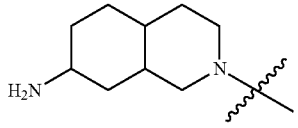 [SMILES: *N1CCC2CCC(N)CC2C1] | 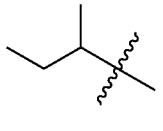 [SMILES: *C(C)CC] | 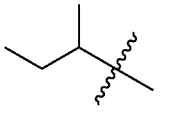 [SMILES: *C(C)CC] | OMe | O |
| 1619 | 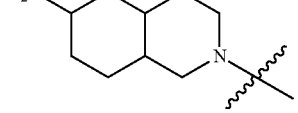 | 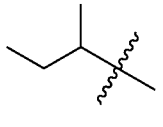 [SMILES: *C(C)CC] | 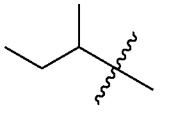 [SMILES: *C(C)CC] | OMe | O |
| 1620 | 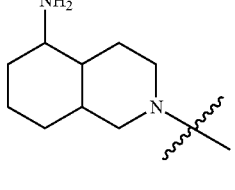 | 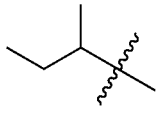 [SMILES: *C(C)CC] | 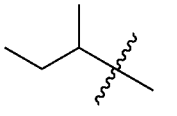 [SMILES: *C(C)CC] | OMe | O |
| 1621 | 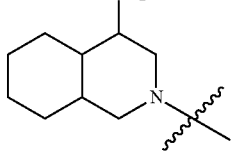 | 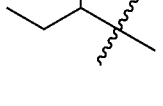 | 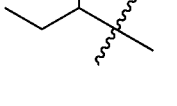 | OMe | O |
| 1622 | 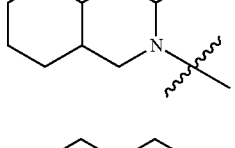 | 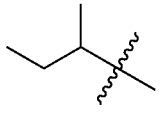 [SMILES: *C(C)CC] | 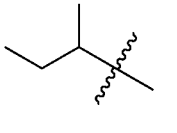 [SMILES: *C(C)CC] | OMe | O |
| 1623 | 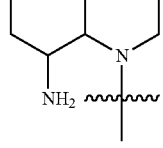 | 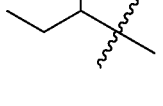 | 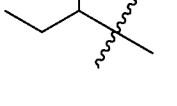 | OMe | O |

TABLE 1-continued

| Cmpd | W | X | Z | A | Q |
|------|---|---|---|---|---|
| 1624 | (decahydroquinoline with H₂N at 7-position, N-linked) | 3-methylpentyl | 3-methylpentyl | OMe | O |
| 1625 | (decahydroquinoline with H₂N at 6-position, N-linked) | 3-methylpentyl | 3-methylpentyl | OMe | O |
| 1626 | (decahydroquinoline with NH₂ at 5-position, N-linked) | 3-methylpentyl | 3-methylpentyl | OMe | O |
| 1627 | (decahydroquinoline with NH₂ at 4-position, N-linked) | 3-methylpentyl | 3-methylpentyl | OMe | O |
| 1628 | (decahydroquinoline with NH₂ at 3-position, N-linked) | 3-methylpentyl | 3-methylpentyl | OMe | O |
| 1629 | (decahydroquinoline with NH₂ at 2-position, N-linked) | 3-methylpentyl | 3-methylpentyl | OMe | O |
| 1630 | (1,2,3,4-tetrahydroquinoline with NH₂ at 8-position, N-linked) | 3-methylpentyl | 3-methylpentyl | OMe | O |

TABLE 1-continued

| Cmpd | W | X | Z | A | Q |
|---|---|---|---|---|---|
| 1631 | 7-amino-1,2,3,4-tetrahydroquinolin-1-yl | 3-methylpentan-3-yl | 3-methylpentan-3-yl | OMe | O |
| 1632 | 6-amino-1,2,3,4-tetrahydroquinolin-1-yl | 3-methylpentan-3-yl | 3-methylpentan-3-yl | OMe | O |
| 1633 | 5-amino-1,2,3,4-tetrahydroquinolin-1-yl | 3-methylpentan-3-yl | 3-methylpentan-3-yl | OMe | O |
| 1634 | 4-amino-1,2,3,4-tetrahydroquinolin-1-yl | 3-methylpentan-3-yl | 3-methylpentan-3-yl | OMe | O |
| 1635 | 3-amino-1,2,3,4-tetrahydroquinolin-1-yl | 3-methylpentan-3-yl | 3-methylpentan-3-yl | OMe | O |
| 1636 | 2-amino-1,2,3,4-tetrahydroquinolin-1-yl | 3-methylpentan-3-yl | 3-methylpentan-3-yl | OMe | O |
| 1637 | 8-amino-2H-quinolin-1-yl | 3-methylpentan-3-yl | 3-methylpentan-3-yl | OMe | O |

TABLE 1-continued

| Cmpd | W | X | Z | A | Q |
|---|---|---|---|---|---|
| 1638 | 7-amino-2H-quinolin-1-yl | 3-pentyl | 3-methylpentan-3-yl | OMe | O |
| 1639 | 6-amino-2H-quinolin-1-yl | 3-pentyl | 3-methylpentan-3-yl | OMe | O |
| 1640 | 5-amino-2H-quinolin-1-yl | 3-pentyl | 3-methylpentan-3-yl | OMe | O |
| 1641 | 4-amino-2H-quinolin-1-yl | 3-pentyl | 3-methylpentan-3-yl | OMe | O |
| 1642 | 3-amino-2H-quinolin-1-yl | 3-pentyl | 3-methylpentan-3-yl | OMe | O |
| 1643 | 2-amino-2H-quinolin-1-yl | 3-pentyl | 3-methylpentan-3-yl | OMe | O |
| 1644 | 1-amino-1H-isoquinolin-2-yl | 3-pentyl | 3-methylpentan-3-yl | OMe | O |
| 1645 | 8-amino-1H-isoquinolin-2-yl | 3-pentyl | 3-methylpentan-3-yl | OMe | O |

TABLE 1-continued

| Cmpd | W | X | Z | A | Q |
|------|---|---|---|---|---|
| 1646 | 7-amino-3,4-dihydroisoquinolin-2(1H)-yl (2-N linked) | 3-pentyl | 3-pentyl | OMe | O |
| 1647 | 6-amino-3,4-dihydroisoquinolin-2(1H)-yl | 3-pentyl | 3-pentyl | OMe | O |
| 1648 | 5-amino-3,4-dihydroisoquinolin-2(1H)-yl | 3-pentyl | 3-pentyl | OMe | O |
| 1649 | 4-amino-3,4-dihydroisoquinolin-2(1H)-yl | 3-pentyl | 3-pentyl | OMe | O |
| 1650 | 3-amino-3,4-dihydroisoquinolin-2(1H)-yl | 3-pentyl | 3-pentyl | OMe | O |
| 1651 | 8-amino-2-oxoquinolin-1(2H)-yl | 3-pentyl | 3-pentyl | OMe | O |
| 1652 | 7-amino-2-oxoquinolin-1(2H)-yl | 3-pentyl | 3-pentyl | OMe | O |
| 1653 | 6-amino-2-oxoquinolin-1(2H)-yl | 3-pentyl | 3-pentyl | OMe | O |
| 1654 | 5-amino-2-oxoquinolin-1(2H)-yl | 3-pentyl | 3-pentyl | OMe | O |

TABLE 1-continued

| Cmpd | W | X | Z | A | Q |
|---|---|---|---|---|---|
| 1655 | 4-amino-1-alkyl-quinolin-2(1H)-one | 3-pentyl | 3-methylpentyl | OMe | O |
| 1656 | 3-amino-1-alkyl-quinolin-2(1H)-one | 3-pentyl | 3-methylpentyl | OMe | O |
| 1657 | 8-amino-2-alkyl-isoquinolin-1(2H)-one | 3-pentyl | 3-methylpentyl | OMe | O |
| 1658 | 7-amino-2-alkyl-isoquinolin-1(2H)-one | 3-pentyl | 3-methylpentyl | OMe | O |
| 1659 | 6-amino-2-alkyl-isoquinolin-1(2H)-one | 3-pentyl | 3-methylpentyl | OMe | O |
| 1660 | 5-amino-2-alkyl-isoquinolin-1(2H)-one | 3-pentyl | 3-methylpentyl | OMe | O |
| 1661 | 4-amino-2-alkyl-isoquinolin-1(2H)-one | 3-pentyl | 3-methylpentyl | OMe | O |
| 1662 | 3-amino-2-alkyl-isoquinolin-1(2H)-one | 3-pentyl | 3-methylpentyl | OMe | O |

US 11,795,192 B2
471                                                                   472
TABLE 1-continued
| Cmpd | W | X | Z | A | Q |
|---|---|---|---|---|---|
| 1663 | 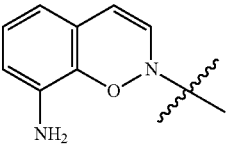 | 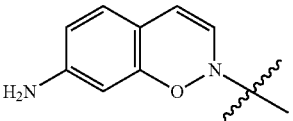 | 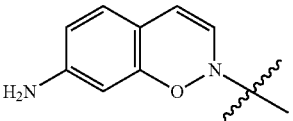 | OMe | O |
| 1664 | 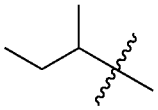 [SMILES: *C(C)CC] | 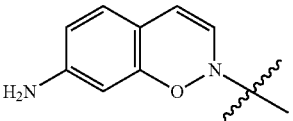 | 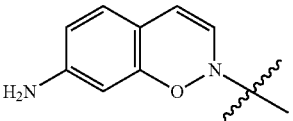 | OMe | O |
| 1665 | 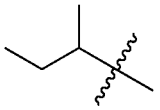 [SMILES: *C(C)CC] | 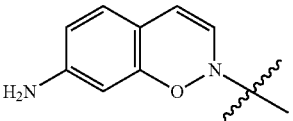 | 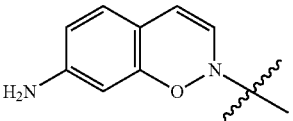 | OMe | O |
| 1666 | 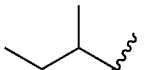 | 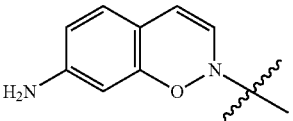 | 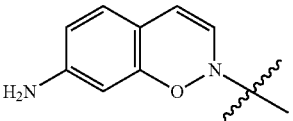 | OMe | O |
| 1667 | 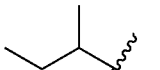 | 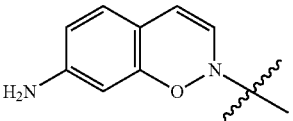 | 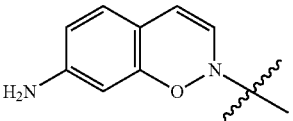 | OMe | O |
| 1668 | 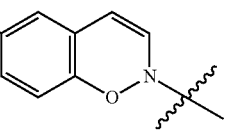 | 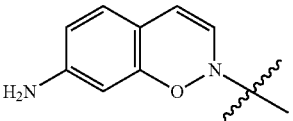 | 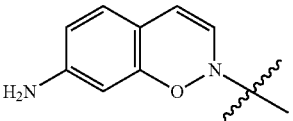 | OMe | O |
| 1669 | 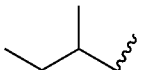 | 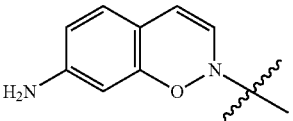 | 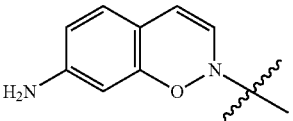 | OMe | O |
| 1670 | 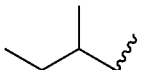 | 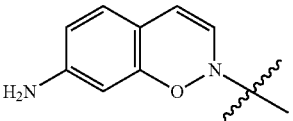 | 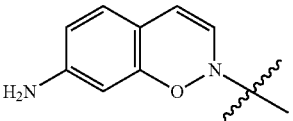 | OMe | O |
| 1671 | 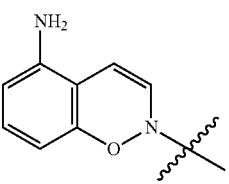 [SMILES: *N1C=Cc2c(N)cccc2O1] | 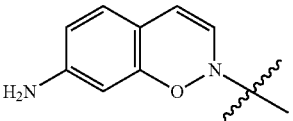 | 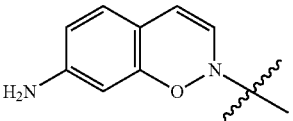 | OMe | O |

TABLE 1-continued

| Cmpd | W | X | Z | A | Q |
|---|---|---|---|---|---|
| 1672 | (2-amino phenoxazine, N-linked) | 3-methylpentyl | 3-methylpentyl | OMe | O |
| 1673 | (1-amino phenothiazine, N-linked) | 3-methylpentyl | 3-methylpentyl | OMe | O |
| 1674 | (2-amino phenothiazine, N-linked) | 3-methylpentyl | 3-methylpentyl | OMe | O |
| 1675 | (amino-azaadamantane) | 3-methylpentyl | 3-methylpentyl | OMe | O |
| 1676 | (amino-dihydroazepine) | 3-methylpentyl | 3-methylpentyl | OMe | O |
| 1677 | (amino-dihydroazepine) | 3-methylpentyl | 3-methylpentyl | OMe | O |
| 1678 | (amino-azepine) | 3-methylpentyl | 3-methylpentyl | OMe | O |

TABLE 1-continued
| Cmpd | W | X | Z | A | Q |
|---|---|---|---|---|---|
| 1679 | 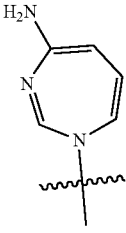 |  |  | OMe | O |
| 1680 | 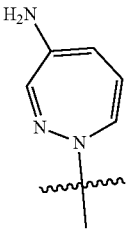 | 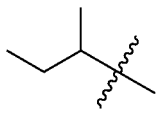 [SMILES: *C(C)CC] | 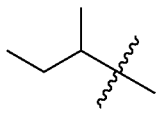 [SMILES: *C(C)CC] | OMe | O |
| 1681 | 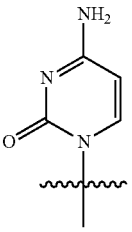 [SMILES: *n1ccc(N)nc1=O] | 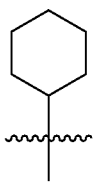 | 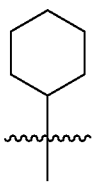 [SMILES: *C1CCCCC1] | OMe | O |
| 1682 | 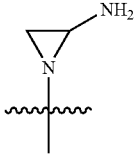 | 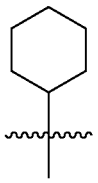 [SMILES: *C1CCCCC1] | 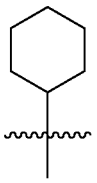 [SMILES: *C1CCCCC1] | OMe | O |
| 1683 | 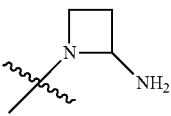 | 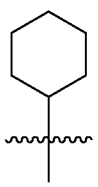 | 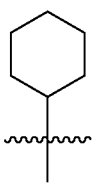 [SMILES: *C1CCCCC1] | OMe | O |
| 1684 | 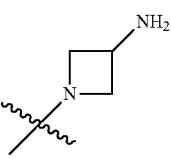 | 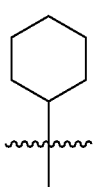 | 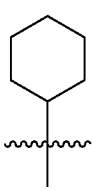 [SMILES: *C1CCCCC1] | OMe | O |
| 1685 | 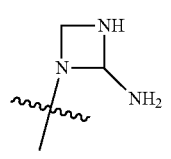 | 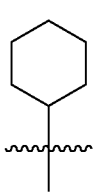 | 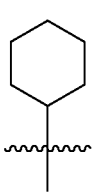 [SMILES: *C1CCCCC1] | OMe | O |

TABLE 1-continued

| Cmpd | W | X | Z | A | Q |
|---|---|---|---|---|---|
| 1686 | 3-amino-azetidinone (N-linked) | cyclohexyl | cyclohexyl | OMe | O |
| 1687 | 4-amino-azetidinone (N-linked) | cyclohexyl | cyclohexyl | OMe | O |
| 1688 | 2-amino-pyrrolidine (N-linked) | cyclohexyl | cyclohexyl | OMe | O |
| 1689 | 3-amino-pyrrolidine (N-linked) | cyclohexyl | cyclohexyl | OMe | O |
| 1690 | 2-amino-2,5-dihydropyrrole (N-linked) | cyclohexyl | cyclohexyl | OMe | O |
| 1691 | 3-amino-2,5-dihydropyrrole (N-linked) | cyclohexyl | cyclohexyl | OMe | O |
| 1692 | 5-amino-3,4-dihydro-2H-pyrrole (N-linked) | cyclohexyl | cyclohexyl | OMe | O |
| 1693 | 4-amino-2,3-dihydro-1H-pyrrole (N-linked) | cyclohexyl | cyclohexyl | OMe | O |

TABLE 1-continued

| Cmpd | W | X | Z | A | Q |
|------|---|---|---|---|---|
| 1694 | 3-amino-2,5-dihydropyrrole (N-linked) | cyclohexyl | cyclohexyl | OMe | O |
| 1695 | 2-amino-2,3-dihydropyrrole (N-linked) | cyclohexyl | cyclohexyl | OMe | O |
| 1696 | 2-amino-pyrrole (N-linked) | cyclohexyl | cyclohexyl | OMe | O |
| 1697 | 3-amino-pyrrole (N-linked) | cyclohexyl | cyclohexyl | OMe | O |
| 1698 | 3-amino-pyrazolidine (N-linked) | cyclohexyl | cyclohexyl | OMe | O |
| 1699 | 4-amino-pyrazolidine (N-linked) | cyclohexyl | cyclohexyl | OMe | O |
| 1700 | 5-amino-pyrazolidine (N-linked) | cyclohexyl | cyclohexyl | OMe | O |

TABLE 1-continued
| Cmpd | W | X | Z | A | Q |
|---|---|---|---|---|---|
| 1701 | 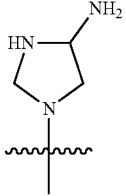 | 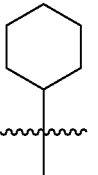 | 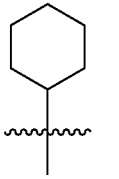 [SMILES: *C1CCCCC1] | OMe | O |
| 1702 | 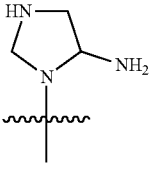 | 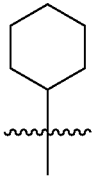 | 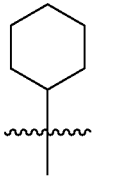 [SMILES: *C1CCCCC1] | OMe | O |
| 1703 | 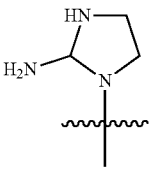 | 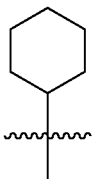 | 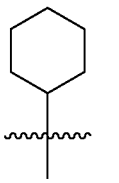 [SMILES: *C1CCCCC1] | OMe | O |
| 1704 | 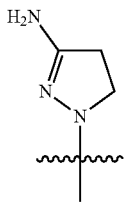 | 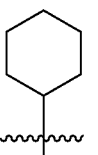 | 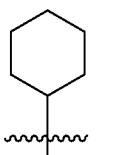 | OMe | O |
| 1705 | 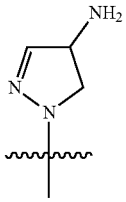 | 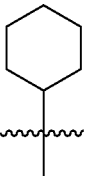 [SMILES: *C1CCCCC1] | 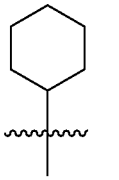 [SMILES: *C1CCCCC1] | OMe | O |
| 1706 | 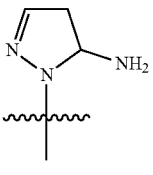 [SMILES: *N1N=CCC1N] | 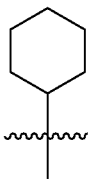 [SMILES: *C1CCCCC1] | 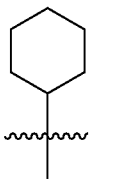 [SMILES: *C1CCCCC1] | OMe | O |
| 1707 | 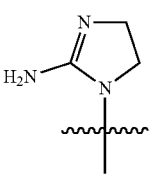 | 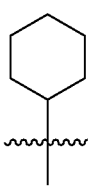 [SMILES: *C1CCCCC1] | 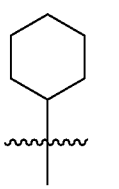 [SMILES: *C1CCCCC1] | OMe | O |
| 1708 | 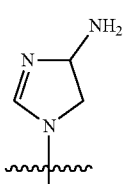 | 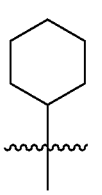 [SMILES: *C1CCCCC1] | 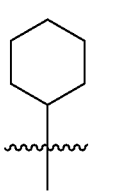 [SMILES: *C1CCCCC1] | OMe | O |

TABLE 1-continued
| Cmpd | W | X | Z | A | Q |
|---|---|---|---|---|---|
| 1709 | 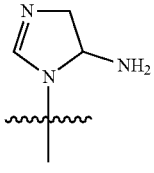 [SMILES: *N1C=NCC1N] | 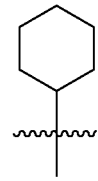 [SMILES: *C1CCCCC1] | 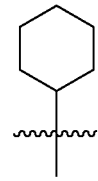 [SMILES: *C1CCCCC1] | OMe | O |
| 1710 | 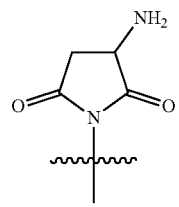 [SMILES: *N1C(=O)CC(N)C1=O] | 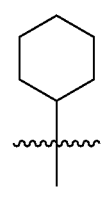 | 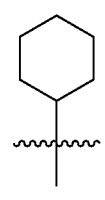 | OMe | O |
| 1711 | 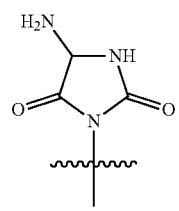 [SMILES: *N1C(=O)NC(N)C1=O] | 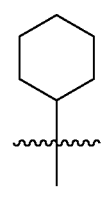 | 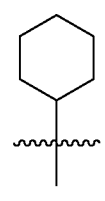 [SMILES: *C1CCCCC1] | OMe | O |
| 1712 | 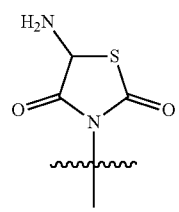 [SMILES: *N1C(=O)SC(N)C1=O] | 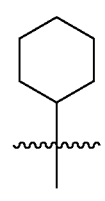 [SMILES: *C1CCCCC1] | 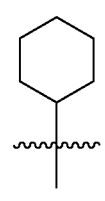 [SMILES: *C1CCCCC1] | OMe | O |
| 1713 | 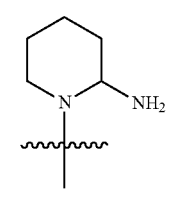 | 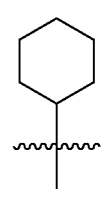 [SMILES: *C1CCCCC1] | 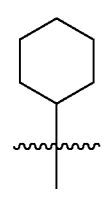 [SMILES: *C1CCCCC1] | OMe | O |
| 1714 | 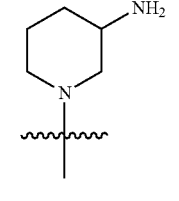 | 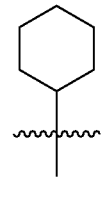 [SMILES: *C1CCCCC1] | 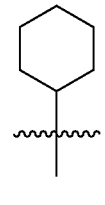 | OMe | O |
| 1715 | 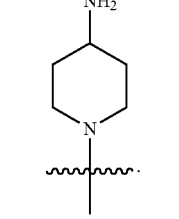 | 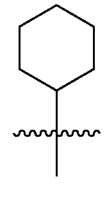 | 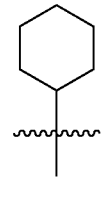 [SMILES: *C1CCCCC1] | OMe | O |

TABLE 1-continued

| Cmpd | W | X | Z | A | Q |
|------|---|---|---|---|---|
| 1716 | 3-amino-piperazin-1-yl (N1-attached, NH at 4) | cyclohexyl | cyclohexyl | OMe | O |
| 1717 | 3-amino-piperazin-1-yl | cyclohexyl | cyclohexyl | OMe | O |
| 1718 | 3-amino-morpholin-4-yl | cyclohexyl | cyclohexyl | OMe | O |
| 1719 | 2-amino-morpholin-4-yl | cyclohexyl | cyclohexyl | OMe | O |
| 1720 | 3-amino-2H-1,2-oxazin-2-yl | cyclohexyl | cyclohexyl | OMe | O |
| 1721 | 4-amino-2H-1,2-oxazin-2-yl | cyclohexyl | cyclohexyl | OMe | O |
| 1722 | 5-amino-2H-1,2-oxazin-2-yl | cyclohexyl | cyclohexyl | OMe | O |

TABLE 1-continued

| Cmpd | W | X | Z | A | Q |
|---|---|---|---|---|---|
| 1723 | (oxazine with NH₂) | cyclohexyl | cyclohexyl | OMe | O |
| 1724 | (oxazine with NH₂) | cyclohexyl | cyclohexyl | OMe | O |
| 1725 | (oxazine with NH₂) | cyclohexyl | cyclohexyl | OMe | O |
| 1726 | (thiomorpholine with H₂N) | cyclohexyl | cyclohexyl | OMe | O |
| 1727 | (thiomorpholine with H₂N) | cyclohexyl | cyclohexyl | OMe | O |
| 1728 | (thiazine with H₂N) | cyclohexyl | cyclohexyl | OMe | O |
| 1729 | (thiazine with H₂N) | cyclohexyl | cyclohexyl | OMe | O |
| 1730 | (thiazine with NH₂) | cyclohexyl | cyclohexyl | OMe | O |

TABLE 1-continued

| Cmpd | W | X | Z | A | Q |
|---|---|---|---|---|---|
| 1731 | 3-amino-2H-1,2-thiazine (N-linked) | cyclohexyl | cyclohexyl | OMe | O |
| 1732 | 3-amino-4H-1,4-thiazine (N-linked) | cyclohexyl | cyclohexyl | OMe | O |
| 1733 | 3-amino-4H-1,4-thiazine (N-linked, isomer) | cyclohexyl | cyclohexyl | OMe | O |
| 1734 | 3-amino-1,1-dioxo-thiomorpholine (N-linked) | cyclohexyl | cyclohexyl | OMe | O |
| 1735 | 2-amino-1,1-dioxo-thiomorpholine (N-linked) | cyclohexyl | cyclohexyl | OMe | O |
| 1736 | 2-amino-5,6-dihydro-4H-cyclopenta[b]pyrrole (N-linked) | cyclohexyl | cyclohexyl | OMe | O |
| 1737 | 3-amino-5,6-dihydro-4H-cyclopenta[b]pyrrole (N-linked) | cyclohexyl | cyclohexyl | OMe | O |

TABLE 1-continued
| Cmpd | W | X | Z | A | Q |
|---|---|---|---|---|---|
| 1738 | 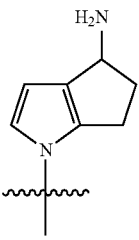 [SMILES: *n1ccc2c1CCC2N] | 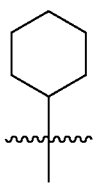 | 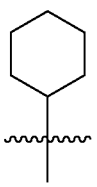 [SMILES: *C1CCCCC1] | OMe | O |
| 1739 | 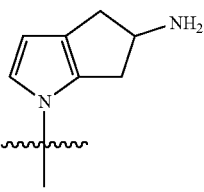 [SMILES: *n1ccc2c1CC(N)C2] | 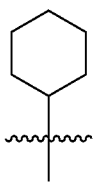 | 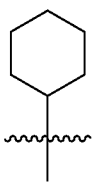 | OMe | O |
| 1740 | 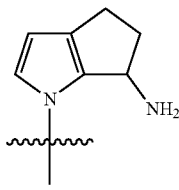 [SMILES: *n1ccc2c1C(N)CC2] | 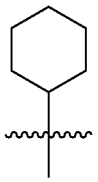 | 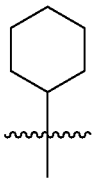 [SMILES: *C1CCCCC1] | OMe | O |
| 1741 | 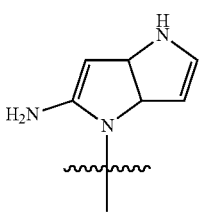 | 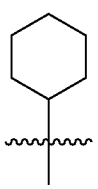 [SMILES: *C1CCCCC1] | 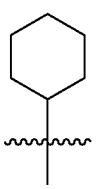 [SMILES: *C1CCCCC1] | OMe | O |
| 1742 | 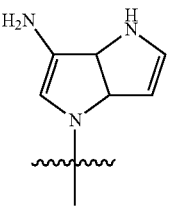 | 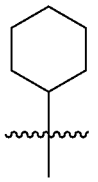 [SMILES: *C1CCCCC1] | 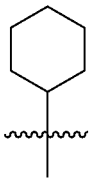 [SMILES: *C1CCCCC1] | OMe | O |
| 1743 | 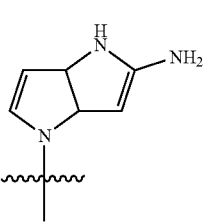 [SMILES: *N1C=CC2NC(N)=CC21] | 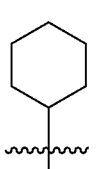 | 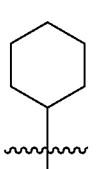 | OMe | O |
| 1744 | 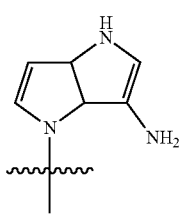 [SMILES: *N1C=CC2NC=C(N)C21] | 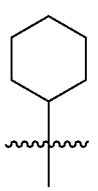 [SMILES: *C1CCCCC1] | 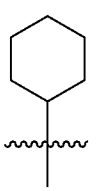 [SMILES: *C1CCCCC1] | OMe | O |

TABLE 1-continued

| Cmpd | W | X | Z | A | Q |
|---|---|---|---|---|---|
| 1745 | 5-amino-1H-pyrrolo[3,2-b]pyrrole (N1-linked) | cyclohexyl | cyclohexyl | OMe | O |
| 1746 | 6-amino-1H-pyrrolo[3,2-b]pyrrole (N4-linked) | cyclohexyl | cyclohexyl | OMe | O |
| 1747 | 2-amino-4H-pyrrolo[3,2-b]pyrrole (N1-linked) | cyclohexyl | cyclohexyl | OMe | O |
| 1748 | 3-amino-4H-pyrrolo[3,2-b]pyrrole (N1-linked) | cyclohexyl | cyclohexyl | OMe | O |
| 1749 | 5-amino-1H-pyrrolo[2,3-b]pyrrole (N4-linked) | cyclohexyl | cyclohexyl | OMe | O |
| 1750 | 6-amino-1H-pyrrolo[2,3-b]pyrrole (N4-linked) | cyclohexyl | cyclohexyl | OMe | O |
| 1751 | 3-amino-1H-pyrrolo[2,3-b]pyrrole (N4-linked) | cyclohexyl | cyclohexyl | OMe | O |

TABLE 1-continued

| Cmpd | W | X | Z | A | Q |
|------|---|---|---|---|---|
| 1752 | 2-amino-1H-pyrrolo[2,3-b]pyrrole (N-linked) | cyclohexyl | cyclohexyl | OMe | O |
| 1753 | 5-amino-furo[2,3-b]pyrrole (N-linked) | cyclohexyl | cyclohexyl | OMe | O |
| 1754 | 4-amino-furo[2,3-b]pyrrole (N-linked) | cyclohexyl | cyclohexyl | OMe | O |
| 1755 | 3-amino-furo[2,3-b]pyrrole (N-linked) | cyclohexyl | cyclohexyl | OMe | O |
| 1756 | 2-amino-furo[3,2-b]pyrrole (N-linked) | cyclohexyl | cyclohexyl | OMe | O |
| 1757 | 5-amino-furo[3,2-b]pyrrole (N-linked) | cyclohexyl | cyclohexyl | OMe | O |
| 1758 | 6-amino-furo[3,2-b]pyrrole (N-linked) | cyclohexyl | cyclohexyl | OMe | O |

TABLE 1-continued

| Cmpd | W | X | Z | A | Q |
|---|---|---|---|---|---|
| 1759 | furo-pyrrole with NH₂ (N-linked) | cyclohexyl | cyclohexyl | OMe | O |
| 1760 | furo-pyrrole with NH₂ (N-linked) | cyclohexyl | cyclohexyl | OMe | O |
| 1761 | thieno-pyrrole with NH₂ (N-linked) | cyclohexyl | cyclohexyl | OMe | O |
| 1762 | thieno-pyrrole with NH₂ (N-linked) | cyclohexyl | cyclohexyl | OMe | O |
| 1763 | thieno-pyrrole with NH₂ (N-linked) | cyclohexyl | cyclohexyl | OMe | O |
| 1764 | thieno-pyrrole with NH₂ (N-linked) | cyclohexyl | cyclohexyl | OMe | O |
| 1765 | thieno-pyrrole with NH₂ (N-linked) | cyclohexyl | cyclohexyl | OMe | O |

TABLE 1-continued
| Cmpd | W | X | Z | A | Q |
|---|---|---|---|---|---|
| 1766 | 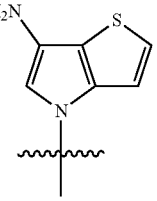 | 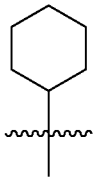 | 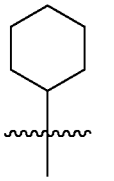 [SMILES: *C1CCCCC1] | OMe | O |
| 1767 | 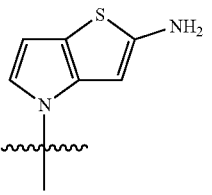 [SMILES: *n1ccc2sc(N)cc21] | 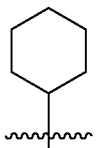 | 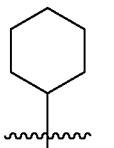 | OMe | O |
| 1768 | 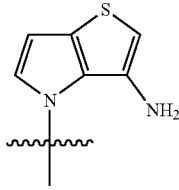 [SMILES: *n1ccc2scc(N)c21] | 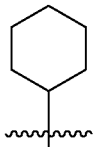 | 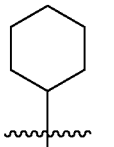 | OMe | O |
| 1769 | 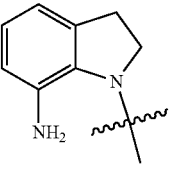 [SMILES: *N1CCc2cccc(N)c21] | 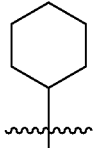 | 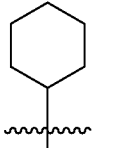 | OMe | O |
| 1770 | 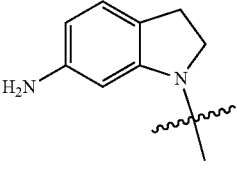 [SMILES: *N1CCc2ccc(N)cc21] | 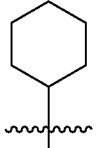 | 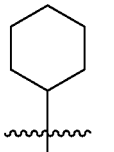 | OMe | O |
| 1771 | 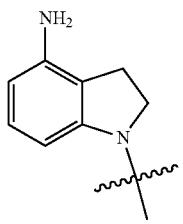 [SMILES: *N1CCc2c(N)cccc21] | 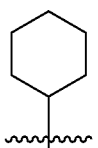 | 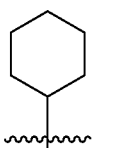 | OMe | O |
| 1772 | 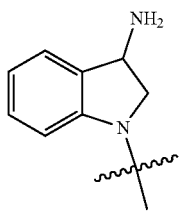 | 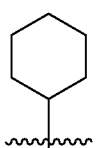 | 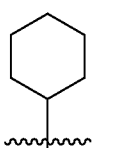 | OMe | O |

TABLE 1-continued
| Cmpd | W | X | Z | A | Q |
|---|---|---|---|---|---|
| 1773 | 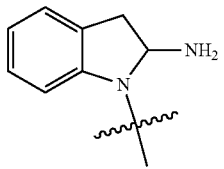 | 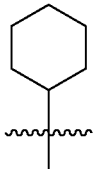 | 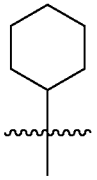 [SMILES: *C1CCCCC1] | OMe | O |
| 1774 | 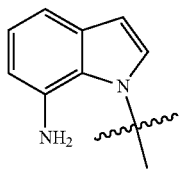 [SMILES: *n1ccc2cccc(N)c21] | 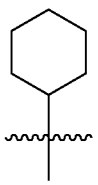 | 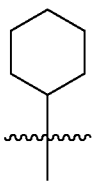 [SMILES: *C1CCCCC1] | OMe | O |
| 1775 | 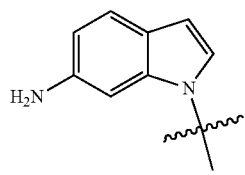 [SMILES: *n1ccc2ccc(N)cc21] | 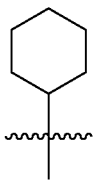 | 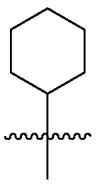 | OMe | O |
| 1776 | 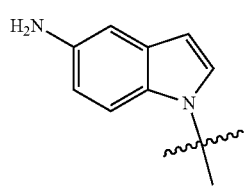 [SMILES: *n1ccc2cc(N)ccc21] | 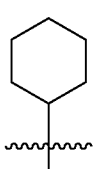 | 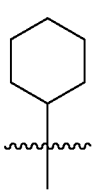 [SMILES: *C1CCCCC1] | OMe | O |
| 1777 | 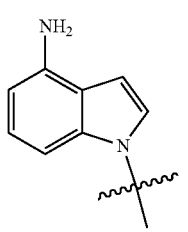 | 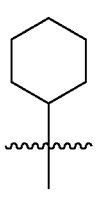 | 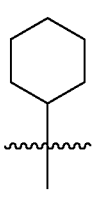 [SMILES: *C1CCCCC1] | OMe | O |
| 1778 | 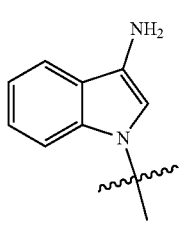 | 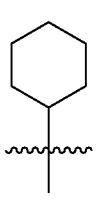 [SMILES: *C1CCCCC1] | 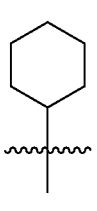 [SMILES: *C1CCCCC1] | OMe | O |
| 1779 | 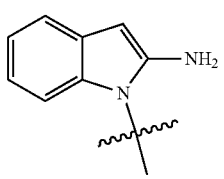 [SMILES: *n1c(N)cc2ccccc21] | 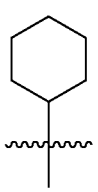 | 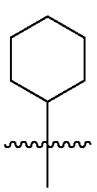 [SMILES: *C1CCCCC1] | OMe | O |

TABLE 1-continued

| Cmpd | W | X | Z | A | Q |
|------|---|---|---|---|---|
| 1780 | 1-aminoisoindole (3-amino, N-linked) | cyclohexyl | cyclohexyl | OMe | O |
| 1781 | 7-aminoisoindole (N-linked) | cyclohexyl | cyclohexyl | OMe | O |
| 1782 | 5-aminoisoindole (N-linked) | cyclohexyl | cyclohexyl | OMe | O |
| 1783 | 7-aminoindazole (N1-linked) | cyclohexyl | cyclohexyl | OMe | O |
| 1784 | 6-aminoindazole (N1-linked) | cyclohexyl | cyclohexyl | OMe | O |
| 1785 | 5-aminoindazole (N1-linked) | cyclohexyl | cyclohexyl | OMe | O |
| 1786 | 4-aminoindazole (N1-linked) | cyclohexyl | cyclohexyl | OMe | O |

TABLE 1-continued

| Cmpd | W | X | Z | A | Q |
|---|---|---|---|---|---|
| 1787 | 3-amino-indazol-1-yl | cyclohexyl | cyclohexyl | OMe | O |
| 1788 | 7-amino-benzimidazol-1-yl | cyclohexyl | cyclohexyl | OMe | O |
| 1789 | 6-amino-benzimidazol-1-yl | cyclohexyl | cyclohexyl | OMe | O |
| 1790 | 5-amino-benzimidazol-1-yl | cyclohexyl | cyclohexyl | OMe | O |
| 1791 | 4-amino-benzimidazol-1-yl | cyclohexyl | cyclohexyl |  | O |
| 1792 | 2-amino-benzimidazol-1-yl | cyclohexyl | cyclohexyl | OMe | O |
| 1793 | 7-amino-pyrrolo[3,2-b]pyridin-1-yl | cyclohexyl | cyclohexyl | OMe | O |
| 1794 | 6-amino-pyrrolo[3,2-b]pyridin-1-yl | cyclohexyl | cyclohexyl | OMe | O |

TABLE 1-continued
| Cmpd | W | X | Z | A | Q |
|---|---|---|---|---|---|
| 1795 | 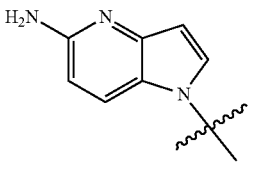 | 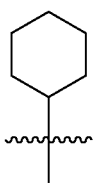 | 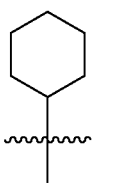 [SMILES: *C1CCCCC1] | OMe | O |
| 1796 | 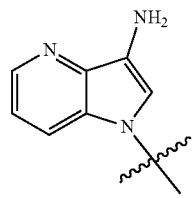 | 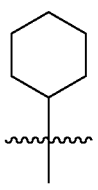 | 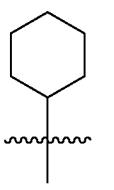 [SMILES: *C1CCCCC1] | OMe | O |
| 1797 | 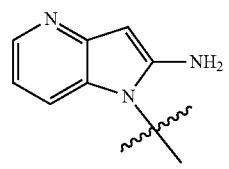 | 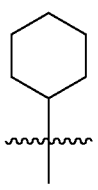 | 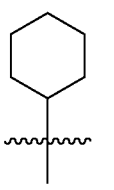 [SMILES: *C1CCCCC1] | OMe | O |
| 1798 | 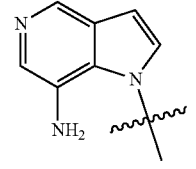 | 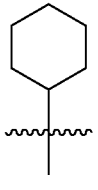 | 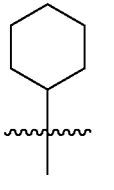 [SMILES: *C1CCCCC1] | OMe | O |
| 1799 | 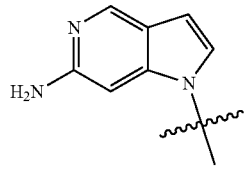 | 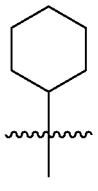 | 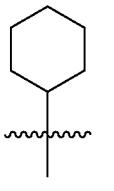 | OMe | O |
| 1800 | 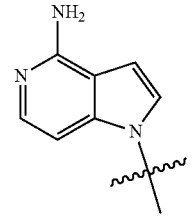 | 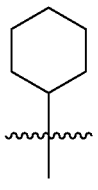 | 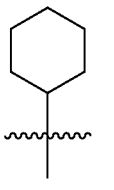 | OMe | O |
| 1801 | 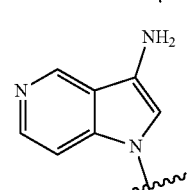 | 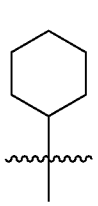 [SMILES: *C1CCCCC1] | 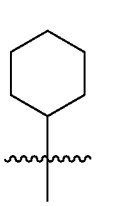 [SMILES: *C1CCCCC1] | OMe | O |
| 1802 | 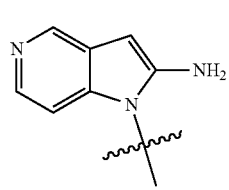 | 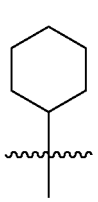 | 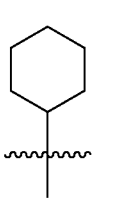 [SMILES: *C1CCCCC1] | OMe | O |

TABLE 1-continued

| Cmpd | W | X | Z | A | Q |
|------|---|---|---|---|---|
| 1803 | 7-amino-pyrrolo[2,3-c]pyridine | cyclohexyl | cyclohexyl | OMe | O |
| 1804 | 5-amino-pyrrolo[2,3-c]pyridine | cyclohexyl | cyclohexyl | OMe | O |
| 1805 | 4-amino-pyrrolo[2,3-c]pyridine | cyclohexyl | cyclohexyl | OMe | O |
| 1806 | 3-amino-pyrrolo[2,3-c]pyridine | cyclohexyl | cyclohexyl | OMe | O |
| 1807 | 2-amino-pyrrolo[2,3-c]pyridine | cyclohexyl | cyclohexyl | OMe | O |
| 1808 | 6-amino-pyrrolo[2,3-b]pyridine | cyclohexyl | cyclohexyl | OMe | O |
| 1809 | 5-amino-pyrrolo[2,3-b]pyridine | cyclohexyl | cyclohexyl | OMe | O |

TABLE 1-continued

| Cmpd | W | X | Z | A | Q |
|---|---|---|---|---|---|
| 1810 | 4-amino-7-azaindol-1-yl (N1-linked via CMe) | cyclohexyl | cyclohexyl | OMe | O |
| 1811 | 3-amino-7-azaindol-1-yl (N1-linked via CMe) | cyclohexyl | cyclohexyl | OMe | O |
| 1812 | 2-amino-7-azaindol-1-yl (N1-linked via CMe) | cyclohexyl | cyclohexyl | OMe | O |
| 1813 | 6-amino-pyrazolo[3,4-b]pyridin-1-yl (N1-linked via CMe) | cyclohexyl | cyclohexyl | OMe | O |
| 1814 | 5-amino-pyrazolo[3,4-b]pyridin-1-yl (N1-linked via CMe) | cyclohexyl | cyclohexyl | OMe | O |
| 1815 | 4-amino-pyrazolo[3,4-b]pyridin-1-yl (N1-linked via CMe) | cyclohexyl | cyclohexyl | OMe | O |
| 1816 | 3-amino-pyrazolo[3,4-b]pyridin-1-yl (N1-linked via CMe) | cyclohexyl | cyclohexyl | OMe | O |

TABLE 1-continued

| Cmpd | W | X | Z | A | Q |
|---|---|---|---|---|---|
| 1817 | 2-amino-imidazo-pyrimidine (N-linked) | cyclohexyl | cyclohexyl | OMe | O |
| 1818 | 4-amino-imidazo-pyrimidine (N9-linked, adenine-like) | cyclohexyl | cyclohexyl | OMe | O |
| 1819 | 8-amino-purine (N9-linked) | cyclohexyl | cyclohexyl | OMe | O |
| 1820 | 7-amino-benzisothiazol-3(2H)-one (N-linked) | cyclohexyl | cyclohexyl | OMe | O |
| 1821 | 6-amino-benzisothiazol-3(2H)-one (N-linked) | cyclohexyl | cyclohexyl | OMe | O |
| 1822 | 5-amino-benzisothiazol-3(2H)-one (N-linked) | cyclohexyl | cyclohexyl | OMe | O |

TABLE 1-continued

| Cmpd | W | X | Z | A | Q |
|------|---|---|---|---|---|
| 1823 | 4-amino-benzisothiazol-3(2H)-one (N-linked) | cyclohexyl | cyclohexyl | OMe | O |
| 1824 | 6-amino-1H-pyrazolo[3,4-d]pyrimidin-4(5H)-one (N1-linked) | cyclohexyl | cyclohexyl | OMe | O |
| 1825 | 4-amino-7H-pyrrolo[2,3-d]pyrimidin-7-yl | piperidinyl | piperidinyl | OMe | O |
| 1826 | 1-amino-decahydroisoquinolin-2-yl | piperidinyl | piperidinyl | OMe | O |
| 1827 | 8-amino-decahydroisoquinolin-2-yl | piperidinyl | piperidinyl | OMe | O |
| 1828 | 7-amino-decahydroisoquinolin-2-yl | piperidinyl | piperidinyl | OMe | O |
| 1829 | 6-amino-decahydroisoquinolin-2-yl | piperidinyl | piperidinyl | OMe | O |

TABLE 1-continued
| Cmpd | W | X | Z | A | Q |
|------|---|---|---|---|---|
| 1830 | 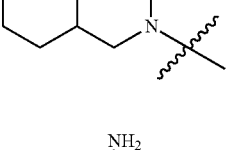 |  |  | OMe | O |
| 1831 | 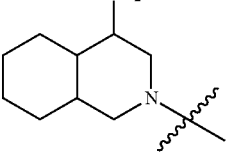 | 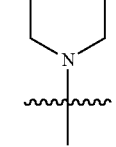 | 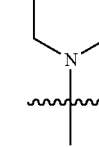 | OMe | O |
| 1832 | 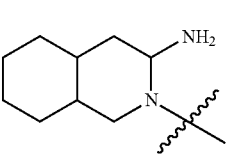 | 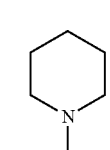 | 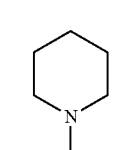 | OMe | O |
| 1833 | 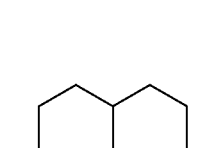 | 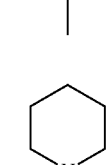 | 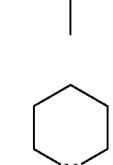 | OMe | O |
| 1834 | 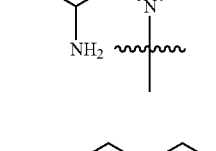 |  |  | OMe | O |
| 1835 | 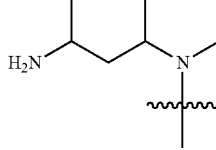 | 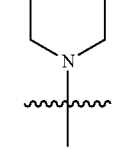 | 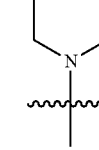 | OMe | O |
| 1836 | 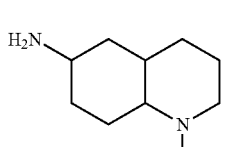 | 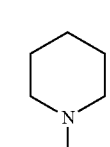 | 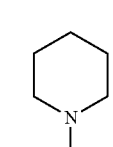 | OMe | O |

TABLE 1-continued
| Cmpd | W | X | Z | A | Q |
|---|---|---|---|---|---|
| 1837 | 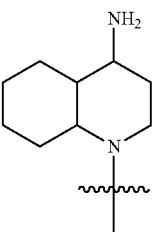 | 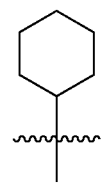 [SMILES: *C1CCCCC1] | 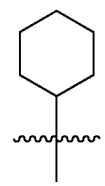 [SMILES: *C1CCCCC1] | OMe | O |
| 1838 | 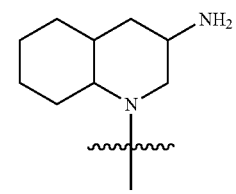 | 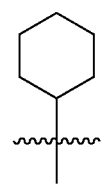 | 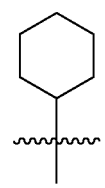 [SMILES: *C1CCCCC1] | OMe | O |
| 1839 | 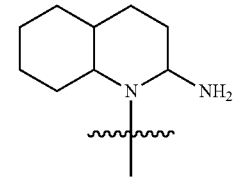 | 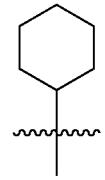 | 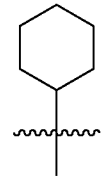 [SMILES: *C1CCCCC1] | OMe | O |
| 1840 | 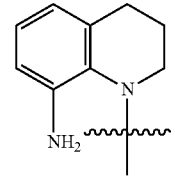 | 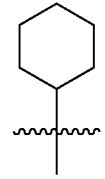 | 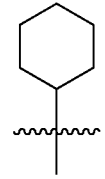 | OMe | O |
| 1841 | 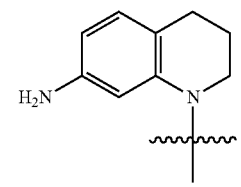 | 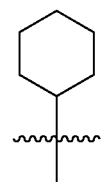 | 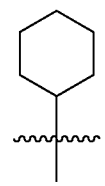 [SMILES: *C1CCCCC1] | OMe | O |
| 1842 | 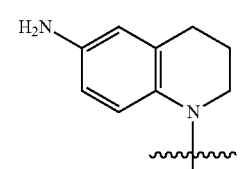 | 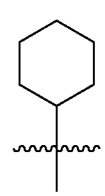 | 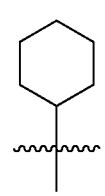 [SMILES: *C1CCCCC1] | OMe | O |
| 1843 | 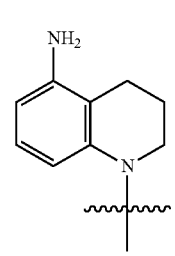 | 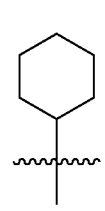 | 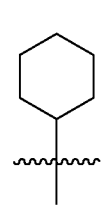 [SMILES: *C1CCCCC1] | OMe | O |

TABLE 1-continued

| Cmpd | W | X | Z | A | Q |
|------|---|---|---|---|---|
| 1844 | 4-amino-1,2,3,4-tetrahydroquinolin-1-yl | cyclohexyl | cyclohexyl | OMe | O |
| 1845 | 3-amino-1,2,3,4-tetrahydroquinolin-1-yl | cyclohexyl | cyclohexyl | OMe | O |
| 1846 | 2-amino-1,2,3,4-tetrahydroquinolin-1-yl | cyclohexyl | cyclohexyl | OMe | O |
| 1847 | 8-amino-1,2-dihydroquinolin-1-yl | cyclohexyl | cyclohexyl | OMe | O |
| 1848 | 7-amino-1,2-dihydroquinolin-1-yl | cyclohexyl | cyclohexyl | OMe | O |
| 1849 | 6-amino-1,2-dihydroquinolin-1-yl | cyclohexyl | cyclohexyl | OMe | O |
| 1850 | 5-amino-1,2-dihydroquinolin-1-yl | cyclohexyl | cyclohexyl | OMe | O |

TABLE 1-continued
| Cmpd | W | X | Z | A | Q |
|---|---|---|---|---|---|
| 1851 |  |  |  | OMe | O |
| 1852 | 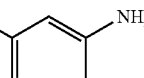 |  |  | OMe | O |
| 1853 | 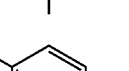 |  |  | OMe | O |
| 1854 |  |  |  | OMe | O |
| 1855 | 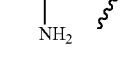 |  |  | OMe | O |
| 1856 | 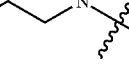 |  |  | OMe | O |
| 1857 | 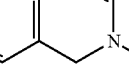 |  |  | OMe | O |
| 1858 | 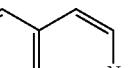 |  |  | OMe | O |

TABLE 1-continued
| Cmpd | W | X | Z | A | Q |
|------|---|---|---|---|---|
| 1859 | 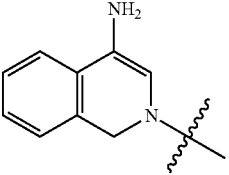 | 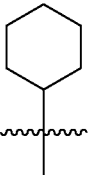 | 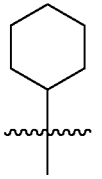 [SMILES: *C1CCCCC1] | OMe | O |
| 1860 | 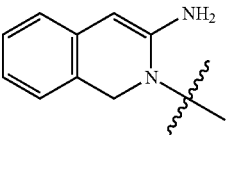 | 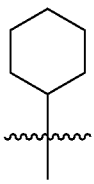 | 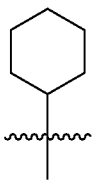 | OMe | O |
| 1861 | 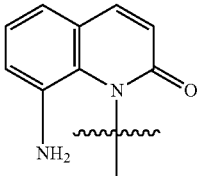 | 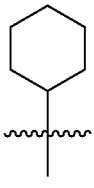 | 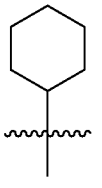 | OMe | O |
| 1862 | 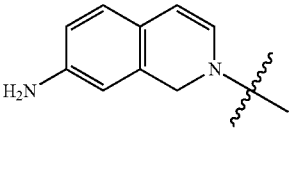 | 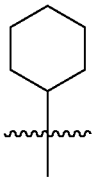 | 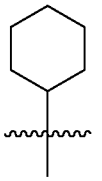 [SMILES: *C1CCCCC1] | OMe | O |
| 1863 | 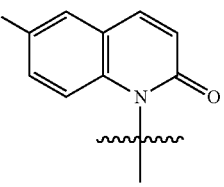 | 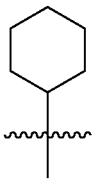 [SMILES: *C1CCCCC1] | 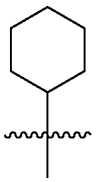 [SMILES: *C1CCCCC1] | OMe | O |
| 1864 | 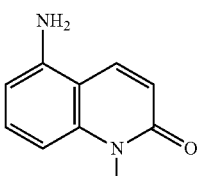 | 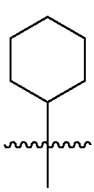 | 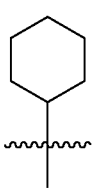 [SMILES: *C1CCCCC1] | OMe | O |
| 1865 | 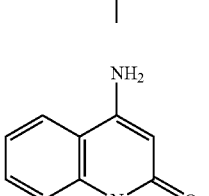 | 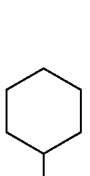 | 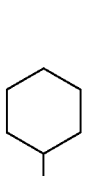 | OMe | O |

| Cmpd | W | X | Z | A | Q |
|---|---|---|---|---|---|
| 1866 | 3-amino-1-methyl-quinolin-2(1H)-one (N-linked) | cyclohexyl | cyclohexyl | OMe | O |
| 1867 | 8-aminoisoquinolin-1(2H)-one (N-linked) | cyclohexyl | cyclohexyl | OMe | O |
| 1868 | 7-aminoisoquinolin-1(2H)-one (N-linked) | cyclohexyl | cyclohexyl | OMe | O |
| 1869 | 6-aminoisoquinolin-1(2H)-one (N-linked) | cyclohexyl | cyclohexyl | OMe | O |
| 1870 | 5-aminoisoquinolin-1(2H)-one (N-linked) | cyclohexyl | cyclohexyl | OMe | O |
| 1871 | 4-aminoisoquinolin-1(2H)-one (N-linked) | cyclohexyl | cyclohexyl | OMe | O |
| 1872 | 3-aminoisoquinolin-1(2H)-one (N-linked) | cyclohexyl | cyclohexyl | OMe | O |
| 1873 | 8-amino-2H-benzo[e][1,2]oxazine (N-linked) | cyclohexyl | cyclohexyl | OMe | O |

TABLE 1-continued

| Cmpd | W | X | Z | A | Q |
|---|---|---|---|---|---|
| 1874 | 7-amino-2H-benzo[e][1,2]oxazine | cyclohexyl | cyclohexyl | OMe | O |
| 1875 | 6-amino-2H-benzo[e][1,2]oxazine | cyclohexyl | cyclohexyl | OMe | O |
| 1876 | 5-amino-2H-benzo[e][1,2]oxazine | cyclohexyl | cyclohexyl | OMe | O |
| 1877 | 4-amino-2H-benzo[e][1,2]oxazine | cyclohexyl | cyclohexyl | OMe | O |
| 1878 | 3-amino-2H-benzo[e][1,2]oxazine | cyclohexyl | cyclohexyl | OMe | O |
| 1879 | 1-amino-9H-carbazol-9-yl | cyclohexyl | cyclohexyl | OMe | O |
| 1880 | 2-amino-9H-carbazol-9-yl | cyclohexyl | cyclohexyl | OMe | O |
| 1881 | 1-amino-10H-phenoxazin-10-yl | cyclohexyl | cyclohexyl | OMe | O |

TABLE 1-continued

| Cmpd | W | X | Z | A | Q |
|------|---|---|---|---|---|
| 1882 | 2-amino-phenoxazin-10-yl | cyclohexyl | cyclohexyl | OMe | O |
| 1883 | 1-amino-phenothiazin-10-yl | cyclohexyl | cyclohexyl | OMe | O |
| 1884 | 2-amino-phenothiazin-10-yl | cyclohexyl | cyclohexyl | OMe | O |
| 1885 | amino-adamantyl (2-azaadamantane) | cyclohexyl | cyclohexyl | OMe | O |
| 1886 | 4-amino-2,7-dihydro-1H-azepin-1-yl | cyclohexyl | cyclohexyl | OMe | O |
| 1887 | 5-amino-2,5-dihydro-1H-azepin-1-yl | cyclohexyl | cyclohexyl | OMe | O |
| 1888 | 4-amino-1H-azepin-1-yl | cyclohexyl | cyclohexyl | OMe | O |

TABLE 1-continued
| Cmpd | W | X | Z | A | Q |
|------|---|---|---|---|---|
| 1889 | 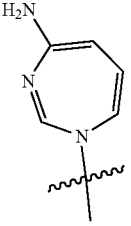 | 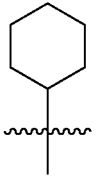 | 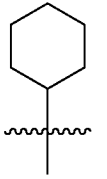 [SMILES: *C1CCCCC1] | OMe | O |
| 1890 | 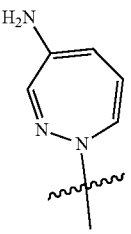 | 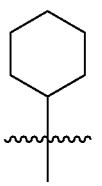 | 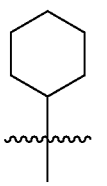 [SMILES: *C1CCCCC1] | OMe | O |
| 1891 | 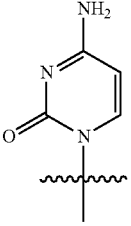 [SMILES: *n1ccc(N)nc1=O] | 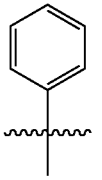 | 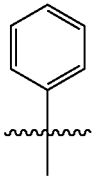 | OMe | O |
| 1892 | 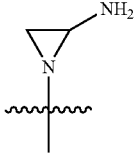 | 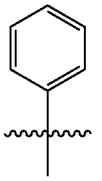 | 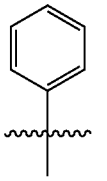 | OMe | O |
| 1893 | 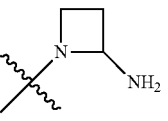 [SMILES: *N1CCC1N] | 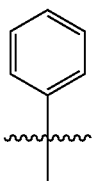 | 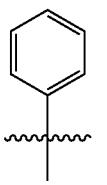 | OMe | O |
| 1894 | 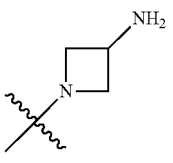 [SMILES: *N1CC(N)C1] | 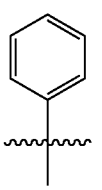 | 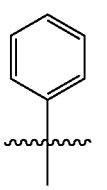 | OMe | O |
| 1895 | 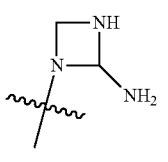 | 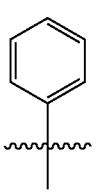 | 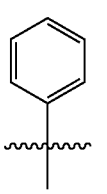 | OMe | O |

TABLE 1-continued

| Cmpd | W | X | Z | A | Q |
|---|---|---|---|---|---|
| 1896 | 3-amino-azetidin-2-one (N-linked) | phenyl | phenyl | OMe | O |
| 1897 | 4-amino-azetidin-2-one (N-linked) | phenyl | phenyl | OMe | O |
| 1898 | 2-amino-pyrrolidin-1-yl | phenyl | phenyl | OMe | O |
| 1899 | 3-amino-pyrrolidin-1-yl | phenyl | phenyl | OMe | O |
| 1900 | 2-amino-2,5-dihydro-pyrrol-1-yl | phenyl | phenyl | OMe | O |
| 1901 | 3-amino-2,5-dihydro-pyrrol-1-yl | phenyl | phenyl | OMe | O |
| 1902 | 5-amino-2,3-dihydro-pyrrol-1-yl | phenyl | phenyl | OMe | O |
| 1903 | 4-amino-2,3-dihydro-pyrrol-1-yl | phenyl | phenyl | OMe | O |

TABLE 1-continued

| Cmpd | W | X | Z | A | Q |
|---|---|---|---|---|---|
| 1904 | 3-amino-2,5-dihydropyrrol-1-yl | phenyl | phenyl | OMe | O |
| 1905 | 2-amino-2,5-dihydropyrrol-1-yl | phenyl | phenyl | OMe | O |
| 1906 | 2-amino-pyrrol-1-yl | phenyl | phenyl | OMe | O |
| 1907 | 3-amino-pyrrol-1-yl | phenyl | phenyl | OMe | O |
| 1908 | 3-amino-pyrazolidin-1-yl | phenyl | phenyl | OMe | O |
| 1909 | 4-amino-pyrazolidin-1-yl | phenyl | phenyl | OMe | O |
| 1910 | 5-amino-pyrazolidin-1-yl | phenyl | phenyl | OMe | O |

TABLE 1-continued

| Cmpd | W | X | Z | A | Q |
|------|---|---|---|---|---|
| 1911 | 3-amino-imidazolidin-1-yl (via quaternary C) | phenyl | phenyl | OMe | O |
| 1912 | 5-amino-imidazolidin-1-yl (via quaternary C) | phenyl | phenyl | OMe | O |
| 1913 | 2-amino-imidazolidin-1-yl (via quaternary C) | phenyl | phenyl | OMe | O |
| 1914 | 3-amino-4,5-dihydro-pyrazol-1-yl (via quaternary C) | phenyl | phenyl | OMe | O |
| 1915 | 4-amino-4,5-dihydro-pyrazol-1-yl (via quaternary C) | phenyl | phenyl | OMe | O |
| 1916 | 5-amino-4,5-dihydro-pyrazol-1-yl (via quaternary C) | phenyl | phenyl | OMe | O |
| 1917 | 2-amino-4,5-dihydro-imidazol-1-yl (via quaternary C) | phenyl | phenyl | OMe | O |
| 1918 | 4-amino-4,5-dihydro-imidazol-1-yl (via quaternary C) | phenyl | phenyl | OMe | O |

TABLE 1-continued

| Cmpd | W | X | Z | A | Q |
| --- | --- | --- | --- | --- | --- |
| 1919 | 4,5-dihydroimidazol-5-amine (N-linked) | phenyl | phenyl | OMe | O |
| 1920 | 3-amino-2,5-dioxopyrrolidin-1-yl | phenyl | phenyl | OMe | O |
| 1921 | 5-aminohydantoin-3-yl | phenyl | phenyl | OMe | O |
| 1922 | 5-amino-2,4-dioxothiazolidin-3-yl | phenyl | phenyl | OMe | O |
| 1923 | 2-aminopiperidin-1-yl | phenyl | phenyl | OMe | O |
| 1924 | 3-aminopiperidin-1-yl | phenyl | phenyl | OMe | O |
| 1925 | 4-aminopiperidin-1-yl | phenyl | phenyl | OMe | O |

TABLE 1-continued

| Cmpd | W | X | Z | A | Q |
|------|---|---|---|---|---|
| 1926 | 3-amino-piperazin-1-yl | phenyl | phenyl | OMe | O |
| 1927 | 3-amino-piperazin-1-yl | phenyl | phenyl | OMe | O |
| 1928 | 3-amino-morpholin-4-yl | phenyl | phenyl | OMe | O |
| 1929 | 2-amino-morpholin-4-yl | phenyl | phenyl | OMe | O |
| 1930 | 3-amino-2H-1,2-oxazin-2-yl | phenyl | phenyl | OMe | O |
| 1931 | 4-amino-2H-1,2-oxazin-2-yl | phenyl | phenyl | OMe | O |
| 1932 | 4-amino-2H-1,2-oxazin-2-yl | phenyl | phenyl | OMe | O |

TABLE 1-continued

| Cmpd | W | X | Z | A | Q |
|---|---|---|---|---|---|
| 1933 | 6-amino-2H-1,2-oxazine (N-linked) | phenyl | phenyl | OMe | O |
| 1934 | 3-amino-4H-1,4-oxazine (N-linked) | phenyl | phenyl | OMe | O |
| 1935 | 2-amino-4H-1,4-oxazine (N-linked) | phenyl | phenyl | OMe | O |
| 1936 | 3-aminothiomorpholine (N-linked) | phenyl | phenyl | OMe | O |
| 1937 | 2-aminothiomorpholine (N-linked) | phenyl | phenyl | OMe | O |
| 1938 | 3-amino-2H-1,2-thiazine (N-linked) | phenyl | phenyl | OMe | O |
| 1939 | 4-amino-2H-1,2-thiazine (N-linked) | phenyl | phenyl | OMe | O |

TABLE 1-continued

| Cmpd | W | X | Z | A | Q |
|---|---|---|---|---|---|
| 1940 | 4-amino-2H-1,2-thiazine (N-linked) | phenyl | phenyl | OMe | O |
| 1941 | 3-amino-2H-1,2-thiazine (N-linked) | phenyl | phenyl | OMe | O |
| 1942 | 3-amino-1,4-thiazine (N-linked) | phenyl | phenyl | OMe | O |
| 1943 | 3-amino-1,4-thiazine (N-linked) | phenyl | phenyl | OMe | O |
| 1944 | 3-amino-thiomorpholine 1,1-dioxide (N-linked) | phenyl | phenyl | OMe | O |
| 1945 | 2-amino-thiomorpholine 1,1-dioxide (N-linked) | phenyl | phenyl | OMe | O |
| 1946 | 2-amino-5,6-dihydro-4H-cyclopenta[b]pyrrole (N-linked) | phenyl | phenyl | OMe | O |

TABLE 1-continued

| Cmpd | W | X | Z | A | Q |
|---|---|---|---|---|---|
| 1947 | H₂N-pyrrole fused cyclopentane, N-linked | phenyl | phenyl | OMe | O |
| 1948 | 4-NH₂ pyrrole fused cyclopentane, N-linked | phenyl | phenyl | OMe | O |
| 1949 | 5-NH₂ pyrrole fused cyclopentane, N-linked | phenyl | phenyl | OMe | O |
| 1950 | 6-NH₂ pyrrole fused cyclopentane, N-linked | phenyl | phenyl | OMe | O |
| 1951 | H₂N-substituted bicyclic dipyrrole, N-linked | phenyl | phenyl | OMe | O |
| 1952 | H₂N-substituted bicyclic dipyrrole, N-linked | phenyl | phenyl | OMe | O |
| 1953 | H₂N-substituted bicyclic dipyrrole, N-linked | phenyl | phenyl | OMe | O |

TABLE 1-continued

| Cmpd | W | X | Z | A | Q |
|---|---|---|---|---|---|
| 1954 | pyrrolo-pyrrole with NH and NH2 | phenyl | phenyl | OMe | O |
| 1955 | pyrrolo-pyrrole with NH and H2N | phenyl | phenyl | OMe | O |
| 1956 | pyrrolo-pyrrole with H2N and NH | phenyl | phenyl | OMe | O |
| 1957 | pyrrolo-pyrrole with NH and NH2 | phenyl | phenyl | OMe | O |
| 1958 | pyrrolo-pyrrole with NH and NH2 | phenyl | phenyl | OMe | O |
| 1959 | pyrrolo-pyrrole with H2N and NH | phenyl | phenyl | OMe | O |
| 1960 | pyrrolo-pyrrole with H2N and NH | phenyl | phenyl | OMe | O |

TABLE 1-continued
| Cmpd | W | X | Z | A | Q |
|---|---|---|---|---|---|
| 1961 | 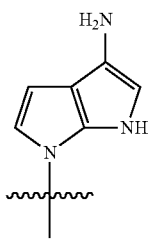 [SMILES: *n1ccc2c(N)c[nH]c21] | 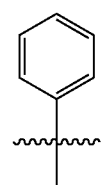 | 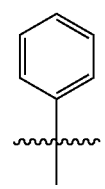 | OMe | O |
| 1962 | 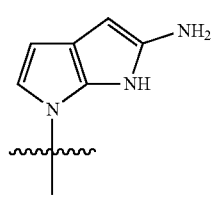 | 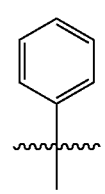 | 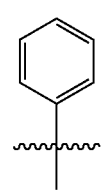 | OMe | O |
| 1963 | 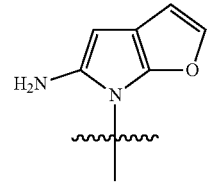 [SMILES: *n1c(N)cc2ccoc21] | 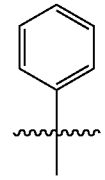 | 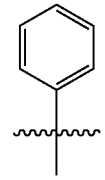 | OMe | O |
| 1964 | 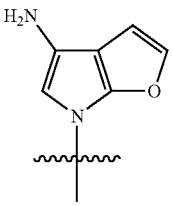 [SMILES: *n1cc(N)c2ccoc21] | 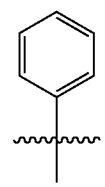 | 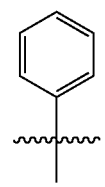 | OMe | O |
| 1965 | 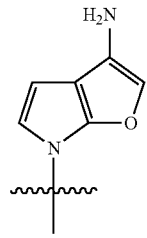 | 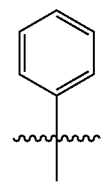 | 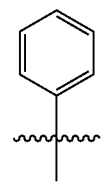 | OMe | O |
| 1966 | 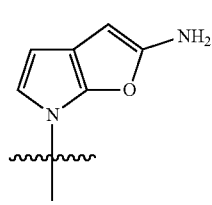 [SMILES: *n1ccc2cc(N)oc21] | 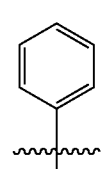 | 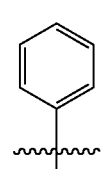 | OMe | O |
| 1967 | 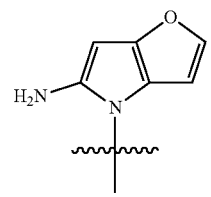 [SMILES: *n1c(N)cc2occc21] | 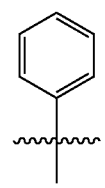 | 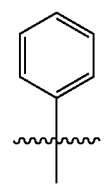 | OMe | O |

TABLE 1-continued

| Cmpd | W | X | Z | A | Q |
|------|---|---|---|---|---|
| 1968 | 5-amino-4H-furo[3,2-b]pyrrole (N-linked) | phenyl | phenyl | OMe | O |
| 1969 | 2-amino-4H-furo[3,2-b]pyrrole (N-linked) | phenyl | phenyl | OMe | O |
| 1970 | 3-amino-4H-furo[3,2-b]pyrrole (N-linked) | phenyl | phenyl | OMe | O |
| 1971 | 5-amino-7H-thieno[2,3-b]pyrrole (N-linked) | phenyl | phenyl | OMe | O |
| 1972 | 4-amino-7H-thieno[2,3-b]pyrrole (N-linked) | phenyl | phenyl | OMe | O |
| 1973 | 3-amino-7H-thieno[2,3-b]pyrrole (N-linked) | phenyl | phenyl | OMe | O |
| 1974 | 2-amino-7H-thieno[2,3-b]pyrrole (N-linked) | phenyl | phenyl | OMe | O |

TABLE 1-continued

| Cmpd | W | X | Z | A | Q |
|---|---|---|---|---|---|
| 1975 | 5-amino-thieno[3,2-b]pyrrol-4-yl (N-linked) | phenyl | phenyl | OMe | O |
| 1976 | 6-amino-thieno[3,2-b]pyrrol-4-yl (N-linked) | phenyl | phenyl | OMe | O |
| 1977 | 2-amino-thieno[3,2-b]pyrrol-4-yl (N-linked) | phenyl | phenyl | OMe | O |
| 1978 | 3-amino-thieno[3,2-b]pyrrol-4-yl (N-linked) | phenyl | phenyl | OMe | O |
| 1979 | 7-amino-indolin-1-yl | phenyl | phenyl | OMe | O |
| 1980 | 6-amino-indolin-1-yl | phenyl | phenyl | OMe | O |
| 1981 | 4-amino-indolin-1-yl | phenyl | phenyl | OMe | O |

TABLE 1-continued

| Cmpd | W | X | Z | A | Q |
|---|---|---|---|---|---|
| 1982 | 3-amino-indoline (N-linked) | phenyl | phenyl | OMe | O |
| 1983 | 2-amino-indoline (N-linked) | phenyl | phenyl | OMe | O |
| 1984 | 7-amino-indole (N-linked) | phenyl | phenyl | OMe | O |
| 1985 | 6-amino-indole (N-linked) | phenyl | phenyl | OMe | O |
| 1986 | 5-amino-indole (N-linked) | phenyl | phenyl | OMe | O |
| 1987 | 4-amino-indole (N-linked) | phenyl | phenyl | OMe | O |
| 1988 | 3-amino-indole (N-linked) | phenyl | phenyl | OMe | O |

TABLE 1-continued

| Cmpd | W | X | Z | A | Q |
|---|---|---|---|---|---|
| 1989 | 1-(indol-2-amine) | phenyl | phenyl | OMe | O |
| 1990 | 2-(isoindol-1-amine) | phenyl | phenyl | OMe | O |
| 1991 | 2-(isoindol-4-amine) | phenyl | phenyl | OMe | O |
| 1992 | 2-(isoindol-5-amine) | phenyl | phenyl | OMe | O |
| 1993 | 1-(indazol-7-amine) | phenyl | phenyl | OMe | O |
| 1994 | 1-(indazol-6-amine) | phenyl | phenyl | OMe | O |
| 1995 | 1-(indazol-5-amine) | phenyl | phenyl | OMe | O |

TABLE 1-continued

| Cmpd | W | X | Z | A | Q |
|---|---|---|---|---|---|
| 1996 | 4-amino-1H-indazol-1-yl (N1-linked) | phenyl | phenyl | OMe | O |
| 1997 | 3-amino-1H-indazol-1-yl (N1-linked) | phenyl | phenyl | OMe | O |
| 1998 | 7-amino-1H-benzimidazol-1-yl | phenyl | phenyl | OMe | O |
| 1999 | 6-amino-1H-benzimidazol-1-yl | phenyl | phenyl | OMe | O |
| 2000 | 5-amino-1H-benzimidazol-1-yl | phenyl | phenyl | OMe | O |
| 2001 | 4-amino-1H-benzimidazol-1-yl | phenyl | phenyl |  | O |
| 2002 | 2-amino-1H-benzimidazol-1-yl | phenyl | phenyl | OMe | O |

TABLE 1-continued

| Cmpd | W | X | Z | A | Q |
|---|---|---|---|---|---|
| 2003 | 7-amino-4-azaindole | phenyl | phenyl | OMe | O |
| 2004 | 6-amino-4-azaindole | phenyl | phenyl | OMe | O |
| 2005 | 5-amino-4-azaindole | phenyl | phenyl | OMe | O |
| 2006 | 3-amino-4-azaindole | phenyl | phenyl | OMe | O |
| 2007 | 2-amino-4-azaindole | phenyl | phenyl | OMe | O |
| 2008 | 7-amino-5-azaindole | phenyl | phenyl | OMe | O |
| 2009 | 6-amino-5-azaindole | phenyl | phenyl | OMe | O |
| 2010 | 4-amino-5-azaindole | phenyl | phenyl | OMe | O |

TABLE 1-continued

| Cmpd | W | X | Z | A | Q |
|---|---|---|---|---|---|
| 2011 | 3-amino-1H-pyrrolo[3,2-c]pyridin-1-yl (N-linked) | phenyl | phenyl | OMe | O |
| 2012 | 2-amino-1H-pyrrolo[3,2-c]pyridin-1-yl | phenyl | phenyl | OMe | O |
| 2013 | 7-amino-1H-pyrrolo[2,3-c]pyridin-1-yl | phenyl | phenyl | OMe | O |
| 2014 | 5-amino-1H-pyrrolo[2,3-c]pyridin-1-yl | phenyl | phenyl | OMe | O |
| 2015 | 4-amino-1H-pyrrolo[2,3-c]pyridin-1-yl | phenyl | phenyl | OMe | O |
| 2016 | 3-amino-1H-pyrrolo[2,3-c]pyridin-1-yl | phenyl | phenyl | OMe | O |
| 2017 | 2-amino-1H-pyrrolo[2,3-c]pyridin-1-yl | phenyl | phenyl | OMe | O |

TABLE 1-continued

| Cmpd | W | X | Z | A | Q |
|---|---|---|---|---|---|
| 2018 | 6-amino-7-azaindol-1-yl | phenyl | phenyl | OMe | O |
| 2019 | 5-amino-7-azaindol-1-yl | phenyl | phenyl | OMe | O |
| 2020 | 4-amino-7-azaindol-1-yl | phenyl | phenyl | OMe | O |
| 2021 | 3-amino-7-azaindol-1-yl | phenyl | phenyl | OMe | O |
| 2022 | 2-amino-7-azaindol-1-yl | phenyl | phenyl | OMe | O |
| 2023 | 6-amino-pyrazolo[3,4-b]pyridin-1-yl | phenyl | phenyl | OMe | O |
| 2024 | 5-amino-pyrazolo[3,4-b]pyridin-1-yl | phenyl | phenyl | OMe | O |

TABLE 1-continued
| Cmpd | W | X | Z | A | Q |
|---|---|---|---|---|---|
| 2025 | 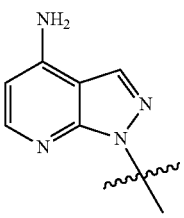 [SMILES: *n1ncc2c(N)ccnc21] | 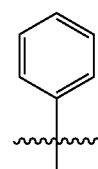 | 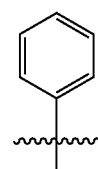 | OMe | O |
| 2026 | 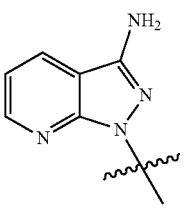 [SMILES: *n1nc(N)c2cccnc21] | 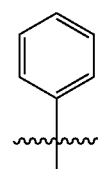 | 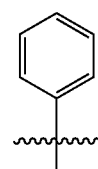 | OMe | O |
| 2027 | 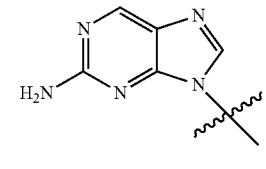 [SMILES: *n1cnc2cnc(N)nc21] | 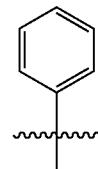 | 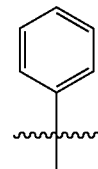 | OMe | O |
| 2028 | 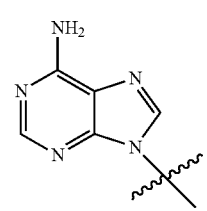 [SMILES: *n1cnc2c(N)ncnc21] | 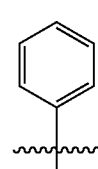 | 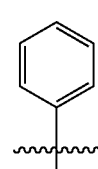 | OMe | O |
| 2029 | 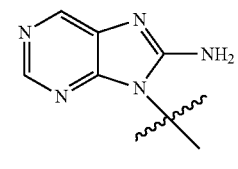 | 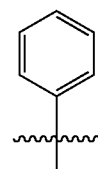 | 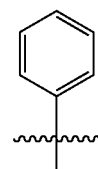 | OMe | O |
| 2030 | 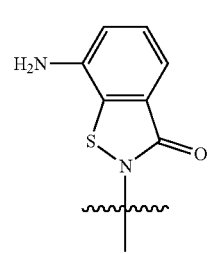 | 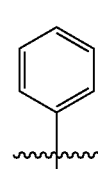 | 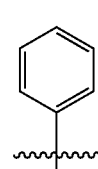 | OMe | O |
| 2031 | 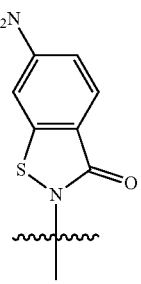 | 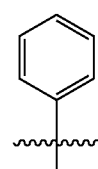 | 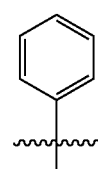 | OMe | O |

US 11,795,192 B2
TABLE 1-continued
| Cmpd | W | X | Z | A | Q |
|------|---|---|---|---|---|
| 2032 | 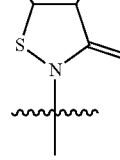 |  |  | OMe | O |
| 2033 | 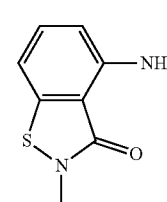 | 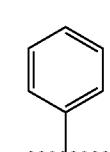 | 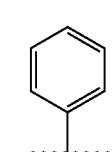 | OMe | O |
| 2034 | 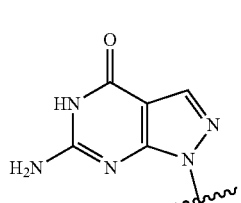 | 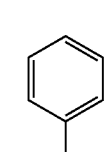 | 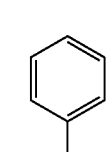 | OMe | O |
| 2035 | 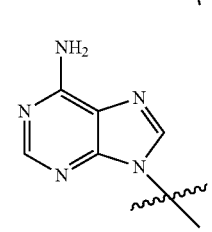 | 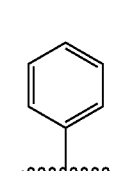 | 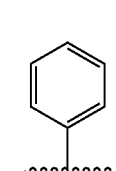 | OMe | O |
| 2036 | 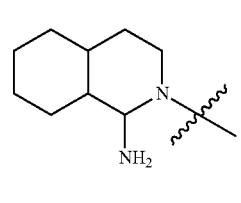 [SMILES: *N1CCC2CCCCC2C1N] | 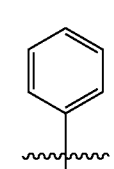 | 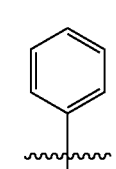 | OMe | O |
| 2037 | 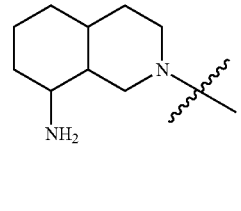 | 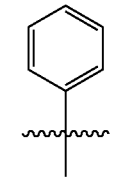 | 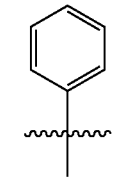 | OMe | O |
| 2038 | 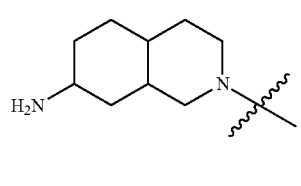 [SMILES: *N1CCC2CCC(N)CC2C1] | 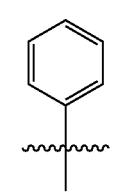 | 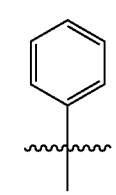 | OMe | O |

TABLE 1-continued

| Cmpd | W | X | Z | A | Q |
|---|---|---|---|---|---|
| 2039 | H₂N-decahydroisoquinoline (amine on cyclohexane ring) | phenyl | phenyl | OMe | O |
| 2040 | decahydroisoquinoline with NH₂ | phenyl | phenyl | OMe | O |
| 2041 | decahydroisoquinoline with NH₂ | phenyl | phenyl | OMe | O |
| 2042 | decahydroisoquinoline with NH₂ | phenyl | phenyl | OMe | O |
| 2043 | decahydroquinoline with NH₂ | phenyl | phenyl | OMe | O |
| 2044 | H₂N-decahydroquinoline | phenyl | phenyl | OMe | O |
| 2045 | H₂N-decahydroquinoline | phenyl | phenyl | OMe | O |
| 2046 | decahydroquinoline with NH₂ | phenyl | phenyl | OMe | O |

TABLE 1-continued
| Cmpd | W | X | Z | A | Q |
|---|---|---|---|---|---|
| 2047 | 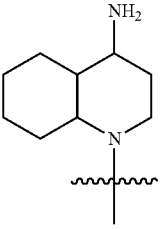 [SMILES: *N1CCC(N)C2CCCCC21] | 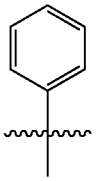 | 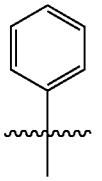 | OMe | O |
| 2048 | 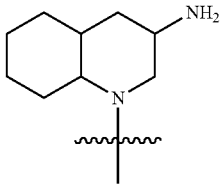 [SMILES: *N1CC(N)CC2CCCCC21] | 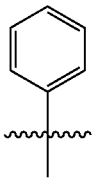 | 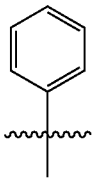 | OMe | O |
| 2049 | 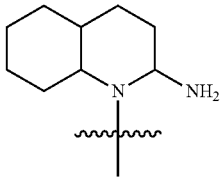 [SMILES: *N1C(N)CCC2CCCCC21] | 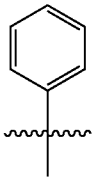 | 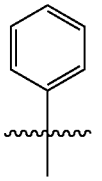 | OMe | O |
| 2050 | 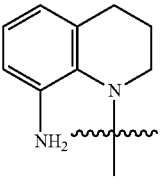 [SMILES: *N1CCCc2cccc(N)c21] | 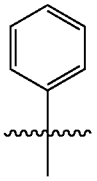 | 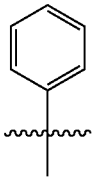 | OMe | O |
| 2051 | 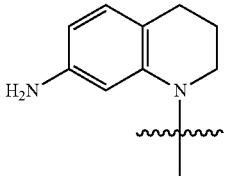 [SMILES: *N1CCCc2ccc(N)cc21] | 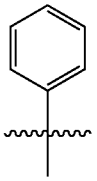 | 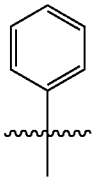 | OMe | O |
| 2052 | 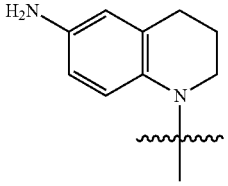 [SMILES: *N1CCCc2cc(N)ccc21] | 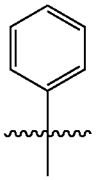 | 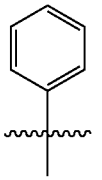 | OMe | O |
| 2053 | 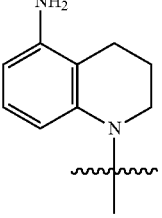 | 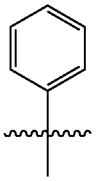 | 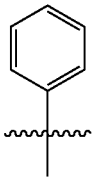 | OMe | O |

TABLE 1-continued

| Cmpd | W | X | Z | A | Q |
|---|---|---|---|---|---|
| 2054 | 4-amino-1,2,3,4-tetrahydroquinolin-1-yl | phenyl | phenyl | OMe | O |
| 2055 | 3-amino-1,2,3,4-tetrahydroquinolin-1-yl | phenyl | phenyl | OMe | O |
| 2056 | 2-amino-1,2,3,4-tetrahydroquinolin-1-yl | phenyl | phenyl | OMe | O |
| 2057 | 8-amino-2H-quinolin-1-yl | phenyl | phenyl | OMe | O |
| 2058 | 7-amino-2H-quinolin-1-yl | phenyl | phenyl | OMe | O |
| 2059 | 6-amino-2H-quinolin-1-yl | phenyl | phenyl | OMe | O |
| 2060 | 5-amino-2H-quinolin-1-yl | phenyl | phenyl | OMe | O |

TABLE 1-continued
| Cmpd | W | X | Z | A | Q |
|---|---|---|---|---|---|
| 2061 | 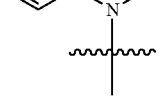 |  |  | OMe | O |
| 2062 | 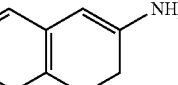 |  |  | OMe | O |
| 2063 |  |  |  | OMe | O |
| 2064 | 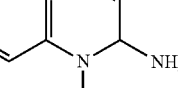 |  |  | OMe | O |
| 2065 | 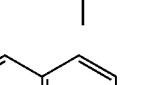 |  |  | OMe | O |
| 2066 | 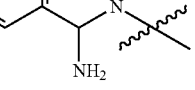 |  |  | OMe | O |
| 2067 | 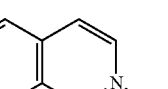 |  |  | OMe | O |
| 2068 |  |  |  | OMe | O |

TABLE 1-continued
| Cmpd | W | X | Z | A | Q |
|---|---|---|---|---|---|
| 2069 | 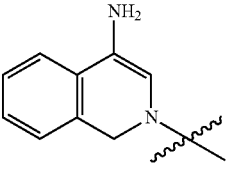 [SMILES: *N1C=C(N)c2ccccc2C1] | 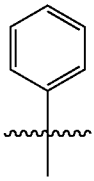 | 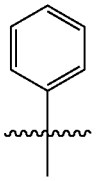 | OMe | O |
| 2070 | 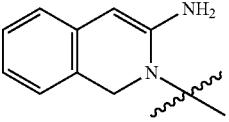 [SMILES: *N1Cc2ccccc2C=C1N] | 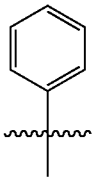 | 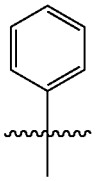 | OMe | O |
| 2071 | 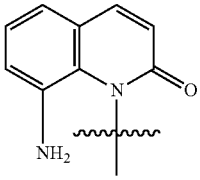 [SMILES: *n1c(=O)ccc2cccc(N)c21] | 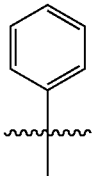 | 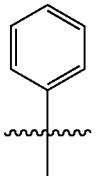 | OMe | O |
| 2072 | 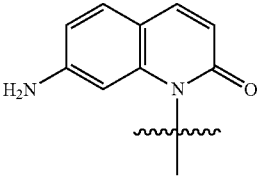 [SMILES: *n1c(=O)ccc2ccc(N)cc21] | 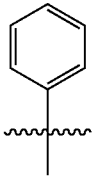 | 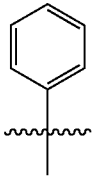 | OMe | O |
| 2073 | 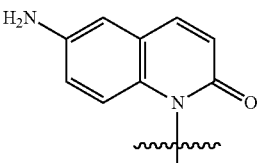 | 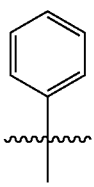 | 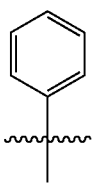 | OMe | O |
| 2074 | 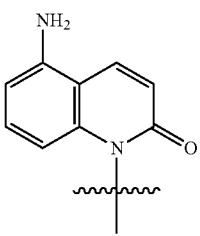 [SMILES: *n1c(=O)ccc2c(N)cccc21] | 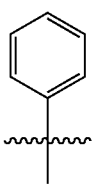 | 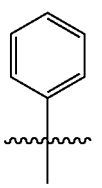 | OMe | O |
| 2075 | 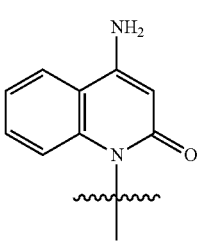 [SMILES: *n1c(=O)cc(N)c2ccccc21] | 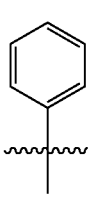 | 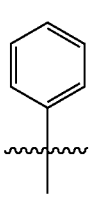 | OMe | O |

TABLE 1-continued
| Cmpd | W | X | Z | A | Q |
|---|---|---|---|---|---|
| 2076 | 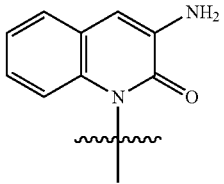 [SMILES: *n1c(=O)c(N)cc2ccccc21] | 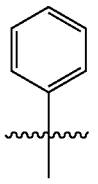 | 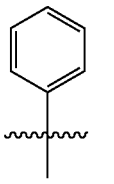 | OMe | O |
| 2077 | 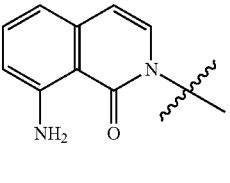 | 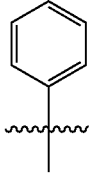 | 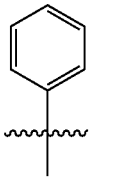 | OMe | O |
| 2078 | 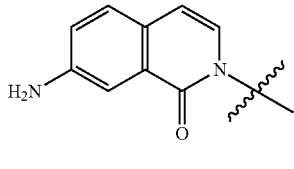 [SMILES: *n1ccc2ccc(N)cc2c1=O] | 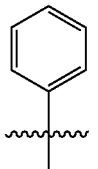 | 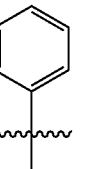 | OMe | O |
| 2079 | 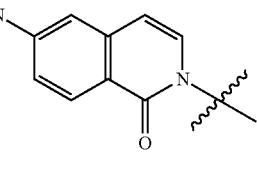 | 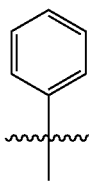 | 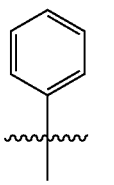 | OMe | O |
| 2080 | 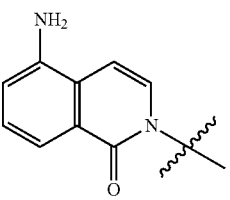 [SMILES: *n1ccc2c(N)cccc2c1=O] | 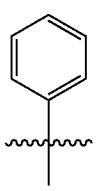 | 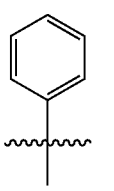 | OMe | O |
| 2081 | 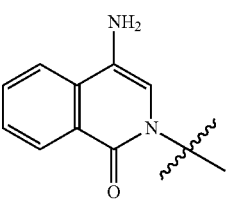 [SMILES: *n1cc(N)c2ccccc2c1=O] | 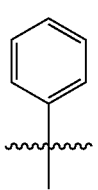 | 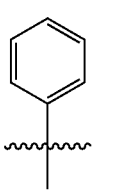 | OMe | O |
| 2082 | 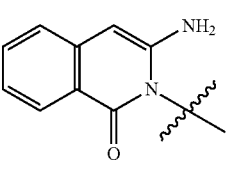 [SMILES: *n1c(N)cc2ccccc2c1=O] | 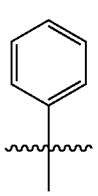 | 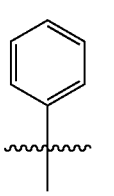 | OMe | O |
| 2083 | 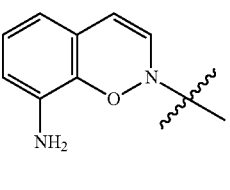 | 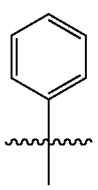 | 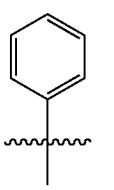 | OMe | O |

TABLE 1-continued
| Cmpd | W | X | Z | A | Q |
|---|---|---|---|---|---|
| 2084 | 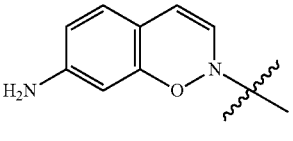 [SMILES: *N1C=Cc2ccc(N)cc2O1] | 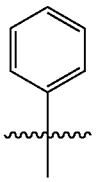 | 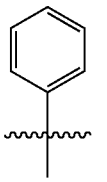 | OMe | O |
| 2085 | 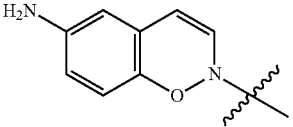 [SMILES: *N1C=Cc2cc(N)ccc2O1] | 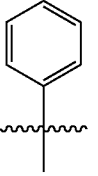 | 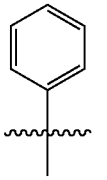 | OMe | O |
| 2086 | 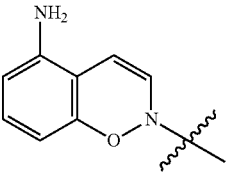 [SMILES: *N1C=Cc2c(N)cccc2O1] | 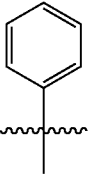 | 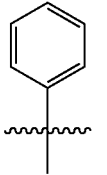 | OMe | O |
| 2087 | 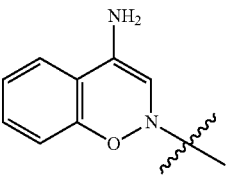 [SMILES: *N1C=C(N)c2ccccc2O1] | 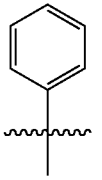 | 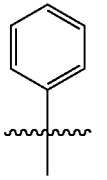 | OMe | O |
| 2088 | 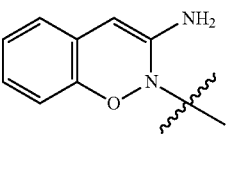 [SMILES: *N1Oc2ccccc2C=C1N] | 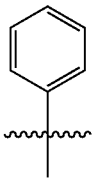 | 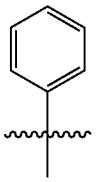 | OMe | O |
| 2089 | 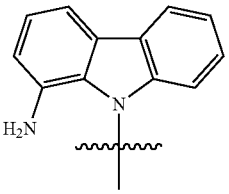 | 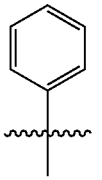 | 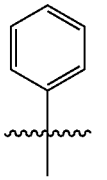 | OMe | O |
| 2090 | 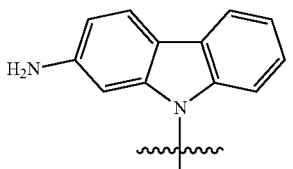 | 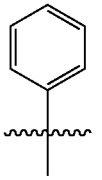 | 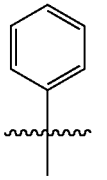 | OMe | O |
| 2091 | 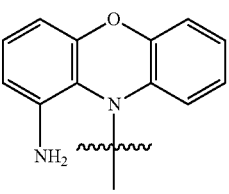 | 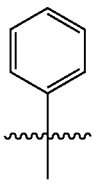 | 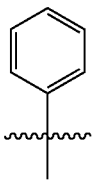 | OMe | O |

TABLE 1-continued
| Cmpd | W | X | Z | A | Q |
|------|---|---|---|---|---|
| 2092 | 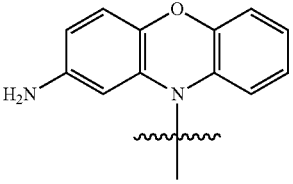 | 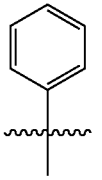 | 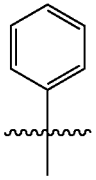 | OMe | O |
| 2093 | 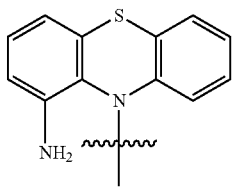 [SMILES: *N1c2ccccc2Sc2cccc(N)c21] | 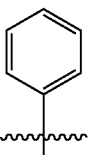 | 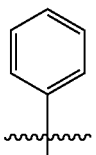 | OMe | O |
| 2094 | 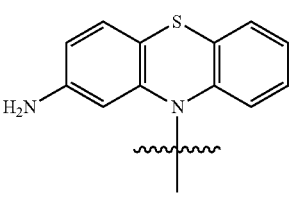 | 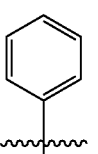 | 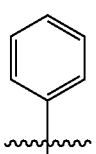 | OMe | O |
| 2095 | 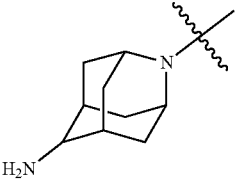 [SMILES: *N1C2CC3CC1CC(C2)C3N] | 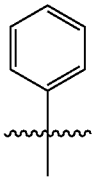 | 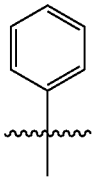 | OMe | O |
| 2096 | 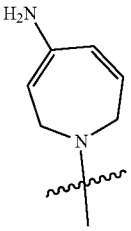 | 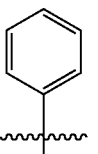 | 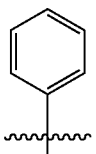 | OMe | O |
| 2097 | 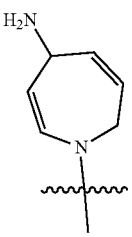 | 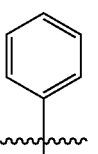 | 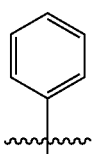 | OMe | O |
| 2098 | 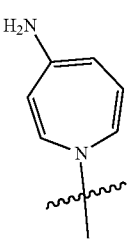 | 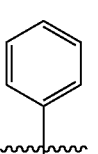 | 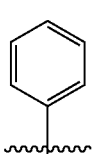 | OMe | O |

TABLE 1-continued
| Cmpd | W | X | Z | A | Q |
|---|---|---|---|---|---|
| 2099 | 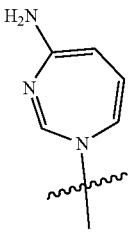 | 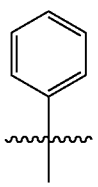 | 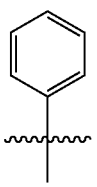 | OMe | O |
| 2100 | 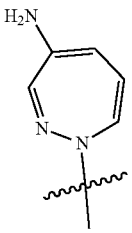 | 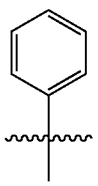 | 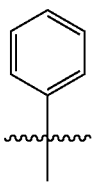 | OMe | O |
| 2101 | 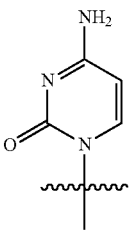 [SMILES: *n1ccc(N)nc1=O] | 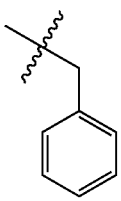 [SMILES: *Cc1ccccc1] | 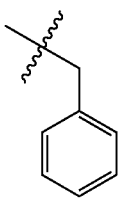 | OMe | O |
| 2102 | 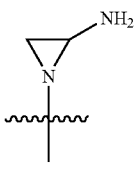 | 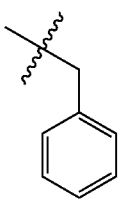 [SMILES: *Cc1ccccc1] | 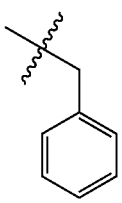 | OMe | O |
| 2103 | 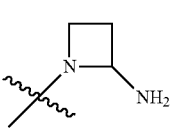 | 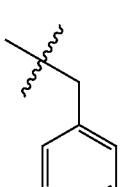 | 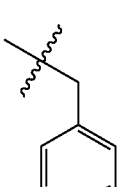 | OMe | O |
| 2104 | 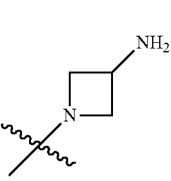 [SMILES: *N1CC(N)C1] | 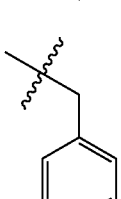 |  | OMe | O |
| 2105 | 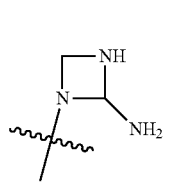 [SMILES: *N1CNC1N] | 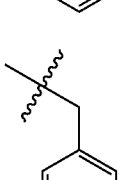 | 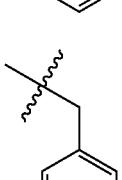 | OMe | O |

TABLE 1-continued

| Cmpd | W | X | Z | A | Q |
|---|---|---|---|---|---|
| 2106 | 3-amino-azetidinone (N-linked) | benzyl | benzyl | OMe | O |
| 2107 | 3-amino-azetidinone (N-linked, alt) | benzyl | benzyl | OMe | O |
| 2108 | 2-amino-pyrrolidine (N-linked) | benzyl | benzyl | OMe | O |
| 2109 | 3-amino-pyrrolidine (N-linked) | benzyl | benzyl | OMe | O |
| 2110 | 2-amino-2,5-dihydro-pyrrole (N-linked) | benzyl | benzyl | OMe | O |
| 2111 | 3-amino-2,5-dihydro-pyrrole (N-linked) | benzyl | benzyl | OMe | O |
| 2112 | 5-amino-3,4-dihydro-2H-pyrrole (N-linked) | benzyl | benzyl | OMe | O |

TABLE 1-continued

| Cmpd | W | X | Z | A | Q |
|---|---|---|---|---|---|
| 2113 | 3-amino-2,3-dihydro-1H-pyrrol-1-yl (via N) | benzyl | benzyl | OMe | O |
| 2114 | 3-amino-2,5-dihydro-1H-pyrrol-1-yl | benzyl | benzyl | OMe | O |
| 2115 | 2-amino-2,3-dihydro-1H-pyrrol-1-yl | benzyl | benzyl | OMe | O |
| 2116 | 2-amino-1H-pyrrol-1-yl | benzyl | benzyl | OMe | O |
| 2117 | 3-amino-1H-pyrrol-1-yl | benzyl | benzyl | OMe | O |
| 2118 | 3-aminopyrazolidin-2-yl | benzyl | benzyl | OMe | O |
| 2119 | 4-aminopyrazolidin-2-yl | benzyl | benzyl | OMe | O |

TABLE 1-continued

| Cmpd | W | X | Z | A | Q |
|---|---|---|---|---|---|
| 2120 | pyrazolidine with NH₂ | benzyl | benzyl | OMe | O |
| 2121 | imidazolidine with NH₂ | benzyl | benzyl | OMe | O |
| 2122 | imidazolidine with NH₂ | benzyl | benzyl | OMe | O |
| 2123 | imidazolidine with NH₂ | benzyl | benzyl | OMe | O |
| 2124 | 4,5-dihydropyrazole with NH₂ | benzyl | benzyl | OMe | O |
| 2125 | 4,5-dihydropyrazole with NH₂ | benzyl | benzyl | OMe | O |
| 2126 | 4,5-dihydropyrazole with NH₂ | benzyl | benzyl | OMe | O |

TABLE 1-continued

| Cmpd | W | X | Z | A | Q |
|---|---|---|---|---|---|
| 2127 | 2-amino-imidazoline (N-linked) | benzyl | benzyl | OMe | O |
| 2128 | 4-amino-imidazoline (N-linked) | benzyl | benzyl | OMe | O |
| 2129 | 5-amino-imidazoline (N-linked) | benzyl | benzyl | OMe | O |
| 2130 | 3-amino-2,5-dioxopyrrolidin-1-yl | benzyl | benzyl | OMe | O |
| 2131 | 5-amino-2,4-dioxoimidazolidin-3-yl | benzyl | benzyl | OMe | O |
| 2132 | 5-amino-2,4-dioxothiazolidin-3-yl | benzyl | benzyl | OMe | O |
| 2133 | 2-aminopiperidin-1-yl | benzyl | benzyl | OMe | O |

TABLE 1-continued
| Cmpd | W | X | Z | A | Q |
|---|---|---|---|---|---|
| 2134 | 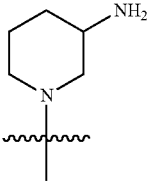 | 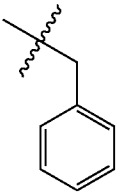 [SMILES: *Cc1ccccc1] | 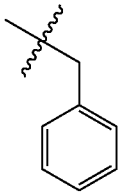 | OMe | O |
| 2135 | 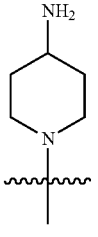 | 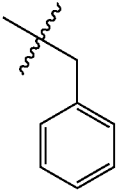 [SMILES: *Cc1ccccc1] | 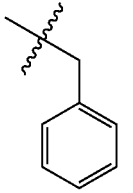 | OMe | O |
| 2136 | 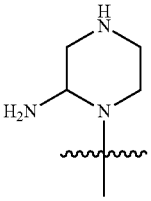 [SMILES: *N1CCNCC1N] | 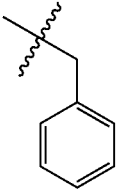 [SMILES: *Cc1ccccc1] | 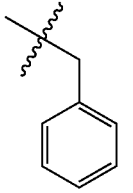 | OMe | O |
| 2137 | 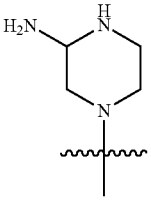 [SMILES: *N1CCNC(N)C1] | 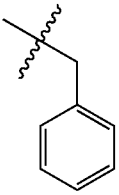 [SMILES: *Cc1ccccc1] | 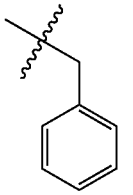 | OMe | O |
| 2138 | 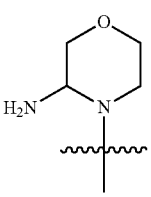 [SMILES: *N1CCOCC1N] | 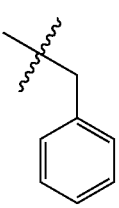 [SMILES: *Cc1ccccc1] | 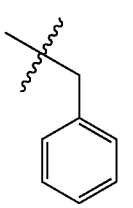 | OMe | O |
| 2139 | 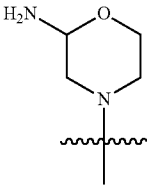 [SMILES: *N1CCOC(N)C1] | 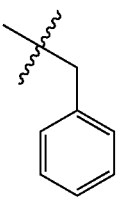 [SMILES: *Cc1ccccc1] | 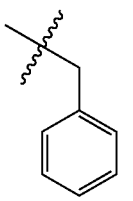 | OMe | O |
| 2140 | 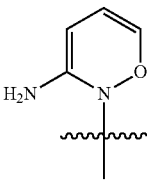 | 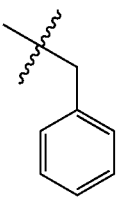 [SMILES: *Cc1ccccc1] | 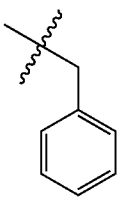 | OMe | O |

TABLE 1-continued

| Cmpd | W | X | Z | A | Q |
|---|---|---|---|---|---|
| 2141 | 4-amino-2H-1,2-oxazine (N-linked) | benzyl | benzyl | OMe | O |
| 2142 | 5-amino-2H-1,2-oxazine (N-linked) | benzyl | benzyl | OMe | O |
| 2143 | 6-amino-2H-1,2-oxazine (N-linked) | benzyl | benzyl | OMe | O |
| 2144 | 3-amino-4H-1,4-oxazine (N-linked) | benzyl | benzyl | OMe | O |
| 2145 | 2-amino-4H-1,4-oxazine (N-linked) | benzyl | benzyl | OMe | O |
| 2146 | 3-amino-thiomorpholine (N-linked) | benzyl | benzyl | OMe | O |
| 2147 | 2-amino-thiomorpholine (N-linked) | benzyl | benzyl | OMe | O |

TABLE 1-continued

| Cmpd | W | X | Z | A | Q |
|---|---|---|---|---|---|
| 2148 | 3-amino-2H-1,2-thiazine (N-linked) | benzyl | benzyl | OMe | O |
| 2149 | 4-amino-2H-1,2-thiazine (N-linked) | benzyl | benzyl | OMe | O |
| 2150 | 4-amino-2H-1,2-thiazine (N-linked) | benzyl | benzyl | OMe | O |
| 2151 | 6-amino-2H-1,2-thiazine (N-linked) | benzyl | benzyl | OMe | O |
| 2152 | 3-amino-4H-1,4-thiazine (N-linked) | benzyl | benzyl | OMe | O |
| 2153 | 3-amino-4H-1,4-thiazine (N-linked) | benzyl | benzyl | OMe | O |
| 2154 | 3-amino-thiomorpholine 1,1-dioxide (N-linked) | benzyl | benzyl | OMe | O |

TABLE 1-continued

| Cmpd | W | X | Z | A | Q |
|---|---|---|---|---|---|
| 2155 | thiomorpholine 1,1-dioxide with NH₂ | CH₂-phenyl | CH₂-phenyl | OMe | O |
| 2156 | 2-amino-dihydrocyclopenta[b]pyrrole (N-linked) | CH₂-phenyl | CH₂-phenyl | OMe | O |
| 2157 | 3-amino-dihydrocyclopenta[b]pyrrole (N-linked) | CH₂-phenyl | CH₂-phenyl | OMe | O |
| 2158 | 4-amino-dihydrocyclopenta[b]pyrrole (N-linked) | CH₂-phenyl | CH₂-phenyl | OMe | O |
| 2159 | 5-amino-dihydrocyclopenta[b]pyrrole (N-linked) | CH₂-phenyl | CH₂-phenyl | OMe | O |
| 2160 | 6-amino-dihydrocyclopenta[b]pyrrole (N-linked) | CH₂-phenyl | CH₂-phenyl | OMe | O |
| 2161 | 2-amino-hexahydropyrrolo[2,3-b]pyrrole | CH₂-phenyl | CH₂-phenyl | OMe | O |

TABLE 1-continued

| Cmpd | W | X | Z | A | Q |
|---|---|---|---|---|---|
| 2162 | 5-amino-1H-pyrrolo[3,2-b]pyrrole, N-linked | benzyl | benzyl | OMe | O |
| 2163 | 2-amino-1H-pyrrolo[2,3-b]pyrrole, N-linked | benzyl | benzyl | OMe | O |
| 2164 | 3-amino-1H-pyrrolo[2,3-b]pyrrole, N-linked | benzyl | benzyl | OMe | O |
| 2165 | 2-amino-pyrrolo[3,2-b]pyrrole, N-linked | benzyl | benzyl | OMe | O |
| 2166 | 5-amino-pyrrolo[3,2-b]pyrrole, N-linked | benzyl | benzyl | OMe | O |
| 2167 | 2-amino-pyrrolo[2,3-b]pyrrole, N-linked | benzyl | benzyl | OMe | O |
| 2168 | 3-amino-pyrrolo[2,3-b]pyrrole, N-linked | benzyl | benzyl | OMe | O |

TABLE 1-continued

| Cmpd | W | X | Z | A | Q |
|---|---|---|---|---|---|
| 2169 | 5-amino-pyrrolo[2,3-b]pyrrole (N-linked) | benzyl | benzyl | OMe | O |
| 2170 | 4-amino-pyrrolo[2,3-b]pyrrole (N-linked) | benzyl | benzyl | OMe | O |
| 2171 | 3-amino-pyrrolo[2,3-b]pyrrole (N-linked) | benzyl | benzyl | OMe | O |
| 2172 | 2-amino-pyrrolo[2,3-b]pyrrole (N-linked) | benzyl | benzyl | OMe | O |
| 2173 | 5-amino-furo[2,3-b]pyrrole (N-linked) | benzyl | benzyl | OMe | O |
| 2174 | 4-amino-furo[2,3-b]pyrrole (N-linked) | benzyl | benzyl | OMe | O |
| 2175 | 3-amino-furo[2,3-b]pyrrole (N-linked) | benzyl | benzyl | OMe | O |

TABLE 1-continued

| Cmpd | W | X | Z | A | Q |
|---|---|---|---|---|---|
| 2176 | 2-amino-furo[3,2-b]pyrrole (N-linked) | benzyl | benzyl | OMe | O |
| 2177 | 5-amino-furo[3,2-b]pyrrole (N-linked) | benzyl | benzyl | OMe | O |
| 2178 | 6-amino-furo[3,2-b]pyrrole (N-linked) | benzyl | benzyl | OMe | O |
| 2179 | 2-amino-furo[2,3-b]pyrrole (N-linked) | benzyl | benzyl | OMe | O |
| 2180 | 3-amino-furo[2,3-b]pyrrole (N-linked) | benzyl | benzyl | OMe | O |
| 2181 | 5-amino-thieno[2,3-b]pyrrole (N-linked) | benzyl | benzyl | OMe | O |
| 2182 | 5-amino-thieno[3,2-b]pyrrole (N-linked) | benzyl | benzyl | OMe | O |

TABLE 1-continued

| Cmpd | W | X | Z | A | Q |
|---|---|---|---|---|---|
| 2183 | 3-amino-thieno[2,3-b]pyrrole N-linked | benzyl | benzyl | OMe | O |
| 2184 | 2-amino-thieno[2,3-b]pyrrole N-linked | benzyl | benzyl | OMe | O |
| 2185 | 5-amino-thieno[3,2-b]pyrrole N-linked | benzyl | benzyl | OMe | O |
| 2186 | 6-amino-thieno[3,2-b]pyrrole N-linked | benzyl | benzyl | OMe | O |
| 2187 | 2-amino-thieno[3,2-b]pyrrole N-linked | benzyl | benzyl | OMe | O |
| 2188 | 3-amino-thieno[3,2-b]pyrrole N-linked | benzyl | benzyl | OMe | O |
| 2189 | 7-amino-2,3-dihydroindole N-linked | benzyl | benzyl | OMe | O |

TABLE 1-continued
| Cmpd | W | X | Z | A | Q |
|---|---|---|---|---|---|
| 2190 | 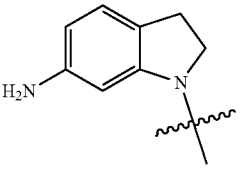 | 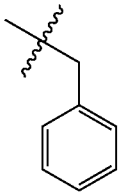 [SMILES: *Cc1ccccc1] | 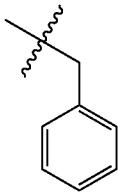 | OMe | O |
| 2191 | 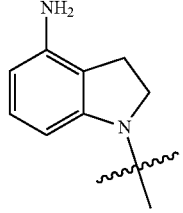 [SMILES: *N1CCc2c(N)cccc21] | 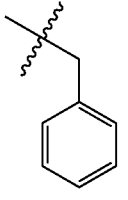 [SMILES: *Cc1ccccc1] | 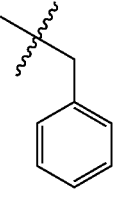 | OMe | O |
| 2192 | 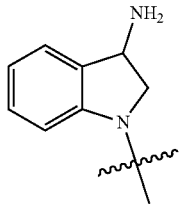 [SMILES: *N1CC(N)c2ccccc21] | 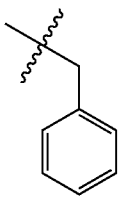 [SMILES: *Cc1ccccc1] | 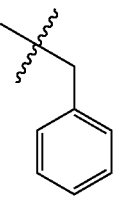 | OMe | O |
| 2193 | 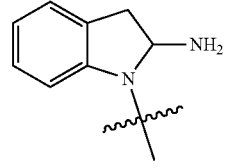 [SMILES: *N1c2ccccc2CC1N] | 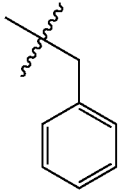 [SMILES: *Cc1ccccc1] | 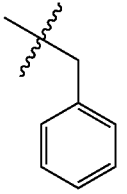 | OMe | O |
| 2194 | 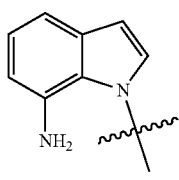 | 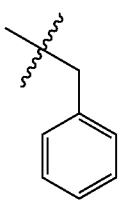 [SMILES: *Cc1ccccc1] | 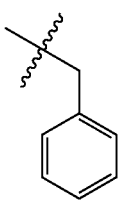 | OMe | O |
| 2195 | 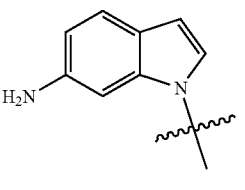 [SMILES: *n1ccc2ccc(N)cc21] | 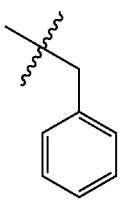 [SMILES: *Cc1ccccc1] | 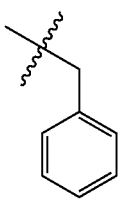 | OMe | O |
| 2196 | 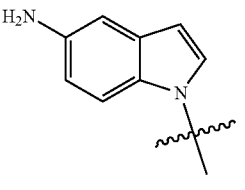 | 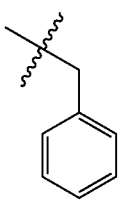 [SMILES: *Cc1ccccc1] | 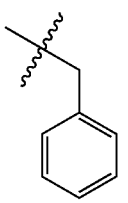 | OMe | O |

TABLE 1-continued

| Cmpd | W | X | Z | A | Q |
|---|---|---|---|---|---|
| 2197 | 4-aminoindol-1-yl | benzyl | benzyl | OMe | O |
| 2198 | 3-aminoindol-1-yl | benzyl | benzyl | OMe | O |
| 2199 | 2-aminoindol-1-yl | benzyl | benzyl | OMe | O |
| 2200 | 1-aminoisoindol-2-yl | benzyl | benzyl | OMe | O |
| 2201 | 7-aminoisoindol-2-yl | benzyl | benzyl | OMe | O |
| 2202 | 6-aminoisoindol-2-yl | benzyl | benzyl | OMe | O |

TABLE 1-continued

| Cmpd | W | X | Z | A | Q |
|------|---|---|---|---|---|
| 2203 | 7-amino-indazol-1-yl | benzyl | benzyl | OMe | O |
| 2204 | 6-amino-indazol-1-yl | benzyl | benzyl | OMe | O |
| 2205 | 5-amino-indazol-1-yl | benzyl | benzyl | OMe | O |
| 2206 | 4-amino-indazol-1-yl | benzyl | benzyl | OMe | O |
| 2207 | 3-amino-indazol-1-yl | benzyl | benzyl | OMe | O |
| 2208 | 7-amino-benzimidazol-1-yl | benzyl | benzyl | OMe | O |
| 2209 | 6-amino-benzimidazol-1-yl | benzyl | benzyl | OMe | O |

TABLE 1-continued
| Cmpd | W | X | Z | A | Q |
|---|---|---|---|---|---|
| 2210 | 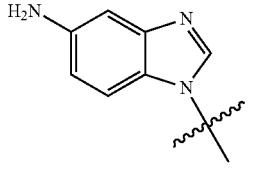 [SMILES: *n1cnc2cc(N)ccc21] | 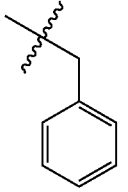 [SMILES: *Cc1ccccc1] | 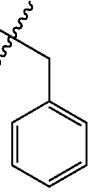 | OMe | O |
| 2211 | 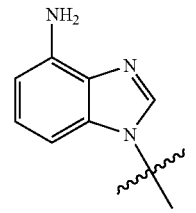 [SMILES: *n1cnc2c(N)cccc21] | 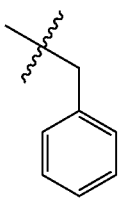 [SMILES: *Cc1ccccc1] | 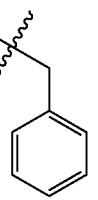 |  | O |
| 2212 | 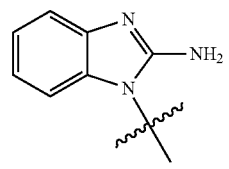 [SMILES: *n1c(N)nc2ccccc21] | 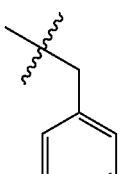 | 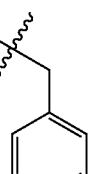 | OMe | O |
| 2213 | 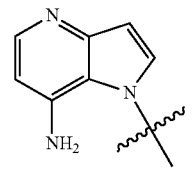 [SMILES: *n1ccc2nccc(N)c21] | 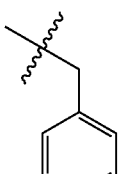 | 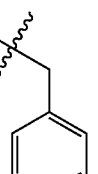 | OMe | O |
| 2214 | 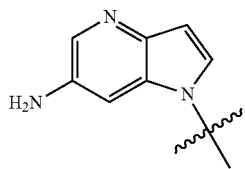 [SMILES: *n1ccc2ncc(N)cc21] | 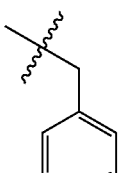 | 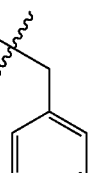 | OMe | O |
| 2215 | 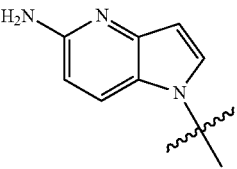 [SMILES: *n1ccc2nc(N)ccc21] | 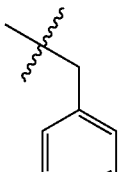 | 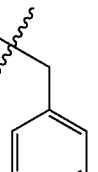 | OMe | O |
| 2216 | 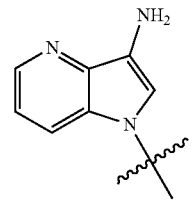 [SMILES: *n1cc(N)c2ncccc21] | 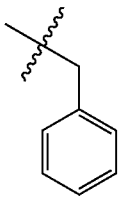 [SMILES: *Cc1ccccc1] | 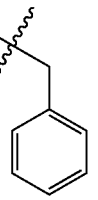 | OMe | O |

TABLE 1-continued

| Cmpd | W | X | Z | A | Q |
|---|---|---|---|---|---|
| 2217 | 2-amino-1H-pyrrolo[3,2-b]pyridine, N1-linked | benzyl | benzyl | OMe | O |
| 2218 | 7-amino-1H-pyrrolo[2,3-c]pyridine, N1-linked | benzyl | benzyl | OMe | O |
| 2219 | 6-amino-1H-pyrrolo[3,2-c]pyridine, N1-linked | benzyl | benzyl | OMe | O |
| 2220 | 4-amino-1H-pyrrolo[3,2-c]pyridine, N1-linked | benzyl | benzyl | OMe | O |
| 2221 | 3-amino-1H-pyrrolo[3,2-c]pyridine, N1-linked | benzyl | benzyl | OMe | O |
| 2222 | 2-amino-1H-pyrrolo[3,2-c]pyridine, N1-linked | benzyl | benzyl | OMe | O |
| 2223 | 7-amino-1H-pyrrolo[2,3-c]pyridine, N1-linked | benzyl | benzyl | OMe | O |

US 11,795,192 B2
TABLE 1-continued
| Cmpd | W | X | Z | A | Q |
|---|---|---|---|---|---|
| 2224 | 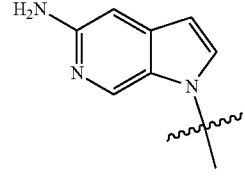 [SMILES: *n1ccc2cc(N)ncc21] | 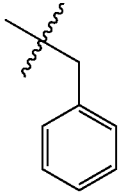 [SMILES: *Cc1ccccc1] | 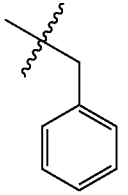 | OMe | O |
| 2225 | 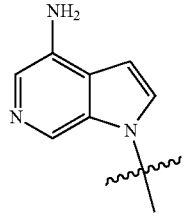 [SMILES: *n1ccc2c(N)cncc21] | 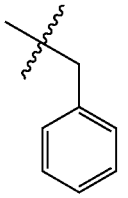 [SMILES: *Cc1ccccc1] | 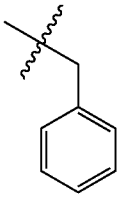 | OMe | O |
| 2226 | 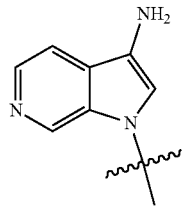 | 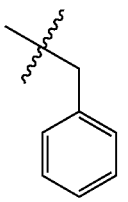 [SMILES: *Cc1ccccc1] | 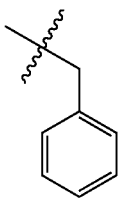 | OMe | O |
| 2227 | 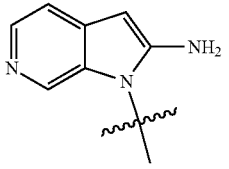 [SMILES: *n1c(N)cc2ccncc21] | 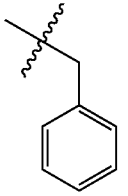 [SMILES: *Cc1ccccc1] | 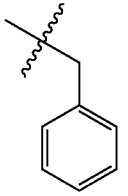 | OMe | O |
| 2228 | 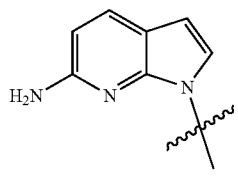 [SMILES: *n1ccc2ccc(N)nc21] | 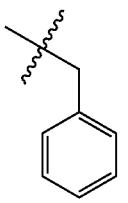 [SMILES: *Cc1ccccc1] | 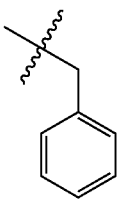 | OMe | O |
| 2229 | 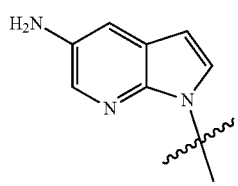 [SMILES: *n1ccc2cc(N)cnc21] | 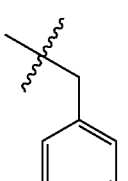 | 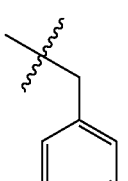 | OMe | O |
| 2230 | 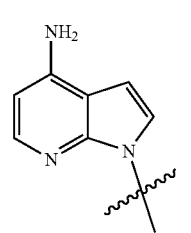 [SMILES: *n1ccc2c(N)ccnc21] | 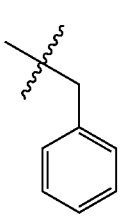 [SMILES: *Cc1ccccc1] | 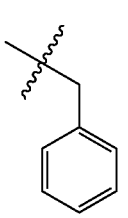 | OMe | O |

TABLE 1-continued

| Cmpd | W | X | Z | A | Q |
|---|---|---|---|---|---|
| 2231 | 3-amino-7-azaindole (N1-linked) | benzyl | benzyl | OMe | O |
| 2232 | 2-amino-7-azaindole (N1-linked) | benzyl | benzyl | OMe | O |
| 2233 | 6-amino-pyrazolo[3,4-b]pyridine (N1-linked) | benzyl | benzyl | OMe | O |
| 2234 | 5-amino-pyrazolo[3,4-b]pyridine (N1-linked) | benzyl | benzyl | OMe | O |
| 2235 | 4-amino-pyrazolo[3,4-b]pyridine (N1-linked) | benzyl | benzyl | OMe | O |
| 2236 | 3-amino-pyrazolo[3,4-b]pyridine (N1-linked) | benzyl | benzyl | OMe | O |
| 2237 | 2-amino-purine (N9-linked) | benzyl | benzyl | OMe | O |

TABLE 1-continued

| Cmpd | W | X | Z | A | Q |
|---|---|---|---|---|---|
| 2238 | 4-amino-pyrazolo[3,4-d]pyrimidin-1-yl | benzyl | benzyl | OMe | O |
| 2239 | 8-amino-purin-9-yl | benzyl | benzyl | OMe | O |
| 2240 | 7-amino-benzo[d]isothiazol-3(2H)-one-2-yl | benzyl | benzyl | OMe | O |
| 2241 | 6-amino-benzo[d]isothiazol-3(2H)-one-2-yl | benzyl | benzyl | OMe | O |
| 2242 | 5-amino-benzo[d]isothiazol-3(2H)-one-2-yl | benzyl | benzyl | OMe | O |
| 2243 | 4-amino-benzo[d]isothiazol-3(2H)-one-2-yl | benzyl | benzyl | OMe | O |

TABLE 1-continued
| Cmpd | W | X | Z | A | Q |
|---|---|---|---|---|---|
| 2244 | 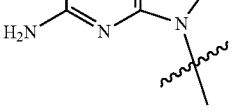 | 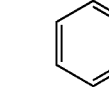 | 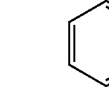 | OMe | O |
| 2245 | 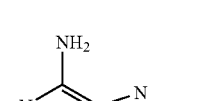 | 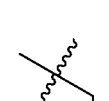 |  | OMe | O |
| 2246 | 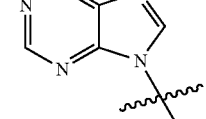 | 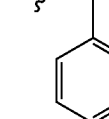 | 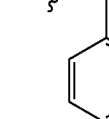 | OMe | O |
| 2247 | 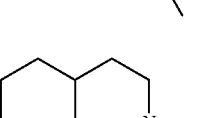 | 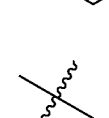 | 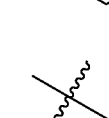 | OMe | O |
| 2248 | 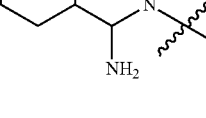 | 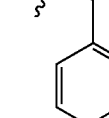 | 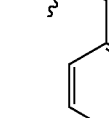 | OMe | O |
| 2249 | 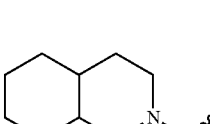 | 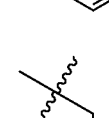 |  | OMe | O |
| 2250 | 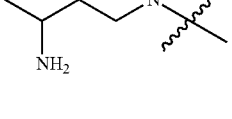 | 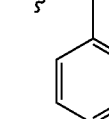 | 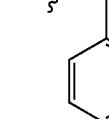 | OMe | O |

TABLE 1-continued

| Cmpd | W | X | Z | A | Q |
|---|---|---|---|---|---|
| 2251 | 4-amino-decahydroisoquinoline (N-linked) | benzyl | benzyl | OMe | O |
| 2252 | 3-amino-decahydroisoquinoline (N-linked) | benzyl | benzyl | OMe | O |
| 2253 | 8-amino-decahydroquinoline (N-linked) | benzyl | benzyl | OMe | O |
| 2254 | 7-amino-decahydroquinoline (N-linked) | benzyl | benzyl | OMe | O |
| 2255 | 6-amino-decahydroquinoline (N-linked) | benzyl | benzyl | OMe | O |
| 2256 | 5-amino-decahydroquinoline (N-linked) | benzyl | benzyl | OMe | O |
| 2257 | 4-amino-decahydroquinoline (N-linked) | benzyl | benzyl | OMe | O |

TABLE 1-continued

| Cmpd | W | X | Z | A | Q |
|---|---|---|---|---|---|
| 2258 | decahydroquinoline with 3-NH₂ | benzyl | benzyl | OMe | O |
| 2259 | decahydroquinoline with 2-NH₂ | benzyl | benzyl | OMe | O |
| 2260 | 1,2,3,4-tetrahydroquinoline with 8-NH₂ | benzyl | benzyl | OMe | O |
| 2261 | 1,2,3,4-tetrahydroquinoline with 7-NH₂ | benzyl | benzyl | OMe | O |
| 2262 | 1,2,3,4-tetrahydroquinoline with 6-NH₂ | benzyl | benzyl | OMe | O |
| 2263 | 1,2,3,4-tetrahydroquinoline with 5-NH₂ | benzyl | benzyl | OMe | O |
| 2264 | 1,2,3,4-tetrahydroquinoline with 4-NH₂ | benzyl | benzyl | OMe | O |

TABLE 1-continued

| Cmpd | W | X | Z | A | Q |
|---|---|---|---|---|---|
| 2265 | 3-amino-1-substituted-1,2,3,4-tetrahydroquinoline | -CH₂-phenyl | -CH₂-phenyl | OMe | O |
| 2266 | 2-amino-1-substituted-1,2,3,4-tetrahydroquinoline | -CH₂-phenyl | -CH₂-phenyl | OMe | O |
| 2267 | 8-amino-1-substituted-1,2-dihydroquinoline | -CH₂-phenyl | -CH₂-phenyl | OMe | O |
| 2268 | 7-amino-1-substituted-1,2-dihydroquinoline | -CH₂-phenyl | -CH₂-phenyl | OMe | O |
| 2269 | 6-amino-1-substituted-1,2-dihydroquinoline | -CH₂-phenyl | -CH₂-phenyl | OMe | O |
| 2270 | 5-amino-1-substituted-1,2-dihydroquinoline | -CH₂-phenyl | -CH₂-phenyl | OMe | O |
| 2271 | 4-amino-1-substituted-1,2-dihydroquinoline | -CH₂-phenyl | -CH₂-phenyl | OMe | O |

TABLE 1-continued

| Cmpd | W | X | Z | A | Q |
|------|---|---|---|---|---|
| 2272 | 3-amino-quinoline (N-linked, methyl) | benzyl | benzyl | OMe | O |
| 2273 | 2-amino-quinoline (N-linked, methyl) | benzyl | benzyl | OMe | O |
| 2274 | 1-amino-isoquinoline (N-linked) | benzyl | benzyl | OMe | O |
| 2275 | 8-amino-isoquinoline (N-linked) | benzyl | benzyl | OMe | O |
| 2276 | 7-amino-isoquinoline (N-linked) | benzyl | benzyl | OMe | O |
| 2277 | 6-amino-isoquinoline (N-linked) | benzyl | benzyl | OMe | O |
| 2278 | 5-amino-isoquinoline (N-linked) | benzyl | benzyl | OMe | O |

TABLE 1-continued
| Cmpd | W | X | Z | A | Q |
|------|---|---|---|---|---|
| 2279 | 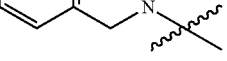 |  | 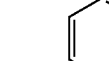 | OMe | O |
| 2280 | 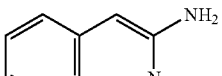 |  |  | OMe | O |
| 2281 | 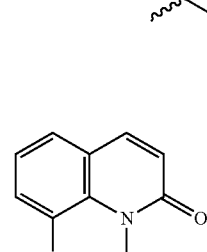 | 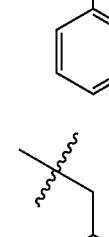 | 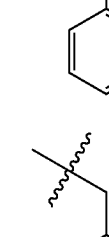 | OMe | O |
| 2282 | 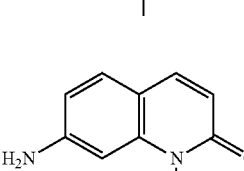 | 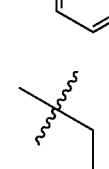 |  | OMe | O |
| 2283 | 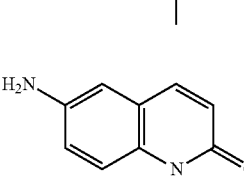 | 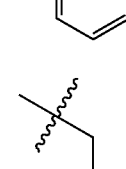 |  | OMe | O |
| 2284 | 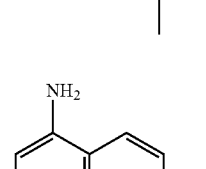 | 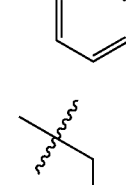 |  | OMe | O |
| 2285 | 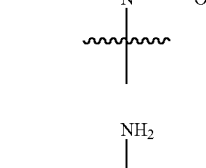 | 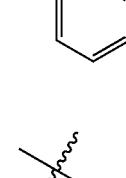 |  | OMe | O |

TABLE 1-continued

| Cmpd | W | X | Z | A | Q |
|---|---|---|---|---|---|
| 2286 | 3-amino-quinolin-2(1H)-one (N1-attached) | benzyl | benzyl | OMe | O |
| 2287 | 8-amino-isoquinolin-1(2H)-one (N2-attached) | benzyl | benzyl | OMe | O |
| 2288 | 7-amino-isoquinolin-1(2H)-one (N2-attached) | benzyl | benzyl | OMe | O |
| 2289 | 6-amino-isoquinolin-1(2H)-one (N2-attached) | benzyl | benzyl | OMe | O |
| 2290 | 5-amino-isoquinolin-1(2H)-one (N2-attached) | benzyl | benzyl | OMe | O |
| 2291 | 4-amino-isoquinolin-1(2H)-one (N2-attached) | benzyl | benzyl | OMe | O |
| 2292 | 3-amino-isoquinolin-1(2H)-one (N2-attached) | benzyl | benzyl | OMe | O |

TABLE 1-continued

| Cmpd | W | X | Z | A | Q |
|---|---|---|---|---|---|
| 2293 | 8-amino-benzo[1,2]oxazine | CH2-Ph | CH2-Ph | OMe | O |
| 2294 | 7-amino-benzo[1,2]oxazine | CH2-Ph | CH2-Ph | OMe | O |
| 2295 | 6-amino-benzo[1,2]oxazine | CH2-Ph | CH2-Ph | OMe | O |
| 2296 | 5-amino-benzo[1,2]oxazine | CH2-Ph | CH2-Ph | OMe | O |
| 2297 | 4-amino-benzo[1,2]oxazine | CH2-Ph | CH2-Ph | OMe | O |
| 2298 | 3-amino-benzo[1,2]oxazine | CH2-Ph | CH2-Ph | OMe | O |
| 2299 | amino-carbazole | CH2-Ph | CH2-Ph | OMe | O |

TABLE 1-continued
| Cmpd | W | X | Z | A | Q |
|---|---|---|---|---|---|
| 2300 | 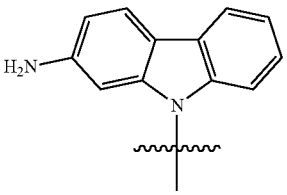 | 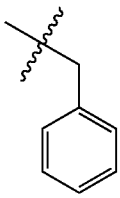 [SMILES: *Cc1ccccc1] | 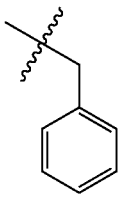 | OMe | O |
| 2301 | 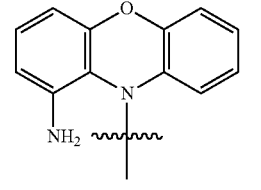 | 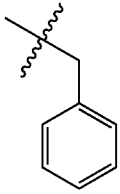 [SMILES: *Cc1ccccc1] | 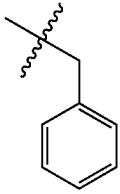 | OMe | O |
| 2302 | 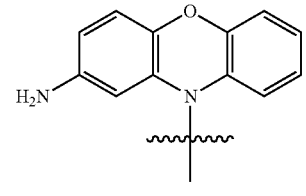 [SMILES: *N1c2ccccc2Oc2ccc(N)cc21] | 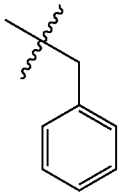 [SMILES: *Cc1ccccc1] | 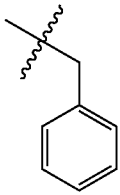 | OMe | O |
| 2303 | 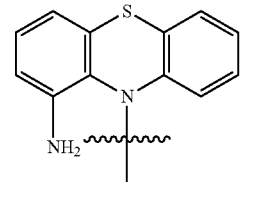 [SMILES: *N1c2ccccc2Sc2cccc(N)c21] | 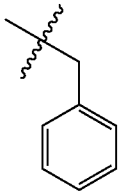 [SMILES: *Cc1ccccc1] | 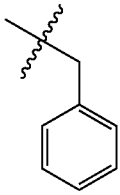 | OMe | O |
| 2304 | 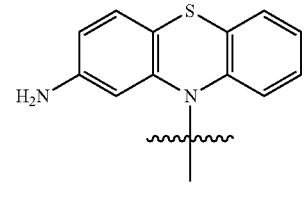 | 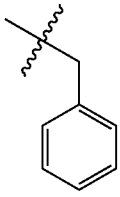 [SMILES: *Cc1ccccc1] | 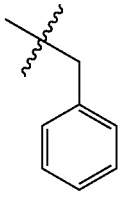 | OMe | O |
| 2305 | 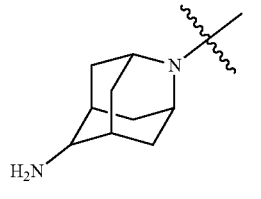 [SMILES: *N1C2CC3CC1CC(C2)C3N] | 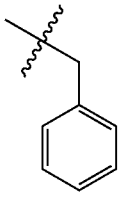 [SMILES: *Cc1ccccc1] | 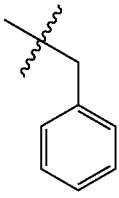 | OMe | O |
| 2306 | 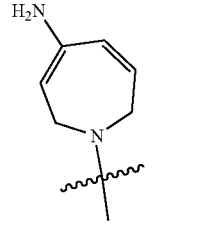 [SMILES: *N1CC=CC(N)=CC1] | 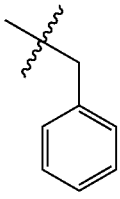 [SMILES: *Cc1ccccc1] | 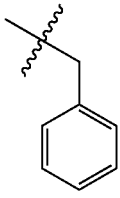 | OMe | O |

TABLE 1-continued
| Cmpd | W | X | Z | A | Q |
|---|---|---|---|---|---|
| 2307 | 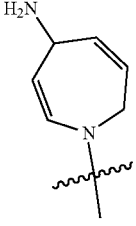 [SMILES: *N1C=CC(N)C=CC1] | 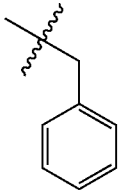 [SMILES: *Cc1ccccc1] | 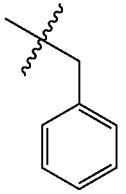 | OMe | O |
| 2308 | 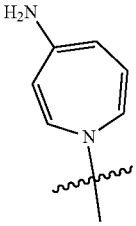 [SMILES: *N1C=CC=C(N)C=C1] | 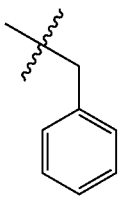 [SMILES: *Cc1ccccc1] | 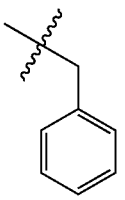 | OMe | O |
| 2309 | 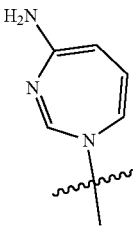 | 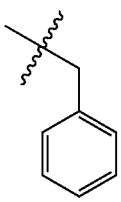 [SMILES: *Cc1ccccc1] | 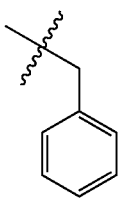 | OMe | O |
| 2310 | 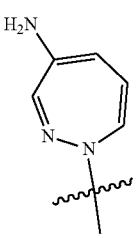 | 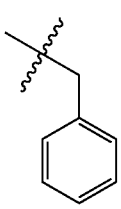 [SMILES: *Cc1ccccc1] | 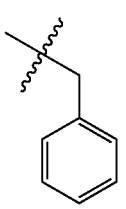 | OMe | O |
| 2311 | 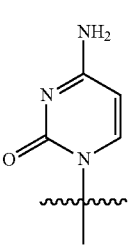 [SMILES: *n1ccc(N)nc1=O] | 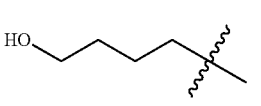 | 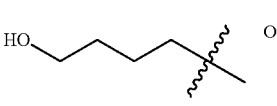 | OMe | O |
| 2312 | 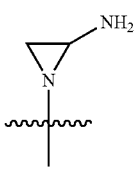 | 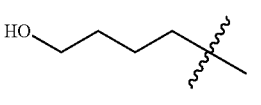 [SMILES: *CCCCO] | 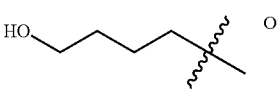 | OMe | O |
| 2313 | 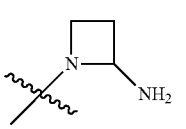 | 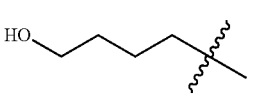 [SMILES: *CCCCO] | 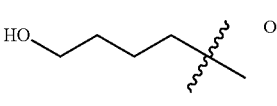 | OMe | O |

TABLE 1-continued

| Cmpd | W | X | Z | A | Q |
|---|---|---|---|---|---|
| 2314 | 3-aminoazetidin-1-yl | HO-(CH2)4- | HO-(CH2)4- | OMe | O |
| 2315 | 2-amino-2,3-dihydroimidazol-1-yl | HO-(CH2)4- | HO-(CH2)4- | OMe | O |
| 2316 | 3-amino-2-oxoazetidin-1-yl | HO-(CH2)4- | HO-(CH2)4- | OMe | O |
| 2317 | 4-amino-2-oxoazetidin-1-yl | HO-(CH2)4- | HO-(CH2)4- | OMe | O |
| 2318 | 2-aminopyrrolidin-1-yl | HO-(CH2)4- | HO-(CH2)4- | OMe | O |
| 2319 | 3-aminopyrrolidin-1-yl | HO-(CH2)4- | HO-(CH2)4- | OMe | O |
| 2320 | 2-amino-2,5-dihydropyrrol-1-yl | HO-(CH2)4- | HO-(CH2)4- | OMe | O |
| 2321 | 3-amino-2,5-dihydropyrrol-1-yl | HO-(CH2)4- | HO-(CH2)4- | OMe | O |
| 2322 | 5-amino-2,3-dihydropyrrol-1-yl | HO-(CH2)4- | HO-(CH2)4- | OMe | O |

TABLE 1-continued

| Cmpd | W | X | Z | A | Q |
|---|---|---|---|---|---|
| 2323 | 3-amino-2,5-dihydropyrrol-1-yl (N-linked with methyl tether) | HO-(CH₂)₄-CH(~)- | HO-(CH₂)₄-CH(~)- | OMe | O |
| 2324 | 3-amino-2,5-dihydropyrrol-1-yl (alt. regiochemistry) | HO-(CH₂)₄-CH(~)- | HO-(CH₂)₄-CH(~)- | OMe | O |
| 2325 | 2-amino-2,5-dihydropyrrol-1-yl | HO-(CH₂)₄-CH(~)- | HO-(CH₂)₄-CH(~)- | OMe | O |
| 2326 | 2-aminopyrrol-1-yl | HO-(CH₂)₄-CH(~)- | HO-(CH₂)₄-CH(~)- | OMe | O |
| 2327 | 3-aminopyrrol-1-yl | HO-(CH₂)₄-CH(~)- | HO-(CH₂)₄-CH(~)- | OMe | O |
| 2328 | 3-aminopyrazolidin-1-yl | HO-(CH₂)₄-CH(~)- | HO-(CH₂)₄-CH(~)- | OMe | O |
| 2329 | 4-aminopyrazolidin-1-yl | HO-(CH₂)₄-CH(~)- | HO-(CH₂)₄-CH(~)- | OMe | O |
| 2330 | 5-aminopyrazolidin-1-yl | HO-(CH₂)₄-CH(~)- | HO-(CH₂)₄-CH(~)- | OMe | O |

TABLE 1-continued
| Cmpd | W | X | Z | A | Q |
|---|---|---|---|---|---|
| 2331 | 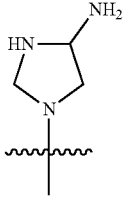 [SMILES: *N1CNC(N)C1] | 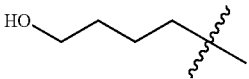 [SMILES: *CCCCO] | 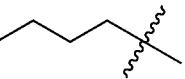 | OMe | O |
| 2332 | 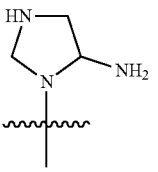 | 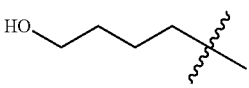 [SMILES: *CCCCO] | 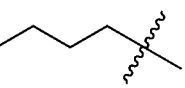 | OMe | O |
| 2333 | 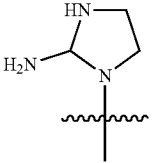 | 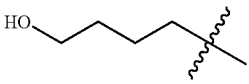 [SMILES: *CCCCO] | 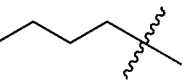 | OMe | O |
| 2334 | 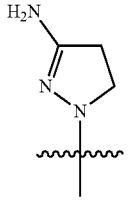 | 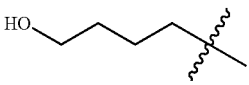 [SMILES: *CCCCO] | 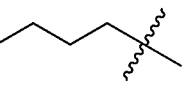 | OMe | O |
| 2335 | 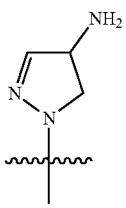 [SMILES: *N1CC(N)C=N1] | 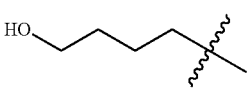 [SMILES: *CCCCO] | 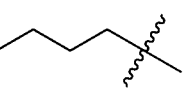 | OMe | O |
| 2336 | 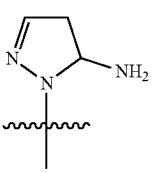 [SMILES: *N1N=CCC1N] | 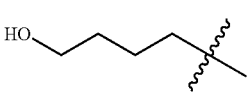 [SMILES: *CCCCO] | 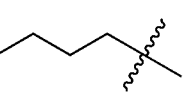 | OMe | O |
| 2337 | 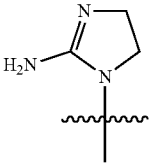 | 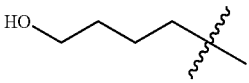 [SMILES: *CCCCO] | 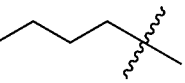 | OMe | O |
| 2338 | 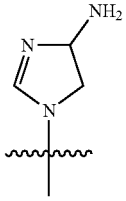 | 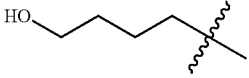 | 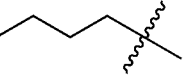 | OMe | O |

TABLE 1-continued

| Cmpd | W | X | Z | A | Q |
|---|---|---|---|---|---|
| 2339 | 2-amino-2,5-dihydro-1H-imidazol-1-yl | HO-(CH2)4-CH< | HO-(CH2)4-CH< | OMe | O |
| 2340 | 3-amino-2,5-dioxopyrrolidin-1-yl | HO-(CH2)4-CH< | HO-(CH2)4-CH< | OMe | O |
| 2341 | 5-amino-2,4-dioxoimidazolidin-3-yl | HO-(CH2)4-CH< | HO-(CH2)4-CH< | OMe | O |
| 2342 | 5-amino-2,4-dioxothiazolidin-3-yl | HO-(CH2)4-CH< | HO-(CH2)4-CH< | OMe | O |
| 2343 | 2-aminopiperidin-1-yl | HO-(CH2)4-CH< | HO-(CH2)4-CH< | OMe | O |
| 2344 | 3-aminopiperidin-1-yl | HO-(CH2)4-CH< | HO-(CH2)4-CH< | OMe | O |
| 2345 | 4-aminopiperidin-1-yl | HO-(CH2)4-CH< | HO-(CH2)4-CH< | OMe | O |

TABLE 1-continued
| Cmpd | W | X | Z | A | Q |
|---|---|---|---|---|---|
| 2346 | 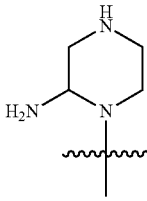 | 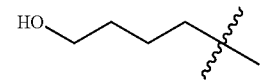 [SMILES: *CCCCO] | 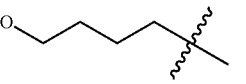 | OMe | O |
| 2347 | 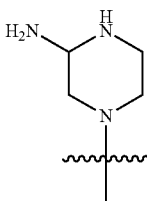 | 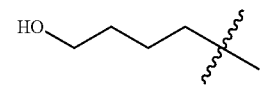 | 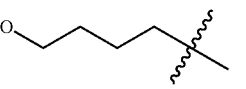 | OMe | O |
| 2348 | 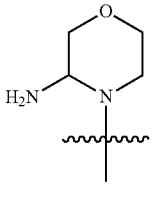 | 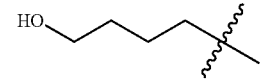 [SMILES: *CCCCO] | 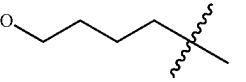 | OMe | O |
| 2349 | 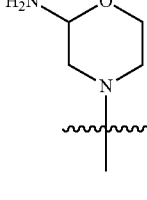 | 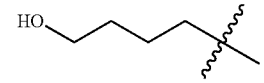 [SMILES: *CCCCO] | 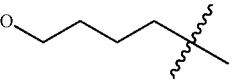 | OMe | O |
| 2350 | 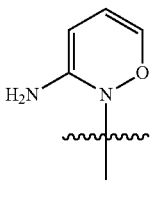 [SMILES: *N1OC=CC=C1N] | 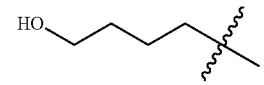 [SMILES: *CCCCO] | 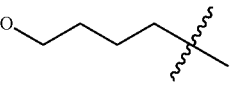 | OMe | O |
| 2351 | 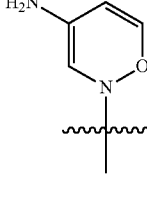 | 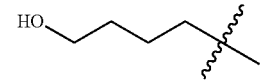 [SMILES: *CCCCO] | 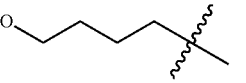 | OMe | O |
| 2352 | 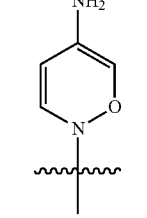 | 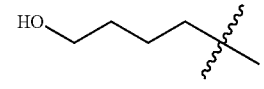 | 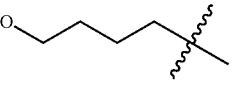 | OMe | O |

TABLE 1-continued
| Cmpd | W | X | Z | A | Q |
|---|---|---|---|---|---|
| 2353 | 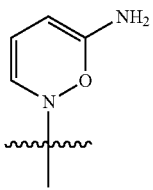 | 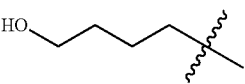 [SMILES: *CCCCO] | 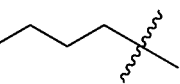 | OMe | O |
| 2354 | 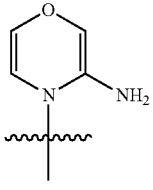 | 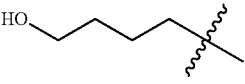 | 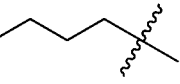 | OMe | O |
| 2355 | 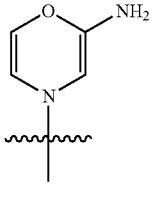 | 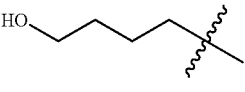 [SMILES: *CCCCO] | 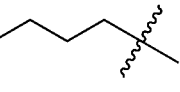 | OMe | O |
| 2356 | 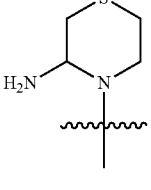 | 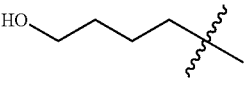 [SMILES: *CCCCO] | 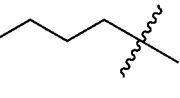 | OMe | O |
| 2357 | 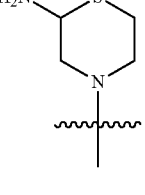 | 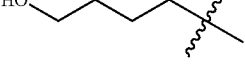 | 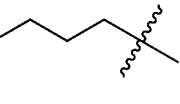 | OMe | O |
| 2358 | 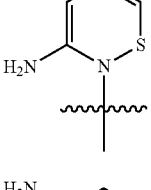 | 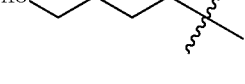 | 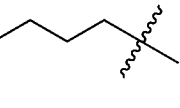 | OMe | O |
| 2359 | 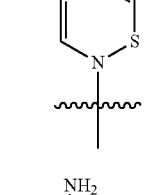 | 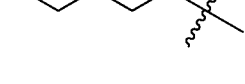 | 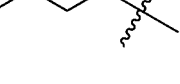 | OMe | O |
| 2360 | 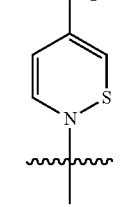 | 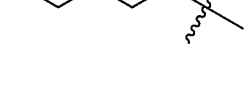 | 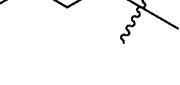 | OMe | O |

TABLE 1-continued

| Cmpd | W | X | Z | A | Q |
|------|---|---|---|---|---|
| 2361 | 3-amino-2H-1,2-thiazine (N-linked) | HO-pentyl- | HO-pentyl- | OMe | O |
| 2362 | 3-amino-4H-1,4-thiazine (N-linked) | HO-pentyl- | HO-pentyl- | OMe | O |
| 2363 | 2-amino-4H-1,4-thiazine (N-linked) | HO-pentyl- | HO-pentyl- | OMe | O |
| 2364 | 3-aminothiomorpholine 1,1-dioxide (N-linked) | HO-pentyl- | HO-pentyl- | OMe | O |
| 2365 | 2-aminothiomorpholine 1,1-dioxide (N-linked) | HO-pentyl- | HO-pentyl- | OMe | O |
| 2366 | 2-amino-5,6-dihydro-4H-cyclopenta[b]pyrrole (N-linked) | HO-pentyl- | HO-pentyl- | OMe | O |
| 2367 | 3-amino-5,6-dihydro-4H-cyclopenta[b]pyrrole (N-linked) | HO-pentyl- | HO-pentyl- | OMe | O |

TABLE 1-continued

| Cmpd | W | X | Z | A | Q |
|---|---|---|---|---|---|
| 2368 | 4-amino-1-(CH)-5,6-dihydrocyclopenta[b]pyrrol-1-yl | HO-(CH₂)₄-CH< | HO-(CH₂)₄-CH< | OMe | O |
| 2369 | 5-amino-1-(CH)-5,6-dihydrocyclopenta[b]pyrrol-1-yl | HO-(CH₂)₄-CH< | HO-(CH₂)₄-CH< | OMe | O |
| 2370 | 6-amino-1-(CH)-5,6-dihydrocyclopenta[b]pyrrol-1-yl | HO-(CH₂)₄-CH< | HO-(CH₂)₄-CH< | OMe | O |
| 2371 | 5-amino-pyrrolo[3,2-b]pyrrolyl | HO-(CH₂)₄-CH< | HO-(CH₂)₄-CH< | OMe | O |
| 2372 | 6-amino-pyrrolo[3,2-b]pyrrolyl | HO-(CH₂)₄-CH< | HO-(CH₂)₄-CH< | OMe | O |
| 2373 | 2-amino-pyrrolo[3,2-b]pyrrolyl | HO-(CH₂)₄-CH< | HO-(CH₂)₄-CH< | OMe | O |
| 2374 | 3-amino-pyrrolo[3,2-b]pyrrolyl | HO-(CH₂)₄-CH< | HO-(CH₂)₄-CH< | OMe | O |

TABLE 1-continued

| Cmpd | W | X | Z | A | Q |
|------|---|---|---|---|---|
| 2375 | 2-amino-4H-pyrrolo[3,2-b]pyrrole, N-linked | HO-(CH₂)₅- | HO-(CH₂)₅- | OMe | O |
| 2376 | 3-amino-4H-pyrrolo[3,2-b]pyrrole, N-linked | HO-(CH₂)₅- | HO-(CH₂)₅- | OMe | O |
| 2377 | 5-amino-1H-pyrrolo[3,2-b]pyrrole, N-linked | HO-(CH₂)₅- | HO-(CH₂)₅- | OMe | O |
| 2378 | 6-amino-1H-pyrrolo[3,2-b]pyrrole, N-linked | HO-(CH₂)₅- | HO-(CH₂)₅- | OMe | O |
| 2379 | 2-amino-pyrrolo[2,3-b]pyrrole, N-linked | HO-(CH₂)₅- | HO-(CH₂)₅- | OMe | O |
| 2380 | 3-amino-pyrrolo[2,3-b]pyrrole, N-linked | HO-(CH₂)₅- | HO-(CH₂)₅- | OMe | O |
| 2381 | 4-amino-pyrrolo[2,3-b]pyrrole, N-linked | HO-(CH₂)₅- | HO-(CH₂)₅- | OMe | O |

TABLE 1-continued

| Cmpd | W | X | Z | A | Q |
|---|---|---|---|---|---|
| 2382 | 2-amino-1H-pyrrolo[2,3-b]pyrrole, N-linked | HO-(CH2)4-C(CH3)- | HO-(CH2)4-C(CH3)- | OMe | O |
| 2383 | 5-amino-furo[2,3-b]pyrrole, N-linked | HO-(CH2)4-C(CH3)- | HO-(CH2)4-C(CH3)- | OMe | O |
| 2384 | 4-amino-furo[2,3-b]pyrrole, N-linked | HO-(CH2)4-C(CH3)- | HO-(CH2)4-C(CH3)- | OMe | O |
| 2385 | 3-amino-furo[2,3-b]pyrrole, N-linked | HO-(CH2)4-C(CH3)- | HO-(CH2)4-C(CH3)- | OMe | O |
| 2386 | 2-amino-furo[2,3-b]pyrrole, N-linked | HO-(CH2)4-C(CH3)- | HO-(CH2)4-C(CH3)- | OMe | O |
| 2387 | 5-amino-furo[3,2-b]pyrrole, N-linked | HO-(CH2)4-C(CH3)- | HO-(CH2)4-C(CH3)- | OMe | O |
| 2388 | 6-amino-furo[3,2-b]pyrrole, N-linked | HO-(CH2)4-C(CH3)- | HO-(CH2)4-C(CH3)- | OMe | O |

TABLE 1-continued

| Cmpd | W | X | Z | A | Q |
|---|---|---|---|---|---|
| 2389 | furo-pyrrole with NH2, N-linked | HO-(CH2)4-C(CH3)< | HO-(CH2)4-C(CH3)< | OMe | O |
| 2390 | furo-pyrrole with NH2, N-linked | HO-(CH2)4-C(CH3)< | HO-(CH2)4-C(CH3)< | OMe | O |
| 2391 | thieno-pyrrole with H2N, N-linked | HO-(CH2)4-C(CH3)< | HO-(CH2)4-C(CH3)< | OMe | O |
| 2392 | thieno-pyrrole with H2N, N-linked | HO-(CH2)4-C(CH3)< | HO-(CH2)4-C(CH3)< | OMe | O |
| 2393 | thieno-pyrrole with H2N, N-linked | HO-(CH2)4-C(CH3)< | HO-(CH2)4-C(CH3)< | OMe | O |
| 2394 | thieno-pyrrole with NH2, N-linked | HO-(CH2)4-C(CH3)< | HO-(CH2)4-C(CH3)< | OMe | O |
| 2395 | thieno-pyrrole with H2N, N-linked | HO-(CH2)4-C(CH3)< | HO-(CH2)4-C(CH3)< | OMe | O |

TABLE 1-continued
| Cmpd | W | X | Z | A | Q |
|------|---|---|---|---|---|
| 2396 | 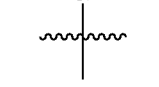 |  |  | OMe | O |
| 2397 | 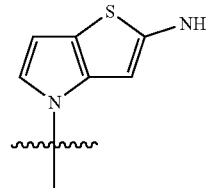 | 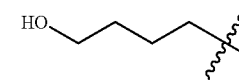 | 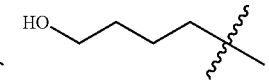 | OMe | O |
| 2398 | 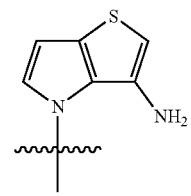 | 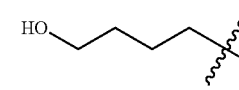 | 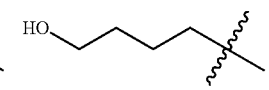 | OMe | O |
| 2399 | 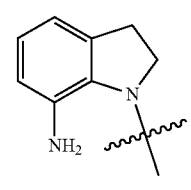 [SMILES: *N1CCc2cccc(N)c21] | 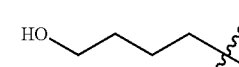 | 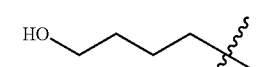 | OMe | O |
| 2400 | 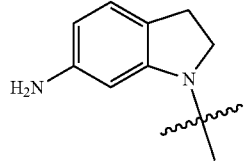 [SMILES: *N1CCc2ccc(N)cc21] | 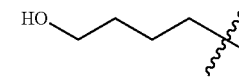 | 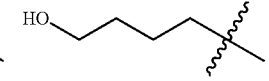 | OMe | O |
| 2401 | 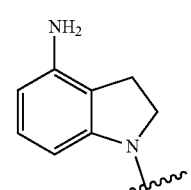 | 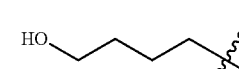 | 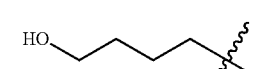 | OMe | O |
| 2402 | 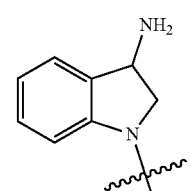 | 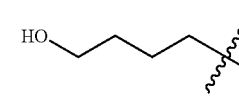 | 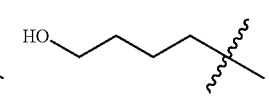 | OMe | O |
| 2403 | 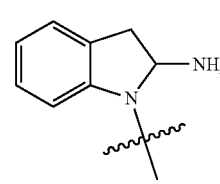 | 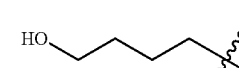 | 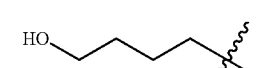 | OMe | O |

TABLE 1-continued
| Cmpd | W | X | Z | A | Q |
|---|---|---|---|---|---|
| 2404 | 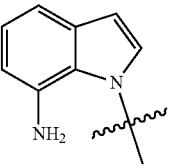 [SMILES: *n1ccc2cccc(N)c21] | 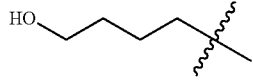 [SMILES: *CCCCO] | 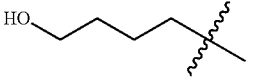 [SMILES: *CCCCO] | OMe | O |
| 2405 | 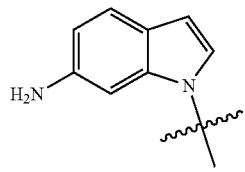 | 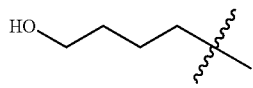 [SMILES: *CCCCO] | 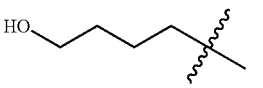 [SMILES: *CCCCO] | OMe | O |
| 2406 | 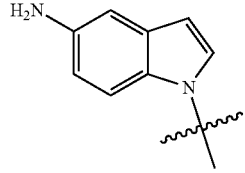 [SMILES: *n1ccc2cc(N)ccc21] | 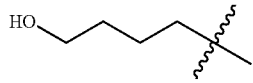 [SMILES: *CCCCO] | 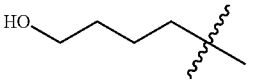 [SMILES: *CCCCO] | OMe | O |
| 2407 | 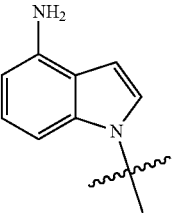 [SMILES: *n1ccc2c(N)cccc21] | 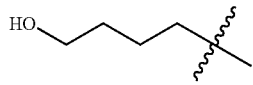 [SMILES: *CCCCO] | 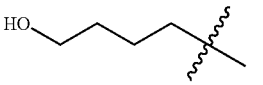 [SMILES: *CCCCO] | OMe | O |
| 2408 | 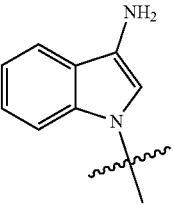 [SMILES: *n1cc(N)c2ccccc21] | 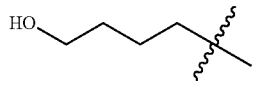 [SMILES: *CCCCO] | 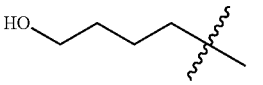 [SMILES: *CCCCO] | OMe | O |
| 2409 | 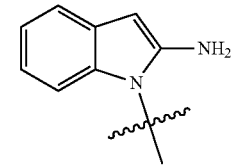 [SMILES: *n1c(N)cc2ccccc21] | 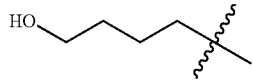 [SMILES: *CCCCO] | 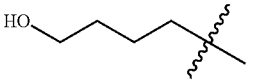 [SMILES: *CCCCO] | OMe | O |
| 2410 | 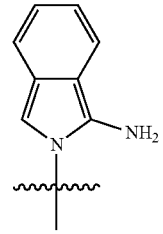 [SMILES: *n1cc2ccccc2c1N] | 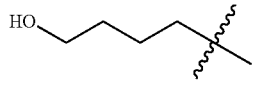 [SMILES: *CCCCO] | 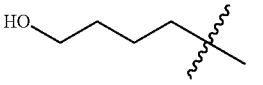 [SMILES: *CCCCO] | OMe | O |

TABLE 1-continued

| Cmpd | W | X | Z | A | Q |
|---|---|---|---|---|---|
| 2411 | 7-amino-2H-isoindol-2-yl | HO-(CH₂)₄-CH(Me)- | HO-(CH₂)₄-CH(Me)- | OMe | O |
| 2412 | 5-amino-2H-isoindol-2-yl | HO-(CH₂)₄-CH(Me)- | HO-(CH₂)₄-CH(Me)- | OMe | O |
| 2413 | 7-amino-1H-indazol-1-yl | HO-(CH₂)₄-CH(Me)- | HO-(CH₂)₄-CH(Me)- | OMe | O |
| 2414 | 6-amino-1H-indazol-1-yl | HO-(CH₂)₄-CH(Me)- | HO-(CH₂)₄-CH(Me)- | OMe | O |
| 2415 | 5-amino-1H-indazol-1-yl | HO-(CH₂)₄-CH(Me)- | HO-(CH₂)₄-CH(Me)- | OMe | O |
| 2416 | 4-amino-1H-indazol-1-yl | HO-(CH₂)₄-CH(Me)- | HO-(CH₂)₄-CH(Me)- | OMe | O |
| 2417 | 3-amino-1H-indazol-1-yl | HO-(CH₂)₄-CH(Me)- | HO-(CH₂)₄-CH(Me)- | OMe | O |

TABLE 1-continued

| Cmpd | W | X | Z | A | Q |
|---|---|---|---|---|---|
| 2418 | benzimidazole-NH₂ (7-amino, N1-linked) | HO-(CH₂)₄-C(Me) | HO-(CH₂)₄-C(Me) | OMe | O |
| 2419 | benzimidazole-NH₂ (6-amino, N1-linked) | HO-(CH₂)₄-C(Me) | HO-(CH₂)₄-C(Me) | OMe | O |
| 2420 | benzimidazole-NH₂ (5-amino, N1-linked) | HO-(CH₂)₄-C(Me) | HO-(CH₂)₄-C(Me) | OMe | O |
| 2421 | benzimidazole-NH₂ (4-amino) | HO-(CH₂)₄-C(Me) | HO-(CH₂)₄-C(Me) |  | O |
| 2422 | benzimidazole-2-NH₂ (N1-linked) | HO-(CH₂)₄-C(Me) | HO-(CH₂)₄-C(Me) | OMe | O |
| 2423 | pyrrolo[3,2-b]pyridine-7-NH₂ (N1-linked) | HO-(CH₂)₄-C(Me) | HO-(CH₂)₄-C(Me) | OMe | O |
| 2424 | pyrrolo[3,2-b]pyridine-6-NH₂ (N1-linked) | HO-(CH₂)₄-C(Me) | HO-(CH₂)₄-C(Me) | OMe | O |
| 2425 | pyrrolo[3,2-b]pyridine-5-NH₂ (N1-linked) | HO-(CH₂)₄-C(Me) | HO-(CH₂)₄-C(Me) | OMe | O |
| 2426 | pyrrolo[3,2-b]pyridine-3-NH₂ (N1-linked) | HO-(CH₂)₄-C(Me) | HO-(CH₂)₄-C(Me) | OMe | O |

TABLE 1-continued

| Cmpd | W | X | Z | A | Q |
|------|---|---|---|---|---|
| 2427 | 2-amino-1H-pyrrolo[3,2-b]pyridin-1-yl (N-linked) | HO-(CH2)4- | HO-(CH2)4- | OMe | O |
| 2428 | 7-amino-1H-pyrrolo[2,3-c]pyridin-1-yl | HO-(CH2)4- | HO-(CH2)4- | OMe | O |
| 2429 | 6-amino-1H-pyrrolo[3,2-c]pyridin-1-yl | HO-(CH2)4- | HO-(CH2)4- | OMe | O |
| 2430 | 4-amino-1H-pyrrolo[3,2-c]pyridin-1-yl | HO-(CH2)4- | HO-(CH2)4- | OMe | O |
| 2431 | 3-amino-1H-pyrrolo[3,2-c]pyridin-1-yl | HO-(CH2)4- | HO-(CH2)4- | OMe | O |
| 2432 | 2-amino-1H-pyrrolo[3,2-c]pyridin-1-yl | HO-(CH2)4- | HO-(CH2)4- | OMe | O |
| 2433 | 7-amino-1H-pyrrolo[2,3-c]pyridin-1-yl | HO-(CH2)4- | HO-(CH2)4- | OMe | O |
| 2434 | 5-amino-1H-pyrrolo[2,3-c]pyridin-1-yl | HO-(CH2)4- | HO-(CH2)4- | OMe | O |

TABLE 1-continued

| Cmpd | W | X | Z | A | Q |
|---|---|---|---|---|---|
| 2435 | 4-amino-6-azaindole (N1-linked) | HO-(CH2)4-C(CH3)< | HO-(CH2)4-C(CH3)< | OMe | O |
| 2436 | 3-amino-6-azaindole (N1-linked) | HO-(CH2)4-C(CH3)< | HO-(CH2)4-C(CH3)< | OMe | O |
| 2437 | 2-amino-6-azaindole (N1-linked) | HO-(CH2)4-C(CH3)< | HO-(CH2)4-C(CH3)< | OMe | O |
| 2438 | 6-amino-7-azaindole (N1-linked) | HO-(CH2)4-C(CH3)< | HO-(CH2)4-C(CH3)< | OMe | O |
| 2439 | 5-amino-7-azaindole (N1-linked) | HO-(CH2)4-C(CH3)< | HO-(CH2)4-C(CH3)< | OMe | O |
| 2440 | 4-amino-7-azaindole (N1-linked) | HO-(CH2)4-C(CH3)< | HO-(CH2)4-C(CH3)< | OMe | O |
| 2441 | 3-amino-7-azaindole (N1-linked) | HO-(CH2)4-C(CH3)< | HO-(CH2)4-C(CH3)< | OMe | O |
| 2442 | 2-amino-7-azaindole (N1-linked) | HO-(CH2)4-C(CH3)< | HO-(CH2)4-C(CH3)< | OMe | O |

TABLE 1-continued

| Cmpd | W | X | Z | A | Q |
|---|---|---|---|---|---|
| 2443 | 6-amino-pyrazolo[3,4-b]pyridin-1-yl | HO-(CH2)4-C(CH3) | HO-(CH2)4-C(CH3) | OMe | O |
| 2444 | 5-amino-pyrazolo[3,4-b]pyridin-1-yl | HO-(CH2)4-C(CH3) | HO-(CH2)4-C(CH3) | OMe | O |
| 2445 | 4-amino-pyrazolo[3,4-b]pyridin-1-yl | HO-(CH2)4-C(CH3) | HO-(CH2)4-C(CH3) | OMe | O |
| 2446 | 3-amino-pyrazolo[3,4-b]pyridin-1-yl | HO-(CH2)4-C(CH3) | HO-(CH2)4-C(CH3) | OMe | O |
| 2447 | 2-amino-purin-9-yl | HO-(CH2)4-C(CH3) | HO-(CH2)4-C(CH3) | OMe | O |
| 2448 | 6-amino-purin-9-yl (adenin-9-yl) | HO-(CH2)4-C(CH3) | HO-(CH2)4-C(CH3) | OMe | O |
| 2449 | 8-amino-purin-9-yl | HO-(CH2)4-C(CH3) | HO-(CH2)4-C(CH3) | OMe | O |
| 2450 | 7-amino-2,3-dihydro-3-oxo-benzisothiazol-2-yl | HO-(CH2)4-C(CH3) | HO-(CH2)4-C(CH3) | OMe | O |

TABLE 1-continued
| Cmpd | W | X | Z | A | Q |
|------|---|---|---|---|---|
| 2451 | 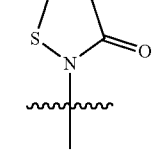 |  |  | OMe | O |
| 2452 | 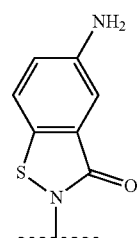 | 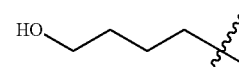 | 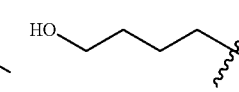 | OMe | O |
| 2453 | 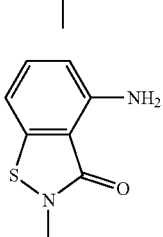 |  |  | OMe | O |
| 2454 | 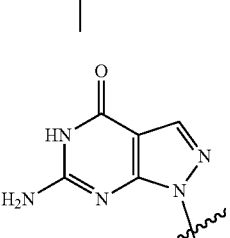 |  |  | OMe | O |
| 2455 | 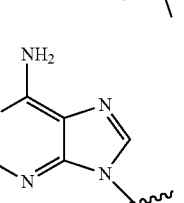 |  |  | OMe | O |
| 2456 | 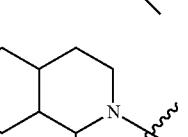 | 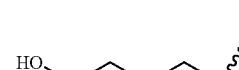 | 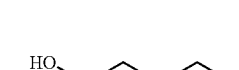 | OMe | O |
| 2457 | 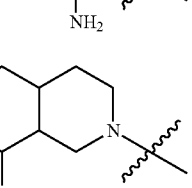 |  |  | OMe | O |

TABLE 1-continued

| Cmpd | W | X | Z | A | Q |
|---|---|---|---|---|---|
| 2458 | 7-amino-decahydroisoquinolinyl (H₂N on one ring, N attached) | HO-(CH₂)₄- | HO-(CH₂)₄- | OMe | O |
| 2459 | 6-amino-decahydroisoquinolinyl | HO-(CH₂)₄- | HO-(CH₂)₄- | OMe | O |
| 2460 | 5-amino-decahydroisoquinolinyl | HO-(CH₂)₄- | HO-(CH₂)₄- | OMe | O |
| 2461 | 4-amino-decahydroisoquinolinyl | HO-(CH₂)₄- | HO-(CH₂)₄- | OMe | O |
| 2462 | 3-amino-decahydroisoquinolinyl | HO-(CH₂)₄- | HO-(CH₂)₄- | OMe | O |
| 2463 | 8-amino-decahydroquinolinyl | HO-(CH₂)₄- | HO-(CH₂)₄- | OMe | O |
| 2464 | 7-amino-decahydroquinolinyl | HO-(CH₂)₄- | HO-(CH₂)₄- | OMe | O |
| 2465 | 6-amino-decahydroquinolinyl | HO-(CH₂)₄- | HO-(CH₂)₄- | OMe | O |

TABLE 1-continued
| Cmpd | W | X | Z | A | Q |
|---|---|---|---|---|---|
| 2466 | 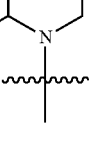 |  |  | OMe | O |
| 2467 | 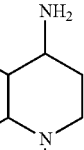 | 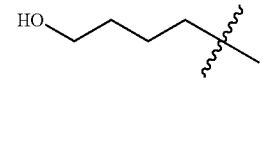 [SMILES: *CCCCO] | 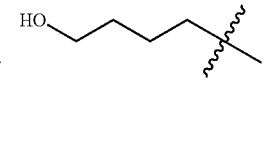 | OMe | O |
| 2468 | 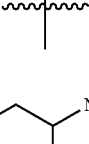 | 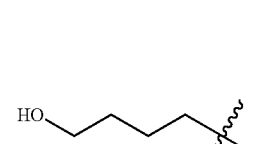 | 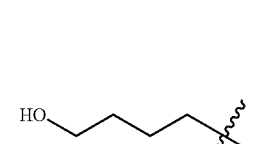 | OMe | O |
| 2469 |  |  |  | OMe | O |
| 2470 | 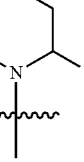 | 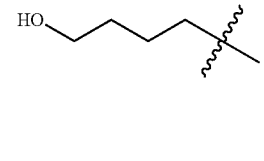 [SMILES: *CCCCO] | 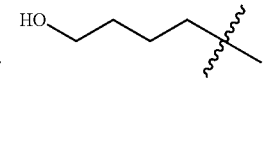 | OMe | O |
| 2471 | 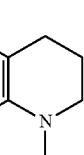 | 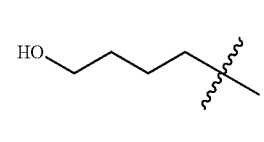 [SMILES: *CCCCO] | 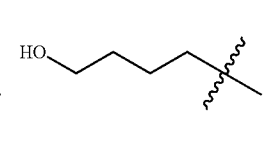 | OMe | O |
| 2472 | 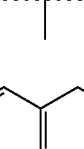 | 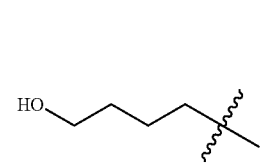 [SMILES: *CCCCO] | 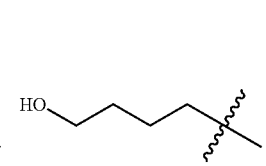 | OMe | O |

TABLE 1-continued

| Cmpd | W | X | Z | A | Q |
|------|---|---|---|---|---|
| 2473 | 5-amino-1,2,3,4-tetrahydroquinolin-1-yl | HO-(CH2)4- | HO-(CH2)4- | OMe | O |
| 2474 | 4-amino-1,2,3,4-tetrahydroquinolin-1-yl | HO-(CH2)4- | HO-(CH2)4- | OMe | O |
| 2475 | 3-amino-1,2,3,4-tetrahydroquinolin-1-yl | HO-(CH2)4- | HO-(CH2)4- | OMe | O |
| 2476 | 2-amino-1,2,3,4-tetrahydroquinolin-1-yl | HO-(CH2)4- | HO-(CH2)4- | OMe | O |
| 2477 | 8-amino-1,2-dihydroquinolin-1-yl | HO-(CH2)4- | HO-(CH2)4- | OMe | O |
| 2478 | 7-amino-1,2-dihydroquinolin-1-yl | HO-(CH2)4- | HO-(CH2)4- | OMe | O |
| 2479 | 6-amino-1,2-dihydroquinolin-1-yl | HO-(CH2)4- | HO-(CH2)4- | OMe | O |

TABLE 1-continued

| Cmpd | W | X | Z | A | Q |
|---|---|---|---|---|---|
| 2480 | 5-amino-2H-quinoline, N-linked | HO-(CH2)4-CH(*)- | HO-(CH2)4-CH(*)- | OMe | O |
| 2481 | 4-amino-2H-quinoline, N-linked | HO-(CH2)4-CH(*)- | HO-(CH2)4-CH(*)- | OMe | O |
| 2482 | 3-amino-2H-quinoline, N-linked | HO-(CH2)4-CH(*)- | HO-(CH2)4-CH(*)- | OMe | O |
| 2483 | 2-amino-2H-quinoline, N-linked | HO-(CH2)4-CH(*)- | HO-(CH2)4-CH(*)- | OMe | O |
| 2484 | 1-amino-1,2-dihydroisoquinoline, N-linked | HO-(CH2)4-CH(*)- | HO-(CH2)4-CH(*)- | OMe | O |
| 2485 | 8-amino-1H-isoquinoline, N-linked | HO-(CH2)4-CH(*)- | HO-(CH2)4-CH(*)- | OMe | O |
| 2486 | 7-amino-1H-isoquinoline, N-linked | HO-(CH2)4-CH(*)- | HO-(CH2)4-CH(*)- | OMe | O |
| 2487 | 6-amino-1H-isoquinoline, N-linked | HO-(CH2)4-CH(*)- | HO-(CH2)4-CH(*)- | OMe | O |

TABLE 1-continued

| Cmpd | W | X | Z | A | Q |
|---|---|---|---|---|---|
| 2488 | 5-amino-1,2-dihydroisoquinolin-2-yl | HO-(CH2)4-C(CH3)< | HO-(CH2)4-C(CH3)< | OMe | O |
| 2489 | 4-amino-1,2-dihydroisoquinolin-2-yl | HO-(CH2)4-C(CH3)< | HO-(CH2)4-C(CH3)< | OMe | O |
| 2490 | 3-amino-1,2-dihydroisoquinolin-2-yl | HO-(CH2)4-C(CH3)< | HO-(CH2)4-C(CH3)< | OMe | O |
| 2491 | 8-amino-2-oxoquinolin-1(2H)-yl | HO-(CH2)4-C(CH3)< | HO-(CH2)4-C(CH3)< | OMe | O |
| 2492 | 7-amino-2-oxoquinolin-1(2H)-yl | HO-(CH2)4-C(CH3)< | HO-(CH2)4-C(CH3)< | OMe | O |
| 2493 | 6-amino-2-oxoquinolin-1(2H)-yl | HO-(CH2)4-C(CH3)< | HO-(CH2)4-C(CH3)< | OMe | O |
| 2494 | 5-amino-2-oxoquinolin-1(2H)-yl | HO-(CH2)4-C(CH3)< | HO-(CH2)4-C(CH3)< | OMe | O |
| 2495 | 4-amino-2-oxoquinolin-1(2H)-yl | HO-(CH2)4-C(CH3)< | HO-(CH2)4-C(CH3)< | OMe | O |

TABLE 1-continued

| Cmpd | W | X | Z | A | Q |
|---|---|---|---|---|---|
| 2496 | 3-amino-quinolin-2(1H)-one (N-linked) | HO-(CH2)4-C(CH3)- | HO-(CH2)4-C(CH3)- | OMe | O |
| 2497 | 8-amino-isoquinolin-1(2H)-one (N-linked) | HO-(CH2)4-C(CH3)- | HO-(CH2)4-C(CH3)- | OMe | O |
| 2498 | 7-amino-isoquinolin-1(2H)-one (N-linked) | HO-(CH2)4-C(CH3)- | HO-(CH2)4-C(CH3)- | OMe | O |
| 2499 | 6-amino-isoquinolin-1(2H)-one (N-linked) | HO-(CH2)4-C(CH3)- | HO-(CH2)4-C(CH3)- | OMe | O |
| 2500 | 5-amino-isoquinolin-1(2H)-one (N-linked) | HO-(CH2)4-C(CH3)- | HO-(CH2)4-C(CH3)- | OMe | O |
| 2501 | 4-amino-isoquinolin-1(2H)-one (N-linked) | HO-(CH2)4-C(CH3)- | HO-(CH2)4-C(CH3)- | OMe | O |
| 2502 | 3-amino-isoquinolin-1(2H)-one (N-linked) | HO-(CH2)4-C(CH3)- | HO-(CH2)4-C(CH3)- | OMe | O |
| 2503 | 8-amino-benzo[e][1,2]oxazine (N-linked) | HO-(CH2)4-C(CH3)- | HO-(CH2)4-C(CH3)- | OMe | O |
| 2504 | 7-amino-benzo[e][1,2]oxazine (N-linked) | HO-(CH2)4-C(CH3)- | HO-(CH2)4-C(CH3)- | OMe | O |

TABLE 1-continued

| Cmpd | W | X | Z | A | Q |
|---|---|---|---|---|---|
| 2505 | 7-amino-benzo[1,2]oxazine | HO-(CH₂)₄- | HO-(CH₂)₄- | OMe | O |
| 2506 | 5-amino-benzo[1,2]oxazine | HO-(CH₂)₄- | HO-(CH₂)₄- | OMe | O |
| 2507 | 4-amino-benzo[1,2]oxazine | HO-(CH₂)₄- | HO-(CH₂)₄- | OMe | O |
| 2508 | 3-amino-benzo[1,2]oxazine | HO-(CH₂)₄- | HO-(CH₂)₄- | OMe | O |
| 2509 | 1-amino-carbazol-9-yl | HO-(CH₂)₄- | HO-(CH₂)₄- | OMe | O |
| 2510 | 2-amino-carbazol-9-yl | HO-(CH₂)₄- | HO-(CH₂)₄- | OMe | O |
| 2511 | 1-amino-phenoxazin-10-yl | HO-(CH₂)₄- | HO-(CH₂)₄- | OMe | O |
| 2512 | 2-amino-phenoxazin-10-yl | HO-(CH₂)₄- | HO-(CH₂)₄- | OMe | O |

TABLE 1-continued

| Cmpd | W | X | Z | A | Q |
|---|---|---|---|---|---|
| 2513 | phenothiazine with NH2 and N-linker | HO-(CH2)4- | HO-(CH2)4- | OMe | O |
| 2514 | phenothiazine with H2N and N-linker | HO-(CH2)4- | HO-(CH2)4- | OMe | O |
| 2515 | aminoadamantane with N-linker | HO-(CH2)4- | HO-(CH2)4- | OMe | O |
| 2516 | H2N-azepine with N-linker | HO-(CH2)4- | HO-(CH2)4- | OMe | O |
| 2517 | H2N-azepine with N-linker | HO-(CH2)4- | HO-(CH2)4- | OMe | O |
| 2518 | H2N-azepine with N-linker | HO-(CH2)4- | HO-(CH2)4- | OMe | O |
| 2519 | H2N-diazepine with N-linker | HO-(CH2)4- | HO-(CH2)4- | OMe | O |

TABLE 1-continued

| Cmpd | W | X | Z | A | Q |
|---|---|---|---|---|---|
| 2520 | (H₂N-diazepine, N-attached) | HO-(CH₂)₄- | HO-(CH₂)₄- | OMe | O |

The present disclosure also provides a compound having the formula:

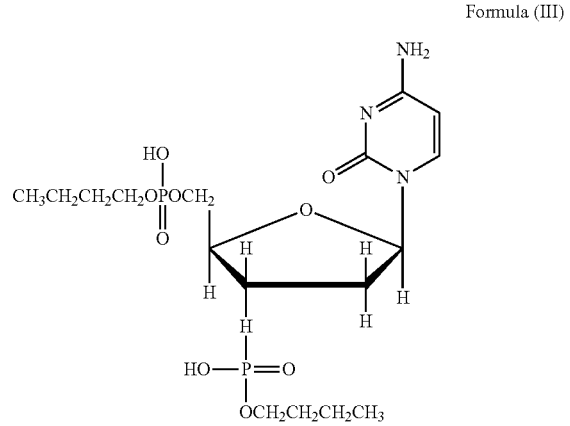

Formula (III)

or a pharmaceutically acceptable salt thereof.

The chemical name of the compound of Formula (III) is sodium ((2R,3S,5R)-5-(4-amino-2-oxopyrimidin-1(2H)-yl)-3-((butoxyoxidophosphor-yl)oxy)tetrahydrofuran-2-yl) methyl butyl phosphate. The molecular formula of the compound of Formula (III) is $C_{17}H_{29}N_3Na_2O_{10}P_2$. The molecular weight of the compound of Formula (III) is 543.11 Da. The compound of Formula (III) is also referred to herein as Nu-8, Compound (III) or Cmpd 1, which such terms are used interchangeably herein. In some embodiments, Nu-8 includes a ribose, two phosphate groups, two butyl groups, and a cytosine.

In some embodiments, the present disclosure also provides a compound of the formula:

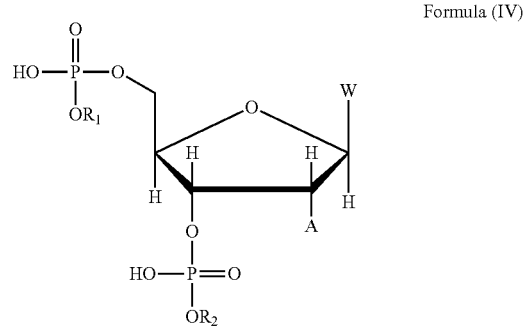

Formula (IV)

wherein A is —H or —OMe; $R_1$ and $R_2$ are each independently selected from isobutyl, benzyl, butyl, and cyclohexyl;

and W is an amino-substituted or guanidino-substituted nitrogen containing heterocyclic moiety; or a pharmaceutically acceptable salt thereof.

In some embodiments, $R_1$ and $R_2$ are both butyl. In other embodiments, $R_1$ and $R_2$ are both isobutyl. In other embodiments, $R_1$ and $R_2$ are both benzyl. In other embodiments, $R_1$ and $R_2$ are both cyclohexyl.

In some embodiments, W is selected from the following amino-substituted moieties:

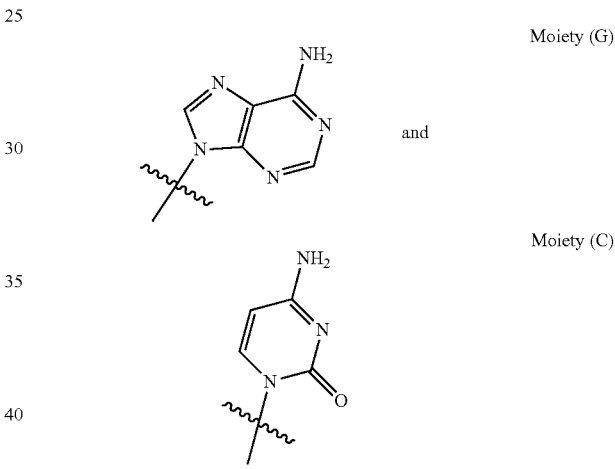

Moiety (G)

and

Moiety (C)

where the wavy line represents a point of attachment to the deoxyribose or ribose moiety.

In some embodiments, $R_1$ and $R_2$ are both butyl, W is moiety (G), and A is —OMe. That is, in some embodiments, the compound of Formula (IV) is a compound of Formula (V).

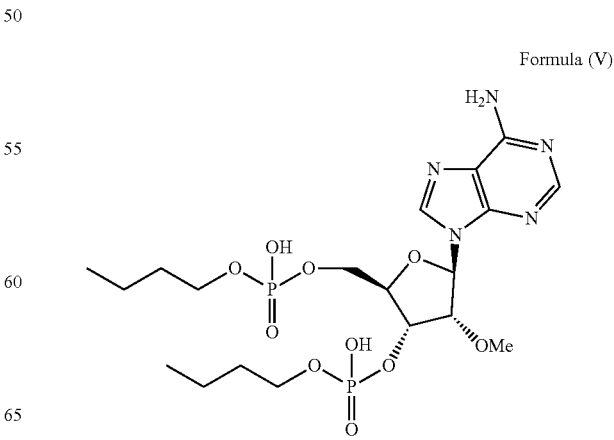

Formula (V)

The chemical name of the compound of Formula (V) is (2R,3R,4R,5R)-5-(6-aminopurin-9-yl)-3-((butoxy(hydroxy)phosphoryl)oxy)-4-methoxytetrahydrofuran-2-yl)methyl butyl hydrogen phosphate. The molecular formula of the compound of Formula (V) is $C_{19}H_{33}N_5O_{10}P_2$. The molecular weight of the compound of Formula (V) is 553.44 Da. The compound of Formula (V) is also referred to herein as LAI-106, Compound (V) or Cmpd 1398 which such terms are used interchangeably herein. In some embodiments, LAI-106 includes a ribose, two phosphate groups, two butyl groups, and a guanine.

In some embodiments, $R_1$ and $R_2$ are both butyl, W is moiety (C), and A is —OMe. That is, in some embodiments, the compound of Formula (IV) is a compound of Formula (VI).

Formula (VI)

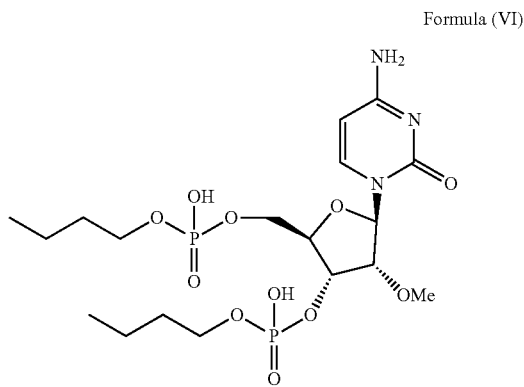 [SMILES: CCCCOP(=O)(O)OC[C@H]1O[C@@H](n2ccc(N)nc2=O)[C@H](OC)[C@@H]1OP(=O)(O)OCCCC]

The chemical name of the compound of Formula (VI) is ((2R,3R,4R,5R)-5-(4-amino-2-oxopyrimidin-1(2H)-yl)-3-((butoxy(hydroxy)phosphoryl)oxy)-4-methoxytetrahydrofuran-2-yl) methyl butyl hydrogen phosphate. The molecular formula of the compound of Formula (VI) is $C_{18}H_{33}N_3O_{11}P_2$. The molecular weight of the compound of Formula (VI) is 529.42 Da. The compound of Formula (VI) is also referred to herein as Nu-10, Compound (VI) or Cmpd 1261, which such terms are used interchangeably herein. In some embodiments, Nu-10 includes a ribose, two phosphate groups, two butyl groups, and a cytosine.

In some embodiments, $R_1$ and $R_2$ are both isobutyl, W is moiety (C), and A is —H. That is, in some embodiments, the compound of Formula (IV) is a compound of Formula (VII).

Formula (VII)

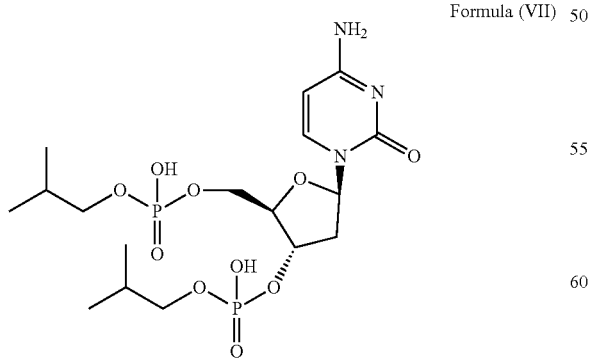

The chemical name of the compound of Formula (VII) is ((2R,3S,5R)-5-(4-amino-2-oxopyrimidin-1(2H)-yl)-3-((hydroxy(isobutoxy)phosphoryl)oxy)tetrahydrofuran-2-yl) methyl isobutyl hydrogen phosphate. The molecular formula of the compound of Formula (VII) is $C_{17}H_{31}N_3O_{10}P_2$. The molecular weight of the compound of Formula (VII) is 499.39 Da. The compound of Formula (VII) is also referred to herein as LAI-101, Compound (VII) or Cmpd 211, which such terms are used interchangeably herein. In some embodiments, LAI-101 includes a ribose, two phosphate groups, two isobutyl groups, and a cytosine.

In some embodiments, $R_1$ and $R_2$ are both benzyl, W is moiety (C), and A is —H. That is, in some embodiments, the compound of Formula (IV) is a compound of Formula (VIII).

Formula (VIII)

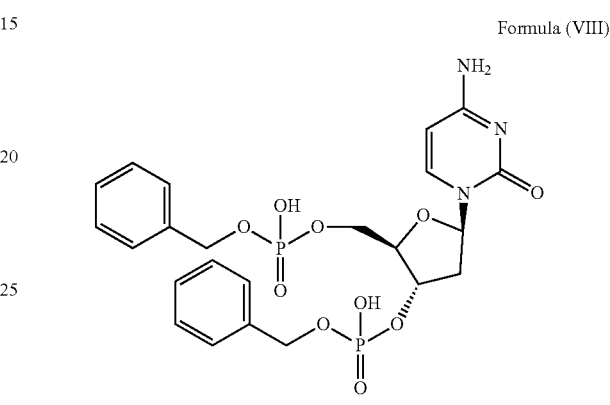

The chemical name of the compound of Formula (VIII) is ((2R,3S,5R)-5-(4-amino-2-oxopyrimidin-1(2H)-yl)-3-(((benzyloxy)(hydroxy)phosphoryl)oxy)tetrahydrofuran-2-yl)methyl benzyl hydrogen phosphate. The molecular formula of the compound of Formula (VIII) is $C_{23}H_{27}N_3O_{10}P_2$. The molecular weight of the compound of Formula (VIII) is 567.42 Da. The compound of Formula (VIII) is also referred to herein as LAI-102, Compound (VIII) or Cmpd 841, which such terms are used interchangeably herein. In some embodiments, LAI-102 includes a ribose, two phosphate groups, two benzyl groups, and a cytosine.

In some embodiments, $R_1$ and $R_2$ are both cyclohexyl, W is moiety (G), and A is —H. That is, in some embodiments, the compound of Formula (IV) is a compound of Formula (IX).

Formula (IX)

The chemical name of the compound of Formula (IX) is (2R,3S,5R)-5-(6-aminopurin-9-yl)-3-((cyclohexyloxy(hydroxy)phosphorypoxy)tetrahydrofuran-2-yl)methyl cyclohexyl hydrogen phosphate. The molecular formula of the compound of Formula (IX) is $C_{22}H_{35}N_5O_9P_2$. The molecular weight of the compound of Formula (IX) is 575.49 Da. The compound of Formula (IX) is also referred to herein as LAI-105, Compound (IX) or Cmpd 558, which such terms are used interchangeably herein. In some embodiments, LAI-105 includes a ribose, two phosphate groups, two cyclohexyl groups, and a guanine.

A compound of the present disclosure is described with reference to a specific compound illustrated herein. In addition, a compound of the present disclosure may exist in any number of different forms or derivatives, all within the scope of the present disclosure. Alternative forms or derivatives, include, for example, pharmaceutically acceptable salts, prodrugs and active metabolites, tautomers, and solid forms, including without limitation different crystal forms, polymorphic or amorphous solids, including hydrates and solvates thereof, and other forms.

Unless specified to the contrary, specification of a compound of the present disclosure herein includes pharmaceutically acceptable salts of such compound. Thus, a compound of the present disclosure can be in the form of pharmaceutically acceptable salts or can be formulated as pharmaceutically acceptable salts. Contemplated pharmaceutically acceptable salt forms of the present disclosure include, without limitation, mono, bis, tris, tetrakis, and so on. Pharmaceutically acceptable salts of the present disclosure are non-toxic in the amounts and concentrations at which such pharmaceutically acceptable salts are administered. The preparation of such pharmaceutically acceptable salts of the present disclosure can facilitate the pharmacological use by altering the physical characteristics of a compound of the present disclosure without preventing it from exerting its physiological effect.

As used herein, the term "pharmaceutically acceptable," with respect to salts and formulation components such as carriers, excipients, and diluents, refers to those salts and components which are not deleterious to a patient and which are compatible with other ingredients, active ingredients, salts or components. Pharmaceutically acceptable includes "veterinarily acceptable," and thus includes both human and non-human mammal applications independently.

As used herein, the term "pharmaceutically acceptable salt" refers to salts commonly used to form alkali metal salts and to form addition salts of free acids or free bases. Such salts include, for example, the physiologically acceptable salts listed in Handbook of Pharmaceutical Salts: Properties, Selection and Use, P. H. Stahl and C. G. Wermuth (Eds.), Wiley-VCH, New York, 2002, which are known to the skilled artisan. Salt formation can occur at one or more positions having labile protons. The pharmaceutically acceptable salts of a compound of the present disclosure include both acid addition salts and base addition salts.

In some embodiments, suitable pharmaceutically acceptable acid addition salts of the compounds of the present disclosure may be prepared from an inorganic acid or an organic acid. Examples of such inorganic acids include without limitation hydrochloric, hydrobromic, hydroiodic, nitric, carbonic, sulfuric, and phosphoric acid. Appropriate organic acids include without limitation aliphatic, cycloaliphatic, aromatic, arylaliphatic, heterocyclic, carboxylic, and sulfonic classes of organic acids, examples of which are formic, acetic, propionic, succinic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, beta-hydroxybutyric, malonic, galactic, and galacturonic acid, to name a few. Pharmaceutically acceptable acidic/anionic salts also include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts, among others.

In some embodiments, suitable pharmaceutically acceptable base addition salts of the compounds of the present disclosure include without limitation metallic salts made from aluminum, calcium, lithium, magnesium, potassium, sodium and zinc, or organic salts made from N,N'-dibenzylethylene-diamine, chloroprocaine, choline, diethanolamine, ethylenediamine, N-methylglucamine, lysine, arginine, and procaine. All of these salts may be prepared by conventional means from a compound of the present disclosure by treating a compound of the present disclosure with the appropriate acid or base. Pharmaceutically acceptable basic/cationic salts also include diethanolamine, ammonium, ethanolamine, piperazine and triethanolamine salts, to name a few. In some embodiments, a pharmaceutically acceptable salt of the present disclosure comprises a monovalent cation or a divalent cation.

In some embodiments, a pharmaceutically acceptable salt of the present disclosure is selected from the group consisting of an ammonium salt, a calcium salt, a sodium salt, a potassium salt, a magnesium salt, and a cobalt salt. In some embodiments, the ammonium salt is ammonium ((2R,3 S,5R)-5-(4-amino-2-oxopyrimidin-1(2H)-yl)-3-((butoxyoxidophosphoryl)oxy)tetrahydrofuran-2-yl)methyl butyl phosphate. In some embodiments, the calcium salt is calcium ((2R,3S,5R)-5-(4-amino-2-oxopyrimidin-1(2H)-yl)-3-((butoxyoxidophosphory)oxy)tetrahydrofuran-2-yl)methyl butyl phosphate. In some embodiments, the sodium salt is sodium ((2R,3S,5R)-5-(4-amino-2-oxopyrimidin-1(2H)-yl)-3-((butoxyoxidophosphoryl)oxy)tetrahydrofuran-2-yl) methyl butyl phosphate. In some embodiments, the potassium salt is potassium ((2R,3S,5R)-5-(4-amino-2-oxopyrimidin-1(2H)-yl)-3-((butoxyoxidophosphoryl)oxy) tetrahydrofuran-2-yl)methyl butyl phosphate. In some embodiments, the magnesium salt is magnesium ((2R,3S, 5R)-5-(4-amino-2-oxopyrimidin-1(2H)-yl)-3-((butoxyoxidophosphoryl)oxy)tetrahydrofuran-2-yl)methyl butyl phosphate. In some embodiments, the cobalt salt is cobalt ((2R, 3S,5R)-5-(4-amino-2-oxopyrimidin-1(2H)-yl)-3-((butoxyoxidophosphoryl)oxy)tetrahydrofuran-2-yl)methyl butyl phosphate.

In some embodiments, a pharmaceutically acceptable salt of the present disclosure is selected from the group consisting of an ammonium salt, a calcium salt, a sodium salt, a potassium salt, a magnesium salt, and a cobalt salt. In some embodiments, the ammonium salt is ammonium (2R,3R,4R, 5R)-5-(6-aminopurin-9-yl)-3-((butoxy(hydroxy)phosphoryl)oxy)-4-methoxytetrahydrofuran-2-yl)methyl butyl hydrogen phosphate. In some embodiments, the calcium salt is calcium (2R,3R,4R,5R)-5-(6-aminopurin-9-yl)-3-((butoxy(hydroxy)phosphoryl)oxy)-4-methoxytetrahydrofuran-2-yl)methyl butyl hydrogen phosphate. In some embodiments, the sodium salt is sodium (2R,3R,4R,5R)-5-(6-aminopurin-9-yl)-3-((butoxy(hydroxy)phosphoryl)oxy)-4- methoxytetrahydrofuran-2-yl)methyl butyl hydrogen phosphate. In some embodiments, the potassium salt is potassium (2R,3R,4R,5R)-5-(6-aminopurin-9-yl)-3-((butoxy(hydroxy)phosphoryl)oxy)-4-methoxytetrahydrofuran-2-yl)methyl butyl hydrogen phosphate. In some embodiments, the magnesium salt is magnesium (2R,3R,4R,5R)-5-(6-aminopurin-9-yl)-3-((butoxy(hydroxy)phosphoryl)oxy)-4-methoxytetrahydrofuran-2-yl)methyl butyl hydrogen phosphate. In some embodiments, the cobalt salt is cobalt (2R,3R,4R,5R)-5-(6-aminopurin-9-yl)-3-((butoxy(hydroxy) phosphoryl)oxy)-4-methoxytetrahydrofuran-2-yl)methyl butyl hydrogen phosphate.

In some embodiments, a pharmaceutically acceptable salt of the present disclosure is selected from the group consisting of an ammonium salt, a calcium salt, a sodium salt, a potassium salt, a magnesium salt, and a cobalt salt. In some embodiments, the ammonium salt is ammonium ((2R,3R,4R,5R)-5-(4-amino-2-oxopyrimidin-1 (2H)-yl)-3-((butoxy(hydroxyl)phosphorypoxy)-4-methoxytetrahydrofuran-2-yl) methyl butyl hydrogen phosphate. In some embodiments, the calcium salt is calcium ((2R,3R,4R,5R)-5-(4-amino-2-oxopyrimidin-1 (2H)-yl)-3-((butoxy(hydroxy)phosphoryl) oxy)-4-methoxytetrahydrofuran-2-yl) methyl butyl hydrogen phosphate. In some embodiments, the sodium salt is sodium ((2R,3R,4R,5R)-5-(4-amino-2-oxopyrimidin-1 (2H)-yl)-3-((butoxy(hydroxy)phosphoryl)oxy)-4-methoxytetrahydrofuran-2-yl) methyl butyl hydrogen phosphate. In some embodiments, the potassium salt is potassium ((2R,3R,4R,5R)-5-(4-amino-2-oxopyrimidin-1(2H)-yl)-3-((butoxy(hydroxy)phosphorypoxy)-4-methoxytetrahydrofuran-2-yl) methyl butyl hydrogen phosphate. In some embodiments, the magnesium salt is magnesium ((2R,3R,4R,5R)-5-(4-amino-2-oxopyrimidin-1(2H)-yl)-3-((butoxy(hydroxy)phosphoryl)oxy)-4-methoxytetrahydrofuran-2-yl) methyl butyl hydrogen phosphate. In some embodiments, the cobalt salt is cobalt ((2R,3R,4R,5R)-5-(4-amino-2-oxopyrimidin-1(2H)-yl)-3-((butoxy(hydroxy)phosphorypoxy)-4-methoxytetrahydrofuran-2-yl) methyl butyl hydrogen phosphate.

In some embodiments, a pharmaceutically acceptable salt of the present disclosure is selected from the group consisting of an ammonium salt, a calcium salt, a sodium salt, a potassium salt, a magnesium salt, and a cobalt salt. In some embodiments, the ammonium salt is ammonium ((2R,3S,5R)-5-(4-amino-2-oxopyrimidin-1(2H)-yl)-3-((hydroxy(isobutoxy)phosphorypoxy)tetrahydrofuran-2-yl)methyl isobutyl hydrogen phosphate. In some embodiments, the calcium salt is calcium ((2R,3S,5R)-5-(4-amino-2-oxopyrimidin-1(2H)-yl)-3-((hydroxy(isobutoxy)phosphorypoxy) tetrahydrofuran-2-yl)methyl isobutyl hydrogen phosphate. In some embodiments, the sodium salt is sodium ((2R,3S,5R)-5-(4-amino-2-oxopyrimidin-1(2H)-yl)-3-((hydroxy(isobutoxy)phosphoryl)oxy)tetrahydrofuran-2-yl)methyl isobutyl hydrogen phosphate. In some embodiments, the potassium salt is potassium ((2R,3 S,5R)-5-(4-amino-2-oxopyrimidin-1(2H)-yl)-3-((hydroxy(isobutoxy)phosphoryl)oxy)tetrahydrofuran-2-yl)methyl isobutyl hydrogen phosphate. In some embodiments, the magnesium salt is magnesium ((2R,3S,5R)-5-(4-amino-2-oxopyrimidin-1 (2H)-yl)-3-((hydroxy(isobutoxy)phosphorypoxy)tetrahydrofuran-2-yl)methyl isobutyl hydrogen phosphate. In some embodiments, the cobalt salt is cobalt ((2R,3S,5R)-5-(4-amino-2-oxopyrimidin-1(2H)-yl)-3-((hydroxy(isobutoxy)phosphoryl)oxy)tetrahydrofuran-2-yl)methyl isobutyl hydrogen phosphate.

In some embodiments, a pharmaceutically acceptable salt of the present disclosure is selected from the group consisting of an ammonium salt, a calcium salt, a sodium salt, a potassium salt, a magnesium salt, and a cobalt salt. In some embodiments, the ammonium salt is ammonium ((2R,3 S,5R)-5-(4-amino-2-oxopyrimidin-1 (2H)-yl)-3-((benzyloxy)(hydroxy)phosphoryl)oxy)tetrahydrofuran-2-yl) methyl benzyl hydrogen phosphate. In some embodiments, the calcium salt is calcium ((2R,3S,5R)-5-(4-amino-2-oxopyrimidin-1(2H)-yl)-3-(((benzyloxy)(hydroxy)phosphoryl)oxy)tetrahydrofuran-2-yl)methyl benzyl hydrogen phosphate. In some embodiments, the sodium salt is sodium ((2R,3S,5R)-5-(4-amino-2-oxopyrimidin-1 (2H)-yl)-3-(abenzyloxy)(hydroxy)phosphoryl)oxy)tetrahydrofuran-2-yl)methyl benzyl hydrogen phosphate. In some embodiments, the potassium salt is potassium ((2R,3S,5R)-5-(4-amino-2-oxopyrimidin-1(2H)-yl)-3-(((benzyloxy)(hydroxy)phosphoryl)oxy)tetrahydrofuran-2-yl)methyl benzyl hydrogen phosphate. In some embodiments, the magnesium salt is magnesium ((2R,3S,5R)-5-(4-amino-2-oxopyrimidin-1 (2H)-yl)-3-(((benzyloxy)(hydroxy)phosphoryl)oxy) tetrahydrofuran-2-yl)methyl benzyl hydrogen phosphate. In some embodiments, the cobalt salt is cobalt ((2R,3S,5R)-5-(4-amino-2-oxopyrimidin-1(2H)-yl)-3-(((benzyloxy)(hydroxy)phosphoryl)oxy)tetrahydrofuran-2-yl)methyl benzyl hydrogen phosphate.

In some embodiments, a pharmaceutically acceptable salt of the present disclosure is selected from the group consisting of an ammonium salt, a calcium salt, a sodium salt, a potassium salt, a magnesium salt, and a cobalt salt. In some embodiments, the ammonium salt is ammonium (2R,3S,5R)-5-(6-aminopurin-9-yl)-3-((cyclohexyloxy(hydroxy) phosphoryl) oxy)tetrahydrofuran-2-yl)methyl cyclohexyl hydrogen phosphate. In some embodiments, the calcium salt is calcium (2R,3S,5R)-5-(6-aminopurin-9-yl)-3-((cyclohexyloxy(hydroxy)phosphoryl)oxy)tetrahydrofuran-2-yl) methyl cyclohexyl hydrogen phosphate. In some embodiments, the sodium salt is sodium (2R,3S,5R)-5-(6-aminopurin-9-yl)-3-((cyclohexyloxy(hydroxy)phosphoryl)oxy)tetrahydrofuran-2-yl)methyl cyclohexyl hydrogen phosphate. In some embodiments, the potassium salt is potassium (2R,3S,5R)-5-(6-aminopurin-9-yl)-3-((cyclohexyloxy(hydroxy) phosphoryl)oxy)tetrahydrofuran-2-yl) methyl cyclohexyl hydrogen phosphate. In some embodiments, the magnesium salt is magnesium (2R,3S,5R)-5-(6-aminopurin-9-yl)-3-((cyclohexyloxy(hydroxy)phosphoryl) oxy)tetrahydrofuran-2-yl)methyl cyclohexyl hydrogen phosphate. In some embodiments, the cobalt salt is cobalt (2R,3S,5R)-5-(6-aminopurin-9-yl)-3-((cyclohexyloxy(hydroxy)phosphoryl)oxy)tetrahydrofuran-2-yl)methyl cyclohexyl hydrogen phosphate.

Pharmaceutically acceptable salts of the present disclosure can be prepared by standard techniques known in the art to which the present disclosure pertains. For example, the free-base form of a compound of the present disclosure can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, including, for example, treatment of the free acid with an appropriate inorganic or organic base.

In addition to the compounds of the present disclosure, the present disclosure also includes prodrugs (e.g., pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Typically, the prodrug is inactive, or less active than the active compound, but may provide one or more advantageous handling, administration, and/or metabolic properties.

Some prodrugs are activated enzymatically to yield the active compound, or a compound may undergo further chemical reaction to yield the active compound. Prodrugs may proceed from prodrug form to active form in a single step or may have one or more intermediate forms which such forms have activity or may be inactive.

As described in The Practice of Medicinal Chemistry, Ch. 31-32 (Ed. Wermuth, Academic Press, San Diego, Calif., 2001), prodrugs can be conceptually divided into two non-exclusive categories, including bioprecursor prodrugs and carrier prodrugs. Generally, bioprecursor prodrugs are compounds that are inactive or have low activity compared to the corresponding active drug compound that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O— and S— dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, and the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Such carrier prodrugs are often advantageous for orally administered drugs. In some instances, the transport moiety provides targeted delivery of the drug. For example, the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity and can be further metabolized to provide an active metabolite.

Metabolites of a compound of the present disclosure may be identified using routine techniques known in the art, and their activities determined using tests such as those described in Bertolini et al., 1997, J. Med. Chem., 40:2011-2016; Shan et al., 1997, J Pharm Sci 86(7):756-757; Bagshawe, 1995, Drug Dev. Res., 34:220-230; Wermuth, supra.

It is understood by those skilled in the art that some compounds may exhibit tautomerism. In such cases, the formulae provided herein expressly depict only one of the possible tautomeric forms. It is therefore to be understood that a compound of the present disclosure intends to represent any tautomeric form of the depicted compound and is not to be limited merely to the specific tautomeric form depicted by the drawing of the compound.

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition (i.e., a free base or free acid of the compound of interest forms an acid/base reaction with a corresponding addition base or addition acid, respectively, resulting in an ionic charge interaction), co-crystals are a new chemical species that is formed between neutral compounds, resulting in the compound and an additional molecular species in the same crystal structure.

In some instances, a compound of the present disclosure is complexed with an acid or a base, including without limitation base addition salts such as, for example, ammonium, diethylamine, ethanolamine, ethylenediamine, diethanolamine, t-butylamine, piperazine, meglumine; acid addition salts, such as, for example, acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate, and tosylate; and amino acids such as, for example, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine.

Additionally, a compound of the present disclosure is intended to cover hydrated or solvated as well as unhydrated or unsolvated forms. Other examples of solvates include without limitation a compound of the present disclosure in combination with a suitable solvent, such as isopropanol, ethanol, methanol, DMSO, ethyl acetate, acetic acid or ethanolamine, and the like.

In some embodiments, a compound of the present disclosure is a protonated compound. As used herein, the term "protonated compound" refers to a compound of the present disclosure that is protonated by adding protons (or positively charged hydrogen ions) to proton acceptor sites of a compound of the present disclosure. In some embodiments, the proton acceptor sites include the phosphate groups of a compound of the present disclosure as well as any additional proton acceptor sites on either the ribose or the butyl groups of a compound of the present disclosure.

As the number of proton acceptor sites that are protonated on a compound of the present disclosure increases, the pH obtained when a compound of the present disclosure is dissolved in water having a pH of 7 decreases and thus the amount of protonation of a compound of the present disclosure can be determined by measuring the pH of solutions of water after addition of a compound of the present disclosure. pH indicates the hydrogen ion concentration of a solution. Solutions with a high concentration of hydrogen ions have a low pH and are therefore acidic, whereas solutions with a low concentration of hydrogen ions have a high pH and are therefore basic. In some embodiments, the compounds of the present disclosure are protonated so that when dissolved in water (pH 7) such compounds form an aqueous solution having a pH of from less than about pH 7 to about pH 1. As used herein, the term "about," when used with numerical values is to be read as including the amount(s) specified and variations of 20%, 10%, 5%, 1%, 0.5%, and 0.1% of the amount specified. In some embodiments, a compound of the present disclosure is a protonated compound having a pH when dissolved in water of from less than about pH 6 to about pH 1. In some embodiments, a compound of the present disclosure is a protonated compound having a pH when dissolved in water of from about pH 5 to about pH 1. In some embodiments, a compound of the present disclosure is a protonated compound having a pH when dissolved in water of from about pH 4.5 to about pH 1. In some embodiments, a compound of the present disclosure is a protonated compound having a pH when dissolved in water of from about pH 4 to about pH 1. In some embodiments, a compound of the present disclosure is a protonated compound having a pH when dissolved in water of from about pH 3 to about pH 1. In some embodiments, a compound of the present disclosure is a protonated compound having a pH when dissolved in water of from about pH 2 to about pH 1. In some embodiments, a compound of the present disclosure is a protonated compound having a pH when dissolved in water of about pH 3 to about pH 5. In some embodiments, a compound of the present disclosure is a protonated compound having a pH when dissolved in water of about pH 3 to about pH 4.

In some embodiments, protonation can be accomplished by incubating a compound of the present disclosure in the presence of a strong acid. Although a compound of the present disclosure can be protonated by adding protons to the reactive sites on the compound, other modifications of a compound of the present disclosure are possible and are intended to be encompassed by the term protonated compound as used herein. In some embodiments, protonated forms of the compounds of the present disclosure can be generated by subjecting the purified, partially purified or crude compounds to a low pH (e.g., acidic) environment. In some embodiments, purified or crude compounds can be protonated with acid, including phosphoric acid, nitric acid, hydrochloric acid, and acetic acid.

Other procedures to prepare a protonated compound of the present disclosure known to the skilled artisan are equally contemplated to be within the scope of the present disclosure. In some embodiments, once the compounds of the present disclosure have been protonated, such compounds may be separated from any undesired components such as, for example, excess acid. The skilled artisan would know of many ways to separate the compounds from undesired components, including but not limited to using an H+-cation exchanger (e.g., H+-SCX). In some embodiments, the compounds of the present disclosure may be subjected to chromatography following protonation. In some embodiments, a compound of the present disclosure is run over a poly(styrene-divinyl benzene) based resin (e.g., Hamilton's PRP-1 or 3 and Polymer Lab's PLRP) following protonation.

In some embodiments, the protonated compounds of the present disclosure can be used directly. In some embodiments, the protonated compounds of the present disclosure can be processed further to remove any excess acid or salt, e.g., via precipitation, reverse phase chromatography, diafiltration or gel filtration. In some embodiments, the protonated compounds of the present disclosure can be concentrated by lyophilization, solvent evaporation, and the like. In some embodiments, when suspended in water or saline, the compounds of the present disclosure generally exhibit a pH of from about pH 3 to about pH 5 depending upon the level of protonation/acidification, which is determined by how much acid is used in the acidification process. In some embodiments, compounds of the present disclosure can be protonated by passage over a cation exchange column charged with hydrogen ions.

In some embodiments, utilization of two butyl groups in a compound of the present disclosure prevents or limits substantial nuclease degradation, including without limitation exonuclease degradation, of a compound of the present disclosure. In some embodiments, the butyl groups are positioned to protect the ribose of a compound of the present disclosure. Percent acid degradation may be determined using analytical HPLC to assess the loss of functional molecules or by other suitable methods. Acid degradation is generally measured as a function of time. In some embodiments, the compounds of the present disclosure are also nuclease resistant, which allows such compounds to maintain activity (e.g., pH stability) in an in vivo setting. Percent degradation of the compounds of the present disclosure in a setting containing a nuclease may be determined by methods known to those skilled in the art, such as, for example, mass spectroscopy. Nuclease degradation is generally measured as a function of time. In some embodiments, a reference compound is employed in determining the extent or rate of acid or nuclease degradation. In some embodiments, the compounds of the present disclosure are 10%, 20%, 30%, 40%, 50%, 70%, 90%, 100%, 150%, 200%, 300%, 500% or 750% more stable than a reference compound.

A compound of the present disclosure in accordance with some embodiments is useful as an antimicrobial having activity against any microbe. As used herein, the terms "microbe," "microbial," and like terms refers to bacteria, fungi, protozoa, viruses, yeast, and the like. As used herein, the term "antimicrobial" refers to a compound of the present disclosure having the ability to kill or inhibit the growth of a microbe, or to attenuate the severity of a microbial infection. A non-limiting list of the bacteria that a compound of the present disclosure is effective against include without limitation gram positive bacteria, gram negative bacteria, slow growing bacteria and acid fast bacteria, and any species included in the following genera: *Aerococcus, Listeria, Streptomyces, Chlamydia, Lactobacillus, Eubacterium, Burkholderia, Stentrophomonas, Achromobacter, Arachnid, Mycobacterium, Peptostreptococcus, Staphylococcus, Corynebacterium, Erysipelothrix, Dermatophilus, Rhodococcus, Pseudomonas, Streptococcus, Bacillus, Peptococcus*, Pneumococcus, *Micrococcus, Neisseria, Klebsiella, Kurthia, Nocardia, Serratia, Rothia, Escherichia, Propionibacterium, Actinomyces, Helicobacter, Enterococcus, Shigella, Vibrio, Clostridium, Salmonella, Yersinia*, and *Haemophilus*.

A non-limiting list of the fungi that a compound of the present disclosure is effective against include without limitation *Trichophyton, Epidermophyton, Microsporum, Candida albicans* and other *Candida* species, *Pityrosporum orbiculare, Trichophyton mentagrophytes, Trichophyton rubrum, Epidermophyton floccosurn*, and *Trichophyton tonsurans*. A non-limiting list of the viruses that a compound of the present disclosure is effective against include without limitation human immunodeficiency virus (HIV), herpes simplex virus (HSV), cytomegalovirus (CMV), Hepatitis B virus (HBV), Hepatitis C virus (HCV), coronaviruses, and influenza virus.

In some embodiments, a compound of the present disclosure is useful in both therapeutic and non-therapeutic medical applications. In some embodiments including non-therapeutic medical applications, the antimicrobial effect of a compound of the present disclosure allows use of a compound of the present disclosure for sterilization (e.g., sterilization of a patient's skin or of a surface or an object, such as, for example, a surgical instrument), or sanitization (e.g., the cleansing of a surface, instrument, as to render the surface free of undesirable concentrations of disease causing microorganisms). In some embodiments, the compounds of the present disclosure are effective in combating microbial contamination of laboratory cultures, consumables (e.g., food or beverage preparations), medical devices, hospital apparatus, or industrial processes. Therapeutic applications of a compound of the present disclosure are described herein.

The present disclosure also provides pharmaceutical compositions. As used herein, the term "pharmaceutical composition" refers to a pharmaceutical preparation that contains a compound of the present disclosure, or a pharmaceutically acceptable salt thereof, and is suitable for administration to a patient for therapeutic purposes. As used herein, the term "patient" refers to a living organism that is treated with a compound of the present disclosure, including without limitation any mammal such as, for example, humans, other primates (e.g., monkeys, chimpanzees, etc.), companion animals (e.g., dogs, cats, horses, etc.), farm animals (e.g., goats, sheep, pigs, cattle, etc.), laboratory animals (e.g., mice, rats, etc.), and wild and zoo animals (e.g., wolves, bears, deer, etc.).

In some embodiments, the composition may include at least one pharmaceutically acceptable component to provide an improved formulation of a compound of the present disclosure, including without limitation one or more pharmaceutically acceptable carriers, excipients or diluents. The carrier, excipient or diluent may take a wide variety of forms depending on the form of preparation desired for administration.

As used herein, the term "carrier" includes without limitation calcium carbonate, calcium phosphate, various sugars, such as lactose, glucose, or sucrose, types of starch, cellulose derivatives, gelatin, lipids, liposomes, nanoparticles, physiologically acceptable liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like.

As used herein, the term "excipient" generally includes without limitation fillers, binders, disintegrants, glidants, lubricants, complexing agents, solubilizers, stabilizer, preservatives, and surfactants, which may be chosen to facilitate administration of the compound by a particular route. Suitable excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil, mineral oil, polyethylene glycol (e.g., PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g., 2-hydroxypropyl-delta-cyclodextrin), polysorbates (e.g., polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g., a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

As the skilled artisan understands, any diluent known in the art may be utilized in accordance with the present disclosure. In some embodiments of the present disclosure, the diluent is water soluble. In some embodiments of the present disclosure, the diluent is water insoluble. As used herein, the term "diluent" includes without limitation water, saline, phosphate buffered saline (PBS), dextrose, glycerol, ethanol, buffered sodium or ammonium acetate solution, or the like, and combinations thereof.

In some embodiments, the pharmaceutical compositions of the present disclosure include at least one additional active ingredient. As used herein, the term "active ingredient" refers to a therapeutically active compound, as well as any prodrugs thereof and pharmaceutically acceptable salts, hydrates, and solvates of the compound and the prodrugs. Additional active ingredients may be combined with a compound of the present disclosure and may be either administered separately or in the same pharmaceutical composition. The amount of additional active ingredients to be given may be determined by one skilled in the art based upon therapy with a compound of the present disclosure.

In some embodiments, the composition is a human pharmaceutical composition. As used herein, the term "human pharmaceutical composition" refers to a pharmaceutical composition intended for administration to a human.

The pharmaceutical compositions of the present disclosure are suitable for administration to a patient by any suitable means, including without limitation those means used to administer conventional antimicrobials. The pharmaceutical compositions of the present disclosure may be administered using any applicable route that would be considered by one of ordinary skill, including without limitation oral, intravenous ("IV") injection or infusion, intravesical, subcutaneous ("SC"), intramuscular ("IM"), intraperitoneal, intradermal, intraocular, inhalation (and intrapulmonary), intranasal, transdermal, epicutaneously, subdermal, topical, mucosal, nasal, ophthalmic, impression into skin, intravaginal, intrauterine, intracervical, and rectal. Such dosage forms should allow a compound of the present disclosure to reach target cells. Other factors are well known in the art and include considerations such as toxicity and dosage forms that retard a compound or composition from exerting its effects. Techniques and formulations generally may be found in Remington: The Science and Practice of Pharmacy, 21st edition, Lippincott, Williams and Wilkins, Philadelphia, Pa., 2005.

In some embodiments, the pharmaceutical compositions of the present disclosure are adapted for topical administration. As used herein, the term "topical administration" refers to administration of a compound of the present disclosure to the skin surface of a patient so that a compound of the present disclosure passes through the skin layer. Transdermal administration and transmucosal administration are also encompassed within the term topical administration. As used herein, the term "transdermal" refers to passage of a compound of the present disclosure across at least one skin layer of a patient. As used herein, "transmucosal" refers to passage of a compound of the present disclosure across a mucous membrane of a patient. Unless otherwise stated or implied, the terms "topical administration," "transdermal administration," and "transmucosal administration" are used interchangeably herein.

A variety of topical delivery systems for delivering bioactive compounds to microbes in a patient are well known in the art. Such systems include without limitation lotions, creams, gels, oils, ointments, solutions, suspensions, emulsions, and the like by choice of appropriate carriers in the art. In some embodiments, the pharmaceutical composition is administered in the form of a gel including a polyhydric alcohol.

Suitable carriers include without limitation vegetable or mineral oils, white petrolatum (e.g., white soft paraffin), branched chain fats or oils, animal fats and high molecular weight alcohol (e.g., greater than C12). In some embodiments, carriers are selected such that a compound of the present disclosure is soluble. In some embodiments, emulsifiers, stabilizers, humectants, and antioxidants may also be included as well as agents imparting color or fragrance, if desired. In some embodiments, an organic solvent or co-solvent such as ethanol or propanol may be employed in the pharmaceutical compositions of the present disclosure. In some embodiments, evaporation of the solvent leaves a residue on the treated surface to inhibit reinfection. In some embodiments, penetrants appropriate to the barrier to be permeated are used. Such penetrants are generally known in the art and include without limitation bile salts and fusidic acid derivatives. In some embodiments, detergents may be used to facilitate permeation. In some embodiments, creams for topical administration are formulated from a mixture of mineral oil, self-emulsifying beeswax, and water in which mixture a compound of the present disclosure, dissolved in a small amount of solvent (e.g., an oil), is admixed. The specific topical delivery system used depends on the location of the microbes.

In some embodiments, other materials may also be added to the topical pharmaceutical compositions of the present disclosure have additional moisturizing effects and to improve the consistency of the pharmaceutical composition. Examples of such compounds include without limitation cetyl esters wax, stearyl alcohol, cetyl alcohol, glycerin, methyl paraben, propyl paraben, quaternium-15, humectants, volatile methylsiloxane fluids, and polydiorganosiloxane-polyoxyalkylene. See, e.g., U.S. Pat. Nos. 5,153,230 and 4,421,769. If it is desirable for the pharmaceutical composition to have additional cleaning effects in some embodiments, chemicals such as sodium lauryl sulfate or a metal salt of a carboxylic acid may be added.

In some embodiments, a wide variety of nonvolatile emollients are useful in the pharmaceutical compositions of the present disclosure. Non-limiting examples of such nonvolatile emollients are listed in McCutcheon's, Vol. 2 Functional Materials, North American Edition, (1992), pp. 137-168, and CTFA Cosmetic Ingredient Handbook, Second Edition (1992) which lists Skin-Conditioning Agents at pp. 572-575 and Skin Protectants at p. 580. In some embodiments, the nonvolatile emollients include silicones, hydrocarbons, esters, and mixtures thereof. In some embodiments, the esters include esters of monofunctional and difunctional fatty acids that have been esterified with alcohols and polyols (i.e., alcohols having two or more hydroxyl groups). In some embodiments, long chain esters of long chain fatty acids are utilized in the pharmaceutical compositions of the present disclosure (i.e., C10-40 fatty acids esterified with C10-40 fatty alcohols). Non-limiting examples of esters useful in the pharmaceutical compositions of the present disclosure include without limitation those selected from the group consisting of diisopropyl adipate, isopropyl myristate, isopropyl palmitate, myristyl propionate, ethylene glycol distearate, 2-ethylhexyl palmitate, isodecyl neopentanoate, C12-15 alcohol benzoate, di-2-ethylhexyl maleate, ceryl palmitate, myristyl myristate, stearyl stearate, cetyl stearate, behenyl behenrate, and mixtures thereof.

Examples of silicone emollients useful in the pharmaceutical compositions of the present disclosure include without limitation polyalkylsiloxanes, cyclic polyalkylsiloxanes, and polyalkylarylsiloxanes. Suitable commercially available polyalkylsiloxanes include the polydimethylsiloxanes, which are also known as dimethicones, non-limiting examples of which include the Vicasil™ series sold by General Electric Company and the Dow Corning™ 200 series sold by Dow Corning Corporation. Commercially available polyalkylsiloxanes include cyclomethicones (Dow Corning™ 244 fluid), Dow Corning™ 344 fluid, Dow Corning™ 245 fluid and Dow Corning™ 345), among others. A suitable commercially available trimethylsiloxysilicate is sold as a mixture with dimethicone as Dow Corning™ 593 fluid. Also useful in the pharmaceutical compositions of the present disclosure are dimethiconols, which are hydroxyl terminated dimethyl silicones. Suitable commercially available dimethiconols are typically sold as mixtures with dimethicone or cyclomethicone (e.g., Dow Corning™ 1401, 1402, and 1403 fluids). Suitable commercially available polyalkylarylsiloxanes include SF1075 methylphenyl fluid (sold by General Electric Company) and 556 Cosmetic Grade phenyl trimethicone fluid (sold by Dow Corning Corporation).

Hydrocarbons suitable for use in the pharmaceutical compositions of the present disclosure include without limitation straight and branched chain hydrocarbons having from about 10 to about 30 carbon atoms. In some embodiments, the straight and branched chain hydrocarbons have from about 12 to about 24 carbon atoms. In some embodiments, the straight and branched chain hydrocarbons have from about 16 to about 22 carbon atoms. Non-limiting examples of such hydrocarbon materials include dodecane, squalane, cholesterol, 5 hydrogenated polyisobutylene, docosane (i.e., a C22 hydrocarbon), hexadecane, and isohexadecane (a commercially available hydrocarbon sold as Permethyl™ 101A by Presperse, South plainfield, N.J.), among others.

In some embodiments, the topical pharmaceutical compositions of the present disclosure include propylene glycol. In some embodiments, propylene glycol acts as a surfactant and assists in penetration, contact, and absorption of a compound of the present disclosure. In some embodiments, propylene glycol serves as a preservative. In some embodiments, the pharmaceutical compositions of the present disclosure include a non-ionic surfactant, such as, for example, polysorbate. Such a surfactant provides better surface contact of the pharmaceutical compositions of the present disclosure with mucosa (such as vaginal mucosa) by further reducing surface tension.

The topical pharmaceutical compositions of the present disclosure optionally may also be formulated with a lipophilic phase, such as, for example, emulsions and liposome dispersions. In some embodiments, liposomal formulations may extend circulation time of a compound of the present disclosure, increase permeability of a compound of the present disclosure, and improve overall efficacy of a compound of the present disclosure as an antimicrobial. In some embodiments, a compound of the present disclosure may be combined with a lipid, cationic lipid or anionic lipid. In some embodiments, the resulting emulsion or liposomal suspension in conjunction with the pH stabilizing qualities of a compound of the present disclosure can effectively increase the in vivo half-life of the activity of a pharmaceutical composition of the present disclosure. Examples of suitable anionic lipids for use with the pharmaceutical compositions of the present disclosure include, but are not limited to, cardiolipin, dimyristoyl, dipalmitoyl, dioleoyl phosphatidyl choline, phosphatidyl glycerol, palmitoyloleoyl phosphatidyl choline, phosphatidyl glycerol, phosphatidic acid, lysophosphatidic acid, phosphatidyl serine, phosphatidyl inositol, and anionic forms of cholesterol.

In some embodiments, a compound of the present disclosure is incorporated into liposomes. In some embodiments, neutral lipids, cholesterol, and/or polyethylene glycol (PEG) are utilized in such liposomes. In some embodiments, the liposomal composition is composed of partially hydrogenated soy phosphatidylcholine (PHSC), cholesterol, methoxy-terminated PEG (mPEG), and/or distearoyl phosphatidyl ethanolamine (DSPE). The liposomes can be prepared according to any suitable method known in the art.

In some embodiments, topical administration is through nasal sprays or suppositories (rectal or vaginal). Suppositories are prepared by mixing a compound of the present disclosure with a lipid vehicle such as *Theobroma* oil, cacao butter, glycerin, gelatin, polyoxyethylene glycols, and the like. In some embodiments, topical administration comprises a transdermal patch or dressing such as a bandage impregnated with a compound of the present disclosure and optionally one or more carriers, excipients or diluents known in the art. In some embodiments, such dressings include without limitation semipermeable films, foams, hydrocolloids, and calcium alginate swabs. In some embodiments, the dosage administration will be continuous rather than intermittent throughout the dosage regimen.

In some embodiments, the pharmaceutical compositions of the present disclosure are adapted for oral administration. As used herein, the term "oral administration" refers to administration of a compound of the present disclosure to the mouth of a patient for ingestion into the gastrointestinal tract. In some embodiments, the pharmaceutical compositions of the present disclosure can be formulated into conventional oral dosage forms including without limitation capsules, tablets, powders, and liquid preparations such as suspensions, solutions, elixirs, syrups, concentrated drops, and the like. In some embodiments, a compound of the present disclosure may be combined with solid excipients, optionally grinding a resulting mixture, and optionally processing the mixture of granules, after adding suitable auxiliaries, if desired, to obtain, for example, tablets, coated tablets, hard capsules, soft capsules, solutions (e.g., aqueous, alcoholic or oily solutions), and the like. In some embodiments, excipients suitable for use in the oral pharmaceutical compositions of the present disclosure include without limitation fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropyl-methyl-cellulose, sodium carboxymethylcellulose (CMC), and/or polyvinylpyrrolidone (PVP or povidone); and oily excipients, including vegetable and animal oils, such as sunflower oil, olive oil, or cod liver oil. In some embodiments, the oral pharmaceutical compositions of the present disclosure may also contain disintegrating agents, such as, for example, cross-linked polyvinylpyrrolidone, agar, or alginic acid, or a salt thereof such as sodium alginate; a lubricant, such as talc or magnesium stearate; a plasticizer, such as glycerol or sorbitol; a sweetening agent such as sucrose, fructose, lactose, or aspartame; a natural or artificial flavoring agent, such as, for example, peppermint, oil of wintergreen, or cherry flavoring; or dye-stuffs or pigments, which may be used for identification or characterization of different doses or combinations. In some embodiments, the oral pharmaceutical compositions of the present disclosure may also contain dragée cores with suitable coatings. In some embodiments, concentrated sugar solutions may be used, which may optionally contain, for example, gum arabic, talc, poly-vinylpyrrolidone, carbopol gel, polyethylene glycol, titanium dioxide, lacquer solutions, and suitable organic solvents or solvent mixtures.

In some embodiments, the pharmaceutical compositions of the present disclosure that can be used orally include without limitation push-fit capsules made of gelatin ("gelcaps"), as well as soft, sealed capsules made of gelatin, and a plasticizer, such as glycerol or sorbitol. In some embodiments, the push-fit capsules can contain a compound of the present disclosure in admixture with filler such as lactose, binders such as starches, and/or lubricants such as talc or magnesium stearate and, optionally, stabilizers. In some embodiments including soft capsules, the active compound may be dissolved or suspended in suitable liquids, such as fatty oils, liquid paraffin, liquid polyethylene glycols, and the like.

In some embodiments, the pharmaceutical compositions of the present disclosure are adapted for inhalation administration. As used herein, the term "inhalation administration" refers to delivery of a compound of the present disclosure by passage through a patient's nose or mouth during inhalation and passage of the compound through the walls of the lungs of the patient. In some embodiments, the pharmaceutical compositions of the present disclosure suitable for inhalation administration may be formulated as dry powder or a suitable solution, suspension or aerosol. In some embodiments, powders and solutions may be formulated with suitable additives known in the art. In some embodiments, powders may include a suitable powder base such as lactose or starch. In some embodiments, solutions may comprise propylene glycol, sterile water, ethanol, sodium chloride, and other additives, such as, for example, acid, alkali, and buffer salts.

In some embodiments, such solutions or suspensions may be administered by inhaling via a spray, pump, atomizer, nebulizer, and the like. In some embodiments, the pharmaceutical compositions of the present disclosure suitable for inhalation administration may also be used in combination with other inhaled therapies, including without limitation corticosteroids such as, for example, fluticasone proprionate, beclomethasone dipropionate, triamcinolone acetonide, budesonide, and mometasone furoate; beta agonists such as, for example, albuterol, salmeterol, and formoterol; anticholinergic agents such as, for example, ipratroprium bromide or tiotropium; vasodilators such as, for example, treprostinal and iloprost; enzymes such as, for example, DNAase; therapeutic proteins; immunoglobulin antibodies; an oligonucleotide, such as, for example, single or double stranded DNA or RNA, siRNA; antibiotics such as, for example, tobramycin; muscarinic receptor antagonists; leukotriene antagonists; cytokine antagonists; protease inhibitors; cromolyn sodium; nedocril sodium; and sodium cromoglycate.

In some embodiments, the pharmaceutical compositions of the present disclosure are adapted for intravesical administration. As used herein, the term "intravesical administration" refers to delivery of a compound of the present disclosure directly into the bladder of a patient. In some embodiments, the pharmaceutical composition is administered via a catheter. In some embodiments, the catheter is a urethral catheter.

In some embodiments, the pharmaceutical compositions of the present disclosure are adapted for parenteral administration. As used herein, the term "parenteral administration" refers to a compound of the present disclosure being injected or infused into a patient and includes without limitation intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In some embodiments, the pharmaceutical compositions of the present disclosure suitable for parenteral administration may be formulated in sterile liquid solutions, including without limitation physiologically compatible buffers or solutions, such as, for example, saline solution, Hank's solution or Ringer's solution. In some embodiments, the pharmaceutical compositions of the present disclosure suitable for parenteral administration may be prepared as dispersions in non-aqueous solutions, such as, for example, glycerol, propylene glycol, ethanol, liquid polyethylene glycols, triacetin, vegetable oils, and the like. In some embodiments, solutions may also contain a preservative, such as, for example, methylparaben, propylparaben, chlorobutanol, phenol, sorbic acid, thimerosal, and the like. In addition, pharmaceutical compositions of the present disclosure suitable for parenteral administration may be formulated in solid form, including, for example, lyophilized forms, and redissolved or suspended prior to use. In some embodiments, the pharmaceutical composition is administered via a needle.

In some embodiments, the present disclosure provides methods and compositions of pretreating a catheter with a compound of the present disclosure, for example, to prevent an infection after the catheter is inserted into a patient. In some embodiments, a method of the present disclosure includes coating a catheter with a compound of the present disclosure prior to inserting the catheter into a patient. In some embodiments, the present disclosure provides a composition comprising a catheter coated with a compound of the present disclosure. In some embodiments, such methods and compositions may be used as a prophylactic treatment of an infection in a patient.

The present disclosure also provides methods of treatment. As used herein, the terms "treating," "treatment," "therapy," and like terms refer to administration of a compound or pharmaceutical composition of the present disclosure in an amount effective to prevent, alleviate or ameliorate one or more symptoms of a disease or condition (i.e., indication) and/or to prolong the survival of the patient being treated. In some embodiments, "treating," "treatment," "therapy," and like terms also include without limitation reducing or eliminating infection in a patient.

In carrying out the methods of the present disclosure, an effective amount of a compound of the present disclosure is administered to a patient in need thereof. As used herein, the term "effective amount," in the context of administration, refers to the amount of a compound or pharmaceutical composition of the present disclosure that when administered to a patient is sufficient to prevent, alleviate or ameliorate one or more symptoms of a disease or condition (i.e., indication) and/or to prolong the survival of the patient being treated. Such an amount should result in no or few adverse events in the treated patient. Similarly, such an amount should result in no or few toxic effects in the treated patient. As those familiar with the art will understand, the amount of a compound or pharmaceutical composition of the present disclosure will vary depending upon a number of factors, including without limitation the activity of a compound of the present disclosure (in vitro, e.g. a compound of the present disclosure vs. target, or in vivo activity in animal efficacy models), pharmacokinetic results in animal models (e.g., biological half-life or bioavailability), the type of patient being treated, the patient's age, size, weight, and general physical condition, the disorder associated with the patient, and the dosing regimen being employed in the treatment.

In some embodiments of the present disclosure, an effective amount of a compound of the present disclosure to be delivered to a patient in need thereof can be quantified by determining micrograms of a compound of the present disclosure per kilogram of patient body weight. In some embodiments, the amount of a compound of the present disclosure administered to a patient is from about 0.1 to about 1000 milligram (mg) of a compound of the present disclosure per kilogram (kg) of patient body weight. In some embodiments, the amount of a compound of the present disclosure administered to a patient is from about 0.1 to about 500 mg of a compound of the present disclosure per kg of patient body weight. In some embodiments, the amount of a compound of the present disclosure administered to a patient is from about 0.1 to about 300 mg of a compound of the present disclosure per kg of patient body weight. In some embodiments, the amount of a compound of the present disclosure administered to a patient is from about 0.1 to about 200 mg of a compound of the present disclosure per kg of patient body weight. In some embodiments, the amount of a compound of the present disclosure administered to a patient is from about 0.1 to about 100 mg of a compound of the present disclosure per kg of patient body weight. As those of ordinary skill in the art understand multiple doses may be used. In some embodiments of the present disclosure, a compound of the present disclosure is administered as a multiple dose regimen. As used herein, the term "multiple dose regimen" refers to a treatment time period of more than one day. In some embodiments of the present disclosure, the multiple dose regimen is a time period of up to about 2 days. In some embodiments of the present disclosure, the multiple dose regimen is a time period of up to about 3 days. In some embodiments of the present disclosure, the multiple dose regimen is a time period of up to about 4 days. In some embodiments of the present disclosure, the multiple dose regimen is a time period of up to about 5 days. In some embodiments of the present disclosure, the multiple dose regimen is a time period of up to about 6 days. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about one month. In some embodiments of the present disclosure, the multiple dose regimen is a time period of up to about two months. In some embodiments of the present disclosure, the multiple dose regimen is a time period of up to about three months. In some embodiments of the present disclosure, the multiple dose regimen is a time period of up to about four months. In some embodiments of the present disclosure, the multiple dose regimen is a time period of up to about five months. In some embodiments of the present disclosure, the multiple dose regimen is a time period of up to about six months. Other time periods may be used herein.

In some embodiments of the present disclosure, a compound of the present disclosure is administered as part of a chronic treatment regimen. As used herein, the term "chronic treatment regimen" refers to treatment with a compound of the present disclosure over an extended period of time during a patient's lifetime. In some embodiments, chronic treatment is lifelong treatment.

In some embodiments of the present disclosure, a compound of the present disclosure is administered as a single dose. In some embodiments of the present disclosure, a compound of the present disclosure is administered as a single unit dose. As used herein, the term "unit dose" is a predetermined amount of a compound of the present disclosure. The amount of a compound of the present disclosure is generally equal to the dosage of a compound of the present disclosure that would be administered to a patient or a convenient fraction of such a dosage such as, for example, one-half or one-third of such a dosage. According to the methods of the present disclosure, the terms "single dose" and "single unit dose" include embodiments wherein the composition can be administered as a single application and administered as multiple applications.

In some embodiment, a compound of the present disclosure may also be used in combination with one or more additional active ingredients for treating the same disease or condition. In some embodiments, such combination use includes administration of a compound of the present disclosure and one or more additional active ingredient at different times, or co-administration of a compound of the present disclosure and one or more additional active ingredients. In some embodiments, dosage may be modified for a compound of the present disclosure or one or more additional active ingredients used in combination, e.g., reduction in the amount dosed relative to a compound of the present disclosure or one or more additional active ingredients used alone, by methods well known to those of ordinary skill in the art. In some embodiments, co-administration includes simultaneous administration of a compound of the present disclosure and an additional active ingredient in the same dosage form, simultaneous administration of a compound of the present disclosure and an additional active ingredient in separate dosage forms, and separate administration of a compound of the present disclosure and an additional active ingredient.

It is understood that use in combination includes use with one or more additional active ingredients or other medical procedure in which the one or more additional active ingredients or other medical procedure may be administered at different times (e.g., within a short time, such as within hours (e.g., 1, 2, 3, 4-24 hours, etc.), or within a longer time (e.g. 1-2 days, 2-4 days, 4-7 days, 1-4 weeks, etc.)) than a compound or pharmaceutical composition of the present disclosure, or at the same time as a compound or pharmaceutical composition of the present disclosure. Use in combination also includes use with one or more additional active ingredients or other medical procedure that is administered once or infrequently, such as surgery, along with a compound or pharmaceutical composition of the present disclosure administered within a short time or longer time before or after the administration of the one or more additional active ingredients or completion of the other medical procedure.

In some embodiments, the present disclosure provides for delivery of a compound or pharmaceutical composition of the present disclosure and one or more additional active ingredients delivered by a different route of administration or by the same route of administration. In some embodiments, the use in combination for any route of administration includes delivery of a compound or pharmaceutical composition of the present disclosure and one or more additional active ingredients delivered by the same route of administration together in any pharmaceutical composition, including pharmaceutical compositions in which the two compounds are chemically linked in such a way that such compounds maintain their therapeutic activity when administered. In some embodiments, the one or more additional active ingredients may be co-administered with a compound or pharmaceutical composition of the present disclosure. In some embodiments, use in combination by co-administration includes administration of co-formulations or formulations of chemically joined compounds, or administration of two or more compounds in separate formulations within a short time of each other (e.g., within an hour, 2 hours, 3 hours, up to 24 hours, etc.), administered by the same or different routes. In some embodiments, co-administration of separate formulations includes co-administration by delivery via one device, for example, the same inhalant device, the same syringe, etc., or administration from separate devices within a short time of each other. In some embodiments, co-formulations of a compound or pharmaceutical composition of the present disclosure and one or more additional active ingredients delivered by the same route includes preparation of the materials together such that they can be administered by one device, including the separate compounds combined in one formulation, or compounds that are modified such that the compounds are chemically joined, yet still maintain their biological activity. In some embodiments, such chemically joined compounds may have a linkage that is substantially maintained in vivo, or the linkage may break down in vivo, separating the two active components.

The present disclosure also provides a method of treating an infection in a patient in need thereof. In some embodiments, the method comprises administering an effective amount of a compound of the present disclosure, or a pharmaceutically acceptable salt thereof, to the patient. As used herein, the term "infection" refers to any microbe infection of a patient's body. Infection includes the invasion of a patient's body by a microbe and subsequent multiplication in the patient's body.

The present disclosure also provides a method of treating an infection of a lower extremity ulcer in a patient in need thereof. In some embodiments, the method comprises administering an effective amount of a compound of the present disclosure, or a pharmaceutically acceptable salt thereof, to the patient. As used herein, the term "infection" refers to any microbe infection of a patient's body. Infection includes the invasion of a patient's body by a microbe and subsequent multiplication in the patient's body. As used herein, the term "lower extremity" refers to a lower limb of a patient's body, including without limitation the hip, thigh, leg, ankle, and foot. As used herein, the term "ulcer" refers to an open wound found anywhere on the lower extremity of a patient.

In some embodiments, the present disclosure provides a method of treating an infection of a diabetic foot ulcer in a patient in need thereof. In some embodiments, the method comprises administering an effective amount of a compound of the present disclosure, or a pharmaceutically acceptable salt thereof, to the patient. In some embodiments, the patient is suffering from Type I diabetes or Type II diabetes. As used herein, the term "diabetic foot ulcer" refers to an open wound located anywhere on the foot of a patient. In some embodiments, the wound is located on the heel, mid-foot, and/or forefoot of the patient's foot. As used herein, the term "treating," in the context of a diabetic foot ulcer, also includes without limitation reducing or eliminating infection in a patient, which, in some embodiments, results in limiting the progression in size, area, and/or depth of the foot ulcer; reducing the size, area, and/or depth of the foot ulcer; increasing the rate of healing and/or reducing time to healing; healing of the foot ulcer (about 100% epithelialization with no drainage); and/or decreased incidence of amputation or slowing in time to amputation.

In some embodiments, the patient is a human. In some embodiments, the administration is topical administration. In some embodiments, the administration is carried out using the compound, or a pharmaceutically acceptable salt thereof, in a lotion, paste, gel, cream, ointment, oil or other viscous composition. In some embodiments, the patient is administered at least one additional active ingredient. In some embodiments, the administration is carried out as a multiple dose regimen. In some embodiments, the multiple dose regimen is a time period of up to about one month. In some embodiments of the present disclosure, the multiple dose regimen is a time period of up to about two months. In some embodiments of the present disclosure, the multiple dose regimen is a time period of up to about three months. In some embodiments of the present disclosure, the multiple dose regimen is a time period of up to about four months. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a method of treating a urinary tract infection in a patient in need thereof. In some embodiments, the method comprises administering an effective amount of a compound of the present disclosure, or a pharmaceutically acceptable salt thereof, to the patient. As used herein, the term "urinary tract" refers to the organs of a patient's body that produce, store, and discharge urine and includes without limitation the kidneys, ureters, bladder, and urethra. As used herein, the term "urinary tract infection" refers to an infection of the urinary tract of a patient and includes without limitation an uncomplicated urinary tract infection and a complicated urinary tract infection. As used herein, the term "uncomplicated urinary tract infection" refers to an infection by a microbe of a structurally and functionally normal urinary tract of a patient. As used herein, the term "complicated urinary tract infection" refers to an infection by a microbe of an abnormal structural and functional urinary tract of a patient. In some embodiments, the complicated urinary tract infection is a catheter-associated urinary tract infection. As used herein, the term "catheter-associated urinary tract infection" refers to a complicated urinary tract infection that occurs in a patient having an indwelling urinary catheter.

In some embodiments, the patient is a human. In some embodiments, the administration is intravesical administration. In some embodiments, the administration is carried out using a compound of the present disclosure, or a pharmaceutically acceptable salt thereof, in a liquid solution or suspension. In some embodiments, the patient is administered at least one additional active ingredient. In some embodiments, the administration is carried out as a multiple dose regimen. In some embodiments of the present disclosure, the multiple dose regimen is a time period of up to about 2 days. In some embodiments of the present disclosure, the multiple dose regimen is a time period of up to about 3 days. In some embodiments of the present disclosure, the multiple dose regimen is a time period of up to about 4 days. In some embodiments of the present disclosure, the multiple dose regimen is a time period of up to about 5 days. In some embodiments of the present disclosure, the multiple dose regimen is a time period of up to about 6 days. In some embodiments of the present disclosure, the multiple dose regimen is a time period of up to about 7 days. In some embodiments of the present disclosure, the multiple dose regimen is a time period of up to about 14 days. In some embodiments of the present disclosure, the administration is carried out as a chronic treatment regimen. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a method of treating a lung infection in a patient in need thereof. In some embodiments, the method comprises administering an effective amount of a compound of the present disclosure, or a pharmaceutically acceptable salt thereof, to the patient. As used herein, the term "lung infection" refers to an infection of one or both of a patient's lungs. In some embodiments, the lung infection arises from a pulmonary condition. As used herein, the term "pulmonary condition" refers to both infection and non-infection induced disease and dysfunction of the respiratory system.

Non-limiting examples of pulmonary conditions include without limitation genetic conditions, acquired conditions, primary conditions, secondary conditions, asthma, chronic obstructive pulmonary disease, cystic fibrosis, bronchiolitis, pneumonia, bronchitis, emphysema, adult respiratory distress syndrome, allergies, lung cancer, small cell lung cancer, primary lung cancer, metastatic lung cancer, bronchiestasis, bronchopulmonary dysplasia, chronic bronchitis, chronic lower respiratory diseases, croup, high altitude pulmonary edema, pulmonary fibrosis, interstitial lung disease, reactive airway disease, lymphangioleiomyomatosis, neonatal respiratory distress syndrome, parainfluenza, pleural effusion, pleurisy, pneumothorax, primary pulmonary hypertension, psittacosis, pulmonary edema secondary to various causes, pulmonary embolism, pulmonary hypertension secondary to various causes, respiratory failure secondary to various causes, sleep apnea, sarcoidosis, smoking, stridor, acute respiratory distress syndrome, infectious diseases, SARS, tuberculosis, psittacosis infection, Q fever, parainfluenza, respiratory syncytial virus, combinations thereof, and conditions caused by any one or combination of the above.

In some embodiments of the present disclosure, a method of treating a lung infection arising from cystic fibrosis in a patient in need thereof is provided. In some embodiments, the method comprises administering an effective amount of a compound of the present disclosure, or a pharmaceutically acceptable salt thereof, to the patient. As used herein, the term "cystic fibrosis" refers to a genetic disease that causes the production of abnormally thick mucus resulting in lung infections and damage to the lungs, digestive system, and other organs in a patient's body.

In some embodiments, the administration is inhalation administration. In some embodiments, the patient is administered at least one additional active ingredient. In some embodiments, the patient is a human. In some embodiments, the administration is carried out using a compound of the present disclosure, or a pharmaceutically acceptable salt thereof, in a liquid solution, suspension or dry powder. In some embodiments, the administration is carried out as a multiple dose regimen. In some embodiments, the multiple dose regimen is a time period of up to about one month. In some embodiments of the present disclosure, the multiple dose regimen is a time period of up to about two months. In some embodiments of the present disclosure, the multiple dose regimen is a time period of up to about three months. In some embodiments of the present disclosure, the multiple dose regimen is a time period of up to about four months. In some embodiments of the present disclosure, the multiple dose regimen is a time period of up to about five months. In some embodiments of the present disclosure, the multiple dose regimen is a time period of up to about six months. In some embodiments of the present disclosure, the multiple dose regimen is a time period of up to about seven months.

In some embodiments of the present disclosure, the multiple dose regimen is a time period of up to about eight months. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

In some embodiments of the present disclosure, a method of treating pneumonia in a patient in need thereof is provided. In some embodiments, the method comprises administering an effective amount of a compound of the present disclosure, or a pharmaceutically acceptable salt thereof, to the patient. As used herein, the term "pneumonia" refers to an infection by a microbe of one or both lungs of a patient resulting in inflammation of lung tissue. In some embodiments, the pneumonia is ventilator acquired pneumonia. As used herein, the term "ventilator acquired pneumonia" refers to pneumonia arising from a patient being connected to a mechanical ventilation machine. Ventilator acquired pneumonia includes pneumonia occurring more than about 48 hours after a patient has been intubated and received mechanical ventilation.

In some embodiments, the administration is inhalation administration. In some embodiments, the patient is administered at least one additional active ingredient. In some embodiments, the patient is a human. In some embodiments, the administration is carried out using a compound of the present disclosure, or a pharmaceutically acceptable salt thereof, in a liquid solution, suspension or dry powder. In some embodiments, the administration is carried out as a multiple dose regimen. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about 21 days. In some embodiments, the multiple dose regimen is a time period of up to about one month. In some embodiments of the present disclosure, the multiple dose regimen is a time period of up to about two months. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a method of treating an infection in a burn wound in a patient in need thereof. In some embodiments, the method comprises administering an effective amount of a compound of the present disclosure, or a pharmaceutically acceptable salt thereof, to the patient. As used herein, the term "burn wound" refers to a burn injury to a patient's body involving damage to a patient's skin and possibly tissues underlying the patient's skin. There are three primary types of burn levels known to one of skill in the art, including without limitation first-, second-, and third-degree burns. In some embodiments, the method of treating an infection in a burn wound contemplated by the present disclosure is used to treat a first-, second-, and/or third-degree burn.

In some embodiments, the patient is a human. In some embodiments, the administration is topical administration.

In some embodiments, the administration is carried out using a compound of the present disclosure, or a pharmaceutically acceptable salt thereof, in lotion, cream, ointment, oil, solution, suspension, emulsion or other viscous composition. In some embodiments, the patient is administered at least one additional active ingredient. In some embodiments, the administration is carried out as a multiple dose regimen. In some embodiments of the present disclosure, the multiple dose regimen is a time period of up to about 2 days. In some embodiments of the present disclosure, the multiple dose regimen is a time period of up to about 3 days. In some embodiments of the present disclosure, the multiple dose regimen is a time period of up to about 4 days. In some embodiments of the present disclosure, the multiple dose regimen is a time period of up to about 5 days. In some embodiments of the present disclosure, the multiple dose regimen is a time period of up to about 6 days. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about 21 days. In some embodiments, the multiple dose regimen is a time period of up to about one month. In some embodiments, the multiple dose regimen is a time period of up to about two months. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a method of treating otitis externa in a patient in need thereof. In some embodiments, the method comprises administering an effective amount of a compound of the present disclosure, or a pharmaceutically acceptable salt thereof, to the patient. As used herein, the term "otitis externa" refers to an infection of the external ear canal of a patient.

In some embodiments, the patient is a human. In some embodiments, the administration is topical administration directly into the patient's external ear canal. In some embodiments, the administration is carried out using a compound of the present disclosure, or a pharmaceutically acceptable salt thereof, in a liquid solution, suspension, lotion, paste, gel, cream, ointment, oil or other viscous composition. In some embodiments, the patient is administered at least one additional active ingredient. In some embodiments, the administration is carried out as a multiple dose regimen. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about 21 days. In some embodiments, the multiple dose regimen is a time period of up to about one month. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a method of treating bacterial vaginosis in a patient in need thereof. In some embodiments, the method comprises administering an effective amount of a compound of the present disclosure, or a pharmaceutically acceptable salt thereof, to the patient. As used herein, the term "bacterial vaginosis" refers to an infection of the vagina of a patient caused by an overgrowth of bacteria naturally found in the vagina.

In some embodiments, the patient is a female human. In some embodiments, the administration is topical administration. In some embodiments, the administration is carried out using a compound of the present disclosure, or a pharmaceutically acceptable salt thereof, in a lotion, gel, cream, ointment, oil, solution, suspension, emulsion or other viscous composition. In some embodiments, the patient is administered at least one additional active ingredient. In some embodiments, the administration is carried out as a multiple dose regimen. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about 21 days. In some embodiments, the multiple dose regimen is a time period of up to about one month. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a method of treating impetigo in a patient in need thereof. In some embodiments, the method comprises administering an effective amount of a compound of the present disclosure, or a pharmaceutically acceptable salt thereof, to the patient. As used herein, the term "impetigo" refers an infection of the skin of a patient that results in vesicles, pustules, yellowish crusts, and the like.

In some embodiments, the patient is a human. In some embodiments, the administration is topical administration. In some embodiments, the administration is carried out using a compound of the present disclosure, or a pharmaceutically acceptable salt thereof, in a lotion, gel, cream, ointment, oil, solution, suspension, emulsion or other viscous composition. In some embodiments, the patient is administered at least one additional active ingredient. In some embodiments, the administration is carried out as a multiple dose regimen. In some embodiments of the present disclosure, the multiple dose regimen is a time period of up to about 2 days. In some embodiments of the present disclosure, the multiple dose regimen is a time period of up to about 3 days. In some embodiments of the present disclosure, the multiple dose regimen is a time period of up to about 4 days. In some embodiments of the present disclosure, the multiple dose regimen is a time period of up to about 5 days. In some embodiments of the present disclosure, the multiple dose regimen is a time period of up to about 6 days. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about 21 days. In some embodiments, the multiple dose regimen is a time period of up to about one month. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a method of treating oral mucositis in a patient in need thereof. In some embodiments, the method comprises administering an effective amount of a compound of the present disclosure, or a pharmaceutically acceptable salt thereof, to the patient. As used herein, the term "oral mucositis" refers to inflammation and ulceration in the mouth. Oral mucositis is a common complication experienced by patients receiving cancer chemotherapy or radiation treatment. Oral mucositis can lead to several problems, including pain, nutritional problems as a result of inability to eat, and increased risk of infection due to open sores in the mucosa. Oral mucositis may also have a significant effect on a cancer patient's quality of life and can limit the effectiveness of certain treatment options (i.e., requiring a reduction in subsequent chemotherapy doses). Oral mucositis is also a significant side effect of bone marrow transplantation.

In some embodiments, the patient is a human. In some embodiments, the administration is topical administration directly into the patient's oral cavity. In some embodiments, the administration is carried out using a compound of the present disclosure, or a pharmaceutically acceptable salt thereof, in a liquid solution, suspension, lotion, paste, gel, cream, ointment, oil or other viscous composition. In some embodiments, the administration is carried out using the compound of the present disclosure in a mouthwash. In some embodiments, the compound of the present disclosure is present in the pharmaceutical composition in an amount from about 1% to about 20% (weight/weight). In some embodiments, the compound of the present disclosure is present in the pharmaceutical composition in an amount from about 5% to about 15% (weight/weight). In some embodiments, the compound of the present disclosure is present in the pharmaceutical composition in an amount from about 30% to about 50% (weight/weight).

In some embodiments, the patient is administered at least one additional active ingredient. In some embodiments, the administration is carried out as a multiple dose regimen. In some embodiments of the present disclosure, the multiple dose regimen is a time period of up to about 7 days. In some embodiments of the present disclosure, the multiple dose regimen is a time period of up to about 14 days. In some embodiments of the present disclosure, the multiple dose regimen is a time period of up to about 21 days. In some embodiments, the multiple dose regimen is a time period of up to about one month. Other time periods may be used herein.

In some embodiments, the administration is carried out one or more times per day. In some embodiments, the administration is carried out one time per day. In some embodiments, the administration is carried out two times per day. In some embodiments, the administration is carried out three times per day. In some embodiments, the administration is carried out four times per day.

The present disclosure also provides a kit. In some embodiments, the kit comprises a compound according to the present disclosure, or a pharmaceutically acceptable salt thereof, or a pharmaceutical composition according to the present disclosure. As used herein, the term "kit" refers to any manufacture, such as, for example, a package, container, and the like, containing a compound according to the present disclosure, or a pharmaceutically acceptable salt thereof, or a pharmaceutical composition according to the present disclosure. In some embodiments, a compound according to the present disclosure, or a pharmaceutically acceptable salt thereof, or a pharmaceutical composition according to the present disclosure is packaged in a vial, bottle, tube, flask or patch, which may be further packaged within a box, envelope, bag, or the like. In some embodiments, a compound according to the present disclosure, or a pharmaceutically acceptable salt thereof, or a pharmaceutical composition according to the present disclosure is approved by the U.S. Food and Drug Administration or similar regulatory agency in the U.S. or a jurisdiction or territory outside the U.S. for administration to a patient. In some embodiments, the kit includes written instructions for use and/or other indication that a compound according to the present disclosure, or a pharmaceutically acceptable salt thereof, or a pharmaceutical composition according to the present disclosure is suitable or approved for administration to a patient. In some embodiments, a compound or composition of the present disclosure is packaged in unit dose or single unit dose form, such as, for example, single unit dose pills, capsules or the like. In some embodiments, the kit includes a dispenser.

The present disclosure also provides the use of a compound of the present disclosure, or a pharmaceutically acceptable salt thereof, for the manufacture of a medicament. As used herein, the term "medicament" refers to a pharmaceutical composition according to the present disclosure. In some embodiments, the pharmaceutical composition is contained in any manufacture, such as, for example, a package, container, and the like.

In addition to the aspects and embodiments described and provided elsewhere in the present disclosure, the following non-limiting list of embodiments are also contemplated.

1. A compound having the formula:

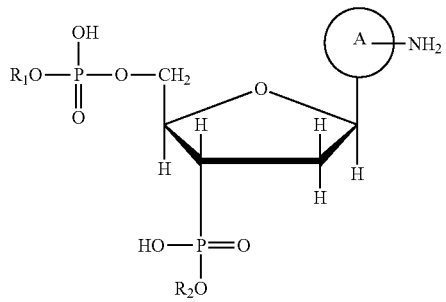

Formula (I)

wherein:

A is a monocyclic, bicyclic, or tricyclic carbocyclic or heterocyclic moiety, and $R_1$ and $R_2$ are each a $C_1$-$C_8$ alkyl moiety; or a pharmaceutically acceptable salt thereof.

2. The compound according to clause 1, wherein $R_1$ and $R_2$ are each butyl.

3. A compound having the formula:

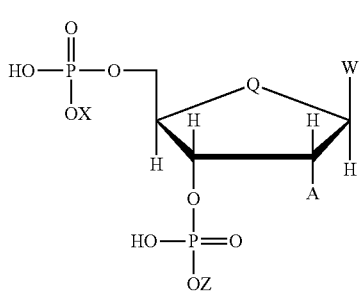

Formula (II)

wherein:

Q is oxygen or sulfur;

W is an amino-substituted or guanidino-substituted nitrogen containing heterocyclic moiety;

X and Z are end blocking groups; and

A is H, alkyl, halogen, alkoxy, alkyl-(O-alkyl), aryl, alkenyl, alkanol or phenol.

4. A compound according to clause 3, wherein W is:

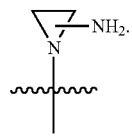

5. A compound according to clause 3, wherein W is:

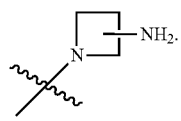

6. A compound according to clause 3, wherein W is:

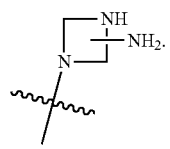

7. A compound according to clause 3, wherein W is:

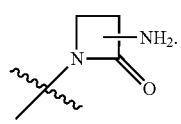

8. A compound according to clause 3, wherein W is:

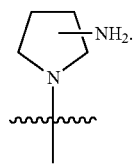

9. A compound according to clause 3, wherein W is:

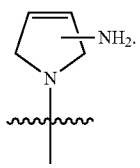

10. A compound according to clause 3, wherein W is:

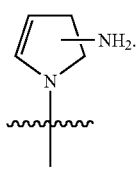

11. A compound according to clause 3, wherein W is:

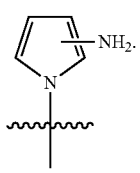

12. A compound according to clause 3, wherein W is:

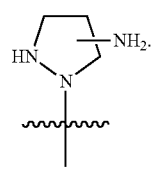

13. A compound according to clause 3, wherein W is:

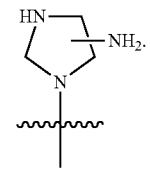

14. A compound according to clause 3, wherein W is:

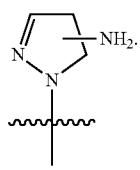

15. A compound according to clause 3, wherein W is:

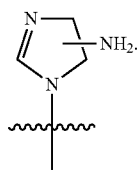

16. A compound according to clause 3, wherein W is:

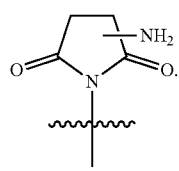

17. A compound according to clause 3, wherein W is:

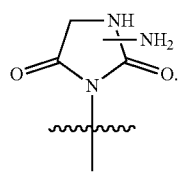

18. A compound according to clause 3, wherein W is:

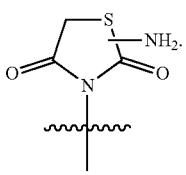

19. A compound according to clause 3, wherein W is:

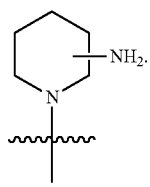

20. A compound according to clause 3, wherein W is:

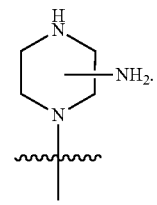

21. A compound according to clause 3, wherein W is:

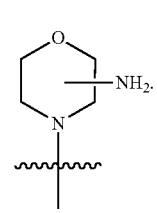

22. A compound according to clause 3, wherein W is:

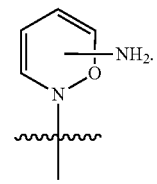

23. A compound according to clause 3, wherein W is:

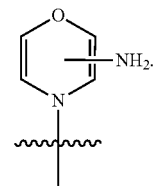

24. A compound according to clause 3, wherein W is:

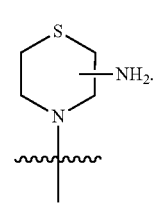

25. A compound according to clause 3, wherein W is:

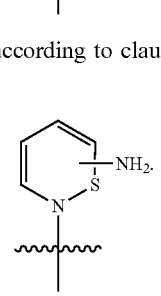

26. A compound according to clause 3, wherein W is:

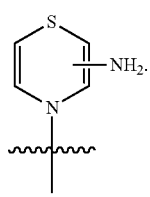

27. A compound according to clause 3, wherein W is:

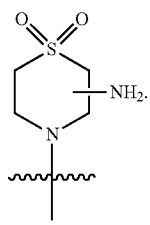

28. A compound according to clause 3, wherein W is:

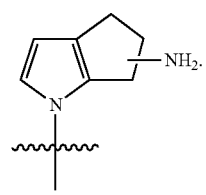

29. A compound according to clause 3, wherein W is:

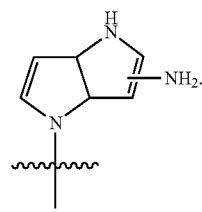

30. A compound according to clause 3, wherein W is:

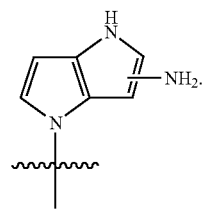

31. A compound according to clause 3, wherein W is:

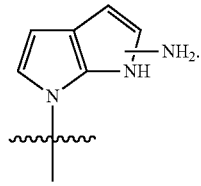

32. A compound according to clause 3, wherein W is:

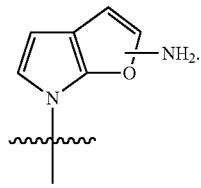

33. A compound according to clause 3, wherein W is:

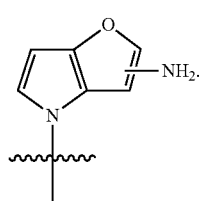

34. A compound according to clause 3, wherein W is:

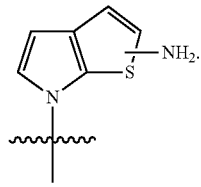

35. A compound according to clause 3, wherein W is:

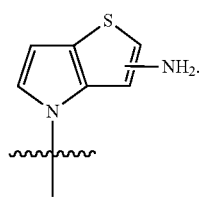

36. A compound according to clause 3, wherein W is:

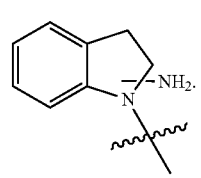

37. A compound according to clause 3, wherein W is:

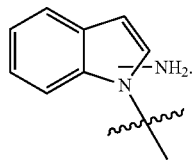

38. A compound according to clause 3, wherein W is:

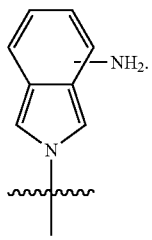

39. A compound according to clause 3, wherein W is:

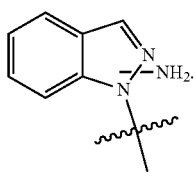

40. A compound according to clause 3, wherein W is:

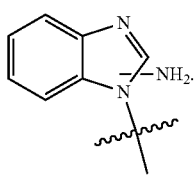

41. A compound according to clause 3, wherein W is:

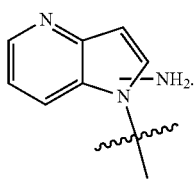

42. A compound according to clause 3, wherein W is:

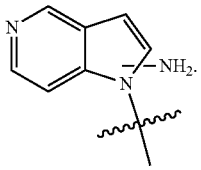

43. A compound according to clause 3, wherein W is:

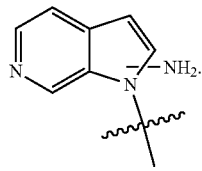

44. A compound according to clause 3, wherein W is:

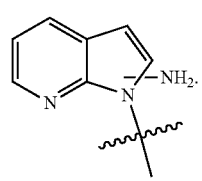

45. A compound according to clause 3, wherein W is:

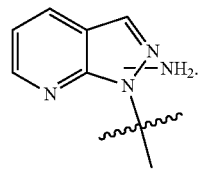

46. A compound according to clause 3, wherein W is:

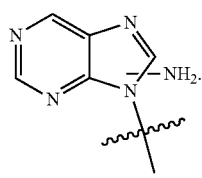

47. A compound according to clause 3, wherein W is:

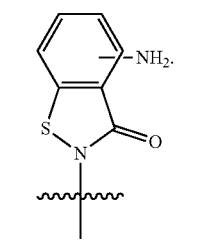

48. A compound according to clause 3, wherein W is:

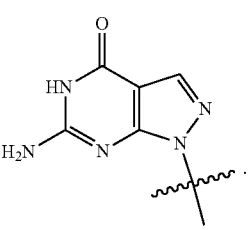 [SMILES: *n1ncc2c(=O)[nH]c(N)nc21]

49. A compound according to clause 3, wherein W is:

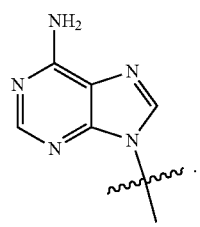 [SMILES: *n1cnc2c(N)ncnc21]

50. A compound according to clause 3, wherein W is:

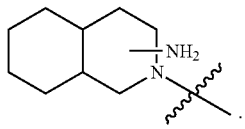

51. A compound according to clause 3, wherein W is:

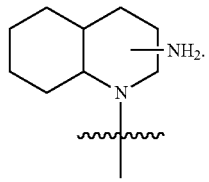

52. A compound according to clause 3, wherein W is:

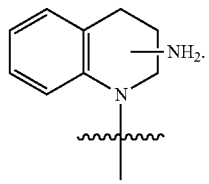

53. A compound according to clause 3, wherein W is:

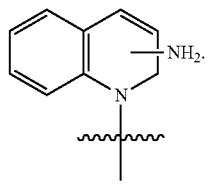

54. A compound according to clause 3, wherein W is:

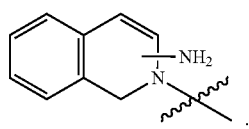

55. A compound according to clause 3, wherein W is:

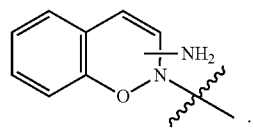

56. A compound according to clause 3, wherein W is:

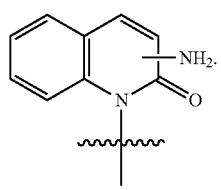

57. A compound according to clause 3, wherein W is:

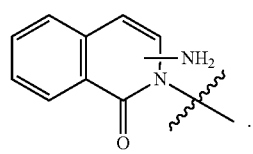

58. A compound according to clause 3, wherein W is:

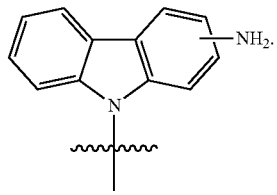

59. A compound according to clause 3, wherein W is:

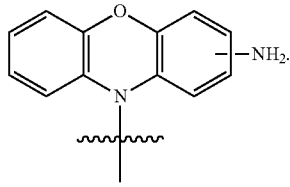

60. A compound according to clause 3, wherein W is:

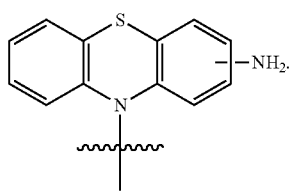

61. A compound according to clause 3, wherein W is:

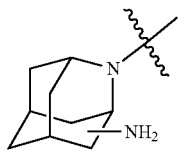

62. A compound according to clause 3, wherein W is:

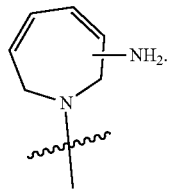

63. A compound according to clause 3, wherein W is:

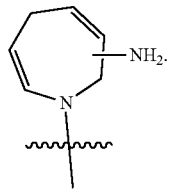

64. A compound according to clause 3, wherein W is:

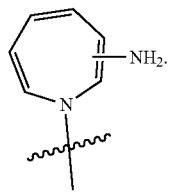

65. A compound according to clause 3, wherein W is:

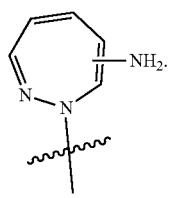

66. A compound according to clause 3, wherein W is:

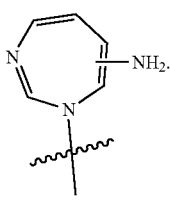

67. A compound according to clause 3, wherein W is:

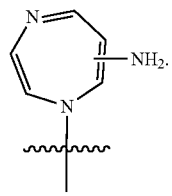

68. A compound according to clause 3, wherein W is:

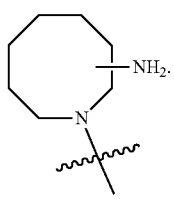

69. A compound according to clause 3, wherein W is a guanidino substituted aziridine.

70. A compound according to clause 3, wherein W is a guanidino substituted azetidine.

71. A compound according to clause 3, wherein W is a guanidino substituted 1,3-azetidine.

72. A compound according to clause 3, wherein W is a guanidino substituted azetidin-2-one (β-lactam).

73. A compound according to clause 3, wherein W is a guanidino substituted pyrrolidine.

74. A compound according to clause 3, wherein W is a guanidino substituted 3-pyrroline.

75. A compound according to clause 3, wherein W is a guanidino substituted 2-pyrroline.

76. A compound according to clause 3, wherein W is a guanidino substituted 1H-pyrrole.

77. A compound according to clause 3, wherein W is a guanidino substituted pyrazolidine.

78. A compound according to clause 3, wherein W is a guanidino substituted imidazolidine.

79. A compound according to clause 3, wherein W is a guanidino substituted 2-pyrazoline.

80. A compound according to clause 3, wherein W is a guanidino substituted 2-imidazoline.

81. A compound according to clause 3, wherein W is a guanidino substituted succinimide.

82. A compound according to clause 3, wherein W is a guanidino substituted hydantoin.

83. A compound according to clause 3, wherein W is a guanidino substituted 2,4-thiazolidinedione.

84. A compound according to clause 3, wherein W is a guanidino substituted piperidine.

85. A compound according to clause 3, wherein W is a guanidino substituted piperazine.

86. A compound according to clause 3, wherein W is a guanidino substituted morpholine.

87. A compound according to clause 3, wherein W is a guanidino substituted 2H-1,2-oxazdine.

88. A compound according to clause 3, wherein W is a guanidino substituted 4H-1,4-oxazdine.

89. A compound according to clause 3, wherein W is a guanidino substituted thiomorpholine.

90. A compound according to clause 3, wherein W is a guanidino substituted 2H-1,2-thiazine.

91. A compound according to clause 3, wherein W is a guanidino substituted 4H-1,4-thiazine.

92. A compound according to clause 3, wherein W is a guanidino substituted thiomorpholine dioxide.

93. A compound according to clause 3, wherein W is a guanidino substituted 1,4,5,6-tetrahydrocyclopenta[b]pyrrole.

94. A compound according to clause 3, wherein W is a guanidino substituted 1,3a,4,6a-tetrahydropyrrolo-[3,2-b]pyrrole. 95. A compound according to clause 3, wherein W is a guanidino substituted 1,4-dihydropyrolo-[3,2-b]pyrrole.

96. A compound according to clause 3, wherein W is a guanidino substituted 1,6-dihydropyrolo-[2,3,-b]pyrrole.

97. A compound according to clause 3, wherein W is a guanidino substituted 6H-furo[2,3-b]pyrrole.

98. A compound according to clause 3, wherein W is a guanidino substituted 4H-furo[3,2-b]pyrrole.

99. A compound according to clause 3, wherein W is a guanidino substituted 6H-thieno[2,3-b]pyrrole. 100. A compound according to clause 3, wherein W is a guanidino substituted 4H-thieno[3,2-b]pyrrole.

101. A compound according to clause 3, wherein W is a guanidino substituted indoline.

102. A compound according to clause 3, wherein W is a guanidino substituted 1H-indole.

103. A compound according to clause 3, wherein W is a guanidino substituted 2H-isoindole.

104. A compound according to clause 3, wherein W is a guanidino substituted 1H-indazole.

105. A compound according to clause 3, wherein W is a guanidino substituted benzimidazole.

106. A compound according to clause 3, wherein W is a guanidino substituted 4-azaindole.

107. A compound according to clause 3, wherein W is a guanidino substituted 5-azaindole.

108. A compound according to clause 3, wherein W is a guanidino substituted 6-azaindole.

109. A compound according to clause 3, wherein W is a guanidino substituted 7-azaindole.

110. A compound according to clause 3, wherein W is a guanidino substituted 7-azaindazole.

111. A compound according to clause 3, wherein W is a guanidino substituted purine.

112. A compound according to clause 3, wherein W is a guanidino substituted 1,2-benzoisothiazole-3(2H)-one.

113. A compound according to clause 3, wherein W is a guanidino substituted guanine.

114. A compound according to clause 3, wherein W is a guanidino substituted adenine.

115. A compound according to clause 3, wherein W is a guanidino substituted decahydroisoquinoline.

116. A compound according to clause 3, wherein W is a guanidino substituted decahydroquinoline.

117. A compound according to clause 3, wherein W is a guanidino substituted 1,2,3,4-tetrahydro-quinoline.

118. A compound according to clause 3, wherein W is a guanidino substituted 1,2-dihydroquinoline.

119. A compound according to clause 3, wherein W is a guanidino substituted 1,2-dihydroisoquinoline.

120. A compound according to clause 3, wherein W is a guanidino substituted 2H-benzo-[e][1,2]oxazine.

121. A compound according to clause 3, wherein W is a guanidino substituted quinolin 2(1H)-one.

122. A compound according to clause 3, wherein W is a guanidino substituted isoquinolin 1(2H)-one.

123. A compound according to clause 3, wherein W is a guanidino substituted carbazole.

124. A compound according to clause 3, wherein W is a guanidino substituted phenoxazine.

125. A compound according to clause 3, wherein W is a guanidino substituted phenothiazine.

126. A compound according to clause 3, wherein W is a guanidino substituted 2-azaadamantane.

127. A compound according to clause 3, wherein W is a guanidino substituted 2,3-dihydroazepine.

128. A compound according to clause 3, wherein W is a guanidino substituted 2,5-dihydroazepine.

129. A compound according to clause 3, wherein W is a guanidino substituted azepine.

130. A compound according to clause 3, wherein W is a guanidino substituted 1,2-azepine.

131. A compound according to clause 3, wherein W is a guanidino substituted 1,3-azepine.

132. A compound according to clause 3, wherein W is a guanidino substituted 1,4-azepine.

133. A compound according to clause 3, wherein W is a guanidino substituted azocane.

134. A compound according to any one of the clauses 3 to 133, wherein X is

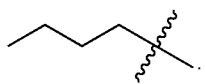 [SMILES: *CCCC]

135. A compound according to any one of the clauses 3 to 133, wherein X is

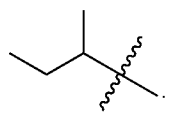

136. A compound according to any one of the clauses 3 to 133, wherein X is

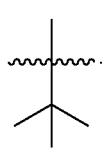 [SMILES: *C(C)(C)C]

137. A compound according to any one of the clauses 3 to 133, wherein X is

751

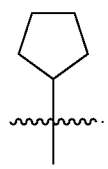

138. A compound according to any one of the clauses 3 to 133, wherein X is

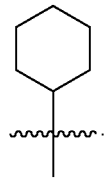

139. A compound according to any one of the clauses 3 to 133, wherein X is

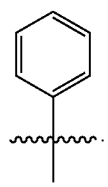

140. A compound according to any one of the clauses 3 to 133, wherein X is

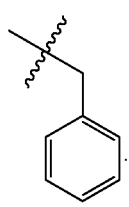

141. A compound according to any one of the clauses 3 to 133, wherein X is

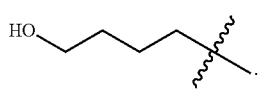

142. A compound according to any one of the clauses 3 to 133, wherein X is

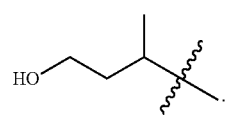

143. A compound according to any one of the clauses 3 to 133, wherein X is

752

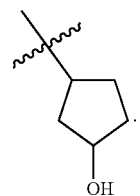 [SMILES: *C1CCC(O)C1]

144. A compound according to any one of the clauses 3 to 133, wherein X is

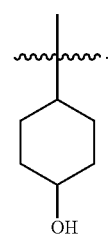

145. A compound according to any one of the clauses 3 to 133, wherein X is

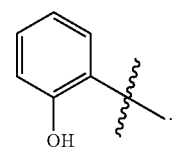

146. A compound according to any one of the clauses 3 to 133, wherein X is

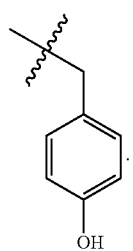

147. A compound according to any one of the clauses 3 to 146, wherein Z is

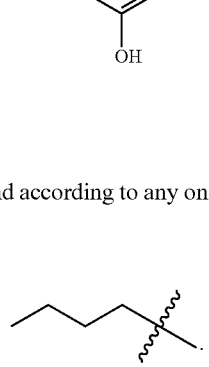

148. A compound according to any one of the clauses 3 to 146, wherein Z is

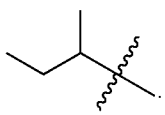 [SMILES: *C(C)CC]

149. A compound according to any one of the clauses 3 to 146, wherein Z is

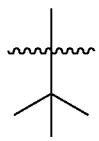

150. A compound according to any one of the clauses 3 to 146, wherein Z is

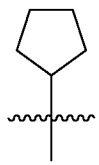

151. A compound according to any one of the clauses 3 to 146, wherein Z is

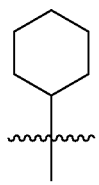

152. A compound according to any one of the clauses 3 to 146, wherein Z is

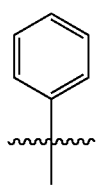

153. A compound according to any one of the clauses 3 to 146, wherein Z is

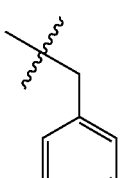

154. A compound according to any one of the clauses 3 to 146, wherein Z is

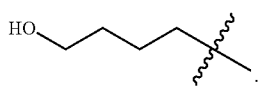

155. A compound according to any one of the clauses 3 to 146, wherein Z is

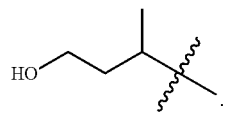

156. A compound according to any one of the clauses 3 to 146, wherein Z is

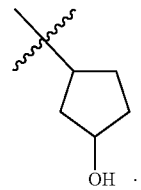 [SMILES: *C1CCC(O)C1]

157. A compound according to any one of the clauses 3 to 146, wherein Z is

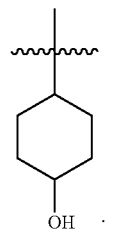 [SMILES: *C1CCC(O)CC1]

158. A compound according to any one of the clauses 3 to 146, wherein Z is

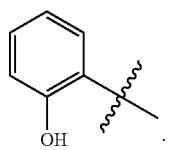 [SMILES: *c1ccccc1O]

159. A compound according to any one of the clauses 3 to 146, wherein Z is

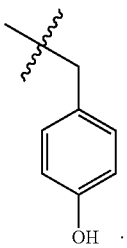 [SMILES: *Cc1ccc(O)cc1]

160. A compound selected from any one of Cmpds 1 to 2,520 as described in TABLE 1.

161. Cmpd 1 as described in TABLE 1. 162. The pharmaceutically acceptable salt of a compound according to clause 160 selected from the group consisting of an ammonium salt, a calcium salt, a sodium salt, a potassium salt, a magnesium salt, and a cobalt salt.

163. The pharmaceutically acceptable salt according to clause 162, wherein the ammonium salt is ammonium ((2R,3S,5R)-5-(4-amino-2-oxopyrimidin-1(2H)-yl)-3-((butoxyoxidophosphor-yl)oxy)tetrahydrofuran-2-yl)methyl butyl phosphate.

164. The pharmaceutically acceptable salt according to clause 162, wherein the calcium salt is calcium ((2R,3 S,5R)-5-(4-amino-2-oxopyrimidin-1(2H)-yl)-3-((butoxyoxidophosphor-yl)oxy)tetrahydrofuran-2-yl)methyl butyl phosphate.

165. The pharmaceutically acceptable salt according to clause 162, wherein the sodium salt is sodium ((2R,3 S,5R)-5-(4-amino-2-oxopyrimidin-1(2H)-yl)-3-((butoxyoxidophosphor-yl)oxy)tetrahydrofuran-2-yl)methyl butyl phosphate.

166. The pharmaceutically acceptable salt according to clause 162, wherein the potassium salt is potassium ((2R, 3S,5R)-5-(4-amino-2-oxopyrimidin-1(2H)-yl)-3-((butoxyoxidophosphor-yl)oxy)tetrahydrofuran-2-yl)methyl butyl phosphate.

167. The pharmaceutically acceptable salt according to clause 162, wherein the magnesium salt is magnesium ((2R,3 S,5R)-5-(4-amino-2-oxopyrimidin-1(2H)-yl)-3-((butoxyoxidophosphor-yl)oxy)tetrahydrofuran-2-yl)methyl butyl phosphate.

168. The pharmaceutically acceptable salt according to clause 162, wherein the cobalt salt is cobalt ((2R,3S,5R)-5-(4-amino-2-oxopyrimidin-1(2H)-yl)-3-((butoxyoxidophosphor-yl)oxy)tetrahydrofuran-2-yl)methyl butyl phosphate.

169. The compound according to clause 160, or a pharmaceutically acceptable salt thereof, wherein the compound, or a pharmaceutically acceptable salt thereof, is a protonated compound having a pH when dissolved in water of about pH 3 to about pH 5.

170. The compound according to clause 160, or a pharmaceutically acceptable salt thereof, wherein the compound, or a pharmaceutically acceptable salt thereof, is a protonated compound having a pH when dissolved in water of about pH 3 to about pH 4.

171. A pharmaceutical composition comprising a compound according to clause 160, or a pharmaceutically acceptable salt thereof, and one or more pharmaceutically acceptable carriers, excipients, or diluents.

172. The pharmaceutical composition of clause 171, wherein the pharmaceutical composition includes at least one additional active ingredient.

173. The pharmaceutical composition of clause 171 or clause 172, wherein the pharmaceutical composition is a human pharmaceutical composition.

174. The pharmaceutical composition of any one of clauses 171 to 173, wherein the pharmaceutical composition is adapted for topical administration.

175. The pharmaceutical composition of any one of clauses 171 to 174, wherein the pharmaceutical composition is administered in the form of a lotion, gel, cream, ointment, oil, solution, suspension, emulsion or other viscous composition.

176. The pharmaceutical composition of any one of clauses 171 to 175, wherein the pharmaceutical composition is administered in the form of a gel including a polyhydric alcohol.

177. The pharmaceutical composition of any one of clauses 171 to 173, wherein the pharmaceutical composition is adapted for oral administration.

178. The pharmaceutical composition of clause 177, wherein the pharmaceutical composition is administered in the form of a capsule, tablet, powder, liquid suspension, solution, elixir, syrup or concentrated drop.

179. The pharmaceutical composition of any one of clauses 171 to 173, wherein the pharmaceutical composition is adapted for inhalation administration.

180. The pharmaceutical composition of clause 179, wherein the pharmaceutical composition is administered in the form of a dry powder, solution, suspension or aerosol.

181. The pharmaceutical composition of any one of clauses 171 to 173, wherein the pharmaceutical composition is adapted for intravesical administration.

182. The pharmaceutical composition of clause 181, wherein the pharmaceutical composition is administered via a catheter.

183. The pharmaceutical composition of any one of clauses 171 to 173, wherein the pharmaceutical composition is adapted for parenteral administration.

184. The pharmaceutical composition of clause 183, wherein the pharmaceutical composition is administered via a needle.

185. A method of treating an infection of a diabetic foot ulcer in a patient in need thereof, the method comprising administering an effective amount of a compound according to clause 160, or a pharmaceutically acceptable salt thereof, to the patient.

186. The method of clause 185, wherein the administration is topical administration.

187. The method of clause 185 or clause 186, wherein the administration is carried out using the compound, or a pharmaceutically acceptable salt thereof, in a lotion, paste, gel, cream, ointment, oil or other viscous composition.

188. The method of any one of clauses 185 to 187, wherein the administration is carried out using the compound, or a pharmaceutically acceptable salt thereof, in a gel.

189. The method of any one of clauses 185 to 188, wherein the patient is administered at least one additional active ingredient.

190. The method of any one of clauses 185 to 189, wherein the patient is a human.

191. The method of any one of clauses 185 to 190, wherein the administration is carried out as a multiple dose regimen.

192. The method of clause 191, wherein the multiple dose regimen is a time period of up to about one month.

193. The method of clause 191, wherein the multiple dose regimen is a time period of up to about two months.

194. The method of clause 191, wherein the multiple dose regimen is a time period of up to about three months.

195. The method of clause 191, wherein the multiple dose regimen is a time period of up to about four months.

196. The method of any one of clauses 185 to 195, wherein the administration is carried out one time per day.

197. A method of treating a complicated urinary tract infection in a patient in need thereof, the method comprising administering an effective amount of a compound according to clause 160, or a pharmaceutically acceptable salt thereof, to the patient.

198. The method of clause 197, wherein the urinary tract infection is a catheter-associated urinary tract infection.

199. The method of clause 197 or clause 198, wherein the administration is intravesical administration.

200. The method of any one of clauses 197 to 199, wherein the administration is carried out using the compound, or a pharmaceutically acceptable salt thereof, in a liquid solution or suspension.

201. The method of any one of clauses 197 to 200, wherein the patient is administered at least one additional active ingredient.

202. The method of any one of clauses 197 to 201, wherein the patient is a human.

203. The method of any one of clauses 197 to 202, wherein the administration is carried out as a multiple dose regimen.

204. The method of clause 203, wherein the multiple dose regimen is a time period of up to about 2 days.

205. The method of clause 203, wherein the multiple dose regimen is a time period of up to about 3 days.

206. The method of clause 203, wherein the multiple dose regimen is a time period of up to about 4 days.

207. The method of clause 203, wherein the multiple dose regimen is a time period of up to about 5 days.

208. The method of clause 203, wherein the multiple dose regimen is a time period of up to about 6 days.

209. The method of clause 203, wherein the multiple dose regimen is a time period of up to about 7 days.

210. The method of clause 203, wherein the multiple dose regimen is a time period of up to about 14 days.

211. The method of any one of clauses 197 to 202, wherein the administration is carried out as a chronic treatment regimen.

212. The method of any one of clauses 197 to 211, wherein the administration is carried out one time per day.

213. A method of treating a lung infection arising from cystic fibrosis in a patient in need thereof, the method comprising administering an effective amount of a compound according to clause 160, or a pharmaceutically acceptable salt thereof, to the patient.

214. The method of clause 213, wherein the administration is inhalation administration.

215. The method of clause 213 or 214, wherein the administration is carried out using the compound, or a pharmaceutically acceptable salt thereof, in a dry powder, solution, suspension or aerosol.

216. The method of any one of clauses 213 to 215, wherein the patient is administered at least one additional active ingredient.

217. The method of any one of clauses 213 to 216, wherein the patient is a human.

218. The method of any one of clauses 213 to 217, wherein the administration is carried out as a multiple dose regimen.

219. The method of clause 213 to 218, wherein the multiple dose regimen is a time period of up to about one month.

220. The method of clause 218, wherein the multiple dose regimen is a time period of up to about two months.

221. The method of clause 218, wherein the multiple dose regimen is a time period of up to about three months.

222. The method of clause 218, wherein the multiple dose regimen is a time period of up to about four months.

223. The method of clause 218, wherein the multiple dose regimen is a time period of up to about five months.

224. The method of clause 218, wherein the multiple dose regimen is a time period of up to about six months.

225. The method of clause 218, wherein the multiple dose regimen is a time period of up to about seven months.

226. The method of clause 218, wherein the multiple dose regimen is a time period of up to about eight months.

227. The method of any one of clauses 213 to 217, wherein the administration is carried out one time per day.

228. A method of treating ventilator acquired pneumonia in a patient in need thereof, the method comprising administering an effective amount of a compound according to clause 160, or a pharmaceutically acceptable salt thereof, to the patient.

229. The method of clause 228, wherein the administration is inhalation administration.

230. The method of clause 228 or clause 229, wherein the administration is carried out using the compound, or a pharmaceutically acceptable salt thereof, in a liquid solution, suspension or dry powder.

231. The method of any one of clauses 228 to 230, wherein the patient is administered at least one additional active ingredient.

232. The method of any one of clauses 228 to 231, wherein the patient is a human.

233. The method of any one of clauses 228 to 232, wherein the administration is carried out as a multiple dose regimen.

234. The method of clause 233, wherein the multiple dose regimen is a time period of up to about 7 days.

235. The method of clause 233, wherein the multiple dose regimen is a time period of up to about 14 days.

236. The method of clause 233, wherein the multiple dose regimen is a time period of up to about 21 days.

237. The method of clause 233, wherein the multiple dose regimen is a time period of up to about one month.

238. The method of any one of clauses 228 to 237, wherein the administration is carried out one time per day.

239. A method of treating an infection in a burn wound in a patient in need thereof, the method comprising administering an effective amount of a compound according to clause 160, or a pharmaceutically acceptable salt thereof, to the patient.

240. The method of clause 239, wherein the administration is topical administration.

241. The method of clause 239 or 240, wherein the administration is carried out using the compound in a lotion, gel, cream, ointment, oil, solution, suspension, emulsion or other viscous composition.

242. The method of any one of clauses 239 to 241, wherein the patient is administered at least one additional active ingredient.

243. The method of any one of clauses 239 to 242, wherein the patient is a human.

244. The method of any one of clauses 239 to 243, wherein the administration is carried out as a multiple dose regimen.

245. The method of clause 244, wherein the multiple dose regimen is a time period of up to about 2 days.

246. The method of clause 244, wherein the multiple dose regimen is a time period of up to about 3 days.

247. The method of clause 244, wherein the multiple dose regimen is a time period of up to about 4 days.

248. The method of clause 244, wherein the multiple dose regimen is a time period of up to about 5 days.

249. The method of clause 244, wherein the multiple dose regimen is a time period of up to about 6 days.

250. The method of clause 244, wherein the multiple dose regimen is a time period of up to about 7 days.

251. The method of clause 244, wherein the multiple dose regimen is a time period of up to about 14 days.

252. The method of clause 244, wherein the multiple dose regimen is a time period of up to about 21 days.

253. The method of clause 244, wherein the multiple dose regimen is a time period of up to about one month.

254. The method of any one of clauses 239 to 253, wherein the administration is carried out one or more times per day.

255. The method of any one of clauses 239 to 253, wherein the administration is carried out one time per day.

256. The method of any one of clauses 239 to 253, wherein the administration is carried out two times per day.

257. The method of any one of clauses 239 to 253, wherein the administration is carried out three times per day.

258. The method of any one of clauses 239 to 253, wherein the administration is carried out four times per day.

259. A method of treating otitis externa in a patient in need thereof, the method comprising administering an effective amount of a compound according to clause 160, or a pharmaceutically acceptable salt thereof, to the patient.

260. The method of clause 259, wherein the administration is topical administration directly into the patient's external ear canal.

261. The method of clause 259 or clause 260, wherein the administration is carried out using the compound in a lotion, gel, cream, ointment, oil, solution, suspension, emulsion or other viscous composition.

262. The method of any one of clauses 259 to 261, wherein the patient is administered at least one additional active ingredient.

263. The method of any one of clauses 259 to 262, wherein the patient is a human.

264. The method of any one of clauses 259 to 263, wherein the administration is carried out as a multiple dose regimen.

265. The method of clause 264, wherein the multiple dose regimen is a time period of up to about 7 days.

266. The method of clause 264, wherein the multiple dose regimen is a time period of up to about 14 days.

267. The method of clause 264, wherein the multiple dose regimen is a time period of up to about 21 days.

268. The method of clause 264, wherein the multiple dose regimen is a time period of up to about one month.

269. The method of any one of clauses 259 to 268, wherein the administration is carried out one or more times per day.

270. The method of any one of clauses 259 to 268, wherein the administration is carried out one time per day.

271. The method of any one of clauses 259 to 268, wherein the administration is carried out two times per day.

272. The method of any one of clauses 259 to 268, wherein the administration is carried out three times per day.

273. A method of treating bacterial vaginosis in a patient in need thereof, the method comprising administering an effective amount of a compound according to clause 160, or a pharmaceutically acceptable salt thereof, to the patient.

274. The method of clause 273, wherein the administration is topical administration.

275. The method of clause 273 or clause 274, wherein the administration is carried out using the compound in a lotion, gel, cream, ointment, oil, solution, suspension, emulsion or other viscous composition.

276. The method of any one of clauses 273 to 275, wherein the administration is carried out using a gel.

277. The method of any one of clauses 273 to 276, wherein the patient is administered at least one additional active ingredient.

278. The method of any one of clauses 273 to 277, wherein the patient is a female human.

279. The method of any one of clauses 273 to 278, wherein the administration is carried out as a multiple dose regimen.

280. The method of clause 279, wherein the multiple dose regimen is a time period of up to about 7 days.

281. The method of clause 279, wherein the multiple dose regimen is a time period of up to about 14 days.

282. The method of clause 279, wherein the multiple dose regimen is a time period of up to about 21 days.

283. The method of any one of clauses 273 to 282, wherein the administration is carried out one or more times per day.

284. The method of any one of clauses 273 to 282, wherein the administration is carried out one time per day.

285. A method of treating impetigo in a patient in need thereof, the method comprising administering an effective amount of a compound according to clause 160, or a pharmaceutically acceptable salt thereof, to the patient.

286. The method of clause 285, wherein the administration is topical administration.

287. The method of clause 285 or clause 286, wherein the administration is carried out using the compound in a lotion, gel, cream, ointment, oil, solution, suspension, emulsion or other viscous composition.

288. The method of any one of clauses 285 to 287, wherein the administration is carried out using a gel.

289. The method of any one of clauses 285 to 288, wherein the patient is administered at least one additional active ingredient.

290. The method of any one of clauses 285 to 289, wherein the patient is a human.

291. The method of any one of clauses 285 to 290, wherein the administration is carried out as a multiple dose regimen.

292. The method of clause 291, wherein the multiple dose regimen is a time period of up to about 2 days.

293. The method of clause 291, wherein the multiple dose regimen is a time period of up to about 3 days.

294. The method of clause 291, wherein the multiple dose regimen is a time period of up to about 4 days.

295. The method of clause 291, wherein the multiple dose regimen is a time period of up to about 5 days.

296. The method of clause 291, wherein the multiple dose regimen is a time period of up to about 6 days.

297. The method of clause 291, wherein the multiple dose regimen is a time period of up to about 7 days.

298. The method of clause 291, wherein the multiple dose regimen is a time period of up to about 14 days.

299. The method of clause 291, wherein the multiple dose regimen is a time period of up to about 21 days.

300. The method of any one of clauses 285 to 299, wherein the administration is carried out one or more times per day.

301. The method of any one of clauses 285 to 299, wherein the administration is carried out one time per day.

302. The method of any one of clauses 285 to 299, wherein the administration is carried out two times per day.

303. A kit comprising the compound according to clause 160, or a pharmaceutically acceptable salt thereof, or a pharmaceutical composition according to any one of clauses 171 to 184.

304. A compound according to clause 160, or a pharmaceutically acceptable salt thereof, for use in therapy.

305. A compound according to clause 160, or a pharmaceutically acceptable salt thereof, for use in the treatment of an infection of a diabetic foot ulcer.

306. A compound according to clause 160, or a pharmaceutically acceptable salt thereof, for use in the treatment of a complicated urinary tract infection.

307. A compound according to clause 160, or a pharmaceutically acceptable salt thereof, for use in the treatment of a lung infection arising from cystic fibrosis.

308. A compound according to clause 160, or a pharmaceutically acceptable salt thereof, for use in the treatment of ventilator acquired pneumonia.

309. A compound according to clause 160, or a pharmaceutically acceptable salt thereof, for use in the treatment of an infection in a burn wound.

310. A compound according to clause 160, or a pharmaceutically acceptable salt thereof, for use in the treatment of otitis externa.

311. A compound according to clause 160, or a pharmaceutically acceptable salt thereof, for use in the treatment of bacterial vaginosis.

312. A compound according to clause 160, or a pharmaceutically acceptable salt thereof, for use in the treatment of impetigo.

313. The use of a compound according to clause 160, or a pharmaceutically acceptable salt thereof, for the manufacture of a medicament.

314. A method of coating a catheter with a compound according to clause 160, or a pharmaceutically acceptable salt thereof, the method comprising coating the catheter with the compound, or a pharmaceutically acceptable salt thereof, prior to inserting the catheter into a patient.

315. A composition comprising a catheter coated with a compound according to clause 160, or a pharmaceutically acceptable salt thereof.

316. A compound having the formula:

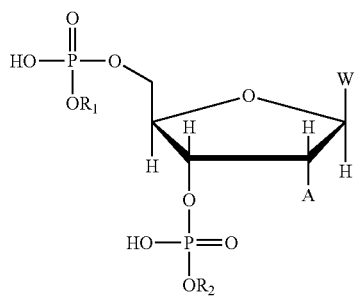

Formula (IV)

wherein:
A is —H or —OMe;
$R_1$ and $R_2$ are each independently selected from isobutyl, benzyl, butyl, and cyclohexyl;
and
W is an amino-substituted or guanidino-substituted nitrogen containing heterocyclic moiety; or
a pharmaceutically acceptable salt thereof.

317. The compound according to clause 316, wherein $R_1$ and $R_2$ are both butyl.

318. The compound according to clause 316, wherein $R_1$ and $R_2$ are both isobutyl.

319. The compound according to clause 316, wherein $R_1$ and $R_2$ are both benzyl.

320. The compound according to clause 316, wherein $R_1$ and $R_2$ are both cyclohexyl.

321. The compound according to clause 316, wherein W is selected from the group consisting of:

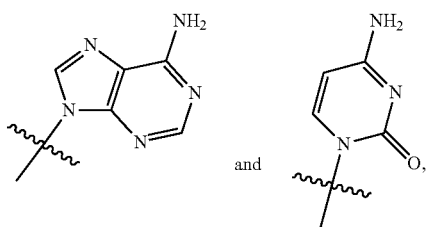 [SMILES: *n1cnc2c(N)ncnc21 ; *n1ccc(N)nc1=O]

where the ⁓ represents a point of attachment to the deoxyribose or ribose moiety.

322. The compound according to clause 317, wherein W is

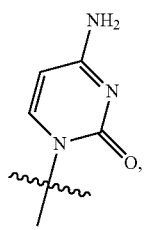 [SMILES: *n1ccc(N)nc1=O]

where the ⁓ represents a point of attachment to the deoxyribose or ribose moiety, and A is —OMe.

323. The compound according to clause 317, wherein W is

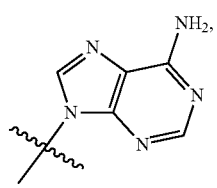 [SMILES: *n1cnc2c(N)ncnc21]

where the ⁓ represents a point of attachment to the deoxyribose or ribose moiety, and A is —OMe.

324. The compound according to clause 318, wherein W is

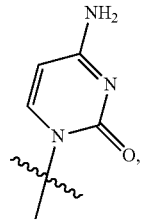 [SMILES: *n1ccc(N)nc1=O]

where the ⁓ represents a point of attachment to the deoxyribose or ribose moiety, and A is —H.

325. The compound according to clause 319, wherein W is

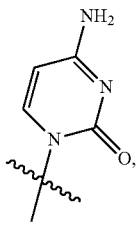 [SMILES: *n1ccc(N)nc1=O]

where the ⌇ represents a point of attachment to the deoxyribose or ribose moiety, and A is —H.

326. The compound according to claim 320, wherein W is

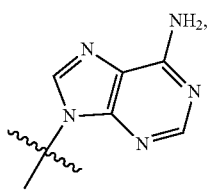 [SMILES: *n1cnc2c(N)ncnc21]

where the ⌇ represents a point of attachment to the deoxyribose or ribose moiety, and A is —H.

327. A pharmaceutical composition comprising a compound according to clause 316, or a pharmaceutically acceptable salt thereof, and one or more pharmaceutically acceptable carriers, excipients, or diluents.

328. A method of treating an infection in a patient in need thereof, the method comprising administering an effective amount of a compound according to clause 316, or a pharmaceutically acceptable salt thereof, to the patient.

329. A method of treating an infection of a lower extremity ulcer in a patient in need thereof, the method comprising administering an effective amount of a compound according to clause 316, or a pharmaceutically acceptable salt thereof, to the patient.

330. A method of treating an infection of a diabetic foot ulcer in a patient in need thereof, the method comprising administering an effective amount of a compound according to clause 316, or a pharmaceutically acceptable salt thereof, to the patient.

331. A method of treating a bladder and/or a urinary tract infection in a patient in need thereof, the method comprising administering an effective amount of a compound according to clause 316, or a pharmaceutically acceptable salt thereof, to the patient.

332. A method of treating a lung infection in a patient in need thereof, the method comprising administering an effective amount of a compound according to clause 316, or a pharmaceutically acceptable salt thereof, to the patient.

333. The method of clause 332, wherein the lung infection arises from a pulmonary condition.

334. The method of clause 333, wherein the pulmonary condition is selected from the group consisting of genetic conditions, acquired conditions, primary conditions, secondary conditions, asthma, chronic obstructive pulmonary disease, cystic fibrosis, bronchiolitis, pneumonia, bronchitis, emphysema, adult respiratory distress syndrome, allergies, lung cancer, small cell lung cancer, primary lung cancer, metastatic lung cancer, bronchiestasis, bronchopulmonary dysplasia, chronic bronchitis, chronic lower respiratory diseases, croup, high altitude pulmonary edema, pulmonary fibrosis, interstitial lung disease, reactive airway disease, lymphangioleiomyomatosis, neonatal respiratory distress syndrome, parainfluenza, pleural effusion, pleurisy, pneumothorax, primary pulmonary hypertension, psittacosis, pulmonary edema secondary to various causes, pulmonary embolism, pulmonary hypertension secondary to various causes, respiratory failure secondary to various causes, sleep apnea, sarcoidosis, smoking, stridor, acute respiratory distress syndrome, infectious diseases, SARS, tuberculosis, psittacosis infection, Q fever, parainfluenza, respiratory syncytial virus, combinations thereof, and conditions caused by any one or combination of the above.

335. A method of treating a lung infection arising from cystic fibrosis in a patient in need thereof, the method comprising administering an effective amount of a compound according to clause 316, or a pharmaceutically acceptable salt thereof, to the patient.

336. A method of treating pneumonia in a patient in need thereof, the method comprising administering an effective amount of a compound according to clause 316, or a pharmaceutically acceptable salt thereof, to the patient.

337. The method of clause 336, wherein the pneumonia is ventilator acquired pneumonia.

338. A method of treating an infection in a burn wound in a patient in need thereof, the method comprising administering an effective amount of a compound according to clause 316, or a pharmaceutically acceptable salt thereof, to the patient.

339. A method of treating otitis externa in a patient in need thereof, the method comprising administering an effective amount of a compound according to clause 316, or a pharmaceutically acceptable salt thereof, to the patient.

340. A method of treating bacterial vaginosis in a patient in need thereof, the method comprising administering an effective amount of a compound according to clause 316, or a pharmaceutically acceptable salt thereof, to the patient.

341. A method of treating impetigo in a patient in need thereof, the method comprising administering an effective amount of a compound according to clause 316, or a pharmaceutically acceptable salt thereof, to the patient.

342. A method of treating oral mucositis in a patient in need thereof, the method comprising administering an effective amount of a compound according to clause 316, or a pharmaceutically acceptable salt thereof, to the patient.

343. A compound according to clause 316, or a pharmaceutically acceptable salt thereof, for use in therapy.

344. The use of a compound according to clause 316, or a pharmaceutically acceptable salt thereof, for the manufacture of a medicament.

345. A compound having the formula:

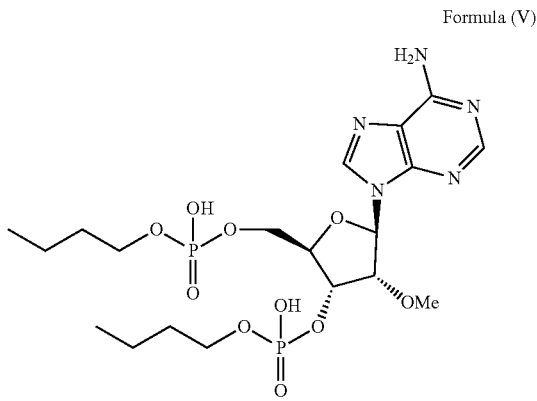 [SMILES: CCCCOP(=O)(O)OC[C@H]1O[C@@H](n2cnc3c(N)ncnc32)[C@H](OC)[C@@H]1OP(=O)(O)OCCCC]

Formula (V)

or a pharmaceutically acceptable salt thereof.

346. A compound having the formula:

Formula (VI)

or a pharmaceutically acceptable salt thereof.

347. A compound having the formula:

Formula (VII)

or a pharmaceutically acceptable salt thereof.

348. A compound having the formula:

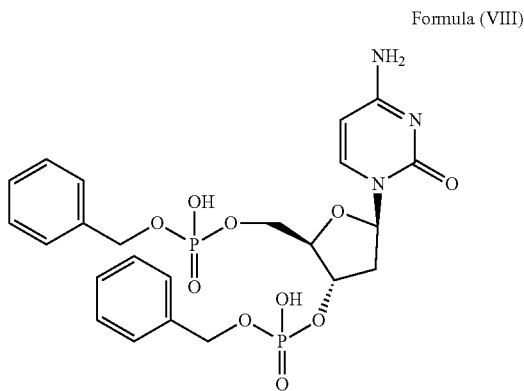 [SMILES: Nc1ccn([C@H]2C[C@H](OP(=O)(O)OCc3ccccc3)[C@@H](COP(=O)(O)OCc3ccccc3)O2)c(=O)n1]

Formula (VIII)

or a pharmaceutically acceptable salt thereof.

349. A compound having the formula:

Formula (IX)

or a pharmaceutically acceptable salt thereof.

350. A pharmaceutical composition comprising a compound according to any one of clauses 345 to 349, or a pharmaceutically acceptable salt thereof, and one or more pharmaceutically acceptable carriers, excipients, or diluents.

351. A method of treating an infection in a patient in need thereof, the method comprising administering an effective amount of a compound according to any one of clauses 345 to 349, or a pharmaceutically acceptable salt thereof, to the patient.

352. A method of treating an infection of a lower extremity ulcer in a patient in need thereof, the method comprising administering an effective amount of a compound according to any one of clauses 345 to 349, or a pharmaceutically acceptable salt thereof, to the patient.

353. A method of treating an infection of a diabetic foot ulcer in a patient in need thereof, the method comprising administering an effective amount of a compound according to any one of clauses 345 to 349, or a pharmaceutically acceptable salt thereof, to the patient.

354. A method of treating a bladder and/or a urinary tract infection in a patient in need thereof, the method comprising administering an effective amount of a compound according to any one of clauses 345 to 349, or a pharmaceutically acceptable salt thereof, to the patient.

355. A method of treating a lung infection in a patient in need thereof, the method comprising administering an effective amount of a compound according to any one of clauses 345 to 349, or a pharmaceutically acceptable salt thereof, to the patient.

356. The method of clause 355, wherein the lung infection arises from a pulmonary condition.

357. The method of clause 356, wherein the pulmonary condition is selected from the group consisting of genetic conditions, acquired conditions, primary conditions, secondary conditions, asthma, chronic obstructive pulmonary disease, cystic fibrosis, bronchiolitis, pneumonia, bronchitis, emphysema, adult respiratory distress syndrome, allergies, lung cancer, small cell lung cancer, primary lung cancer, metastatic lung cancer, bronchiestasis, bronchopulmonary dysplasia, chronic bronchitis, chronic lower respiratory diseases, croup, high altitude pulmonary edema, pulmonary fibrosis, interstitial lung disease, reactive airway disease, lymphangioleiomyomatosis, neonatal respiratory distress syndrome, parainfluenza, pleural effusion, pleurisy, pneumothorax, primary pulmonary hypertension, psittacosis, pulmonary edema secondary to various causes, pulmonary embolism, pulmonary hypertension secondary to various causes, respiratory failure secondary to various causes, sleep apnea, sarcoidosis, smoking, stridor, acute respiratory distress syndrome, infectious diseases, SARS, tuberculosis, psittacosis infection, Q fever, parainfluenza, respiratory syncytial virus, combinations thereof, and conditions caused by any one or combination of the above.

358. A method of treating a lung infection arising from cystic fibrosis in a patient in need thereof, the method comprising administering an effective amount of a compound according to any one of clauses 345 to 349, or a pharmaceutically acceptable salt thereof, to the patient.

359. A method of treating pneumonia in a patient in need thereof, the method comprising administering an effective amount of a compound according to any one of clauses 345 to 349, or a pharmaceutically acceptable salt thereof, to the patient.

360. The method of clause 336, wherein the pneumonia is ventilator acquired pneumonia.

361. A method of treating an infection in a burn wound in a patient in need thereof, the method comprising administering an effective amount of a compound according to any one of clauses 345 to 349, or a pharmaceutically acceptable salt thereof, to the patient.

362. A method of treating otitis externa in a patient in need thereof, the method comprising administering an effective amount of a compound according to any one of clauses 345 to 349, or a pharmaceutically acceptable salt thereof, to the patient.

363. A method of treating bacterial vaginosis in a patient in need thereof, the method comprising administering an effective amount of a compound according to any one of clauses 345 to 349, or a pharmaceutically acceptable salt thereof, to the patient.

364. A method of treating impetigo in a patient in need thereof, the method comprising administering an effective amount of a compound according to any one of clauses 345 to 349, or a pharmaceutically acceptable salt thereof, to the patient.

365. A method of treating oral mucositis in a patient in need thereof, the method comprising administering an effective amount of a compound according to any one of clauses 345 to 349, or a pharmaceutically acceptable salt thereof, to the patient.

366. A compound according to any one of clauses 345 to 349, or a pharmaceutically acceptable salt thereof, for use in therapy.

367. The use of a compound according to any one of clauses 345 to 349, or a pharmaceutically acceptable salt thereof; for the manufacture of a medicament.

EXAMPLES

Examples related to the present disclosure are described below. In most cases, alternative techniques can be used. The examples are intended to be illustrative and are not limiting or restrictive of the scope of the invention as set forth in the claims.

EXAMPLE 1

General Synthesis Scheme of a Compound of Formula (II) Having an Amino Substituted Nitrogen Containing Heterocyclic Moiety Step 1. Protection of the Amino Substituted Nitrogen Containing Heterocycle

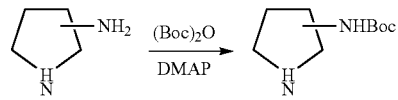

An amino substituted nitrogen containing heterocycle is treated with di-tert-butyl dicarbonate ((BOC)$_2$O) in the presence of a base such as 4-(dimethylamino) pyridine (DMAP) in an organic solvent such as methanol to Boc protect the exocyclic amine nitrogen.

Step-2. Nucleobase Glycosylation

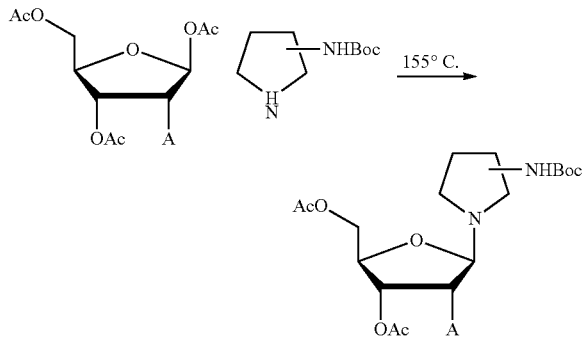

The Boc protected amino substituted nitrogen containing heterocycle prepared in Step 1 is coupled under thermal conditions to an acetyl protected ribose/deoxyribose derivative that is electrophilic at the anomeric carbon.

Step-3. Deprotection of Acetyl Group

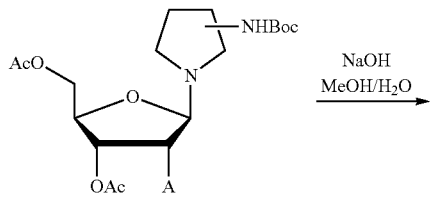

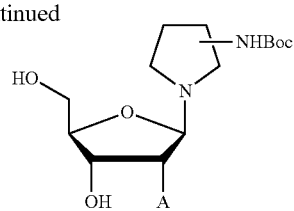

The glycosylated nucleobase prepared in Step 2 is treated with NaOH, MeOH, and H₂O to deprotect the acetyl protecting group and provide the primary and secondary hydroxy groups.

Step-4. Preparation of Phosphitylating Reagent

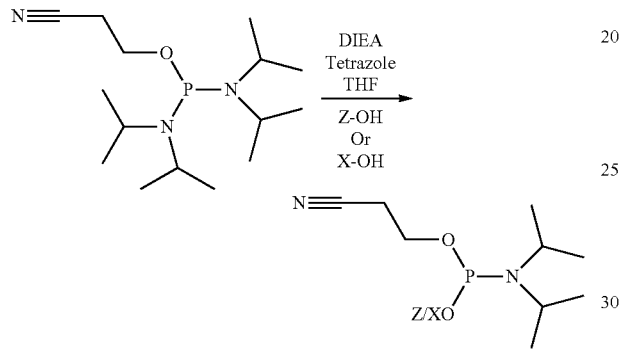

Step 4 can occur as a precursor to Step 5 and is an independent process to Steps 1-3. An alcohol is reacted with the phosphinamide in THF with tetrazole as a catalyst in the presence of N,N-diisopropylethylamine (DIPEA).

Step-5. Phosphitylation

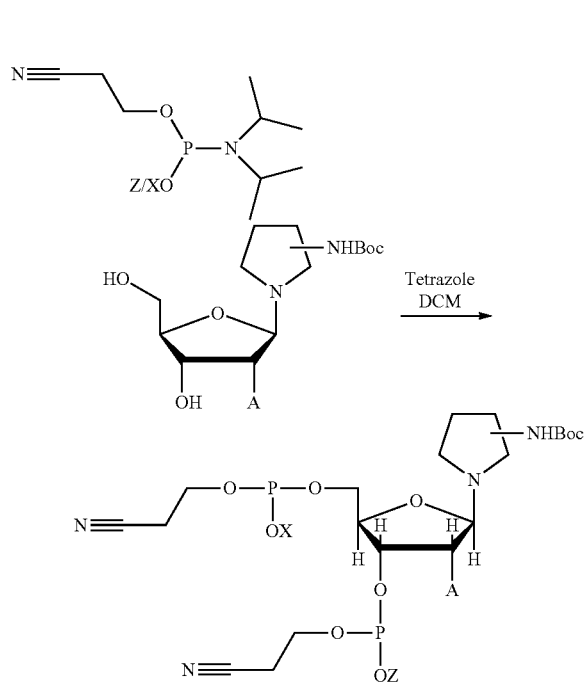

The Boc-protected species nucleobase prepared in Step 3 is bis-phosphinylated with the phosphitylating reagent prepared in Step 4 and tetrazole as catalyst in dichloromethane (DCM).

Step-6. Oxidation

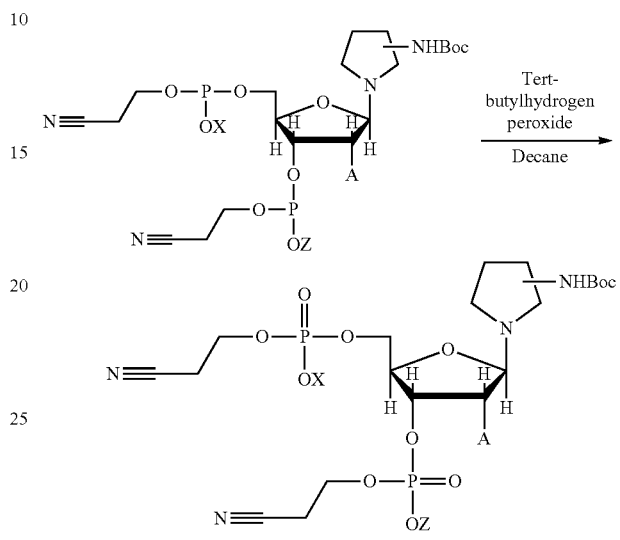

The bis-phosphonate is generated by oxidation of the bis-phosphinylated compound prepared in Step 5 with tert-butylhydroperoxide (TBTH) in the presence of decane.

Step-7. Deprotection of the Amino Substituted Nitrogen Containing Heterocycle

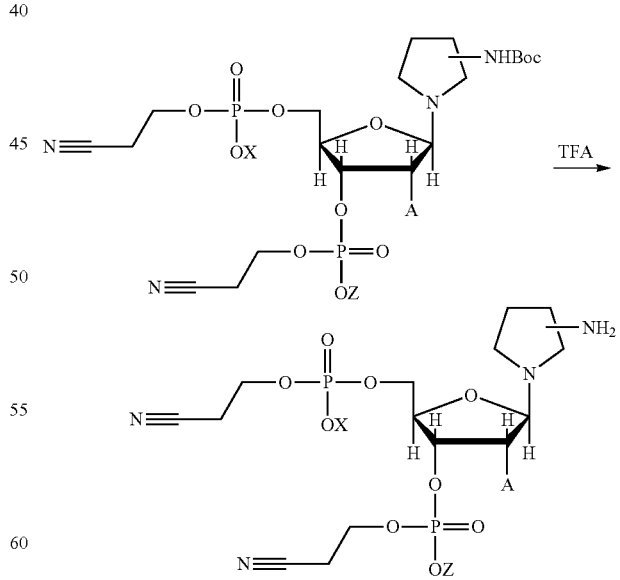

Removal of the Boc protecting group of the amino substituted nitrogen containing heterocycle prepared in Step 6 is conducted in DCM in the presence of trifluoroacetic acid (TFA).

Step-8. Deprotection of the Phosphodiester
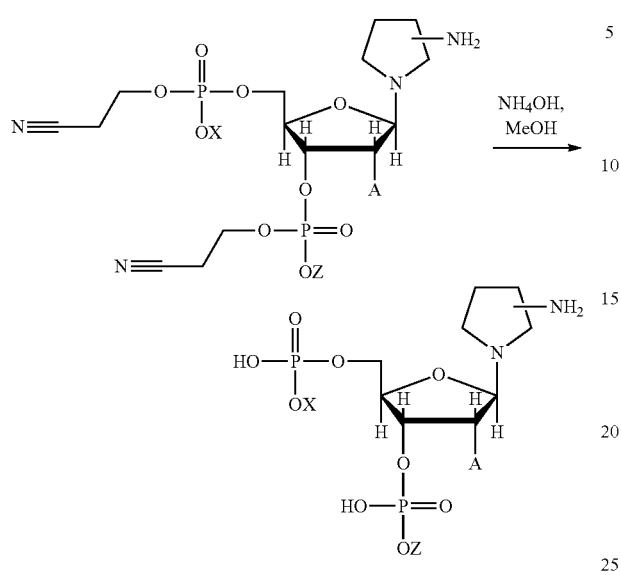
Hydrolysis of the β-cyanoethyl protecting group of the phosphodiester prepared in Step 7 with methanolic ammonium hydroxide (NH$_4$OH, MeOH) provides the target compound.
EXAMPLE 2
Synthesis of Nu-8
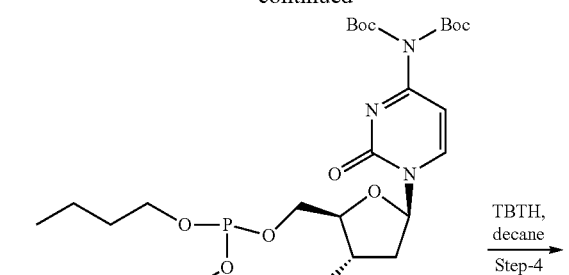
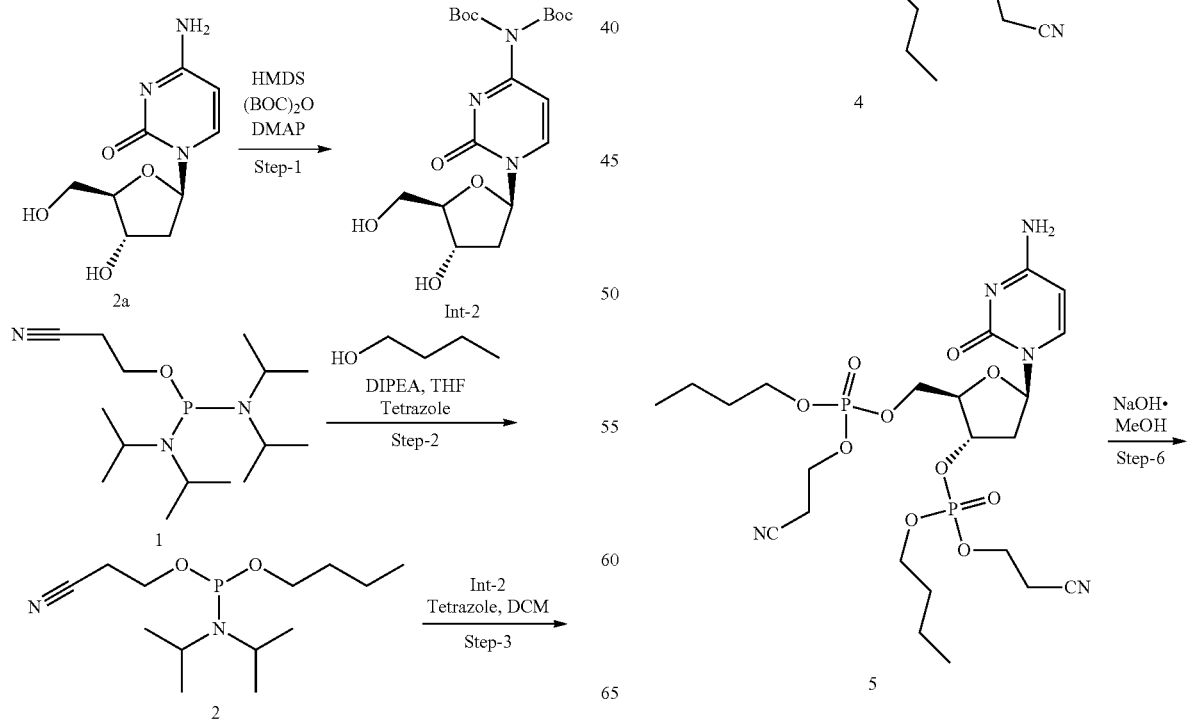

-continued

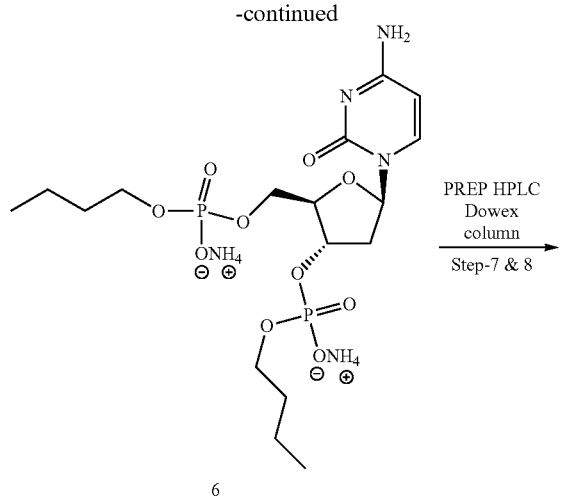

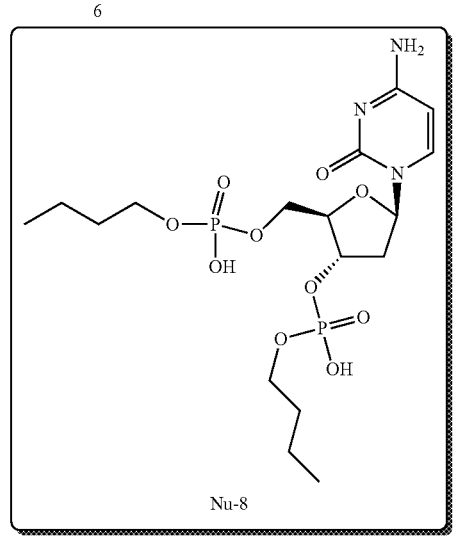

Nu-8

Step-1. Protection of the Amine (Building Block Key Intermediate)

Cytidine 2a is added to hexamethyldisilazane (HMDS), 4-(dimethylamino)pyridine (DMAP), trimethylsilyl trifluoromethanesulfonate, and di-tert-butyl dicarbonate ((BOC) 20) in methanol to protect the nitrogen atoms of 2a by generating BOC-protected compound Int-2.

Step-2. Preparation of Phosphitylating Reagent (Building Block Key Intermediate)

n-Butanol is reacted with the phosphinamide 1 in THF with tetrazole as a catalyst in the presence of N,N-diisopoylethylamine (DIEA). The crude product is chromatographed on neutral alumina eluting with hexane and then 2% ethyl acetate in hexane. The pure fraction is combined (by TLC) and evaporated to a residue under vacuo.

Step-3. Coupling of Key Intermediates

BOC-protected species Int-2 is bis-phosphinylated with reagent 2 in dichloromethane (DCM)/dimethyl formamide (DMF) solvent and tetrazole as catalyst to produce 3. The reaction mixture is concentrated to a residue and the crude product is immediately oxidized in the next step.

Steps-4 & 5. Oxidation and Amino Deprotection

The crude product 3 is oxidized with tert-butylhydroperoxide (TBHP) in the presence of decane to generate the bis-phosphonate species 4. Removal of the BOC groups is carried in DCM in the presence of trifluoroacetic acid (TFA) to yield 5. The crude product is chromatographed on silica gel eluting with ethyl acetate. The pure fractions (by TLC) are combined and evaporated to a residue under vacuo.

Step-6. Deprotection of the Phosphodiester

Hydrolysis of 5 with methanolic ammonium hydroxide ($NH_4OH$, MeOH) gives crude (I) ammonium salt (6).

Steps-7 & 8. Purification

Purification by preparative HPLC of 6 and conversion to the free acid with Dowex 50WX8-200 resin is carried out. Evaporation of the aqueous eluate provides (I) that is diluted with purified water to provide a 20% solution at its ambient pH.

EXAMPLE 3

Synthesis of Nu-8 Sodium Salt

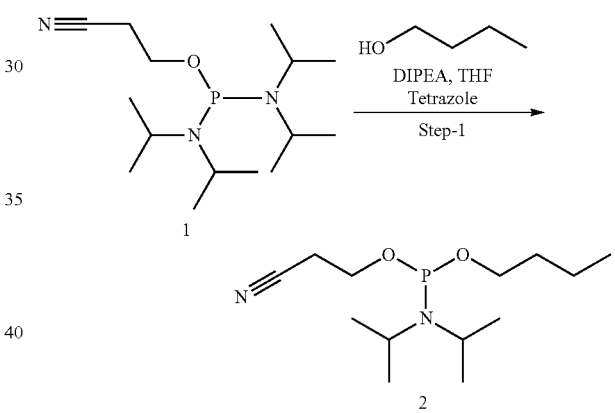

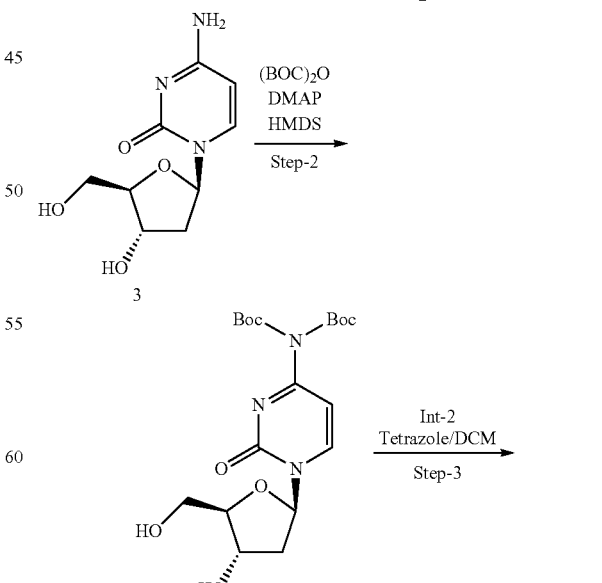

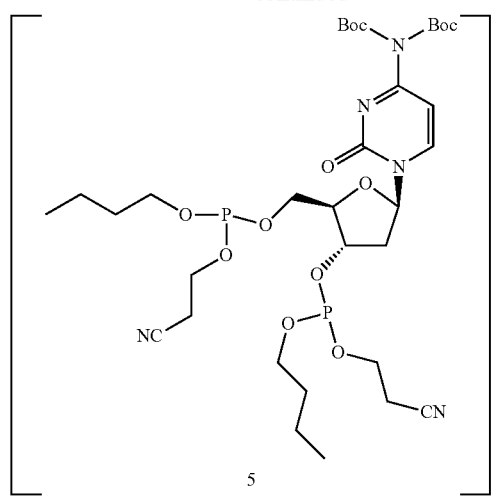

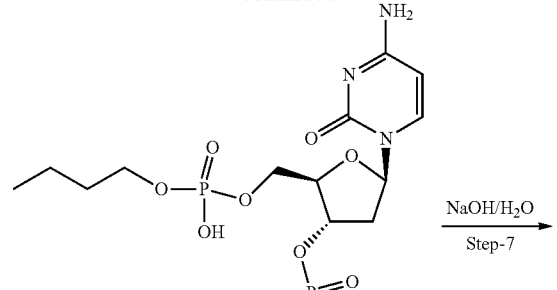

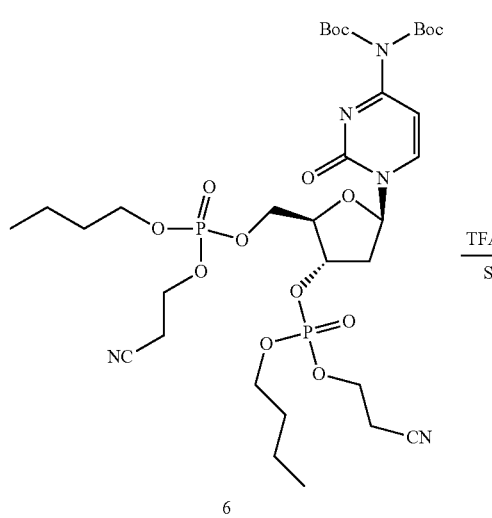

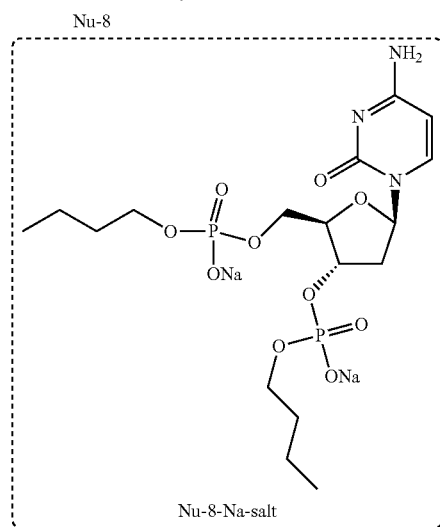

Synthesis of Compound-2

To a solution of compound-1 (1.0 kg, 3.3222 mol) in THF (6 L) is added DIEA (1.370 mL, 8.3055 mol) and tetrazole (230 g, 3.3222 mol) followed by n-butanol (275 mL, 2.99 mol) in THF (6 L) is added drop wise at 0° C. for 12 h. The reaction mixture is stirred at room temperature for 24 h. The progress of the reaction is monitored by TLC and after completion of the reaction, solid is filtered off. Filtrate is evaporated under reduced pressure at 40° C. to afford crude compound. Crude compound is dissolved in ethyl acetate (5 L). Organic layer is washed with water (3 L) and brine (2 L). Organic layer is dried over anhydrous $Na_2SO_4$ filtered and the solvent is evaporated under reduced pressure to obtain crude compound. The crude compound is purified by column chromatography over basic lumina ($Al_2O_3$), Compound eluted with 0-2% EtOAc in petroleum ether to afford Compound-2.(700 g, 76.92%) as pale yellow liquid. H-NMR (400 MHz, chloroform-d) δ 4.18-4.07 (m, 1H), 4.02 (q, J=6.6 Hz, 1H), 3.93-3.74 (m, 4H), 2.65 (td, J=6.5, 3.6 Hz, 2H), 1.31-1.23 (m, 4H), 1.18 (dd, J=6.8, 3.8 Hz, 12H), 0.93 (td, J=7.4, 3.1 Hz, 3H). LC-MS: 275 (M+H).

Synthesis of Compound-4

To solution of compound-3 (300 g, 1.321 mol) in hexamethyldisilazane (638 g, 3.964 mol) is added DMAP (16.11 g, 0.132 mol) followed by TMSOTf (7.22 g, 0.039 mol) is added at 0° C. and the resulting reaction mixture is stirred for 1 h at room temperature. After consumption of starting material, Boc-anhydride (1.4 L, 6.605 mol) is added at 0° C. for 1 h and the reaction mixture is stirred for 16 h at room temperature. To the reaction is added methanol (3 L) followed by triethylamine (1.5 L) is added at 0° C. for 1 h and the reaction mixture is stirred for 20 h at room temperature. Reaction mixture is concentrated under reduced pressure to get crude compound. Crude compound is diluted with ethyl acetate (3 L) and washed with water (1.0 L) and brine (1.0 L) solution; organic layer is dried over anhydrous $Na_2SO_4$, filtered and the solvent is evaporated under reduced pressure to get afford crude compound. The crude compound is purified by column chromatography silica gel (100-200 mesh) compound eluted 0-3% MeOH in DCM to afford Compound-4 (180 g, 31.89%) as off white solid. H-NMR (300 MHz, DMSO-d6) δ8.41 (d, J=7.5 Hz, 1H), 6.84 (d, J=7.5 Hz, 1H), 6.06 (t, J=6.2 Hz, 1H), 5.28 (d, J=4.3 Hz, 1H), 5.07 (q, J=4.6, 4.0 Hz, 1H), 4.21 (q, J=4.1 Hz, 1H), 3.87 (q, J=3.7 Hz, 1H), 3.71-3.49 (m, 2F1), 2.32 (m, 1H), 2.03 (dt, J=13.0, 6.2 Hz, 1H), 1.49 (s, 18H), LC-MS: 275 (M+H).

Synthesis of Compound-6

To a stirred solution of compound-4 (180 g, 0.421 mol) in THF (1.0 L) is added DIEA (348 mL, 2.105 mol) and tetrazole (176 g, 2.526 mol) at 0° C. To the resulting reaction mixture is added a solution of compound-2 (519 g, 1.896 mol) in THF (800 mL) drop wise at 0° C. for 1 h. The reaction mixture is stirred at room temperature for 16 h. After completion of the reaction, tert-butyl peroxide in decane (505 mL, 5 M) is added drop wise at 0° C. and the reaction mixture is stirred for 6 h at room temperature. The reaction is monitored by TLC. After completion of the reaction, the reaction mixture is concentrated at 40° C. and diluted with ethyl acetate (3 L) and washed with water (1 L) and brine (1 L) solution. Organic layer is dried over anhydrous $Na_2SO_4$ filtered and the solvent is evaporated under reduced pressure to get afford crude compound (350 g crude). The crude compound is purified by column chromatography through silica gel (100-200 mesh) column eluted with 0-5% MeOH in DCM. All collected pure fractions are concentrated to afford pure Compound-6 (220 g, 64.83%) as a wine red liquid. H-NMR (300 MHz, DMSO-d6) δ 8.19 (dd, J=7.6, 1.3 Hz, 1H), 6.88 (d, J=7.5 Hz, 1H), 6.13 (t, J=10.5 Hz, 1H), 4.99 (s, 1H), 4.44 (s, 1H), 4.26-3.96 (m, 10H), 3.00-2.84 (m, 4H), 2.57-2.79 (m, 2H), 1.70-1.54 (m, 4H), 1.50 (s, 18H), 1.35 (m, 4H), 0.88 (qd, J=7.5, 2.5 Hz, 6H); LC-MS: 806 (M+H).

Synthesis of Compound-7

To a solution of Compound-6 (220 g, 0.273 mol) in DCM (4.4 L) is added TFA (210 mL, 2.732 mol) dropwise at 0° C. The reaction mixture is stirred at room temperature for 24 h. The reaction is monitored by TLC. After completion of the reaction, solvent is evaporated under reduced pressure to afford crude compound. The crude compound is purified by column chromatography silica gel (230-400 mesh). Compound eluted with 0-10% MeOH in DCM. All collected pure fractions are concentrated to afford pure Compound-7 (170 g, 84.67%) as a pale yellow liquid. H-NMR (300 MHz, DMSO-d6) δ 7.61 (d, J=7.5 Hz, 1H), 7.27 (d, J=13.9 Hz, 2H), 6.19 (t, J=6.9 Hz, 1H), 5.74 (d, J=7.4 Hz, 1H), 4.96 (s, 1H), 4.10-3.93 (m, 11H), 2.93 (q, J=6.2 Hz, 4H), 2.29 (d, J=13.1 Hz, 2H), 1.61 (h, J=7.1 Hz, 4H), 1.35 (p, J=7.3 Hz, 4H), 0.89 (dq, J=7.9, 4.2 Hz, 6H); LC-MS: 606 (M+H).

Synthesis of Nu-8

To a stirred solution of Compound-7 (720 g, 1.1900 mol) in MeOH (5.0 L) is added aq. ammonia (600 mL) at 0° C. The reaction mixture is stirred at room temperature for 4 h. The reaction is monitored by TLC. After completion of the reaction, evaporate the MeOH under reduced pressure the aqueous layer is washed with DCM (1.5 L). The aqueous layer is passed through Dowex-H$^+$ resin. The water is removed under reduced pressure to afford Nu-8 (260 g, 43.84%) as an off white solid. H-NMR (300 MHz, DMSO-d6) δ 8.94 (s, 1H), 8.49 (s, 1H), 7.97 (d, J=7.8 Hz, 1H), 6.08 (t, J=6.1 Hz, 1H), 5.95 (d, J=7.7 Hz, 1H), 4.76 (q, J=5.8 Hz, 1H), 4.15 (q, J=4.1 Hz, 1H), 4.08 (s, 1H), 3.83 (m, 6H), 2.43 (t, J=5.6 Hz, 2H), 1.67-1.44 (m, 4H), 1.44-1.26 (m, 4H), 0.95-0.82 (m, 6H), LC-MS: 500.15 (M+H).

Synthesis of Nu-8 Sodium Salt

To a stirred solution of compound-Nu-8 (260 g, 0.478 mol) in water (2.6 L), 1 N NaOH (950 mL) is added dropwise at 0° C. The reaction mixture is stirred at room temperature for 2 h. The reaction is monitored by TLC. After completion of the reaction, aqueous layer is washed with DCM (1.5 L). The aqueous layer is evaporated under reduced pressure to afford Nu-8 sodium salt (265 g, 93%) as off white solid. H-NMR (300 MHz, DMSO-d6) δ 7.81 (d, J=7.2 Hz, 1H), 7.2 (bs, 1H), 7.0 (bs, 1H), 6.16 (t, J=4 Hz, 1H), 5.71 (d, J=7.6 Hz, 1H), 4.69 (bs, 1H), 3.75 (m, 1H), 3.71 (m, 1H), 3.8 (m, 4H), 2.2 (q, 1H), 1.89-1.96-1.44 (m, 1H), 1.49-1.39 (m, 4H), 1.34-1.23 (m, 4H), 0.88-0.84 (m, 6H).

EXAMPLE 4

Comparative Physical Property Studies of Bisphosphocin® Compounds Nu-2, Nu-4, and Nu-5, and the Compound of Formula (I)

The structures of known Bisphosphocin® compounds Nu-2, Nu-4, and Nu-5 are shown below:

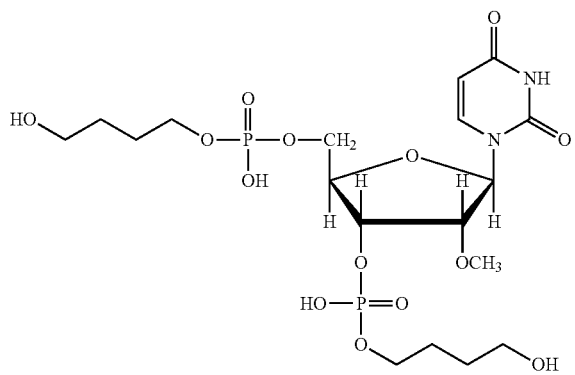

Nu-2

-continued

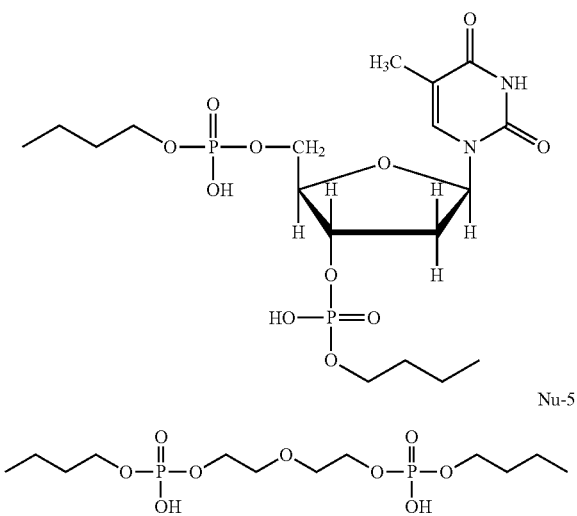

pH studies are conducted to show the pH of Nu-8 compared to Bisphosphocin® compounds Nu-2, Nu-4, and Nu-5. 20 mg/mL Nu-2 solution is prepared by diluting 2 mL of 250 mg/mL Nu-2 solution with 23 mL DI water. 20 mg/mL Nu-4 and Nu-5 solutions are prepared in the same way. 401.65 mg Nu-8 is weighed in a 5 mL volumetric flask and diluted with DI water to volume. 20 mg/mL Nu-8 solution is prepared by diluting 5 mL of 80.3 mg/mL Nu-8 solution with 15 mL DI water. The pH values of 4 Nu-2, Nu-4, Nu-5, and Nu-8 at 20 mg/mL are measured with a calibrated pH meter. The results are shown in TABLE 2. Also shown in TABLE 2 is a summary of other physical properties of the compound of Formula (I) and reference compounds Nu-2, Nu-4, and Nu-5.

TABLE 2

|  | Nu-2 | Nu-4 | Nu-5 | Nu-8 |
|---|---|---|---|---|
| pH (2% solution) | 0.99 | 0.94 | 0.93 | 1.49 |
| pKa | 2.30 | 2.30 | 2.28 | 3.20 |
| Solubility | — | — | — | 137 |
| Pow | 0.0407 | 0.0592 | 0.0480 | 0.0662 |

Nu-8 prepared in a 2% aqueous solution provides the most basic (highest pH) solution compared to reference compounds Nu-2, Nu-4, and Nu-5. Without wishing to be bound to any particular theory, it is believed that the presence of a free exocyclic amino group in the structure of Nu-8 alters the pH of Nu-8 in solution, which in turn caused Nu-8 to act more rapidly and to be more potent at higher pH levels than Bisphosphocins® Nu-2, Nu-4, and Nu-5.

Additionally, pKa measurements show that Nu-8 has the lowest acid dissociation constant compared to Bisphosphocins® Nu-2, Nu-4, and Nu-5, which is a measurement of the dissociation of the molecule into hydrogen ion(s) and corresponding conjugate base. Without wishing to be bound to any particular theory, it is believed that Nu-8 does not have as many acidic protons in its structure that can dissociate into solution as hydrogen ions compared to the number of acidic protons present in reference Bisphosphocin® compounds Nu-2, Nu-4, and Nu-5. The reference Bisphosphocins® compounds have acidic protons such as hydroxyl protons and methyl ester protons, which can dissociate into solution.

In summary, Nu-8 prepared in a 2% aqueous solution provides the most basic (highest pH) solution and acts more rapidly and is more potent at higher pH levels compared to reference compounds Nu-2, Nu-4, and Nu-5.

EXAMPLE 5

Use of Nu-8 in the Treatment of *Helicobacter Pylori* in Mice

Animals

The mouse strain used in this study is C57/BL6 ranging from 5-6 weeks in age and 18-22 grams in weight. Mice are housed five to a cage with free access to food and water in accordance with NIH guidelines.

Bacterial Strain

A bacterial strain of *Helicobacter pylori* SS1 (CagA+, VacA+) is adapted for the mouse model from a human clinical isolate and validated in this infection model.

Infection

At 6 days prior to infection, a frozen stock is streaked onto one to two Columbia 5% sheep blood agar plates, and the plates are microaerophilically incubated for 72 hours at 37° C. After 72 hours, the plate growth is subcultured onto five Columbia 5% sheep blood agar plates and is incubated as before. After another 72 hours of incubation, the plates are removed, and the plate growth is suspended in sterile 0.9% saline to an OD of 1.5-2.0 at 530 nm. This OD is approximately equal to 1.0e+09 CFU/mL, which is used to orally infect the mice on all 3 infection days. To infect mice, the mice are orally dosed 0.25 mL of the 1.0e+09 CFU/mL via a 20-22 G gavage needle. Mice need to be fasted only before the first infection.

Treatment

At 1 week post-infection, mice are treated with Nu-8. Multiple dose antibiotic therapies are administered orally at 0.2 mL/dose. Antibiotics are administered 2 times per day and continued for 7 days. The control group is administered the vehicle alone.

Sampling

Food is removed from cages 18 hours prior to euthanizing animals and each cage is clearly labeled that the animals are being experimentally fasted. Mice are euthanized ($CO_2$ & cervical dislocation). After mice are euthanized, each stomach is removed by cutting the esophagus away from the superior aspect of the stomach and the duodenum away from the pyloric region. The excised stomach is placed into a sterile petri dish and the luminal contents are rinsed away with sterile 1X PBS. Each rinsed stomach is placed into a 14-mL Falcon tube containing 2 mL of 1×PBS and stored on ice. Each stomach is homogenized, 10-fold serial diluted in 1×PBS, spot plated onto Columbia agar with 3.5% laked horse blood±the DENT selective antibiotic supplement, and microaerophilically incubated for 5 days at 37° C. Then, colonies are counted.

Dose Response

Nu-8 is administered at various doses (mg/kg), orally, twice-a-day for 7 days. The formulations, concentration and dose volumes for treatment is established prior to dosing. The positive control group consists of a triple therapy regimen (omeprazole, amoxicillin, and clarithromycin). Negative control used dosing solution without drugs. The doing schedule is shown in TABLE 3. The inoculation and treatment schedule is shown in TABLE 4.

TABLE 3

| Group | Compound | Dose | Conc Dose Volume | Regimen | # animals[a] |
|---|---|---|---|---|---|
| 1 | Nu-8 | 0.2 mg | 1 mg/mL, 0.2 mL | PO; bid x 7 days | 16 |
| 2 |  | 1.0 mg | 5 mg/mL, 0.2 mL |  | 16 |
| 3 |  | 2.0 mg | 10 mg/mL, 0.2 mL |  | 16 |
| 4 | PrevPac | 31 mg/kg | 31 mg/kg | bid x 7 days | 16 |

TABLE 3-continued

| Group | Compound | Dose | Conc Dose Volume | Regimen | # animals[a] |
|---|---|---|---|---|---|
| 5 | Vehicle | na | na | bid x 7 days | 5 |
| 6 | Infection controls | na | na | bid x 7 days | 20 |

[a]8 animals each for therapeutic and relapse endpoints

TABLE 4

| Day | Procedure |
|---|---|
| −11 | Infection |
| −10 |  |
| −9 | Infection |
| −8 |  |
| −7 | Infection |
| 0 | Treatment & Control sample |
| 1 | Treatment |
| 2 |  |
| 3 |  |
| 4 |  |
| 5 |  |
| 6 |  |
| 7 | Day 7 sample |
| 14 | Day 14 sample |

Results

Mice are infected on three days with inoculums of 6.16, 6.6 and 6.37 log 10 CFU. One week following the last infection (Day 0— treatment initiated) mean stomach titers are 6.74 $\log_{10}$ CFU. Counts remain consistent over the next two weeks with mean titers for the untreated control groups of 6.86 and 6.66 $_{log10}$ CFU on days 7 and 14, respectively (see TABLE 5, which shows mean bacterial stomach tiers of H. pylori SS1 in mice following treatment with Nu-8 and Prevpac). Nu-8 exhibits a dose response with bacterial stomach tiers of 5.62, 5.21, and 4.74 on Day 7 and 6.2, 5.67, and 5.81 log 10 CFU on Day 14 for the dose solutions of 1, 5, and 10 mg/mL, respectively. Prevpac (e.g., clarithromycin, omeprazole and Amoxicillin) reduces bacterial titers to 3.22 $_{log10}$ CFU on Day 7 which rebounds to 6.19 $_{log10}$ CFU by Day 14. Although treatment with Nu-8 is less effective than the triple therapy regimen on Day 7, Nu-8 exhibits less of a rebound by Day 14 (7 days after the last administered dose) than Prevpac with lower counts for the 5 and 10 mg/mL dose groups (see TABLE 5). In summary, these results support the use of Nu-8 as a longer-term treatment of H. pylon infections, which such results would be expected against other gram negative bacteria.

TABLE 5

| Group | Test | Dose | Conc Dose Vol | Regimen | Time-points | Log10 | SD |
|---|---|---|---|---|---|---|---|
| 1 | Cp, [pim (I) | 0.2 mg | 1 mg/mL, 0.2 mL | PO, bid for 7 days | +7 Davs | 5.62 | 0.6 |
|   |   |   |   |   | +14 Days | 6.2 | 0.86 |
| 2 |   | 1.0 mg | 5 mg/mL, 0.2 mL | PO, bid for 7 days | +7 Days | 5.21 | 0.26 |
|   |   |   |   |   | +14 Days | 5.67 | 0.23 |
| 3 |   | 2 mg | 10 mg/mL, 0.2 mL | PO, bid for 7 days; | +7 Days | 4.74 | 0.68 |
|   |   |   |   |   | +14 Days | 5.81 | 0.74 |
| 4 | PREVPAC | 31 mg/kg | 31 mg/kg | PO, bid for 7 days | +7 Days | 3.22 | 0.52 |
|   |   |   |   |   | +14 Days | 6.19 | 0.69 |
| 5 | Vehicle Treated | na | na | PO, bid for 7 days | +7 Days | 6.59 | 0.12 |
|   |   |   |   |   | Day 0 | 6.74 | 0.37 |
| 6 | Untreated Controls | na | na | na |   |   |   |
|   |   |   |   | na | +7 Days | 6.86 | 0.54 |
|   |   |   |   | na | +14 Days | 6.66 | 0.76 |

EXAMPLE 6

Bacterial Cytological Profiling for Assessing Structure Activity Relationship of Nu-8 Compared with Bisphosphocin® Compounds Nu-3, Nu-4, and Nu-5

The structure of known Bisphosphocin® compound Nu-3 is shown below:

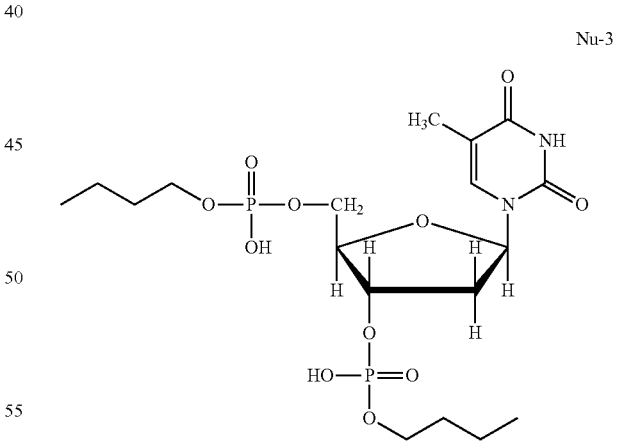

Nu-3

Methods and Materials

This bacterial cytological profiling (BCP) study uses methods and materials described previously by Nonejuie, P., Burkart, M., Poglianoa, K., Pogiano, J. (2013). Bacterial cytological profiling rapidly identifies the cellular pathways targeted by antibacterial molecules. Proc. Natl. Acad. Sci. U.S.A. 110(40):16169-16174. doi: 10.1073/pnas.1311066110.

Wild type strains of E. coli ATCC 25922 or P.aeruginosa K2732 are grown in rich media (unbuffered 2x Lysogeny broth [LB]) at 30 C to an OD600-0.4. These cultures are then split and each sample treated with the appropriate concentration of Nu-8 in unbuffered or buffered LB (final mixture $OD_{600}$~0.1). Cells exposed without Nu-8 are buffered to pH 4 with phosphoric acid.

The BCP is performed in LB media buffered to pH 4. The minimum inhibitory concentration (MIC) is measured for Nu-3, Nu-4, Nu-5, and Nu-8 against each bacterial strain. As one of ordinary skill in the art understands, minimum inhibitory concentrations are the lowest concentration of an antimicrobial that will inhibit the visible growth of a microorganism after overnight incubation. Cells are treated with each of Nu-3, Nu-4, Nu-5, and Nu-8 at three different concentrations (1, 0.5, and 0.25x MIC) and samples are collected at 30 min and 2 and 4 h for imaging. Cellular viability is assayed at three time points (5 minutes and 4 and 24 h following the onset of treatment).

For imaging *E. coli*, treated cells are stained with 1 μg/ML FM4-64, 2 μg/mL DAPI, and 0.5 μM SYTOXGreen (Molecular Probes/Invitrogen). *P.aeruginosa* samples are stained 0.5 μM SYTOX Green, 28 μg/mL DAPI, and 4.5 μg/mL FM 4-64. Cells are transferred to an agarose pad (20% LB, 1% agarose) for imaging as described in Pogliano, J., Osborne, N., Sharp, M. D., Abanes-De Mello, A., Perez, A., Sun, Y.-L. and Pogliano, K. (1999), A vital stain for studying membrane dynamics in bacteria: a novel mechanism controlling septation during *Bacillus subtilis* sporulation. Molecular Microbiology, 31: 1149-1159. doi:10.1046/j 0.1365-2958.1999.01255.x.

Results

The BCP results indicate that each of Nu-3, Nu-4, Nu-5, and Nu-8 affect the cell envelope in both *E coli* (ATCC 25922) and *P aeruginosa* (K2732). Treatment with Nu-3, Nu-4, Nu-5, and Nu-8 causes DNA condensation at higher treatment concentrations (buffered pH 4) for *E. coli* (ATCC 25922). Nu-4, Nu-5, and Nu-8 increase cell membrane permeability (buffered pH 4 or in unbuffered LB) for both *E. coli* (ATCC 25922) and *P. aeruginosa* (K2732), while Nu-3, Nu-4, and Nu-5 cause cell wall deformations (unbuffered LB) for *E. coli* (ATCC 25922). Treatment with Nu-8 manifests rapid and marked reduction in cell viability and is superior in effect to Nu-3, Nu-4, and Nu-5. Specifically, Nu-8 reduces cell viability to <102 CFU/mL within minutes from an initial CFU/mL of $10^9$. Nu-3, Nu-4 and Nu-5 also reduce CFU/mL to <102-3 at a slower rate within hours of treatment.

In summary, these results support the use of Nu-8 in treatment of infection in which a fast-acting antimicrobial mechanism is preferred, such as, for example, urinary tract infections and bacterial infections associated with diabetic foot ulcers, among others.

EXAMPLE 7

Bisphosphocin® Compounds Nu-3 and Nu-5 and Nu-8 Antimicrobial Efficacy at Incremental pH Increases Against *E. coli* and *P. aeruginosa*

MIC testing is conducted using the broth (Mueller Hinton Broth) microdilution procedures relevant to each organism group as established by the Clinical and Laboratory Standards Institute (CLSI; 3-7). MIC plates are prepared in accordance with CLSI (3-7). To prepare the test plates, automated liquid handlers are used to conduct serial dilutions and liquid transfers. Automated liquid handlers utilized in this study include the Multidrop 384 (Labsystems, Helsinki, Finland) and the Biomek 2000 (Beckman Coulter, Fullerton CA). The solution is diluted to desired pH using 1 M Citric Acid or 1 M NaOH buffer. A standardized inoculum of each test organism is prepared per CLSI methods (3,5-7) to equal a 0.5 McFarland standard in the appropriate media followed by an additional 1:20 dilution (1:10 for anaerobes).

The plates are then inoculated with 10 μL of the diluted 0.5 McFarland suspension using the Biomek 2000 from low to high drug concentration, resulting in a final concentration of approximately $5 \times 10^5$ CFU/mL per well. An un-inoculated plate is incubated for the purpose of assessing solubility of the drug in the test media. The plates are stacked 3 to 4 high, covered with a sterile lid on the top plate, and incubated for 18 to 24 hours according to CLSI. The MIC is recorded as the lowest concentration of respective compound that inhibited visible growth of the organism.

As demonstrated in TABLE 6, Nu-8 MIC efficacy is greater than Bisphosphocin® Compounds Nu-3 and Nu-5 at equivalent pH against *E. coli* and *P. aeruginosa*. Specifically, Nu-8 antimicrobial activity is better than Nu-3 and Nu-5 in pH range (pH 3-4) deemed important for clinical use in several administration routes, such as, for example, topical, inhalation, and intravesical.

TABLE 6

|  | pH 1 | pH 3 | pH 4 | pH 5 | pH 7 |
|---|---|---|---|---|---|
|  |  | (MIC) mg/mL |  |  |  |
| *E. coli* |  |  |  |  |  |
| Nu-3 | 12.5 | >100 | — | >100 | >100 |
| Nu-5 | 6.25 | 100 | — | 100 | 100 |
| Nu-8 | 9.8 | 37.5 | 75 | >75 | >75 |
| *P. aeruginosa* |  |  |  |  |  |
| Nu-3 | 12.5 | >100 | — | >100 | >100 |
| Nu-5 | 6.25 | 100 | — | 100 | 100 |
| Nu-8 | 9.38 | 18.75 | 37.5 | 75 | >75 |

EXAMPLE 8

Bacterial Cytological Profiling of Nu-3 Versus Nu-8 Against Gram Negative and Gram Positive Bacteria at pH 4, 5.5, and 7

Methods and Materials

This bacterial cytological profiling (BCP) investigation uses methods and materials described previously by Nonejuie, P., Burkart, M., Poglianoa, K., Pogiano, J. (2013). Bacterial cytological profiling rapidly identifies the cellular pathways targeted by antibacterial molecules. Proc. Natl. Acad. Sci. U.S.A. 110(40):16169-16174. doi: 10.1073/pnas.1311066110.

For viable cell counts, cells are grown to $OD_{600}$≈0.4 and diluted 1:1 into buffered or unbuffered media containing various compound concentrations. Samples are then collected and serially diluted (1:10) on a 96 well plate. Five microliters from each well are spotted on LB plates, incubated at 30° C., and viable cells are counted the next day.

Samples are collected at 10, 30, 120, and 240 min of exposure for viable cell count and imaging. For imaging, *E. coli* and *S. aureus* 200 μL of treated cells per time point are stained with 0.8 μg/mL FM4-64, 1.5 μg/mL DAPI, and 0.4 μM SYTOXGreen (Molecular Probes/Invitrogen). *P.aeruginosa* samples are stained 0.4 μM SYTOX Green, 28 μg/mL DAPI, and 1 μg/mL FM 4-64. Cells are transferred to an agarose pad (20% LB, 1% agarose) for imaging.

For Nu-3 and Nu-8 stocks (at pH 4, 5.5 and 7), stock concentration is 500 mg/mL. For pH 4, the stocks are prepared by dissolving Nu-3 in 25 mM citrate buffer and Nu-8 in 350 mM citric acid. For pH 5.5, the stocks are prepared by dissolving Nu-3 in 25 mM citric-phosphate and Nu-8 in 25 mM critic. For pH 7, the stocks are prepared by dissolving Nu-3 and Nu-8 in 25 mM Sorensen phosphate buffer. 2X LB (lysogeny broth) solutions are prepared with 50 mM citrate buffer for pH 4, 50 mM citrate-phosphate buffer for pH 5.5, and 50 mM Sorensen phosphate buffer for pH 7.

Results

Under the experimental conditions of BCP procedure performed at pH 4 and above, Nu-8 is more effective than Nu-3 (at equimolar concentrations) against wild type $E.\ coli$ (ATCC 25922), wild type $P.\ aeruginosa$ (PAO1; K2732), and methicillin susceptible $S.\ aureus$ (ATCC 29213) in rapidly altering cell viability, cell growth, and cell permeability over a range of exposure times, concentrations, and in buffered media (Linnaeus Bioscience 10-2-2017 Report). $E.\ coli$ in culture at pH 4, 5.5, and 7 without treatment is unaffected. $E.\ coli$ cell growth, cell viability, and cell permeability up to 24 h of the study remain consistent relative to similar parameters assayed at neutral pH. At pH 4, Nu-8 is more effective than Nu-3 at similar concentrations (112.5 and 225 mg/mL) markedly decreasing cell viability within 10 min of treatment (cell viability decreases from log $10^7$CFU/mL to <log $10^3$ CFU/mL), whereas Nu-3 at 112.5 mg/mL slows cell growth during 240 min of treatment leading to lower cell viability at 24 h (cell growth delay up to 240 min $10^7$ CFR/mL [pH 4 alone, cell growth at 240 min 108 CFU/mL] decreases to $10^{4.5}$ CFU/mL by 24 h), and at 225 mg/mL reduces cell viability within 240 min (<$10^3$ CFU/mL). Cell viability occurs before apparent changes in cell permeability are detected at 10 min of treatment. At pH 5.5 and 7, Nu-8 alters $E.\ coli$ cell permeability and reduces cell viability and growth whereas Nu-3 is ineffective.

$P.\ aeruginosa$ at pH 4 alone is rapidly affected with reduced cell growth and viability and increased maximal 100% cell permeability (within 10 to 30 min of treatment). At pH 5.5 and 7 alone, cell growth and cell viability, and cell permeability are unaffected (relative to similar parameters assayed at neutral pH). Nu-3 and Nu-8 at pH 4 are generally additive in effect to that observed at pH 4 alone and reduce cell viability. Nu-8 at 56.5 mg/mL is more effective in reducing cell viability (<$10^3$ CFU/mL) within 30 min relative to Nu-3 at twice the concentration (112.5 mg/mL), which reduces cell viability within 120 min (<$10^3$ CFU/mL). At 112.5 mg/mL, Nu-8 lowers cell viability within 10 min (<$10^3$ CFU/mL) beyond that occurring with a similar Nu-3 treatment as well as with pH 4 alone (~$10^6$ CFU/mL by 10 min). Also at pH 5.5 and 7, Nu-8 at 112.5 mg/mL is more active causing<20% increase in cell permeability and reduction in cell growth relative to Nu-3 at 112.5 mg/mL, which produces little change in cell permeability (<6%) and no effect on cell growth. At pH 7, only Nu-8 (225 mg/mL) increases cell permeability (~37% with 10 min) which subsequently is not persistent and cell growth is slightly lower than that at pH 7 alone.

$S.\ aureus$ at pH 4 alone exhibits reduced cell growth and cell viability and a slight increase in cell permeability (<8%). At pH 5.5 alone, cell growth is inhibited up to 240 min and later recovered by 24 h and cell permeability is unaffected. At pH 7, all cell parameters are unaffected. At pH 4, Nu-8 at 125 mg/mL slightly increases cell permeability (<4.3%) with enhanced killing activity (103 CFU/mL by 240 min from 1075 CFU/mL at study start, and <103 CFU/mL at 24 h) compared to cell viability at pH 4 alone (~$10^7$ CFU/mL at 240 min and 104 CFU/mL at 24 h). Nu-3 at 125 mg/mL produces low cell permeability (<10%) and slight reduction in cell growth resembling that at pH 4 alone. At 250 mg/mL, Nu-8 reduces cell viability within 10 min (~$10^4$ CFU/mL) without recovery later (<$10^3$ CFU/mL) and increases cell permeability (~60%). Nu-3 at 250 mg/mL is less active producing a slight increase in cell permeability (<10%) with reduced cell viability within 240 min to 24 h (<103 CFU/mL). At pH 5.5 and 7, both Nu-3 and Nu-8 (125 mg/mL and 250 mg/mL) slightly reduce cell growth up to 24 h with minimal effect on cell permeability (<5%).

In summary, this study demonstrates that Nu-8 will outperform Nu-3 across a pH range 3-4 planned for clinical use.

EXAMPLE 9

Nu-8 Antimicrobial Activity Against Strain Commonly Associated with Bacteria Bacterial strains evaluated in this study include $Escherichia\ coli$, $Klebsiella$ spp, $Serratia\ marcescens$, $Proteus\ mirabilis/vulgaris$, $Citrobacter$ spp, $Providencia$ spp, $Morganella\ morganii$, $Pseudomonas\ aeruginosa$, $Staphylococcus\ aureus$ (MRSA only), and $Enterococcus\ faecalis$. Nu-8 test solutions are adjusted to pH 3.5 with citric acid, and MIC is evaluated per the CLSI methods in Mueller-Hinton broth supplemented accordingly to facilitate growth of specific strains.

MICs of the Nu-8 at pH 3.5 are measured in human and mouse urine and are comparable to those of Nu-8 in Mueller Hinton broth under similar conditions. TABLE 7 demonstrates Nu-8 MIC against the bacterial strains identified therein.

TABLE 7

| Test Organisms (# of isolates) | Nu-8 MIC (mg/mL) at pH 3.5 ($MIC_{50}$ and $MIC_{90}$) |
|---|---|
| Gram-negative | |
| $Escherichia\ coli$ (5) | 37.5 |
| $Klebsiella\ pneumoniae$ (5) (includes | 37.5-75 |
| $Serratia\ marcescens$ (5) | 37.5-75 |
| $Proteus\ mirabilis/vulgaris$ (5) | 4.69-18.75 |
| $Citrobacter$ species (5) | 18.75-37.5 |
| $Providencia$ species (5) | 9.38-37.5 |
| $Morganella\ morganii$ (5) | 18.75 |
| $Haemophilus\ influenzae$ (5) | 4.69-9.38 |
| Other | |
| $Pseudomonas\ aeruginosa$ (20) | 9.38-18.75 (18.75 and 18.75) |
| Gram-positive | |
| $Staphylococcus\ aureus$ (20) (MRSA | 9.38-37.5 (18.75 and 37.5) |
| $Enterococcus\ faecalis$ (5) (both VSE | 4.69-18.75 |
| $Streptococcus\ pneumoniae$ (PRSP) | 9.38-18.75 |

The MICs are also determined using lysogeny broth (LB) at pH 4 as the growth medium. Under these conditions, Nu-8 is active against $E.\ coli$ and $P.\ aeruginosa$ with MICs of 54 and 27 mg/mL, respectively.

In summary, these results demonstrate that Nu-8 is effective against gram negative and gram-positive bacteria, which is deemed important for clinical use in several administration routes, such as, for example, topical, inhalation, and intravesical.

EXAMPLE 10

Initial Efficacy Evaluation of Nu-8 Against *Escherichia Coli* in a Urinary Tract Infection Model in BALB/c Mice Female BALB/c mice (20-22 g) ordered from Envigo are acclimated to housing conditions and handled in accordance with Animal Use Protocol (AUP) number TP-08. Animals are fed irradiated Teklad Global 29 18 Rodent Diet and water ad libitum. Mice are housed 6/cage in static cages with irradiated ⅛" Teklad corn cobbedding 7902 inside bioBubble® clean rooms that provide H.E.P.A filtered air into the bubble environment at 100 complete air changes per hour. The environment is controlled to a temperature range of 74°±4° F. and a humidity range of 30-70%. All procedures carried out in this experiment are conducted in compliance with the laws, regulations, and guidelines of the National Institutes of Health and with the approval of the TransPharm Preclinical Solutions Animal Care and Use Committee.

A clinical isolate of *Escherichia coli* (strain CFT073, TPPS 1041) are procured from the University of Michigan.

The organism is grown overnight at 37° C. in ambient atmosphere on trypticase soy agar plates supplemented with 5% sheep blood cells. The culture is aseptically swabbed and transferred to tubes of trypticase soy broth. The optical density is determined at 600 nm. The culture is diluted to provide an inoculum of approximately 7.5 $\log_{10}$ CFU per mouse in a volume of 30 µL. Instillation of the bacterial challenge constituted time 0 hour for the study. Inoculum counts are estimated before inoculation by optical density and confirmed after inoculation by dilution and back counts.

One hour prior to bacterial challenge, water is removed from animal cages. On Day 0 at 0 hours, mice are anesthetized using isoflurane and urine is expressed from the bladder by applying gentle pressure to the abdomen with the thumb. Mice are infected with bacteria via transurethral injection in a volume of 30 µL. Water is returned to the cages immediately following the challenge. Challenge is performed in a BL2 surgical suite. The final count of the challenge inoculum demonstrated a delivered burden of 7.8 $\log_{10}$ organisms per mouse.

Nu-8 (Test article) is prepared immediately before each dosing. Nu-8 is dissolved in sterile saline and adjusted to pH 3.5 with phosphoric acid. At 23 hours post-challenge, water is removed from animal cages. One hour later, mice are anesthetized using isoflurane and residual urine is expressed from the bladder. Mice are treated with test article or controls via transurethral dosing in a volume of 30 µL, according to TABLE 8 (showing Animal Challenge and Treatment Schedule). Harvest time is the time when the mice organs are processed. All treatments are administered in a BSL2 surgical suite. Immediately following treatment administration, the urethral opening is occluded using a cyanoacrylate tissue ad.

TABLE 8

| | | Challenge | | Treatment | | | Har- |
|---|---|---|---|---|---|---|---|
| Grp | N | E. Coli | ROA | Description | ROA | Dose (mg/kg) | Dose vest TimeTime[a] |
| 1 | 6 | 7.5 $\log_{10}$ | Trans-urethral | Saline pH 3.5 | Trans-urethral | NA | 24 hr 60 min |
| 2 | | | | Gentamicin | | 50 | 60 min |
| 3 | | | | Nu-8 pH 3.5 | | 1025 | 20 min |
| 4 | | | | Nu-8 pH 3.5 | | 1025 | 60 min |

[a] Relative to challenge at 0 hour

The primary endpoint used to assess progress of the infection is mean bacterial burden per gram of urinary bladder tissue. At 60 or 20 minutes following treatment administration and urethral occlusion, mice are euthanized by $CO_2$ asphyxiation. The urinary bladder is aseptically removed, weighed, and homogenized in 1 mL TSB using a mini bead-beater. The resulting homogenate is serially diluted (neat to 10-7) and grown overnight at ° C. on ambient atmosphere trypticase soy agar plates supplemented with 5% sheep blood cells. Colony forming units (CFU) are enumerated and the total bacterial burden per gram of urinary bladder tissue homogenate is calculated.

The geometric mean CFU, along with standard error of the mean (SEM), are calculated using Microsoft Excel and bar charts are prepared for the data using GraphPad Prism v. 7.0.

Statistical comparisons are made between groups by comparing the geometric mean bacterial burden of different treatment groups in Excel, using a Student's t-test assuming unequal variance. Two-tailed P-values≤0.05 are considered significant.

At 60 minutes post-treatment, vehicle-treated mice in Group 1 demonstrated an average bladder CFU burden of 5.3 $\log_{10}$, while gentamicin-treated animals in Group 2 showed 6.1 $\log_{10}$ CFU. At 20 minutes post-treatment, mice treated with Nu-8 showed a significant decrease in mean bladder CFU burden (2.9 $\log_{10}$) when compared to the vehicle-treated control group. At 60 minutes, these mice showed a burden of 3.7 $\log_{10}$ CFU.

In summary, Nu-8 showed a statistically significant decrease in *E. coli* in animal bladders in 20 minutes post-treatment, which confirms Nu-8 is effective against *E. Coli* in a urinary tract infection animal model. These results are a predictive model for human therapies.

EXAMPLE 11

Confirmatory Efficacy Evaluation of Nu-8 Against *Escherichia Coli* in a Urinary Tract Infection Model in BALB/c Mice Female BALB/c mice (20-22 g) ordered from Envigo are acclimated to housing conditions and handled in accordance with Animal Use Protocol (AUP) number TP-08. Animals are fed irradiated Teklad Global 29 18 Rodent Diet and water ad libitum. Mice are housed 6/cage in static cages with irradiated ⅛" Teklad corn cobbedding 7902 inside bioBubble® clean rooms that provide H.E.P.A filtered air into the bubble environment at 100 complete air changes per hour. The environment is controlled to a temperature range of 74°±4° F. and a humidity range of 30-70%. All procedures carried out in this experiment are conducted in compliance with the laws, regulations, and guidelines of the National Institutes of Health and with the approval of the TransPharm Preclinical Solutions Animal Care and Use Committee.

A clinical isolate of *Escherichia coli* (strain CFT073, TPPS 1041) are procured from the University of Michigan.

The organism is grown overnight at 37° C. in ambient atmosphere on trypticase soy agar plates supplemented with 5% sheep blood cells. The culture is aseptically swabbed and transferred to tubes of trypticase soy broth. The optical density is determined at 600 nm. The culture is diluted to provide an inoculum of approximately 7.5 $\log_{10}$ CFU per mouse in a volume of 30 μL. Instillation of the bacterial challenge constituted time 0 hour for the study. Inoculum counts are estimated before inoculation by optical density and confirmed after inoculation by dilution and back counts.

One hour prior to bacterial challenge, water is removed from animal cages. On Day 0 at 0 hours, mice are anesthetized using isoflurane and urine is expressed from the bladder by applying gentle pressure to the abdomen with the thumb. Mice are infected with bacteria via transurethral injection in a volume of 30 μL. Water is returned to the cages immediately following the challenge. Challenge is performed in a BL2 surgical suite. The final count of the challenge inoculum demonstrated a delivered burden of 7.8 $\log_{10}$ organisms per mouse.

Nu-8 (Test article) is prepared immediately before each dosing. Nu-8 is dissolved in sterile saline and adjusted to pH 3.5 with phosphoric acid. At 23 hours post-challenge, water is removed from animal cages. One hour later, mice are anesthetized using isoflurane and residual urine is expressed from the bladder. Mice are treated with test article or controls via transurethral dosing in a volume of 30 μL according to TABLE 9 (showing Animal Challenge and Treatment Schedule). All treatments are administered in a BSL2 surgical suite.

Immediately following treatment administration, the urethral opening is occluded using Locktite gel superglue. One drop of glue is placed at the urethral opening and the opening is held together for 5-10 seconds using tissue forceps to ensure the urethral opening is occluded and the adhesive is dry. Animals remained under anesthetic following urethral occlusion. Mice are rotated (front to back) every 5 minutes while under anesthesia.

TABLE 9

| | | Challenge | | Treatment | | | Har- |
|---|---|---|---|---|---|---|---|
| Grp | N | E. Coli | ROA | Description | ROA | Dose (mg/kg) | Dose vest Time Time[a] |
| 1 | 6 | 7.5 $\log_{10}$ | Transurethral | PBS pH 3.5 | Transurethral | NA | 24 hr / 20 min |
| 2 | | | | Nu-8 pH 3.5 | | 205 | 20 min |
| 3 | | | | Nu-8 pH 3.5 | | 410 | 20 min |
| 4 | | | | Nu-8 pH 3.5 | | 820 | 10 min |
| 5 | | | | Nu-8 pH 3.5 | | 820 | 20 min |

[a]Relative to challenge at 0 hour

The primary endpoint used to assess progress of the infection is mean bacterial burden per gram of urinary bladder tissue. At 10 or 20 minutes following treatment administration and urethral occlusion, mice are euthanized by $CO_2$ asphyxiation. The abdominal cavity is dissected to expose the bladder and the urethra is clamped near the bladder to prevent urine leakage. Care is taken not to express urine from the bladder during removal by cutting the urethra distal to the lamp. The bladder (with urine) is aseptically removed and transferred to a pre-weighed vial with 1 mL TSB. The bladder is then cut to release urine into the vial along with the tissue. The tissue is weighed and homogenized using a mini-bead beater. The resulting homogenate is serially diluted (neat to 10-7), plated in 5 μL duplicate spots, and grown overnight at 37° C. in ambient atmosphere on trypticase soy agar plates supplemented with 5% sheep blood cells. The undiluted (neat) homogenate is also plated in 100 μL volume for each sample. Colony forming units (CFU) are enumerated and the total bacterial burden per gram of urinary bladder tissue homogenate is calculated.

The geometric mean CFU, along with standard error of the mean (SEM), are calculated using Microsoft Excel, and bar charts are prepared for the data using GraphPad Prism v.7.0. Statistical comparisons are made between groups by comparing the geometric mean bacterial burden of different treatment groups in Excel, using a Student's t-test assuming unequal variance. Two-tailed P-values≤0.05 are considered significant.

At 10 minutes post-treatment, animals treated with 820 mg/kg Nu-8 showed an average bladder CFU burden of 6.3 log 10.

At 20 minutes post-treatment, vehicle-treated mice in Group 1 demonstrated an average of 6.8 log 10 CFU/g tissue. Mice which received Nu-8 at 205, 410, and 820 mg/kg showed bacterial burdens of 6.5, 5.0, and 5.4 log 10, respectively.

In summary, Nu-8 showed a decrease in *E. coli* in animal bladders in 20 minutes post-treatment, which confirms Nu-8 is effective against *E. Coli* in a urinary tract infection animal model. These results are a predictive model for human therapies.

EXAMPLE 12

Urinary Tract Infection (UTI) Model in Rats Induced by *Escherichia coli* with Transurethral Treatment Female Sprague-Dawley rats (n=6/group) are intraurethrally infected with the pre-determined inoculum size of *E. coli*. At the specified time following infection with (depending on the in vivo growth curve), the animals are anaesthetized (ketamine/xylazine) and treated by transurethral administration with neutral saline (group 1), saline pH 3.5 adjusted with phosphoric acid (group 2), test compound Nu-8 pH 3.5 at 103 and 207 mg/kg (groups 3 and 4, respectively). When adjusting pH, the volume of phosphoric acid added are monitored and the final concentration of the pH adjusted dose solution are subsequently determined. The goal is to have the final concentration after pH adjustment within 10% of the desired dose so the final concentration after pH adjustment are reported. Volume of administration will be 300 μL. TABLE 10 (Animal Challenge and Treatment Schedule) summarizes the study groups.

TABLE 10

| | | Inoculum size CFU/300 μL/rat (*E. coli* ATCC25922) | | Treatment 4 hrs post | Terminal procedures (urine sampling directly |
|---|---|---|---|---|---|
| Group No | N | 1st Infection | 2nd Infection | 2nd infection (300 μL intraurethrally) | from bladder) |
| 1 | 10 | 1 × 10^8 | 1 × 10^8 | Control saline neutral pH | 60 minutes post |
| 2 | 10 | | | Control saline pH 3.5 | |

TABLE 10-continued

| | | Inoculum size CFU/300 µL/rat (*E. coli* ATCC25922) | | Treatment 4 hrs post | Terminal procedures (urine sampling directly |
|---|---|---|---|---|---|
| Group No | N | 1st Infection | 2nd Infection | 2nd infection (300 µL intraurethrally) | from bladder) |
| 3 | 10 | | | Nu-8 pH 3.5; 103 mg/kg | treatment |
| 4 | 10 | | | Nu-8 pH 3.5; 207 mg/kg | |

Two hours prior to each infection animals are water deprived. Each animal is infected twice with 24 hrs difference by transurethral administration of 300 µL of bacterial suspension under light ketamine and xylazine anaesthesia. Prior to infection, urine is evacuated by digital pressure, cannula is gently inserted into the bladder via urethra and 300 µL, of bacterial suspension is inserted into the bladder. After infection cannula is gently removed, the animal is held in upside down position for 1 min, then placed into a cage.

Animals from all groups are sacrificed by exsanguination on K2EDTA anticoagulant (under ketamine/xylazine anaesthesia) 60 minutes following treatment, and urine are sampled under sterile conditions for CFU determination.

The mean CFU log 10 per mL of bladder tissue (tissue plus urine) per group was 5.67, 5.53 and 4.60 Log 10 CFUs/mL bladder tissue for pH 3.5 solutions of saline, and Nu-8 doses of 103 mg/kg and 207 mg/kg at 60 min, respectively. The Log 10 CFUs/mL bladder tissue for saline control at pH 7 was 5.51. Statistically significant reduction in CFU counts is observed in group treated with Nu-8 at a dose of 207 mg/kg BW as compared to saline pH3.5 control group. There is no statistically significant difference in CFU counts between groups treated with Nu-8 and saline pH 7 control group.

In summary, this rat study confirms the mouse studies shown in in EXAMPLES 10 and 11, all of which demonstrate that Nu-8 shows a statistically significant decrease in *E. coli* in animal bladders in 20 minutes post-treatment. The results of this study again confirms that Nu-8 is effective against *E. Coli* in a urinary tract infection animal model. These results are a predictive model for human therapies.

EXAMPLE 13

Nu-8 Treatment of Human Patient Having Complicated Urinary Tract Infection

A human patient is identified as having a complicated urinary tract infection. A pharmaceutical composition in the form of a liquid solution containing an effective amount of Nu-8 is administered intravesically to the patient via a catheter. The patient is monitored until symptoms are alleviated or ameliorated, and the pharmaceutical composition may be administered one or more additional times if it is determined that such administration is necessary or helpful for treatment.

EXAMPLE 14

Nu-8 Treatment of Human Patient Having a Lung Infection Arising from Cystic Fibrosis A human patient is identified as having a lung infection arising from cystic fibrosis. A pharmaceutical composition in the form of a liquid solution containing an effective amount of Nu-8 is administered inhalationally to the patient via a nebulizer. The patient is monitored until symptoms are alleviated or ameliorated, and the pharmaceutical composition may be administered one or more additional times if it is determined that such administration is necessary or helpful for treatment.

EXAMPLE 15

Nu-8 Treatment of Human Patient Having an Infection of a Diabetic Foot Ulcer

A human patient is identified as having a diabetic foot ulcer. A pharmaceutical composition in the form of a gel containing an effective amount of Nu-8 is administered topically to the patient at the location of the diabetic foot ulcer. The patient is monitored until symptoms are alleviated or ameliorated, and the pharmaceutical composition may be administered one or more additional times if it is determined that such administration is necessary or helpful for treatment.

EXAMPLE 16

Nu-8 Treatment of Human Patient Having Ventilator Acquired Pneumonia

A human patient is identified as having ventilator acquired pneumonia. A pharmaceutical composition in the form of a liquid solution containing an effective amount of Nu-8 is administered inhalationally to the patient via a nebulizer. The patient is monitored until symptoms are alleviated or ameliorated, and the pharmaceutical composition may be administered one or more additional times if it is determined that such administration is necessary or helpful for treatment.

EXAMPLE 17

Nu-8 Treatment of Human Patient Having an Infection in a Burn Wound

A human patient is identified as having an infection in a burn wound. A pharmaceutical composition in the form of a gel containing an effective amount of Nu-8 is administered topically to the patient at the location of the burn wound. The patient is monitored until symptoms are alleviated or ameliorated, and the pharmaceutical composition may be administered one or more additional times if it is determined that such administration is necessary or helpful for treatment.

EXAMPLE 18

Nu-8 Treatment of Human Patient Having Impetigo

A human patient is identified as having impetigo. A pharmaceutical composition in the form of a gel containing an effective amount of Nu-8 is administered topically to the patient at the location of the vesicles, pustules and/or yellowish crusts. The patient is monitored until symptoms are alleviated or ameliorated, and the pharmaceutical composition may be administered one or more additional times if it is determined that such administration is necessary or helpful for treatment.

EXAMPLE 19

Nu-8 Treatment of Human Patient Having Otitis Externa

A human patient is identified as having otitis externa. A pharmaceutical composition in the form of a liquid solution containing an effective amount of Nu-8 is administered topically directly into the patient's external ear canal. The patient is monitored until symptoms are alleviated or ameliorated, and the pharmaceutical composition may be administered one or more additional times if it is determined that such administration is necessary or helpful for treatment.

EXAMPLE 20

Nu-8 Treatment of Female Human Patient Having Bacterial Vaginosis

A female human patient is identified as having bacterial vaginosis. A pharmaceutical composition in the form of a gel containing an effective amount of Nu-8 is administered topically onto or into the patient's vagina. The patient is monitored until symptoms are alleviated or ameliorated, and the pharmaceutical composition may be administered one or more additional times if it is determined that such administration is necessary or helpful for treatment.

EXAMPLE 21

Preparation of ((2R,3S,5R)-5-(4-amino-2-oxopyrimidin-1(2H)-yl)-3-((hydroxy(isobutoxy)phosphoryl)-oxy)tetrahydrofuran-2-yl)methyl isobutyl hydrogen phosphate (LAI-101)

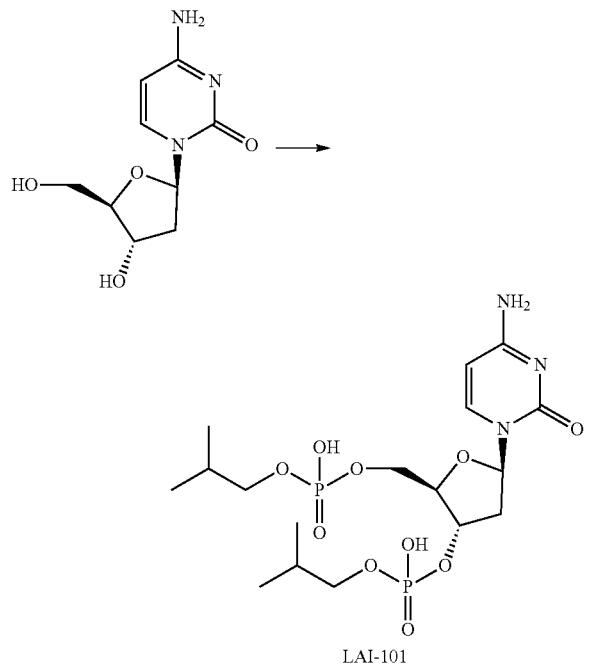

LAI-101

To a stirred solution of 4-amino-1-((2R,4S,5R)-4-hydroxy-5-(hydroxymethyl) tetrahydrofuran-2-yl)pyrimidin-2 (1H)-one (Cas No 951-77-9) (2.5 g, 11.00 mmol) in trimethyl phosphate (25 ml) with 4A molecular sieve (w/w) was added phosphorous oxychloride (2.5 ml, 26.40 mmol) at 0° C. under a $N_2$ atmosphere and stirred at 0° C. for 2 h. Then isobutanol (3 ml, 33.00 mmol) was added to the reaction mixture and the reaction was stirred at 0° C. for another 2 h. The reaction was monitored by LCMS and after completion the reaction mixture was poured into diethyl ether (500 ml) and quenched with 10% saturated sodium bicarbonate solution (30 ml). The aqueous layer was acidified by 1N HCl (15 ml) to pH~2.0 and lyophilized to obtain the crude compound which was purified by preparative HPLC to afford LAI-101 (501.96 mg, 9% yield) as a white solid.

Preparative HPLC Conditions: Column/dimensions: SUN FIRE $C_{18}$(19*150 mm), 5μ; mobile phase A: 0.1% TFA in water; mobile phase B: $CH_3CN$; flow rate: 18 ml/min; gradient (Time/% B): 0/5, 1/5, 12/30, 12.1/100, 16/100, 16.1/5, 18/5; solubility: $CH_3CN$+THF; LCMS: 91%; 500.48 [M+H]+; UPLC: 92%; 1H NMR (400 MHz, DMSO-d6): δ 8.02 (s, 1H), 7.82 (d, J=7.2 Hz, 1H), 7.57 (s, 1H), 6.08 (t, J=6 Hz, 1H), 5.81 (d, J=7.6 Hz, 1H), 4.77 (s, 1H), 4.10-4.00 (m, 3H), 3.78-3.64 (m, 1H), 3.63-3.49 (m, 4H), 2.39-2.32 (m, 1H), 2.27-2.25 (m, 1H), 1.85-1.77 (m, 2H), 0.91-0.84 (m, 12H).

EXAMPLE 22

Preparation of ((2R,3S,5R)-5-(4-amino-2-oxopyrimidin-1(2H)-yl)-3-(((benzyloxy)(hydroxy)-phosphoryl)oxy)tetrahydrofuran-2-yl)methyl benzyl hydrogen phosphate (LAI-102)

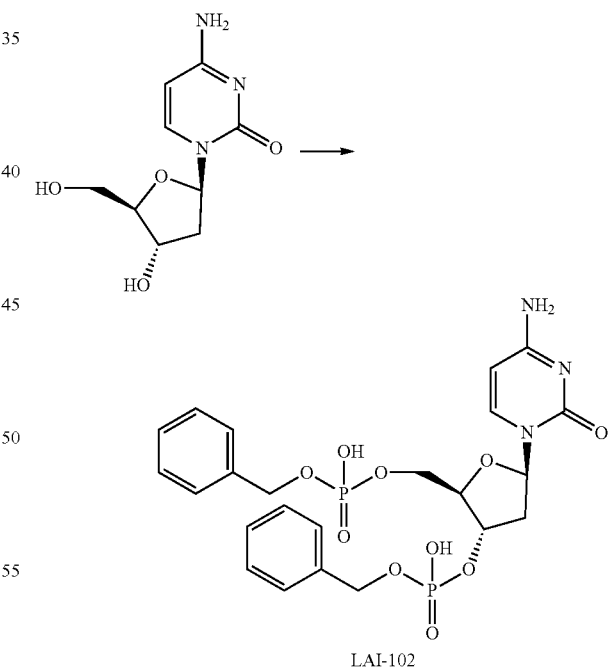

LAI-102

To a stirred solution of 4-amino-1-((2R,4S,5R)-4-hydroxy-5-(hydroxymethyl) tetrahydrofuran-2-yl)pyrimidin-2 (1H)-one (Cas No 951-77-9) (2.5 g, 11.00 mmol) in trimethyl phosphate (25 ml) with 4A molecular sieve (w/w) was added phosphorous oxychloride (5.14 ml, 55.01 mmol) at 0° C. under a $N_2$ atmosphere and stirred 0° C. for 2 h. Then benzyl alcohol (5.7 ml, 55.01 mmol) was added, and reaction mixture was stirred at 0° C. for another 2 h. The reaction mixture was monitored by LCMS and after completion the reaction mixture was poured in diethyl ether (500 ml) and quenched with 10% saturated sodium bicarbonate solution (30 ml). The aqueous layer was acidified with IN HCl (15 ml) to 2.0 and lyophilized to obtain the crude compound which was purified by preparative HPLC to afford LAI-102 (550 mg, 7.2% yield) as a white solid.

Preparative HPLC conditions: Column/dimensions: Luna omega (19*250, 5um); mobile phase A: 0.1% TFA in water; mobile phase B: CH$_3$CN; gradient (Time/% B): 0/5, 2/5, 6/20, 16/20, 16.1/100, 20/100, 20.1/5, 23/5; flow rate: 18 ml/min; solubility: THF; LCMS: 95%; 568.33 [M+H]$^+$; UPLC: 93%; $^1$H NMR 400 MHz, DMSO-d6: δ 8.49 (bs, 1H), 7.91-7.84 (m, 2H), 7.37-7.27 (m, 10H), 6.06 (t, J=6.4 Hz, 1H), 5.87 (d, J=7.6 Hz, 1H), 4.93-4.80 (m, 5H), 4.17-3.90 (m, 3H), 2.38-2.32 (m, 1H), 2.29-2.26 (m, 1H).

EXAMPLE 23

Preparation of ((2R,3R,4R,5R)-5-(4-amino-2-oxopyrimidin-1(2H)-yl)-3-((butoxy(hydroxy)phosphoryl)oxy)-4-methoxytetrahydrofuran-2-yl)methyl butyl hydrogen phosphate (Nu-10)

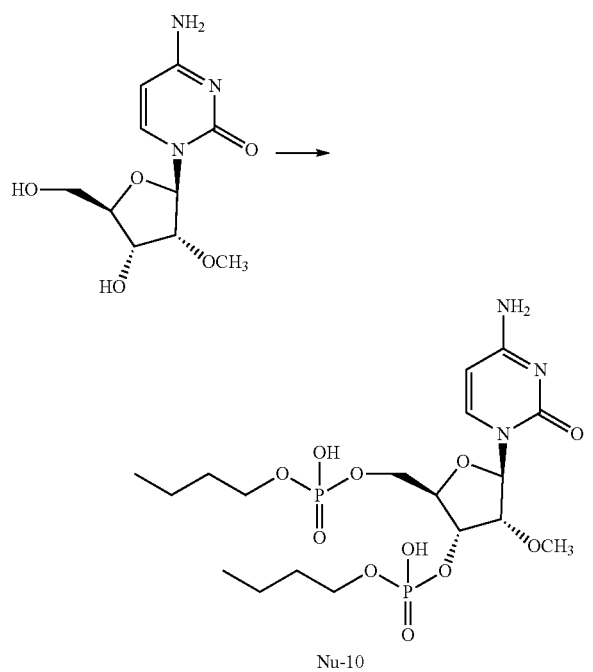

Nu-10

To a stirred solution of 4-amino-1-42R,3R,4R,5R)-4-hydroxy-5-(hydroxymethyl)-3-methoxytetrahydrofuran-2-yl)pyrimidin-2(1H)-one (Cas No: 2140-72-9) (3 g, 11.66 mmol) in trimethyl phosphate (30 ml) with 4A molecular sieve (w/w) was added phosphorous oxychloride (5.5 ml, 58.32 mmole) at 0° C. under a N$_2$ atmosphere and stirred at 0° C. for 2 h. Then 1-butanol (5.33 ml, 58.32 mmol) was added to the reaction mixture and was stirred at 0° C. for another 2 h.

The reaction was monitored by LCMS and after completion the reaction mixture was poured into diethyl ether (600 ml) and quenched with 10% saturated sodium bicarbonate solution (36 ml). The aqueous layer was acidified with 1N HCl (18 ml) to pH~2.0 and lyophilized to obtain crude compound which was purified by preparative HPLC to afford Nu-10 (530 mg, 6% yield) as a white solid.

Preparative HPLC Conditions: Column/dimensions: Luna omega (19*250, 5 um); mobile phase A: 0.1% TFA in water; mobile phase B: CH$_3$CN; gradient (Time/% B): 0/10, 1/10, 5/25, 12/25, 12.1/100, 14/100, 14.1/10, 17/10; flow rate: 18 ml/min; solubility: THF; LCMS: 99%; 530.37 [M+H]$^+$; UPLC: 98%; $^1$H NMR (400 MHz, DMSO-d6): δ 9.00 (bs, 1H), 8.08 (d, J=8 Hz, 2H), 5.94 (d, J=7.6 Hz, 1H), 5.76 (m, 1H), 4.56-4.53 (m, 1H), 4.17-4.12 (m, 3H), 3.97-3.96 (m, 1H), 3.85-3.46 (m, 4H), 3.41 (s, 3H), 1.58-1.49 (m, 4H), 1.36-1.28 (m, 4H), 0.90-0.85 (m, 6H).

EXAMPLE 24

Preparation of ((2R,3S,5R)-5-(6-amino-9H-purin-9-yl)-3-(((cyclohexyloxy)(hydroxy)phosphoryl)oxy)tetrahydrofuran-2-yl)methyl cyclohexyl hydrogen phosphate (LAI-105)

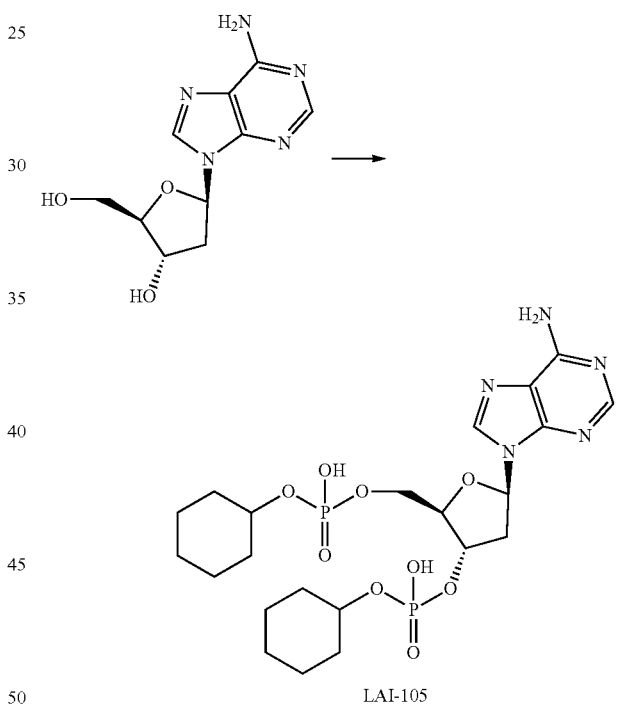

LAI-105

To a stirred solution of (2R,3S,5R)-5-(6-amino-9H-purin-9-yl)-2-(hydroxymethyl) tetrahydrofuran-3-ol (Cas No 961-07-9) (3.5 g, 13.93 mmol) in trimethyl phosphate (35 ml) with 4A molecular sieve (w/w) was added phosphorous oxychloride (6.5 ml, 69.65 mmol) at 0° C. under a N$_2$ atmosphere and stirred at 0° C. for 2 h. Then cyclohexanol (6.4 ml, 69.65 mmol) was added and reaction mixture was stirred at 0° C. for another 2 h. The reaction was monitored by LCMS and after completion the reaction mixture was poured into diethyl ether (700 ml) and quenched with 10% saturated sodium bicarbonate solution (42 ml). The aqueous layer was acidified with 1N HCl (21 ml) at pH~2.0 and lyophilized to obtain the crude compound which was purified by preparative HPLC to afford LAI-105 (325 mg, 4%) as a white solid.

Preparative HPLC Conditions: Column/dimensions: GEMINI NX C18 (21.5*250 mm 5 μm); mobile phase A: 0.1% TFA in water (aq); mobile phase B: Acetonitrile (org); gradient (Time/% B): 0/10, 1/10, 10/45, 11.49/45, 11.50/100, 13/100, 13.10/10, 14.50/10; flow rate: 18 ml/min; solubility: Acetonitrile+THF; LCMS: 99%; 576.39 [M+H]$^+$; UPLC: 96%; $^1$H NMR (400 MHz, DMSO-d6): δ 8.36 (s, 1H), 8.19 (s, 1H), 7.60 (bs, 2H), 6.39 (t, J=7.2 Hz, 1H), 4.27-4.26 (m, 1H), 4.20-4.19 (m, 1H), 4.13-4.12 (m, 2H), 4.04-4.00 (m, 1H), 3.00-2.97 (m, 1H), 2.51-5.49 (m, 1H), 1.86-1.78 (m, 4H), 1.68-1.65 (m, 4H), 1.17-1.35 (m, 12H).

EXAMPLE 25

Preparation of ((2R,3R,4R,5R)-5-(6-amino-9H-purin-9-yl)-3-((butoxy(hydroxy)phosphoryl)oxy)-4-methoxytetrahydrofuran-2-yl)methyl butyl hydrogen phosphate (LAI-106)

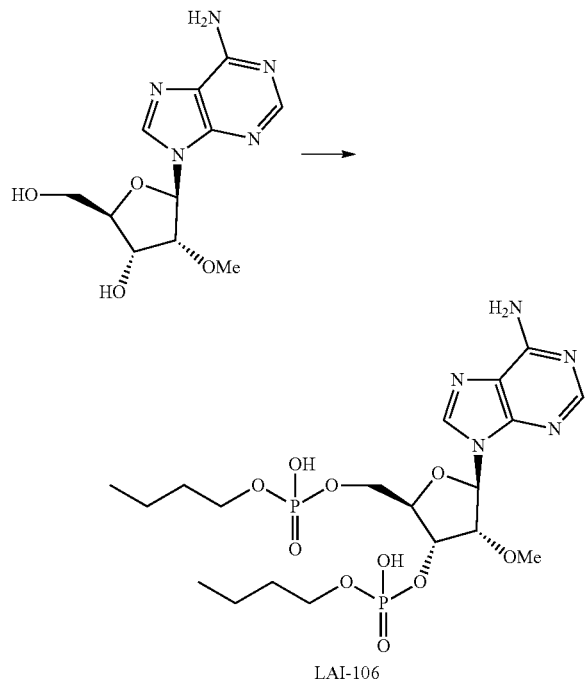

LAI-106

To a stirred solution of (2R,3R,4R,5R)-5-(6-amino-9H-purin-9-yl)-2-(hydroxymethyl)-4-methoxytetrahydrofuran-3-ol (Cas No 2140-79-6) (5.0 g, 17.78 mmol) in trimethyl phosphate (50 ml) with 4A molecular sieve (w/w) was added phosphorous oxychloride (8.4 ml, 88.88 mmol) at 0° C. under a N$_2$ atmosphere and stirred at 0° C. for 2 h. Then n-butanol (8.1 ml, 88.88 mmol) was added, and reaction mixture was stirred at 0° C. for another 2 h. The reaction was monitored by LCMS and after completion the reaction mixture was poured in diethyl ether (1000 ml) and quenched with 10% saturated sodium bicarbonate solution (75 ml). The aqueous layer was acidified with 1N HCl (40 ml) at pH=2.0 and lyophilized to obtain crude compound which was purified by reverse phase purification (REVELERIS RP FLASH CARTRIDGE 120G; 20% CH$_3$CN in 0.1% FA in water) to afford LAI-106 (1.6 g, 16% yield) as a white solid.

LCMS: 91%; 554.38 [M+H]$^+$; UPLC: 92%; $^1$H NMR (400 MHz, DMSO-d6): δ 8.40 (s, 1H), 8.21 (s, 1H), 7.68 (bs, 2H), 6.05 (d, 1H), 5.09-4.98 (m, 1H), 4.61-4.32 (m, 1H), 4.35-4.36 (m, 1H), 4.20-4.05 (m, 2H), 3.93-3.80 (m, 4H), 3.38 (s, 3H), 1.58-1.48 (m, 4H), 1.36-1.27 (m, 4H), 0.90-0.82 (m, 6H).

EXAMPLE 26

Single-Cell Antimicrobial Activity of LAI-101, LAI-102, Nu-10, LAI-105, and LAI-106

MIC was determined as per Example 9 using LAI-101, LAI-102, Nu-10, LAI-105, LAI-106, Nu-3, and Nu-8 against a single isolate of *Escherichia coli, Pseudomonas aeruginosa, Staphylococcus aureus* (MRSA only), and *Candida Albicans*. The MIC results are provided in Table 11. For all microbe species, the LAI-101, LAI-102, Nu-10, LAI-105, and LAI-106 all perform at least as well as, and in many experiments better than, Nu-8 and Nu-3, which are both already quite active compounds.

TABLE 11

| Compound | E. coli MIC (mg/mL) | P. aeruginosa MIC (mg/mL) | S. aureus MIC (mg/mL) | C. Albicans MIC (mg/mL) |
|---|---|---|---|---|
| LAI-101 | 5 | 5 | 5 | 50 |
| LAI-102 | 5 | 25 | 25 | 50 |
| Nu-10 | 1 | 5 | 5 | 5 |
| LAI-105 | >5 | 5 | >5 | >5 |
| LAI-106 | 1 | 5 | 5 | 25 |
| Nu-3 | 25 | 25 | >50 | 25 |
| Nu-8 | >50 | >50 | >50 | >50 |

EXAMPLE 27

Cell Population Antimicrobial Activity of Nu-10, Nu-8, and Nu-3

Log$_{10}$ 5 CFU of *E. coli* (ATCC 25922) were suspended in saline. Additionally, a sample of the saline only was prepared as a vehicle control (V.C.). Solutions of Nu-3, Nu-8, and Nu-10 at varying concentrations were adjusted to pH 3.5 with citric acid and added to the *E. coli* suspensions. At each time point (0, 1, 2.5, 5, 10, and 20 minutes), the treated bacterial suspensions were plated and incubated for 24 hrs, and each plate was read to determine the CFU count.

Figure 2:
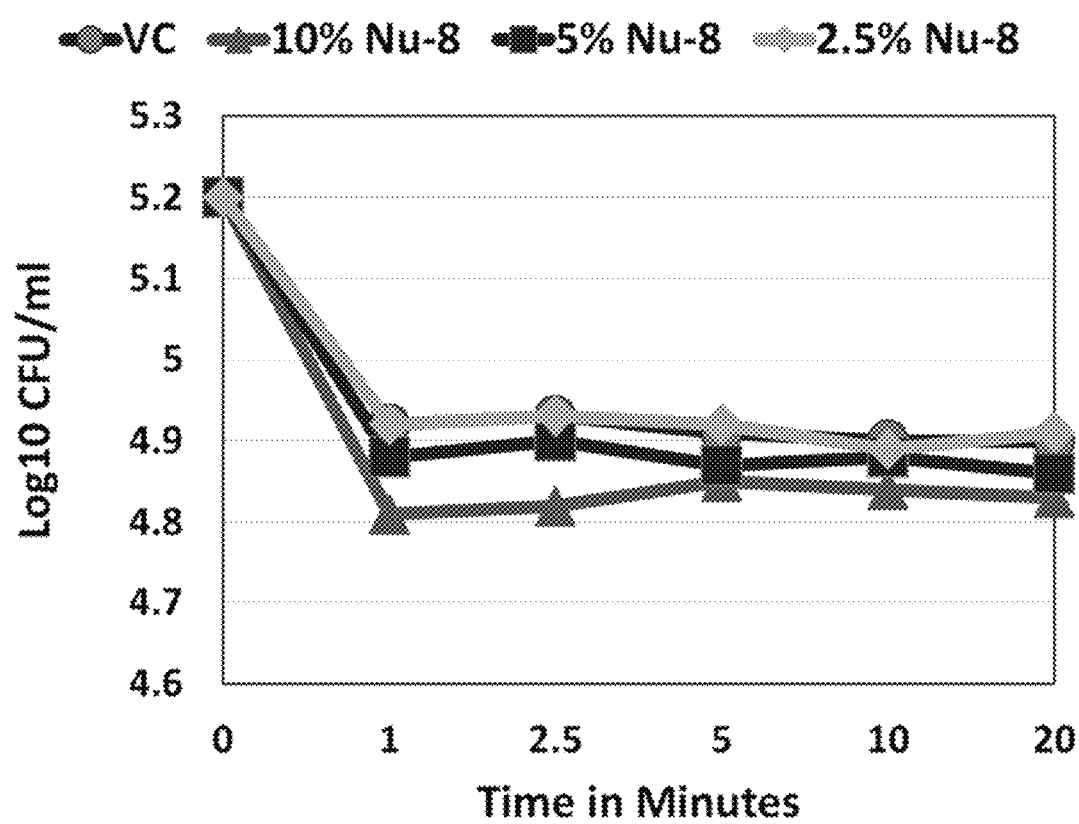
FIG. 2 shows a graph of $Log_{10}$ CFU vs. time for Nu-8 at 2.5%, 0.5%, and 0.1% solutions according to embodiments.
Figure 3:
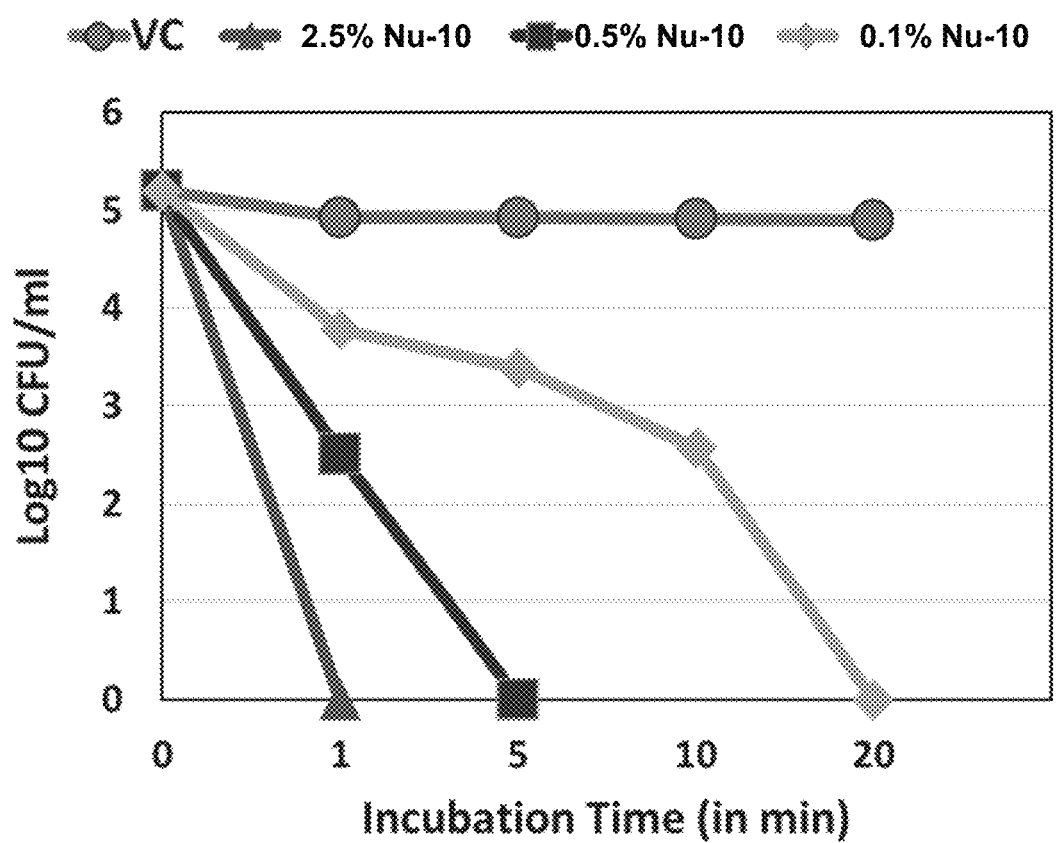
FIG. 3 shows a graph of $Log_{10}$ CFU vs. time for Nu-10 at 0.1%, 0.5%, and 2.5% solutions according to embodiments.

Tables 12-14 provide the time kill assay data for Nu-3 (Table 12), Nu-8 (Table 13) and Nu-10 (Table 14) against *E. coli*. These data are also presented graphically in FIG. 1 (Nu-3), FIG. 2 (Nu-8), and FIG. 3 (Nu-10).

TABLE 12

| | Log$_{10}$ CFU/mL | | | | | |
|---|---|---|---|---|---|---|
| | 0 min | 1 min | 2.5 min | 5 min | 10 min | 20 min |
| Vehicle Control | 5.20 | 4.93 | 4.93 | 4.91 | 4.90 | 4.90 |
| 10% Nu-3 | 5.20 | 2.85 | 0.00 | 0.00 | 0.00 | 0.00 |
| 5% Nu-3 | 5.20 | 3.00 | 2.10 | 0.00 | 0.00 | 0.00 |
| 2.5% Nu-3 | 5.20 | 3.38 | 2.55 | 1.99 | 0.00 | 0.00 |

TABLE 13

| | Log₁₀ CFU/mL | | | | | |
|---|---|---|---|---|---|---|
| | 0 min | 1 min | 2.5 min | 5 min | 10 min | 20 min |
| Vehicle Control | 5.20 | 4.93 | 4.93 | 4.91 | 4.90 | 4.90 |
| 10% Nu-8 | 5.20 | 4.86 | 4.79 | 4.76 | 4.71 | 4.75 |
| 5% Nu-8 | 5.20 | 4.88 | 4.92 | 4.90 | 4.95 | 4.90 |
| 2.5% Nu-8 | 5.20 | 4.93 | 4.90 | 4.93 | 4.90 | 4.93 |

TABLE 14

| | Log₁₀ CFU/mL | | | | | |
|---|---|---|---|---|---|---|
| | 0 min | 1 min | 2.5 min | 5 min | 10 min | 20 min |
| Vehicle Control | 5.20 | 4.93 | 4.93 | 4.91 | 4.90 | 4.90 |
| 2.5% Nu-10 | 5.20 | 0.00 | 0.00 | 0.00 | 0.00 | 0.00 |
| 0.5% Nu-10 | 5.20 | 2.51 | 0.00 | 0.00 | 0.00 | 0.00 |
| 0.1% Nu-10 | 5.20 | 3.78 | 3.38 | 2.57 | 0.00 | 0.00 |

Nu-10 was active, showing a complete kill of the bacteria within 1 minute at a concentration of 2.5% and a complete kill of the bacteria within 10 mins at a concentration of 0.1%. Nu-3 was less active with a complete kill of the bacteria within 2.5 mins at a concentration of 10% and a complete kill of the bacteria within 10 mins at a concentration of 2.5%. Nu-8 was the least active with a modest kill at 20 mins and at a concentration of 10%.

EXAMPLE 28

Treatment of Human Patient Having an Infection

A human patient is identified as having an infection. A pharmaceutical composition in the form of a liquid solution containing an effective amount of any compound described herein, such as Nu-8 or Nu-10, is administered in a manner consistent with the particular infection diagnosed. The patient is monitored until symptoms are alleviated or ameliorated, and the pharmaceutical composition may be administered one or more additional times if it is determined that such administration is necessary or helpful for treatment.

EXAMPLE 29

Treatment of Human Patient Having an Infection of a Lower Extremity

A human patient is identified as having an infection of a lower extremity. A pharmaceutical composition in the form of a gel containing an effective amount of any compound described herein, such as Nu-8 or Nu-10, is administered topically to the patient at the location of the infection of the lower extremity. The patient is monitored until symptoms are alleviated or ameliorated, and the pharmaceutical composition may be administered one or more additional times if it is determined that such administration is necessary or helpful for treatment.

EXAMPLE 30

Treatment of Human Patient Having an Infection of a Diabetic Foot Ulcer

A human patient is identified as having a diabetic foot ulcer. A pharmaceutical composition in the form of a gel containing an effective amount of any compound described herein, such as Nu-8 or Nu-10, is administered topically to the patient at the location of the diabetic foot ulcer. The patient is monitored until symptoms are alleviated or ameliorated, and the pharmaceutical composition may be administered one or more additional times if it is determined that such administration is necessary or helpful for treatment.

EXAMPLE 31

Treatment of Human Patient Having Bladder and/or a Urinary Tract Infection

A human patient is identified as having a bladder and/or a urinary tract infection. A pharmaceutical composition in the form of a liquid solution containing an effective amount of any compound described herein, such as Nu-8 or Nu-10, is administered intravesically to the patient via a catheter. The patient is monitored until symptoms are alleviated or ameliorated, and the pharmaceutical composition may be administered one or more additional times if it is determined that such administration is necessary or helpful for treatment.

EXAMPLE 32

Treatment of Human Patient Having a Lung Infection

A human patient is identified as having a lung infection. A pharmaceutical composition in the form of a liquid solution containing an effective amount of any compound described herein, such as Nu-8 or Nu-10, is administered inhalationally to the patient via a nebulizer. The patient is monitored until symptoms are alleviated or ameliorated, and the pharmaceutical composition may be administered one or more additional times if it is determined that such administration is necessary or helpful for treatment.

EXAMPLE 33

Treatment of Human Patient Having a Lung Infection Arising from Cystic Fibrosis

A human patient is identified as having a lung infection arising from cystic fibrosis. A pharmaceutical composition in the form of a liquid solution containing an effective amount of any compound described herein, such as Nu-8 or Nu-10, is administered inhalationally to the patient via a nebulizer. The patient is monitored until symptoms are alleviated or ameliorated, and the pharmaceutical composition may be administered one or more additional times if it is determined that such administration is necessary or helpful for treatment.

EXAMPLE 34

Treatment of Human Patient Having Pneumonia

A human patient is identified as having pneumonia. A pharmaceutical composition in the form of a liquid solution containing an effective amount of any compound described herein, such as Nu-8 or Nu-10, is administered inhalationally to the patient via a nebulizer. The patient is monitored until symptoms are alleviated or ameliorated, and the pharmaceutical composition may be administered one or more additional times if it is determined that such administration is necessary or helpful for treatment.

EXAMPLE 35

Treatment of Human Patient Having Ventilator Acquired Pneumonia

A human patient is identified as having ventilator acquired pneumonia. A pharmaceutical composition in the form of a liquid solution containing an effective amount of any compound described herein, such as Nu-8 or Nu-10, is administered inhalationally to the patient via a nebulizer. The patient is monitored until symptoms are alleviated or ameliorated, and the pharmaceutical composition may be administered one or more additional times if it is determined that such administration is necessary or helpful for treatment.

EXAMPLE 36

Treatment of Human Patient Having an Infection in a Burn Wound

A human patient is identified as having an infection in a burn wound. A pharmaceutical composition in the form of a gel containing an effective amount of any compound described herein, such as Nu-8 or Nu-10, is administered topically to the patient at the location of the burn wound. The patient is monitored until symptoms are alleviated or ameliorated, and the pharmaceutical composition may be administered one or more additional times if it is determined that such administration is necessary or helpful for treatment.

EXAMPLE 37

Treatment of Human Patient Having Otitis Externa

A human patient is identified as having otitis externa. A pharmaceutical composition in the form of a liquid solution containing an effective amount of any compound described herein, such as Nu-8 or Nu-10, is administered topically directly into the patient's external ear canal. The patient is monitored until symptoms are alleviated or ameliorated, and the pharmaceutical composition may be administered one or more additional times if it is determined that such administration is necessary or helpful for treatment.

EXAMPLE 38

Treatment of Female Human Patient Having Bacterial Vaginosis

A female human patient is identified as having bacterial vaginosis. A pharmaceutical composition in the form of a gel containing an effective amount of any compound described herein, such as Nu-8 or Nu-10, is administered topically onto or into the patient's vagina. The patient is monitored until symptoms are alleviated or ameliorated, and the pharmaceutical composition may be administered one or more additional times if it is determined that such administration is necessary or helpful for treatment.

EXAMPLE 39

Treatment of Human Patient Having Impetigo

A human patient is identified as having impetigo. A pharmaceutical composition in the form of a gel containing an effective amount of any compound described herein, such as Nu-8 or Nu-10, is administered topically to the patient at the location of the vesicles, pustules and/or yellowish crusts. The patient is monitored until symptoms are alleviated or ameliorated, and the pharmaceutical composition may be administered one or more additional times if it is determined that such administration is necessary or helpful for treatment.

EXAMPLE 40

Treatment of Human Patient Having Oral Mucositis

A human patient is identified as having oral mucositis. A pharmaceutical composition in the form of a liquid solution containing an effective amount of any compound described herein, such as Nu-8 or Nu-10, is administered topically directly into the patient's external ear canal. The patient is monitored until symptoms are alleviated or ameliorated, and the pharmaceutical composition may be administered one or more additional times if it is determined that such administration is necessary or helpful for treatment.

While embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A compound having the formula:

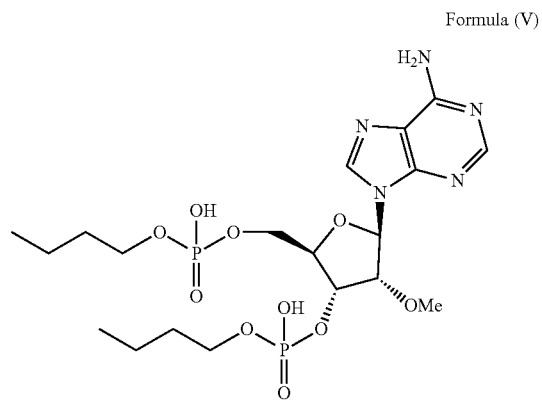 [SMILES: CCCCOP(=O)(O)OC[C@H]1O[C@@H](n2cnc3c(N)ncnc32)[C@H](OC)[C@@H]1OP(=O)(O)OCCCC]

Formula (V)

or a pharmaceutically acceptable salt thereof.

2. A compound having the formula:

Formula (VI)

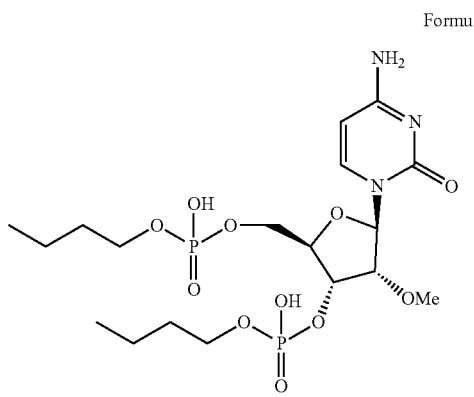

or a pharmaceutically acceptable salt thereof.

3. A compound having the formula:

Formula (VII)

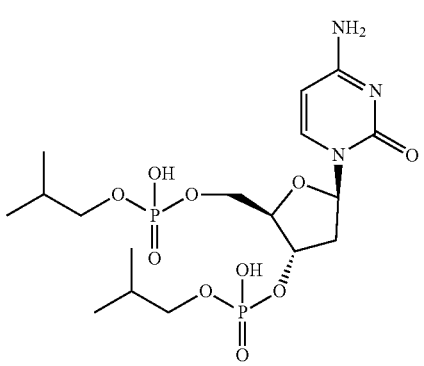

or a pharmaceutically acceptable salt thereof.

4. A compound having the formula:

Formula (VIII)

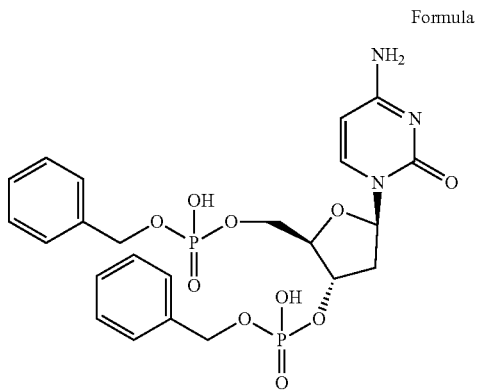

or a pharmaceutically acceptable salt thereof.

5. A compound having the formula:

Formula (IX)

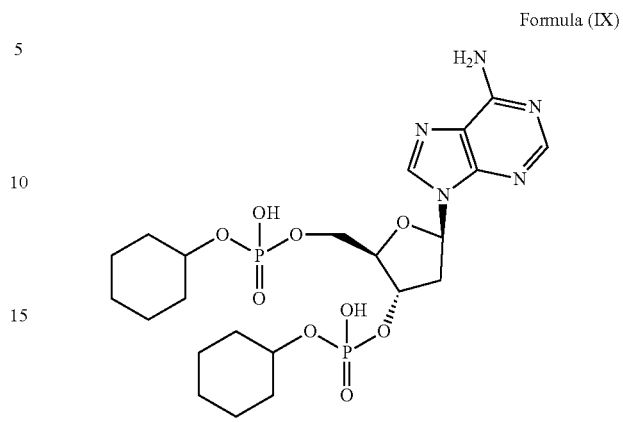

or a pharmaceutically acceptable salt thereof.

6. A pharmaceutical composition comprising a compound according to claim 2, or a pharmaceutically acceptable salt thereof, and one or more pharmaceutically acceptable carriers, excipients, or diluents.

7. A method of treating an infection in a patient in need thereof, the method comprising administering an effective amount of a compound according to claim 2, or a pharmaceutically acceptable salt thereof, to the patient.

8. A method of treating an infection of at least one of a wound or an ulcer in a patient in need thereof, the method comprising administering an effective amount of a compound according to claim 2, or a pharmaceutically acceptable salt thereof, to the patient.

9. A method of treating an infection of a diabetic foot ulcer in a patient in need thereof, the method comprising administering an effective amount of a compound according to claim 2, or a pharmaceutically acceptable salt thereof, to the patient.

10. A method of treating a bladder and/or a urinary tract infection in a patient in need thereof, the method comprising administering an effective amount of a compound according to claim 2, or a pharmaceutically acceptable salt thereof, to the patient.

11. A method of treating a lung infection in a patient in need thereof, the method comprising administering an effective amount of a compound according to claim 2, or a pharmaceutically acceptable salt thereof, to the patient.

12. The method of claim 11, wherein the lung infection arises from a pulmonary condition.

13. The method of claim 12, Wherein the pulmonary condition is selected from the group consisting of genetic conditions, acquired conditions, primary conditions, secondary conditions, asthma, chronic obstructive pulmonary disease, cystic fibrosis, bronchiolitis, pneumonia, bronchitis, emphysema, adult respiratory distress syndrome, allergies, lung cancer, small cell lung cancer, primary lung cancer, metastatic, lung cancer, bronchiestasis, bronchopulmonary dysplasia, chronic bronchitis, chronic lower respiratory diseases, croup, high altitude pulmonary edema, pulmonary fibrosis, interstitial lung disease, reactive airway disease, lymphangioleiomyomatosis, neonatal respiratory distress syndrome, parainfluenza, pleural effusion, pleurisy, pneumothorax, primary pulmonary hypertension, psittacosis, pulmonary edema secondary to various causes, pulmonary embolism, pulmonary hypertension secondary to various causes, respiratory failure secondary to various causes, sleep apnea, sarcoidosis, smoking, stridor, acute respiratory distress syndrome, infectious diseases, SARS, tuberculosis, psittacosis infection, Q fever, parainfluenza, respiratory syncytial virus, combinations thereof, and conditions caused by any one or combination of the above.

14. A method of treating cystic fibrosis in a patient in need thereof, the method comprising administering an effective amount of a compound according to claim 2, or a pharmaceutically acceptable salt thereof, to the patient.

15. A method of treating pneumonia in a patient in need thereof, the method comprising administering an effective amount of a compound according to claim 2, or a pharmaceutically acceptable salt thereof, to the patient.

16. The method of claim 15, wherein the pneumonia is ventilator acquired pneumonia.

17. A method of treating an infection in a burn wound in a patient in need thereof, the method comprising administering an effective amount of a compound according to claim 2, or a pharmaceutically acceptable salt thereof, to the patient.

18. A method of treating otitis externa in a patient in need thereof, the method comprising administering an effective amount of a compound according to claim 2, or a pharmaceutically acceptable salt thereof, to the patient.

19. A method of treating bacterial vaginosis in a patient in need thereof, the method comprising administering an effective amount of a compound according to claim 2, or a pharmaceutically acceptable salt thereof, to the patient.

20. A method of treating impetigo in a patient in need thereof, the method comprising administering an effective amount of a compound according to claim 2, or a pharmaceutically acceptable salt thereof, to the patient.

21. A method of treating oral mucositis in a patient in need thereof, the method comprising administering an effective amount of a compound according to claim 2, or a pharmaceutically acceptable salt thereof, to the patient.

* * * * *

UNITED STATES PATENT AND TRADEMARK OFFICE
CERTIFICATE OF CORRECTION

PATENT NO. : 11,795,192 B2
APPLICATION NO. : 17/890102
DATED : October 24, 2023
INVENTOR(S) : Steven A. Kates et al.

It is certified that error appears in the above-identified patent and that said Letters Patent is hereby corrected as shown below:

In the Specification

At Column 713, Line 19, please replace "(hydroxyl)phosphorypoxy)" with "(hydroxyl)phosphoryl)oxy".
At Column 713, Line 46, please replace "(isobutoxy)phosphorypoxy)" with "(hydroxyl)phosphoryl)oxy".
At Column 713, Line 49, please replace "((hydroxy(isobutoxy)phosphorypoxy)" with "((hydroxy(isobutoxy)phosphoryl)oxy)".
At Column 713, Line 60, please replace "((hydroxy(isobutoxy)phosphorypoxy)" with "((hydroxy(isobutoxy)phosphoryl)oxy)".
At Column 770, Line 34, please replace "(TBTH)" with "(TBHP)".
At Column 772, Line 9, please replace "TBTH" with "TBHP".
At Column 773, Line 55-56, please replace "N,N-diisopoylethylamine (DIEA)" with "N,N-diisopropylethylamine (DIPEA)".
At Column 775, Line 8, please replace "TBTH" with "TBHP".
At Column 776, Line 44, please replace "DIEA" with "DIPEA".
At Column 777, Line 28, please replace "DIEA" with "DIPEA".
At Column 778, Line 48, please replace "Nu-4" with "Nu-3".
At Column 779, Line 1, please replace "Nu-4" with "Nu-3".
At Column 779, Line 25, please replace "Nu-4" with "Nu-3".
At Column 779, Line 28, please replace "Nu-4" with "Nu-3".
At Column 779, Line 33, please replace "Nu-4" with "Nu-3".
At Column 779, Line 37, please replace "Nu-4" with "Nu-3".
At Column 779, Line 41, please replace "Nu-4" with "Nu-3".
At Column 779, Line 49, please replace "Nu-4" with "Nu-3".
At Column 779, Line 54, please replace "Nu-4" with "Nu-3".
At Column 779, Line 64, please replace "Nu-4" with "Nu-3".
At Column 780, Line 4, please replace "Nu-4" with "Nu-3".

Signed and Sealed this
Twenty-fifth Day of June, 2024

Katherine Kelly Vidal
*Director of the United States Patent and Trademark Office*